(12) United States Patent
Frincke

(10) Patent No.: US 9,115,168 B2
(45) Date of Patent: Aug. 25, 2015

(54) STEROIDS HAVING 7-OXYGEN AND 17-HETEROARYL SUBSTITUTION-3

(71) Applicant: Harbor Therapeutics, Inc., San Diego, CA (US)

(72) Inventor: James M. Frincke, San Diego, CA (US)

(73) Assignee: NEURMEDIX, INC., San Diego, CA (US)

( * ) Notice: Subject to any disclaimer, the term of this patent is extended or adjusted under 35 U.S.C. 154(b) by 211 days.

(21) Appl. No.: 14/027,842

(22) Filed: Sep. 16, 2013

(65) Prior Publication Data

US 2014/0018337 A1 Jan. 16, 2014

Related U.S. Application Data

(60) Division of application No. 13/095,528, filed on Apr. 27, 2011, now Pat. No. 8,569,275, which is a continuation-in-part of application No. 11/549,875, filed on Oct. 16, 2006, now Pat. No. 7,935,839, which is a continuation of application No. 10/651,515, filed on Aug. 28, 2003, now abandoned.

(60) Provisional application No. 60/407,146, filed on Aug. 28, 2002, provisional application No. 60/408,332, filed on Sep. 4, 2002, provisional application No. 60/479,257, filed on Jun. 17, 2003.

(51) Int. Cl.
  *C07J 13/00* (2006.01)
  *C07J 43/00* (2006.01)
  *C07J 41/00* (2006.01)

(52) U.S. Cl.
  CPC .............. *C07J 43/003* (2013.01); *C07J 13/005* (2013.01); *C07J 41/0011* (2013.01)

(58) Field of Classification Search
  None
  See application file for complete search history.

(56) References Cited

U.S. PATENT DOCUMENTS

| | | | |
|---|---|---|---|
| 4,548,749 A | 10/1985 | van Leusen | |
| 5,424,304 A | 6/1995 | Bettolini | |
| 5,604,213 A | 2/1997 | Barrie | |
| 5,677,293 A | 10/1997 | Peet | |
| 5,914,325 A | 6/1999 | Droesche | |
| 5,965,548 A | 10/1999 | Peet | |
| 5,994,335 A | 11/1999 | Brodie | |
| 6,143,736 A | 11/2000 | Upasani et al. | |
| 6,277,838 B1 | 8/2001 | Upasani et al. | |
| 7,482,334 B2 | 1/2009 | Frincke et al. | |
| 7,514,420 B2 | 4/2009 | Lardy et al. | |
| 7,696,189 B1 | 4/2010 | Frincke | |
| 2003/0060425 A1 | 3/2003 | Ahlem et al. | |
| 2003/0083231 A1 | 5/2003 | Ahlem et al. | |
| 2004/0138187 A1 | 7/2004 | Reading et al. | |
| 2006/0073099 A1 | 4/2006 | Frincke et al. | |
| 2006/0088473 A1 | 4/2006 | Dowding et al. | |
| 2007/0014719 A1 | 1/2007 | Reading et al. | |
| 2007/0077201 A1 | 4/2007 | Reading et al. | |
| 2008/0051380 A1 | 2/2008 | Auerbach | |
| 2011/0118219 A1 | 5/2011 | Njar et al. | |

FOREIGN PATENT DOCUMENTS

| | | |
|---|---|---|
| EP | 0551952(A2) | 7/1993 |
| EP | 0721461(B1) | 2/1999 |
| EP | 0752860(B1) | 8/2000 |
| EP | 1038880(A2) | 9/2000 |
| EP | 1336602(A1) | 8/2003 |
| WO | WO 90/10462(A1) | 9/1990 |
| WO | WO 93/20097 A1 | 10/1993 |
| WO | WO 95/21617(A1) | 8/1995 |
| WO | WO 96/40043(A1) | 12/1996 |
| WO | WO 01/23405(A1) | 4/2001 |
| WO | WO 01/30802(A2) | 5/2001 |
| WO | WO 02/069977(A1) | 9/2002 |
| WO | WO 2004/019953 (A1) | 3/2004 |
| WO | WO 2004/089304 (A2) | 10/2004 |
| WO | WO 2006/021776 (A1) | 3/2006 |
| WO | WO 2006/093993 (A1) | 9/2006 |
| WO | WO 2006/110172 (A2) | 9/2007 |
| WO | WO 2008/039566 (A2) | 4/2008 |
| WO | WO 2009/120565 (A2) | 10/2009 |

OTHER PUBLICATIONS

Wicha, J. et al. (1981) "Synthesis of 17α-pyridyl- and 17α-pyridonyl-androstane derivatives" *Heterocycles* 16: 521-524.
Wicha, J. et al. (1984) "Cardiotonic Steroids. Part 7. Synthesis of 17α-pyridylandrostane derivatives" *Bull. Pol. Acad. Sci.* 32: 75-83.
Wicha, J. et al. (1985) "Cardiotonic Steroids. Part 8. Synthesis of 17.beta.(3'-pyridyl)-14.beta.-Androst-4-ene-3.beta.14-diol from 17-Oxoandrostane Derivatives" *Bull. Pol. Acad. Sci.* 33:19-27.
Fernandez-Mateos, A. et al. (1998) *J. Chem. Res.* (S) 760-1.

(Continued)

*Primary Examiner* — Savitha Rao
*Assistant Examiner* — Gregg Polansky
(74) *Attorney, Agent, or Firm* — Daryl D. Muenchau

(57) ABSTRACT

The invention relates to the use of compounds to ameliorate or treat a condition such as a cystic fibrosis, neutropenia or other exemplified conditions. Exemplary compounds that can be used include 7β-hydroxy-17-(3-pyridyl)-androst-4,16-diene-3-one and other androst-4,16-diene compounds substituted at the 17-position with a heterocycle moiety and at the 3- and 7-positions with a hydroxyl, ester, ether or other disclosed moiety.

14 Claims, No Drawings

(56) References Cited

OTHER PUBLICATIONS

Wicha, J. et al. (1983) "Synthesis and molecular-biological activity of the pyridine analogue of cardiotonic steroids" *Heterocycles* 20: 231-234.

Barton, D.H.R. et al. (1985) "A new synthesis of pyrroles from nitroalkenes" *J. Chem. Soc. Chem. Comm.* 16: 1098-1100.

Kamernitskii, A.V. et al. (1987) "Alkaline cyclization of carboethoxyhydrozones of 21-hydroxyl-20-ketosteroids to 17α-(1',3',4'-oxadiazin-2'-ones) and its correlation with the geometry of the hydrozone fragment:" *Bull. Acad. Sci. (USSR)* 36: 173-175.

Fetizon, M. et al. (1990) "1,4-dioxene(2,3-dihydro-1,4-dioxine) in orgqnic synthesis. Part 9. Preparation of biologically active sidechains from 17-oxosteroids" *J. Chem. Soc. Perkin Trans 1* 1990: 1107-1110.

Barton, D.H.R. et al. (1990) "A useful synthesis of pyrroles from nitroolefins" *Tet.* 46: 7578-7598.

Barlaam, B. et al. (1993) "A new synthesis of substituted dienes by reductive elimination of allylic nitro derivatives" *Tet. Lett.* 34: 1023-1026.

van Leuson, D. et al. (1994) "Synthesis of 17-(2-methoxy-3-oxazolin-4-yl-, 17-3-oxazolin-4-yl)-, and 17-(2-oxazolin-4-ylidene)-sustituted steroids and their use as precursors of corticosteroids" *J. Org. Chem.* 59: 5650-5657.

Potter, G.A. et al. (1995) "Novel steroidal inhibitors of human cytochrome $P450_{17\beta}$, ($17\beta$-hdroxylase-$C_{17,20}$-lyase): potential agents for the treatment of prostatic cancer" *J. Med. Chem.* 38: 2463-2471.

Burkhart, J.P. et al. (1996) "Inhibition of steroid $C_{17(20)}$ lyase with C-17-heteroaryl steroids" *Bioorg. Med. Chem.* 4: 1411-1420.

Njar, V.C. et al. (1996) "Nucleophillic vinylic 'addition-elimination' substitution reaction of 3α-acetoxy-17-chloro-16-formylandrosta-5,16-diene: a novel and general route to 17-substituted steroids. Part 1-Synthesis of novel 17-azolyl-$\Delta^{16}$ steroids: inhibitors of 17β-hydroxylase/17,20-lyase (17β-lyase)" *Bioorg. Med. Chem Lett.* 6: 2777-2782.

Ling, Y. et al. (1997) 17-imidazolyl, pyrazolyl, and isoxazolyl androstene derivatives. Novel steroidal inhibitors of human cytochrome $C_{17,20}$ lyase ($P450_{17\beta}$) *J. Med. Chem.* 40: 3297-3304.

Njar, V.C. et al. (1998) "Novel 17-azolyl steroids, potent inhibitors of human cytochrome 17β-hydroxylase-C17,20-lyase ($P450_{17\beta}$): potential agents for the treatment of prostate cancer" *J. Med. Chem.* 41: 902-912.

Zhuang, Y. et al. (2000) "Novel imidazolyl and triazolyl substituted biphenyl compounds: synthesis and evaluations as nonsteroidal inhibitors of human 17β-hydroxylase-C17, 20 lyase (P450 17)" *Bioorg. Med. Chem.* 8: 1245-1252.

Haidar, S. et al. (2001) "Novelsteroidal pyrimidyl inhibitors of P450 17 (17β-hydroxylase/C17-20-lyase)" *Arch. Pharm.* 334: 373-374.

Zhu, N. et al. (2003) "Novel $P450_{17\beta}$ inhibitors: 17-(2'-oxazolyl)- and 17-(2'-thiazolyl-androstene derivatives" *Steroids* 68: 603-612.

Handratta, V.D. et al. (2005) "Novel C-17-heteroaryl steroidal CYP17 inhibitors/antiandrogens: synthesis, in vitro biological activity, pharmacokinetics, and anti-tumor activity in the LAPC4 human prostate cancer xenograft model" *J. Med. Chem.* 48: 2972-2984.

Chao, J. et al. (2006) "A versatile synthesis of 17-heteroaryl androstenes via paladium-mediated cross-coupling with heteroaryl boronic acids" *Steroids* 71: 585-590.

Moreria, V.M.A. et al. (2007) "Synthesis and evaluation of novel 17-indazole androstene derivatives as CYP17 inhibitors" *Steroids* 72: 939-948.

STEROIDS HAVING 7-OXYGEN AND 17-HETEROARYL SUBSTITUTION-3

CROSS REFERENCE TO RELATED APPLICATIONS

This application is division of pending U.S. application Ser. No. 13/095,528, filed on Apr. 27, 2011, which is a continuation in part of U.S. application Ser. No. 11/549,875, filed Oct. 16, 2006, now U.S. Pat. No. 7,935,839, which is a continuation of U.S. application Ser. No. 10/651,515, now abandoned, filed Aug. 28, 2003, which claims priorty to abandoned U.S. provisional application Ser. No. 60/407,146, filed Aug. 28, 2002, U.S. abandoned provisional application Ser. No. 60/408,332, filed Sep. 4, 2002 and abandoned U.S. provisional application Ser. No. 60/479,257, filed Jun. 17, 2003, all of which are incorporated herein by reference.

FIELD OF THE INVENTION

The invention relates to methods to use compounds, such as 3β-hydroxy-16α-fluoro-17β-aminoandrost-5-ene, 3β-hydroxy-16β-fluoro-17β-aminoandrost-5-ene, 3β-hydroxy-17β-aminoandrost-5-ene, 1α,3β-dihydroxy-4α-fluoroandrost-5-ene, 1α,3β,17β-trihydroxy-4α-fluoroandrost-5-ene, 1β,3β-dihydroxy-6-bromoandrost-5-ene-17-one, 1α-fluoro-3β,12α-dihydroxyandrost-5-ene-17-one, 1α-fluoro-3β,4α-dihydroxyandrost-5-ene and 4α-fluoro-3β,6α,17β-trihydroxyandrostane to treat, ameliorate or prevent neutropenia, cystic fibrosis conditions or other pathological or disease conditions or their symptoms.

BACKGROUND

Immune dysregulation can be a component of many pathological diseases or conditions. Such dysregulation may be a factor that favors the establishment, maintenance or progression of these diseases or conditions. Deficient immune responses or immune suppression can enhance a mammal's susceptibility to infection or to the development of cancer. Conversely, excessive or inappropriate immune responses can play a role in the establishment or progression of unwanted inflammation or autoimmune conditions. It would thus be advantageous to utilize agents that can modulate immune responses and to at least partially reverse immune dysregulation when such dysregulation is a component of a given pathological condition. Some agents are known that can ameliorate some aspects of immune dysregulation, but typically such agents have their own unwanted effects on either the host's immune system or other organs or tissues. Agents such as glucocorticoid steroids have been used to reduce unwanted inflammation in a number of clinical conditions, but such compounds often have serious limitations, such as inducing immune suppression or causing unwanted mood changes.

Human and mammalian immune responses to infections or other conditions are often characterized by responses mediated by different immune effector cell populations. In some situations, helper T cells designated Th1 in the murine system, facilitate immune effector functions that are typically dominated by cell-mediated responses. In other cases, helper T cells designated Th2 cells facilitate immune effector functions that are typically dominated by humoral responses. A vigorous Th1 response is usually desirable to help clear infections or to slow the progression of an infection. When a subject's immune response is biased to, or dominated by, a Th2-type response, the cytokines associated with the Th2 response tend to suppress the immune system's capacity to mount a vigorous Th1 response at the same time. The converse is also generally true. When mammalian immune responses begin to result in an increasing Th1 response, Th2 responses tend to weaken. Insufficient Th1 responses may be associated with progression of some infections or other conditions, see, e.g., M. Clerici and G. M. Shearer, *Immunol. Today* 14:107-111, 1993; M. Clerici and G. M. Shearer, *Immunol. Today* 15:575-581, 1994.

There is a current need for cost-effective pharmaceutical agents and treatment methods for treating various immune dysregulation conditions. The invention provides compounds that can be used in such treatments to treat or ameliorate one or more aspects of immune dysregulation conditions. Such agents can be used to treat autoimmune or inflammation conditions, immune suppression conditions, infections, blood cell deficiencies and other described conditions. The agents and methods are useful to ameliorate these conditions or one or more symptoms associated with any of these conditions. The use of these agents can be combined with one or more conventional treatments for these disorders.

DESCRIPTION OF THE INVENTION

Summary of Invention Embodiments

In principal embodiments the invention provides therapeutic treatment methods.

The methods include a method to prevent, treat, ameliorate or slow the progression of cystic fibrosis, sickle cell disease, neutropenia or thrombocytpoenia in a subject, or to treat a symptom of the cystic fibrosis, sickle cell disease, neutropenia or thrombocytopenia, comprising administering to a subject, or delivering to the subject's tissues, an effective amount of a formula 1 compound having the structure 5, 6, 7, 8, 9, 10, 11, 12, 13 or 14

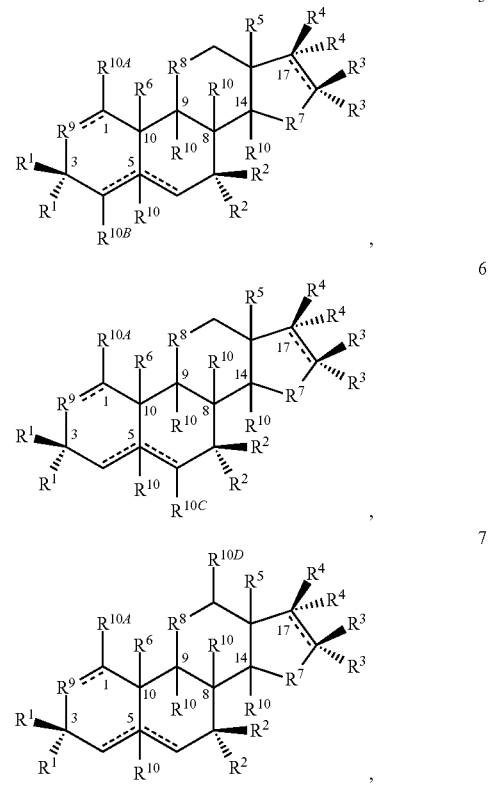

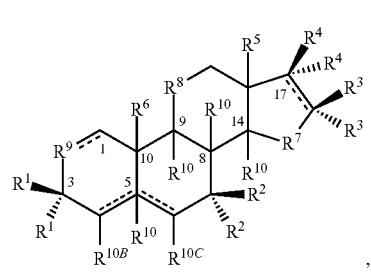

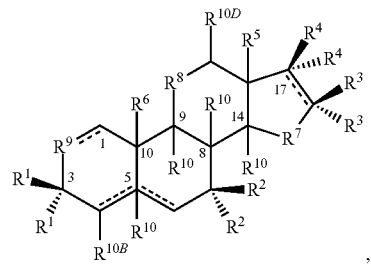

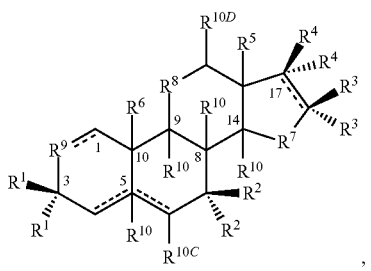

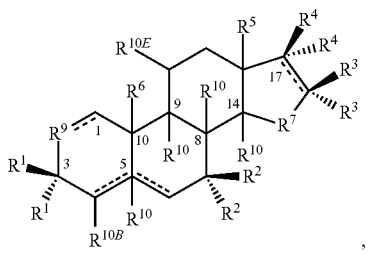

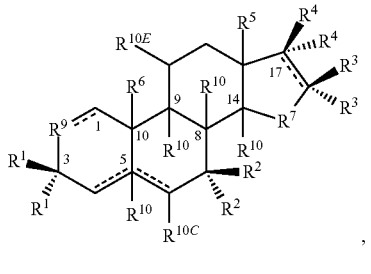

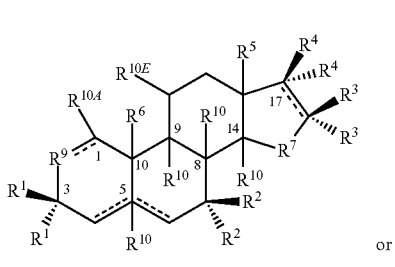

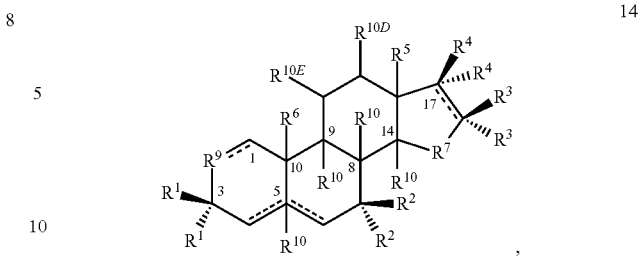

or a metabolic precursor or a metabolite thereof, wherein $R^{10}$ moieties at the 5 (if present), 8, 9 and 14 positions respectively are in the α,α,α,α, α,α,α,β, α,α,β,α, α,β,α,α, β,α,α,α, α,α,β,β, α,β,α,β, β,α,α,β, β,α,β,α, β,β,α,α, α,β,β, α, α,β,β,β, β,α,β,β, β, β,α,β, β,β,β,α or β,β,β,β configurations, wherein $R^{10A}$, $R^{10B}$, $R^{10C}$, $R^{10D}$ and $R^{10E}$ respectively are in the α,α, α,β, β,α or β,β configurations, wherein, each $R^1$, $R^2$, $R^3$, $R^4$, $R^5$, $R^6$, $R^{10}$, $R^{10A}$, $R^{10B}$, $R^{10C}$, $R^{10D}$ and $R^{10E}$ independently are —H, —OH, —OR$^{PR}$, —SR$^{PR}$, —N(R$^{PR}$)$_2$, —O—Si—(R$^{13}$)$_3$, —CHO, —CHS, —CN, —SCN, —NO$_2$, —NH$_2$, —COOH, —OSO$_3$H, —OPO$_3$H, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate, a carbamate, a halogen, an optionally substituted alkyl group, an optionally substituted alkenyl group, an optionally substituted alkynyl group, an optionally substituted aryl moiety, an optionally substituted heteroaryl moiety, an optionally substituted heterocycle, an optionally substituted monosaccharide, an optionally substituted oligosaccharide, a nucleoside, a nucleotide, an oligonucleotide, a polymer, or, one more of $R^1$, $R^2$, $R^3$, $R^4$, $R^5$, $R^6$, $R^{10}$, $R^{10A}$, $R^{10B}$, $R^{10C}$, $R^{10D}$ and $R^{10E}$ are =O, =S, =N—OH, =CH$_2$, =CH—CH$_3$, or an independently selected spiro ring and the hydrogen atom or the second variable group that is bonded to the same carbon atom is absent, or, one or more of two adjacent $R^1$-$R^6$, $R^{10}$, $R^{10A}$, $R^{10B}$, $R^{10C}$, $R^{10D}$ and $R^{10E}$ comprise an independently selected epoxide, acetal, a thioacetal, ketal or thioketal;

$R^7$ is —C(R$^{10}$)$_2$—, —C(R$^{10}$)$_2$—C(R$^{10}$)$_2$—, —C(R$^{10}$)$_2$—C(R$^{10}$)$_2$—C(R$^{10}$)$_2$—, —C(R$^{10}$)$_2$—O—C(R$^{10}$)$_2$—, —C(R$^{10}$)$_2$—S—C(R$^{10}$)$_2$—, —C(R$^{10}$)$_2$—NR$^{PR}$—C(R$^{10}$)$_2$—, —O—, —O—C(R$^{10}$)$_2$—, —S—, —S—C(R$^{10}$)$_2$—, —NR$^{PR}$— or —NR$^{PR}$—C(R$^{10}$)$_2$—;

$R^8$ and $R^9$ independently are —C(R$^{10}$)$_2$—, —C(R$^{10}$)$_2$—C(R$^{10}$)$_2$—, —O—, —O—C(R$^{10}$)$_2$—, —S—, —S—C(R$^{10}$)$_2$—, —NR$^{PR}$— or —NR$^{PR}$—C(R$^{10}$)$_2$—, or one or both of $R^8$ or $R^9$ independently are absent, leaving a 5-membered ring;

$R^{13}$ independently is C$_{1-6}$ alkyl; and

R$^{PR}$ independently is —H or a protecting group. In typical embodiments, one or two of $R^{10A}$, $R^{10B}$, $R^{10C}$, $R^{10D}$ and $R^{10E}$ are not hydrogen or one $R^4$ is —NH$_2$, an opotionally substituted amine, —N(R$^{PR}$)$^2$, =NOH, =NO-optionally substituted alkyl, an amide or an N-linked amino acid.

Other embodiments include (1) certain new formula 1 compounds, which are new chemical entities, (2) compositions that comprise a formula 1 compound and another compound or an excipient, (3) formulations that comprise a formula 1 compound and 1, 2, 3, 4, 5, 6 or more excipients. The formulations can be designed for human pharmaceutical use or they can be suitable for veterinary use. Therapeutic use embodiments include (1) use of a formula 1 compound for the preparation of a medicament and (2) use of a formula 1 compound for the preparation of a medicament for the prophylaxis or treatment of a condition or symptom disclosed herein.

Other embodiments are as described elsewhere in the specification including the claims.

Definitions

As used herein and unless otherwise stated or implied by context, terms that are used herein have the meanings defined below. Unless otherwise contraindicated or implied, e.g., by including mutually exclusive elements or options, in these definitions and throughout this specification, the terms "a" and "an" mean one or more and the term "or" means and/or.

Reference to an androstane compound, e.g., $3\beta,16\alpha,17\beta$-trihydroxyandrostane, means that the hydrogen atom at the 5-position is in the $\alpha$-configuration. For androstanes with hydrogen in the $\beta$-configuration, the compound name will specify this configuration, e.g., $3\beta,16\alpha,17\beta$-trihydroxy-$5\beta$-androstane.

An "invention formulation", "formulation", "pharmaceutical formulation" or the like means a composition that one can administer to a subject, e.g., human, mammal or other animal, without further manipulations that change the ingredients or the ingredient proportions that are present. Formulations will typically comprise a single formula 1 compound and one or more excipients. Formulations are suitable for human or veterinary applications and would typically have expected characteristics for the formulation, e.g., parenteral formulations for human use would usually be sterile and stored in a suitable closed container.

When referring to mixtures that contain a formula 1 compound, an "invention composition", "composition" or the like means a composition, that is a formulation or that can be an intermediate one can use, e.g., to make a formulation or a formula 1 compound. Compositions also include other types of mixtures, e.g., (1) reagents for assays or cells that are optionally contacted with a formula 1 compound or mixtures of compounds and (2) compounds used to make a formula 1 compound or by-products of formula 1 compound synthesis or analysis. Invention compositions include compositions where further processing may be required before it is a formulation, e.g., mixing or addition of a desired amount of an excipient.

Phrases such as "administration of a compound of formula 1", "treatment with a formula 1 compound", "use of a formula 1 compound" or similar terms mean that the compound(s) is administered to, contacted with or delivered to, the subject or to the subject's cells or tissues in vitro or in vivo by one or more suitable methods, e.g., in vivo delivery can be by an oral, topical, subcutaneous, parenteral, buccal or sublingual route.

Expressions such as "a formula 1 compound(s)", "a formula 1 compound" and the like mean invention compositions or formulations where one or more than one formula 1 compound is present, e.g., in a composition, or is used in the disclosed method, typically 1, 2, 3 or 4, usually 1. Any reference to a "formula 1 compound", "one or more compounds of formula 1" or the like means that the formula 1 compound can have the formula 2 structure or any other structure disclosed herein that is within the definition of formula 1 compounds. The phrase formula 1 compound or formula 1 compound(s) is sometimes abbreviated as "F1C" or "F1C(s)" and formula 1 compounds may be abbreviated as "F1Cs".

Reference to subject matter "as disclosed herein" such as a "therapeutic treatment or agent as disclosed herein", a "dosing protocol as disclosed herein" or a "clinical condition or symptom as disclosed herein" or the like means a treatment, agent, protocol, condition, symptom or the like that is described herein or in any reference that is cited herein.

An "excipient", "carrier", "pharmaceutically acceptable excipient", "pharmaceutically acceptable carrier" or similar terms mean one or more component(s) or ingredient(s) that is acceptable in the sense of being compatible with the other ingredients of invention compositions or formulations and not overly deleterious to the patient, animal, tissues or cells to which the F1C, composition or formulation is to be administered.

A "subject" means a human or animal. Usually the animal is a mammal or vertebrate such as a primate, rodent, lagomorph, domestic animal or game animal. Primates include chimpanzees, cynomologous monkeys, spider monkeys, and macaques, e.g., *Rhesus* or *Pan*. Rodents and lagomorphs include mice, rats, woodchucks, ferrets, rabbits and hamsters.

The terms "effective amount", "effective dose" or the like with reference to a F1C(s) mean an amount of the F1C(s) that is sufficient to elicit a desired response, e.g., detectable restoration of normal immune responsiveness in an immunodeficient subject to which it is administered, e.g., a human, or to detectable modulation or amelioration of an immune or cellular parameter or a clinical condition or symptom. An effective amount, e.g., for human therapeutic use, may be a single dose or two or more subdoses of a F1C administered in one day, or it may be administered as multiple doses over a period of time, e.g., over 1, 2, 3, 4 or about 7 days to about 1 year.

Terms such as "use", "treat", "treatment", "address" or the like in the context of using the F1Cs in the treatment methods or other methods disclosed herein mean that a F1C is administered to a subject, delivered to the subject's tissues or contacted with tissues, cells or cell free systems in vivo or in vitro, e.g., as described herein or a reference cited herein. Typically such use or treatment results in, e.g., (1) detectable improvement in or amelioration of the condition or symptom being treated, (2) detectable modulation in the activity, level or numbers of a relevant biomolecule, therapeutic immune cell population or a pathological cell population, (3) slowing of the progression of a condition or delaying its onset, or reduction of the severity of a symptom(s) of the condition or (4) another detectable response as described herein.

Thus, a F1C use or treatment typically results in detectable modulation in a relevant immune parameter such as modulation of the level, activity or relative amount of a target effector or suppressor immune cell population, interleukin, cytokine, chemokine, immunoglobulin compared to a suitable control, e.g., untreated. A F1C treatment can also cause modulation of the level or activity of a relevant transcription factor, enzyme, cell biological activity or level or activity of the etiological agent of the disease such as a pathogen, tumor cell or autoreactive immune cell subset. A treatment with a F1C may be used to delay or prevent the onset of a disease, symptom or complication or to ameliorate or slow the progression of a preexisting disease, condition, symptom or complication, or to facilitate elimination of a disease, condition, symptom or complication.

"Alkyl" as used here means linked normal, secondary, tertiary or cyclic carbon atoms, i.e., linear, branched, cyclic or any combination thereof. Alkyl moieties, as used herein, may be saturated, or unsaturated, i.e., the moiety may comprise one, two, three or more independently selected double bonds or triple bonds. Unsaturated alkyl moieties include moieties as described for alkenyl and alkynyl moieties described below. The number of carbon atoms in an alkyl group or moiety can vary and typically is 1 to about 50, e.g., about 1-30 or about 1-20, unless otherwise specified, e.g., $C_{1-8}$ alkyl or C1-C8 alkyl means an alkyl moiety containing 1, 2, 3, 4, 5, 6, 7 or 8 carbon atoms. When an alkyl group is specified, species may include methyl, ethyl, 1-propyl (n-propyl), 2-propyl (i-propyl, —CH(CH$_3$)$_2$), 1-butyl (n-butyl), 2-methyl-1-propyl (i-butyl, —CH$_2$CH(CH$_3$)$_2$), 2-butyl (s-butyl, —CH(CH$_3$)CH$_2$CH$_3$), 2-methyl-2-propyl (t-butyl, —C(CH$_3$)$_3$), 1-pentyl (n-pentyl), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl, 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), cyclopropyl (—CH<CH$_2$CH$_2$), cyclobutyl (—CH<CH$_2$CH$_2$CH$_2$), cyclopentyl, cyclohexyl, cycloheptyl, cyclooctyl, —(CH$_2$)$_n$—(CHCH$_3$)$_m$—(CH$_2$)$_o$—CH$_3$, —(CH$_2$)$_n$—(CHC$_2$H$_5$)$_m$—(OH$_2$)$_o$—OH$_3$ and species and groups described below for alkenyl, alkynyl groups aryl groups, arylalkyl groups alkylaryl groups and the like, where n, m and o independently are 0, 1, 2, 3, 4, 5, 6, 7 or 8.

For any group or moiety described by a given range of carbon atoms, the designated range means that any individual number of carbon atoms is described. Thus, reference to, e.g., "C1-C4 optionally substituted alkyl", "$C_{2-6}$ alkenyl", or "C2-C6 optionally substituted alkenyl", specifically means that a 1, 2, 3 or 4 carbon optionally substituted alkyl moiety as defined herein is present, or a 2, 3, 4, 5 or 6 carbon alkenyl or optionally substituted alkenyl moiety as defined herein is present. All such designations are expressly intended to disclose all of the individual carbon atom groups and thus "C1-C4 optionally substituted alkyl" means, e.g., 3 carbon alkyl, 4 carbon substituted alkyl and the like are disclosed and can be expressly referred to or named.

"Alkenyl" as used here means a moiety that comprises linked normal, secondary, tertiary or cyclic carbon atoms, i.e., linear, branched, cyclic or any combination thereof, that comprises one or more double bonds (e.g., —CH═CH—), e.g., 1, 2, 3, 4, 5, 6 or more, typically 1 or 2. The number of carbon atoms in an alkenyl group or moiety can vary and typically is 2 to about 50, e.g., about 2-30 or about 2-20, unless otherwise specified, e.g., $C_{2-8}$ alkenyl or C2-8 alkenyl means an alkenyl moiety containing 2, 3, 4, 5, 6, 7 or 8 carbon atoms. When an alkenyl group is specified, species may include methylene (═CH$_2$), methylmethylene (═CH—CH$_3$), ethylmethylene (═CH—CH$_2$—CH$_3$), ═CH—CH$_2$—CH$_2$—CH$_3$, vinyl (—CH═CH$_2$), allyl, —(CH$_2$)$_n$—(CH═CH)—(CH$_2$)$_m$—CH$_3$, —(CH$_2$)$_n$—(CCH$_3$═CH)—(CH$_2$)$_m$—CH$_3$, —(CH$_2$)$_n$—(CH═CCH$_3$)—(CH$_2$)$_m$—CH$_3$ and —(CH$_2$)$_n$—(CH═CH)$_{0-1}$—(CH$_2$)$_m$—CH$_2$CH═CH$_2$, where n and m independently are 0, 1, 2, 3, 4, 5, 6, 7 or 8.

"Alkynyl" as used here means a moiety that comprises linked normal, secondary, tertiary or cyclic carbon atoms, i.e., linear, branched, cyclic or any combination thereof, that comprises one or more triple bonds (—C≡C—), e.g., 1, 2, 3, 4, 5, 6 or more, typically 1 or 2 triple bonds, optionally comprising 1, 2, 3, 4, 5, 6 or more double bonds, with the remaining bonds being single bonds. The number of carbon atoms in an alkenyl group or moiety can vary and typically is 2 to about 50, e.g., about 2-30 or about 2-20, unless otherwise specified, e.g., $C_{2-8}$ alkynyl or C2-8 alkynyl means an alkynyl moiety containing 2, 3, 4, 5, 6, 7 or 8 carbon atoms. When an alkynyl group is specified, groups and species may include —CCH, —CCCH$_3$, —CCCH$_2$CH$_3$, —CCC$_3$H$_7$, —CCCH$_2$C$_3$H$_7$, —(CH$_2$)$_n$—(C≡C)—(CH$_2$)$_m$—CH$_3$, and —(CH$_2$)$_n$—(C≡C)$_{0-1}$—(CH$_2$)$_m$—CH$_2$C≡CH, where n and m independently are 0, 1, 2, 3, 4, 5, 6, 7 or 8.

"Aryl" means an aromatic ring or fused ring system with no ring heteroatoms, e.g., phenyl or naphthyl.

"Arylalkyl" means a moiety where an alkyl group is bonded to an aryl group, i.e., -alkyl-aryl, where alkyl and aryl groups are as described above, e.g., —CH$_2$—C$_6$H$_5$ or —CH$_2$CH(CH$_3$)—C$_6$H$_5$.

"Alkylaryl" means a moiety where an aryl group is bonded to an alkyl group, i.e., -aryl-alkyl, where aryl and alkyl groups are as described above, e.g., —C$_6$H$_4$—CH$_3$ or —C$_6$H$_4$—CH$_2$CH(CH$_3$).

"Substituted alkyl", "substituted alkenyl", "substituted alkynyl", substituted alkylaryl", "substituted arylalkyl", "substituted heterocycle", "substituted aryl", "substituted monosaccharide" and the like mean an alkyl, alkenyl, alkynyl, alkylaryl, arylalkyl heterocycle, aryl, monosaccharide or other group or moiety as defined or disclosed herein that has a substituent(s) that replaces a hydrogen atom(s) or a substituent(s) that interrupts a carbon atom chain. Substituted heterocycles may thus have a substituent bonded to a ring carbon or a ring heteroatom such as a nitrogen.

Substituents are independently chosen when more than one is present. Alkenyl and alkynyl groups that comprise a substituent(s), are optionally substituted at a carbon that is one or more methylene moiety removed from the double bond, e.g., the substituent is optionally separated by one, two, three or more independently selected —CH$_2$—, —CH(C$_{1-6}$ optionally substituted alkyl)-, —CH(C$_{1-6}$ optionally substituted alkenyl)-, —CH(C$_{1-6}$ optionally substituted alkynyl)-, —CH (optionally substituted heterocycle)-, —CH(optionally substituted aryl-optionally substituted alkyl)- or —CH(optionally substituted alkyl-optionally substituted aryl)-moieties.

"Heterocycle" or "heterocyclic" includes by way of example and not limitation the heterocycles described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 1960, 82:5566. Heterocycles are typically bonded to the steroid nucleus through a carbon, nitrogen or sulfur atom in the heterocycle ring.

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Typically, nitrogen bonded heterocycles include 1-aziridyl, 1-azetedyl, 1-pyrrolyl, 1-imidazolyl, 1-pyrazolyl, and 1-piperidinyl.

"Heteroaryl" means an aromatic ring or two or more fused rings that contain one or more aromatic rings where the ring or fused rings comprise 1, 2, 3 or more heteroatoms, usually oxygen (—O—), nitrogen (—NX—) or sulfur (—S—) where X is —H, a protecting group or $C_{1-6}$ optionally substituted alkyl, usually —H. Examples are as described for heterocycle.

"Alcohol" as used herein means an alcohol that comprises a $C_{1-12}$ alkyl moiety substituted at a hydrogen atom with one hydroxyl group. Alcohols include methanol, ethanol, n-propanol, i-propanol, n-butanol, i-butanol, s-butanol, t-butanol, n-pentanol, i-pentanol, n-hexanol, cyclohexanol, n-heptanol, n-octanol, n-nonanol and n-decanol. The carbon atoms in alcohols can be straight, branched or cyclic. Alcohol includes any subset of the foregoing, e.g., $C_{1-4}$ alcohols (alcohols having 1, 2, 3 or 4 carbon atoms).

"Halogen" means fluorine, chlorine, bromine or iodine.

"Protecting group" means a moiety that prevents or reduces the atom or functional group to which it is linked from participating in unwanted reactions. For example, for —$OR^{PR}$, $R^{PR}$ may be hydrogen or a protecting group for the oxygen atom found in a hydroxyl, while for —C(O)—$OR^{PR}$, $R^{PR}$ may be hydrogen or a carboxylprotecting group, for —$SR^{PR}$, $R^{PR}$ may be hydrogen or a protecting group for sulfur in thiols for instance, and for —$NHR^{PR}$ or —$N(R^{PR})_2$—, $R^{PR}$ may be hydrogen or a nitrogen atom protecting group for primary or secondary amines. Hydroxyl, amine, ketones and other reactive groups are found in F1Cs at, e.g., $R^1$ or $R^2$. These groups may require protection against reactions taking place elsewhere in the molecule. The protecting groups for oxygen, sulfur or nitrogen atoms are usually used to prevent unwanted reactions with electrophilic compounds, such as acylating agents used, e.g., in steroid chemistry.

"Ester" means a moiety that contains a —C(O)—O— structure. Typically, esters as used here comprise an organic moiety containing about 1-50 carbon atoms (e.g., about 2-20 carbon atoms) and 0 to about 10 independently selected heteroatoms (e.g., O, S, N, P, Si), where the organic moiety is bonded to a formula 1 steroid nucleus at, e.g., $R^1$ or $R^2$ through the —C(O)—O— structure, e.g., organic moiety-C(O)—O-steroid or organic moiety-O—C(O)-steroid. The organic moiety usually comprises one or more of any of the organic groups described herein, e.g., $C_{1-20}$ alkyl moieties, $C_{2-20}$ alkenyl moieties, $C_{2-20}$ alkynyl moieties, aryl moieties, $C_{2-9}$ heterocycles or substituted derivatives of any of these, e.g., comprising 1, 2, 3, 4 or more substituents, where each substituent is independently chosen. Exemplary substitutions for hydrogen or carbon atoms in these organic groups are as described above for substituted alkyl and other substituted moieties. Substitutions are independently chosen. The organic moiety includes compounds defined by the $R_4$ variable. The organic moieties exclude obviously unstable moieties, e.g., —O—O—, except where such unstable moieties are transient species that one can use to make a compound with sufficient chemical stability for one or more of the uses described herein, including for synthesis of the formula 1 or other compounds. The substitutions listed above are typically substituents that one can use to replace one or more carbon atoms, e.g., —O— or —O(O)—, or one or more hydrogen atom, e.g., halogen, —$NH_2$ or —OH. Exemplary esters include one or more independently selected acetate, enanthate, propionate, isopropionate, isobutyrate, butyrate, valerate, caproate, isocaproate, hexanoate, heptanoate, octanoate, nonanoate, decanoate, undecanoate, phenylacetate or benzoate, which are typically hydroxyl esters.

"Acetal", "thioacetal", "ketal", "thioketal" "spiro ring" and the like mean a cyclic organic moiety that is bonded to a steroid ring atom in the F1Cs, e.g., steroid nucleus atoms at one, two or more of the 1, 2, 3, 4, 6, 7, 11, 12, 15, 16, 17, 18 or 19 positions. Typically, acetals comprise an organic moiety containing about 1-20 carbon atoms (e.g., about 1-10 carbon atoms) and 0 to about 10 independently selected heteroatoms (e.g., O, S, N, P, Si). For acetals (or ketals), the steroid nucleus atoms are usually carbons and the acetal is bonded to a steroid carbon through two oxygen atoms. Thioacetals (or thioketals) are bonded to the steroid nucleus through one oxygen and one sulfur atom or, more often, through two sulfur atoms. One, two or more of e.g., $R^1$, $R^2$, $R^3$, $R^4$, $R^{10}$ at the 2, 11 or 15 positions, $R^{10A}$, $R^{10B}$, $R^{10C}$ and $R^{10D}$, may be an independently selected acetal, thioacetal or spiro ring in any of the F1Cs disclosed herein. The oxygen or sulfur atoms in ketals and thioketals are linked by an optionally substituted alkyl moiety. Typically the alkyl moiety is an optionally substituted C1-C6 alkylene or branched alkyl structure such as —$C(CH_3)_2$—, —$CH(CH_3)$—, —$CH_2$—, —$CH_2$—$CH_2$—, —$C[(C2-C4\ alkyl)_2]_{1,2,3}$— or —$[CH(C2-C4\ alkyl)]_{1,\ 2,\ 3}$-. Acetals include moieties having the structure —O—$[C(R^{36})_2]_{1-6}$—O—, —O—$CH_2$—$[C(R^{36})_2]_2$—O—, —O—$CH_2$—$CH_2$—$[C(R^{36})_2]_2$—O—, —O—$CH_2$—$[C(R^{36})_2]_2$—$CH_2$—O—, and —O—$CH_2$—$C(R^{36})_2$—O—, where each $R^{36}$ independently is —H, —OH, =O, =S, —SH, —F, —Cl, —Br, —I or an organic moiety such as C1-C6 alkyl (e.g., methyl, ethyl, hydroxymethyl or halomethyl), C2-C6 alkenyl, C2-C6 alkenyl, aryl or an heterocycle, any of which are optionally substituted, e.g., —$CF_3$ or —$CH_2OH$. In some of these embodiments, one $R^{36}$ is —H and the other is another atom or moiety, e.g., —OH, methyl or a halogen. In other embodiments, neither $R^{36}$ is —H, e.g., both are methyl. Thioacetals include moieties that comprise a —S—$[C(R^{36})_2]_{1-6}$—O— or —S—$[C(R^{36})_2]_{1-6}$—S— structure where the open valences are bonded to the same carbon on the steroid nucleus. Other exemplary acetal and thioacetals are —O—$C(CH_3)_2$—O—, —O—$CH_2$—$CH_2$—$CH_2$—O—, —O—$CH_2$—$CH_2$—O—, —O—$CH_2$—O—, —O—$C(CH_3)$ (heterocycle)-O—, —O—CH(heterocycle)-O—, —O—C(CH$_3$)(aryl)-O—, —O—CH(aryl)-O—, —S—C(CH$_3$)$_2$—O—, —S—C(CH$_3$)$_2$—S—, —S—CH$_2$—CH$_2$—O—, —S—CH$_2$—CH$_2$—S—, —S—CH$_2$—CH$_2$—O—, —S—CH$_2$—S—, —O—C(CH$_3$)$_2$—CH$_2$—O—, —O—C(CH$_3$)$_2$—C(CH$_3$)$_2$—O—, —S—C(CH$_3$)$_2$—CH$_2$—O— and —O—C(CH$_3$)$_2$—CH$_2$—S—. Some of these moieties can serve as protecting groups for a ketone or hydroxyl, e.g., acetals such as —O—CH$_2$—CH$_2$—CH$_2$—O— or —O—CH$_2$—CH$_2$—O— for ketones, which form a spiro ring that can be removed by chemical synthesis methods or by metabolism in cells or biological fluids. For any spiro ring disclosed herein and unless otherwise specified, the 1$^{st}$ and 2$^{nd}$ open valences can be bonded to the carbon in the steroid nucleus in the α- and β-configurations respectively or in the α- and β-configurations respectively. For example, in a spiro —NH—CH$_2$—CH$_2$—O— structure, the 1$^{st}$ open valence, i.e., at the nitrogen atom, can be, e.g., at the 17-position in the β-configuration and the 2$^{nd}$ open valence, i.e., at the oxygen, would then be in the α-configuration.

"Amide", "amide derivative" and the like mean an organic moiety as described for ester that comprises a —C(O)—NR$^{PR}$— or —C(O)—NH— moiety, where R$^{PR}$ is —H or a protecting group. In some embodiments, the —C(O)NR$^{PR}$— group is linked to the steroid nucleus at a variable group such as R$^1$-R$^6$, R$^{10}$, R$^{15}$, R$^{17}$ or R$^{18}$, i.e., organic moiety —C(O)NR$^{PR}$-steroid, organic moiety-C(O)—NH-steroid or steroid-C(O)NR$^{PR}$-organic moiety. The organic moiety is as described above for esters.

"Ether" means an organic moiety as described for ester that comprises 1, 2, 3, 4 or more —O— moieties, usually 1 or 2. In some embodiments, the —O— group is linked to the steroid nucleus at a variable group such as R$^1$-R$^6$, R$^{10}$, R$^{15}$, R$^{17}$ or R$^{18}$, e.g., organic moiety-O-steroid. The organic moiety is as described above for esters.

"Acyl group" or "acyl" means an organic moiety as described for ester that comprises 1, 2, 3, 4 or more —C(O)— groups. In some embodiments, the —C(O)— group is linked to the steroid nucleus at a variable group such as R$^1$-R$^6$, R$^{10}$, R$^{15}$, R$^{17}$ or R$^{18}$, e.g., organic moiety-C(O)-steroid. The organic moiety is as described above for esters.

"Carbonate" means an organic moiety as described for ester that comprises 1, 2, 3, 4 or more —O—C(O)—O— structures. Typically, carbonate groups as used here comprise an organic moiety containing about 1-50 carbon atoms and 0 to about 10 independently selected heteroatoms (e.g., O, S, N, P, Si) linked to a formula 1 steroid nucleus at a variable group such as R$^1$-R$^6$, R$^{10}$, R$^{15}$, R$^{17}$ or R$^{18}$, through the —O—C(O)—O— structure, e.g., organic moiety-O—C(O)—O-steroid. The organic moiety is as described above for esters.

"Carbamate" means an organic moiety as described for ester that comprises 1, 2, 3, 4 or more —O—C(O)NR$^{PR}$— structures where R$^{PR}$ is —H, a protecting group or an organic moiety as described for ester. Typically, carbamate groups as used here comprise an organic moiety containing about 1-50 carbon atoms and 0 to about 10 independently selected heteroatoms (e.g., O, S, N, P, Si) linked to a formula 1 steroid nucleus at a variable group such as R$^1$-R$^6$, R$^{10}$, R$^{15}$, R$^{17}$ or R$^{18}$, through the —O—C(O)—NR$^{PR}$— structure, e.g., organic moiety-O—C(O)—NR$^{PR}$-steroid or steroid-O—C(O)—NR$^{PR}$-organic moiety. The organic moiety is as described above for esters.

Optionally substituted alkyl group, optionally substituted alkenyl group, optionally substituted alkynyl group, optionally substituted aryl moiety and optionally substituted heterocycle mean an alkyl, alkenyl, alkynyl, aryl or heterocycle moiety that contains an optional substitution(s). Such moieties include C$_{1-20}$ alkyl moieties, C$_{2-20}$ alkenyl moieties, C$_{2-20}$ alkynyl moieties, aryl moieties, C$_{2-9}$ heterocycles or substituted derivatives of any of these.

As used herein, position numbers that are given for the F1Cs use the numbering convention for cholesterol.

As used herein, "innate immunity" refers to one or more components typically associated with nonspecific immune defense mechanisms in a subject. These components include the alternate complement pathway, e.g., Factor B, Factor D and properdin; NK cells, phagocytes (monocytes, macrophages), neutrophils, eosinophils, dendritic cells, fibrocytes; anti-microbial chemicals, e.g., one or more of defensins; physical barriers—skin, mucosal epithelium; or certain interleukins, chemokines, cytokines, lung or alveolar macrophage respiratory burst activity or a lung surfactant protein such as surfactant protein A or surfactant protein D. Innate immunity plays a role in resistance to intracellular parasite infections, e.g., white blood cell infection, a liver infection, and other infections, e.g., lymph node infections. Detectable enhancement of innate immunity mechanism by F1Cs or method described herein can also enhance phagolysosome fusion or movement, which some pathogens, e.g., intracellular bacteria such as mycobacteria, or *Listeria* inhibit.

Terms such as "immune dysregulation", "immune dysregulation condition", "unwanted immune response" and the like mean that a subject has or is subject to developing an immune response that is not desirable or is suboptimal for the subject's condition. Such dysregulation or unwanted responses can arise from various clinical conditions or diseases or as a result of treatment of such conditions or diseases, e.g., inflammation, autoimmunity, organ or tissue transplant rejection (e.g., allograft, xenograft), infections, cancers, chemotherapy treatments, trauma, allergy conditions or in conditions where a subject mounts a Th1, Tc1, Th2 or Tc2 immune response that is considered to be pathogenic, ineffective, insufficient or suboptimal. Immune dysregulation conditions are as described herein or in the cited references.

Terms such as "cellular response", "cellular activity", "biological response", "biological activity" and the like mean a response or activity that is detectably modulated in response to the presence of a F1C. Such responses or activities can be direct effects or indirect effects on one or more cellular activities or on the expression or level of one or more molecules that the affected cell(s) bind, sequester, synthesize or respond to. Such responses or activities include a detectable change in the synthesis or level of one or more cytokines, growth factors, transcription factors (including receptors and their cofactors), enzymes, Th1- or Th2-associated antibody subtype responses or the like. Typically, the cytokines, growth factors, transcription factors, enzymes or antibodies that are modulated are involved in the amelioration of a pathological condition or in the establishment, maintenance, severity or progression of a pathological condition.

As used herein, references to CD molecules, specific immune cell subsets, immune responses and the like, generally use nomenclature that applies to molecules, cells or the like that are found in humans. Analogs or counterparts of such molecules, cells or the like in other species may have a differing nomenclature, but are included in this invention. A description of the nomenclature and function of various CD molecules and immune cell subsets are as found in the scientific literature. References to Th0, Th1 or Th2 cells and references to Th1 or Th2 immune responses in the context of human patients refers to the human counterparts of the murine Th0, Th1 or Th2 immune cells or responses. For reviews see, e.g., A. K. Abbas et al., editors, *Cellular and Molecular Immunology*, W.B. Saunders Company, third edition, 1997, ISBN 0-7216-4024-9, pages 4-469, and I. Kimber and M. K. Selgrade, editors, *T Lymphocyte Subpopulations in Immunotoxicology*, John Wiley & Sons Ltd., 1998, ISBN 0-471-97194-4, pages 1-53.

"Immunosuppressive molecule" means molecules such as cyclosporin, cyclohexamide, mitomycin C, adriamycin, taxol and amphotericin B. These molecules tend to have toxicities toward the immune system and are directly or indirectly immunosuppressive, e.g., they are toxic to dividing cells, they inhibit proliferation of immune cell precursors or they can downregulate an otherwise desired or improved immune response or condition.

"Nuclear hormone receptor" means a gene product, typically as a protein monomer or dimer that can bind to a ligand and affect transcription of one or more genes. Ligands include, e.g., certain natural steroids, steroid analogs, F1Cs or another ligand such as a lipid, e.g., a prostaglandin, or the like. Nuclear hormone receptors include orphan steroid receptors, which typically function as heterodimers and the classical steroid receptors, e.g., androgen receptor ("AR"), estrogen receptor α ("ERα"), estrogen receptor β ("ERβ"), that function as homodimers.

Salts of F1Cs.

Invention embodiments include salts and complexes of F1Cs, including pharmaceutically acceptable or salts that are relatively non-toxic. Some of the F1Cs have one or more moieties that carry at least a partial positive or negative charge in aqueous solutions, typically at a pH of about 4-10, that can participate in forming a salt, a complex, a composition with partial salt and partial complex properties or other noncovalent interactions, all of which we refer to as a "salt(s)". Salts are usually biologically compatible or pharmaceutically acceptable or non-toxic, particularly for mammalian cells. Salts that are biologically toxic are optionally used with synthetic intermediates of F1Cs. When a water-soluble composition is desired, monovalent salts are usually used.

Metal salts typically are prepared by reacting the metal hydroxide with a compound of this invention. Examples of metal salts that are optionally prepared in this way are salts containing $Li^+$, $Na^+$, and $K^+$. A less soluble metal salt can be precipitated from the solution of a more soluble salt by adding a suitable metal compound. Invention salts may be formed from acid addition of certain organic acids, such as organic carboxylic acids, and inorganic acids, such as alkylsulfonic acids or hydrogen halide acids, to acidic or basic centers on F1Cs, such as basic centers on the invention pyrimidine base analogs. Metal salts include ones containing $Na^+$, $Li^+$, $K^+$, $Ca^{++}$ or $Mg^{++}$.

Salts are produced by standard methods, including dissolving free base in an aqueous, aqueous-alcohol or aqueous-organic solution containing the selected acid, optionally followed by evaporating the solution. The free base is reacted in an organic solution containing the acid, in which case the salt usually separates directly or one can concentrate the solution.

Suitable amine salts include amines having sufficient basicity to form a stable salt, usually amines of low toxicity including trialkyl amines (tripropylamine, triethylamine, trimethylamine), procaine, dibenzylamine, N-benzyl-betaphenethylamine, ephenamine, N,N'-dibenzylethylenediamine, N-ethylpiperidine, benzylamine and dicyclohexylamine.

Salts include organic sulfonic acid or organic carboxylic acid salts, made for example by addition of the acids to basic centers, typically amines. Exemplary sulfonic acids include $C_{6-16}$ aryl sulfonic acids, $C_{6-16}$ heteroaryl sulfonic acids and $C_{1-16}$ alkyl sulfonic acids such as phenyl sulfonic acid, a-naphthalene sulfonic acid, β-naphthalene sulfonic acid, (S)-camphorsulfonic acid, methyl ($CH_3SO_3H$), ethyl ($C_2H_5SO_3H$), n-propyl, i-propyl, n-butyl, s-butyl, i-butyl, t-butyl, pentyl and hexyl sulfonic acids. Exemplary organic carboxylic and other acids include $C_{1-16}$ alkyl, $C_{6-16}$ aryl carboxylic acids and $C_{4-16}$ heteroaryl carboxylic acids such as acetic, glycolic, lactic, pyruvic, malonic, glutaric, tartaric, citric, fumaric, succinic, malic, maleic, oxalic, hydroxymaleic, benzoic, hydroxybenzoic, phenylacetic, cinnamic, salicylic, nicotinic, 2-phenoxybenzoic, methanesulfonic, pamoic, propionic, toluenesulfonic and trifluoroacetic acids.

Invention salts include those made from inorganic acids, e.g., HF, HCl, HBr, HI, $H_2SO_4$, $H_3PO_4$, $Na_2CO_3$, $K_2CO_3$, $CaCO_3$, $MgCO_3$ and $NaClO_3$. Suitable anions, which are optionally present with a cation such a $Ca^{++}$, $Mg^{++}$, $Li^+$, $Na^+$ or $K^+$, include arsenate, arsenite formate, sorbate, chlorate, perchlorate, periodate, dichromate, glycodeoxycholate, cholate, deoxycholate, desoxycholate, taurocholate, taurodeoxycholate, taurolithocholate, tetraborate, nitrate, nitrite, sulfite, sulfamate, hyposulfite, bisulfite, metabisulfite, thiosulfate, thiocyanate, silicate, metasilicate, $CN^-$, gluconate, gulcuronate, hippurate, picrate, hydrosulfite, hexafluorophosphate, hypochlorite, hypochlorate, borate, metaborate, tungstate and urate.

Salts also include the F1C salts with one or more amino acids. Many amino acids are suitable, especially the naturally-occurring amino acids found as protein components, although the amino acid typically is one bearing a side chain with a basic or acidic group, e.g., lysine, arginine, histidine or glutamic acid, or a neutral group such as glycine, serine, threonine, alanine, isoleucine, or leucine.

Embodiments of Formula 1 Compounds.

For formula 1 compounds ("F1Cs"), 2, 3 or more of $R^1$, $R^2$, $R^3$ and $R^4$ are usually not —H, and typically one or both $R^1$ and $R^4$, $R^3$ and $R^4$, $R^2$, $R^3$ and $R^4$ or $R^2$ and $R^4$ are not —H, and/or 1 or 2 of $R^{10A}$, $R^{10B}$, $R^{10C}$ and $R_{10D}$ are optionally not —H. For any F1C disclosed herien, steroid nucleus carbon atoms that contain two variable groups (e.g., two $R^{10}$ at $R^8$ or $R^9$ or two $R^3$ or $R^4$ at the 16- or 17-position), each variable group is independently selected and each can thus be the same or different, e.g., both can be methyl, ethyl, methoxy, ethoxy, —F, —Cl, —Br, —I, or they can be different. As is apparent from the F1C structures, a double bond can be present at either the 4-5 position or at the 5-6 position, but not at both positions at the same time. Steroid nucleus carbon atoms refers generally to the carbons that make up the rings in F1Cs and carbons, if present, that are bonded to the 10, 13 and 17 positions. Additional carbons that may be at the 17-position are typically numbered using the cholesterol numbering system, although any other suitable nomenclature can be used to describe species or genera of F1C. Exemplary F1C embodiments are described below.

F1Cs include 16α-bromoepiandrosterone ("BrEA") hemihydrate

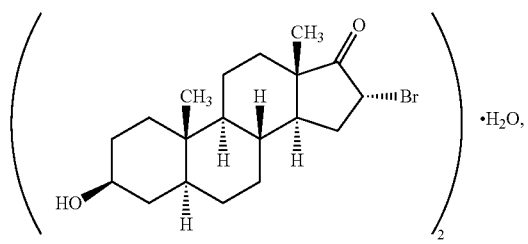

which has previously been described, e.g., WO 00/56757. BrEA hemihydrate is used as a F1C either as a pure compound or substantially free of other forms of BrEA, such as amorphous BrEA or anhydrous BrEA.

F1Cs include compounds having the structure 5, 6, 7, 8, 9 and 10,

5

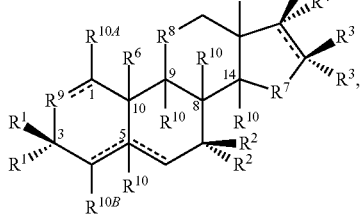

6

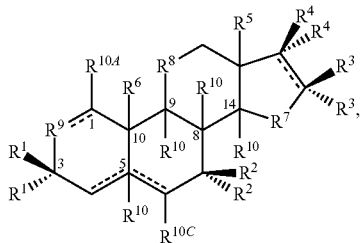

7

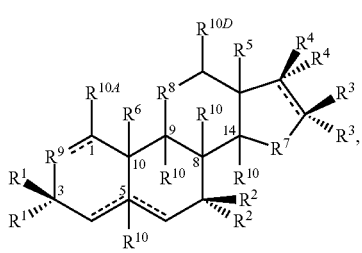

8

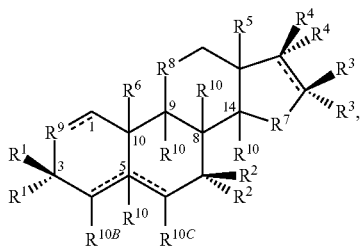

9

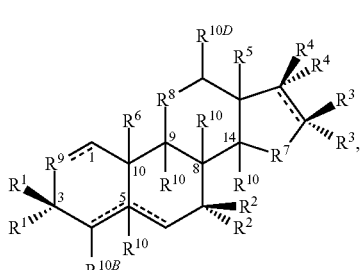

10

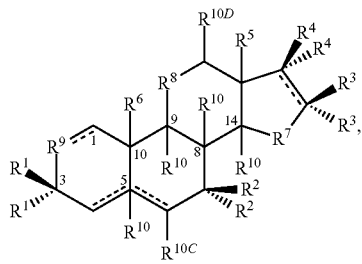

or a metabolic precursor, a metabolite or salt thereof, wherein each $R^1$, $R^2$, $R^3$, $R^4$, $R^{10}$ at the 2, 11 and 15 positions, $R^{10A}$, $R^{10B}$, $R^{10C}$ and $R^{10D}$ independently are —H, —OH, —OR$^{PR}$, —SR$^{PR}$, —N(R$^{PR}$)$_2$, —O—Si—(R$^{10}$)$_3$, —CHO, —CHS, —CN, —SCN, —NO$_2$, —ONO$_2$, —N$_3$, —NH$_2$, —COOH, —OSO$_3$H, —OPO$_3$H, =O, =S, =NOH, =CH$_2$, =CH$_2$CH$_3$, =N—NH—C(=NH)—N(R$^{PR}$)$_2$, =N—NH—C(=NH)—NH$_2$, an ester, a thioester, a thionoester, a phosphoester, a phosphothioester, a phosphonoester, a phosphiniester, a sulfite ester, a sulfate ester, a sulfoxide, a sulfamate, a sulfonate, a sulfamide, a sulfinamide, a sulfurous diamide, an amide, an amino acid, a peptide, an ether, a thioether, an acyl group, a thioacyl group, a carbonate, a carbamate, a halogen, an acetal, a thioacetal a spiro ring, an optionally substituted alkyl group, an optionally substituted alkenyl group, an optionally substituted alkynyl group, an optionally substituted aryl moiety, an optionally substituted heteroaryl moiety, an optionally substituted heterocycle, an optionally substituted monosaccharide, an optionally substituted oligosaccharide, a nucleoside, a nucleotide, an oligonucleotide, a polymer, or, one or more of two adjacent $R^1$-$R^4$, $R^{10}$, $R^{10A}$, $R^{10B}$, $R^{10C}$ and $R^{10D}$ are an independently selected epoxide or cyclopropyl ring;

$R^5$, $R^6$ and $R^{10}$ at the 5 (if present), 8, 9 and 14 positions independently are —H, —CH$_3$, —C$_2$H$_5$, —OH, —OR$^{PR}$, —SR$^{PR}$, —N(R$^{PR}$)$_2$, —O—Si—(R$^{13}$)$_3$, —CHO, —CHS, —CN, —SCN, —N$_3$, —COOH, —OS(O)(O)OH, an ester, a thioester, a thionoester, a sulfite ester, a sulfate ester, a sulfoxide, a sulfamate, a sulfonate, a sulfamide, a sulfinamide, a sulfurous diamide, an amide, an amino acid, a peptide, an ether, a thioether, an acyl group, a thioacyl group, a carbonate, a carbamate, a halogen, an optionally substituted alkyl group, an optionally substituted alkenyl group, an optionally substituted alkynyl group, an optionally substituted aryl moiety, an optionally substituted heteroaryl moiety, an optionally substituted heterocycle, an optionally substituted monosaccharide, an optionally substituted oligosaccharide, or, one, two or more of $R^5$, $R^6$ and $R^{10}$ at the 5, 8, 9 and 14 positions, together with a carbon atom that is adjacent to the carbon to which the $R^5$, $R^6$ or $R^{10}$ at the 5, 8, 9 or 14 position is bonded are an independently selected epoxide or cyclopropyl ring;

$R^7$ is —C(R$^{10}$)$_2$—, —C(R$^{10}$)$_2$—C(R$^{10}$)$_2$—, —C(R$^{10}$)$_2$—C(R$^{10}$)$_2$—C(R$^{10}$)$_2$—, —C(R$^{10}$)$_2$—O—C(R$^{10}$)$_2$—, —C(R$^{10}$)$_2$—S—C(R$^{10}$)$_2$—, C(R$^{10}$)$_2$—NR$^{PR}$—C(R$^{10}$)$_2$—, —O—, —O—C(R$^{10}$)$_2$—, —S—, —S—C(R$^{10}$)$_2$—, —NR$^{PR}$—, —NH— or —NR$^{PR}$—C(R$^{10}$)$_2$—;

$R^8$ and $R^9$ independently are —C(R$^{10}$)$_2$—, —C(R$^{10}$)$_2$—C(R$^{10}$)$_2$—, —O—, —O—C(R$^{10}$)$_2$—, —S—, —S—C(R$^{10}$)$_2$—, —NR$^{PR}$— or —NR$^{PR}$—C(R$^{10}$)$_2$—, or one or both of $R^8$ or $R^9$ independently are absent, leaving a 5-membered ring;

$R^{13}$ independently is $C_{1-6}$ alkyl; and $R^{PR}$ independently are —H, a protecting group or together are a protecting group, wherein 0, 1, 2, 3 or 4 of $R^{10A}$, $R^{10B}$, $R^{10C}$ and $R^{10D}$ are —H, $R^5$ and $R^6$ respectively are in the ββ, α,β, β,α or α,α configurations, and wherein $R^{10}$ moieties at the 5 (if present), 8, 9 and 14 positions respectively are in the α,α,α,α, α,α,α,β, α,α,β,α, α,β,α,α, β,α,α,α, α,α,β,β, α,β, α,β, β,α,α,β, β,α,β,α, β,β,α,α, α,β,β,α, α,β,β,β, β,α,β,β, β,β,α,β, β,β,β,α or β,β,β,β configurations. For any of the F1Cs of structure 5, 6, 7, 8, 9 or 10 where two variable groups are bonded to the same carbon, e.g., $R^1$, $R^2$, $R^3$, $R^4$ or $R^{10}$ at the 11 position, the each variable group at that position is independently selected.

In the F1Cs, each $R^1$, $R^2$, $R^3$, $R^4$, $R^{10}$ at the 2, 11 and 15 positions, is independently selected. In some embodiments one of the $R^1$, $R^2$, $R^3$, $R^4$, $R^{10}$ at the 2, 11 and 15 positions is hydrogen and the other is —H another moiety, but usually 2, 3, 4, 5 or 6 of the remaining variable groups are not —H, i.e., they are another moiety as defined for those groups. In other embodiments, both $R^1$, $R^2$, $R^3$, $R^4$, $R^{10}$ at the 2, 11 and 15 positions, are independently selected moieties other than hydrogen, i.e., they are another moiety as defined for those groups such as a C1-C20 organic moiety or C1-C20 optionally substituted alkyl group. In many embodiments $R^1$ at the 1-position in the β-configuration or $R^1$ at the 1-position in the α-configuration is not —H and $R^4$ at the 1-position in the β-configuration or $R^1$ at the 1-position in the α-configuration is not —H.

Other embodiments of species and genera of F1Cs include compounds of structures B, C, D, E, F and G

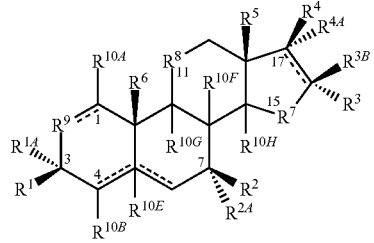
B

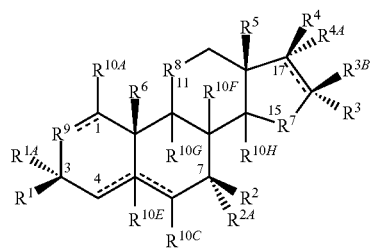
C

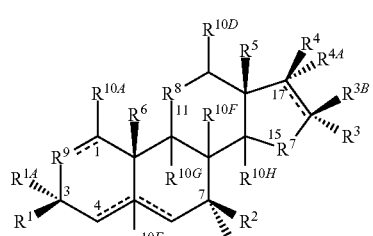
D

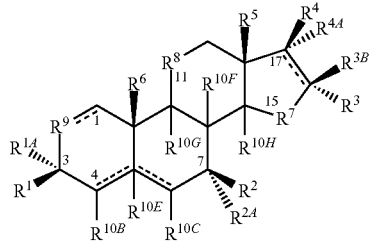
E

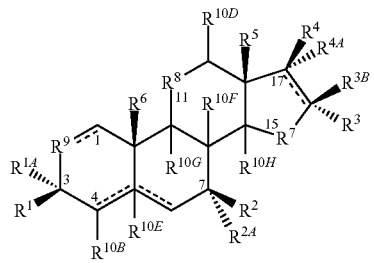
F

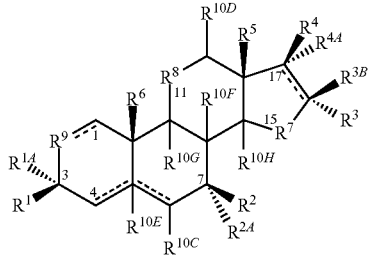
G where the dotted lines represent double or single bonds, each $R^{10A}$, $R^{10B}$, $R^{10C}$, $R^{10D}$, $R^{10E}$ (when present), $R^{10F}$, $R^{10G}$ and $R^{10H}$ is an independently selected single bonded $R^{10}$ moiety in the α-configuration or the β-configuration, or each $R^{10A}$, $R^{10B}$, $R^{10C}$ and $R^{10D}$ is an independently selected double bonded $R^{10}$ moiety (e.g., =O or =CH$_2$), $R^{1A}$ is a single bonded $R^1$ moiety in the α-configuration, or $R^{1A}$ together with $R^1$ is a double bonded moiety (e.g., =O, =NOH, =CH$_2$ or =CH—CH$_3$), $R^{2A}$ is a single bonded $R^2$ moiety in the α-configuration, or $R^{2A}$ together with $R^2$ is a double bonded moiety, $R^{3B}$ is a single bonded $R^3$ moiety in the β-configuration, or $R^{3B}$ together with $R^3$ is a double bonded moiety, or $R^{3B}$ is absent if a double bond is present at the 16-17 position, $R^{4A}$ is a single bonded $R^4$ moiety in the α-configuration, or $R^{4A}$ together with $R^4$ is a double bonded moiety, or $R^{4A}$ is absent if a double bond is present at the 16-17 position, and $R^5$, $R^6$, $R^7$, $R^8$ and $R^9$ are as previously defined. When a double bond is present at the 4-5 or the 5-6 positions, $R^{10E}$ is absent. For these structures, $R^{10A}$, $R^{10B}$, $R^{10C}$ and $R^{10D}$ may be in the α,α, α,β, β,α, or β,β configurations respectively, while $R^{10E}$, $R^{10F}$, $R^{10G}$ and $R^{10H}$ may be in the α,α,α,α, α,α,α,β, α,α,β,α, α,β,α,α, β,α,α,α, α,α,β,β, α,β,α,β, β,α,α,β, β,α,β,α, β,β,α,α, α,β,β,α, α,β,β,β, β,α,β, β, β,β,α,β, β,β,β,α or β,β,β,β configurations respectively, typically the α,β,α,α or β,β,α,α configurations.

Thus, when $R_{10E}$, $R_{10F}$, $R^{10G}$ and $R^{10H}$ respectively are in the α,β,α,α configurations and $R^{10A}$ and $R^{10B}$ or $R^{10A}$ and $R^{10C}$ or $R^{10A}$ and $R^{10D}$ or $R^{10B}$ and $R^{10C}$ or $R^{10B}$ and $R^{10D}$ or $R^{10C}$ and $R^{10D}$ are both in α-configurations exemplary B, C, D, E, F and G structures include B
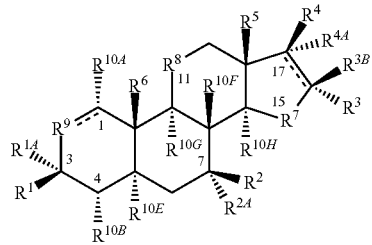
C
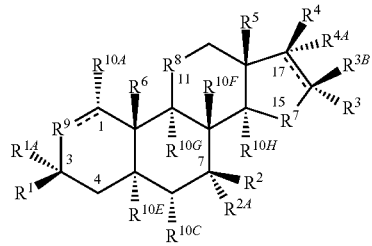
D
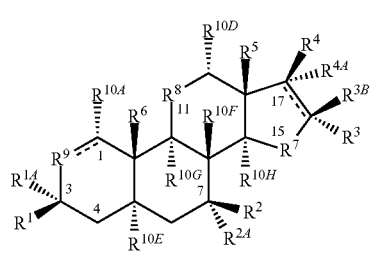
E
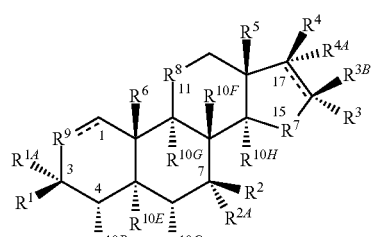
F
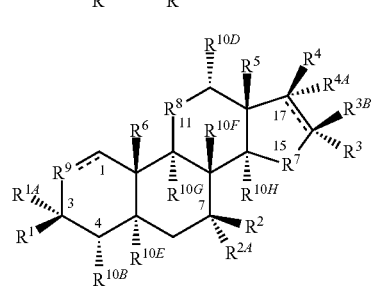
G
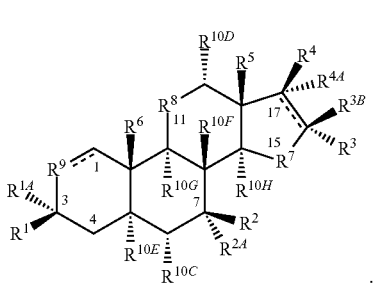
Similarly, when $R^{10E}$, $R^{10F}$, $R^{10G}$ and $R^{10H}$ respectively are in the α,β,α,α configurations and $R^{10A}$ and $R^{10B}$ or $R^{10A}$ and $R^{10C}$ or $R^{10A}$ and $R^{10D}$ or $R^{10B}$ and $R^{10C}$ or $R^{10B}$ and $R^{10D}$ or $R^{10C}$ and $R^{10D}$ respectively are in the β,α configurations exemplary B, C, D, E, F and G structures include
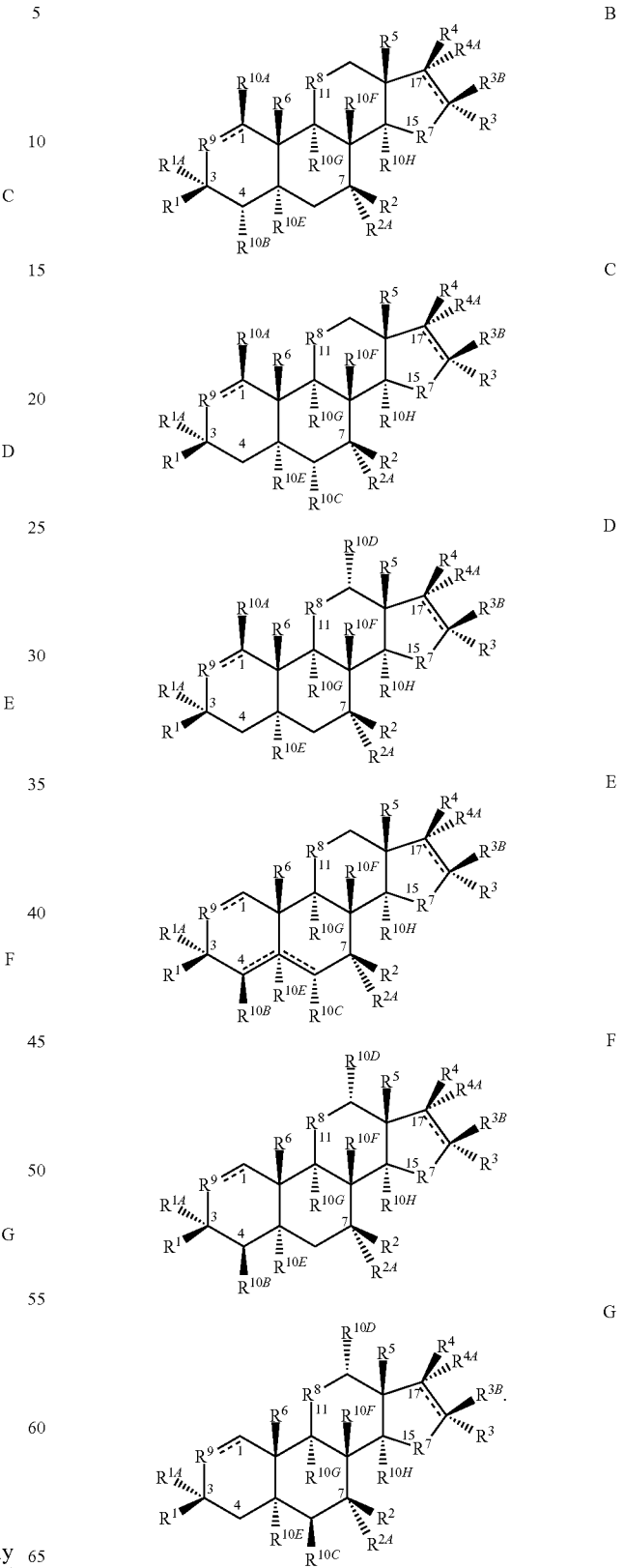

When $R^{10E}$, $R^{10F}$, $R^{10G}$ and $R^{10H}$ respectively are in the α,β,α,α configurations and $R^{10A}$ and $R^{10B}$ or $R^{10A}$ and $R^{10C}$ or $R^{10A}$ and $R^{10D}$ or $R^{10B}$ and $R^{10C}$ or $R^{10B}$ and $R^{10D}$ or $R^{10C}$ and $R^{10D}$ respectively are in the α,β configurations exemplary B, C, D, E, F and G structures include B
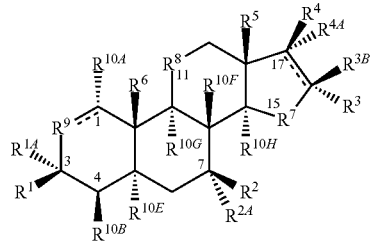

C
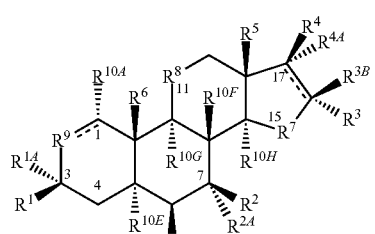

D
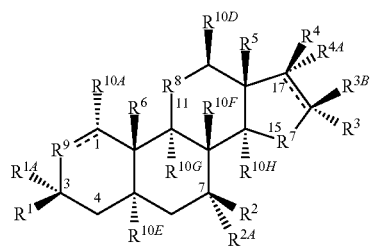

E
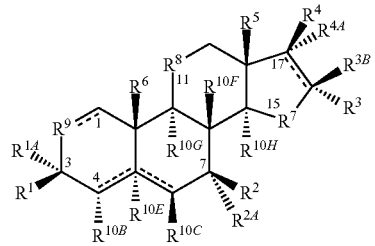

F
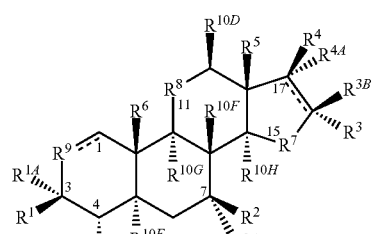

G
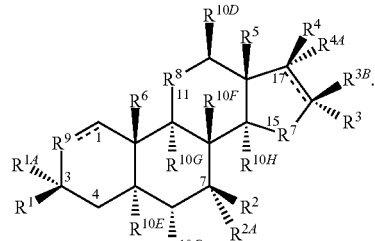

When $R^{10E}$, $R^{10F}$, $R^{10G}$ and $R^{10H}$ respectively are in the α,β,α,α configurations and $R^{10A}$ and $R^{10B}$ or $R^{10A}$ and $R^{10C}$ or $R^{10A}$ and $R^{10D}$ or $R^{10B}$ and $R^{10C}$ or $R^{10B}$ and $R^{10D}$ or $R^{10C}$ and $R^{10D}$ respectively are in the β,β configurations exemplary B, C, D, E, F and G structures include B
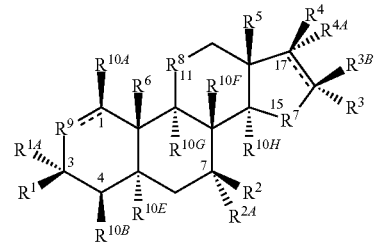

C
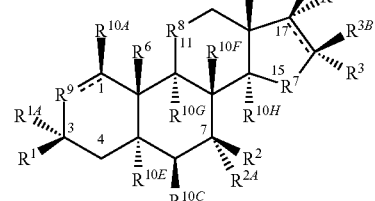

D
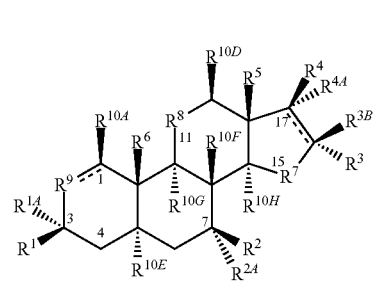

E
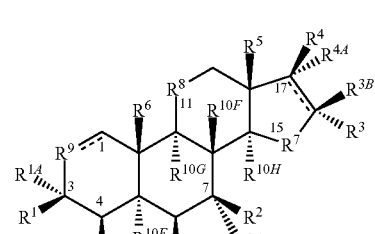

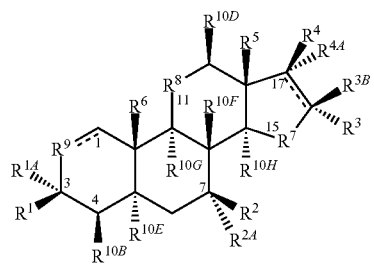
F
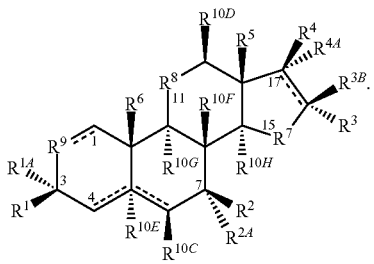
G
When $R^{10E}$, $R^{10F}$, $R^{10G}$ and $R^{10H}$ respectively are in the β,β,α,α configurations exemplary B, C, D, E, F and G structures include
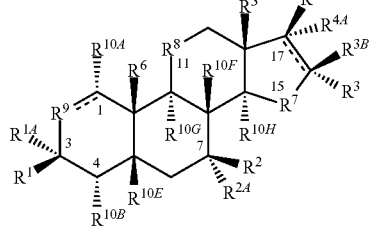
B
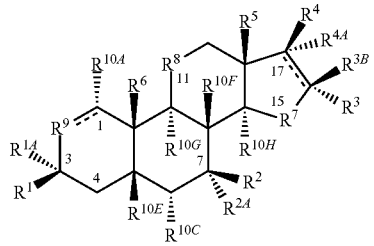
C
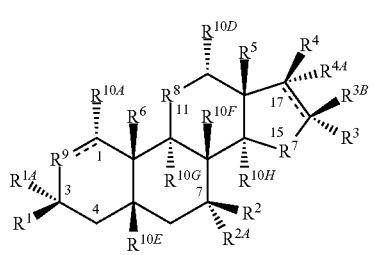
D
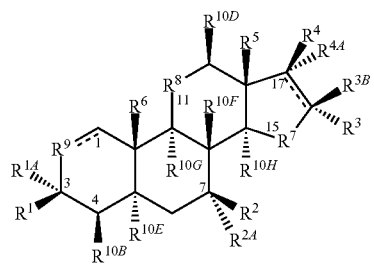
E
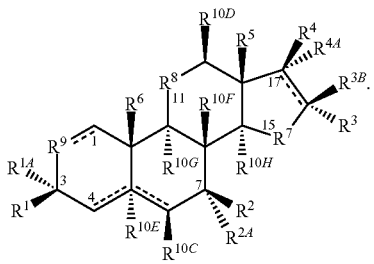
F
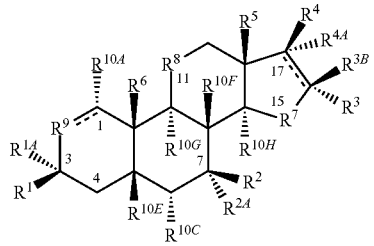
G
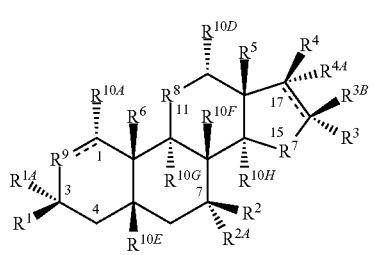
B
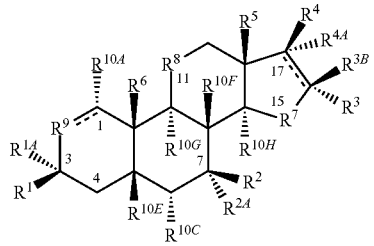
C
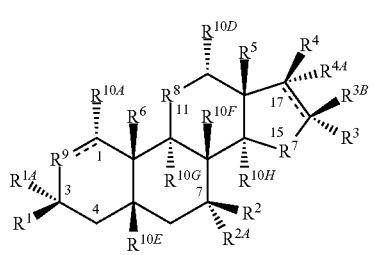
D E
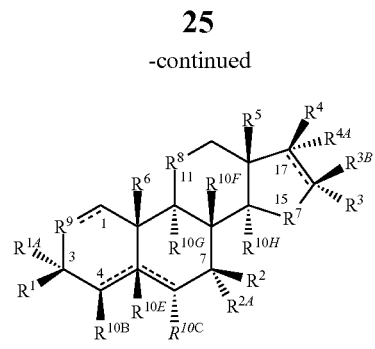
F
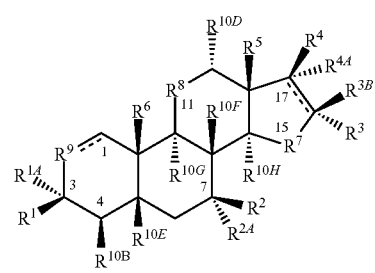
G
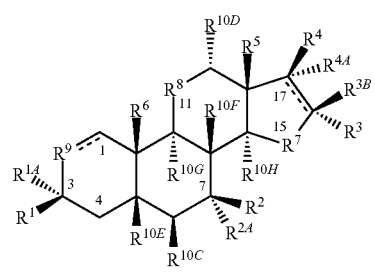
B
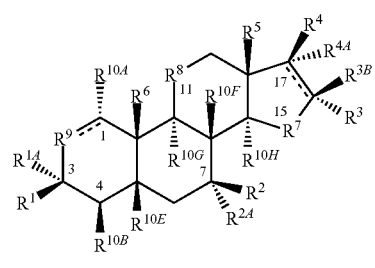
C
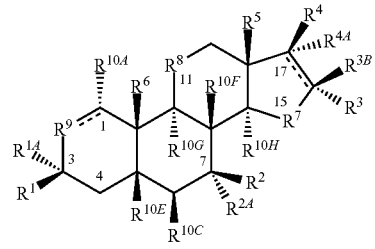
D
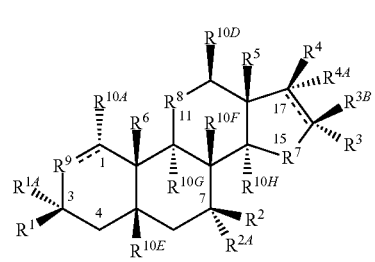
E
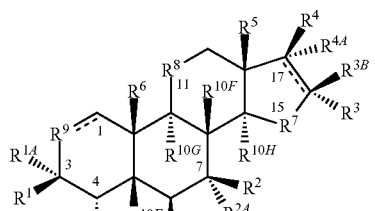
F
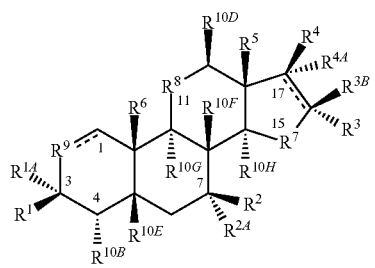
G
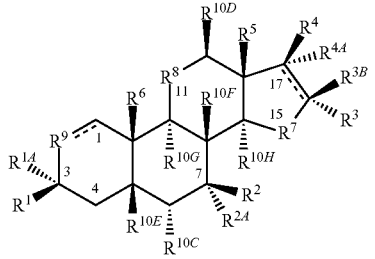
B
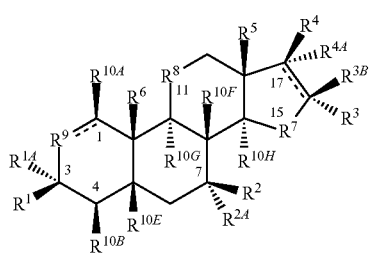
C
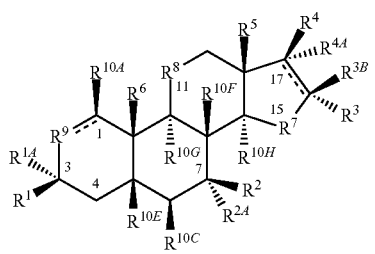
D
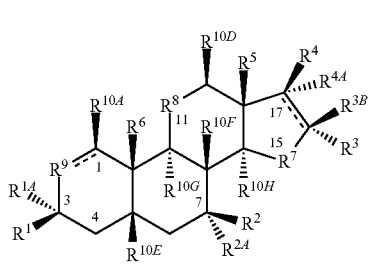

E
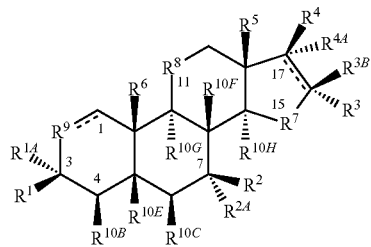
F
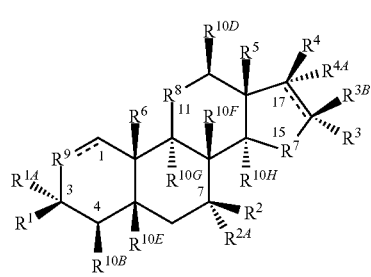
G
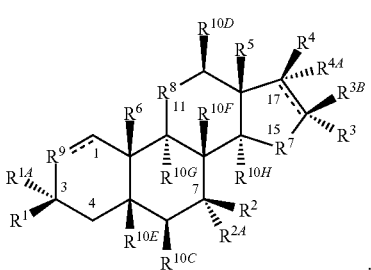
When a double bond is present at the 5-6 position, and $R^{10F}$, $R^{10G}$ and $R^{10H}$ respectively are in the β,α,α configurations exemplary B, C, D, E, F and G structures include
B
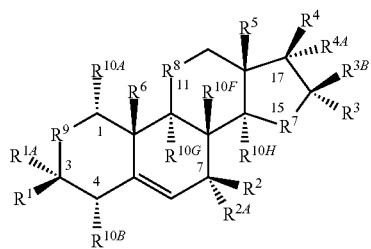
C
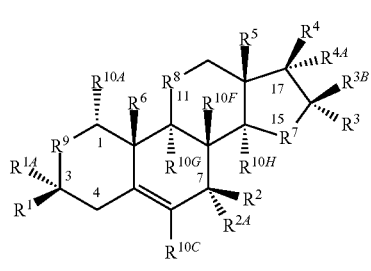
D
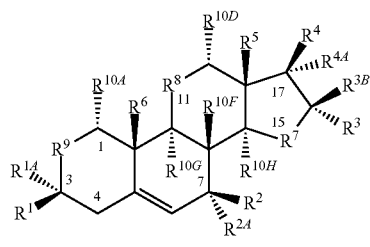
E
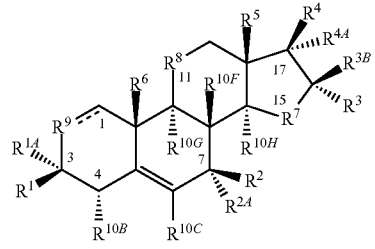
F
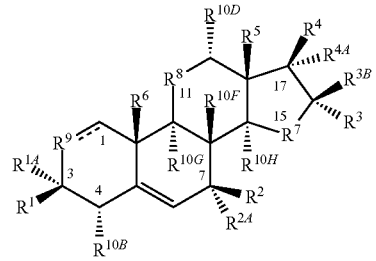
G
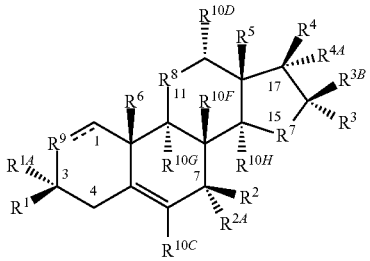
When a double bond is present at the 1-2 and 5-6 positions, and $R^{10F}$, $R^{10G}$ and $R^{10H}$ respectively are in the β,α,α configurations exemplary B, C, D, E, F and G structures include
B
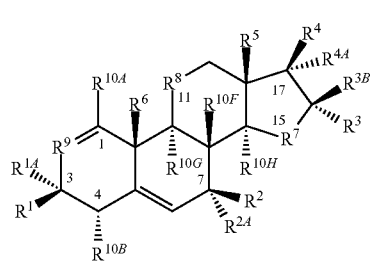

-continued
C
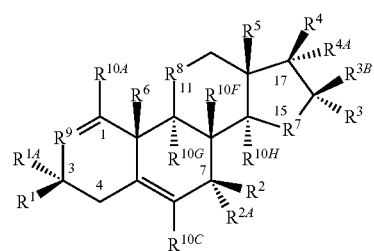
D
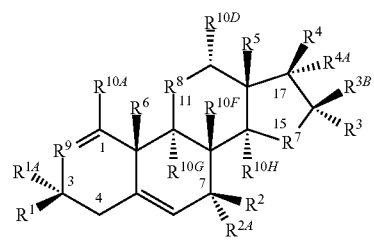
E
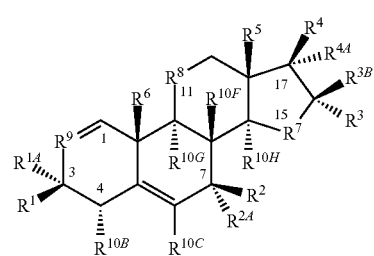
F
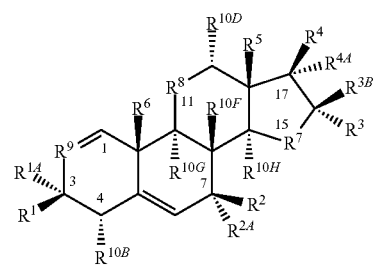
G
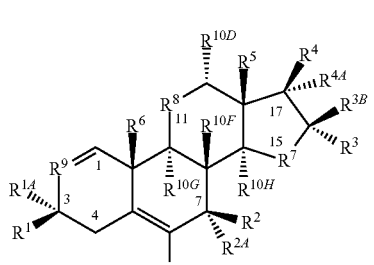
When a double bond is present at the 5-6 and 16-17 positions, and $R^{10F}$, $R^{10G}$ and $R^{10H}$ respectively are in the β,α,α configurations exemplary B, C, D, E, F and G structures include
B
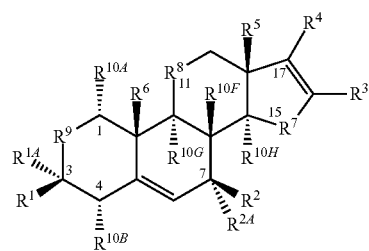
C
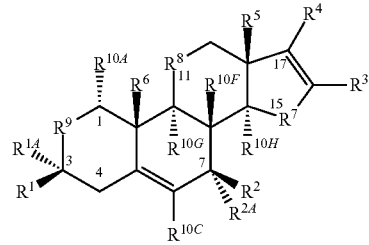
D
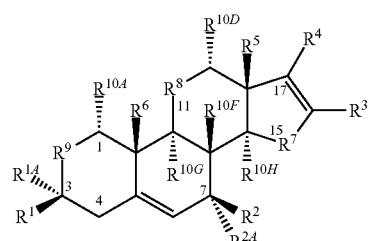
E
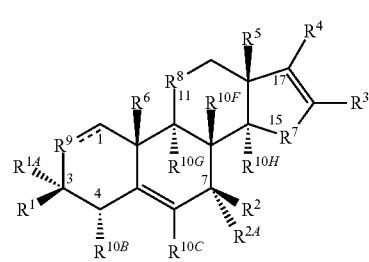
F
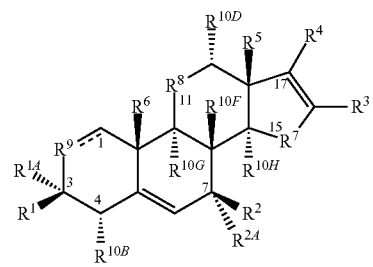
G
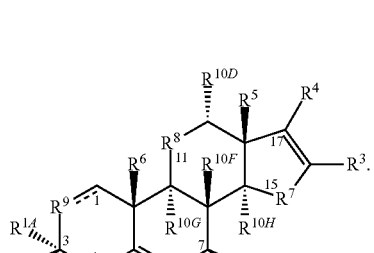

Thus, exemplary F1C, e.g., 2, 5, 6, 7, 8, 9, 10, B, C, D, E, F and G structures are characterized as having the following:

(1) a double bond at the 5-6 position, no double bonds with $R^{10E}$ at the 5 position in the α-configuration, no double bonds with $R^{10E}$ in the β-configuration, a double bond at the 4-5 position, a double bond at the 1-2 position with $R^{10E}$ in the α-configuration, a double bond at the 1-2 position with $R^{10E}$ in the β-configuration, double bonds at the 1-2 and 4-5 positions, double bonds at the 1-2 and 5-6 positions, a double bond at the 16-17 position with $R^{10E}$ in the α-configuration, a double bond at the 16-17 position with $R^{10E}$ in the β-configuration, double bonds at the 4-5 and 16-17 positions, double bonds at the 5-6 and 16-17 positions, double bonds at the 1-2 and 16-17 positions with $R^{10E}$ in the β-configuration, double bonds at the 1-2 and 16-17 positions with $R^{10E}$ in the β-configuration, double bonds at the 1-2, 5-6 and 16-17 positions or double bonds at the 1-2, 4-5 and 16-17 positions, and (2) $R^{10A}$, $R^{10B}$, $R^{10C}$ and $R^{10D}$ are independently selected $R^{10}$ groups in the α,α, α,β, β,α, or β,β configurations respectively, and (3) $R^{10E}$, $R^{10F}$, $R^{10G}$ and $R^{10H}$ are independently selected $R^{10}$ groups in the α,α,α,α, α,α,α,β, α,α,β,α, α,β,α,α, β,α,α,α, α,α,β,β, α,β,α,β, β,α,α,β, β,α,β,α, β,β,α,α, α,β,β,α, α,β,β,β, β,α,β,β, β,β,α,β, β,β,β,α or β,β,β,β configurations respectively, and (4) $R^{1A}$, $R^{2A}$, $R^{3B}$ and $R^{4A}$ are —H, $R^{1A}$ is not —H and $R^{2A}$, $R^{3B}$ and $R^{4A}$ are —H, $R^{2A}$ is not —H and $R^{1A}$, $R^{3B}$ and $R^{4A}$ are —H, $R^{3B}$ is not —H and $R^{1A}$, $R^{2A}$ and $R^{4A}$ are —H, $R^{4A}$ is not —H and $R^{1A}$, $R^{2A}$ and $R^{3B}$ are —H, $R^{1A}$ and $R^{2A}$ are not —H and $R^{3B}$ and $R^{4A}$ are —H, $R^{1A}$ and $R^{3B}$ are not —H and $R^{2A}$ and $R^{4A}$ are —H, $R^{1A}$ and $R^{4A}$ are not —H and $R^{2A}$ and $R^{3B}$ are —H, $R^{2A}$ and $R^{3B}$ are not —H and $R^{1A}$ and $R^{4A}$ are —H, $R^{2A}$ and $R^{4A}$ are not —H and $R^{1A}$ and $R^{3B}$ are —H, $R^{3B}$ and $R^{4A}$ are not —H and $R^{1A}$ and $R^{2A}$ are —H, $R^{1A}$, $R^{2A}$ and $R^{3B}$ are not —H and $R^{4A}$ is —H, $R^{1A}$, $R^{2A}$ and $R^{4A}$ are not —H and $R^{3B}$ is —H, $R^{1A}$, $R^{3B}$ and $R^{4A}$ are not —H and $R^{2A}$ is —H, $R^{2A}$, $R^{3B}$ and $R^{4A}$ are not —H and $R^{1A}$ is —H, $R^{1A}$, $R^{2A}$, $R^{3B}$ and $R^{4A}$ are not —H and $R^{1A}$ and $R^{2A}$ are —H and $R^{3B}$ and $R^{4A}$ are absent (i.e., a 16-17 double bond is present), $R^{1A}$ is —H and $R^{2A}$ is not —H and $R^{3B}$ and $R^{4A}$ are absent, $R^{2A}$ is —H and $R^{1A}$ is not —H and $R^{3B}$ and $R^{4A}$ are absent, or, $R^{1A}$ and $R^{2A}$ are not —H and $R^{3B}$ and $R^{4A}$ are absent, where each $R^{1A}$, $R^{2A}$, $R^{3B}$ and $R^{4A}$ are independently selected, and (5) each $R^1$, $R^2$, $R^3$ and $R^4$ are independently selected.

For these exemplary formula B, C, D, E, F and G structures and any other FiC strutures disclosed herein, each $R^1$, $R^{1A}$, $R^2$, $R^{2A}$, $R^3$, $R^{3B}$, $R^4$, $R^{4A}$, $R^{10}$, $R^{10A}$, $R^{10B}$, $R^{10C}$, $R^{10D}$, $R^{10E}$, $R^{10F}$ and $R^{10G}$ are an independently selected atom or moiety as described herein, e.g., —H, —OH, =O, —SH, =S, —F, —Cl, —Br, —I, —CN, —SCN, —N$_3$, —NH—C1-C8 optionally substituted alkyl, —N(C1-C8 optionally substituted alkyl)$_2$ where each optionally substituted alkyl moiety is the same or different, protected ketone, e.g., ethylene ketal (—O—CH$_2$—CH$_2$—O—), —NO$_2$, —ONO$_2$, —(CH$_2$)$_n$—CH(O), —(CH$_2$)$_n$—COOH, —(CH$_2$)$_n$—COOR$^{PR}$, —(CH$_2$)$_n$—NHCH$_3$, —(CH$_2$)$_n$—NHR$^{PR}$, where n is 1, 2, 3 or 4 and R$^{PR}$ is —H or a protecting group, or a group such as:

optionally substituted alkyl, e.g., —CH$_3$, —C$_2$H$_5$, —CH$_2$CH$_2$CH$_3$, —CH$_2$CH$_2$CH$_2$CH$_3$, —CH$_2$CH$_2$OCH$_2$CH$_3$, —CH$_2$OH, —CH$_2$CH$_2$OH, —CHOHCH$_3$, —CH(OC(O)CH$_3$)—CH$_3$, —CH(OR$^{PR}$)—CH$_3$, —CF$_3$, —(CH$_2$)$_t$—NH$_2$, —(CH$_2$)$_2$—NH$_2$, —(CH$_2$)$_3$—NH$_2$, —CH$_2$—NHCH$_3$, —(CH$_2$)$_2$—NHCH$_3$, —(CH$_2$)$_3$—NHCH$_3$, —(CH$_2$)$_t$—N(CH$_3$)$_2$, —(CH$_2$)$_n$—CH$_2$OH, where n is 1, 2, 3 or 4 and R$^{PR}$ is —H or a protecting group, or optionally substituted alkenyl, e.g., —CH=CH$_2$, —CH=CHF, —CH=CHCl, —CH=CHBr, —CH=CHI, —CH=CH—(CH$_2$)$_n$—OH, —CH=NCH$_3$, —CH=NR$^{PR}$, —CH=N—CH$_3$, —CH=CH—CH$_3$, —CH=CH—(CH$_2$)$_n$—COOR$^{PR}$, —CH=CH—(CH$_2$)$_n$—NHR$^{PR}$, —CH=CH—CH$_2$—OR$^{PR}$, where R$^{PR}$ is —H or a protecting group, or optionally substituted alkynyl, e.g., —C≡CH, —C≡C—(CH$_2$)$_m$—OH, —C≡C-halogen, —C≡C—CH$_3$, —C≡CCF$_3$, —C≡CCH$_2$F, —C≡CCH$_2$Cl, —C≡CCH$_2$Br, —C≡CCH$_2$I, —C≡C—CH$_2$OH, —C≡C—CH$_2$-halogen, —C≡C—CH$_2$—C(O)OR$^{PR}$, —C≡C—CH$_2$—CH$_3$, —C≡C—CH$_2$—CH$_2$OH, —C≡C—(CH$_2$)$_n$—C$_6$H$_5$, —C≡C—(CH$_2$)$_n$—C$_6$H$_4$OH, —C≡C—(CH$_2$)$_n$—C$_6$H$_4$COOR$^{PR}$, —C≡C—(CH$_2$)$_n$—C$_6$H$_3$(OH)$_2$, —C≡C—(CH$_2$)$_n$—C$_6$H$_4$F, —C≡C—(CH$_2$)$_n$—C$_6$H$_4$Br, —C≡C—CH$_2$—CH$_2$—C(O)OR$^{PR}$, —C≡C—(CH$_2$)$_n$—CH$_3$, —C≡C—CH(CH$_3$)—(CH$_2$)$_n$—CH$_3$, —C≡C—(CH$_2$)$_n$—CHOR$^{PR}$, —C≡C—CH(CH$_3$)—(CH$_2$)$_n$—CHOR$^{PR}$, —C≡C—(CH$_2$)$_n$—CHCOOR$^{PR}$, —C≡C—CH(CH$_3$)—(CH$_2$)$_n$—NHR$^{PR}$, —C≡C—(CH$_2$)$_n$—NHR$^{PR}$, —C≡C—(CH$_2$)$_n$—C(O)NHR$^{PR}$, where n is 0, 1, 2, 3, 4, 5 or 6, n is 1, 2, 3 or 4 and R$^{PR}$ is —H or a protecting group, or optionally substituted aryl, optionally substituted alkylaryl, optionally substituted alkenylaryl or optionally substituted alkynylaryl, e.g., optionally substituted phenyl, optionally substituted benzyl, —(CH$_2$)$_n$—C$_6$H$_4$OH, —(CH$_2$)$_n$—C$_6$H$_4$OR$^{PR}$, —(CH$_2$)$_n$—C$_6$H$_3$(OH)$_2$, —(CH$_2$)$_n$—C$_6$H$_4$F, —(CH$_2$)$_n$—C$_6$H$_4$Br, —(CH$_2$)$_n$—C$_6$H$_4$C(O)OR$^{PR}$, —(CH$_2$)$_n$—C$_6$H$_4$C(O)SR$^{PR}$, or analogs where the aromatic ring contains 1, 2, 3 or 4 independently chosen substituents such as independently chosen halogen, —OH, —SH, —NO$_2$, —CN, —SCN, —N$_3$, C1-C6 ester, C1-C6 alkyl, C1-C6 ether, C1-C6 thioether, —OR$^{PR}$, —(CH$_2$)$_n$—C(O)OR$^{PR}$, —(CH$_2$)$_n$—NHR$^{PR}$, —(CH$_2$)$_n$—OR$^{PR}$ or —(CH$_2$)$_m$—O—(CH$_2$)$_m$—OR$^{PR}$ where n is 0, 1, 2, 3, 4, 5 or 6, m independently are 1, 2 or 3 and R$^{PR}$ independently are —H or a protecting group, or ether, e.g., optionally substituted alkoxy, optionally substituted alkenyloxy, optionally substituted alkynyloxy, optionally substituted aryloxy, —OCH$_3$, —OC$_2$H$_5$, —OC$_3$H$_7$, —OC$_4$H$_9$, —OC$_2$H$_3$, —OC$_3$H$_5$, —OC$_4$H$_7$, —O—C(CH$_3$)$_3$, —OCH$_2$CH$_2$OH, —O(CH$_2$)$_2$—O—CH$_3$, —O(CH$_2$)$_3$—O—CH$_3$, —O—CH(CH$_3$)CH$_3$, —O—CH$_2$CH$_2$CH$_3$, —O—C1-C20 organic moiety where the organic moiety is, e.g., —CH$_3$, —C$_2$H$_5$, i-propyl, n-propyl, t-butyl, n-butyl, l-butyl, n-hexyl, n-octyl, n-decyl, —(CH$_2$)$_{1-8}$—OH, —CHO, —(CH$_2$)$_{1-8}$—NH$_2$, —(OH$_2$)$_{1-8}$—C(O)—OH, or ester, e.g., —OC(O)CH$_3$, —OC(O)O$_2$H$_5$, —OC(O)O$_2$H$_3$, —OC(O)CH$_2$CH$_2$CH$_3$, —OC(O)CH(CH$_3$)$_2$, —O—C(O)—(CH$_2$)$_2$—C(O)OH, —O—C(O)—(CH$_2$)$_2$—C(O)OR$^{PR}$, —OC(O)—(CH$_2$)$_m$—CH$_3$, —OC(O)C$_6$H$_5$, —OC(O)CH$_2$C$_6$H$_5$, a C2-C20 ester such as —O—C(O)—CH$_3$, —O—C(O)—CF$_3$, —O—C(O)—OCl$_3$, —O—C(O)—C$_2$H$_5$, —O—C(O)—C$_4$H$_7$, —O—C(O)—C$_6$H$_5$, —O—C(O)—(CH$_2$)$_2$—CH$_3$, —O—C(O)—(CH$_2$)$_3$—CH$_3$, —O—C(O)—(OH$_2$)$_4$—CH$_3$, —O—C(O)—(OH$_2$)$_5$—CH$_3$, —O—C(O)—(OH$_2$)$_6$—CH$_3$, —O—C(O)-2 furanyl, —O—C(O)-2 thiophenyl, —O—C(O)-2 pyrrolyl, —O—C(O)-2 pyrimidinyl, —O—C(O)-3 pyrimidinyl, —O—C(O)-2 pyridyl, —O—C(O)-3 pyridyl, —O—C(O)-heterocycle, —O—C(O)—(CH$_2$)$_m$—C(O)O—C1-C10 optionally substituted alkyl, —O—C(O)—C$_{1-12}$ optionally substituted alkyl, —OC(O)—(CH$_2$)$_q$—C(O)OH, —OC(O)—(CH$_2$)$_q$—C(O)O—C$_{1-8}$ optionally substituted alkyl, where the optionally substituted alkyl optionally is methyl, ethyl, i-propyl, n-propyl, t-butyl, n-butyl, n-hexyl, n-octyl, n-decyl, —CH$_2$OH, —CH$_2$OR$^{PR}$, —(CH$_2$)$_n$—CH$_3$, —(CH$_2$)$_n$—OH, —$(CH_2)_n$—Br, —$(CH_2)_n$—$NH_2$, —$(CH_2)_n$—C(O)—$OR^{PR}$, —$(CH_2)_n$—O—$CH_3$, —$CF_3$, wherein $R^{PR}$ independently are —H, a protecting group such as C1-C10 optionally substituted alkyl (e.g., —$CH_3$, —$C_2H_5$, —$C_3H_6OH$) or together are a protecting group, m is 0, 1, 2, 3, 4, 5 or 6 and q is 0, 1, 2, 3, 4, 5 or 6, or optionally substituted amine, e.g., —$NH_2$, —$NH_3^+Cl^-$, —$NH_3^+Br^-$, —$NH_3^+I^-$, alkylamine, dialkylamine, —NH—$CH_3$, —$N(CH_3)_2$, —$N^+(CH_3)_3$, —$N^+(C_2H_5)_3$, —NHOH, —$NHR^{PR}$, —$N(R^{PR})_2$, —NH—C(O)$CH_3$, —NH—C(O)$CF_3$, —$N(C(O)CF_3)_2$, —NH—C(O)$CCl_3$, —$N(C(O)CCl_3)_2$, —NH—C(O)$C_6H_5$, —$N(C(O)C_6H_5)_2$, —NH—$C_2H_5$, —$N(C_2H_5)_2$, —NH—$CH_2OH$, —NH—$CH_2$—$CH_2OH$, —NH—$C_3H_7$, —NH—C(=NH)—$N(CH_3)$—$CH_2$—C(O)$OR^{PR}$, —$N(CH_3)_2$, —$N(C_2H_5)_2$, —$N(CH_3)(C_2H_5)$—N$(CH_2OH)(CH_3)$, —N=C[$(CH_2)_n$—H]—OH, —NH—NH—C(O)-optionally substituted alkyl, —NH—C(NH-optionally substituted alkyl)=N-optionally substituted alkyl, —N=C[$(CH_2)_n$—H]-O-optionally substituted alkyl, —NH-organic moiety, —NH—C(O)-organic moiety, e.g., —NH—C(O)—$CH_3$, —NH—$(CH_2)_n$-optionally substituted phenyl, —NH-optionally substituted alkyl, —N(optionally substituted alkyl)$_2$, —N(C(O)-optionally substituted alkyl)$_2$, —NH—C(O)-optionally substituted alkyl or —NH—$(CH_2)_n$-optionally substituted alkyl, or optionally substituted amide, e.g., —C(O)—$NH_2$, —C(O)—NH—$C(CH_3)_3$, —C(O)—$NH_2$, —C(O)—NH—$CH_3$, —C(O)—NH—$(CH_2)_m$—$CH_3$, —C(O)—NH—$(CH_2)_m$—$NH_2$, —C(O)—NH—$(CH_2)_m$—$NHR^{PR}$, —NH—C(O)H, —NH—C(O)—$CH_2$—$CH_2$—C(O)OH, —NH—C(O)—$CH_2$—$CH_2$—C(O)$OR^{PR}$, —NH—C(O)—$(CH_2)_m$—C(O)OH, —NH—C(O)—$(CH_2)_m$—C(O)$OR^{PR}$, —NH—C(O)—$CH_3$, —NH—C(O)—$(CH_2)_m$—$NH_2$, —NH—C(O)—$(CH_2)_m$—$NHR^{PR}$, —NH—C(O)—O—$C(CH_3)_3$, —NH—C(O)—O—$CH_3$, —C(O)—NH-organic moiety, —C(O)—NH-optionally substituted alkyl, —C(O)—$NR^{49}$—(O)$_p$-organic moiety, —C(O)—NH—(O)$_p$—$(CH_2)$, optionally substituted phenyl, —C(O)—NH—$(CH_2)_n$—(O)$_p$-optionally substituted alkyl, —NH—C(O)—(O)$_p$-optionally substituted alkyl, —NH—C(S)—(O)$_p$-optionally substituted alkyl, wherein m independently are 1, 2, 3, 4, 5 or 6, n independently are 0, 1, 2, 3 or 4 and p is 0 or 1, or —O—Si(C1-C6 alkyl)$_3$ where each alkyl is independently chosen, e.g., —O—Si$(CH_3)_3$, —O—Si$[C(CH_3)_3](CH_3)_2$, —O—Si$[C(CH_3)_3](C_2H_5)_2$, or optionally substituted heterocycle or —O—[C(O)]$_m$—$(CH_2)_n$-optionally substituted heterocycle, —$(CH_2)_n$-optionally substituted heterocycle, e.g., 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, 1-aziridyl, 1-azetedyl, 1-pyrrolyl, 1-imidazolyl, 1-pyrazolyl or 1-piperidinyl, wherein m is 0 or 1 and n is 0, 1, 2 or 3, e.g., m and n are both 0, m is 1 and n is 0, m is 0 and n is 1, m and n are both 1, or carboxyl which is optionally substituted, e.g., —C(O)OH, —C(O)$OR^{PR}$, —C(O)OM, —C(O)O—$CH_3$, —C(O)—O—$(CH_2)_n$—$CH_3$, —C(O)O-organic moiety, —C(O)O—$(CH_2)_n$-optionally substituted phenyl or —C(O)O—$(CH_2)_n$-optionally substituted alkyl, wherein the phenyl or alkyl moieties are optionally substituted with 1, 2 or 3 independently selected with substituents described herein, e.g., —F, —Cl, —Br, —I, —OH, —$CH_3$, —$C_2H_5$, —O—$CH_3$, —O—$C_2H_5$, —$NO_2$, —CN, —SCN, —$NH_2$, —C(O)$OR^{PR}$ or —$(CH_2)_{1-4}$—C(O)—$OR^{PR}$, where n is 0, 1, 2, 3, 4, 5 or 6, $R^{PR}$ is —H or a protecting group such as methyl, ethyl, propyl or butyl, and M is a metal such as an alkali metal, e.g., $Li^+$, $Na^+$ or $K^+$ or M is another counter ion such as an ammonium ion, or carbonate, e.g., —O—C(O)—O—$CH_3$, —O—C(O)—O—$(CH_2)_n$-$CH_3$, —O—C(O)—O—$CH(CH_3)$—$(CH_2)_n$—$CH_3$, —O—C(O)—O-organic moiety, —O—C(O)—C$(CH_2)_n$-optionally substituted phenyl or —C(O)—O—$(CH_2)_n$-optionally substituted alkyl, or carbamate, e.g., —O—C(O)—$NH_2$, —O—C(O)—NH—$CH_3$, —O—C(O)—NH—$C_2H_5$, —O—C(O)—NH—$C_3H_7$, —O—C(O)—NH—$C_4H_9$, —O—C(O)—NH—$C_2H_3$, —O—C(O)—NH—$C_3H_5$, —O—C(O)—NH—$C_4H_7$, —O—C(O)—$NHR^{PR}$, —O—C(O)—NH-organic moiety, —O—C(O)—$NR^{48}$-organic moiety, —NH—C(O)—O-organic moiety, —$NR^{48}$—C(O)—O-organic moiety, wherein the organic moiety is as described herein, or optionally substituted oxime, e.g., =NOH, =NOCH$_3$, =NOC$_2$H$_5$, =NOC$_3$H$_7$, =N—$(CH_2)_n$—(X)$_q$—$(CH_2)_n$-optionally substituted alkyl, where X is —O—, —C(O)—, —S— or —NH— and the optionally substituted alkyl moiety is as described herein, an acetal or spiro ring, e.g., —O—$CH_2$—O—, —O—$(CH_2)_2$—O—, —O—$(CH_2)_3$—O— or —[C(R$^{36}$)$_2$]$_{1-4}$—O—, —O—C(O)—$CH_2$—, —O—C(O)—$CH_2$—$CH_2$—, —O—C(O)—$CH_2$—$CH_2$—$CH_2$—, —O—C(O)—CHR$^{10}$—, —O—C(O)—CHR$^{10}$—CHR$^{10}$—, —O—C(O)—(CHR$^{10}$)$_3$—, —NH—$(CH_2)_2$—O—, —NH—$(CH_2)_2$—NH—, —NH—$(CH_2)_2$—S—, —$CH_2$—N=CH—NH—, —NH—$(CH_2)_3$—O—, —NH—$(CH_2)_3$—S—, —NH—$(CH_2)_3$—O—, where R$^{10}$ are independently selected and optionally independently are —H, —F, —Cl, —Br, —I, —$CH_3$, —$C_2H_5$, —$CF_3$, —$C_2F_5$, —$CH_2CF_3$, —OH, —CN, —SCN, —$OCH_3$ or —$OC_2H_5$, and where each R$^{36}$ independently is —H, —F, —Cl, —Br, —I or an organic moiety such as C1-C10 optionally substituted alkyl (e.g., methyl or ethyl), C2-10 alkenyl, aryl or a heterocycle, any of which are optionally substituted as described herein, e.g., —$CF_3$ or —$CH_2OH$, or thioacetal, e.g., —S—$CH_2$—O—, —S—$(CH_2)_2$—O—, —S—$(CH_2)_3$—O—, —S—$CH_2$—S—, —S—$(CH_2)_2$—S—, —S—$(CH_2)_3$—S— or —S—[C(R$^{36}$)$_2$]$_{1-4}$—S— where each R$^{36}$ independently is —H, —F, —Cl, —Br, —I or an organic moiety such as C1-C10 optionally substituted alkyl (e.g., methyl or ethyl), C2-10 alkenyl, aryl or a heterocycle, any of which are optionally substituted as described herein, e.g., —$CF_3$ or —$CH_2OH$.

For any of these exemplary F1C, e.g., the B, C, D, E, F and G structures, some embodiments are characterized by the presence of one or two independently selected substitutions at $R^{10A}$, $R^{10B}$, $R^{10C}$ and $R^{10D}$ optionally:

(a) $R^{10E}$ (when present at the 5-position), $R^{10F}$, $R^{10G}$ and $R^{10H}$ are independently selected $R^{10}$ groups in the α,β,α,α or β,β,α,α configurations respectively, $R^1$ is an oxygen-bonded, nitrogen-bonded or a sulfur-bonded moiety such as —OH, =O, —SH, =NOH, —NH(C1-C8 optionally substituted alkyl), an ester, an ether, a thioester, or a thioether, $R^{1A}$ is —H, absent, a carbon-bonded moiety such as an acyl moiety, optionally substituted alkyl or optionally substituted alkylaryl, $R^2$ is a halogen or an oxygen-bonded or a sulfur-bonded moiety, $R^{2A}$ is —H, absent, a carbon-bonded moiety, $R^3$ is a halogen or an oxygen-bonded or a sulfur-bonded moiety, $R^{3B}$ is —H, absent, a carbon-bonded moiety, $R^4$ is a halogen, an oxygen-bonded or a sulfur-bonded moiety, $R^{4A}$ is —H, absent, a carbon-bonded moiety such as an acyl moiety, optionally substituted alkyl or optionally substituted alkylaryl, (b) $R^{10E}$ (if present), $R^{10F}$, $R^{10G}$ and $R^{10H}$ are independently selected $R^{10}$ groups in the α,β,α,α or β,β,α,α configurations respectively, $R^{1A}$ is —H, an oxygen-bonded, nitrogen-bonded or a sulfur-bonded moiety, $R^1$ is —H, a carbon-bonded moiety, $R^2$ is a halogen or an oxygen-bonded or a sulfur-bonded moiety, $R^{2A}$ is —H, absent, a carbon-bonded moiety, $R^3$ is a halogen or an oxygen-bonded or a sulfur-bonded moiety, $R^{3B}$ is —H, absent, a carbon-bonded moiety, $R^4$ is a halogen, an oxygen-bonded or a sulfur-bonded moiety, $R^{4A}$ is —H, absent or a carbon-bonded moiety, (c) $R^{10E}$ (if present), $R^{10F}$, $R^{10G}$ and $R^{10H}$ are independently selected $R^{10}$ groups in the α,β,α,α or β,β,α,α configurations respectively, $R^1$ is an oxygen-bonded, nitrogen-bonded or a sulfur-bonded moiety, $R^{1A}$ is —H, absent or a carbon-bonded moiety, $R^2$ is a halogen or an oxygen-bonded or a sulfur-bonded moiety, $R^{2A}$ is —H, absent or a carbon-bonded moiety, $R^3$ is a halogen or an oxygen-bonded or a sulfur-bonded moiety, $R^{3B}$ is —H, absent or a carbon-bonded moiety, $R^{4A}$ is a halogen, an oxygen-bonded or a sulfur-bonded moiety, $R^4$ is —H, a halogen or a carbon-bonded moiety, (d) $R^{10E}$ (if present), $R^{10F}$, $R^{10G}$ and $R^{10H}$ are independently selected $R^{10}$ groups in the α,β,α,α or β,β,α,α configurations respectively, $R^1$ is an oxygen-bonded, nitrogen-bonded or a sulfur-bonded moiety, $R^{1A}$ is —H, absent, a carbon-bonded moiety, $R^2$ is a halogen or an oxygen-bonded or a sulfur-bonded moiety, $R^{2A}$ is —H, absent or a carbon-bonded moiety, $R^3$ is a halogen or an oxygen-bonded or a sulfur-bonded moiety, $R^{3B}$ is —H, absent or a carbon-bonded moiety, $R^4$ is a halogen, an oxygen-bonded or a sulfur-bonded moiety, $R^{4A}$ is —H, absent or a carbon-bonded moiety, (e) $R^{10E}$ (if present), $R^{10F}$, $R^{10G}$ and $R^{10H}$ are independently selected $R^{10}$ groups in the α,β,α,α or β,β,α,α configurations respectively, $R^1$ is an oxygen-bonded, nitrogen-bonded or a sulfur-bonded moiety, $R^{1A}$ is —H, absent or a carbon-bonded moiety, $R^2$ is a halogen or an oxygen-bonded or a sulfur-bonded moiety, $R^{2A}$ is —H, absent or a carbon-bonded moiety, $R^{3B}$ is a halogen or an oxygen-bonded or a sulfur-bonded moiety, $R^3$ is —H, a carbon-bonded moiety, $R^4$ is a halogen, an oxygen-bonded or a sulfur-bonded moiety, $R^{4A}$ is —H, absent or a carbon-bonded moiety, (f) $R^{10E}$ (if present), $R^{10F}$, $R^{10G}$ and $R^{10H}$ are independently selected $R^{10}$ groups in the α,β,α,α or β,β,α,α configurations respectively, $R^{1A}$ is —H, an oxygen-bonded, nitrogen-bonded or a sulfur-bonded moiety, $R^1$ is —H, a carbon-bonded moiety, $R^2$ is a halogen or an oxygen-bonded or a sulfur-bonded moiety, $R^{2A}$ is —H, absent or a carbon-bonded moiety, $R^3$ is a halogen or an oxygen-bonded or a sulfur-bonded moiety, $R^{3B}$ is —H, absent or a carbon-bonded moiety, $R^{4A}$ is a halogen, an oxygen-bonded or a sulfur-bonded moiety, $R^4$ is —H, a carbon-bonded moiety, or (g) $R^{10E}$ (if present), $R^{10F}$, $R^{10G}$ and $R^{10H}$ are independently selected $R^{10}$ groups in the α,β,α,α or β,β,α,α configurations respectively, $R^1$ is a halogen or an oxygen-bonded, nitrogen-bonded, carbon bonded or a sulfur-bonded moiety, $R^{1A}$ is —H, a carbon-bonded or nitrogen-bonded moiety and $R^2$, $R^{2A}$, $R^3$ $R^{3B}$, $R^4$ and $R^{4A}$ are as described any of in the foregoing embodiments or elsewhere herein. In any of these embodiments, $R^5$-$R^9$ are independently selected moieties as described herein and the oxygen-bonded, nitrogen-bonded, carbon bonded or sulfur-bonded moieties at $R^1$, $R^{1A}$, $R^2$, $R^{2A}$, $R^3$, $R^{3B}$, $R^4$, and $R^{4A}$ include atoms or groups described herein. These embodiments contain formula B, C, D, E, F and G compounds wherein one or two of $R^1$, $R^{1A}$, $R^2$, $R^{2A}$, $R^3$, $R^{3B}$, $R^4$, and $R^{4A}$ are independently selected nitrogen-bonded moieties, one, two or three of $R^1$, $R^{1A}$, $R^2$, $R^{2A}$, $R^3$, $R^{3B}$, $R^4$, and $R^{4A}$ are independently selected carbon-bonded moieties and one, two, three, four or five of $R^2$, $R^{2A}$, $R^3$, $R^{3B}$, $R^4$, and $R^{4A}$ are independently selected or halogen atoms or oxygen-bonded or sulfur-bonded moieties.

These embodiments contain F1C, such as the B, C, D, E, F and G structures wherein $R^4$ and $R^{4A}$ are present, i.e., no 16-17 double bond is present, and both are the same, such as optionally substituted alkyl, halogen, ether, ester, thioether, thioester, e.g., —$OR^{PR}$, —$SR^{PR}$, —F, —Cl, —Br, —I, methyl, ethyl, methoxy, ethoxy acetate or propionate. However, in many embodiments, when they are both present, $R^4$ and $R^{4A}$ are two independently selected dissimilar moieties defined herein, e.g., independently selected —H, —OH, —$OR^{PR}$, an ester (e.g., —OC(O)—CH$_3$, —OC(O)—C$_2$H$_5$, —OC(O)—C3 alkyl, —OC(O)—C4 alkyl,), ether (e.g., —OCH$_3$, —OC$_2$H$_5$, —OCH$_2$CH$_2$CH$_3$, or —OCH(CH$_3$)CH$_3$, —O—C4 alkyl, —O—C5 alkyl or —O—C6 alkyl), a thioester, a thioether, an acyl moiety, a carbonate, a carbamate an amide, a monosaccharide, a disaccharide, or an amino acid, optionally substituted alkyl, optionally substituted alkenyl, optionally substituted alkynyl or another moiety described herein.

For any F1C, examples of dissimilar $R^4$ and $R^{4A}$ moieties at the 17-position include (α-ester, β-optionally substituted alkynyl), (β-ester, α-optionally substituted alkynyl), α-thioester, β-optionally substituted alkynyl), (β-thioester, α-optionally substituted alkynyl), (α-ester, β-optionally substituted alkenyl), (β-ester, α-optionally substituted alkenyl), α-thioester, β-optionally substituted alkenyl), (β-thioester, α-optionally substituted alkenyl), (α-optionally substituted alkyl, (β-ester), (β-optionally substituted alkyl, α-ester), α-optionally substituted alkyl, β-optionally substituted amine), (β-optionally substituted alkyl, α-optionally substituted amine), (α-optionally substituted alkyl, (β-halogen)-, (β-optionally substituted alkyl, α-halogen), (α-halogen, β-optionally substituted alkyl), (β-halogen, α-optionally substituted alkyl), (β-ester, α-acyl), (α-ester, (β-acyl), (β-ester, α-C(O)—C1-C10 optionally substituted alkyl), (α-ester, β-C(O)—C1-C10 optionally substituted alkyl), (β-thioester, α-C(O)—C1-C10 optionally substituted alkyl), (β-CH, α-ester), (α-OH, (β-ester), (β-OH, α-ether), (α-OH, β-ether), (β-CH, α-acyl), (α-OH, (β-acyl), (α-F, β-optionally substituted alkyl), (β-F, α-optionally substituted alkyl), (α-OH, β-optionally substituted alkynyl), (β-CH, α-optionally substituted alkynyl), (α-OH, β-C≡CCH$_2$-halogen), (β-CH, α-C≡CCH$_2$-halogen), (α-OH, β-C≡C-halogen), (β-OH, α-C≡C-halogen), (α-cyclopropyl, β-optionally substituted alkyl where the epoxy is formed with an adjacent steroid nucleus atom), (β-cyclopropyl, α-optionally substituted alkyl), (α-optionally substituted alkyl, β-NH—C1-C8 optionally substituted alkyl), (β-optionally substituted alkyl, α-NH-C1-C8 optionally substituted alkyl), (α-ether, β-NH—C1-C8 optionally substituted alkyl), (α-C(O)CH$_3$, β-NH—C1C-8 optionally substituted alkyl), (β-C(O)CH$_3$, α-NH—C1-C8 optionally substituted alkyl), and other combinations of groups that are within the scope of $R^4$ and $R^{4A}$. Such moieties, which are the same or different can also be at 1, 2, 3 or more $R^1$ and $R^{1A}$, $R^2$ and $R^{2A}$, $R^3$ and $R^{3B}$ variable groups, and/or the $R^{10}$ variable groups at $R^7$, $R^8$ and $R^9$.

Specific dissimilar $R^4$ and $R^{4A}$ moieties include, e.g., (α-F, β-CH$_3$), (β-F, α-CH$_3$), (α-F, β-C$_2$H$_5$), (β-F, α-C$_2$H$_5$), (α-F, β-CH$_3$), (β-F, α-CH$_3$), (α-Br, β-CH$_3$), (β-Br, α-CH$_3$), (α-OH, β-CCCH$_3$), (β-CH, α-CCCH$_3$), (α-OH, β-CCCH$_2$OH), (β-CH, α-CCCH$_2$OH), (α-OH, β-CCH), (β-CH, α-CCH), (α-CH$_3$, β-OC(O)CH$_3$), (β-CH$_3$, α-OC(O)CH$_3$), (α-C$_2$H$_5$, β-OC(O)CH$_3$), (β-C$_2$H$_5$, α-OC(O)CH$_3$), (α-C$_3$H$_7$, β-OC(O)CH$_3$), (β-C$_3$H$_7$, α-OC(O)CH$_3$), (α-C$_4$H$_9$, β-OC(O)CH$_3$), (β-C$_4$H$_9$, α-OC(O)CH$_3$), (α-C$_2$H$_3$, β-OC(O)

$CH_3$), ($\beta$-$C_2H_3$, $\alpha$-OC(O)$CH_3$), ($\alpha$-$C_2H_4$OH, $\beta$-OC(O)$CH_3$), ($\beta$-$C_2H_4$OH, $\alpha$-OC(O)$CH_3$), ($\alpha$-$C_3H_5$, $\beta$-OC(O)$CH_3$), ($\beta$-$C_3H_5$, $\alpha$-OC(O)$CH_3$), ($\alpha$-$C_4H_7$, $\beta$-OC(O)$CH_3$), ($\beta$-$C_4H_7$, $\alpha$-OC(O)$CH_3$), ($\alpha$-$C_3H_3$, $\beta$-OC(O)$CH_3$), ($\beta$-$C_3H_3$, $\alpha$-OC(O)$CH_3$), ($\alpha$-$C_4H_5$, $\beta$-OC(O)$CH_3$), ($\beta$-$C_4H_5$, $\alpha$-OC(O)$CH_3$), ($\alpha$-$CH_3$, $\beta$—OC(O)$C_2H_5$), ($\beta$-$CH_3$, $\alpha$-OC(O)$C_2H_5$), ($\alpha$-$C_2H_5$, $\beta$—OC(O)$C_2H_5$), ($\beta$-$C_2H_5$, $\alpha$-OC(O)$C_2H_5$), ($\alpha$-$C_3H_7$, $\beta$-OC(O)$C_2H_5$), ($\beta$-$C_3H_7$, $\alpha$-OC(O)$C_2H_5$), ($\alpha$-$C_4H_9$, $\beta$-OC(O)$C_2H_5$), ($\beta$-$C_4H_9$, $\alpha$-OC(O)$C_2H_5$), ($\alpha$-$C_2H_3$, $\beta$-OC(O)$C_2H_5$), ($\beta$-$C_2H_3$, $\alpha$-OC(O)$C_2H_5$), ($\alpha$-$C_2H_4$OH, $\beta$-OC(O)$C_2H_5$), ($\beta$-$C_2H_{40}$H, $\alpha$-OC(O)$C_2H_5$), ($\alpha$-$C_3H_5$, $\beta$-OC(O)$C_2H_5$), ($\beta$-$C_3H_5$, $\alpha$-OC(O)$C_2H_5$), ($\alpha$-$C_4H_7$, $\beta$—OC(O)$C_2H_5$), ($\beta$-$C_4H_7$, $\alpha$-OC(O)$C_2H_5$), ($\alpha$-$C_3H_3$, $\beta$-OC(O)$C_2H_5$), ($\beta$-$C_3H_3$, $\alpha$-OC(O)$C_2H_5$), ($\alpha$-$C_4H_5$, $\beta$-OC(O)$C_2H_5$), ($\beta$-$C_4H_5$, $\alpha$-OC(O)$C_2H_5$), ($\alpha$-C(O)$CH_3$, $\beta$-OC(O)$CH_3$), ($\beta$-C(O)$CH_3$, $\alpha$-OC(O)$CH_3$), ($\alpha$-C(O)$C_2H_5$, $\beta$-OC(O)$CH_3$), ($\beta$-C(O)$C_2H_5$, $\alpha$-OC(O)$CH_3$), ($\alpha$-C(O)$CH_3$, $\beta$-NH—$CH_3$) and ($\beta$-C(O)$CH_3$, $\alpha$-NH—$CH_3$)

Additional embodiments of the F1Cs include any F1Cs or any 2, 5, 6, 7, 8, 9, 10, B, C, D, E, F or G structures, e.g., any of the F1Cs or F1C genera disclosed herein, wherein one or both of $R^5$ or $R^6$ independently are —H, —$CH_2SH$, —CHO, —$CH_2NRPR$, —$CH_2NH_2$, —$C_4H_9$, —$C_3H_7$, —$C_2H_5$, —$CH_3$, —$C_2H_4$OH, —$C_2H_4SH$, —$C_2H_4NH_2$, —$CH_2$CHO, —$CH_2CH_2NR^{PR}$, —$CH_2CH_2$OH, —$CH_2CH_2SH$, —$CH_2CH_2C_6H_5$, —$CH_2C_6H_5$, —$C_6H_5$ or optionally substituted alkyl wherein any phenyl ($C_6H_5$) moiety in the foregoing groups is optionally substituted at the phenyl ring with 1, 2, 3, 4 or 5 moieties independently selected from those described for esters herein and including C1-C6 alkyl (optionally substituted with 1 or 2 independently selected —OH, —SH, —O—, —S— or —NH—) C1-C6 alkoxy, —F, —Cl, —Br, —I, —CN, —$NO_2$, —OH, —SH, —$COOR^{PR}$, —$NHR^{PR}$ and —C(O)—C1-C6 alkyl. Typically $R^5$ or $R^6$ are both in the $\beta$-configuration, but they may be in, e.g., the $\alpha,\beta$ or $\beta,\alpha$ configurations respectively.

Specific F1Cs that can be used in the clinical treatments and other methods described herein include the following groups of compounds.

Group 1.

Exemplary embodiments include the formula 1 compounds named according to the compound structure designations given in Tables A and B below. Each compound named in Table B is depicted as a compound having formula B

B where $R^5$ and $R^6$ are both —$CH_3$, there is no double bond at the 1-2-, 4-5-, 5-6 or 16-17 positions, $R^7$, $R^8$ and $R^9$ are all —$CH_2$—, $R^{10A}$, $R^{10B}$, $R^{10C}$, $R^{10D}$, $R^{10E}$, $R^{10F}$, $R^{10G}$ and $R^{10H}$ are all —H and $R^1$, $R^2$, $R^3$ and $R^4$ are the substituents designated in Table A. The compounds named according to Tables A and B are referred to as "group 1" compounds.

Compounds named in Table B are named by numbers assigned to $R^1$, $R^2$, $R^3$ and $R^4$ according to the following compound naming convention, $R^1.R^2.R^3.R^4$, using the numbered chemical substituents in Table A. Each Table A number specifies a different structure for each of $R^1$, $R^2$, $R^3$ and $R^4$. When $R^1$, $R^2$, $R^3$ or $R^4$ is a divalent moiety, e.g., =O, the hydrogen at the corresponding position is absent. Thus, the group 1 compound named 1.2.1.1 is a formula B structure with a $\beta$-hydroxyl bonded to carbons at the 3- and 7-positions (the variable groups $R^1$ and $R^2$ respectively), an $\alpha$-bromine bonded to carbon 16 (the variable group $R^3$) and double bonded oxygen (=O) at carbon 17 (the variable group $R^4$), i.e., 1.2.4.1 is 3$\beta$,7$\beta$-dihydroxy-16$\alpha$-fluoro-17$\beta$-aminoandrostane and has the structure 1.2.4.1

Similarly, group 1 compound 1.2.7.1 is 3$\beta$,7$\beta$-dihydroxy-16-oxo-17$\beta$-aminoandrostane and compound 1.1.4.1 is 3$\beta$-hydroxy-16$\alpha$-fluoro-17$\beta$-aminoandrostane.

TABLE A

| | $R^1$ |
|---|---|
| 1 | —OH |
| 2 | =O |
| 3 | —SH |
| 4 | =S |
| 5 | —$NH_2$ |
| 6 | —NH—C(O)$CH_3$ |
| 7 | —H |
| 8 | —$CH_3$ |
| 9 | —O—S(O)(O)—$OC_2H_5$ |
| 10 | —O—S(O)(O)—$O^-Na^+$ |
| | $R^2$ |
| 1 | —H |
| 2 | —OH |
| 3 | =O |
| 4 | —$CH_3$ |
| 5 | —$OCH_3$ |
| 6 | —F |
| 7 | —Cl |
| 8 | —Br |
| 9 | —I |
| 10 | =$CH_2$ |
| | $R^3$ |
| 1 | —Br |
| 2 | —Cl |
| 3 | —I |
| 4 | —F |
| 5 | —H |
| 6 | —OH |
| 7 | =O |
| 8 | —O—C(O)—$CH_3$ |
| 9 | —O—C(O)—$CH_2CH_3$ |
| 10 | =$CH_2$ |
| | $R^4$ |
| 1 | —$NH_2$ |
| 2 | —NH—C(O)$CH_3$ |
| 3 | =NOH |
| 4 | —NH—$CH_3$ |

TABLE A-continued

| | |
|---|---|
| 5 | —N(CH$_3$)$_2$ |
| 6 | —N$^+$(CH$_3$)$_3$ |
| 7 | —NH—C$_2$H$_5$ |
| 8 | —NHOH |
| 9 | —OH |
| 10 | =O |

TABLE B 1.1.1.1, 1.1.1.2, 1.1.1.3, 1.1.1.4, 1.1.1.5, 1.1.1.6, 1.1.1.7, 1.1.1.8, 1.1.1.9, 1.1.1.10, 1.1.2.1, 1.1.2.2, 1.1.2.3, 1.1.2.4, 1.1.2.5, 1.1.2.6, 1.1.2.7, 1.1.2.8, 1.1.2.9, 1.1.2.10, 1.1.3.1, 1.1.3.2, 1.1.3.3, 1.1.3.4, 1.1.3.5, 1.1.3.6, 1.1.3.7, 1.1.3.8, 1.1.3.9, 1.1.3.10, 1.1.4.1, 1.1.4.2, 1.1.4.3, 1.1.4.4, 1.1.4.5, 1.1.4.6, 1.1.4.7, 1.1.4.8, 1.1.4.9, 1.1.4.10, 1.1.5.1, 1.1.5.2, 1.1.5.3, 1.1.5.4, 1.1.5.5, 1.1.5.6, 1.1.5.7, 1.1.5.8, 1.1.5.9, 1.1.5.10, 1.1.6.1, 1.1.6.2, 1.1.6.3, 1.1.6.4, 1.1.6.5, 1.1.6.6, 1.1.6.7, 1.1.6.8, 1.1.6.9, 1.1.6.10, 1.1.7.1, 1.1.7.2, 1.1.7.3, 1.1.7.4, 1.1.7.5, 1.1.7.6, 1.1.7.7, 1.1.7.8, 1.1.7.9, 1.1.7.10, 1.1.8.1, 1.1.8.2, 1.1.8.3, 1.1.8.4, 1.1.8.5, 1.1.8.6, 1.1.8.7, 1.1.8.8, 1.1.8.9, 1.1.8.10, 1.1.9.1, 1.1.9.2, 1.1.9.3, 1.1.9.4, 1.1.9.5, 1.1.9.6, 1.1.9.7, 1.1.9.8, 1.1.9.9, 1.1.9.10, 1.1.10.1, 1.1.10.2, 1.1.10.3, 1.1.10.4, 1.1.10.5, 1.1.10.6, 1.1.10.7, 1.1.10.8, 1.1.10.9, 1.1.10.10, 1.2.1.1, 1.2.1.2, 1.2.1.3, 1.2.1.4, 1.2.1.5, 1.2.1.6, 1.2.1.7, 1.2.1.8, 1.2.1.9, 1.2.1.10, 1.2.2.1, 1.2.2.2, 1.2.2.3, 1.2.2.4, 1.2.2.5, 1.2.2.6, 1.2.2.7, 1.2.2.8, 1.2.2.9, 1.2.2.10, 1.2.3.1, 1.2.3.2, 1.2.3.3, 1.2.3.4, 1.2.3.5, 1.2.3.6, 1.2.3.7, 1.2.3.8, 1.2.3.9, 1.2.3.10, 1.2.4.1, 1.2.4.2, 1.2.4.3, 1.2.4.4, 1.2.4.5, 1.2.4.6, 1.2.4.7, 1.2.4.8, 1.2.4.9, 1.2.4.10, 1.2.5.1, 1.2.5.2, 1.2.5.3, 1.2.5.4, 1.2.5.5, 1.2.5.6, 1.2.5.7, 1.2.5.8, 1.2.5.9, 1.2.5.10, 1.2.6.1, 1.2.6.2, 1.2.6.3, 1.2.6.4, 1.2.6.5, 1.2.6.6, 1.2.6.7, 1.2.6.8, 1.2.6.9, 1.2.6.10, 1.2.7.1, 1.2.7.2, 1.2.7.3, 1.2.7.4, 1.2.7.5, 1.2.7.6, 1.2.7.7, 1.2.7.8, 1.2.7.9, 1.2.7.10, 1.2.8.1, 1.2.8.2, 1.2.8.3, 1.2.8.4, 1.2.8.5, 1.2.8.6, 1.2.8.7, 1.2.8.8, 1.2.8.9, 1.2.8.10, 1.2.9.1, 1.2.9.2, 1.2.9.3, 1.2.9.4, 1.2.9.5, 1.2.9.6, 1.2.9.7, 1.2.9.8, 1.2.9.9, 1.2.9.10, 1.2.10.1, 1.2.10.2, 1.2.10.3, 1.2.10.4, 1.2.10.5, 1.2.10.6, 1.2.10.7, 1.2.10.8, 1.2.10.9, 1.2.10.10, 1.3.1.1, 1.3.1.2, 1.3.1.3, 1.3.1.4, 1.3.1.5, 1.3.1.6, 1.3.1.7, 1.3.1.8, 1.3.1.9, 1.3.1.10, 1.3.2.1, 1.3.2.2, 1.3.2.3, 1.3.2.4, 1.3.2.5, 1.3.2.6, 1.3.2.7, 1.3.2.8, 1.3.2.9, 1.3.2.10, 1.3.3.1, 1.3.3.2, 1.3.3.3, 1.3.3.4, 1.3.3.5, 1.3.3.6, 1.3.3.7, 1.3.3.8, 1.3.3.9, 1.3.3.10, 1.3.4.1, 1.3.4.2, 1.3.4.3, 1.3.4.4, 1.3.4.5, 1.3.4.6, 1.3.4.7, 1.3.4.8, 1.3.4.9, 1.3.4.10, 1.3.5.1, 1.3.5.2, 1.3.5.3, 1.3.5.4, 1.3.5.5, 1.3.5.6, 1.3.5.7, 1.3.5.8, 1.3.5.9, 1.3.5.10, 1.3.6.1, 1.3.6.2, 1.3.6.3, 1.3.6.4, 1.3.6.5, 1.3.6.6, 1.3.6.7, 1.3.6.8, 1.3.6.9, 1.3.6.10, 1.3.7.1, 1.3.7.2, 1.3.7.3, 1.3.7.4, 1.3.7.5, 1.3.7.6, 1.3.7.7, 1.3.7.8, 1.3.7.9, 1.3.7.10, 1.3.8.1, 1.3.8.2, 1.3.8.3, 1.3.8.4, 1.3.8.5, 1.3.8.6, 1.3.8.7, 1.3.8.8, 1.3.8.9, 1.3.8.10, 1.3.9.1, 1.3.9.2, 1.3.9.3, 1.3.9.4, 1.3.9.5, 1.3.9.6, 1.3.9.7, 1.3.9.8, 1.3.9.9, 1.3.9.10, 1.3.10.1, 1.3.10.2, 1.3.10.3, 1.3.10.4, 1.3.10.5, 1.3.10.6, 1.3.10.7, 1.3.10.8, 1.3.10.9, 1.3.10.10, 1.4.1.1, 1.4.1.2, 1.4.1.3, 1.4.1.4, 1.4.1.5, 1.4.1.6, 1.4.1.7, 1.4.1.8, 1.4.1.9, 1.4.1.10, 1.4.2.1, 1.4.2.2, 1.4.2.3, 1.4.2.4, 1.4.2.5, 1.4.2.6, 1.4.2.7, 1.4.2.8, 1.4.2.9, 1.4.2.10, 1.4.3.1, 1.4.3.2, 1.4.3.3, 1.4.3.4, 1.4.3.5, 1.4.3.6, 1.4.3.7, 1.4.3.8, 1.4.3.9, 1.4.3.10, 1.4.4.1, 1.4.4.2, 1.4.4.3, 1.4.4.4, 1.4.4.5, 1.4.4.6, 1.4.4.7, 1.4.4.8, 1.4.4.9, 1.4.4.10, 1.4.5.1, 1.4.5.2, 1.4.5.3, 1.4.5.4, 1.4.5.5, 1.4.5.6, 1.4.5.7, 1.4.5.8, 1.4.5.9, 1.4.5.10, 1.4.6.1, 1.4.6.2, 1.4.6.3, 1.4.6.4, 1.4.6.5, 1.4.6.6, 1.4.6.7, 1.4.6.8, 1.4.6.9, 1.4.6.10, 1.4.7.1, 1.4.7.2, 1.4.7.3, 1.4.7.4, 1.4.7.5, 1.4.7.6, 1.4.7.7, 1.4.7.8, 1.4.7.9, 1.4.7.10, 1.4.8.1, 1.4.8.2, 1.4.8.3, 1.4.8.4, 1.4.8.5, 1.4.8.6, 1.4.8.7, 1.4.8.8, 1.4.8.9, 1.4.8.10, 1.4.9.1, 1.4.9.2, 1.4.9.3, 1.4.9.4, 1.4.9.5, 1.4.9.6, 1.4.9.7, 1.4.9.8, 1.4.9.9, 1.4.9.10, 1.4.10.1, 1.4.10.2, 1.4.10.3, 1.4.10.4, 1.4.10.5, 1.4.10.6, 1.4.10.7, 1.4.10.8, 1.4.10.9, 1.4.10.10, 1.5.1.1, 1.5.1.2, 1.5.1.3, 1.5.1.4, 1.5.1.5, 1.5.1.6, 1.5.1.7, 1.5.1.8, 1.5.1.9, 1.5.1.10, 1.5.2.1, 1.5.2.2, 1.5.2.3, 1.5.2.4, 1.5.2.5, 1.5.2.6, 1.5.2.7, 1.5.2.8, 1.5.2.9, 1.5.2.10, 1.5.3.1, 1.5.3.2, 1.5.3.3, 1.5.3.4, 1.5.3.5, 1.5.3.6, 1.5.3.7, 1.5.3.8, 1.5.3.9, 1.5.3.10, 1.5.4.1, 1.5.4.2, 1.5.4.3, 1.5.4.4, 1.5.4.5, 1.5.4.6, 1.5.4.7, 1.5.4.8, 1.5.4.9, 1.5.4.10, 1.5.5.1, 1.5.5.2, 1.5.5.3, 1.5.5.4, 1.5.5.5, 1.5.5.6, 1.5.5.7, 1.5.5.8, 1.5.5.9, 1.5.5.10, 1.5.6.1, 1.5.6.2, 1.5.6.3, 1.5.6.4, 1.5.6.5, 1.5.6.6, 1.5.6.7, 1.5.6.8, 1.5.6.9, 1.5.6.10, 1.5.7.1, 1.5.7.2, 1.5.7.3, 1.5.7.4, 1.5.7.5, 1.5.7.6, 1.5.7.7, 1.5.7.8, 1.5.7.9, 1.5.7.10, 1.5.8.1, 1.5.8.2, 1.5.8.3, 1.5.8.4, 1.5.8.5, 1.5.8.6, 1.5.8.7, 1.5.8.8, 1.5.8.9, 1.5.8.10, 1.5.9.1, 1.5.9.2, 1.5.9.3, 1.5.9.4, 1.5.9.5, 1.5.9.6, 1.5.9.7, 1.5.9.8, 1.5.9.9, 1.5.9.10, 1.5.10.1, 1.5.10.2, 1.5.10.3, 1.5.10.4, 1.5.10.5, 1.5.10.6, 1.5.10.7, 1.5.10.8, 1.5.10.9, 1.5.10.10, 1.6.1.1, 1.6.1.2, 1.6.1.3, 1.6.1.4, 1.6.1.5, 1.6.1.6, 1.6.1.7, 1.6.1.8, 1.6.1.9, 1.6.1.10, 1.6.2.1, 1.6.2.2, 1.6.2.3, 1.6.2.4, 1.6.2.5, 1.6.2.6, 1.6.2.7, 1.6.2.8, 1.6.2.9, 1.6.2.10, 1.6.3.1, 1.6.3.2, 1.6.3.3, 1.6.3.4, 1.6.3.5, 1.6.3.6, 1.6.3.7, 1.6.3.8, 1.6.3.9, 1.6.3.10, 1.6.4.1, 1.6.4.2, 1.6.4.3, 1.6.4.4, 1.6.4.5, 1.6.4.6, 1.6.4.7, 1.6.4.8, 1.6.4.9, 1.6.4.10, 1.6.5.1, 1.6.5.2, 1.6.5.3, 1.6.5.4, 1.6.5.5, 1.6.5.6, 1.6.5.7, 1.6.5.8, 1.6.5.9, 1.6.5.10, 1.6.6.1, 1.6.6.2, 1.6.6.3, 1.6.6.4, 1.6.6.5, 1.6.6.6, 1.6.6.7, 1.6.6.8, 1.6.6.9, 1.6.6.10, 1.6.7.1, 1.6.7.2, 1.6.7.3, 1.6.7.4, 1.6.7.5, 1.6.7.6, 1.6.7.7, 1.6.7.8, 1.6.7.9, 1.6.7.10, 1.6.8.1, 1.6.8.2, 1.6.8.3, 1.6.8.4, 1.6.8.5, 1.6.8.6, 1.6.8.7, 1.6.8.8, 1.6.8.9, 1.6.8.10, 1.6.9.1, 1.6.9.2, 1.6.9.3, 1.6.9.4, 1.6.9.5, 1.6.9.6, 1.6.9.7, 1.6.9.8, 1.6.9.9, 1.6.9.10, 1.6.10.1, 1.6.10.2, 1.6.10.3, 1.6.10.4, 1.6.10.5, 1.6.10.6, 1.6.10.7, 1.6.10.8, 1.6.10.9, 1.6.10.10, 1.7.1.1, 1.7.1.2, 1.7.1.3, 1.7.1.4, 1.7.1.5, 1.7.1.6, 1.7.1.7, 1.7.1.8, 1.7.1.9, 1.7.1.10, 1.7.2.1, 1.7.2.2, 1.7.2.3, 1.7.2.4, 1.7.2.5, 1.7.2.6, 1.7.2.7, 1.7.2.8, 1.7.2.9, 1.7.2.10, 1.7.3.1, 1.7.3.2, 1.7.3.3, 1.7.3.4, 1.7.3.5, 1.7.3.6, 1.7.3.7, 1.7.3.8, 1.7.3.9, 1.7.3.10, 1.7.4.1, 1.7.4.2, 1.7.4.3, 1.7.4.4, 1.7.4.5, 1.7.4.6, 1.7.4.7, 1.7.4.8, 1.7.4.9, 1.7.4.10, 1.7.5.1, 1.7.5.2, 1.7.5.3, 1.7.5.4, 1.7.5.5, 1.7.5.6, 1.7.5.7, 1.7.5.8, 1.7.5.9, 1.7.5.10, 1.7.6.1, 1.7.6.2, 1.7.6.3, 1.7.6.4, 1.7.6.5, 1.7.6.6, 1.7.6.7, 1.7.6.8, 1.7.6.9, 1.7.6.10, 1.7.7.1, 1.7.7.2, 1.7.7.3, 1.7.7.4, 1.7.7.5, 1.7.7.6, 1.7.7.7, 1.7.7.8, 1.7.7.9, 1.7.7.10, 1.7.8.1, 1.7.8.2, 1.7.8.3, 1.7.8.4, 1.7.8.5, 1.7.8.6, 1.7.8.7, 1.7.8.8, 1.7.8.9, 1.7.8.10, 1.7.9.1, 1.7.9.2, 1.7.9.3, 1.7.9.4, 1.7.9.5, 1.7.9.6, 1.7.9.7, 1.7.9.8, 1.7.9.9, 1.7.9.10, 1.7.10.1, 1.7.10.2, 1.7.10.3, 1.7.10.4, 1.7.10.5, 1.7.10.6, 1.7.10.7, 1.7.10.8, 1.7.10.9, 1.7.10.10, 1.8.1.1, 1.8.1.2, 1.8.1.3, 1.8.1.4, 1.8.1.5, 1.8.1.6, 1.8.1.7, 1.8.1.8, 1.8.1.9, 1.8.1.10, 1.8.2.1, 1.8.2.2, 1.8.2.3, 1.8.2.4, 1.8.2.5, 1.8.2.6, 1.8.2.7, 1.8.2.8, 1.8.2.9, 1.8.2.10, 1.8.3.1, 1.8.3.2, 1.8.3.3, 1.8.3.4, 1.8.3.5, 1.8.3.6, 1.8.3.7, 1.8.3.8, 1.8.3.9, 1.8.3.10, 1.8.4.1, 1.8.4.2, 1.8.4.3, 1.8.4.4, 1.8.4.5, 1.8.4.6, 1.8.4.7, 1.8.4.8, 1.8.4.9, 1.8.4.10, 1.8.5.1, 1.8.5.2, 1.8.5.3, 1.8.5.4, 1.8.5.5, 1.8.5.6, 1.8.5.7, 1.8.5.8, 1.8.5.9, 1.8.5.10, 1.8.6.1, 1.8.6.2, 1.8.6.3, 1.8.6.4, 1.8.6.5, 1.8.6.6, 1.8.6.7, 1.8.6.8, 1.8.6.9, 1.8.6.10, 1.8.7.1, 1.8.7.2, 1.8.7.3, 1.8.7.4, 1.8.7.5, 1.8.7.6, 1.8.7.7, 1.8.7.8, 1.8.7.9, 1.8.7.10, 1.8.8.1, 1.8.8.2, 1.8.8.3, 1.8.8.4, 1.8.8.5, 1.8.8.6, 1.8.8.7, 1.8.8.8, 1.8.8.9, 1.8.8.10, 1.8.9.1, 1.8.9.2, 1.8.9.3, 1.8.9.4, 1.8.9.5, 1.8.9.6, 1.8.9.7, 1.8.9.8, 1.8.9.9, 1.8.9.10, 1.8.10.1, 1.8.10.2, 1.8.10.3, 1.8.10.4, 1.8.10.5, 1.8.10.6, 1.8.10.7, 1.8.10.8, 1.8.10.9, 1.8.10.10, 1.9.1.1, 1.9.1.2, 1.9.1.3, 1.9.1.4, 1.9.1.5, 1.9.1.6, 1.9.1.7, 1.9.1.8, 1.9.1.9, 1.9.1.10, 1.9.2.1, 1.9.2.2, 1.9.2.3, 1.9.2.4, 1.9.2.5, 1.9.2.6, 1.9.2.7, 1.9.2.8, 1.9.2.9, 1.9.2.10, 1.9.3.1, 1.9.3.2, 1.9.3.3, 1.9.3.4, 1.9.3.5, 1.9.3.6, 1.9.3.7, 1.9.3.8, 1.9.3.9, 1.9.3.10, 1.9.4.1, 1.9.4.2, 1.9.4.3, 1.9.4.4, 1.9.4.5, 1.9.4.6, 1.9.4.7, 1.9.4.8, 1.9.4.9, 1.9.4.10, 1.9.5.1, 1.9.5.2, 1.9.5.3, 1.9.5.4, 1.9.5.5,

TABLE B-continued 1.9.5.6, 1.9.5.7, 1.9.5.8, 1.9.5.9, 1.9.5.10, 1.9.6.1, 1.9.6.2, 1.9.6.3, 1.9.6.4, 1.9.6.5, 1.9.6.6, 1.9.6.7, 1.9.6.8, 1.9.6.9, 1.9.6.10, 1.9.7.1, 1.9.7.2, 1.9.7.3, 1.9.7.4, 1.9.7.5, 1.9.7.6, 1.9.7.7, 1.9.7.8, 1.9.7.9, 1.9.7.10, 1.9.8.1, 1.9.8.2, 1.9.8.3, 1.9.8.4, 1.9.8.5, 1.9.8.6, 1.9.8.7, 1.9.8.8, 1.9.8.9, 1.9.8.10, 1.9.9.1, 1.9.9.2, 1.9.9.3, 1.9.9.4, 1.9.9.5, 1.9.9.6, 1.9.9.7, 1.9.9.8, 1.9.9.9, 1.9.9.10, 1.9.10.1, 1.9.10.2, 1.9.10.3, 1.9.10.4, 1.9.10.5, 1.9.10.6, 1.9.10.7, 1.9.10.8, 1.9.10.9, 1.9.10.10, 1.10.1.1, 1.10.1.2, 1.10.1.3, 1.10.1.4, 1.10.1.5, 1.10.1.6, 1.10.1.7, 1.10.1.8, 1.10.1.9, 1.10.1.10, 1.10.2.1, 1.10.2.2, 1.10.2.3, 1.10.2.4, 1.10.2.5, 1.10.2.6, 1.10.2.7, 1.10.2.8, 1.10.2.9, 1.10.2.10, 1.10.3.1, 1.10.3.2, 1.10.3.3, 1.10.3.4, 1.10.3.5, 1.10.3.6, 1.10.3.7, 1.10.3.8, 1.10.3.9, 1.10.3.10, 1.10.4.1, 1.10.4.2, 1.10.4.3, 1.10.4.4, 1.10.4.5, 1.10.4.6, 1.10.4.7, 1.10.4.8, 1.10.4.9, 1.10.4.10, 1.10.5.1, 1.10.5.2, 1.10.5.3, 1.10.5.4, 1.10.5.5, 1.10.5.6, 1.10.5.7, 1.10.5.8, 1.10.5.9, 1.10.5.10, 1.10.6.1, 1.10.6.2, 1.10.6.3, 1.10.6.4, 1.10.6.5, 1.10.6.6, 1.10.6.7, 1.10.6.8, 1.10.6.9, 1.10.6.10, 1.10.7.1, 1.10.7.2, 1.10.7.3, 1.10.7.4, 1.10.7.5, 1.10.7.6, 1.10.7.7, 1.10.7.8, 1.10.7.9, 1.10.7.10, 1.10.8.1, 1.10.8.2, 1.10.8.3, 1.10.8.4, 1.10.8.5, 1.10.8.6, 1.10.8.7, 1.10.8.8, 1.10.8.9, 1.10.8.10, 1.10.9.1, 1.10.9.2, 1.10.9.3, 1.10.9.4, 1.10.9.5, 1.10.9.6, 1.10.9.7, 1.10.9.8, 1.10.9.9, 1.10.9.10, 1.10.10.1, 1.10.10.2, 1.10.10.3, 1.10.10.4, 1.10.10.5, 1.10.10.6, 1.10.10.7, 1.10.10.8, 1.10.10.9, 1.10.10.10, 2.1.1.1, 2.1.1.2, 2.1.1.3, 2.1.1.4, 2.1.1.5, 2.1.1.6, 2.1.1.7, 2.1.1.8, 2.1.1.9, 2.1.1.10, 2.1.2.1, 2.1.2.2, 2.1.2.3, 2.1.2.4, 2.1.2.5, 2.1.2.6, 2.1.2.7, 2.1.2.8, 2.1.2.9, 2.1.2.10, 2.1.3.1, 2.1.3.2, 2.1.3.3, 2.1.3.4, 2.1.3.5, 2.1.3.6, 2.1.3.7, 2.1.3.8, 2.1.3.9, 2.1.3.10, 2.1.4.1, 2.1.4.2, 2.1.4.3, 2.1.4.4, 2.1.4.5, 2.1.4.6, 2.1.4.7, 2.1.4.8, 2.1.4.9, 2.1.4.10, 2.1.5.1, 2.1.5.2, 2.1.5.3, 2.1.5.4, 2.1.5.5, 2.1.5.6, 2.1.5.7, 2.1.5.8, 2.1.5.9, 2.1.5.10, 2.1.6.1, 2.1.6.2, 2.1.6.3, 2.1.6.4, 2.1.6.5, 2.1.6.6, 2.1.6.7, 2.1.6.8, 2.1.6.9, 2.1.6.10, 2.1.7.1, 2.1.7.2, 2.1.7.3, 2.1.7.4, 2.1.7.5, 2.1.7.6, 2.1.7.7, 2.1.7.8, 2.1.7.9, 2.1.7.10, 2.1.8.1, 2.1.8.2, 2.1.8.3, 2.1.8.4, 2.1.8.5, 2.1.8.6, 2.1.8.7, 2.1.8.8, 2.1.8.9, 2.1.8.10, 2.1.9.1, 2.1.9.2, 2.1.9.3, 2.1.9.4, 2.1.9.5, 2.1.9.6, 2.1.9.7, 2.1.9.8, 2.1.9.9, 2.1.9.10, 2.1.10.1, 2.1.10.2, 2.1.10.3, 2.1.10.4, 2.1.10.5, 2.1.10.6, 2.1.10.7, 2.1.10.8, 2.1.10.9, 2.1.10.10, 2.2.1.1, 2.2.1.2, 2.2.1.3, 2.2.1.4, 2.2.1.5, 2.2.1.6, 2.2.1.7, 2.2.1.8, 2.2.1.9, 2.2.1.10, 2.2.2.1, 2.2.2.2, 2.2.2.3, 2.2.2.4, 2.2.2.5, 2.2.2.6, 2.2.2.7, 2.2.2.8, 2.2.2.9, 2.2.2.10, 2.2.3.1, 2.2.3.2, 2.2.3.3, 2.2.3.4, 2.2.3.5, 2.2.3.6, 2.2.3.7, 2.2.3.8, 2.2.3.9, 2.2.3.10, 2.2.4.1, 2.2.4.2, 2.2.4.3, 2.2.4.4, 2.2.4.5, 2.2.4.6, 2.2.4.7, 2.2.4.8, 2.2.4.9, 2.2.4.10, 2.2.5.1, 2.2.5.2, 2.2.5.3, 2.2.5.4, 2.2.5.5, 2.2.5.6, 2.2.5.7, 2.2.5.8, 2.2.5.9, 2.2.5.10, 2.2.6.1, 2.2.6.2, 2.2.6.3, 2.2.6.4, 2.2.6.5, 2.2.6.6, 2.2.6.7, 2.2.6.8, 2.2.6.9, 2.2.6.10, 2.2.7.1, 2.2.7.2, 2.2.7.3, 2.2.7.4, 2.2.7.5, 2.2.7.6, 2.2.7.7, 2.2.7.8, 2.2.7.9, 2.2.7.10, 2.2.8.1, 2.2.8.2, 2.2.8.3, 2.2.8.4, 2.2.8.5, 2.2.8.6, 2.2.8.7, 2.2.8.8, 2.2.8.9, 2.2.8.10, 2.2.9.1, 2.2.9.2, 2.2.9.3, 2.2.9.4, 2.2.9.5, 2.2.9.6, 2.2.9.7, 2.2.9.8, 2.2.9.9, 2.2.9.10, 2.2.10.1, 2.2.10.2, 2.2.10.3, 2.2.10.4, 2.2.10.5, 2.2.10.6, 2.2.10.7, 2.2.10.8, 2.2.10.9, 2.2.10.10, 2.3.1.1, 2.3.1.2, 2.3.1.3, 2.3.1.4, 2.3.1.5, 2.3.1.6, 2.3.1.7, 2.3.1.8, 2.3.1.9, 2.3.1.10, 2.3.2.1, 2.3.2.2, 2.3.2.3, 2.3.2.4, 2.3.2.5, 2.3.2.6, 2.3.2.7, 2.3.2.8, 2.3.2.9, 2.3.2.10, 2.3.3.1, 2.3.3.2, 2.3.3.3, 2.3.3.4, 2.3.3.5, 2.3.3.6, 2.3.3.7, 2.3.3.8, 2.3.3.9, 2.3.3.10, 2.3.4.1, 2.3.4.2, 2.3.4.3, 2.3.4.4, 2.3.4.5, 2.3.4.6, 2.3.4.7, 2.3.4.8, 2.3.4.9, 2.3.4.10, 2.3.5.1, 2.3.5.2, 2.3.5.3, 2.3.5.4, 2.3.5.5, 2.3.5.6, 2.3.5.7, 2.3.5.8, 2.3.5.9, 2.3.5.10, 2.3.6.1, 2.3.6.2, 2.3.6.3, 2.3.6.4, 2.3.6.5, 2.3.6.6, 2.3.6.7, 2.3.6.8, 2.3.6.9, 2.3.6.10, 2.3.7.1, 2.3.7.2, 2.3.7.3, 2.3.7.4, 2.3.7.5, 2.3.7.6, 2.3.7.7, 2.3.7.8, 2.3.7.9, 2.3.7.10, 2.3.8.1, 2.3.8.2, 2.3.8.3, 2.3.8.4, 2.3.8.5, 2.3.8.6, 2.3.8.7, 2.3.8.8, 2.3.8.9, 2.3.8.10, 2.3.9.1, 2.3.9.2, 2.3.9.3, 2.3.9.4, 2.3.9.5, 2.3.9.6, 2.3.9.7, 2.3.9.8, 2.3.9.9, 2.3.9.10, 2.3.10.1, 2.3.10.2, 2.3.10.3, 2.3.10.4, 2.3.10.5, 2.3.10.6, 2.3.10.7, 2.3.10.8, 2.3.10.9, 2.3.10.10, 2.4.1.1, 2.4.1.2, 2.4.1.3, 2.4.1.4, 2.4.1.5, 2.4.1.6, 2.4.1.7, 2.4.1.8, 2.4.1.9, 2.4.1.10, 2.4.2.1, 2.4.2.2, 2.4.2.3, 2.4.2.4, 2.4.2.5, 2.4.2.6, 2.4.2.7, 2.4.2.8, 2.4.2.9, 2.4.2.10, 2.4.3.1, 2.4.3.2, 2.4.3.3, 2.4.3.4, 2.4.3.5, 2.4.3.6, 2.4.3.7, 2.4.3.8, 2.4.3.9, 2.4.3.10, 2.4.4.1, 2.4.4.2, 2.4.4.3, 2.4.4.4, 2.4.4.5, 2.4.4.6, 2.4.4.7, 2.4.4.8, 2.4.4.9, 2.4.4.10, 2.4.5.1, 2.4.5.2, 2.4.5.3, 2.4.5.4, 2.4.5.5, 2.4.5.6, 2.4.5.7, 2.4.5.8, 2.4.5.9, 2.4.5.10, 2.4.6.1, 2.4.6.2, 2.4.6.3, 2.4.6.4, 2.4.6.5, 2.4.6.6, 2.4.6.7, 2.4.6.8, 2.4.6.9, 2.4.6.10, 2.4.7.1, 2.4.7.2, 2.4.7.3, 2.4.7.4, 2.4.7.5, 2.4.7.6, 2.4.7.7, 2.4.7.8, 2.4.7.9, 2.4.7.10, 2.4.8.1, 2.4.8.2, 2.4.8.3, 2.4.8.4, 2.4.8.5, 2.4.8.6, 2.4.8.7, 2.4.8.8, 2.4.8.9, 2.4.8.10, 2.4.9.1, 2.4.9.2, 2.4.9.3, 2.4.9.4, 2.4.9.5, 2.4.9.6, 2.4.9.7, 2.4.9.8, 2.4.9.9, 2.4.9.10, 2.4.10.1, 2.4.10.2, 2.4.10.3, 2.4.10.4, 2.4.10.5, 2.4.10.6, 2.4.10.7, 2.4.10.8, 2.4.10.9, 2.4.10.10, 2.5.1.1, 2.5.1.2, 2.5.1.3, 2.5.1.4, 2.5.1.5, 2.5.1.6, 2.5.1.7, 2.5.1.8, 2.5.1.9, 2.5.1.10, 2.5.2.1, 2.5.2.2, 2.5.2.3, 2.5.2.4, 2.5.2.5, 2.5.2.6, 2.5.2.7, 2.5.2.8, 2.5.2.9, 2.5.2.10, 2.5.3.1, 2.5.3.2, 2.5.3.3, 2.5.3.4, 2.5.3.5, 2.5.3.6, 2.5.3.7, 2.5.3.8, 2.5.3.9, 2.5.3.10, 2.5.4.1, 2.5.4.2, 2.5.4.3, 2.5.4.4, 2.5.4.5, 2.5.4.6, 2.5.4.7, 2.5.4.8, 2.5.4.9, 2.5.4.10, 2.5.5.1, 2.5.5.2, 2.5.5.3, 2.5.5.4, 2.5.5.5, 2.5.5.6, 2.5.5.7, 2.5.5.8, 2.5.5.9, 2.5.5.10, 2.5.6.1, 2.5.6.2, 2.5.6.3, 2.5.6.4, 2.5.6.5, 2.5.6.6, 2.5.6.7, 2.5.6.8, 2.5.6.9, 2.5.6.10, 2.5.7.1, 2.5.7.2, 2.5.7.3, 2.5.7.4, 2.5.7.5, 2.5.7.6, 2.5.7.7, 2.5.7.8, 2.5.7.9, 2.5.7.10, 2.5.8.1, 2.5.8.2, 2.5.8.3, 2.5.8.4, 2.5.8.5, 2.5.8.6, 2.5.8.7, 2.5.8.8, 2.5.8.9, 2.5.8.10, 2.5.9.1, 2.5.9.2, 2.5.9.3, 2.5.9.4, 2.5.9.5, 2.5.9.6, 2.5.9.7, 2.5.9.8, 2.5.9.9, 2.5.9.10, 2.5.10.1, 2.5.10.2, 2.5.10.3, 2.5.10.4, 2.5.10.5, 2.5.10.6, 2.5.10.7, 2.5.10.8, 2.5.10.9, 2.5.10.10, 2.6.1.1, 2.6.1.2, 2.6.1.3, 2.6.1.4, 2.6.1.5, 2.6.1.6, 2.6.1.7, 2.6.1.8, 2.6.1.9, 2.6.1.10, 2.6.2.1, 2.6.2.2, 2.6.2.3, 2.6.2.4, 2.6.2.5, 2.6.2.6, 2.6.2.7, 2.6.2.8, 2.6.2.9, 2.6.2.10, 2.6.3.1, 2.6.3.2, 2.6.3.3, 2.6.3.4, 2.6.3.5, 2.6.3.6, 2.6.3.7, 2.6.3.8, 2.6.3.9, 2.6.3.10, 2.6.4.1, 2.6.4.2, 2.6.4.3, 2.6.4.4, 2.6.4.5, 2.6.4.6, 2.6.4.7, 2.6.4.8, 2.6.4.9, 2.6.4.10, 2.6.5.1, 2.6.5.2, 2.6.5.3, 2.6.5.4, 2.6.5.5, 2.6.5.6, 2.6.5.7, 2.6.5.8, 2.6.5.9, 2.6.5.10, 2.6.6.1, 2.6.6.2, 2.6.6.3, 2.6.6.4, 2.6.6.5, 2.6.6.6, 2.6.6.7, 2.6.6.8, 2.6.6.9, 2.6.6.10, 2.6.7.1, 2.6.7.2, 2.6.7.3, 2.6.7.4, 2.6.7.5, 2.6.7.6, 2.6.7.7, 2.6.7.8, 2.6.7.9, 2.6.7.10, 2.6.8.1, 2.6.8.2, 2.6.8.3, 2.6.8.4, 2.6.8.5, 2.6.8.6, 2.6.8.7, 2.6.8.8, 2.6.8.9, 2.6.8.10, 2.6.9.1, 2.6.9.2, 2.6.9.3, 2.6.9.4, 2.6.9.5, 2.6.9.6, 2.6.9.7, 2.6.9.8, 2.6.9.9, 2.6.9.10, 2.6.10.1, 2.6.10.2, 2.6.10.3, 2.6.10.4, 2.6.10.5, 2.6.10.6, 2.6.10.7, 2.6.10.8, 2.6.10.9, 2.6.10.10, 2.7.1.1, 2.7.1.2, 2.7.1.3, 2.7.1.4, 2.7.1.5, 2.7.1.6, 2.7.1.7, 2.7.1.8, 2.7.1.9, 2.7.1.10, 2.7.2.1, 2.7.2.2, 2.7.2.3, 2.7.2.4, 2.7.2.5, 2.7.2.6, 2.7.2.7, 2.7.2.8, 2.7.2.9, 2.7.2.10, 2.7.3.1, 2.7.3.2, 2.7.3.3, 2.7.3.4, 2.7.3.5, 2.7.3.6, 2.7.3.7, 2.7.3.8, 2.7.3.9, 2.7.3.10, 2.7.4.1, 2.7.4.2, 2.7.4.3, 2.7.4.4, 2.7.4.5, 2.7.4.6, 2.7.4.7, 2.7.4.8, 2.7.4.9, 2.7.4.10, 2.7.5.1, 2.7.5.2, 2.7.5.3, 2.7.5.4, 2.7.5.5, 2.7.5.6, 2.7.5.7, 2.7.5.8, 2.7.5.9, 2.7.5.10, 2.7.6.1, 2.7.6.2, 2.7.6.3, 2.7.6.4, 2.7.6.5, 2.7.6.6, 2.7.6.7, 2.7.6.8, 2.7.6.9, 2.7.6.10, 2.7.7.1, 2.7.7.2, 2.7.7.3, 2.7.7.4, 2.7.7.5, 2.7.7.6, 2.7.7.7, 2.7.7.8, 2.7.7.9, 2.7.7.10, 2.7.8.1, 2.7.8.2, 2.7.8.3, 2.7.8.4, 2.7.8.5, 2.7.8.6, 2.7.8.7, 2.7.8.8, 2.7.8.9, 2.7.8.10, 2.7.9.1, 2.7.9.2, 2.7.9.3, 2.7.9.4, 2.7.9.5, 2.7.9.6, 2.7.9.7, 2.7.9.8, 2.7.9.9, 2.7.9.10, 2.7.10.1, 2.7.10.2, 2.7.10.3, 2.7.10.4, 2.7.10.5, 2.7.10.6, 2.7.10.7, 2.7.10.8, 2.7.10.9, 2.7.10.10, 2.8.1.1, 2.8.1.2, 2.8.1.3, 2.8.1.4, 2.8.1.5, 2.8.1.6, 2.8.1.7, 2.8.1.8, 2.8.1.9, 2.8.1.10, 2.8.2.1, 2.8.2.2, 2.8.2.3, 2.8.2.4, 2.8.2.5, 2.8.2.6, 2.8.2.7, 2.8.2.8, 2.8.2.9, 2.8.2.10, 2.8.3.1, 2.8.3.2, 2.8.3.3, 2.8.3.4, 2.8.3.5, 2.8.3.6, 2.8.3.7, 2.8.3.8, 2.8.3.9, 2.8.3.10, 2.8.4.1, 2.8.4.2, 2.8.4.3, 2.8.4.4, 2.8.4.5, 2.8.4.6, 2.8.4.7, 2.8.4.8, 2.8.4.9, 2.8.4.10, 2.8.5.1, 2.8.5.2, 2.8.5.3, 2.8.5.4, 2.8.5.5, 2.8.5.6, 2.8.5.7, 2.8.5.8, 2.8.5.9, 2.8.5.10, 2.8.6.1, 2.8.6.2, 2.8.6.3, 2.8.6.4, 2.8.6.5, 2.8.6.6, 2.8.6.7, 2.8.6.8, 2.8.6.9, 2.8.6.10, 2.8.7.1, 2.8.7.2, 2.8.7.3, 2.8.7.4, 2.8.7.5, 2.8.7.6, 2.8.7.7, 2.8.7.8, 2.8.7.9, 2.8.7.10, 2.8.8.1, 2.8.8.2, 2.8.8.3, 2.8.8.4, 2.8.8.5, 2.8.8.6, 2.8.8.7, 2.8.8.8, 2.8.8.9, 2.8.8.10, 2.8.9.1, 2.8.9.2, 2.8.9.3, 2.8.9.4, 2.8.9.5, 2.8.9.6, TABLE B-continued 2.8.9.7, 2.8.9.8, 2.8.9.9, 2.8.9.10, 2.8.10.1, 2.8.10.2, 2.8.10.3, 2.8.10.4, 2.8.10.5, 2.8.10.6, 2.8.10.7, 2.8.10.8, 2.8.10.9, 2.8.10.10, 2.9.1.1, 2.9.1.2, 2.9.1.3, 2.9.1.4, 2.9.1.5, 2.9.1.6, 2.9.1.7, 2.9.1.8, 2.9.1.9, 2.9.1.10, 2.9.2.1, 2.9.2.2, 2.9.2.3, 2.9.2.4, 2.9.2.5, 2.9.2.6, 2.9.2.7, 2.9.2.8, 2.9.2.9, 2.9.2.10, 2.9.3.1, 2.9.3.2, 2.9.3.3, 2.9.3.4, 2.9.3.5, 2.9.3.6, 2.9.3.7, 2.9.3.8, 2.9.3.9, 2.9.3.10, 2.9.4.1, 2.9.4.2, 2.9.4.3, 2.9.4.4, 2.9.4.5, 2.9.4.6, 2.9.4.7, 2.9.4.8, 2.9.4.9, 2.9.4.10, 2.9.5.1, 2.9.5.2, 2.9.5.3, 2.9.5.4, 2.9.5.5, 2.9.5.6, 2.9.5.7, 2.9.5.8, 2.9.5.9, 2.9.5.10, 2.9.6.1, 2.9.6.2, 2.9.6.3, 2.9.6.4, 2.9.6.5, 2.9.6.6, 2.9.6.7, 2.9.6.8, 2.9.6.9, 2.9.6.10, 2.9.7.1, 2.9.7.2, 2.9.7.3, 2.9.7.4, 2.9.7.5, 2.9.7.6, 2.9.7.7, 2.9.7.8, 2.9.7.9, 2.9.7.10, 2.9.8.1, 2.9.8.2, 2.9.8.3, 2.9.8.4, 2.9.8.5, 2.9.8.6, 2.9.8.7, 2.9.8.8, 2.9.8.9, 2.9.8.10, 2.9.9.1, 2.9.9.2, 2.9.9.3, 2.9.9.4, 2.9.9.5, 2.9.9.6, 2.9.9.7, 2.9.9.8, 2.9.9.9, 2.9.9.10, 2.9.10.1, 2.9.10.2, 2.9.10.3, 2.9.10.4, 2.9.10.5, 2.9.10.6, 2.9.10.7, 2.9.10.8, 2.9.10.9, 2.9.10.10, 2.10.1.1, 2.10.1.2, 2.10.1.3, 2.10.1.4, 2.10.1.5, 2.10.1.6, 2.10.1.7, 2.10.1.8, 2.10.1.9, 2.10.1.10, 2.10.2.1, 2.10.2.2, 2.10.2.3, 2.10.2.4, 2.10.2.5, 2.10.2.6, 2.10.2.7, 2.10.2.8, 2.10.2.9, 2.10.2.10, 2.10.3.1, 2.10.3.2, 2.10.3.3, 2.10.3.4, 2.10.3.5, 2.10.3.6, 2.10.3.7, 2.10.3.8, 2.10.3.9, 2.10.3.10, 2.10.4.1, 2.10.4.2, 2.10.4.3, 2.10.4.4, 2.10.4.5, 2.10.4.6, 2.10.4.7, 2.10.4.8, 2.10.4.9, 2.10.4.10, 2.10.5.1, 2.10.5.2, 2.10.5.3, 2.10.5.4, 2.10.5.5, 2.10.5.6, 2.10.5.7, 2.10.5.8, 2.10.5.9, 2.10.5.10, 2.10.6.1, 2.10.6.2, 2.10.6.3, 2.10.6.4, 2.10.6.5, 2.10.6.6, 2.10.6.7, 2.10.6.8, 2.10.6.9, 2.10.6.10, 2.10.7.1, 2.10.7.2, 2.10.7.3, 2.10.7.4, 2.10.7.5, 2.10.7.6, 2.10.7.7, 2.10.7.8, 2.10.7.9, 2.10.7.10, 2.10.8.1, 2.10.8.2, 2.10.8.3, 2.10.8.4, 2.10.8.5, 2.10.8.6, 2.10.8.7, 2.10.8.8, 2.10.8.9, 2.10.8.10, 2.10.9.1, 2.10.9.2, 2.10.9.3, 2.10.9.4, 2.10.9.5, 2.10.9.6, 2.10.9.7, 2.10.9.8, 2.10.9.9, 2.10.9.10, 2.10.10.1, 2.10.10.2, 2.10.10.3, 2.10.10.4, 2.10.10.5, 2.10.10.6, 2.10.10.7, 2.10.10.8, 2.10.10.9, 2.10.10.10, 3.1.1.1, 3.1.1.2, 3.1.1.3, 3.1.1.4, 3.1.1.5, 3.1.1.6, 3.1.1.7, 3.1.1.8, 3.1.1.9, 3.1.1.10, 3.1.2.1, 3.1.2.2, 3.1.2.3, 3.1.2.4, 3.1.2.5, 3.1.2.6, 3.1.2.7, 3.1.2.8, 3.1.2.9, 3.1.2.10, 3.1.3.1, 3.1.3.2, 3.1.3.3, 3.1.3.4, 3.1.3.5, 3.1.3.6, 3.1.3.7, 3.1.3.8, 3.1.3.9, 3.1.3.10, 3.1.4.1, 3.1.4.2, 3.1.4.3, 3.1.4.4, 3.1.4.5, 3.1.4.6, 3.1.4.7, 3.1.4.8, 3.1.4.9, 3.1.4.10, 3.1.5.1, 3.1.5.2, 3.1.5.3, 3.1.5.4, 3.1.5.5, 3.1.5.6, 3.1.5.7, 3.1.5.8, 3.1.5.9, 3.1.5.10, 3.1.6.1, 3.1.6.2, 3.1.6.3, 3.1.6.4, 3.1.6.5, 3.1.6.6, 3.1.6.7, 3.1.6.8, 3.1.6.9, 3.1.6.10, 3.1.7.1, 3.1.7.2, 3.1.7.3, 3.1.7.4, 3.1.7.5, 3.1.7.6, 3.1.7.7, 3.1.7.8, 3.1.7.9, 3.1.7.10, 3.1.8.1, 3.1.8.2, 3.1.8.3, 3.1.8.4, 3.1.8.5, 3.1.8.6, 3.1.8.7, 3.1.8.8, 3.1.8.9, 3.1.8.10, 3.1.9.1, 3.1.9.2, 3.1.9.3, 3.1.9.4, 3.1.9.5, 3.1.9.6, 3.1.9.7, 3.1.9.8, 3.1.9.9, 3.1.9.10, 3.1.10.1, 3.1.10.2, 3.1.10.3, 3.1.10.4, 3.1.10.5, 3.1.10.6, 3.1.10.7, 3.1.10.8, 3.1.10.9, 3.1.10.10, 3.2.1.1, 3.2.1.2, 3.2.1.3, 3.2.1.4, 3.2.1.5, 3.2.1.6, 3.2.1.7, 3.2.1.8, 3.2.1.9, 3.2.1.10, 3.2.2.1, 3.2.2.2, 3.2.2.3, 3.2.2.4, 3.2.2.5, 3.2.2.6, 3.2.2.7, 3.2.2.8, 3.2.2.9, 3.2.2.10, 3.2.3.1, 3.2.3.2, 3.2.3.3, 3.2.3.4, 3.2.3.5, 3.2.3.6, 3.2.3.7, 3.2.3.8, 3.2.3.9, 3.2.3.10, 3.2.4.1, 3.2.4.2, 3.2.4.3, 3.2.4.4, 3.2.4.5, 3.2.4.6, 3.2.4.7, 3.2.4.8, 3.2.4.9, 3.2.4.10, 3.2.5.1, 3.2.5.2, 3.2.5.3, 3.2.5.4, 3.2.5.5, 3.2.5.6, 3.2.5.7, 3.2.5.8, 3.2.5.9, 3.2.5.10, 3.2.6.1, 3.2.6.2, 3.2.6.3, 3.2.6.4, 3.2.6.5, 3.2.6.6, 3.2.6.7, 3.2.6.8, 3.2.6.9, 3.2.6.10, 3.2.7.1, 3.2.7.2, 3.2.7.3, 3.2.7.4, 3.2.7.5, 3.2.7.6, 3.2.7.7, 3.2.7.8, 3.2.7.9, 3.2.7.10, 3.2.8.1, 3.2.8.2, 3.2.8.3, 3.2.8.4, 3.2.8.5, 3.2.8.6, 3.2.8.7, 3.2.8.8, 3.2.8.9, 3.2.8.10, 3.2.9.1, 3.2.9.2, 3.2.9.3, 3.2.9.4, 3.2.9.5, 3.2.9.6, 3.2.9.7, 3.2.9.8, 3.2.9.9, 3.2.9.10, 3.2.10.1, 3.2.10.2, 3.2.10.3, 3.2.10.4, 3.2.10.5, 3.2.10.6, 3.2.10.7, 3.2.10.8, 3.2.10.9, 3.2.10.10, 3.3.1.1, 3.3.1.2, 3.3.1.3, 3.3.1.4, 3.3.1.5, 3.3.1.6, 3.3.1.7, 3.3.1.8, 3.3.1.9, 3.3.1.10, 3.3.2.1, 3.3.2.2, 3.3.2.3, 3.3.2.4, 3.3.2.5, 3.3.2.6, 3.3.2.7, 3.3.2.8, 3.3.2.9, 3.3.2.10, 3.3.3.1, 3.3.3.2, 3.3.3.3, 3.3.3.4, 3.3.3.5, 3.3.3.6, 3.3.3.7, 3.3.3.8, 3.3.3.9, 3.3.3.10, 3.3.4.1, 3.3.4.2, 3.3.4.3, 3.3.4.4, 3.3.4.5, 3.3.4.6, 3.3.4.7, 3.3.4.8, 3.3.4.9, 3.3.4.10, 3.3.5.1, 3.3.5.2, 3.3.5.3, 3.3.5.4, 3.3.5.5, 3.3.5.6, 3.3.5.7, 3.3.5.8, 3.3.5.9, 3.3.5.10, 3.3.6.1, 3.3.6.2, 3.3.6.3, 3.3.6.4, 3.3.6.5, 3.3.6.6, 3.3.6.7, 3.3.6.8, 3.3.6.9, 3.3.6.10, 3.3.7.1, 3.3.7.2, 3.3.7.3, 3.3.7.4, 3.3.7.5, 3.3.7.6, 3.3.7.7, 3.3.7.8, 3.3.7.9, 3.3.7.10, 3.3.8.1, 3.3.8.2, 3.3.8.3, 3.3.8.4, 3.3.8.5, 3.3.8.6, 3.3.8.7, 3.3.8.8, 3.3.8.9, 3.3.8.10, 3.3.9.1, 3.3.9.2, 3.3.9.3, 3.3.9.4, 3.3.9.5, 3.3.9.6, 3.3.9.7, 3.3.9.8, 3.3.9.9, 3.3.9.10, 3.3.10.1, 3.3.10.2, 3.3.10.3, 3.3.10.4, 3.3.10.5, 3.3.10.6, 3.3.10.7, 3.3.10.8, 3.3.10.9, 3.3.10.10, 3.4.1.1, 3.4.1.2, 3.4.1.3, 3.4.1.4, 3.4.1.5, 3.4.1.6, 3.4.1.7, 3.4.1.8, 3.4.1.9, 3.4.1.10, 3.4.2.1, 3.4.2.2, 3.4.2.3, 3.4.2.4, 3.4.2.5, 3.4.2.6, 3.4.2.7, 3.4.2.8, 3.4.2.9, 3.4.2.10, 3.4.3.1, 3.4.3.2, 3.4.3.3, 3.4.3.4, 3.4.3.5, 3.4.3.6, 3.4.3.7, 3.4.3.8, 3.4.3.9, 3.4.3.10, 3.4.4.1, 3.4.4.2, 3.4.4.3, 3.4.4.4, 3.4.4.5, 3.4.4.6, 3.4.4.7, 3.4.4.8, 3.4.4.9, 3.4.4.10, 3.4.5.1, 3.4.5.2, 3.4.5.3, 3.4.5.4, 3.4.5.5, 3.4.5.6, 3.4.5.7, 3.4.5.8, 3.4.5.9, 3.4.5.10, 3.4.6.1, 3.4.6.2, 3.4.6.3, 3.4.6.4, 3.4.6.5, 3.4.6.6, 3.4.6.7, 3.4.6.8, 3.4.6.9, 3.4.6.10, 3.4.7.1, 3.4.7.2, 3.4.7.3, 3.4.7.4, 3.4.7.5, 3.4.7.6, 3.4.7.7, 3.4.7.8, 3.4.7.9, 3.4.7.10, 3.4.8.1, 3.4.8.2, 3.4.8.3, 3.4.8.4, 3.4.8.5, 3.4.8.6, 3.4.8.7, 3.4.8.8, 3.4.8.9, 3.4.8.10, 3.4.9.1, 3.4.9.2, 3.4.9.3, 3.4.9.4, 3.4.9.5, 3.4.9.6, 3.4.9.7, 3.4.9.8, 3.4.9.9, 3.4.9.10, 3.4.10.1, 3.4.10.2, 3.4.10.3, 3.4.10.4, 3.4.10.5, 3.4.10.6, 3.4.10.7, 3.4.10.8, 3.4.10.9, 3.4.10.10, 3.5.1.1, 3.5.1.2, 3.5.1.3, 3.5.1.4, 3.5.1.5, 3.5.1.6, 3.5.1.7, 3.5.1.8, 3.5.1.9, 3.5.1.10, 3.5.2.1, 3.5.2.2, 3.5.2.3, 3.5.2.4, 3.5.2.5, 3.5.2.6, 3.5.2.7, 3.5.2.8, 3.5.2.9, 3.5.2.10, 3.5.3.1, 3.5.3.2, 3.5.3.3, 3.5.3.4, 3.5.3.5, 3.5.3.6, 3.5.3.7, 3.5.3.8, 3.5.3.9, 3.5.3.10, 3.5.4.1, 3.5.4.2, 3.5.4.3, 3.5.4.4, 3.5.4.5, 3.5.4.6, 3.5.4.7, 3.5.4.8, 3.5.4.9, 3.5.4.10, 3.5.5.1, 3.5.5.2, 3.5.5.3, 3.5.5.4, 3.5.5.5, 3.5.5.6, 3.5.5.7, 3.5.5.8, 3.5.5.9, 3.5.5.10, 3.5.6.1, 3.5.6.2, 3.5.6.3, 3.5.6.4, 3.5.6.5, 3.5.6.6, 3.5.6.7, 3.5.6.8, 3.5.6.9, 3.5.6.10, 3.5.7.1, 3.5.7.2, 3.5.7.3, 3.5.7.4, 3.5.7.5, 3.5.7.6, 3.5.7.7, 3.5.7.8, 3.5.7.9, 3.5.7.10, 3.5.8.1, 3.5.8.2, 3.5.8.3, 3.5.8.4, 3.5.8.5, 3.5.8.6, 3.5.8.7, 3.5.8.8, 3.5.8.9, 3.5.8.10, 3.5.9.1, 3.5.9.2, 3.5.9.3, 3.5.9.4, 3.5.9.5, 3.5.9.6, 3.5.9.7, 3.5.9.8, 3.5.9.9, 3.5.9.10, 3.5.10.1, 3.5.10.2, 3.5.10.3, 3.5.10.4, 3.5.10.5, 3.5.10.6, 3.5.10.7, 3.5.10.8, 3.5.10.9, 3.5.10.10, 3.6.1.1, 3.6.1.2, 3.6.1.3, 3.6.1.4, 3.6.1.5, 3.6.1.6, 3.6.1.7, 3.6.1.8, 3.6.1.9, 3.6.1.10, 3.6.2.1, 3.6.2.2, 3.6.2.3, 3.6.2.4, 3.6.2.5, 3.6.2.6, 3.6.2.7, 3.6.2.8, 3.6.2.9, 3.6.2.10, 3.6.3.1, 3.6.3.2, 3.6.3.3, 3.6.3.4, 3.6.3.5, 3.6.3.6, 3.6.3.7, 3.6.3.8, 3.6.3.9, 3.6.3.10, 3.6.4.1, 3.6.4.2, 3.6.4.3, 3.6.4.4, 3.6.4.5, 3.6.4.6, 3.6.4.7, 3.6.4.8, 3.6.4.9, 3.6.4.10, 3.6.5.1, 3.6.5.2, 3.6.5.3, 3.6.5.4, 3.6.5.5, 3.6.5.6, 3.6.5.7, 3.6.5.8, 3.6.5.9, 3.6.5.10, 3.6.6.1, 3.6.6.2, 3.6.6.3, 3.6.6.4, 3.6.6.5, 3.6.6.6, 3.6.6.7, 3.6.6.8, 3.6.6.9, 3.6.6.10, 3.6.7.1, 3.6.7.2, 3.6.7.3, 3.6.7.4, 3.6.7.5, 3.6.7.6, 3.6.7.7, 3.6.7.8, 3.6.7.9, 3.6.7.10, 3.6.8.1, 3.6.8.2, 3.6.8.3, 3.6.8.4, 3.6.8.5, 3.6.8.6, 3.6.8.7, 3.6.8.8, 3.6.8.9, 3.6.8.10, 3.6.9.1, 3.6.9.2, 3.6.9.3, 3.6.9.4, 3.6.9.5, 3.6.9.6, 3.6.9.7, 3.6.9.8, 3.6.9.9, 3.6.9.10, 3.6.10.1, 3.6.10.2, 3.6.10.3, 3.6.10.4, 3.6.10.5, 3.6.10.6, 3.6.10.7, 3.6.10.8, 3.6.10.9, 3.6.10.10, 3.7.1.1, 3.7.1.2, 3.7.1.3, 3.7.1.4, 3.7.1.5, 3.7.1.6, 3.7.1.7, 3.7.1.8, 3.7.1.9, 3.7.1.10, 3.7.2.1, 3.7.2.2, 3.7.2.3, 3.7.2.4, 3.7.2.5, 3.7.2.6, 3.7.2.7, 3.7.2.8, 3.7.2.9, 3.7.2.10, 3.7.3.1, 3.7.3.2, 3.7.3.3, 3.7.3.4, 3.7.3.5, 3.7.3.6, 3.7.3.7, 3.7.3.8, 3.7.3.9, 3.7.3.10, 3.7.4.1, 3.7.4.2, 3.7.4.3, 3.7.4.4, 3.7.4.5, 3.7.4.6, 3.7.4.7, 3.7.4.8, 3.7.4.9, 3.7.4.10, 3.7.5.1, 3.7.5.2, 3.7.5.3, 3.7.5.4, 3.7.5.5, 3.7.5.6, 3.7.5.7, 3.7.5.8, 3.7.5.9, 3.7.5.10, 3.7.6.1, 3.7.6.2, 3.7.6.3, 3.7.6.4, 3.7.6.5, 3.7.6.6, 3.7.6.7, 3.7.6.8, 3.7.6.9, 3.7.6.10, 3.7.7.1, 3.7.7.2, 3.7.7.3, 3.7.7.4, 3.7.7.5, 3.7.7.6, 3.7.7.7, 3.7.7.8, 3.7.7.9, 3.7.7.10, 3.7.8.1, 3.7.8.2, 3.7.8.3, 3.7.8.4, 3.7.8.5, 3.7.8.6, 3.7.8.7, 3.7.8.8, 3.7.8.9, 3.7.8.10, 3.7.9.1, 3.7.9.2, 3.7.9.3, 3.7.9.4, 3.7.9.5, 3.7.9.6, 3.7.9.7, 3.7.9.8, 3.7.9.9, 3.7.9.10, 3.7.10.1, 3.7.10.2, 3.7.10.3, 3.7.10.4, 3.7.10.5, 3.7.10.6, 3.7.10.7, 3.7.10.8, 3.7.10.9, 3.7.10.10, 3.8.1.1, 3.8.1.2, 3.8.1.3, 3.8.1.4, 3.8.1.5, 3.8.1.6, 3.8.1.7, 3.8.1.8, 3.8.1.9, 3.8.1.10, 3.8.2.1, 3.8.2.2, 3.8.2.3, 3.8.2.4, 3.8.2.5, 3.8.2.6, 3.8.2.7, 3.8.2.8, 3.8.2.9, 3.8.2.10, 3.8.3.1, 3.8.3.2, 3.8.3.3, 3.8.3.4, 3.8.3.5, 3.8.3.6, TABLE B-continued 3.8.3.7, 3.8.3.8, 3.8.3.9, 3.8.3.10, 3.8.4.1, 3.8.4.2, 3.8.4.3, 3.8.4.4, 3.8.4.5, 3.8.4.6, 3.8.4.7, 3.8.4.8, 3.8.4.9, 3.8.4.10, 3.8.5.1, 3.8.5.2, 3.8.5.3, 3.8.5.4, 3.8.5.5, 3.8.5.6, 3.8.5.7, 3.8.5.8, 3.8.5.9, 3.8.5.10, 3.8.6.1, 3.8.6.2, 3.8.6.3, 3.8.6.4, 3.8.6.5, 3.8.6.6, 3.8.6.7, 3.8.6.8, 3.8.6.9, 3.8.6.10, 3.8.7.1, 3.8.7.2, 3.8.7.3, 3.8.7.4, 3.8.7.5, 3.8.7.6, 3.8.7.7, 3.8.7.8, 3.8.7.9, 3.8.7.10, 3.8.8.1, 3.8.8.2, 3.8.8.3, 3.8.8.4, 3.8.8.5, 3.8.8.6, 3.8.8.7, 3.8.8.8, 3.8.8.9, 3.8.8.10, 3.8.9.1, 3.8.9.2, 3.8.9.3, 3.8.9.4, 3.8.9.5, 3.8.9.6, 3.8.9.7, 3.8.9.8, 3.8.9.9, 3.8.9.10, 3.8.10.1, 3.8.10.2, 3.8.10.3, 3.8.10.4, 3.8.10.5, 3.8.10.6, 3.8.10.7, 3.8.10.8, 3.8.10.9, 3.8.10.10, 3.9.1.1, 3.9.1.2, 3.9.1.3, 3.9.1.4, 3.9.1.5, 3.9.1.6, 3.9.1.7, 3.9.1.8, 3.9.1.9, 3.9.1.10, 3.9.2.1, 3.9.2.2, 3.9.2.3, 3.9.2.4, 3.9.2.5, 3.9.2.6, 3.9.2.7, 3.9.2.8, 3.9.2.9, 3.9.2.10, 3.9.3.1, 3.9.3.2, 3.9.3.3, 3.9.3.4, 3.9.3.5, 3.9.3.6, 3.9.3.7, 3.9.3.8, 3.9.3.9, 3.9.3.10, 3.9.4.1, 3.9.4.2, 3.9.4.3, 3.9.4.4, 3.9.4.5, 3.9.4.6, 3.9.4.7, 3.9.4.8, 3.9.4.9, 3.9.4.10, 3.9.5.1, 3.9.5.2, 3.9.5.3, 3.9.5.4, 3.9.5.5, 3.9.5.6, 3.9.5.7, 3.9.5.8, 3.9.5.9, 3.9.5.10, 3.9.6.1, 3.9.6.2, 3.9.6.3, 3.9.6.4, 3.9.6.5, 3.9.6.6, 3.9.6.7, 3.9.6.8, 3.9.6.9, 3.9.6.10, 3.9.7.1, 3.9.7.2, 3.9.7.3, 3.9.7.4, 3.9.7.5, 3.9.7.6, 3.9.7.7, 3.9.7.8, 3.9.7.9, 3.9.7.10, 3.9.8.1, 3.9.8.2, 3.9.8.3, 3.9.8.4, 3.9.8.5, 3.9.8.6, 3.9.8.7, 3.9.8.8, 3.9.8.9, 3.9.8.10, 3.9.9.1, 3.9.9.2, 3.9.9.3, 3.9.9.4, 3.9.9.5, 3.9.9.6, 3.9.9.7, 3.9.9.8, 3.9.9.9, 3.9.9.10, 3.9.10.1, 3.9.10.2, 3.9.10.3, 3.9.10.4, 3.9.10.5, 3.9.10.6, 3.9.10.7, 3.9.10.8, 3.9.10.9, 3.9.10.10, 3.10.1.1, 3.10.1.2, 3.10.1.3, 3.10.1.4, 3.10.1.5, 3.10.1.6, 3.10.1.7, 3.10.1.8, 3.10.1.9, 3.10.1.10, 3.10.2.1, 3.10.2.2, 3.10.2.3, 3.10.2.4, 3.10.2.5, 3.10.2.6, 3.10.2.7, 3.10.2.8, 3.10.2.9, 3.10.2.10, 3.10.3.1, 3.10.3.2, 3.10.3.3, 3.10.3.4, 3.10.3.5, 3.10.3.6, 3.10.3.7, 3.10.3.8, 3.10.3.9, 3.10.3.10, 3.10.4.1, 3.10.4.2, 3.10.4.3, 3.10.4.4, 3.10.4.5, 3.10.4.6, 3.10.4.7, 3.10.4.8, 3.10.4.9, 3.10.4.10, 3.10.5.1, 3.10.5.2, 3.10.5.3, 3.10.5.4, 3.10.5.5, 3.10.5.6, 3.10.5.7, 3.10.5.8, 3.10.5.9, 3.10.5.10, 3.10.6.1, 3.10.6.2, 3.10.6.3, 3.10.6.4, 3.10.6.5, 3.10.6.6, 3.10.6.7, 3.10.6.8, 3.10.6.9, 3.10.6.10, 3.10.7.1, 3.10.7.2, 3.10.7.3, 3.10.7.4, 3.10.7.5, 3.10.7.6, 3.10.7.7, 3.10.7.8, 3.10.7.9, 3.10.7.10, 3.10.8.1, 3.10.8.2, 3.10.8.3, 3.10.8.4, 3.10.8.5, 3.10.8.6, 3.10.8.7, 3.10.8.8, 3.10.8.9, 3.10.8.10, 3.10.9.1, 3.10.9.2, 3.10.9.3, 3.10.9.4, 3.10.9.5, 3.10.9.6, 3.10.9.7, 3.10.9.8, 3.10.9.9, 3.10.9.10, 3.10.10.1, 3.10.10.2, 3.10.10.3, 3.10.10.4, 3.10.10.5, 3.10.10.6, 3.10.10.7, 3.10.10.8, 3.10.10.9, 3.10.10.10, 4.1.1.1, 4.1.1.2, 4.1.1.3, 4.1.1.4, 4.1.1.5, 4.1.1.6, 4.1.1.7, 4.1.1.8, 4.1.1.9, 4.1.1.10, 4.1.2.1, 4.1.2.2, 4.1.2.3, 4.1.2.4, 4.1.2.5, 4.1.2.6, 4.1.2.7, 4.1.2.8, 4.1.2.9, 4.1.2.10, 4.1.3.1, 4.1.3.2, 4.1.3.3, 4.1.3.4, 4.1.3.5, 4.1.3.6, 4.1.3.7, 4.1.3.8, 4.1.3.9, 4.1.3.10, 4.1.4.1, 4.1.4.2, 4.1.4.3, 4.1.4.4, 4.1.4.5, 4.1.4.6, 4.1.4.7, 4.1.4.8, 4.1.4.9, 4.1.4.10, 4.1.5.1, 4.1.5.2, 4.1.5.3, 4.1.5.4, 4.1.5.5, 4.1.5.6, 4.1.5.7, 4.1.5.8, 4.1.5.9, 4.1.5.10, 4.1.6.1, 4.1.6.2, 4.1.6.3, 4.1.6.4, 4.1.6.5, 4.1.6.6, 4.1.6.7, 4.1.6.8, 4.1.6.9, 4.1.6.10, 4.1.7.1, 4.1.7.2, 4.1.7.3, 4.1.7.4, 4.1.7.5, 4.1.7.6, 4.1.7.7, 4.1.7.8, 4.1.7.9, 4.1.7.10, 4.1.8.1, 4.1.8.2, 4.1.8.3, 4.1.8.4, 4.1.8.5, 4.1.8.6, 4.1.8.7, 4.1.8.8, 4.1.8.9, 4.1.8.10, 4.1.9.1, 4.1.9.2, 4.1.9.3, 4.1.9.4, 4.1.9.5, 4.1.9.6, 4.1.9.7, 4.1.9.8, 4.1.9.9, 4.1.9.10, 4.1.10.1, 4.1.10.2, 4.1.10.3, 4.1.10.4, 4.1.10.5, 4.1.10.6, 4.1.10.7, 4.1.10.8, 4.1.10.9, 4.1.10.10, 4.2.1.1, 4.2.1.2, 4.2.1.3, 4.2.1.4, 4.2.1.5, 4.2.1.6, 4.2.1.7, 4.2.1.8, 4.2.1.9, 4.2.1.10, 4.2.2.1, 4.2.2.2, 4.2.2.3, 4.2.2.4, 4.2.2.5, 4.2.2.6, 4.2.2.7, 4.2.2.8, 4.2.2.9, 4.2.2.10, 4.2.3.1, 4.2.3.2, 4.2.3.3, 4.2.3.4, 4.2.3.5, 4.2.3.6, 4.2.3.7, 4.2.3.8, 4.2.3.9, 4.2.3.10, 4.2.4.1, 4.2.4.2, 4.2.4.3, 4.2.4.4, 4.2.4.5, 4.2.4.6, 4.2.4.7, 4.2.4.8, 4.2.4.9, 4.2.4.10, 4.2.5.1, 4.2.5.2, 4.2.5.3, 4.2.5.4, 4.2.5.5, 4.2.5.6, 4.2.5.7, 4.2.5.8, 4.2.5.9, 4.2.5.10, 4.2.6.1, 4.2.6.2, 4.2.6.3, 4.2.6.4, 4.2.6.5, 4.2.6.6, 4.2.6.7, 4.2.6.8, 4.2.6.9, 4.2.6.10, 4.2.7.1, 4.2.7.2, 4.2.7.3, 4.2.7.4, 4.2.7.5, 4.2.7.6, 4.2.7.7, 4.2.7.8, 4.2.7.9, 4.2.7.10, 4.2.8.1, 4.2.8.2, 4.2.8.3, 4.2.8.4, 4.2.8.5, 4.2.8.6, 4.2.8.7, 4.2.8.8, 4.2.8.9, 4.2.8.10, 4.2.9.1, 4.2.9.2, 4.2.9.3, 4.2.9.4, 4.2.9.5, 4.2.9.6, 4.2.9.7, 4.2.9.8, 4.2.9.9, 4.2.9.10, 4.2.10.1, 4.2.10.2, 4.2.10.3, 4.2.10.4, 4.2.10.5, 4.2.10.6, 4.2.10.7, 4.2.10.8, 4.2.10.9, 4.2.10.10, 4.3.1.1, 4.3.1.2, 4.3.1.3, 4.3.1.4, 4.3.1.5, 4.3.1.6, 4.3.1.7, 4.3.1.8, 4.3.1.9, 4.3.1.10, 4.3.2.1, 4.3.2.2, 4.3.2.3, 4.3.2.4, 4.3.2.5, 4.3.2.6, 4.3.2.7, 4.3.2.8, 4.3.2.9, 4.3.2.10, 4.3.3.1, 4.3.3.2, 4.3.3.3, 4.3.3.4, 4.3.3.5, 4.3.3.6, 4.3.3.7, 4.3.3.8, 4.3.3.9, 4.3.3.10, 4.3.4.1, 4.3.4.2, 4.3.4.3, 4.3.4.4, 4.3.4.5, 4.3.4.6, 4.3.4.7, 4.3.4.8, 4.3.4.9, 4.3.4.10, 4.3.5.1, 4.3.5.2, 4.3.5.3, 4.3.5.4, 4.3.5.5, 4.3.5.6, 4.3.5.7, 4.3.5.8, 4.3.5.9, 4.3.5.10, 4.3.6.1, 4.3.6.2, 4.3.6.3, 4.3.6.4, 4.3.6.5, 4.3.6.6, 4.3.6.7, 4.3.6.8, 4.3.6.9, 4.3.6.10, 4.3.7.1, 4.3.7.2, 4.3.7.3, 4.3.7.4, 4.3.7.5, 4.3.7.6, 4.3.7.7, 4.3.7.8, 4.3.7.9, 4.3.7.10, 4.3.8.1, 4.3.8.2, 4.3.8.3, 4.3.8.4, 4.3.8.5, 4.3.8.6, 4.3.8.7, 4.3.8.8, 4.3.8.9, 4.3.8.10, 4.3.9.1, 4.3.9.2, 4.3.9.3, 4.3.9.4, 4.3.9.5, 4.3.9.6, 4.3.9.7, 4.3.9.8, 4.3.9.9, 4.3.9.10, 4.3.10.1, 4.3.10.2, 4.3.10.3, 4.3.10.4, 4.3.10.5, 4.3.10.6, 4.3.10.7, 4.3.10.8, 4.3.10.9, 4.3.10.10, 4.4.1.1, 4.4.1.2, 4.4.1.3, 4.4.1.4, 4.4.1.5, 4.4.1.6, 4.4.1.7, 4.4.1.8, 4.4.1.9, 4.4.1.10, 4.4.2.1, 4.4.2.2, 4.4.2.3, 4.4.2.4, 4.4.2.5, 4.4.2.6, 4.4.2.7, 4.4.2.8, 4.4.2.9, 4.4.2.10, 4.4.3.1, 4.4.3.2, 4.4.3.3, 4.4.3.4, 4.4.3.5, 4.4.3.6, 4.4.3.7, 4.4.3.8, 4.4.3.9, 4.4.3.10, 4.4.4.1, 4.4.4.2, 4.4.4.3, 4.4.4.4, 4.4.4.5, 4.4.4.6, 4.4.4.7, 4.4.4.8, 4.4.4.9, 4.4.4.10, 4.4.5.1, 4.4.5.2, 4.4.5.3, 4.4.5.4, 4.4.5.5, 4.4.5.6, 4.4.5.7, 4.4.5.8, 4.4.5.9, 4.4.5.10, 4.4.6.1, 4.4.6.2, 4.4.6.3, 4.4.6.4, 4.4.6.5, 4.4.6.6, 4.4.6.7, 4.4.6.8, 4.4.6.9, 4.4.6.10, 4.4.7.1, 4.4.7.2, 4.4.7.3, 4.4.7.4, 4.4.7.5, 4.4.7.6, 4.4.7.7, 4.4.7.8, 4.4.7.9, 4.4.7.10, 4.4.8.1, 4.4.8.2, 4.4.8.3, 4.4.8.4, 4.4.8.5, 4.4.8.6, 4.4.8.7, 4.4.8.8, 4.4.8.9, 4.4.8.10, 4.4.9.1, 4.4.9.2, 4.4.9.3, 4.4.9.4, 4.4.9.5, 4.4.9.6, 4.4.9.7, 4.4.9.8, 4.4.9.9, 4.4.9.10, 4.4.10.1, 4.4.10.2, 4.4.10.3, 4.4.10.4, 4.4.10.5, 4.4.10.6, 4.4.10.7, 4.4.10.8, 4.4.10.9, 4.4.10.10, 4.5.1.1, 4.5.1.2, 4.5.1.3, 4.5.1.4, 4.5.1.5, 4.5.1.6, 4.5.1.7, 4.5.1.8, 4.5.1.9, 4.5.1.10, 4.5.2.1, 4.5.2.2, 4.5.2.3, 4.5.2.4, 4.5.2.5, 4.5.2.6, 4.5.2.7, 4.5.2.8, 4.5.2.9, 4.5.2.10, 4.5.3.1, 4.5.3.2, 4.5.3.3, 4.5.3.4, 4.5.3.5, 4.5.3.6, 4.5.3.7, 4.5.3.8, 4.5.3.9, 4.5.3.10, 4.5.4.1, 4.5.4.2, 4.5.4.3, 4.5.4.4, 4.5.4.5, 4.5.4.6, 4.5.4.7, 4.5.4.8, 4.5.4.9, 4.5.4.10, 4.5.5.1, 4.5.5.2, 4.5.5.3, 4.5.5.4, 4.5.5.5, 4.5.5.6, 4.5.5.7, 4.5.5.8, 4.5.5.9, 4.5.5.10, 4.5.6.1, 4.5.6.2, 4.5.6.3, 4.5.6.4, 4.5.6.5, 4.5.6.6, 4.5.6.7, 4.5.6.8, 4.5.6.9, 4.5.6.10, 4.5.7.1, 4.5.7.2, 4.5.7.3, 4.5.7.4, 4.5.7.5, 4.5.7.6, 4.5.7.7, 4.5.7.8, 4.5.7.9, 4.5.7.10, 4.5.8.1, 4.5.8.2, 4.5.8.3, 4.5.8.4, 4.5.8.5, 4.5.8.6, 4.5.8.7, 4.5.8.8, 4.5.8.9, 4.5.8.10, 4.5.9.1, 4.5.9.2, 4.5.9.3, 4.5.9.4, 4.5.9.5, 4.5.9.6, 4.5.9.7, 4.5.9.8, 4.5.9.9, 4.5.9.10, 4.5.10.1, 4.5.10.2, 4.5.10.3, 4.5.10.4, 4.5.10.5, 4.5.10.6, 4.5.10.7, 4.5.10.8, 4.5.10.9, 4.5.10.10, 4.6.1.1, 4.6.1.2, 4.6.1.3, 4.6.1.4, 4.6.1.5, 4.6.1.6, 4.6.1.7, 4.6.1.8, 4.6.1.9, 4.6.1.10, 4.6.2.1, 4.6.2.2, 4.6.2.3, 4.6.2.4, 4.6.2.5, 4.6.2.6, 4.6.2.7, 4.6.2.8, 4.6.2.9, 4.6.2.10, 4.6.3.1, 4.6.3.2, 4.6.3.3, 4.6.3.4, 4.6.3.5, 4.6.3.6, 4.6.3.7, 4.6.3.8, 4.6.3.9, 4.6.3.10, 4.6.4.1, 4.6.4.2, 4.6.4.3, 4.6.4.4, 4.6.4.5, 4.6.4.6, 4.6.4.7, 4.6.4.8, 4.6.4.9, 4.6.4.10, 4.6.5.1, 4.6.5.2, 4.6.5.3, 4.6.5.4, 4.6.5.5, 4.6.5.6, 4.6.5.7, 4.6.5.8, 4.6.5.9, 4.6.5.10, 4.6.6.1, 4.6.6.2, 4.6.6.3, 4.6.6.4, 4.6.6.5, 4.6.6.6, 4.6.6.7, 4.6.6.8, 4.6.6.9, 4.6.6.10, 4.6.7.1, 4.6.7.2, 4.6.7.3, 4.6.7.4, 4.6.7.5, 4.6.7.6, 4.6.7.7, 4.6.7.8, 4.6.7.9, 4.6.7.10, 4.6.8.1, 4.6.8.2, 4.6.8.3, 4.6.8.4, 4.6.8.5, 4.6.8.6, 4.6.8.7, 4.6.8.8, 4.6.8.9, 4.6.8.10, 4.6.9.1, 4.6.9.2, 4.6.9.3, 4.6.9.4, 4.6.9.5, 4.6.9.6, 4.6.9.7, 4.6.9.8, 4.6.9.9, 4.6.9.10, 4.6.10.1, 4.6.10.2, 4.6.10.3, 4.6.10.4, 4.6.10.5, 4.6.10.6, 4.6.10.7, 4.6.10.8, 4.6.10.9, 4.6.10.10, 4.7.1.1, 4.7.1.2, 4.7.1.3, 4.7.1.4, 4.7.1.5, 4.7.1.6, 4.7.1.7, 4.7.1.8, 4.7.1.9, 4.7.1.10, 4.7.2.1, 4.7.2.2, 4.7.2.3, 4.7.2.4, 4.7.2.5, 4.7.2.6, 4.7.2.7, 4.7.2.8, 4.7.2.9, 4.7.2.10, 4.7.3.1, 4.7.3.2, 4.7.3.3, 4.7.3.4, 4.7.3.5, 4.7.3.6, 4.7.3.7, 4.7.3.8, 4.7.3.9, 4.7.3.10, 4.7.4.1, 4.7.4.2, 4.7.4.3, 4.7.4.4, 4.7.4.5, 4.7.4.6, 4.7.4.7, 4.7.4.8, 4.7.4.9, 4.7.4.10, 4.7.5.1, 4.7.5.2, 4.7.5.3, 4.7.5.4, 4.7.5.5, 4.7.5.6, 4.7.5.7, 4.7.5.8, 4.7.5.9, 4.7.5.10, 4.7.6.1, 4.7.6.2, 4.7.6.3, 4.7.6.4, 4.7.6.5, 4.7.6.6, 4.7.6.7, 4.7.6.8, 4.7.6.9, 4.7.6.10, 4.7.7.1, 4.7.7.2, 4.7.7.3, 4.7.7.4, 4.7.7.5, 4.7.7.6, 4.7.7.7, TABLE B-continued 4.7.7.8, 4.7.7.9, 4.7.7.10, 4.7.8.1, 4.7.8.2, 4.7.8.3, 4.7.8.4, 4.7.8.5, 4.7.8.6, 4.7.8.7, 4.7.8.8, 4.7.8.9, 4.7.8.10, 4.7.9.1, 4.7.9.2, 4.7.9.3, 4.7.9.4, 4.7.9.5, 4.7.9.6, 4.7.9.7, 4.7.9.8, 4.7.9.9, 4.7.9.10, 4.7.10.1, 4.7.10.2, 4.7.10.3, 4.7.10.4, 4.7.10.5, 4.7.10.6, 4.7.10.7, 4.7.10.8, 4.7.10.9, 4.7.10.10, 4.8.1.1, 4.8.1.2, 4.8.1.3, 4.8.1.4, 4.8.1.5, 4.8.1.6, 4.8.1.7, 4.8.1.8, 4.8.1.9, 4.8.1.10, 4.8.2.1, 4.8.2.2, 4.8.2.3, 4.8.2.4, 4.8.2.5, 4.8.2.6, 4.8.2.7, 4.8.2.8, 4.8.2.9, 4.8.2.10, 4.8.3.1, 4.8.3.2, 4.8.3.3, 4.8.3.4, 4.8.3.5, 4.8.3.6, 4.8.3.7, 4.8.3.8, 4.8.3.9, 4.8.3.10, 4.8.4.1, 4.8.4.2, 4.8.4.3, 4.8.4.4, 4.8.4.5, 4.8.4.6, 4.8.4.7, 4.8.4.8, 4.8.4.9, 4.8.4.10, 4.8.5.1, 4.8.5.2, 4.8.5.3, 4.8.5.4, 4.8.5.5, 4.8.5.6, 4.8.5.7, 4.8.5.8, 4.8.5.9, 4.8.5.10, 4.8.6.1, 4.8.6.2, 4.8.6.3, 4.8.6.4, 4.8.6.5, 4.8.6.6, 4.8.6.7, 4.8.6.8, 4.8.6.9, 4.8.6.10, 4.8.7.1, 4.8.7.2, 4.8.7.3, 4.8.7.4, 4.8.7.5, 4.8.7.6, 4.8.7.7, 4.8.7.8, 4.8.7.9, 4.8.7.10, 4.8.8.1, 4.8.8.2, 4.8.8.3, 4.8.8.4, 4.8.8.5, 4.8.8.6, 4.8.8.7, 4.8.8.8, 4.8.8.9, 4.8.8.10, 4.8.9.1, 4.8.9.2, 4.8.9.3, 4.8.9.4, 4.8.9.5, 4.8.9.6, 4.8.9.7, 4.8.9.8, 4.8.9.9, 4.8.9.10, 4.8.10.1, 4.8.10.2, 4.8.10.3, 4.8.10.4, 4.8.10.5, 4.8.10.6, 4.8.10.7, 4.8.10.8, 4.8.10.9, 4.8.10.10, 4.9.1.1, 4.9.1.2, 4.9.1.3, 4.9.1.4, 4.9.1.5, 4.9.1.6, 4.9.1.7, 4.9.1.8, 4.9.1.9, 4.9.1.10, 4.9.2.1, 4.9.2.2, 4.9.2.3, 4.9.2.4, 4.9.2.5, 4.9.2.6, 4.9.2.7, 4.9.2.8, 4.9.2.9, 4.9.2.10, 4.9.3.1, 4.9.3.2, 4.9.3.3, 4.9.3.4, 4.9.3.5, 4.9.3.6, 4.9.3.7, 4.9.3.8, 4.9.3.9, 4.9.3.10, 4.9.4.1, 4.9.4.2, 4.9.4.3, 4.9.4.4, 4.9.4.5, 4.9.4.6, 4.9.4.7, 4.9.4.8, 4.9.4.9, 4.9.4.10, 4.9.5.1, 4.9.5.2, 4.9.5.3, 4.9.5.4, 4.9.5.5, 4.9.5.6, 4.9.5.7, 4.9.5.8, 4.9.5.9, 4.9.5.10, 4.9.6.1, 4.9.6.2, 4.9.6.3, 4.9.6.4, 4.9.6.5, 4.9.6.6, 4.9.6.7, 4.9.6.8, 4.9.6.9, 4.9.6.10, 4.9.7.1, 4.9.7.2, 4.9.7.3, 4.9.7.4, 4.9.7.5, 4.9.7.6, 4.9.7.7, 4.9.7.8, 4.9.7.9, 4.9.7.10, 4.9.8.1, 4.9.8.2, 4.9.8.3, 4.9.8.4, 4.9.8.5, 4.9.8.6, 4.9.8.7, 4.9.8.8, 4.9.8.9, 4.9.8.10, 4.9.9.1, 4.9.9.2, 4.9.9.3, 4.9.9.4, 4.9.9.5, 4.9.9.6, 4.9.9.7, 4.9.9.8, 4.9.9.9, 4.9.9.10, 4.9.10.1, 4.9.10.2, 4.9.10.3, 4.9.10.4, 4.9.10.5, 4.9.10.6, 4.9.10.7, 4.9.10.8, 4.9.10.9, 4.9.10.10, 4.10.1.1, 4.10.1.2, 4.10.1.3, 4.10.1.4, 4.10.1.5, 4.10.1.6, 4.10.1.7, 4.10.1.8, 4.10.1.9, 4.10.1.10, 4.10.2.1, 4.10.2.2, 4.10.2.3, 4.10.2.4, 4.10.2.5, 4.10.2.6, 4.10.2.7, 4.10.2.8, 4.10.2.9, 4.10.2.10, 4.10.3.1, 4.10.3.2, 4.10.3.3, 4.10.3.4, 4.10.3.5, 4.10.3.6, 4.10.3.7, 4.10.3.8, 4.10.3.9, 4.10.3.10, 4.10.4.1, 4.10.4.2, 4.10.4.3, 4.10.4.4, 4.10.4.5, 4.10.4.6, 4.10.4.7, 4.10.4.8, 4.10.4.9, 4.10.4.10, 4.10.5.1, 4.10.5.2, 4.10.5.3, 4.10.5.4, 4.10.5.5, 4.10.5.6, 4.10.5.7, 4.10.5.8, 4.10.5.9, 4.10.5.10, 4.10.6.1, 4.10.6.2, 4.10.6.3, 4.10.6.4, 4.10.6.5, 4.10.6.6, 4.10.6.7, 4.10.6.8, 4.10.6.9, 4.10.6.10, 4.10.7.1, 4.10.7.2, 4.10.7.3, 4.10.7.4, 4.10.7.5, 4.10.7.6, 4.10.7.7, 4.10.7.8, 4.10.7.9, 4.10.7.10, 4.10.8.1, 4.10.8.2, 4.10.8.3, 4.10.8.4, 4.10.8.5, 4.10.8.6, 4.10.8.7, 4.10.8.8, 4.10.8.9, 4.10.8.10, 4.10.9.1, 4.10.9.2, 4.10.9.3, 4.10.9.4, 4.10.9.5, 4.10.9.6, 4.10.9.7, 4.10.9.8, 4.10.9.9, 4.10.9.10, 4.10.10.1, 4.10.10.2, 4.10.10.3, 4.10.10.4, 4.10.10.5, 4.10.10.6, 4.10.10.7, 4.10.10.8, 4.10.10.9, 4.10.10.10, 5.1.1.1, 5.1.1.2, 5.1.1.3, 5.1.1.4, 5.1.1.5, 5.1.1.6, 5.1.1.7, 5.1.1.8, 5.1.1.9, 5.1.1.10, 5.1.2.1, 5.1.2.2, 5.1.2.3, 5.1.2.4, 5.1.2.5, 5.1.2.6, 5.1.2.7, 5.1.2.8, 5.1.2.9, 5.1.2.10, 5.1.3.1, 5.1.3.2, 5.1.3.3, 5.1.3.4, 5.1.3.5, 5.1.3.6, 5.1.3.7, 5.1.3.8, 5.1.3.9, 5.1.3.10, 5.1.4.1, 5.1.4.2, 5.1.4.3, 5.1.4.4, 5.1.4.5, 5.1.4.6, 5.1.4.7, 5.1.4.8, 5.1.4.9, 5.1.4.10, 5.1.5.1, 5.1.5.2, 5.1.5.3, 5.1.5.4, 5.1.5.5, 5.1.5.6, 5.1.5.7, 5.1.5.8, 5.1.5.9, 5.1.5.10, 5.1.6.1, 5.1.6.2, 5.1.6.3, 5.1.6.4, 5.1.6.5, 5.1.6.6, 5.1.6.7, 5.1.6.8, 5.1.6.9, 5.1.6.10, 5.1.7.1, 5.1.7.2, 5.1.7.3, 5.1.7.4, 5.1.7.5, 5.1.7.6, 5.1.7.7, 5.1.7.8, 5.1.7.9, 5.1.7.10, 5.1.8.1, 5.1.8.2, 5.1.8.3, 5.1.8.4, 5.1.8.5, 5.1.8.6, 5.1.8.7, 5.1.8.8, 5.1.8.9, 5.1.8.10, 5.1.9.1, 5.1.9.2, 5.1.9.3, 5.1.9.4, 5.1.9.5, 5.1.9.6, 5.1.9.7, 5.1.9.8, 5.1.9.9, 5.1.9.10, 5.1.10.1, 5.1.10.2, 5.1.10.3, 5.1.10.4, 5.1.10.5, 5.1.10.6, 5.1.10.7, 5.1.10.8, 5.1.10.9, 5.1.10.10, 5.2.1.1, 5.2.1.2, 5.2.1.3, 5.2.1.4, 5.2.1.5, 5.2.1.6, 5.2.1.7, 5.2.1.8, 5.2.1.9, 5.2.1.10, 5.2.2.1, 5.2.2.2, 5.2.2.3, 5.2.2.4, 5.2.2.5, 5.2.2.6, 5.2.2.7, 5.2.2.8, 5.2.2.9, 5.2.2.10, 5.2.3.1, 5.2.3.2, 5.2.3.3, 5.2.3.4, 5.2.3.5, 5.2.3.6, 5.2.3.7, 5.2.3.8, 5.2.3.9, 5.2.3.10, 5.2.4.1, 5.2.4.2, 5.2.4.3, 5.2.4.4, 5.2.4.5, 5.2.4.6, 5.2.4.7, 5.2.4.8, 5.2.4.9, 5.2.4.10, 5.2.5.1, 5.2.5.2, 5.2.5.3, 5.2.5.4, 5.2.5.5, 5.2.5.6, 5.2.5.7, 5.2.5.8, 5.2.5.9, 5.2.5.10, 5.2.6.1, 5.2.6.2, 5.2.6.3, 5.2.6.4, 5.2.6.5, 5.2.6.6, 5.2.6.7, 5.2.6.8, 5.2.6.9, 5.2.6.10, 5.2.7.1, 5.2.7.2, 5.2.7.3, 5.2.7.4, 5.2.7.5, 5.2.7.6, 5.2.7.7, 5.2.7.8, 5.2.7.9, 5.2.7.10, 5.2.8.1, 5.2.8.2, 5.2.8.3, 5.2.8.4, 5.2.8.5, 5.2.8.6, 5.2.8.7, 5.2.8.8, 5.2.8.9, 5.2.8.10, 5.2.9.1, 5.2.9.2, 5.2.9.3, 5.2.9.4, 5.2.9.5, 5.2.9.6, 5.2.9.7, 5.2.9.8, 5.2.9.9, 5.2.9.10, 5.2.10.1, 5.2.10.2, 5.2.10.3, 5.2.10.4, 5.2.10.5, 5.2.10.6, 5.2.10.7, 5.2.10.8, 5.2.10.9, 5.2.10.10, 5.3.1.1, 5.3.1.2, 5.3.1.3, 5.3.1.4, 5.3.1.5, 5.3.1.6, 5.3.1.7, 5.3.1.8, 5.3.1.9, 5.3.1.10, 5.3.2.1, 5.3.2.2, 5.3.2.3, 5.3.2.4, 5.3.2.5, 5.3.2.6, 5.3.2.7, 5.3.2.8, 5.3.2.9, 5.3.2.10, 5.3.3.1, 5.3.3.2, 5.3.3.3, 5.3.3.4, 5.3.3.5, 5.3.3.6, 5.3.3.7, 5.3.3.8, 5.3.3.9, 5.3.3.10, 5.3.4.1, 5.3.4.2, 5.3.4.3, 5.3.4.4, 5.3.4.5, 5.3.4.6, 5.3.4.7, 5.3.4.8, 5.3.4.9, 5.3.4.10, 5.3.5.1, 5.3.5.2, 5.3.5.3, 5.3.5.4, 5.3.5.5, 5.3.5.6, 5.3.5.7, 5.3.5.8, 5.3.5.9, 5.3.5.10, 5.3.6.1, 5.3.6.2, 5.3.6.3, 5.3.6.4, 5.3.6.5, 5.3.6.6, 5.3.6.7, 5.3.6.8, 5.3.6.9, 5.3.6.10, 5.3.7.1, 5.3.7.2, 5.3.7.3, 5.3.7.4, 5.3.7.5, 5.3.7.6, 5.3.7.7, 5.3.7.8, 5.3.7.9, 5.3.7.10, 5.3.8.1, 5.3.8.2, 5.3.8.3, 5.3.8.4, 5.3.8.5, 5.3.8.6, 5.3.8.7, 5.3.8.8, 5.3.8.9, 5.3.8.10, 5.3.9.1, 5.3.9.2, 5.3.9.3, 5.3.9.4, 5.3.9.5, 5.3.9.6, 5.3.9.7, 5.3.9.8, 5.3.9.9, 5.3.9.10, 5.3.10.1, 5.3.10.2, 5.3.10.3, 5.3.10.4, 5.3.10.5, 5.3.10.6, 5.3.10.7, 5.3.10.8, 5.3.10.9, 5.3.10.10, 5.4.1.1, 5.4.1.2, 5.4.1.3, 5.4.1.4, 5.4.1.5, 5.4.1.6, 5.4.1.7, 5.4.1.8, 5.4.1.9, 5.4.1.10, 5.4.2.1, 5.4.2.2, 5.4.2.3, 5.4.2.4, 5.4.2.5, 5.4.2.6, 5.4.2.7, 5.4.2.8, 5.4.2.9, 5.4.2.10, 5.4.3.1, 5.4.3.2, 5.4.3.3, 5.4.3.4, 5.4.3.5, 5.4.3.6, 5.4.3.7, 5.4.3.8, 5.4.3.9, 5.4.3.10, 5.4.4.1, 5.4.4.2, 5.4.4.3, 5.4.4.4, 5.4.4.5, 5.4.4.6, 5.4.4.7, 5.4.4.8, 5.4.4.9, 5.4.4.10, 5.4.5.1, 5.4.5.2, 5.4.5.3, 5.4.5.4, 5.4.5.5, 5.4.5.6, 5.4.5.7, 5.4.5.8, 5.4.5.9, 5.4.5.10, 5.4.6.1, 5.4.6.2, 5.4.6.3, 5.4.6.4, 5.4.6.5, 5.4.6.6, 5.4.6.7, 5.4.6.8, 5.4.6.9, 5.4.6.10, 5.4.7.1, 5.4.7.2, 5.4.7.3, 5.4.7.4, 5.4.7.5, 5.4.7.6, 5.4.7.7, 5.4.7.8, 5.4.7.9, 5.4.7.10, 5.4.8.1, 5.4.8.2, 5.4.8.3, 5.4.8.4, 5.4.8.5, 5.4.8.6, 5.4.8.7, 5.4.8.8, 5.4.8.9, 5.4.8.10, 5.4.9.1, 5.4.9.2, 5.4.9.3, 5.4.9.4, 5.4.9.5, 5.4.9.6, 5.4.9.7, 5.4.9.8, 5.4.9.9, 5.4.9.10, 5.4.10.1, 5.4.10.2, 5.4.10.3, 5.4.10.4, 5.4.10.5, 5.4.10.6, 5.4.10.7, 5.4.10.8, 5.4.10.9, 5.4.10.10, 5.5.1.1, 5.5.1.2, 5.5.1.3, 5.5.1.4, 5.5.1.5, 5.5.1.6, 5.5.1.7, 5.5.1.8, 5.5.1.9, 5.5.1.10, 5.5.2.1, 5.5.2.2, 5.5.2.3, 5.5.2.4, 5.5.2.5, 5.5.2.6, 5.5.2.7, 5.5.2.8, 5.5.2.9, 5.5.2.10, 5.5.3.1, 5.5.3.2, 5.5.3.3, 5.5.3.4, 5.5.3.5, 5.5.3.6, 5.5.3.7, 5.5.3.8, 5.5.3.9, 5.5.3.10, 5.5.4.1, 5.5.4.2, 5.5.4.3, 5.5.4.4, 5.5.4.5, 5.5.4.6, 5.5.4.7, 5.5.4.8, 5.5.4.9, 5.5.4.10, 5.5.5.1, 5.5.5.2, 5.5.5.3, 5.5.5.4, 5.5.5.5, 5.5.5.6, 5.5.5.7, 5.5.5.8, 5.5.5.9, 5.5.5.10, 5.5.6.1, 5.5.6.2, 5.5.6.3, 5.5.6.4, 5.5.6.5, 5.5.6.6, 5.5.6.7, 5.5.6.8, 5.5.6.9, 5.5.6.10, 5.5.7.1, 5.5.7.2, 5.5.7.3, 5.5.7.4, 5.5.7.5, 5.5.7.6, 5.5.7.7, 5.5.7.8, 5.5.7.9, 5.5.7.10, 5.5.8.1, 5.5.8.2, 5.5.8.3, 5.5.8.4, 5.5.8.5, 5.5.8.6, 5.5.8.7, 5.5.8.8, 5.5.8.9, 5.5.8.10, 5.5.9.1, 5.5.9.2, 5.5.9.3, 5.5.9.4, 5.5.9.5, 5.5.9.6, 5.5.9.7, 5.5.9.8, 5.5.9.9, 5.5.9.10, 5.5.10.1, 5.5.10.2, 5.5.10.3, 5.5.10.4, 5.5.10.5, 5.5.10.6, 5.5.10.7, 5.5.10.8, 5.5.10.9, 5.5.10.10, 5.6.1.1, 5.6.1.2, 5.6.1.3, 5.6.1.4, 5.6.1.5, 5.6.1.6, 5.6.1.7, 5.6.1.8, 5.6.1.9, 5.6.1.10, 5.6.2.1, 5.6.2.2, 5.6.2.3, 5.6.2.4, 5.6.2.5, 5.6.2.6, 5.6.2.7, 5.6.2.8, 5.6.2.9, 5.6.2.10, 5.6.3.1, 5.6.3.2, 5.6.3.3, 5.6.3.4, 5.6.3.5, 5.6.3.6, 5.6.3.7, 5.6.3.8, 5.6.3.9, 5.6.3.10, 5.6.4.1, 5.6.4.2, 5.6.4.3, 5.6.4.4, 5.6.4.5, 5.6.4.6, 5.6.4.7, 5.6.4.8, 5.6.4.9, 5.6.4.10, 5.6.5.1, 5.6.5.2, 5.6.5.3, 5.6.5.4, 5.6.5.5, 5.6.5.6, 5.6.5.7, 5.6.5.8, 5.6.5.9, 5.6.5.10, 5.6.6.1, 5.6.6.2, 5.6.6.3, 5.6.6.4, 5.6.6.5, 5.6.6.6, 5.6.6.7, 5.6.6.8, 5.6.6.9, 5.6.6.10, 5.6.7.1, 5.6.7.2, 5.6.7.3, 5.6.7.4, 5.6.7.5, 5.6.7.6, 5.6.7.7, 5.6.7.8, 5.6.7.9, 5.6.7.10, 5.6.8.1, 5.6.8.2, 5.6.8.3, 5.6.8.4, 5.6.8.5, 5.6.8.6, 5.6.8.7, 5.6.8.8, 5.6.8.9, 5.6.8.10, 5.6.9.1, 5.6.9.2, 5.6.9.3, 5.6.9.4, 5.6.9.5, 5.6.9.6, 5.6.9.7, 5.6.9.8, 5.6.9.9, 5.6.9.10, 5.6.10.1, 5.6.10.2, 5.6.10.3, 5.6.10.4, 5.6.10.5, 5.6.10.6, 5.6.10.7, 5.6.10.8, 5.6.10.9, 5.6.10.10, 5.7.1.1, 5.7.1.2, 5.7.1.3, 5.7.1.4, 5.7.1.5, 5.7.1.6, 5.7.1.7, TABLE B-continued 5.7.1.8, 5.7.1.9, 5.7.1.10, 5.7.2.1, 5.7.2.2, 5.7.2.3, 5.7.2.4, 5.7.2.5, 5.7.2.6, 5.7.2.7, 5.7.2.8, 5.7.2.9, 5.7.2.10, 5.7.3.1, 5.7.3.2, 5.7.3.3, 5.7.3.4, 5.7.3.5, 5.7.3.6, 5.7.3.7, 5.7.3.8, 5.7.3.9, 5.7.3.10, 5.7.4.1, 5.7.4.2, 5.7.4.3, 5.7.4.4, 5.7.4.5, 5.7.4.6, 5.7.4.7, 5.7.4.8, 5.7.4.9, 5.7.4.10, 5.7.5.1, 5.7.5.2, 5.7.5.3, 5.7.5.4, 5.7.5.5, 5.7.5.6, 5.7.5.7, 5.7.5.8, 5.7.5.9, 5.7.5.10, 5.7.6.1, 5.7.6.2, 5.7.6.3, 5.7.6.4, 5.7.6.5, 5.7.6.6, 5.7.6.7, 5.7.6.8, 5.7.6.9, 5.7.6.10, 5.7.7.1, 5.7.7.2, 5.7.7.3, 5.7.7.4, 5.7.7.5, 5.7.7.6, 5.7.7.7, 5.7.7.8, 5.7.7.9, 5.7.7.10, 5.7.8.1, 5.7.8.2, 5.7.8.3, 5.7.8.4, 5.7.8.5, 5.7.8.6, 5.7.8.7, 5.7.8.8, 5.7.8.9, 5.7.8.10, 5.7.9.1, 5.7.9.2, 5.7.9.3, 5.7.9.4, 5.7.9.5, 5.7.9.6, 5.7.9.7, 5.7.9.8, 5.7.9.9, 5.7.9.10, 5.7.10.1, 5.7.10.2, 5.7.10.3, 5.7.10.4, 5.7.10.5, 5.7.10.6, 5.7.10.7, 5.7.10.8, 5.7.10.9, 5.7.10.10, 5.8.1.1, 5.8.1.2, 5.8.1.3, 5.8.1.4, 5.8.1.5, 5.8.1.6, 5.8.1.7, 5.8.1.8, 5.8.1.9, 5.8.1.10, 5.8.2.1, 5.8.2.2, 5.8.2.3, 5.8.2.4, 5.8.2.5, 5.8.2.6, 5.8.2.7, 5.8.2.8, 5.8.2.9, 5.8.2.10, 5.8.3.1, 5.8.3.2, 5.8.3.3, 5.8.3.4, 5.8.3.5, 5.8.3.6, 5.8.3.7, 5.8.3.8, 5.8.3.9, 5.8.3.10, 5.8.4.1, 5.8.4.2, 5.8.4.3, 5.8.4.4, 5.8.4.5, 5.8.4.6, 5.8.4.7, 5.8.4.8, 5.8.4.9, 5.8.4.10, 5.8.5.1, 5.8.5.2, 5.8.5.3, 5.8.5.4, 5.8.5.5, 5.8.5.6, 5.8.5.7, 5.8.5.8, 5.8.5.9, 5.8.5.10, 5.8.6.1, 5.8.6.2, 5.8.6.3, 5.8.6.4, 5.8.6.5, 5.8.6.6, 5.8.6.7, 5.8.6.8, 5.8.6.9, 5.8.6.10, 5.8.7.1, 5.8.7.2, 5.8.7.3, 5.8.7.4, 5.8.7.5, 5.8.7.6, 5.8.7.7, 5.8.7.8, 5.8.7.9, 5.8.7.10, 5.8.8.1, 5.8.8.2, 5.8.8.3, 5.8.8.4, 5.8.8.5, 5.8.8.6, 5.8.8.7, 5.8.8.8, 5.8.8.9, 5.8.8.10, 5.8.9.1, 5.8.9.2, 5.8.9.3, 5.8.9.4, 5.8.9.5, 5.8.9.6, 5.8.9.7, 5.8.9.8, 5.8.9.9, 5.8.9.10, 5.8.10.1, 5.8.10.2, 5.8.10.3, 5.8.10.4, 5.8.10.5, 5.8.10.6, 5.8.10.7, 5.8.10.8, 5.8.10.9, 5.8.10.10, 5.9.1.1, 5.9.1.2, 5.9.1.3, 5.9.1.4, 5.9.1.5, 5.9.1.6, 5.9.1.7, 5.9.1.8, 5.9.1.9, 5.9.1.10, 5.9.2.1, 5.9.2.2, 5.9.2.3, 5.9.2.4, 5.9.2.5, 5.9.2.6, 5.9.2.7, 5.9.2.8, 5.9.2.9, 5.9.2.10, 5.9.3.1, 5.9.3.2, 5.9.3.3, 5.9.3.4, 5.9.3.5, 5.9.3.6, 5.9.3.7, 5.9.3.8, 5.9.3.9, 5.9.3.10, 5.9.4.1, 5.9.4.2, 5.9.4.3, 5.9.4.4, 5.9.4.5, 5.9.4.6, 5.9.4.7, 5.9.4.8, 5.9.4.9, 5.9.4.10, 5.9.5.1, 5.9.5.2, 5.9.5.3, 5.9.5.4, 5.9.5.5, 5.9.5.6, 5.9.5.7, 5.9.5.8, 5.9.5.9, 5.9.5.10, 5.9.6.1, 5.9.6.2, 5.9.6.3, 5.9.6.4, 5.9.6.5, 5.9.6.6, 5.9.6.7, 5.9.6.8, 5.9.6.9, 5.9.6.10, 5.9.7.1, 5.9.7.2, 5.9.7.3, 5.9.7.4, 5.9.7.5, 5.9.7.6, 5.9.7.7, 5.9.7.8, 5.9.7.9, 5.9.7.10, 5.9.8.1, 5.9.8.2, 5.9.8.3, 5.9.8.4, 5.9.8.5, 5.9.8.6, 5.9.8.7, 5.9.8.8, 5.9.8.9, 5.9.8.10, 5.9.9.1, 5.9.9.2, 5.9.9.3, 5.9.9.4, 5.9.9.5, 5.9.9.6, 5.9.9.7, 5.9.9.8, 5.9.9.9, 5.9.9.10, 5.9.10.1, 5.9.10.2, 5.9.10.3, 5.9.10.4, 5.9.10.5, 5.9.10.6, 5.9.10.7, 5.9.10.8, 5.9.10.9, 5.9.10.10, 5.10.1.1, 5.10.1.2, 5.10.1.3, 5.10.1.4, 5.10.1.5, 5.10.1.6, 5.10.1.7, 5.10.1.8, 5.10.1.9, 5.10.1.10, 5.10.2.1, 5.10.2.2, 5.10.2.3, 5.10.2.4, 5.10.2.5, 5.10.2.6, 5.10.2.7, 5.10.2.8, 5.10.2.9, 5.10.2.10, 5.10.3.1, 5.10.3.2, 5.10.3.3, 5.10.3.4, 5.10.3.5, 5.10.3.6, 5.10.3.7, 5.10.3.8, 5.10.3.9, 5.10.3.10, 5.10.4.1, 5.10.4.2, 5.10.4.3, 5.10.4.4, 5.10.4.5, 5.10.4.6, 5.10.4.7, 5.10.4.8, 5.10.4.9, 5.10.4.10, 5.10.5.1, 5.10.5.2, 5.10.5.3, 5.10.5.4, 5.10.5.5, 5.10.5.6, 5.10.5.7, 5.10.5.8, 5.10.5.9, 5.10.5.10, 5.10.6.1, 5.10.6.2, 5.10.6.3, 5.10.6.4, 5.10.6.5, 5.10.6.6, 5.10.6.7, 5.10.6.8, 5.10.6.9, 5.10.6.10, 5.10.7.1, 5.10.7.2, 5.10.7.3, 5.10.7.4, 5.10.7.5, 5.10.7.6, 5.10.7.7, 5.10.7.8, 5.10.7.9, 5.10.7.10, 5.10.8.1, 5.10.8.2, 5.10.8.3, 5.10.8.4, 5.10.8.5, 5.10.8.6, 5.10.8.7, 5.10.8.8, 5.10.8.9, 5.10.8.10, 5.10.9.1, 5.10.9.2, 5.10.9.3, 5.10.9.4, 5.10.9.5, 5.10.9.6, 5.10.9.7, 5.10.9.8, 5.10.9.9, 5.10.9.10, 5.10.10.1, 5.10.10.2, 5.10.10.3, 5.10.10.4, 5.10.10.5, 5.10.10.6, 5.10.10.7, 5.10.10.8, 5.10.10.9, 5.10.10.10, 6.1.1.1, 6.1.1.2, 6.1.1.3, 6.1.1.4, 6.1.1.5, 6.1.1.6, 6.1.1.7, 6.1.1.8, 6.1.1.9, 6.1.1.10, 6.1.2.1, 6.1.2.2, 6.1.2.3, 6.1.2.4, 6.1.2.5, 6.1.2.6, 6.1.2.7, 6.1.2.8, 6.1.2.9, 6.1.2.10, 6.1.3.1, 6.1.3.2, 6.1.3.3, 6.1.3.4, 6.1.3.5, 6.1.3.6, 6.1.3.7, 6.1.3.8, 6.1.3.9, 6.1.3.10, 6.1.4.1, 6.1.4.2, 6.1.4.3, 6.1.4.4, 6.1.4.5, 6.1.4.6, 6.1.4.7, 6.1.4.8, 6.1.4.9, 6.1.4.10, 6.1.5.1, 6.1.5.2, 6.1.5.3, 6.1.5.4, 6.1.5.5, 6.1.5.6, 6.1.5.7, 6.1.5.8, 6.1.5.9, 6.1.5.10, 6.1.6.1, 6.1.6.2, 6.1.6.3, 6.1.6.4, 6.1.6.5, 6.1.6.6, 6.1.6.7, 6.1.6.8, 6.1.6.9, 6.1.6.10, 6.1.7.1, 6.1.7.2, 6.1.7.3, 6.1.7.4, 6.1.7.5, 6.1.7.6, 6.1.7.7, 6.1.7.8, 6.1.7.9, 6.1.7.10, 6.1.8.1, 6.1.8.2, 6.1.8.3, 6.1.8.4, 6.1.8.5, 6.1.8.6, 6.1.8.7, 6.1.8.8, 6.1.8.9, 6.1.8.10, 6.1.9.1, 6.1.9.2, 6.1.9.3, 6.1.9.4, 6.1.9.5, 6.1.9.6, 6.1.9.7, 6.1.9.8, 6.1.9.9, 6.1.9.10, 6.1.10.1, 6.1.10.2, 6.1.10.3, 6.1.10.4, 6.1.10.5, 6.1.10.6, 6.1.10.7, 6.1.10.8, 6.1.10.9, 6.1.10.10, 6.2.1.1, 6.2.1.2, 6.2.1.3, 6.2.1.4, 6.2.1.5, 6.2.1.6, 6.2.1.7, 6.2.1.8, 6.2.1.9, 6.2.1.10, 6.2.2.1, 6.2.2.2, 6.2.2.3, 6.2.2.4, 6.2.2.5, 6.2.2.6, 6.2.2.7, 6.2.2.8, 6.2.2.9, 6.2.2.10, 6.2.3.1, 6.2.3.2, 6.2.3.3, 6.2.3.4, 6.2.3.5, 6.2.3.6, 6.2.3.7, 6.2.3.8, 6.2.3.9, 6.2.3.10, 6.2.4.1, 6.2.4.2, 6.2.4.3, 6.2.4.4, 6.2.4.5, 6.2.4.6, 6.2.4.7, 6.2.4.8, 6.2.4.9, 6.2.4.10, 6.2.5.1, 6.2.5.2, 6.2.5.3, 6.2.5.4, 6.2.5.5, 6.2.5.6, 6.2.5.7, 6.2.5.8, 6.2.5.9, 6.2.5.10, 6.2.6.1, 6.2.6.2, 6.2.6.3, 6.2.6.4, 6.2.6.5, 6.2.6.6, 6.2.6.7, 6.2.6.8, 6.2.6.9, 6.2.6.10, 6.2.7.1, 6.2.7.2, 6.2.7.3, 6.2.7.4, 6.2.7.5, 6.2.7.6, 6.2.7.7, 6.2.7.8, 6.2.7.9, 6.2.7.10, 6.2.8.1, 6.2.8.2, 6.2.8.3, 6.2.8.4, 6.2.8.5, 6.2.8.6, 6.2.8.7, 6.2.8.8, 6.2.8.9, 6.2.8.10, 6.2.9.1, 6.2.9.2, 6.2.9.3, 6.2.9.4, 6.2.9.5, 6.2.9.6, 6.2.9.7, 6.2.9.8, 6.2.9.9, 6.2.9.10, 6.2.10.1, 6.2.10.2, 6.2.10.3, 6.2.10.4, 6.2.10.5, 6.2.10.6, 6.2.10.7, 6.2.10.8, 6.2.10.9, 6.2.10.10, 6.3.1.1, 6.3.1.2, 6.3.1.3, 6.3.1.4, 6.3.1.5, 6.3.1.6, 6.3.1.7, 6.3.1.8, 6.3.1.9, 6.3.1.10, 6.3.2.1, 6.3.2.2, 6.3.2.3, 6.3.2.4, 6.3.2.5, 6.3.2.6, 6.3.2.7, 6.3.2.8, 6.3.2.9, 6.3.2.10, 6.3.3.1, 6.3.3.2, 6.3.3.3, 6.3.3.4, 6.3.3.5, 6.3.3.6, 6.3.3.7, 6.3.3.8, 6.3.3.9, 6.3.3.10, 6.3.4.1, 6.3.4.2, 6.3.4.3, 6.3.4.4, 6.3.4.5, 6.3.4.6, 6.3.4.7, 6.3.4.8, 6.3.4.9, 6.3.4.10, 6.3.5.1, 6.3.5.2, 6.3.5.3, 6.3.5.4, 6.3.5.5, 6.3.5.6, 6.3.5.7, 6.3.5.8, 6.3.5.9, 6.3.5.10, 6.3.6.1, 6.3.6.2, 6.3.6.3, 6.3.6.4, 6.3.6.5, 6.3.6.6, 6.3.6.7, 6.3.6.8, 6.3.6.9, 6.3.6.10, 6.3.7.1, 6.3.7.2, 6.3.7.3, 6.3.7.4, 6.3.7.5, 6.3.7.6, 6.3.7.7, 6.3.7.8, 6.3.7.9, 6.3.7.10, 6.3.8.1, 6.3.8.2, 6.3.8.3, 6.3.8.4, 6.3.8.5, 6.3.8.6, 6.3.8.7, 6.3.8.8, 6.3.8.9, 6.3.8.10, 6.3.9.1, 6.3.9.2, 6.3.9.3, 6.3.9.4, 6.3.9.5, 6.3.9.6, 6.3.9.7, 6.3.9.8, 6.3.9.9, 6.3.9.10, 6.3.10.1, 6.3.10.2, 6.3.10.3, 6.3.10.4, 6.3.10.5, 6.3.10.6, 6.3.10.7, 6.3.10.8, 6.3.10.9, 6.3.10.10, 6.4.1.1, 6.4.1.2, 6.4.1.3, 6.4.1.4, 6.4.1.5, 6.4.1.6, 6.4.1.7, 6.4.1.8, 6.4.1.9, 6.4.1.10, 6.4.2.1, 6.4.2.2, 6.4.2.3, 6.4.2.4, 6.4.2.5, 6.4.2.6, 6.4.2.7, 6.4.2.8, 6.4.2.9, 6.4.2.10, 6.4.3.1, 6.4.3.2, 6.4.3.3, 6.4.3.4, 6.4.3.5, 6.4.3.6, 6.4.3.7, 6.4.3.8, 6.4.3.9, 6.4.3.10, 6.4.4.1, 6.4.4.2, 6.4.4.3, 6.4.4.4, 6.4.4.5, 6.4.4.6, 6.4.4.7, 6.4.4.8, 6.4.4.9, 6.4.4.10, 6.4.5.1, 6.4.5.2, 6.4.5.3, 6.4.5.4, 6.4.5.5, 6.4.5.6, 6.4.5.7, 6.4.5.8, 6.4.5.9, 6.4.5.10, 6.4.6.1, 6.4.6.2, 6.4.6.3, 6.4.6.4, 6.4.6.5, 6.4.6.6, 6.4.6.7, 6.4.6.8, 6.4.6.9, 6.4.6.10, 6.4.7.1, 6.4.7.2, 6.4.7.3, 6.4.7.4, 6.4.7.5, 6.4.7.6, 6.4.7.7, 6.4.7.8, 6.4.7.9, 6.4.7.10, 6.4.8.1, 6.4.8.2, 6.4.8.3, 6.4.8.4, 6.4.8.5, 6.4.8.6, 6.4.8.7, 6.4.8.8, 6.4.8.9, 6.4.8.10, 6.4.9.1, 6.4.9.2, 6.4.9.3, 6.4.9.4, 6.4.9.5, 6.4.9.6, 6.4.9.7, 6.4.9.8, 6.4.9.9, 6.4.9.10, 6.4.10.1, 6.4.10.2, 6.4.10.3, 6.4.10.4, 6.4.10.5, 6.4.10.6, 6.4.10.7, 6.4.10.8, 6.4.10.9, 6.4.10.10, 6.5.1.1, 6.5.1.2, 6.5.1.3, 6.5.1.4, 6.5.1.5, 6.5.1.6, 6.5.1.7, 6.5.1.8, 6.5.1.9, 6.5.1.10, 6.5.2.1, 6.5.2.2, 6.5.2.3, 6.5.2.4, 6.5.2.5, 6.5.2.6, 6.5.2.7, 6.5.2.8, 6.5.2.9, 6.5.2.10, 6.5.3.1, 6.5.3.2, 6.5.3.3, 6.5.3.4, 6.5.3.5, 6.5.3.6, 6.5.3.7, 6.5.3.8, 6.5.3.9, 6.5.3.10, 6.5.4.1, 6.5.4.2, 6.5.4.3, 6.5.4.4, 6.5.4.5, 6.5.4.6, 6.5.4.7, 6.5.4.8, 6.5.4.9, 6.5.4.10, 6.5.5.1, 6.5.5.2, 6.5.5.3, 6.5.5.4, 6.5.5.5, 6.5.5.6, 6.5.5.7, 6.5.5.8, 6.5.5.9, 6.5.5.10, 6.5.6.1, 6.5.6.2, 6.5.6.3, 6.5.6.4, 6.5.6.5, 6.5.6.6, 6.5.6.7, 6.5.6.8, 6.5.6.9, 6.5.6.10, 6.5.7.1, 6.5.7.2, 6.5.7.3, 6.5.7.4, 6.5.7.5, 6.5.7.6, 6.5.7.7, 6.5.7.8, 6.5.7.9, 6.5.7.10, 6.5.8.1, 6.5.8.2, 6.5.8.3, 6.5.8.4, 6.5.8.5, 6.5.8.6, 6.5.8.7, 6.5.8.8, 6.5.8.9, 6.5.8.10, 6.5.9.1, 6.5.9.2, 6.5.9.3, 6.5.9.4, 6.5.9.5, 6.5.9.6, 6.5.9.7, 6.5.9.8, 6.5.9.9, 6.5.9.10, 6.5.10.1, 6.5.10.2, 6.5.10.3, 6.5.10.4, 6.5.10.5, 6.5.10.6, 6.5.10.7, 6.5.10.8, 6.5.10.9, 6.5.10.10, 6.6.1.1, 6.6.1.2, 6.6.1.3, 6.6.1.4, 6.6.1.5, 6.6.1.6, 6.6.1.7, 6.6.1.8, 6.6.1.9, 6.6.1.10, 6.6.2.1, 6.6.2.2, 6.6.2.3, 6.6.2.4, 6.6.2.5, 6.6.2.6, 6.6.2.7, 6.6.2.8, 6.6.2.9, 6.6.2.10, 6.6.3.1, 6.6.3.2, 6.6.3.3, 6.6.3.4, 6.6.3.5, 6.6.3.6, 6.6.3.7, 6.6.3.8, 6.6.3.9, 6.6.3.10, 6.6.4.1, 6.6.4.2, 6.6.4.3, 6.6.4.4, 6.6.4.5, 6.6.4.6, 6.6.4.7, 6.6.4.8, 6.6.4.9, 6.6.4.10, 6.6.5.1, 6.6.5.2, 6.6.5.3, 6.6.5.4, 6.6.5.5, 6.6.5.6, 6.6.5.7, 6.6.5.8, TABLE B-continued 6.6.5.9, 6.6.5.10, 6.6.6.1, 6.6.6.2, 6.6.6.3, 6.6.6.4, 6.6.6.5, 6.6.6.6, 6.6.6.7, 6.6.6.8, 6.6.6.9, 6.6.6.10, 6.6.7.1, 6.6.7.2, 6.6.7.3, 6.6.7.4, 6.6.7.5, 6.6.7.6, 6.6.7.7, 6.6.7.8, 6.6.7.9, 6.6.7.10, 6.6.8.1, 6.6.8.2, 6.6.8.3, 6.6.8.4, 6.6.8.5, 6.6.8.6, 6.6.8.7, 6.6.8.8, 6.6.8.9, 6.6.8.10, 6.6.9.1, 6.6.9.2, 6.6.9.3, 6.6.9.4, 6.6.9.5, 6.6.9.6, 6.6.9.7, 6.6.9.8, 6.6.9.9, 6.6.9.10, 6.6.10.1, 6.6.10.2, 6.6.10.3, 6.6.10.4, 6.6.10.5, 6.6.10.6, 6.6.10.7, 6.6.10.8, 6.6.10.9, 6.6.10.10, 6.7.1.1, 6.7.1.2, 6.7.1.3, 6.7.1.4, 6.7.1.5, 6.7.1.6, 6.7.1.7, 6.7.1.8, 6.7.1.9, 6.7.1.10, 6.7.2.1, 6.7.2.2, 6.7.2.3, 6.7.2.4, 6.7.2.5, 6.7.2.6, 6.7.2.7, 6.7.2.8, 6.7.2.9, 6.7.2.10, 6.7.3.1, 6.7.3.2, 6.7.3.3, 6.7.3.4, 6.7.3.5, 6.7.3.6, 6.7.3.7, 6.7.3.8, 6.7.3.9, 6.7.3.10, 6.7.4.1, 6.7.4.2, 6.7.4.3, 6.7.4.4, 6.7.4.5, 6.7.4.6, 6.7.4.7, 6.7.4.8, 6.7.4.9, 6.7.4.10, 6.7.5.1, 6.7.5.2, 6.7.5.3, 6.7.5.4, 6.7.5.5, 6.7.5.6, 6.7.5.7, 6.7.5.8, 6.7.5.9, 6.7.5.10, 6.7.6.1, 6.7.6.2, 6.7.6.3, 6.7.6.4, 6.7.6.5, 6.7.6.6, 6.7.6.7, 6.7.6.8, 6.7.6.9, 6.7.6.10, 6.7.7.1, 6.7.7.2, 6.7.7.3, 6.7.7.4, 6.7.7.5, 6.7.7.6, 6.7.7.7, 6.7.7.8, 6.7.7.9, 6.7.7.10, 6.7.8.1, 6.7.8.2, 6.7.8.3, 6.7.8.4, 6.7.8.5, 6.7.8.6, 6.7.8.7, 6.7.8.8, 6.7.8.9, 6.7.8.10, 6.7.9.1, 6.7.9.2, 6.7.9.3, 6.7.9.4, 6.7.9.5, 6.7.9.6, 6.7.9.7, 6.7.9.8, 6.7.9.9, 6.7.9.10, 6.7.10.1, 6.7.10.2, 6.7.10.3, 6.7.10.4, 6.7.10.5, 6.7.10.6, 6.7.10.7, 6.7.10.8, 6.7.10.9, 6.7.10.10, 6.8.1.1, 6.8.1.2, 6.8.1.3, 6.8.1.4, 6.8.1.5, 6.8.1.6, 6.8.1.7, 6.8.1.8, 6.8.1.9, 6.8.1.10, 6.8.2.1, 6.8.2.2, 6.8.2.3, 6.8.2.4, 6.8.2.5, 6.8.2.6, 6.8.2.7, 6.8.2.8, 6.8.2.9, 6.8.2.10, 6.8.3.1, 6.8.3.2, 6.8.3.3, 6.8.3.4, 6.8.3.5, 6.8.3.6, 6.8.3.7, 6.8.3.8, 6.8.3.9, 6.8.3.10, 6.8.4.1, 6.8.4.2, 6.8.4.3, 6.8.4.4, 6.8.4.5, 6.8.4.6, 6.8.4.7, 6.8.4.8, 6.8.4.9, 6.8.4.10, 6.8.5.1, 6.8.5.2, 6.8.5.3, 6.8.5.4, 6.8.5.5, 6.8.5.6, 6.8.5.7, 6.8.5.8, 6.8.5.9, 6.8.5.10, 6.8.6.1, 6.8.6.2, 6.8.6.3, 6.8.6.4, 6.8.6.5, 6.8.6.6, 6.8.6.7, 6.8.6.8, 6.8.6.9, 6.8.6.10, 6.8.7.1, 6.8.7.2, 6.8.7.3, 6.8.7.4, 6.8.7.5, 6.8.7.6, 6.8.7.7, 6.8.7.8, 6.8.7.9, 6.8.7.10, 6.8.8.1, 6.8.8.2, 6.8.8.3, 6.8.8.4, 6.8.8.5, 6.8.8.6, 6.8.8.7, 6.8.8.8, 6.8.8.9, 6.8.8.10, 6.8.9.1, 6.8.9.2, 6.8.9.3, 6.8.9.4, 6.8.9.5, 6.8.9.6, 6.8.9.7, 6.8.9.8, 6.8.9.9, 6.8.9.10, 6.8.10.1, 6.8.10.2, 6.8.10.3, 6.8.10.4, 6.8.10.5, 6.8.10.6, 6.8.10.7, 6.8.10.8, 6.8.10.9, 6.8.10.10, 6.9.1.1, 6.9.1.2, 6.9.1.3, 6.9.1.4, 6.9.1.5, 6.9.1.6, 6.9.1.7, 6.9.1.8, 6.9.1.9, 6.9.1.10, 6.9.2.1, 6.9.2.2, 6.9.2.3, 6.9.2.4, 6.9.2.5, 6.9.2.6, 6.9.2.7, 6.9.2.8, 6.9.2.9, 6.9.2.10, 6.9.3.1, 6.9.3.2, 6.9.3.3, 6.9.3.4, 6.9.3.5, 6.9.3.6, 6.9.3.7, 6.9.3.8, 6.9.3.9, 6.9.3.10, 6.9.4.1, 6.9.4.2, 6.9.4.3, 6.9.4.4, 6.9.4.5, 6.9.4.6, 6.9.4.7, 6.9.4.8, 6.9.4.9, 6.9.4.10, 6.9.5.1, 6.9.5.2, 6.9.5.3, 6.9.5.4, 6.9.5.5, 6.9.5.6, 6.9.5.7, 6.9.5.8, 6.9.5.9, 6.9.5.10, 6.9.6.1, 6.9.6.2, 6.9.6.3, 6.9.6.4, 6.9.6.5, 6.9.6.6, 6.9.6.7, 6.9.6.8, 6.9.6.9, 6.9.6.10, 6.9.7.1, 6.9.7.2, 6.9.7.3, 6.9.7.4, 6.9.7.5, 6.9.7.6, 6.9.7.7, 6.9.7.8, 6.9.7.9, 6.9.7.10, 6.9.8.1, 6.9.8.2, 6.9.8.3, 6.9.8.4, 6.9.8.5, 6.9.8.6, 6.9.8.7, 6.9.8.8, 6.9.8.9, 6.9.8.10, 6.9.9.1, 6.9.9.2, 6.9.9.3, 6.9.9.4, 6.9.9.5, 6.9.9.6, 6.9.9.7, 6.9.9.8, 6.9.9.9, 6.9.9.10, 6.9.10.1, 6.9.10.2, 6.9.10.3, 6.9.10.4, 6.9.10.5, 6.9.10.6, 6.9.10.7, 6.9.10.8, 6.9.10.9, 6.9.10.10, 6.10.1.1, 6.10.1.2, 6.10.1.3, 6.10.1.4, 6.10.1.5, 6.10.1.6, 6.10.1.7, 6.10.1.8, 6.10.1.9, 6.10.1.10, 6.10.2.1, 6.10.2.2, 6.10.2.3, 6.10.2.4, 6.10.2.5, 6.10.2.6, 6.10.2.7, 6.10.2.8, 6.10.2.9, 6.10.2.10, 6.10.3.1, 6.10.3.2, 6.10.3.3, 6.10.3.4, 6.10.3.5, 6.10.3.6, 6.10.3.7, 6.10.3.8, 6.10.3.9, 6.10.3.10, 6.10.4.1, 6.10.4.2, 6.10.4.3, 6.10.4.4, 6.10.4.5, 6.10.4.6, 6.10.4.7, 6.10.4.8, 6.10.4.9, 6.10.4.10, 6.10.5.1, 6.10.5.2, 6.10.5.3, 6.10.5.4, 6.10.5.5, 6.10.5.6, 6.10.5.7, 6.10.5.8, 6.10.5.9, 6.10.5.10, 6.10.6.1, 6.10.6.2, 6.10.6.3, 6.10.6.4, 6.10.6.5, 6.10.6.6, 6.10.6.7, 6.10.6.8, 6.10.6.9, 6.10.6.10, 6.10.7.1, 6.10.7.2, 6.10.7.3, 6.10.7.4, 6.10.7.5, 6.10.7.6, 6.10.7.7, 6.10.7.8, 6.10.7.9, 6.10.7.10, 6.10.8.1, 6.10.8.2, 6.10.8.3, 6.10.8.4, 6.10.8.5, 6.10.8.6, 6.10.8.7, 6.10.8.8, 6.10.8.9, 6.10.8.10, 6.10.9.1, 6.10.9.2, 6.10.9.3, 6.10.9.4, 6.10.9.5, 6.10.9.6, 6.10.9.7, 6.10.9.8, 6.10.9.9, 6.10.9.10, 6.10.10.1, 6.10.10.2, 6.10.10.3, 6.10.10.4, 6.10.10.5, 6.10.10.6, 6.10.10.7, 6.10.10.8, 6.10.10.9, 6.10.10.10, 7.1.1.1, 7.1.1.2, 7.1.1.3, 7.1.1.4, 7.1.1.5, 7.1.1.6, 7.1.1.7, 7.1.1.8, 7.1.1.9, 7.1.1.10, 7.1.2.1, 7.1.2.2, 7.1.2.3, 7.1.2.4, 7.1.2.5, 7.1.2.6, 7.1.2.7, 7.1.2.8, 7.1.2.9, 7.1.2.10, 7.1.3.1, 7.1.3.2, 7.1.3.3, 7.1.3.4, 7.1.3.5, 7.1.3.6, 7.1.3.7, 7.1.3.8, 7.1.3.9, 7.1.3.10, 7.1.4.1, 7.1.4.2, 7.1.4.3, 7.1.4.4, 7.1.4.5, 7.1.4.6, 7.1.4.7, 7.1.4.8, 7.1.4.9, 7.1.4.10, 7.1.5.1, 7.1.5.2, 7.1.5.3, 7.1.5.4, 7.1.5.5, 7.1.5.6, 7.1.5.7, 7.1.5.8, 7.1.5.9, 7.1.5.10, 7.1.6.1, 7.1.6.2, 7.1.6.3, 7.1.6.4, 7.1.6.5, 7.1.6.6, 7.1.6.7, 7.1.6.8, 7.1.6.9, 7.1.6.10, 7.1.7.1, 7.1.7.2, 7.1.7.3, 7.1.7.4, 7.1.7.5, 7.1.7.6, 7.1.7.7, 7.1.7.8, 7.1.7.9, 7.1.7.10, 7.1.8.1, 7.1.8.2, 7.1.8.3, 7.1.8.4, 7.1.8.5, 7.1.8.6, 7.1.8.7, 7.1.8.8, 7.1.8.9, 7.1.8.10, 7.1.9.1, 7.1.9.2, 7.1.9.3, 7.1.9.4, 7.1.9.5, 7.1.9.6, 7.1.9.7, 7.1.9.8, 7.1.9.9, 7.1.9.10, 7.1.10.1, 7.1.10.2, 7.1.10.3, 7.1.10.4, 7.1.10.5, 7.1.10.6, 7.1.10.7, 7.1.10.8, 7.1.10.9, 7.1.10.10, 7.2.1.1, 7.2.1.2, 7.2.1.3, 7.2.1.4, 7.2.1.5, 7.2.1.6, 7.2.1.7, 7.2.1.8, 7.2.1.9, 7.2.1.10, 7.2.2.1, 7.2.2.2, 7.2.2.3, 7.2.2.4, 7.2.2.5, 7.2.2.6, 7.2.2.7, 7.2.2.8, 7.2.2.9, 7.2.2.10, 7.2.3.1, 7.2.3.2, 7.2.3.3, 7.2.3.4, 7.2.3.5, 7.2.3.6, 7.2.3.7, 7.2.3.8, 7.2.3.9, 7.2.3.10, 7.2.4.1, 7.2.4.2, 7.2.4.3, 7.2.4.4, 7.2.4.5, 7.2.4.6, 7.2.4.7, 7.2.4.8, 7.2.4.9, 7.2.4.10, 7.2.5.1, 7.2.5.2, 7.2.5.3, 7.2.5.4, 7.2.5.5, 7.2.5.6, 7.2.5.7, 7.2.5.8, 7.2.5.9, 7.2.5.10, 7.2.6.1, 7.2.6.2, 7.2.6.3, 7.2.6.4, 7.2.6.5, 7.2.6.6, 7.2.6.7, 7.2.6.8, 7.2.6.9, 7.2.6.10, 7.2.7.1, 7.2.7.2, 7.2.7.3, 7.2.7.4, 7.2.7.5, 7.2.7.6, 7.2.7.7, 7.2.7.8, 7.2.7.9, 7.2.7.10, 7.2.8.1, 7.2.8.2, 7.2.8.3, 7.2.8.4, 7.2.8.5, 7.2.8.6, 7.2.8.7, 7.2.8.8, 7.2.8.9, 7.2.8.10, 7.2.9.1, 7.2.9.2, 7.2.9.3, 7.2.9.4, 7.2.9.5, 7.2.9.6, 7.2.9.7, 7.2.9.8, 7.2.9.9, 7.2.9.10, 7.2.10.1, 7.2.10.2, 7.2.10.3, 7.2.10.4, 7.2.10.5, 7.2.10.6, 7.2.10.7, 7.2.10.8, 7.2.10.9, 7.2.10.10, 7.3.1.1, 7.3.1.2, 7.3.1.3, 7.3.1.4, 7.3.1.5, 7.3.1.6, 7.3.1.7, 7.3.1.8, 7.3.1.9, 7.3.1.10, 7.3.2.1, 7.3.2.2, 7.3.2.3, 7.3.2.4, 7.3.2.5, 7.3.2.6, 7.3.2.7, 7.3.2.8, 7.3.2.9, 7.3.2.10, 7.3.3.1, 7.3.3.2, 7.3.3.3, 7.3.3.4, 7.3.3.5, 7.3.3.6, 7.3.3.7, 7.3.3.8, 7.3.3.9, 7.3.3.10, 7.3.4.1, 7.3.4.2, 7.3.4.3, 7.3.4.4, 7.3.4.5, 7.3.4.6, 7.3.4.7, 7.3.4.8, 7.3.4.9, 7.3.4.10, 7.3.5.1, 7.3.5.2, 7.3.5.3, 7.3.5.4, 7.3.5.5, 7.3.5.6, 7.3.5.7, 7.3.5.8, 7.3.5.9, 7.3.5.10, 7.3.6.1, 7.3.6.2, 7.3.6.3, 7.3.6.4, 7.3.6.5, 7.3.6.6, 7.3.6.7, 7.3.6.8, 7.3.6.9, 7.3.6.10, 7.3.7.1, 7.3.7.2, 7.3.7.3, 7.3.7.4, 7.3.7.5, 7.3.7.6, 7.3.7.7, 7.3.7.8, 7.3.7.9, 7.3.7.10, 7.3.8.1, 7.3.8.2, 7.3.8.3, 7.3.8.4, 7.3.8.5, 7.3.8.6, 7.3.8.7, 7.3.8.8, 7.3.8.9, 7.3.8.10, 7.3.9.1, 7.3.9.2, 7.3.9.3, 7.3.9.4, 7.3.9.5, 7.3.9.6, 7.3.9.7, 7.3.9.8, 7.3.9.9, 7.3.9.10, 7.3.10.1, 7.3.10.2, 7.3.10.3, 7.3.10.4, 7.3.10.5, 7.3.10.6, 7.3.10.7, 7.3.10.8, 7.3.10.9, 7.3.10.10, 7.4.1.1, 7.4.1.2, 7.4.1.3, 7.4.1.4, 7.4.1.5, 7.4.1.6, 7.4.1.7, 7.4.1.8, 7.4.1.9, 7.4.1.10, 7.4.2.1, 7.4.2.2, 7.4.2.3, 7.4.2.4, 7.4.2.5, 7.4.2.6, 7.4.2.7, 7.4.2.8, 7.4.2.9, 7.4.2.10, 7.4.3.1, 7.4.3.2, 7.4.3.3, 7.4.3.4, 7.4.3.5, 7.4.3.6, 7.4.3.7, 7.4.3.8, 7.4.3.9, 7.4.3.10, 7.4.4.1, 7.4.4.2, 7.4.4.3, 7.4.4.4, 7.4.4.5, 7.4.4.6, 7.4.4.7, 7.4.4.8, 7.4.4.9, 7.4.4.10, 7.4.5.1, 7.4.5.2, 7.4.5.3, 7.4.5.4, 7.4.5.5, 7.4.5.6, 7.4.5.7, 7.4.5.8, 7.4.5.9, 7.4.5.10, 7.4.6.1, 7.4.6.2, 7.4.6.3, 7.4.6.4, 7.4.6.5, 7.4.6.6, 7.4.6.7, 7.4.6.8, 7.4.6.9, 7.4.6.10, 7.4.7.1, 7.4.7.2, 7.4.7.3, 7.4.7.4, 7.4.7.5, 7.4.7.6, 7.4.7.7, 7.4.7.8, 7.4.7.9, 7.4.7.10, 7.4.8.1, 7.4.8.2, 7.4.8.3, 7.4.8.4, 7.4.8.5, 7.4.8.6, 7.4.8.7, 7.4.8.8, 7.4.8.9, 7.4.8.10, 7.4.9.1, 7.4.9.2, 7.4.9.3, 7.4.9.4, 7.4.9.5, 7.4.9.6, 7.4.9.7, 7.4.9.8, 7.4.9.9, 7.4.9.10, 7.4.10.1, 7.4.10.2, 7.4.10.3, 7.4.10.4, 7.4.10.5, 7.4.10.6, 7.4.10.7, 7.4.10.8, 7.4.10.9, 7.4.10.10, 7.5.1.1, 7.5.1.2, 7.5.1.3, 7.5.1.4, 7.5.1.5, 7.5.1.6, 7.5.1.7, 7.5.1.8, 7.5.1.9, 7.5.1.10, 7.5.2.1, 7.5.2.2, 7.5.2.3, 7.5.2.4, 7.5.2.5, 7.5.2.6, 7.5.2.7, 7.5.2.8, 7.5.2.9, 7.5.2.10, 7.5.3.1, 7.5.3.2, 7.5.3.3, 7.5.3.4, 7.5.3.5, 7.5.3.6, 7.5.3.7, 7.5.3.8, 7.5.3.9, 7.5.3.10, 7.5.4.1, 7.5.4.2, 7.5.4.3, 7.5.4.4, 7.5.4.5, 7.5.4.6, 7.5.4.7, 7.5.4.8, 7.5.4.9, 7.5.4.10, 7.5.5.1, 7.5.5.2, 7.5.5.3, 7.5.5.4, 7.5.5.5, 7.5.5.6, 7.5.5.7, 7.5.5.8, 7.5.5.9, 7.5.5.10, 7.5.6.1, 7.5.6.2, 7.5.6.3, 7.5.6.4, 7.5.6.5, 7.5.6.6, 7.5.6.7, 7.5.6.8, 7.5.6.9, 7.5.6.10, 7.5.7.1, 7.5.7.2, 7.5.7.3, 7.5.7.4, 7.5.7.5, 7.5.7.6, 7.5.7.7, 7.5.7.8, 7.5.7.9, 7.5.7.10, 7.5.8.1, 7.5.8.2, 7.5.8.3, 7.5.8.4, 7.5.8.5, 7.5.8.6, 7.5.8.7, 7.5.8.8, 7.5.8.9, 7.5.8.10, 7.5.9.1, 7.5.9.2, 7.5.9.3, 7.5.9.4, 7.5.9.5, 7.5.9.6, 7.5.9.7, 7.5.9.8, 7.5.9.9, TABLE B-continued 7.5.9.10, 7.5.10.1, 7.5.10.2, 7.5.10.3, 7.5.10.4, 7.5.10.5, 7.5.10.6, 7.5.10.7, 7.5.10.8, 7.5.10.9, 7.5.10.10, 7.6.1.1, 7.6.1.2, 7.6.1.3, 7.6.1.4, 7.6.1.5, 7.6.1.6, 7.6.1.7, 7.6.1.8, 7.6.1.9, 7.6.1.10, 7, 6.2.1, 7.6.2.2, 7.6.2.3, 7.6.2.4, 7.6.2.5, 7.6.2.6, 7.6.2.7, 7.6.2.8, 7.6.2.9, 7.6.2.10, 7.6.3.1, 7.6.3.2, 7.6.3.3, 7.6.3.4, 7.6.3.5, 7.6.3.6, 7.6.3.7, 7.6.3.8, 7.6.3.9, 7.6.3.10, 7.6.4.1, 7.6.4.2, 7.6.4.3, 7.6.4.4, 7.6.4.5, 7.6.4.6, 7.6.4.7, 7.6.4.8, 7.6.4.9, 7.6.4.10, 7.6.5.1, 7.6.5.2, 7.6.5.3, 7.6.5.4, 7.6.5.5, 7.6.5.6, 7.6.5.7, 7.6.5.8, 7.6.5.9, 7.6.5.10, 7.6.6.1, 7.6.6.2, 7.6.6.3, 7.6.6.4, 7.6.6.5, 7.6.6.6, 7.6.6.7, 7.6.6.8, 7.6.6.9, 7.6.6.10, 7.6.7.1, 7.6.7.2, 7.6.7.3, 7.6.7.4, 7.6.7.5, 7.6.7.6, 7.6.7.7, 7.6.7.8, 7.6.7.9, 7.6.7.10, 7.6.8.1, 7.6.8.2, 7.6.8.3, 7.6.8.4, 7.6.8.5, 7.6.8.6, 7.6.8.7, 7.6.8.8, 7.6.8.9, 7.6.8.10, 7.6.9.1, 7.6.9.2, 7.6.9.3, 7.6.9.4, 7.6.9.5, 7.6.9.6, 7.6.9.7, 7.6.9.8, 7.6.9.9, 7.6.9.10, 7.6.10.1, 7.6.10.2, 7.6.10.3, 7.6.10.4, 7.6.10.5, 7.6.10.6, 7.6.10.7, 7.6.10.8, 7.6.10.9, 7.6.10.10, 7.7.1.1, 7.7.1.2, 7.7.1.3, 7.7.1.4, 7.7.1.5, 7.7.1.6, 7.7.1.7, 7.7.1.8, 7.7.1.9, 7.7.1.10, 7.7.2.1, 7.7.2.2, 7.7.2.3, 7.7.2.4, 7.7.2.5, 7.7.2.6, 7.7.2.7, 7.7.2.8, 7.7.2.9, 7.7.2.10, 7.7.3.1, 7.7.3.2, 7.7.3.3, 7.7.3.4, 7.7.3.5, 7.7.3.6, 7.7.3.7, 7.7.3.8, 7.7.3.9, 7.7.3.10, 7.7.4.1, 7.7.4.2, 7.7.4.3, 7.7.4.4, 7.7.4.5, 7.7.4.6, 7.7.4.7, 7.7.4.8, 7.7.4.9, 7.7.4.10, 7.7.5.1, 7.7.5.2, 7.7.5.3, 7.7.5.4, 7.7.5.5, 7.7.5.6, 7.7.5.7, 7.7.5.8, 7.7.5.9, 7.7.5.10, 7.7.6.1, 7.7.6.2, 7.7.6.3, 7.7.6.4, 7.7.6.5, 7.7.6.6, 7.7.6.7, 7.7.6.8, 7.7.6.9, 7.7.6.10, 7.7.7.1, 7.7.7.2, 7.7.7.3, 7.7.7.4, 7.7.7.5, 7.7.7.6, 7.7.7.7, 7.7.7.8, 7.7.7.9, 7.7.7.10, 7.7.8.1, 7.7.8.2, 7.7.8.3, 7.7.8.4, 7.7.8.5, 7.7.8.6, 7.7.8.7, 7.7.8.8, 7.7.8.9, 7.7.8.10, 7.7.9.1, 7.7.9.2, 7.7.9.3, 7.7.9.4, 7.7.9.5, 7.7.9.6, 7.7.9.7, 7.7.9.8, 7.7.9.9, 7.7.9.10, 7.7.10.1, 7.7.10.2, 7.7.10.3, 7.7.10.4, 7.7.10.5, 7.7.10.6, 7.7.10.7, 7.7.10.8, 7.7.10.9, 7.7.10.10, 7.8.1.1, 7.8.1.2, 7.8.1.3, 7.8.1.4, 7.8.1.5, 7.8.1.6, 7.8.1.7, 7.8.1.8, 7.8.1.9, 7.8.1.10, 7.8.2.1, 7.8.2.2, 7.8.2.3, 7.8.2.4, 7.8.2.5, 7.8.2.6, 7.8.2.7, 7.8.2.8, 7.8.2.9, 7.8.2.10, 7.8.3.1, 7.8.3.2, 7.8.3.3, 7.8.3.4, 7.8.3.5, 7.8.3.6, 7.8.3.7, 7.8.3.8, 7.8.3.9, 7.8.3.10, 7.8.4.1, 7.8.4.2, 7.8.4.3, 7.8.4.4, 7.8.4.5, 7.8.4.6, 7.8.4.7, 7.8.4.8, 7.8.4.9, 7.8.4.10, 7.8.5.1, 7.8.5.2, 7.8.5.3, 7.8.5.4, 7.8.5.5, 7.8.5.6, 7.8.5.7, 7.8.5.8, 7.8.5.9, 7.8.5.10, 7.8.6.1, 7.8.6.2, 7.8.6.3, 7.8.6.4, 7.8.6.5, 7.8.6.6, 7.8.6.7, 7.8.6.8, 7.8.6.9, 7.8.6.10, 7.8.7.1, 7.8.7.2, 7.8.7.3, 7.8.7.4, 7.8.7.5, 7.8.7.6, 7.8.7.7, 7.8.7.8, 7.8.7.9, 7.8.7.10, 7.8.8.1, 7.8.8.2, 7.8.8.3, 7.8.8.4, 7.8.8.5, 7.8.8.6, 7.8.8.7, 7.8.8.8, 7.8.8.9, 7.8.8.10, 7.8.9.1, 7.8.9.2, 7.8.9.3, 7.8.9.4, 7.8.9.5, 7.8.9.6, 7.8.9.7, 7.8.9.8, 7.8.9.9, 7.8.9.10, 7.8.10.1, 7.8.10.2, 7.8.10.3, 7.8.10.4, 7.8.10.5, 7.8.10.6, 7.8.10.7, 7.8.10.8, 7.8.10.9, 7.8.10.10, 7.9.1.1, 7.9.1.2, 7.9.1.3, 7.9.1.4, 7.9.1.5, 7.9.1.6, 7.9.1.7, 7.9.1.8, 7.9.1.9, 7.9.1.10, 7.9.2.1, 7.9.2.2, 7.9.2.3, 7.9.2.4, 7.9.2.5, 7.9.2.6, 7.9.2.7, 7.9.2.8, 7.9.2.9, 7.9.2.10, 7.9.3.1, 7.9.3.2, 7.9.3.3, 7.9.3.4, 7.9.3.5, 7.9.3.6, 7.9.3.7, 7.9.3.8, 7.9.3.9, 7.9.3.10, 7.9.4.1, 7.9.4.2, 7.9.4.3, 7.9.4.4, 7.9.4.5, 7.9.4.6, 7.9.4.7, 7.9.4.8, 7.9.4.9, 7.9.4.10, 7.9.5.1, 7.9.5.2, 7.9.5.3, 7.9.5.4, 7.9.5.5, 7.9.5.6, 7.9.5.7, 7.9.5.8, 7.9.5.9, 7.9.5.10, 7.9.6.1, 7.9.6.2, 7.9.6.3, 7.9.6.4, 7.9.6.5, 7.9.6.6, 7.9.6.7, 7.9.6.8, 7.9.6.9, 7.9.6.10, 7.9.7.1, 7.9.7.2, 7.9.7.3, 7.9.7.4, 7.9.7.5, 7.9.7.6, 7.9.7.7, 7.9.7.8, 7.9.7.9, 7.9.7.10, 7.9.8.1, 7.9.8.2, 7.9.8.3, 7.9.8.4, 7.9.8.5, 7.9.8.6, 7.9.8.7, 7.9.8.8, 7.9.8.9, 7.9.8.10, 7.9.9.1, 7.9.9.2, 7.9.9.3, 7.9.9.4, 7.9.9.5, 7.9.9.6, 7.9.9.7, 7.9.9.8, 7.9.9.9, 7.9.9.10, 7.9.10.1, 7.9.10.2, 7.9.10.3, 7.9.10.4, 7.9.10.5, 7.9.10.6, 7.9.10.7, 7.9.10.8, 7.9.10.9, 7.9.10.10, 7.10.1.1, 7.10.1.2, 7.10.1.3, 7.10.1.4, 7.10.1.5, 7.10.1.6, 7.10.1.7, 7.10.1.8, 7.10.1.9, 7.10.1.10, 7.10.2.1, 7.10.2.2, 7.10.2.3, 7.10.2.4, 7.10.2.5, 7.10.2.6, 7.10.2.7, 7.10.2.8, 7.10.2.9, 7.10.2.10, 7.10.3.1, 7.10.3.2, 7.10.3.3, 7.10.3.4, 7.10.3.5, 7.10.3.6, 7.10.3.7, 7.10.3.8, 7.10.3.9, 7.10.3.10, 7.10.4.1, 7.10.4.2, 7.10.4.3, 7.10.4.4, 7.10.4.5, 7.10.4.6, 7.10.4.7, 7.10.4.8, 7.10.4.9, 7.10.4.10, 7.10.5.1, 7.10.5.2, 7.10.5.3, 7.10.5.4, 7.10.5.5, 7.10.5.6, 7.10.5.7, 7.10.5.8, 7.10.5.9, 7.10.5.10, 7.10.6.1, 7.10.6.2, 7.10.6.3, 7.10.6.4, 7.10.6.5, 7.10.6.6, 7.10.6.7, 7.10.6.8, 7.10.6.9, 7.10.6.10, 7.10.7.1, 7.10.7.2, 7.10.7.3, 7.10.7.4, 7.10.7.5, 7.10.7.6, 7.10.7.7, 7.10.7.8, 7.10.7.9, 7.10.7.10, 7.10.8.1, 7.10.8.2, 7.10.8.3, 7.10.8.4, 7.10.8.5, 7.10.8.6, 7.10.8.7, 7.10.8.8, 7.10.8.9, 7.10.8.10, 7.10.9.1, 7.10.9.2, 7.10.9.3, 7.10.9.4, 7.10.9.5, 7.10.9.6, 7.10.9.7, 7.10.9.8, 7.10.9.9, 7.10.9.10, 7.10.10.1, 7.10.10.2, 7.10.10.3, 7.10.10.4, 7.10.10.5, 7.10.10.6, 7.10.10.7, 7.10.10.8, 7.10.10.9, 7.10.10.10, 8.1.1.1, 8.1.1.2, 8.1.1.3, 8.1.1.4, 8.1.1.5, 8.1.1.6, 8.1.1.7, 8.1.1.8, 8.1.1.9, 8.1.1.10, 8.1.2.1, 8.1.2.2, 8.1.2.3, 8.1.2.4, 8.1.2.5, 8.1.2.6, 8.1.2.7, 8.1.2.8, 8.1.2.9, 8.1.2.10, 8.1.3.1, 8.1.3.2, 8.1.3.3, 8.1.3.4, 8.1.3.5, 8.1.3.6, 8.1.3.7, 8.1.3.8, 8.1.3.9, 8.1.3.10, 8.1.4.1, 8.1.4.2, 8.1.4.3, 8.1.4.4, 8.1.4.5, 8.1.4.6, 8.1.4.7, 8.1.4.8, 8.1.4.9, 8.1.4.10, 8.1.5.1, 8.1.5.2, 8.1.5.3, 8.1.5.4, 8.1.5.5, 8.1.5.6, 8.1.5.7, 8.1.5.8, 8.1.5.9, 8.1.5.10, 8.1.6.1, 8.1.6.2, 8.1.6.3, 8.1.6.4, 8.1.6.5, 8.1.6.6, 8.1.6.7, 8.1.6.8, 8.1.6.9, 8.1.6.10, 8.1.7.1, 8.1.7.2, 8.1.7.3, 8.1.7.4, 8.1.7.5, 8.1.7.6, 8.1.7.7, 8.1.7.8, 8.1.7.9, 8.1.7.10, 8.1.8.1, 8.1.8.2, 8.1.8.3, 8.1.8.4, 8.1.8.5, 8.1.8.6, 8.1.8.7, 8.1.8.8, 8.1.8.9, 8.1.8.10, 8.1.9.1, 8.1.9.2, 8.1.9.3, 8.1.9.4, 8.1.9.5, 8.1.9.6, 8.1.9.7, 8.1.9.8, 8.1.9.9, 8.1.9.10, 8.1.10.1, 8.1.10.2, 8.1.10.3, 8.1.10.4, 8.1.10.5, 8.1.10.6, 8.1.10.7, 8.1.10.8, 8.1.10.9, 8.1.10.10, 8.2.1.1, 8.2.1.2, 8.2.1.3, 8.2.1.4, 8.2.1.5, 8.2.1.6, 8.2.1.7, 8.2.1.8, 8.2.1.9, 8.2.1.10, 8.2.2.1, 8.2.2.2, 8.2.2.3, 8.2.2.4, 8.2.2.5, 8.2.2.6, 8.2.2.7, 8.2.2.8, 8.2.2.9, 8.2.2.10, 8.2.3.1, 8.2.3.2, 8.2.3.3, 8.2.3.4, 8.2.3.5, 8.2.3.6, 8.2.3.7, 8.2.3.8, 8.2.3.9, 8.2.3.10, 8.2.4.1, 8.2.4.2, 8.2.4.3, 8.2.4.4, 8.2.4.5, 8.2.4.6, 8.2.4.7, 8.2.4.8, 8.2.4.9, 8.2.4.10, 8.2.5.1, 8.2.5.2, 8.2.5.3, 8.2.5.4, 8.2.5.5, 8.2.5.6, 8.2.5.7, 8.2.5.8, 8.2.5.9, 8.2.5.10, 8.2.6.1, 8.2.6.2, 8.2.6.3, 8.2.6.4, 8.2.6.5, 8.2.6.6, 8.2.6.7, 8.2.6.8, 8.2.6.9, 8.2.6.10, 8.2.7.1, 8.2.7.2, 8.2.7.3, 8.2.7.4, 8.2.7.5, 8.2.7.6, 8.2.7.7, 8.2.7.8, 8.2.7.9, 8.2.7.10, 8.2.8.1, 8.2.8.2, 8.2.8.3, 8.2.8.4, 8.2.8.5, 8.2.8.6, 8.2.8.7, 8.2.8.8, 8.2.8.9, 8.2.8.10, 8.2.9.1, 8.2.9.2, 8.2.9.3, 8.2.9.4, 8.2.9.5, 8.2.9.6, 8.2.9.7, 8.2.9.8, 8.2.9.9, 8.2.9.10, 8.2.10.1, 8.2.10.2, 8.2.10.3, 8.2.10.4, 8.2.10.5, 8.2.10.6, 8.2.10.7, 8.2.10.8, 8.2.10.9, 8.2.10.8, 8.3.1.1, 8.3.1.2, 8.3.1.3, 8.3.1.4, 8.3.1.5, 8.3.1.6, 8.3.1.7, 8.3.1.8, 8.3.1.9, 8.3.1.10, 8.3.2.1, 8.3.2.2, 8.3.2.3, 8.3.2.4, 8.3.2.5, 8.3.2.6, 8.3.2.7, 8.3.2.8, 8.3.2.9, 8.3.2.10, 8.3.3.1, 8.3.3.2, 8.3.3.3, 8.3.3.4, 8.3.3.5, 8.3.3.6, 8.3.3.7, 8.3.3.8, 8.3.3.9, 8.3.3.10, 8.3.4.1, 8.3.4.2, 8.3.4.3, 8.3.4.4, 8.3.4.5, 8.3.4.6, 8.3.4.7, 8.3.4.8, 8.3.4.9, 8.3.4.10, 8.3.5.1, 8.3.5.2, 8.3.5.3, 8.3.5.4, 8.3.5.5, 8.3.5.6, 8.3.5.7, 8.3.5.8, 8.3.5.9, 8.3.5.10, 8.3.6.1, 8.3.6.2, 8.3.6.3, 8.3.6.4, 8.3.6.5, 8.3.6.6, 8.3.6.7, 8.3.6.8, 8.3.6.9, 8.3.6.10, 8.3.7.1, 8.3.7.2, 8.3.7.3, 8.3.7.4, 8.3.7.5, 8.3.7.6, 8.3.7.7, 8.3.7.8, 8.3.7.9, 8.3.7.10, 8.3.8.1, 8.3.8.2, 8.3.8.3, 8.3.8.4, 8.3.8.5, 8.3.8.6, 8.3.8.7, 8.3.8.8, 8.3.8.9, 8.3.8.10, 8.3.9.1, 8.3.9.2, 8.3.9.3, 8.3.9.4, 8.3.9.5, 8.3.9.6, 8.3.9.7, 8.3.9.8, 8.3.9.9, 8.3.9.10, 8.3.10.1, 8.3.10.2, 8.3.10.3, 8.3.10.4, 8.3.10.5, 8.3.10.6, 8.3.10.7, 8.3.10.8, 8.3.10.9, 8.3.10.10, 8.4.1.1, 8.4.1.2, 8.4.1.3, 8.4.1.4, 8.4.1.5, 8.4.1.6, 8.4.1.7, 8.4.1.8, 8.4.1.9, 8.4.1.10, 8.4.2.1, 8.4.2.2, 8.4.2.3, 8.4.2.4, 8.4.2.5, 8.4.2.6, 8.4.2.7, 8.4.2.8, 8.4.2.9, 8.4.2.10, 8.4.3.1, 8.4.3.2, 8.4.3.3, 8.4.3.4, 8.4.3.5, 8.4.3.6, 8.4.3.7, 8.4.3.8, 8.4.3.9, 8.4.3.10, 8.4.4.1, 8.4.4.2, 8.4.4.3, 8.4.4.4, 8.4.4.5, 8.4.4.6, 8.4.4.7, 8.4.4.8, 8.4.4.9, 8.4.4.10, 8.4.5.1, 8.4.5.2, 8.4.5.3, 8.4.5.4, 8.4.5.5, 8.4.5.6, 8.4.5.7, 8.4.5.8, 8.4.5.9, 8.4.5.10, 8.4.6.1, 8.4.6.2, 8.4.6.3, 8.4.6.4, 8.4.6.5, 8.4.6.6, 8.4.6.7, 8.4.6.8, 8.4.6.9, 8.4.6.10, 8.4.7.1, 8.4.7.2, 8.4.7.3, 8.4.7.4, 8.4.7.5, 8.4.7.6, 8.4.7.7, 8.4.7.8, 8.4.7.9, 8.4.7.10, 8.4.8.1, 8.4.8.2, 8.4.8.3, 8.4.8.4, 8.4.8.5, 8.4.8.6, 8.4.8.7, 8.4.8.8, 8.4.8.9, 8.4.8.10, 8.4.9.1, 8.4.9.2, 8.4.9.3, 8.4.9.4, 8.4.9.5, 8.4.9.6, 8.4.9.7, 8.4.9.8, 8.4.9.9, 8.4.9.10, 8.4.10.1, 8.4.10.2, 8.4.10.3, 8.4.10.4, 8.4.10.5, 8.4.10.6, 8.4.10.7, 8.4.10.8, 8.4.10.9, 8.4.10.10, 8.5.1.1, 8.5.1.2, 8.5.1.3, 8.5.1.4, 8.5.1.5, 8.5.1.6, 8.5.1.7, 8.5.1.8, 8.5.1.9, 8.5.1.10, 8.5.2.1, 8.5.2.2, 8.5.2.3, 8.5.2.4, 8.5.2.5, 8.5.2.6, 8.5.2.7, 8.5.2.8, 8.5.2.9, 8.5.2.10, 8.5.3.1, 8.5.3.2, 8.5.3.3, 8.5.3.4, 8.5.3.5, 8.5.3.6, 8.5.3.7, 8.5.3.8, 8.5.3.9, TABLE B-continued 8.5.3.10, 8.5.4.1, 8.5.4.2, 8.5.4.3, 8.5.4.4, 8.5.4.5, 8.5.4.6, 8.5.4.7, 8.5.4.8, 8.5.4.9, 8.5.4.10, 8.5.5.1,
8.5.5.2, 8.5.5.3, 8.5.5.4, 8.5.5.5, 8.5.5.6, 8.5.5.7, 8.5.5.8, 8.5.5.9, 8.5.5.10, 8.5.6.1, 8.5.6.2, 8.5.6.3,
8.5.6.4, 8.5.6.5, 8.5.6.6, 8.5.6.7, 8.5.6.8, 8.5.6.9, 8.5.6.10, 8.5.7.1, 8.5.7.2, 8.5.7.3, 8.5.7.4, 8.5.7.5,
8.5.7.6, 8.5.7.7, 8.5.7.8, 8.5.7.9, 8.5.7.10, 8.5.8.1, 8.5.8.2, 8.5.8.3, 8.5.8.4, 8.5.8.5, 8.5.8.6, 8.5.8.7,
8.5.8.8, 8.5.8.9, 8.5.8.10, 8.5.9.1, 8.5.9.2, 8.5.9.3, 8.5.9.4, 8.5.9.5, 8.5.9.6, 8.5.9.7, 8.5.9.8, 8.5.9.9,
8.5.9.10, 8.5.10.1, 8.5.10.2, 8.5.10.3, 8.5.10.4, 8.5.10.5, 8.5.10.6, 8.5.10.7, 8.5.10.8, 8.5.10.9, 8.5.10.10,
8.6.1.1, 8.6.1.2, 8.6.1.3, 8.6.1.4, 8.6.1.5, 8.6.1.6, 8.6.1.7, 8.6.1.8, 8.6.1.9, 8.6.1.10, 8.6.2.1, 8.6.2.2,
8.6.2.3, 8.6.2.4, 8.6.2.5, 8.6.2.6, 8.6.2.7, 8.6.2.8, 8.6.2.9, 8.6.2.10, 8.6.3.1, 8.6.3.2, 8.6.3.3, 8.6.3.4,
8.6.3.5, 8.6.3.6, 8.6.3.7, 8.6.3.8, 8.6.3.9, 8.6.3.10, 8.6.4.1, 8.6.4.2, 8.6.4.3, 8.6.4.4, 8.6.4.5, 8.6.4.6,
8.6.4.7, 8.6.4.8, 8.6.4.9, 8.6.4.10, 8.6.5.1, 8.6.5.2, 8.6.5.3, 8.6.5.4, 8.6.5.5, 8.6.5.6, 8.6.5.7, 8.6.5.8,
8.6.5.9, 8.6.5.10, 8.6.6.1, 8.6.6.2, 8.6.6.3, 8.6.6.4, 8.6.6.5, 8.6.6.6, 8.6.6.7, 8.6.6.8, 8.6.6.9, 8.6.6.10,
8.6.7.1, 8.6.7.2, 8.6.7.3, 8.6.7.4, 8.6.7.5, 8.6.7.6, 8.6.7.7, 8.6.7.8, 8.6.7.9, 8.6.7.10, 8.6.8.1, 8.6.8.2,
8.6.8.3, 8.6.8.4, 8.6.8.5, 8.6.8.6, 8.6.8.7, 8.6.8.8, 8.6.8.9, 8.6.8.10, 8.6.9.1, 8.6.9.2, 8.6.9.3, 8.6.9.4,
8.6.9.5, 8.6.9.6, 8.6.9.7, 8.6.9.8, 8.6.9.9, 8.6.9.10, 8.6.10.1, 8.6.10.2, 8.6.10.3, 8.6.10.4, 8.6.10.5,
8.6.10.6, 8.6.10.7, 8.6.10.8, 8.6.10.9, 8.6.10.10, 8.7.1.1, 8.7.1.2, 8.7.1.3, 8.7.1.4, 8.7.1.5, 8.7.1.6, 8.7.1.7,
8.7.1.8, 8.7.1.9, 8.7.1.10, 8.7.2.1, 8.7.2.2, 8.7.2.3, 8.7.2.4, 8.7.2.5, 8.7.2.6, 8.7.2.7, 8.7.2.8, 8.7.2.9,
8.7.2.10, 8.7.3.1, 8.7.3.2, 8.7.3.3, 8.7.3.4, 8.7.3.5, 8.7.3.6, 8.7.3.7, 8.7.3.8, 8.7.3.9, 8.7.3.10, 8.7.4.1,
8.7.4.2, 8.7.4.3, 8.7.4.4, 8.7.4.5, 8.7.4.6, 8.7.4.7, 8.7.4.8, 8.7.4.9, 8.7.4.10, 8.7.5.1, 8.7.5.2, 8.7.5.3,
8.7.5.4, 8.7.5.5, 8.7.5.6, 8.7.5.7, 8.7.5.8, 8.7.5.9, 8.7.5.10, 8.7.6.1, 8.7.6.2, 8.7.6.3, 8.7.6.4, 8.7.6.5,
8.7.6.6, 8.7.6.7, 8.7.6.8, 8.7.6.9, 8.7.6.10, 8.7.7.1, 8.7.7.2, 8.7.7.3, 8.7.7.4, 8.7.7.5, 8.7.7.6, 8.7.7.7,
8.7.7.8, 8.7.7.9, 8.7.7.10, 8.7.8.1, 8.7.8.2, 8.7.8.3, 8.7.8.4, 8.7.8.5, 8.7.8.6, 8.7.8.7, 8.7.8.8, 8.7.8.9,
8.7.8.10, 8.7.9.1, 8.7.9.2, 8.7.9.3, 8.7.9.4, 8.7.9.5, 8.7.9.6, 8.7.9.7, 8.7.9.8, 8.7.9.9, 8.7.9.10, 8.7.10.1,
8.7.10.2, 8.7.10.3, 8.7.10.4, 8.7.10.5, 8.7.10.6, 8.7.10.7, 8.7.10.8, 8.7.10.9, 8.7.10.10, 8.8.1.1, 8.8.1.2,
8.8.1.3, 8.8.1.4, 8.8.1.5, 8.8.1.6, 8.8.1.7, 8.8.1.8, 8.8.1.9, 8.8.1.10, 8.8.2.1, 8.8.2.2, 8.8.2.3, 8.8.2.4,
8.8.2.5, 8.8.2.6, 8.8.2.7, 8.8.2.8, 8.8.2.9, 8.8.2.10, 8.8.3.1, 8.8.3.2, 8.8.3.3, 8.8.3.4, 8.8.3.5, 8.8.3.6,
8.8.3.7, 8.8.3.8, 8.8.3.9, 8.8.3.10, 8.8.4.1, 8.8.4.2, 8.8.4.3, 8.8.4.4, 8.8.4.5, 8.8.4.6, 8.8.4.7, 8.8.4.8,
8.8.4.9, 8.8.4.10, 8.8.5.1, 8.8.5.2, 8.8.5.3, 8.8.5.4, 8.8.5.5, 8.8.5.6, 8.8.5.7, 8.8.5.8, 8.8.5.9, 8.8.5.10,
8.8.6.1, 8.8.6.2, 8.8.6.3, 8.8.6.4, 8.8.6.5, 8.8.6.6, 8.8.6.7, 8.8.6.8, 8.8.6.9, 8.8.6.10, 8.8.7.1, 8.8.7.2,
8.8.7.3, 8.8.7.4, 8.8.7.5, 8.8.7.6, 8.8.7.7, 8.8.7.8, 8.8.7.9, 8.8.7.10, 8.8.8.1, 8.8.8.2, 8.8.8.3, 8.8.8.4,
8.8.8.5, 8.8.8.6, 8.8.8.7, 8.8.8.8, 8.8.8.9, 8.8.8.10, 8.8.9.1, 8.8.9.2, 8.8.9.3, 8.8.9.4, 8.8.9.5, 8.8.9.6,
8.8.9.7, 8.8.9.8, 8.8.9.9, 8.8.9.10, 8.8.10.1, 8.8.10.2, 8.8.10.3, 8.8.10.4, 8.8.10.5, 8.8.10.6, 8.8.10.7,
8.8.10.8, 8.8.10.9, 8.8.10.10, 8.9.1.1, 8.9.1.2, 8.9.1.3, 8.9.1.4, 8.9.1.5, 8.9.1.6, 8.9.1.7, 8.9.1.8, 8.9.1.9,
8.9.1.10, 8.9.2.1, 8.9.2.2, 8.9.2.3, 8.9.2.4, 8.9.2.5, 8.9.2.6, 8.9.2.7, 8.9.2.8, 8.9.2.9, 8.9.2.10, 8.9.3.1,
8.9.3.2, 8.9.3.3, 8.9.3.4, 8.9.3.5, 8.9.3.6, 8.9.3.7, 8.9.3.8, 8.9.3.9, 8.9.3.10, 8.9.4.1, 8.9.4.2, 8.9.4.3,
8.9.4.4, 8.9.4.5, 8.9.4.6, 8.9.4.7, 8.9.4.8, 8.9.4.9, 8.9.4.10, 8.9.5.1, 8.9.5.2, 8.9.5.3, 8.9.5.4, 8.9.5.5,
8.9.5.6, 8.9.5.7, 8.9.5.8, 8.9.5.9, 8.9.5.10, 8.9.6.1, 8.9.6.2, 8.9.6.3, 8.9.6.4, 8.9.6.5, 8.9.6.6, 8.9.6.7,
8.9.6.8, 8.9.6.9, 8.9.6.10, 8.9.7.1, 8.9.7.2, 8.9.7.3, 8.9.7.4, 8.9.7.5, 8.9.7.6, 8.9.7.7, 8.9.7.8, 8.9.7.9,
8.9.7.10, 8.9.8.1, 8.9.8.2, 8.9.8.3, 8.9.8.4, 8.9.8.5, 8.9.8.6, 8.9.8.7, 8.9.8.8, 8.9.8.9, 8.9.8.10, 8.9.9.1,
8.9.9.2, 8.9.9.3, 8.9.9.4, 8.9.9.5, 8.9.9.6, 8.9.9.7, 8.9.9.8, 8.9.9.9, 8.9.9.10, 8.9.10.1, 8.9.10.2, 8.9.10.3,
8.9.10.4, 8.9.10.5, 8.9.10.6, 8.9.10.7, 8.9.10.8, 8.9.10.9, 8.9.10.10, 8.10.1.1, 8.10.1.2, 8.10.1.3, 8.10.1.4,
8.10.1.5, 8.10.1.6, 8.10.1.7, 8.10.1.8, 8.10.1.9, 8.10.1.10, 8.10.2.1, 8.10.2.2, 8.10.2.3, 8.10.2.4, 8.10.2.5,
8.10.2.6, 8.10.2.7, 8.10.2.8, 8.10.2.9, 8.10.2.10, 8.10.3.1, 8.10.3.2, 8.10.3.3, 8.10.3.4, 8.10.3.5, 8.10.3.6,
8.10.3.7, 8.10.3.8, 8.10.3.9, 8.10.3.10, 8.10.4.1, 8.10.4.2, 8.10.4.3, 8.10.4.4, 8.10.4.5, 8.10.4.6, 8.10.4.7,
8.10.4.8, 8.10.4.9, 8.10.4.10, 8.10.5.1, 8.10.5.2, 8.10.5.3, 8.10.5.4, 8.10.5.5, 8.10.5.6, 8.10.5.7, 8.10.5.8,
8.10.5.9, 8.10.5.10, 8.10.6.1, 8.10.6.2, 8.10.6.3, 8.10.6.4, 8.10.6.5, 8.10.6.6, 8.10.6.7, 8.10.6.8, 8.10.6.9,
8.10.6.10, 8.10.7.1, 8.10.7.2, 8.10.7.3, 8.10.7.4, 8.10.7.5, 8.10.7.6, 8.10.7.7, 8.10.7.8, 8.10.7.9, 8.10.7.10,
8.10.8.1, 8.10.8.2, 8.10.8.3, 8.10.8.4, 8.10.8.5, 8.10.8.6, 8.10.8.7, 8.10.8.8, 8.10.8.9, 8.10.8.10, 8.10.9.1,
8.10.9.2, 8.10.9.3, 8.10.9.4, 8.10.9.5, 8.10.9.6, 8.10.9.7, 8.10.9.8, 8.10.9.9, 8.10.9.10, 8.10.10.1,
8.10.10.2, 8.10.10.3, 8.10.10.4, 8.10.10.5, 8.10.10.6, 8.10.10.7, 8.10.10.8, 8.10.10.9, 8.10.10.10, 9.1.1.1,
9.1.1.2, 9.1.1.3, 9.1.1.4, 9.1.1.5, 9.1.1.6, 9.1.1.7, 9.1.1.8, 9.1.1.9, 9.1.1.10, 9.1.2.1, 9.1.2.2, 9.1.2.3,
9.1.2.4, 9.1.2.5, 9.1.2.6, 9.1.2.7, 9.1.2.8, 9.1.2.9, 9.1.2.10, 9.1.3.1, 9.1.3.2, 9.1.3.3, 9.1.3.4, 9.1.3.5,
9.1.3.6, 9.1.3.7, 9.1.3.8, 9.1.3.9, 9.1.3.10, 9.1.4.1, 9.1.4.2, 9.1.4.3, 9.1.4.4, 9.1.4.5, 9.1.4.6, 9.1.4.7,
9.1.4.8, 9.1.4.9, 9.1.4.10, 9.1.5.1, 9.1.5.2, 9.1.5.3, 9.1.5.4, 9.1.5.5, 9.1.5.6, 9.1.5.7, 9.1.5.8, 9.1.5.9,
9.1.5.10, 9.1.6.1, 9.1.6.2, 9.1.6.3, 9.1.6.4, 9.1.6.5, 9.1.6.6, 9.1.6.7, 9.1.6.8, 9.1.6.9, 9.1.6.10, 9.1.7.1,
9.1.7.2, 9.1.7.3, 9.1.7.4, 9.1.7.5, 9.1.7.6, 9.1.7.7, 9.1.7.8, 9.1.7.9, 9.1.7.10, 9.1.8.1, 9.1.8.2, 9.1.8.3,
9.1.8.4, 9.1.8.5, 9.1.8.6, 9.1.8.7, 9.1.8.8, 9.1.8.9, 9.1.8.10, 9.1.9.1, 9.1.9.2, 9.1.9.3, 9.1.9.4, 9.1.9.5,
9.1.9.6, 9.1.9.7, 9.1.9.8, 9.1.9.9, 9.1.9.10, 9.1.10.1, 9.1.10.2, 9.1.10.3, 9.1.10.4, 9.1.10.5, 9.1.10.6,
9.1.10.7, 9.1.10.8, 9.1.10.9, 9.1.10.10, 9.2.1.1, 9.2.1.2, 9.2.1.3, 9.2.1.4, 9.2.1.5, 9.2.1.6, 9.2.1.7, 9.2.1.8,
9.2.1.9, 9.2.1.10, 9.2.2.1, 9.2.2.2, 9.2.2.3, 9.2.2.4, 9.2.2.5, 9.2.2.6, 9.2.2.7, 9.2.2.8, 9.2.2.9, 9.2.2.10,
9.2.3.1, 9.2.3.2, 9.2.3.3, 9.2.3.4, 9.2.3.5, 9.2.3.6, 9.2.3.7, 9.2.3.8, 9.2.3.9, 9.2.3.10, 9.2.4.1, 9.2.4.2,
9.2.4.3, 9.2.4.4, 9.2.4.5, 9.2.4.6, 9.2.4.7, 9.2.4.8, 9.2.4.9, 9.2.4.10, 9.2.5.1, 9.2.5.2, 9.2.5.3, 9.2.5.4,
9.2.5.5, 9.2.5.6, 9.2.5.7, 9.2.5.8, 9.2.5.9, 9.2.5.10, 9.2.6.1, 9.2.6.2, 9.2.6.3, 9.2.6.4, 9.2.6.5, 9.2.6.6,
9.2.6.7, 9.2.6.8, 9.2.6.9, 9.2.6.10, 9.2.7.1, 9.2.7.2, 9.2.7.3, 9.2.7.4, 9.2.7.5, 9.2.7.6, 9.2.7.7, 9.2.7.8,
9.2.7.9, 9.2.7.10, 9.2.8.1, 9.2.8.2, 9.2.8.3, 9.2.8.4, 9.2.8.5, 9.2.8.6, 9.2.8.7, 9.2.8.8, 9.2.8.9, 9.2.8.10,
9.2.9.1, 9.2.9.2, 9.2.9.3, 9.2.9.4, 9.2.9.5, 9.2.9.6, 9.2.9.7, 9.2.9.8, 9.2.9.9, 9.2.9.10, 9.2.10.1, 9.2.10.2,
9.2.10.3, 9.2.10.4, 9.2.10.5, 9.2.10.6, 9.2.10.7, 9.2.10.8, 9.2.10.9, 9.2.10.10, 9.3.1.1, 9.3.1.2, 9.3.1.3,
9.3.1.4, 9.3.1.5, 9.3.1.6, 9.3.1.7, 9.3.1.8, 9.3.1.9, 9.3.1.10, 9.3.2.1, 9.3.2.2, 9.3.2.3, 9.3.2.4, 9.3.2.5,
9.3.2.6, 9.3.2.7, 9.3.2.8, 9.3.2.9, 9.3.2.10, 9.3.3.1, 9.3.3.2, 9.3.3.3, 9.3.3.4, 9.3.3.5, 9.3.3.6, 9.3.3.7,
9.3.3.8, 9.3.3.9, 9.3.3.10, 9.3.4.1, 9.3.4.2, 9.3.4.3, 9.3.4.4, 9.3.4.5, 9.3.4.6, 9.3.4.7, 9.3.4.8, 9.3.4.9,
9.3.4.10, 9.3.5.1, 9.3.5.2, 9.3.5.3, 9.3.5.4, 9.3.5.5, 9.3.5.6, 9.3.5.7, 9.3.5.8, 9.3.5.9, 9.3.5.10, 9.3.6.1,
9.3.6.2, 9.3.6.3, 9.3.6.4, 9.3.6.5, 9.3.6.6, 9.3.6.7, 9.3.6.8, 9.3.6.9, 9.3.6.10, 9.3.7.1, 9.3.7.2, 9.3.7.3,
9.3.7.4, 9.3.7.5, 9.3.7.6, 9.3.7.7, 9.3.7.8, 9.3.7.9, 9.3.7.10, 9.3.8.1, 9.3.8.2, 9.3.8.3, 9.3.8.4, 9.3.8.5,
9.3.8.6, 9.3.8.7, 9.3.8.8, 9.3.8.9, 9.3.8.10, 9.3.9.1, 9.3.9.2, 9.3.9.3, 9.3.9.4, 9.3.9.5, 9.3.9.6, 9.3.9.7,
9.3.9.8, 9.3.9.9, 9.3.9.10, 9.3.10.1, 9.3.10.2, 9.3.10.3, 9.3.10.4, 9.3.10.5, 9.3.10.6, 9.3.10.7, 9.3.10.8,
9.3.10.9, 9.3.10.10, 9.4.1.1, 9.4.1.2, 9.4.1.3, 9.4.1.4, 9.4.1.5, 9.4.1.6, 9.4.1.7, 9.4.1.8, 9.4.1.9, 9.4.1.10,
9.4.2.1, 9.4.2.2, 9.4.2.3, 9.4.2.4, 9.4.2.5, 9.4.2.6, 9.4.2.7, 9.4.2.8, 9.4.2.9, 9.4.2.10, 9.4.3.1, 9.4.3.2,
9.4.3.3, 9.4.3.4, 9.4.3.5, 9.4.3.6, 9.4.3.7, 9.4.3.8, 9.4.3.9, 9.4.3.10, 9.4.4.1, 9.4.4.2, 9.4.4.3, 9.4.4.4,
9.4.4.5, 9.4.4.6, 9.4.4.7, 9.4.4.8, 9.4.4.9, 9.4.4.10, 9.4.5.1, 9.4.5.2, 9.4.5.3, 9.4.5.4, 9.4.5.5, 9.4.5.6,
9.4.5.7, 9.4.5.8, 9.4.5.9, 9.4.5.10, 9.4.6.1, 9.4.6.2, 9.4.6.3, 9.4.6.4, 9.4.6.5, 9.4.6.6, 9.4.6.7, 9.4.6.8,
9.4.6.9, 9.4.6.10, 9.4.7.1, 9.4.7.2, 9.4.7.3, 9.4.7.4, 9.4.7.5, 9.4.7.6, 9.4.7.7, 9.4.7.8, 9.4.7.9, 9.4.7.10, TABLE B-continued 9.4.8.1, 9.4.8.2, 9.4.8.3, 9.4.8.4, 9.4.8.5, 9.4.8.6, 9.4.8.7, 9.4.8.8, 9.4.8.9, 9.4.8.10, 9.4.9.1, 9.4.9.2, 9.4.9.3, 9.4.9.4, 9.4.9.5, 9.4.9.6, 9.4.9.7, 9.4.9.8, 9.4.9.9, 9.4.9.10, 9.4.10.1, 9.4.10.2, 9.4.10.3, 9.4.10.4, 9.4.10.5, 9.4.10.6, 9.4.10.7, 9.4.10.8, 9.4.10.9, 9.4.10.10, 9.5.1.1, 9.5.1.2, 9.5.1.3, 9.5.1.4, 9.5.1.5, 9.5.1.6, 9.5.1.7, 9.5.1.8, 9.5.1.9, 9.5.1.10, 9.5.2.1, 9.5.2.2, 9.5.2.3, 9.5.2.4, 9.5.2.5, 9.5.2.6, 9.5.2.7, 9.5.2.8, 9.5.2.9, 9.5.2.10, 9.5.3.1, 9.5.3.2, 9.5.3.3, 9.5.3.4, 9.5.3.5, 9.5.3.6, 9.5.3.7, 9.5.3.8, 9.5.3.9, 9.5.3.10, 9.5.4.1, 9.5.4.2, 9.5.4.3, 9.5.4.4, 9.5.4.5, 9.5.4.6, 9.5.4.7, 9.5.4.8, 9.5.4.9, 9.5.4.10, 9.5.5.1, 9.5.5.2, 9.5.5.3, 9.5.5.4, 9.5.5.5, 9.5.5.6, 9.5.5.7, 9.5.5.8, 9.5.5.9, 9.5.5.10, 9.5.6.1, 9.5.6.2, 9.5.6.3, 9.5.6.4, 9.5.6.5, 9.5.6.6, 9.5.6.7, 9.5.6.8, 9.5.6.9, 9.5.6.10, 9.5.7.1, 9.5.7.2, 9.5.7.3, 9.5.7.4, 9.5.7.5, 9.5.7.6, 9.5.7.7, 9.5.7.8, 9.5.7.9, 9.5.7.10, 9.5.8.1, 9.5.8.2, 9.5.8.3, 9.5.8.4, 9.5.8.5, 9.5.8.6, 9.5.8.7, 9.5.8.8, 9.5.8.9, 9.5.8.10, 9.5.9.1, 9.5.9.2, 9.5.9.3, 9.5.9.4, 9.5.9.5, 9.5.9.6, 9.5.9.7, 9.5.9.8, 9.5.9.9, 9.5.9.10, 9.5.10.2, 9.5.10.3, 9.5.10.4, 9.5.10.5, 9.5.10.6, 9.5.10.7, 9.5.10.8, 9.5.10.9, 9.5.10.10, 9.6.1.1, 9.6.1.2, 9.6.1.3, 9.6.1.4, 9.6.1.5, 9.6.1.6, 9.6.1.7, 9.6.1.8, 9.6.1.9, 9.6.1.10, 9.6.2.1, 9.6.2.2, 9.6.2.3, 9.6.2.4, 9.6.2.5, 9.6.2.6, 9.6.2.7, 9.6.2.8, 9.6.2.9, 9.6.2.10, 9.6.3.1, 9.6.3.2, 9.6.3.3, 9.6.3.4, 9.6.3.5, 9.6.3.6, 9.6.3.7, 9.6.3.8, 9.6.3.9, 9.6.3.10, 9.6.4.1, 9.6.4.2, 9.6.4.3, 9.6.4.4, 9.6.4.5, 9.6.4.6, 9.6.4.7, 9.6.4.8, 9.6.4.9, 9.6.4.10, 9.6.5.1, 9.6.5.2, 9.6.5.3, 9.6.5.4, 9.6.5.5, 9.6.5.6, 9.6.5.7, 9.6.5.8, 9.6.5.9, 9.6.5.10, 9.6.6.1, 9.6.6.2, 9.6.6.3, 9.6.6.4, 9.6.6.5, 9.6.6.6, 9.6.6.7, 9.6.6.8, 9.6.6.9, 9.6.6.10, 9.6.7.1, 9.6.7.2, 9.6.7.3, 9.6.7.4, 9.6.7.5, 9.6.7.6, 9.6.7.7, 9.6.7.8, 9.6.7.9, 9.6.7.10, 9.6.8.1, 9.6.8.2, 9.6.8.3, 9.6.8.4, 9.6.8.5, 9.6.8.6, 9.6.8.7, 9.6.8.8, 9.6.8.9, 9.6.8.10, 9.6.9.1, 9.6.9.2, 9.6.9.3, 9.6.9.4, 9.6.9.5, 9.6.9.6, 9.6.9.7, 9.6.9.8, 9.6.9.9, 9.6.9.10, 9.6.10.1, 9.6.10.2, 9.6.10.3, 9.6.10.4, 9.6.10.5, 9.6.10.6, 9.6.10.7, 9.6.10.8, 9.6.10.9, 9.6.10.10, 9.7.1.1, 9.7.1.2, 9.7.1.3, 9.7.1.4, 9.7.1.5, 9.7.1.6, 9.7.1.7, 9.7.1.8, 9.7.1.9, 9.7.1.10, 9.7.2.1, 9.7.2.2, 9.7.2.3, 9.7.2.4, 9.7.2.5, 9.7.2.6, 9.7.2.7, 9.7.2.8, 9.7.2.9, 9.7.2.10, 9.7.3.1, 9.7.3.2, 9.7.3.3, 9.7.3.4, 9.7.3.5, 9.7.3.6, 9.7.3.7, 9.7.3.8, 9.7.3.9, 9.7.3.10, 9.7.4.1, 9.7.4.2, 9.7.4.3, 9.7.4.4, 9.7.4.5, 9.7.4.6, 9.7.4.7, 9.7.4.8, 9.7.4.9, 9.7.4.10, 9.7.5.1, 9.7.5.2, 9.7.5.3, 9.7.5.4, 9.7.5.5, 9.7.5.6, 9.7.5.7, 9.7.5.8, 9.7.5.9, 9.7.5.10, 9.7.6.1, 9.7.6.2, 9.7.6.3, 9.7.6.4, 9.7.6.5, 9.7.6.6, 9.7.6.7, 9.7.6.8, 9.7.6.9, 9.7.6.10, 9.7.7.1, 9.7.7.2, 9.7.7.3, 9.7.7.4, 9.7.7.5, 9.7.7.6, 9.7.7.7, 9.7.7.8, 9.7.7.9, 9.7.7.10, 9.7.8.1, 9.7.8.2, 9.7.8.3, 9.7.8.4, 9.7.8.5, 9.7.8.6, 9.7.8.7, 9.7.8.8, 9.7.8.9, 9.7.8.10, 9.7.9.1, 9.7.9.2, 9.7.9.3, 9.7.9.4, 9.7.9.5, 9.7.9.6, 9.7.9.7, 9.7.9.8, 9.7.9.9, 9.7.9.10, 9.7.10.1, 9.7.10.2, 9.7.10.3, 9.7.10.4, 9.7.10.5, 9.7.10.6, 9.7.10.7, 9.7.10.8, 9.7.10.9, 9.7.10.10, 9.8.1.1, 9.8.1.2, 9.8.1.3, 9.8.1.4, 9.8.1.5, 9.8.1.6, 9.8.1.7, 9.8.1.8, 9.8.1.9, 9.8.1.10, 9.8.2.1, 9.8.2.2, 9.8.2.3, 9.8.2.4, 9.8.2.5, 9.8.2.6, 9.8.2.7, 9.8.2.8, 9.8.2.9, 9.8.2.10, 9.8.3.1, 9.8.3.2, 9.8.3.3, 9.8.3.4, 9.8.3.5, 9.8.3.6, 9.8.3.7, 9.8.3.8, 9.8.3.9, 9.8.3.10, 9.8.4.1, 9.8.4.2, 9.8.4.3, 9.8.4.4, 9.8.4.5, 9.8.4.6, 9.8.4.7, 9.8.4.8, 9.8.4.9, 9.8.4.10, 9.8.5.1, 9.8.5.2, 9.8.5.3, 9.8.5.4, 9.8.5.5, 9.8.5.6, 9.8.5.7, 9.8.5.8, 9.8.5.9, 9.8.5.10, 9.8.6.1, 9.8.6.2, 9.8.6.3, 9.8.6.4, 9.8.6.5, 9.8.6.6, 9.8.6.7, 9.8.6.8, 9.8.6.9, 9.8.6.10, 9.8.7.1, 9.8.7.2, 9.8.7.3, 9.8.7.4, 9.8.7.5, 9.8.7.6, 9.8.7.7, 9.8.7.8, 9.8.7.9, 9.8.7.10, 9.8.8.1, 9.8.8.2, 9.8.8.3, 9.8.8.4, 9.8.8.5, 9.8.8.6, 9.8.8.7, 9.8.8.8, 9.8.8.9, 9.8.8.10, 9.8.9.1, 9.8.9.2, 9.8.9.3, 9.8.9.4, 9.8.9.5, 9.8.9.6, 9.8.9.7, 9.8.9.8, 9.8.9.9, 9.8.9.10, 9.8.10.1, 9.8.10.2, 9.8.10.3, 9.8.10.4, 9.8.10.5, 9.8.10.6, 9.8.10.7, 9.8.10.8, 9.8.10.9, 9.8.10.10, 9.9.1.1, 9.9.1.2, 9.9.1.3, 9.9.1.4, 9.9.1.5, 9.9.1.6, 9.9.1.7, 9.9.1.8, 9.9.1.9, 9.9.1.10, 9.9.2.1, 9.9.2.2, 9.9.2.3, 9.9.2.4, 9.9.2.5, 9.9.2.6, 9.9.2.7, 9.9.2.8, 9.9.2.9, 9.9.2.10, 9.9.3.1, 9.9.3.2, 9.9.3.3, 9.9.3.4, 9.9.3.5, 9.9.3.6, 9.9.3.7, 9.9.3.8, 9.9.3.9, 9.9.3.10, 9.9.4.1, 9.9.4.2, 9.9.4.3, 9.9.4.4, 9.9.4.5, 9.9.4.6, 9.9.4.7, 9.9.4.8, 9.9.4.9, 9.9.4.10, 9.9.5.1, 9.9.5.2, 9.9.5.3, 9.9.5.4, 9.9.5.5, 9.9.5.6, 9.9.5.7, 9.9.5.8, 9.9.5.9, 9.9.5.10, 9.9.6.1, 9.9.6.2, 9.9.6.3, 9.9.6.4, 9.9.6.5, 9.9.6.6, 9.9.6.7, 9.9.6.8, 9.9.6.9, 9.9.6.10, 9.9.7.1, 9.9.7.2, 9.9.7.3, 9.9.7.4, 9.9.7.5, 9.9.7.6, 9.9.7.7, 9.9.7.8, 9.9.7.9, 9.9.7.10, 9.9.8.1, 9.9.8.2, 9.9.8.3, 9.9.8.4, 9.9.8.5, 9.9.8.6, 9.9.8.7, 9.9.8.8, 9.9.8.9, 9.9.8.10, 9.9.9.1, 9.9.9.2, 9.9.9.3, 9.9.9.4, 9.9.9.5, 9.9.9.6, 9.9.9.7, 9.9.9.8, 9.9.9.9, 9.9.9.10, 9.9.10.1, 9.9.10.2, 9.9.10.3, 9.9.10.4, 9.9.10.5, 9.9.10.6, 9.9.10.7, 9.9.10.8, 9.9.10.9, 9.9.10.10, 9.10.1.1, 9.10.1.2, 9.10.1.3, 9.10.1.4, 9.10.1.5, 9.10.1.6, 9.10.1.7, 9.10.1.8, 9.10.1.9, 9.10.1.10, 9.10.2.1, 9.10.2.2, 9.10.2.3, 9.10.2.4, 9.10.2.5, 9.10.2.6, 9.10.2.7, 9.10.2.8, 9.10.2.9, 9.10.2.10, 9.10.3.1, 9.10.3.2, 9.10.3.3, 9.10.3.4, 9.10.3.5, 9.10.3.6, 9.10.3.7, 9.10.3.8, 9.10.3.9, 9.10.3.10, 9.10.4.1, 9.10.4.2, 9.10.4.3, 9.10.4.4, 9.10.4.5, 9.10.4.6, 9.10.4.7, 9.10.4.8, 9.10.4.9, 9.10.4.10, 9.10.5.1, 9.10.5.2, 9.10.5.3, 9.10.5.4, 9.10.5.5, 9.10.5.6, 9.10.5.7, 9.10.5.8, 9.10.5.9, 9.10.5.10, 9.10.6.1, 9.10.6.2, 9.10.6.3, 9.10.6.4, 9.10.6.5, 9.10.6.6, 9.10.6.7, 9.10.6.8, 9.10.6.9, 9.10.6.10, 9.10.7.1, 9.10.7.2, 9.10.7.3, 9.10.7.4, 9.10.7.5, 9.10.7.6, 9.10.7.7, 9.10.7.8, 9.10.7.9, 9.10.7.10, 9.10.8.1, 9.10.8.2, 9.10.8.3, 9.10.8.4, 9.10.8.5, 9.10.8.6, 9.10.8.7, 9.10.8.8, 9.10.8.9, 9.10.8.10, 9.10.9.1, 9.10.9.2, 9.10.9.3, 9.10.9.4, 9.10.9.5, 9.10.9.6, 9.10.9.7, 9.10.9.8, 9.10.9.9, 9.10.9.10, 9.10.10.1, 9.10.10.2, 9.10.10.3, 9.10.10.4, 9.10.10.5, 9.10.10.6, 9.10.10.7, 9.10.10.8, 9.10.10.9, 9.10.10.10, 10.1.1.1, 10.1.1.2, 10.1.1.3, 10.1.1.4, 10.1.1.5, 10.1.1.6, 10.1.1.7, 10.1.1.8, 10.1.1.9, 10.1.1.10, 10.1.2.1, 10.1.2.2, 10.1.2.3, 10.1.2.4, 10.1.2.5, 10.1.2.6, 10.1.2.7, 10.1.2.8, 10.1.2.9, 10.1.2.10, 10.1.3.1, 10.1.3.2, 10.1.3.3, 10.1.3.4, 10.1.3.5, 10.1.3.6, 10.1.3.7, 10.1.3.8, 10.1.3.9, 10.1.3.10, 10.1.4.1, 10.1.4.2, 10.1.4.3, 10.1.4.4, 10.1.4.5, 10.1.4.6, 10.1.4.7, 10.1.4.8, 10.1.4.9, 10.1.4.10, 10.1.5.1, 10.1.5.2, 10.1.5.3, 10.1.5.4, 10.1.5.5, 10.1.5.6, 10.1.5.7, 10.1.5.8, 10.1.5.9, 10.1.5.10, 10.1.6.1, 10.1.6.2, 10.1.6.3, 10.1.6.4, 10.1.6.5, 10.1.6.6, 10.1.6.7, 10.1.6.8, 10.1.6.9, 10.1.6.10, 10.1.7.1, 10.1.7.2, 10.1.7.3, 10.1.7.4, 10.1.7.5, 10.1.7.6, 10.1.7.7, 10.1.7.8, 10.1.7.9, 10.1.7.10, 10.1.8.1, 10.1.8.2, 10.1.8.3, 10.1.8.4, 10.1.8.5, 10.1.8.6, 10.1.8.7, 10.1.8.8, 10.1.8.9, 10.1.8.10, 10.1.9.1, 10.1.9.2, 10.1.9.3, 10.1.9.4, 10.1.9.5, 10.1.9.6, 10.1.9.7, 10.1.9.8, 10.1.9.9, 10.1.9.10, 10.1.10.1, 10.1.10.2, 10.1.10.3, 10.1.10.4, 10.1.10.5, 10.1.10.6, 10.1.10.7, 10.1.10.8, 10.1.10.9, 10.1.10.10, 10.2.1.1, 10.2.1.2, 10.2.1.3, 10.2.1.4, 10.2.1.5, 10.2.1.6, 10.2.1.7, 10.2.1.8, 10.2.1.9, 10.2.1.10, 10.2.2.1, 10.2.2.2, 10.2.2.3, 10.2.2.4, 10.2.2.5, 10.2.2.6, 10.2.2.7, 10.2.2.8, 10.2.2.9, 10.2.2.10, 10.2.3.1, 10.2.3.2, 10.2.3.3, 10.2.3.4, 10.2.3.5, 10.2.3.6, 10.2.3.7, 10.2.3.8, 10.2.3.9, 10.2.3.10, 10.2.4.1, 10.2.4.2, 10.2.4.3, 10.2.4.4, 10.2.4.5, 10.2.4.6, 10.2.4.7, 10.2.4.8, 10.2.4.9, 10.2.4.10, 10.2.5.1, 10.2.5.2, 10.2.5.3, 10.2.5.4, 10.2.5.5, 10.2.5.6, 10.2.5.7, 10.2.5.8, 10.2.5.9, 10.2.5.10, 10.2.6.1, 10.2.6.2, 10.2.6.3, 10.2.6.4, 10.2.6.5, 10.2.6.6, 10.2.6.7, 10.2.6.8, 10.2.6.9, 10.2.6.10, 10.2.7.1, 10.2.7.2, 10.2.7.3, 10.2.7.4, 10.2.7.5, 10.2.7.6, 10.2.7.7, 10.2.7.8, 10.2.7.9, 10.2.7.10, 10.2.8.1, 10.2.8.2, 10.2.8.3, 10.2.8.4, 10.2.8.5, 10.2.8.6, 10.2.8.7, 10.2.8.8, 10.2.8.9, 10.2.8.10, 10.2.9.1, 10.2.9.2, 10.2.9.3, 10.2.9.4, 10.2.9.5, 10.2.9.6, 10.2.9.7, 10.2.9.8, 10.2.9.9, 10.2.9.10, 10.2.10.1, 10.2.10.2, 10.2.10.3, 10.2.10.4, 10.2.10.5, 10.2.10.6, 10.2.10.7, 10.2.10.8, 10.2.10.9, 10.2.10.10, 10.3.1.1, 10.3.1.2, 10.3.1.3, 10.3.1.4, 10.3.1.5, 10.3.1.6, 10.3.1.7, 10.3.1.8, 10.3.1.9, 10.3.1.10, 10.3.2.1, 10.3.2.2, 10.3.2.3, 10.3.2.4, 10.3.2.5, 10.3.2.6, 10.3.2.7, 10.3.2.8, 10.3.2.9, 10.3.2.10, 10.3.3.1, 10.3.3.2, 10.3.3.3, 10.3.3.4, 10.3.3.5, 10.3.3.6, 10.3.3.7, 10.3.3.8, 10.3.3.9, 10.3.3.10, 10.3.4.1, 10.3.4.2, 10.3.4.3, 10.3.4.4, 10.3.4.5, 10.3.4.6, 10.3.4.7, 10.3.4.8, 10.3.4.9, 10.3.4.10, 10.3.5.1, 10.3.5.2, 10.3.5.3, 10.3.5.4, 10.3.5.5, 10.3.5.6, 10.3.5.7, 10.3.5.8, 10.3.5.9, 10.3.5.10, 10.3.6.1, 10.3.6.2, 10.3.6.3, 10.3.6.4, 10.3.6.5, 10.3.6.6, 10.3.6.7, 10.3.6.8, 10.3.6.9, 10.3.6.10, 10.3.7.1, 10.3.7.2, 10.3.7.3, 10.3.7.4, 10.3.7.5, 10.3.7.6, 10.3.7.7, 10.3.7.8, 10.3.7.9, 10.3.7.10, 10.3.8.1, 10.3.8.2, 10.3.8.3, 10.3.8.4, 10.3.8.5, 10.3.8.6, 10.3.8.7, 10.3.8.8, 10.3.8.9, 10.3.8.10, 10.3.9.1, 10.3.9.2,

TABLE B-continued 10.3.9.3, 10.3.9.4, 10.3.9.5, 10.3.9.6, 10.3.9.7, 10.3.9.8, 10.3.9.9, 10.3.9.10, 10.3.10.1, 10.3.10.2, 10.3.10.3, 10.3.10.4, 10.3.10.5, 10.3.10.6, 10.3.10.7, 10.3.10.8, 10.3.10.9, 10.3.10.10, 10.4.1.1, 10.4.1.2, 10.4.1.3, 10.4.1.4, 10.4.1.5, 10.4.1.6, 10.4.1.7, 10.4.1.8, 10.4.1.9, 10.4.1.10, 10.4.2.1, 10.4.2.2, 10.4.2.3, 10.4.2.4, 10.4.2.5, 10.4.2.6, 10.4.2.7, 10.4.2.8, 10.4.2.9, 10.4.2.10, 10.4.3.1, 10.4.3.2, 10.4.3.3, 10.4.3.4, 10.4.3.5, 10.4.3.6, 10.4.3.7, 10.4.3.8, 10.4.3.9, 10.4.3.10, 10.4.4.1, 10.4.4.2, 10.4.4.3, 10.4.4.4, 10.4.4.5, 10.4.4.6, 10.4.4.7, 10.4.4.8, 10.4.4.9, 10.4.4.10, 10.4.5.1, 10.4.5.2, 10.4.5.3, 10.4.5.4, 10.4.5.5, 10.4.5.6, 10.4.5.7, 10.4.5.8, 10.4.5.9, 10.4.5.10, 10.4.6.1, 10.4.6.2, 10.4.6.3, 10.4.6.4, 10.4.6.5, 10.4.6.6, 10.4.6.7, 10.4.6.8, 10.4.6.9, 10.4.6.10, 10.4.7.1, 10.4.7.2, 10.4.7.3, 10.4.7.4, 10.4.7.5, 10.4.7.6, 10.4.7.7, 10.4.7.8, 10.4.7.9, 10.4.7.10, 10.4.8.1, 10.4.8.2, 10.4.8.3, 10.4.8.4, 10.4.8.5, 10.4.8.6, 10.4.8.7, 10.4.8.8, 10.4.8.9, 10.4.8.10, 10.4.9.1, 10.4.9.2, 10.4.9.3, 10.4.9.4, 10.4.9.5, 10.4.9.6, 10.4.9.7, 10.4.9.8, 10.4.9.9, 10.4.9.10, 10.4.10.1, 10.4.10.2, 10.4.10.3, 10.4.10.4, 10.4.10.5, 10.4.10.6, 10.4.10.7, 10.4.10.8, 10.4.10.9, 10.4.10.10, 10.5.1.1, 10.5.1.2, 10.5.1.3, 10.5.1.4, 10.5.1.5, 10.5.1.6, 10.5.1.7, 10.5.1.8, 10.5.1.9, 10.5.1.10, 10.5.2.1, 10.5.2.2, 10.5.2.3, 10.5.2.4, 10.5.2.5, 10.5.2.6, 10.5.2.7, 10.5.2.8, 10.5.2.9, 10.5.2.10, 10.5.3.1, 10.5.3.2, 10.5.3.3, 10.5.3.4, 10.5.3.5, 10.5.3.6, 10.5.3.7, 10.5.3.8, 10.5.3.9, 10.5.3.10, 10.5.4.1, 10.5.4.2, 10.5.4.3, 10.5.4.4, 10.5.4.5, 10.5.4.6, 10.5.4.7, 10.5.4.8, 10.5.4.9, 10.5.4.10, 10.5.5.1, 10.5.5.2, 10.5.5.3, 10.5.5.4, 10.5.5.5, 10.5.5.6, 10.5.5.7, 10.5.5.8, 10.5.5.9, 10.5.5.10, 10.5.6.1, 10.5.6.2, 10.5.6.3, 10.5.6.4, 10.5.6.5, 10.5.6.6, 10.5.6.7, 10.5.6.8, 10.5.6.9, 10.5.6.10, 10.5.7.1, 10.5.7.2, 10.5.7.3, 10.5.7.4, 10.5.7.5, 10.5.7.6, 10.5.7.7, 10.5.7.8, 10.5.7.9, 10.5.7.10, 10.5.8.1, 10.5.8.2, 10.5.8.3, 10.5.8.4, 10.5.8.5, 10.5.8.6, 10.5.8.7, 10.5.8.8, 10.5.8.9, 10.5.8.10, 10.5.9.1, 10.5.9.2, 10.5.9.3, 10.5.9.4, 10.5.9.5, 10.5.9.6, 10.5.9.7, 10.5.9.8, 10.5.9.9, 10.5.9.10, 10.5.10.1, 10.5.10.2, 10.5.10.3, 10.5.10.4, 10.5.10.5, 10.5.10.6, 10.5.10.7, 10.5.10.8, 10.5.10.9, 10.5.10.10, 10.6.1.1, 10.6.1.2, 10.6.1.3, 10.6.1.4, 10.6.1.5, 10.6.1.6, 10.6.1.7, 10.6.1.8, 10.6.1.9, 10.6.1.10, 10.6.2.1, 10.6.2.2, 10.6.2.3, 10.6.2.4, 10.6.2.5, 10.6.2.6, 10.6.2.7, 10.6.2.8, 10.6.2.9, 10.6.2.10, 10.6.3.1, 10.6.3.2, 10.6.3.3, 10.6.3.4, 10.6.3.5, 10.6.3.6, 10.6.3.7, 10.6.3.8, 10.6.3.9, 10.6.3.10, 10.6.4.1, 10.6.4.2, 10.6.4.3, 10.6.4.4, 10.6.4.5, 10.6.4.6, 10.6.4.7, 10.6.4.8, 10.6.4.9, 10.6.4.10, 10.6.5.1, 10.6.5.2, 10.6.5.3, 10.6.5.4, 10.6.5.5, 10.6.5.6, 10.6.5.7, 10.6.5.8, 10.6.5.9, 10.6.5.10, 10.6.6.1, 10.6.6.2, 10.6.6.3, 10.6.6.4, 10.6.6.5, 10.6.6.6, 10.6.6.7, 10.6.6.8, 10.6.6.9, 10.6.6.10, 10.6.7.1, 10.6.7.2, 10.6.7.3, 10.6.7.4, 10.6.7.5, 10.6.7.6, 10.6.7.7, 10.6.7.8, 10.6.7.9, 10.6.7.10, 10.6.8.1, 10.6.8.2, 10.6.8.3, 10.6.8.4, 10.6.8.5, 10.6.8.6, 10.6.8.7, 10.6.8.8, 10.6.8.9, 10.6.8.10, 10.6.9.1, 10.6.9.2, 10.6.9.3, 10.6.9.4, 10.6.9.5, 10.6.9.6, 10.6.9.7, 10.6.9.8, 10.6.9.9, 10.6.9.10, 10.6.10.1, 10.6.10.2, 10.6.10.3, 10.6.10.4, 10.6.10.5, 10.6.10.6, 10.6.10.7, 10.6.10.8, 10.6.10.9, 10.6.10.10, 10.7.1.1, 10.7.1.2, 10.7.1.3, 10.7.1.4, 10.7.1.5, 10.7.1.6, 10.7.1.7, 10.7.1.8, 10.7.1.9, 10.7.1.10, 10.7.2.1, 10.7.2.2, 10.7.2.3, 10.7.2.4, 10.7.2.5, 10.7.2.6, 10.7.2.7, 10.7.2.8, 10.7.2.9, 10.7.2.10, 10.7.3.1, 10.7.3.2, 10.7.3.3, 10.7.3.4, 10.7.3.5, 10.7.3.6, 10.7.3.7, 10.7.3.8, 10.7.3.9, 10.7.3.10, 10.7.4.1, 10.7.4.2, 10.7.4.3, 10.7.4.4, 10.7.4.5, 10.7.4.6, 10.7.4.7, 10.7.4.8, 10.7.4.9, 10.7.4.10, 10.7.5.1, 10.7.5.2, 10.7.5.3, 10.7.5.4, 10.7.5.5, 10.7.5.6, 10.7.5.7, 10.7.5.8, 10.7.5.9, 10.7.5.10, 10.7.6.1, 10.7.6.2, 10.7.6.3, 10.7.6.4, 10.7.6.5, 10.7.6.6, 10.7.6.7, 10.7.6.8, 10.7.6.9, 10.7.6.10, 10.7.7.1, 10.7.7.2, 10.7.7.3, 10.7.7.4, 10.7.7.5, 10.7.7.6, 10.7.7.7, 10.7.7.8, 10.7.7.9, 10.7.7.10, 10.7.8.1, 10.7.8.2, 10.7.8.3, 10.7.8.4, 10.7.8.5, 10.7.8.6, 10.7.8.7, 10.7.8.8, 10.7.8.9, 10.7.8.10, 10.7.9.1, 10.7.9.2, 10.7.9.3, 10.7.9.4, 10.7.9.5, 10.7.9.6, 10.7.9.7, 10.7.9.8, 10.7.9.9, 10.7.9.10, 10.7.10.1, 10.7.10.2, 10.7.10.3, 10.7.10.4, 10.7.10.5, 10.7.10.6, 10.7.10.7, 10.7.10.8, 10.7.10.9, 10.7.10.10, 10.8.1.1, 10.8.1.2, 10.8.1.3, 10.8.1.4, 10.8.1.5, 10.8.1.6, 10.8.1.7, 10.8.1.8, 10.8.1.9, 10.8.1.10, 10.8.2.1, 10.8.2.2, 10.8.2.3, 10.8.2.4, 10.8.2.5, 10.8.2.6, 10.8.2.7, 10.8.2.8, 10.8.2.9, 10.8.2.10, 10.8.3.1, 10.8.3.2, 10.8.3.3, 10.8.3.4, 10.8.3.5, 10.8.3.6, 10.8.3.7, 10.8.3.8, 10.8.3.9, 10.8.3.10, 10.8.4.1, 10.8.4.2, 10.8.4.3, 10.8.4.4, 10.8.4.5, 10.8.4.6, 10.8.4.7, 10.8.4.8, 10.8.4.9, 10.8.4.10, 10.8.5.1, 10.8.5.2, 10.8.5.3, 10.8.5.4, 10.8.5.5, 10.8.5.6, 10.8.5.7, 10.8.5.8, 10.8.5.9, 10.8.5.10, 10.8.6.1, 10.8.6.2, 10.8.6.3, 10.8.6.4, 10.8.6.5, 10.8.6.6, 10.8.6.7, 10.8.6.8, 10.8.6.9, 10.8.6.10, 10.8.7.1, 10.8.7.2, 10.8.7.3, 10.8.7.4, 10.8.7.5, 10.8.7.6, 10.8.7.7, 10.8.7.8, 10.8.7.9, 10.8.7.10, 10.8.8.1, 10.8.8.2, 10.8.8.3, 10.8.8.4, 10.8.8.5, 10.8.8.6, 10.8.8.7, 10.8.8.8, 10.8.8.9, 10.8.8.10, 10.8.9.1, 10.8.9.2, 10.8.9.3, 10.8.9.4, 10.8.9.5, 10.8.9.6, 10.8.9.7, 10.8.9.8, 10.8.9.9, 10.8.9.10, 10.8.10.1, 10.8.10.2, 10.8.10.3, 10.8.10.4, 10.8.10.5, 10.8.10.6, 10.8.10.7, 10.8.10.8, 10.8.10.9, 10.8.10.10, 10.9.1.1, 10.9.1.2, 10.9.1.3, 10.9.1.4, 10.9.1.5, 10.9.1.6, 10.9.1.7, 10.9.1.8, 10.9.1.9, 10.9.1.10, 10.9.2.1, 10.9.2.2, 10.9.2.3, 10.9.2.4, 10.9.2.5, 10.9.2.6, 10.9.2.7, 10.9.2.8, 10.9.2.9, 10.9.2.10, 10.9.3.1, 10.9.3.2, 10.9.3.3, 10.9.3.4, 10.9.3.5, 10.9.3.6, 10.9.3.7, 10.9.3.8, 10.9.3.9, 10.9.3.10, 10.9.4.1, 10.9.4.2, 10.9.4.3, 10.9.4.4, 10.9.4.5, 10.9.4.6, 10.9.4.7, 10.9.4.8, 10.9.4.9, 10.9.4.10, 10.9.5.1, 10.9.5.2, 10.9.5.3, 10.9.5.4, 10.9.5.5, 10.9.5.6, 10.9.5.7, 10.9.5.8, 10.9.5.9, 10.9.5.10, 10.9.6.1, 10.9.6.2, 10.9.6.3, 10.9.6.4, 10.9.6.5, 10.9.6.6, 10.9.6.7, 10.9.6.8, 10.9.6.9, 10.9.6.10, 10.9.7.1, 10.9.7.2, 10.9.7.3, 10.9.7.4, 10.9.7.5, 10.9.7.6, 10.9.7.7, 10.9.7.8, 10.9.7.9, 10.9.7.10, 10.9.8.1, 10.9.8.2, 10.9.8.3, 10.9.8.4, 10.9.8.5, 10.9.8.6, 10.9.8.7, 10.9.8.8, 10.9.8.9, 10.9.8.10, 10.9.9.1, 10.9.9.2, 10.9.9.3, 10.9.9.4, 10.9.9.5, 10.9.9.6, 10.9.9.7, 10.9.9.8, 10.9.9.9, 10.9.9.10, 10.9.10.1, 10.9.10.2, 10.9.10.3, 10.9.10.4, 10.9.10.5, 10.9.10.6, 10.9.10.7, 10.9.10.8, 10.9.10.9, 10.9.10.10, 10.10.1.1, 10.10.1.2, 10.10.1.3, 10.10.1.4, 10.10.1.5, 10.10.1.6, 10.10.1.7, 10.10.1.8, 10.10.1.9, 10.10.1.10, 10.10.2.1, 10.10.2.2, 10.10.2.3, 10.10.2.4, 10.10.2.5, 10.10.2.6, 10.10.2.7, 10.10.2.8, 10.10.2.9, 10.10.2.10, 10.10.3.1, 10.10.3.2, 10.10.3.3, 10.10.3.4, 10.10.3.5, 10.10.3.6, 10.10.3.7, 10.10.3.8, 10.10.3.9, 10.10.3.10, 10.10.4.1, 10.10.4.2, 10.10.4.3, 10.10.4.4, 10.10.4.5, 10.10.4.6, 10.10.4.7, 10.10.4.8, 10.10.4.9, 10.10.4.10, 10.10.5.1, 10.10.5.2, 10.10.5.3, 10.10.5.4, 10.10.5.5, 10.10.5.6, 10.10.5.7, 10.10.5.8, 10.10.5.9, 10.10.5.10, 10.10.6.1, 10.10.6.2, 10.10.6.3, 10.10.6.4, 10.10.6.5, 10.10.6.6, 10.10.6.7, 10.10.6.8, 10.10.6.9, 10.10.6.10, 10.10.7.1, 10.10.7.2, 10.10.7.3, 10.10.7.4, 10.10.7.5, 10.10.7.6, 10.10.7.7, 10.10.7.8, 10.10.7.9, 10.10.7.10, 10.10.8.1, 10.10.8.2, 10.10.8.3, 10.10.8.4, 10.10.8.5, 10.10.8.6, 10.10.8.7, 10.10.8.8, 10.10.8.9, 10.10.8.10, 10.10.9.1, 10.10.9.2, 10.10.9.3, 10.10.9.4, 10.10.9.5, 10.10.9.6, 10.10.9.7, 10.10.9.8, 10.10.9.9, 10.10.9.10, 10.10.10.1, 10.10.10.2, 10.10.10.3, 10.10.10.4, 10.10.10.5, 10.10.10.6, 10.10.10.7, 10.10.10.8, 10.10.10.9, 10.10.10.10

Additional exemplary formula B compound groups include the following compound groups disclosed below. Unless otherwise specified, the configurations of all hydrogen atoms and R groups for the following compound groups are as defined for the group 1 compounds of formula B above. As is apparent from the description, each of the compound groups disclose a significant number of unique compounds or generic structures. The compounds or generic structures specifically described in any of the compound groups are thus exemplary only and the remaining compounds or structures in each group are described by Tables A and B as noted in each group.

As used in the description of compounds in the compound groups, the definitive structure of compounds in the various compound groups is specified only by the structure defining portion of the compound group and in Tables A and B, which together definitively name or specifies individual compound or genus structures. The structure defining portion of the compound groups is generally contained in the first sentence the compound groups below. This applies regardless of any name or structure, including chemical names in the exemplary compounds that are named in some of the compound groups. Thus, any name or structure for any compound or compound genus that refers to a compound or genus in a compound group and is given anywhere in the disclosure is intended only to refer to the compound or genus that is definitively specified by the compound groups together with Tables A and B.

Group 2. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$ is hydrogen in the β-configuration. As examples, group 2 compound 1.2.7.1 is 3β,7β-dihydroxy-16-oxo-17β-amino-5β-androstane and compound 1.1.4.1 is 3β-hydroxy-16α-fluoro-17β-amino-5β-androstane.

Group 3.

This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 5-6 position is present. Thus, group 3 compound 1.2.7.1 is 3β,7β-dihydroxy-16-oxo-17β-aminoandrost-5-ene and compound 1.1.4.1 is 3β-hydroxy-16α-fluoro-17β-aminoandrost-5-ene.

Group 4.

This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus as described for group 1 compounds, except that double bonds at the 1-2- and 5-6 positions are present. Thus, group 4 compound 1.2.7.1 is 3β,7β-dihydroxy-16-oxo-17β-aminoandrost-1,5-diene and compound 1.1.4.1 is 3β-hydroxy-16α-fluoro-17β-aminoandrost-1,5-diene.

Group 5.

This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 1-2 position is present. Thus, group 5 compound 1.2.7.1 is 3β,7β-dihydroxy-16-oxo-17β-aminoandrost-1-ene and compound 1.1.4.1 is 3β-hydroxy-16α-fluoro-17β-aminoandrost-1-ene.

Group 6.

This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 1-2 position is present and hydrogen at the 5-position is in the β-configuration. Thus, group 5A compound 1.2.7.1 is 3β,7β-dihydroxy-16-oxo-17β-amino-5β-androst-1-ene and 5A compound 1.1.4.1 is 3β-hydroxy-16α-fluoro-17β-amino-5β-androst-1-ene.

Group 7.

This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 4-5 position is present. Thus, group 6 compound 1.2.7.1 is 3β,7β-dihydroxy-16-oxo-17β-aminoandrost-4-ene and compound 1.1.4.1 is 3β-hydroxy-16α-fluoro-17β-aminoandrost-4-ene.

Group 8.

This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds at both the 1-2 and 4-5 positions are present. Thus, group 7 compound 1.2.7.1 is 3β,7β-dihydroxy-16-oxo-17β-aminoandrost-1,4-diene and compound 1.1.4.1 is 3β-hydroxy-16α-fluoro-17β-aminoandrost-1,4-diene.

Group 9.

This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 16-17 position is present. For this group and other compound groups that contain a 16-17 double bond, the $R^3$ and $R^4$ moieties will only be single bonded. Moieties such as =O are thus not included as $R^3$ or $R^4$ substituents in the compound group, since this would give rise to a pentavalent carbon at the 16- or 17-position. Thus, group 8 compound 1.2.7.1 does not represent any compound since a 16-17 double bond and an =O at 16 can not both be present at the same time, while group 8 compound 1.1.4.1 is 3β-hydroxy-16-fluoro-17-aminoandrost-16-ene.

Group 10.

This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 16-17 position is present and hydrogen at the 5-position is in the β-configuration. Thus, group 8A compound 1.2.7.1 is 3β,7β-dihydroxy-16-oxo-17β-amino-5β-androst-16-ene and 8A compound 1.1.4.1 is 3β-hydroxy-16α-fluoro-17β-amino-5,β-androst-16-ene.

Group 11.

This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds at the 16-17 and 5-6 positions are present. Thus, group 9 compound 1.1.4.1 is 3β-hydroxy-16-fluoro-17-aminoandrost-5,16-diene.

Group 12.

This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds at the 16-17 and 1-2 positions are present. Thus, group 10 compound 1.1.4.1 is 3β-hydroxy-16-fluoro-17-aminoandrost-1,16-diene.

Group 13.

This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 16-17 and 1-2 positions are present and hydrogen at the 5-position is in the β-configuration. Thus, group 10A compound 1.2.7.1 is 3β,7β-dihydroxy-16-oxo-17β-amino-5β-androst-1,16-diene and 10A compound 1.1.4.1 is 3β-hydroxy-16α-fluoro-17β-amino-5β-androst-1,16-diene.

Group 14.

This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds at the 16-17 and 4-5 positions are present. Thus, group 11 compound 1.1.4.1 is 3β-hydroxy-16-fluoro-17-aminoandrost-4,5-diene.

Group 15.

This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds at the 1-2, 16-17 and 4-5 positions are present. Thus, group 12 compound 1.1.4.1 is 3β-hydroxy-16-fluoro-17-aminoandrost-1,4,16-triene.

Group 16.

This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds at the 1-2, 16-17 and 5-6 positions are present. Thus, group 12 compound 1.1.4.1 is 3β-hydroxy-16-fluoro-17-aminoandrost-1,5,16-triene.

Group 17.

This group contains compounds from groups 1-13 above wherein, for single bonded $R^1$, $R^2$, $R^3$ and $R^4$ moieties, $R^1$, $R^2$, $R^3$ and $R^4$ respectively are in the α,β,α,β, β,β,α,α, β,α,α,β, α,α,α,β, β,β,β,β, β,β,βα, α,β,β,β, β,α,β,β, α,α,α,α, α, β,α,β,α, α,β,β,α, α,α,β,α, α,β,α,α or α,α,β,β configurations. Thus, when $R^1$, $R^2$, $R^3$ and $R^4$ respectively are in the α,β,α,β configurations, group 14 compound 1.2.7.1 from group 3 (also referred to as group 14-3 compound 1.2.7.1) is 3α,7β-dihydroxy-16-oxo-17β-aminoandrost-5-ene and compound 1.1.4.1 from group 3 (also referred to as group 14-3 compound 1.1.4.1) is 3α-hydroxy-16α-fluoro-17β-aminoandrost-5-ene. When $R^1$, $R^2$, $R^3$ and $R^4$ respectively are in the α,β,α,β configurations, group 14 compound 1.2.7.1 from group 1 (also referred to as group 14-1 compound 1.2.7.1) is 3α,7β-dihydroxy-16-oxo-17β-aminoandrostane and group 14-1 compound 1.1.4.1 is 3α-hydroxy-16α-fluoro-17β-aminoandrostane. Similarly, when $R^1$, $R^2$, $R^3$ and $R^4$ respectively are in the α,β,α,βconfigurations, group 14-6 compound 1.2.7.1 is 3α,7β-dihydroxy-16-oxo-17β-aminoandrost-4-ene and group 14-6 compound 1.1.4.1 is 3α-hydroxy-16α-fluoro-17β-aminoandrost-4-ene.

Group 18.

This group contains compounds in groups 1-14 above wherein $R^{10F}$, $R^{10G}$ and $R^{10H}$ respectively are in the β,α,β, β,β,α, α,β,β, β,β,β, α,α,α, α,β,α or α,α,β configurations. Thus, when $R^{10F}$, $R^{10G}$ and $R^{10H}$ respectively are in the β,α,β configurations, group 15 compound 1.2.7.1 from group 3 is 3β,7β-dihydroxy-16-oxo-17β-amino-14β-androst-5-ene and compound 1.1.4.1 from group 3 is 3β-hydroxy-16α-fluoro-17β-amino-14β-androst-5-ene. When $R^{10E}$, $R^{10F}$, $R^{10G}$ and $R^{10H}$ respectively are in the α,β,α,β configurations, group 15 compound 1.2.7.1 from group 1 is 3α,7β-dihydroxy-16-oxo-17β-amino-14β-androstane and compound 1.1.4.1 from group 1 is 3α-hydroxy-16α-fluoro-17β-amino-14β-androstane. When $R^{10F}$, $R^{10G}$ and $R^{10H}$ respectively are in the β,α,βconfigurations and $R^1$, $R^2$, $R^3$ and $R^4$ respectively are in the α,β,α,β configurations as included in group 14, group 15-14-3 compound 1.2.7.1 (compound 1.2.7.1 from groups 14 and 3) is 3α,7β-dihydroxy-16-oxo-17β-amino-14β-androst-5-ene and group 15-14-3 compound 1.1.4.1 is 3α-hydroxy-16α-fluoro-17β-amino-14β-androst-5-ene. When $R^{10G}$ is —F in the α-configuration and $R^{10F}$ and $R^{10H}$ are —H in the β- and α-configurations respectively, group 15-3 compound 1.1.4.1 is 3β-hydroxy-9α,16α-difluoro-17β-aminoandrost-5-ene and 15-3 compound 1.1.5.1 is 3β-hydroxy-9α-fluoro-17β-aminoandrost-5-ene.

Group 19.

This group contains compounds in groups 1-15 above wherein 1 or 2 of $R^{10A}$, $R^{10B}$, $R^{10C}$ and $R^{10D}$ are not —H and are an independently chosen moiety as defined herein, e.g., optionally substituted alkyl, —CH₃, halogen, —$SR^{PR}$ or —$OR^{PR}$, wherein each $R^{10A}$, $R^{10B}$, $R^{10C}$ and $R^{10D}$ is independently in the α-configuration or the β-configuration and $R^{PR}$ independently are —H or a protecting group. Thus, when $R^{10C}$ and $R^{10D}$ are both not —H, they can be in the β,β, β,α, α,β or α,α configurations respectively. Similarly, when $R^{10B}$ and $R^{10D}$ are both not —H, they can be in the β,β, β,α, α,β or α,α configurations respectively, or, when $R^{10B}$ is not —H and $R^{10A}$, $R^{10C}$ and $R^{10D}$ are all —H, $R^{10B}$ can be in the α-configuration or the β-configuration. Thus, when $R^{10C}$ is —Cl in the α-configuration, group 16-3 compound 1.2.7.1 is 3β,7β-dihydroxy-6-chloro-16-oxo-17β-aminoandrost-5-ene and group 16-3 compound 1.1.4.1 is 3β-hydroxy-6-chloro-16α-fluoro-17β-aminoandrost-5-ene. When $R^{10C}$ is —Br in the α-configuration, group 16-1 compound 1.2.7.1 is 3β,7β-dihydroxy-6α-bromo-16-oxo-17β-aminoandrostane and group 16-1 compound 1.1.4.1 is 3β-hydroxy-6α-bromo-16α-fluoro-17β-aminoandrostane.

Group 20.

This group contains compounds in groups 1-16 above wherein (1) one or both of $R^5$ and $R^6$ are not —CH₃ and they independently are a moiety as defined herein, and (2) $R^5$ and $R^6$ are in the β,β, β,α, α,β or α,α configurations respectively. Thus, $R^5$ and $R^6$ independently can be —H, —CH₃, —C₂H₅, —C₃H₇, optionally substituted alkyl, —OH, —F, —Cl, —Br, —I or another single bonded moiety as defined herein in the β,β, β,α, α,β or α,α configurations. When, for example, $R^5$ is —CH₃, $R^6$ is —H and both are in the β-configuration, group 17-1 compound 1.2.7.1 is 3β,7β-dihydroxy-16-oxo-17β-amino-19-norandrostane and group 17-1 compound 1.1.4.1 is 3β-hydroxy-16α-fluoro-17β-amino-19-norandrostane. When $R^5$ is —CH₃, $R^6$ is —H and both are in the β-configuration, group 17-3 compound 1.2.7.1 is 3β,7β-dihydroxy-16-oxo-17β-amino-19-norandrost-5-ene and group 17-3 compound 1.1.4.1 is 3β-hydroxy-16α-fluoro-17β-amino-19-norandrost-5-ene. When $R^5$ is —CH₃, $R^6$ is —H and both are in the β-configuration, $R^{10G}$ is —F in the α-configuration and $R^{10F}$ and $R^{10H}$ are —H in the β- and α-configurations respectively, group 17-15-3 compound 1.1.4.1 is 3β-hydroxy-9α,16α-difluoro-17β-amino-19-norandrost-5-ene and 17-15-3 compound 1.1.5.1 is 3β-hydroxy-9α-fluoro-17β-amino-19-norandrost-5-ene.

Group 21.

This group contains compounds in groups 1-17 above wherein $R^7$ is not —CH₂— and is another $R^7$ moiety defined herein, e.g., —O—, —NH—, —S—, —CH₂—CH₂— or —C($R^{10}$)₂— where each $R^{10}$ is an independently chosen moiety described herein. Exemplary $R^7$ include —C(halogen)₂- such as —CF₂—, —CH(α-optionally substituted alkyl), —CH(β-optionally substituted alkyl), —CH(α-OH), —CH(β-OH) or —C(optionally substituted alkyl)₂- such as —C(CH₃)₂— or —C(C₂H₅)(CH₃)—. Each optionally substituted alkyl group can contain 1, 2, 3, 4, 5, 6, 7, 8 or more carbon atoms as defined previously.

Group 22.

This group contains compounds in groups 1-18 above wherein $R^8$ is not —CH₂— and is another $R^8$ moiety defined herein, e.g., —O—, —NH—, —S— or —C($R^{10}$)₂— where each $R^{10}$ is an independently chosen moiety described herein. Exemplary $R^8$ include —C(halogen)₂- such as —CF₂—, —CH(α-optionally substituted alkyl), —CH(β-optionally substituted alkyl) or —C(optionally substituted alkyl)₂- such as —C(CH₃)₂— or —C(C₂H₅)(CH₃)—. Each optionally substituted alkyl group can contain 1, 2, 3, 4, 5, 6, 7, 8 or more carbon atoms as defined previously. In some embodiments, when one or both $R^{10}$ at $R^8$ is —OH, —SH, =O, an ester, a thioester, or another moiety that can give rise to a hydroxyl group by metabolism or hydrolysis, $R^2$ and/or $R^{10D}$ is not —H. As examples, group 19-3 compound 1.1.4.1 is 3β-hydroxy-11-oxa-16α-fluoro-17β-aminoandrost-5-ene and 19-3 compound 1.1.5.1 is 3β-hydroxy-11-oxa-17β-aminoandrost-5-ene. When $R^8$ is —O—, $R^5$ is —CH$_3$, $R^6$ is —H and both are in the β-configuration, $R^{10G}$ is —F in the α-configuration and $R^{10F}$ and $R^{10H}$ are —H in the β- and α-configurations respectively, group 19-17-15-3 compound 1.1.4.1 is 3β-hydroxy-9α,16α-difluoro-11-oxa-17β-amino-19-norandrost-5-ene and 19-17-15-3 compound 1.1.5.1 is 3β-hydroxy-9α-fluoro-11-oxa-17β-amino-19-norandrost-5-ene.

Group 23.

This group contains compounds in groups 1-19 above wherein $R^9$ is not —CH$_2$— and is another $R^9$ moiety defined herein, e.g., —O—, —NH—, —S— or —C($R^{10}$)$_2$— where each $R^{10}$ is an independently chosen moiety as defined herein. Exemplary $R^9$ include —C(halogen)$_2$- such as —CF$_2$—, —CH(α-OH), —CH(β-OH) or —C(optionally substituted alkyl)$_2$-such as —C(CH$_3$)$_2$— or —C(C$_2$H$_5$)(CH$_3$)—. Each optionally substituted alkyl group can contain 1, 2, 3, 4, 5, 6, 7, 8 or more carbon atoms as defined previously. For groups that contain a double bond at the 1-2 position such as groups 5 and 7, $R^9$ can be —N=, but $R^9$ will not be —O— or —S— due to improper bonding, i.e., —O= and —S= are not present in the steroid ring.

Group 24.

This group contains compounds in groups 1-20 above where $R^4$ substituents 1-10 listed in Table A are replaced with the following groups: 1—optionally substituted amine, 2—optionally substituted amide, 3—optionally substituted oxime, 4—optionally substituted alkyl, 5—optionally substituted alkenyl, 6—optionally substituted alkynyl, 7—optionally substituted aryl, 8—optionally substituted heterocycle, 9—ether, e.g., methoxy, ethoxy or methoxymethyl and 10—ester, e.g., acetate, propionate, enanthate or trifluoroacetate. Any of these groups can be a moiety defined herein for that group. Thus, for Table A substituent 1, optionally substituted amine, the $R^4$ group includes moieties such as —NH$_3^+$Cl$^-$, —NH$_3^+$Br$^-$, —NH$_3^+$I$^-$, optionally substituted alkylamine, di-optionally substituted alkylamine, —NHR$^{PR}$, —N(R$^{PR}$)$_2$ and —NH—CH$_3$, where $R^{PR}$ are a protecting group. Similarly, optionally substituted amide includes moieties such as —C(O)—NH$_2$, —C(O)—NH—C(CH$_3$)$_3$ and —C(O)—NH$_2$, which are described herein. Other R4 moieties include =N—OCH$_3$, =N—OC$_2$H$_5$, =N—OC$_3$H$_7$ and =N—O-optionally substituted alkyl. Group 21-3 compound 1.1.6.1 (i.e., group 21 compound 1.1.6.1 from group 3) is 3β,16α-dihydroxy-17β-optionally substituted amine-androst-5-ene and 21-3 compound 1.1.4.1 is 3β-hydroxy-16α-fluoro-17β-optionally substituted amine-androst-5-ene, where the optionally substituted amine is a moiety described herein such as an amine salt, an optionally substituted alkylamine or an optionally substituted dialkylamine like —NH$_3^+$Cl$^-$, —NHCH$_3$, —N(CH$_3$)$_2$ and —NH—(CH$_2$)$_2$—OH. Similarly, group 21-1 compound 1.1.6.1 (i.e., group 21 compound 1.1.6.1 from group 1) is 3β,16α-dihydroxy-17β-optionally substituted amine-androstane and 21-1 compound 1.1.4.1 is 3β-hydroxy-16α-fluoro-17β-optionally substituted amine-androstane.

Group 25.

This group contains compounds in groups 1-20 above where $R^4$ substituents 1-10 listed in Table A are replaced with the following groups: 1 -phosphate thioether, 2 -thionoester, 3 -amino acid, 4 -peptide, 5 -dipeptide, 6 -optionally substituted heterocycle, 7 - optionally substituted carboxyl, 8 -carbonate, 9 -carbamate and 10 -phosphothioester. Amino acids for substituent 3 are as described herein and include, e.g., —NH—CH$_2$—C(O)OH, —NH—CH$_2$—C(O)OR$^{PR}$, —NH—CH$_2$—CH$_2$—C(O)OH, —NH—CH$_2$—CH$_2$—C(O)OR$^{PR}$, —NH—CH(CH$_3$)—C(O)OH, —NH—CH(CH$_3$)—CH$_2$—C(O)OH, —NH—CH(CH$_3$)—CH$_2$—C(O)OR$^{PR}$, —NH—CH$_2$—CH$_2$—CH$_2$—C(O)OH, —NH—CH$_2$—CH$_2$—CH$_2$—C(O)OR$^{PR}$, —O—C(O)—CH$_2$—NH$_2$, —O—C(O)—CH$_2$—NHR$^{PR}$, —O—C(O)—CH$_2$—CH$_2$—NH$_2$, —O—C(O)—CH$_2$—CH$_2$—NHR$^{PR}$ or for ionizable groups such as free carboxyls or amines, a salt such as a Na$^+$ or K$^+$ salt for carboxyls or a salt such as HCl or HBr salt for amines.

Group 26.

This group contains compounds in groups 1-20 above where $R^4$ substituents 1-10 listed in Table A are replaced with the following groups: 1 —N-pyrrolidine, 2 —N-1-pyrazolone, 3 —N2-pyrazolone, 4 —N-imidazolidin-2-one, 5 —N1-imidazole, 6 —N1-4,5-dihydroimidazole, 7 —N-morpholine, 8 —N1-pyridine, 9 —N-piperidine, 10 —N-piperazine. As examples, group 26A-3 compound 1.1.6.1 (i.e., group 26A compound 1.1.6.1 from group 3) is 3β,16α-dihydroxy-17β-N-pyrrolidinylandrost-5-ene, 26A-3 compound 1.1.4.1 is 3β-hydroxy-16α-fluoro-17β-N-pyrrolidinylandrost-5-ene, group 26A-4 compound 1.1.6.1 (i.e., group 26A compound 1.1.6.1 from group 4) is 3β,16α-dihydroxy-17β-N-pyrrolidinylandrost-1,5-diene and 26A-4 compound 1.1.4.1 is 3β-hydroxy-16α-fluoro-17β-N-pyrrolidinylandrost-1,5-diene.

Group 27.

This group contains compounds in groups 1-20 above where $R^4$ substituents 1-10 listed in Table A are replaced with the following groups: 1 —N-piperazine substituted at N4 with optionally substituted alkyl, 2 —N-indole, 3 —N-indoline, 4 —N-quinolidine, 5 —NH—C(O)—CH$_2$—CH$_2$—C(O)—OH, 6 —NH—C(O)—CH$_2$—C(O)—OH, 7 —NH—C(O)—CH$_2$—CH$_2$—C(O)—OR$^{PR}$, 8 —NH—C(O)—CH$_2$—C(O)—OR$^{PR}$, 9 —NH—C(O)—(CH$_2$)$_3$—C(O)—OH, 10 —NH—C(O)—(CH$_2$)$_3$—C(O)—OR$^{PR}$. Ionizable moieties such as free carboxyl groups include salts, e.g., Na$^+$ or K$^+$. $R^{PR}$ is a protecting group.

Group 28.

This group contains compounds in groups 1-34 above where $R^3$ substituents 1-10 listed in Table A are replaced with the following groups: 1 -optionally substituted amine, 2 -optionally substituted amide, 3 -optionally substituted oxime, 4 -optionally substituted alkyl, 5 -optionally substituted alkenyl, 6 -optionally substituted alkynyl, 7 -optionally substituted aryl, 8 -optionally substituted heterocycle, 9 -ether and 10 -ester. Any of these groups can be a moiety defined herein for that group.

Group 29.

This group contains compounds in groups 1-34 above where $R^3$ substituents 1-10 listed in Table A are replaced with the following groups: 1 -phosphate thioether, 2 -thionoester, 3 -amino acid, 4 -peptide, 5 -dipeptide, 6 -optionally substituted heterocycle, 7 -optionally substituted carboxyl, 8 -carbonate, 9 -carbamate and 10 -phosphothioester.

Group 30.

This group contains compounds in groups 1-34 above where $R^3$ substituents 1-10 listed in Table A are replaced with the following groups: 1 —N-pyrrolidine, 2 —N1-pyrazolone, 3 —N2-pyrazolone, 4 —N-imidazolidin-2-one, 5 —N1-imidazole, 6 —N1-4,5-dihydroimidazole, 7 —N-morpholine, 8 —N1-pyridine, 9 —N-piperidine, 10—N-piperazine.

Group 31.

This group contains compounds in groups 1-34 above where $R^3$ substituents 1-10 listed in Table A are replaced with the following groups: 1 —N-piperazine substituted at N4 with optionally substituted alkyl, 2 —N-indole, 3 —N-indoline, 4 —N-quinolidine, 5 —NH—C(O)—CH$_2$—CH$_2$—C(O)—OH, 6 —NH—C(O)—CH$_2$—C(O)—OH, 7 —NH—C(O)—CH$_2$—CH$_2$—C(O)—OR$^{PR}$, 8 —NH—C(O)—CH$_2$—C(O)—OR$^{PR}$, 9 —NH—C(O)—(CH$_2$)$_3$—C(O)—OH, 10 —NH—C(O)—(CH$_2$)$_3$—C(O)—OR$^{PR}$. Ionizable moieties such as free carboxyl groups include salts, e.g., Na$^+$ or K$^+$. $R^{PR}$ is a protecting group.

Group 32.

This group contains compounds in groups 1-41 above where $R^2$ substituents 1-10 listed in Table A are replaced with the following groups: 1 -optionally substituted amine, 2 -optionally substituted amide, 3 -optionally substituted oxime, 4 -optionally substituted alkyl, 5 -optionally substituted alkenyl, 6 -optionally substituted alkynyl, 7 -optionally substituted aryl, 8 -optionally substituted heterocycle, 9 -ether and 10 -ester. Any of these groups can be a moiety defined herein for that group.

Group 33.

This group contains compounds in groups 1-41 above where $R^2$ substituents 1-10 listed in Table A are replaced with the following groups: 1 -phosphate thioether, 2 -thionoester, 3 -amino acid, 4 -peptide, 5 -dipeptide, 6 -optionally substituted heterocycle, 7 -optionally substituted carboxyl, 8 -carbonate, 9 -carbamate and 10 -phosphothioester.

Group 34.

This group contains compounds in groups 1-41 above where $R^2$ substituents 1-10 listed in Table A are replaced with the following groups: 1 —N-pyrrolidine, 2 —N1-pyrazolone, 3 —N$^2$-pyrazolone, 4 —N-imidazolidin-2-one, 5 —N1-imidazole, 6 —N1 4,5-dihydroimidazole, 7 —N-morpholine, 8 —N1-pyridine, 9 —N-piperidine, 10—N-piperazine.

Group 35.

This group contains compounds in groups 1-48 above wherein $R^4$ is single bonded and a second $R^4$ that is not —H is present. The second $R^4$ can be a moiety defined herein for $R^4$, e.g., optionally substituted alkyl, halogen, —SH or —OH.

Group 36.

This group contains compounds in groups 1-49 above wherein $R^1$ is single bonded and a second $R^1$ that is not —H is present. The second $R^1$ can be a moiety defined herein for $R^1$, e.g., optionally substituted alkyl, halogen, —SH or —OH.

Group 37.

This group contains compounds in groups 1-50 above wherein $R^3$ is single bonded and a second $R^3$ that is not —H is present. The second $R^3$ can be a moiety defined herein for $R^3$, e.g., optionally substituted alkyl, halogen, —SH or —OH.

Group 38.

This group contains compounds in groups 1-51 above wherein $R^2$ is single bonded and a second $R^2$ that is not —H is present. The second $R^2$ can be a moiety defined herein for $R^2$, e.g., optionally substituted alkyl, halogen, —SH or —OH.

Analytical Characterization and Reference Standards.

Individual F1Cs described or disclosed herein are suitable for use as standards for determining chemical or physical properties using one, two or more analytical methods, e.g., for use in HPLC, reverse phase HPLC, MS (mass spectrometry), quadrupole MS, GC-MS, LC-MS, NMR (nuclear magnetic resonance spectrometry), $^2$H-NMR, $^3$H-NMR, $^{13}$C-NMR, $^{14}$C-NMR, infrared spectrometry (IR), Fourier transform-IR, optical rotary dispersion, loss on drying for water and solvent measurement, Karl Fisher titration for water determination, differential scanning calorimetry, melting point, density, refractive index, solubility characteristics in organic solvents, aqueous systems or aqueous-organic solvent mixtures, the partition coefficient in immiscible solvent systems, e.g., octanol:water partition coefficient, heat stability or epimerization rate or characteristics of a given enantiomer. These analytical or chemical properties of each F1C are collectively referred to as analytical characteristics. For general methods, see, e.g., H. L. J. Makin et al., eds. *Steroid Analysis* 1995, Chapman & Hall, ISBN 0751401285. Thus, to aid in the determination of, e.g., the structure of a metabolite of a F1C or a structurally related compound, the parent compound or another structurally related F1C could be used as a standard. Metabolism of F1Cs will often include one or more of oxidation, reduction, hydroxylation or conjugation, e.g., oxidation or reduction to a —OH or =O moiety, or conjugation with a moiety such as sulfate, phosphate, amino acid, dipeptide or a monosaccharide such as glucuronic acid at, e.g., the 2, 3, 6, 7, 11, 15, 16, 17 or other positions on the steroid nucleus. In these embodiments, the appropriate use of a F1C of known structure as a standard can aid in or verify the identification of metabolites that are projected to have closely related structures. Information regarding the identification can be useful or sometimes is necessary for, e.g., obtaining regulatory approval to market a therapeutic agent such as a F1C or understanding the potential biological role that a F1C or its metabolite can play in one of the applications disclosed herein or in a cited reference.

Embodiments include a method (the "characterization method") to characterize or at least partially characterize a formula 1 compound that is at least partially uncharacterized for one or more given chemical or analytical properties, e.g., a known or potential metabolite of a parent formula 1 compound, comprising (a) providing a formula 1 compound having one, two or more known characteristics, e.g., a known or at least partially known or characterized chemical structure, XRD spectrum or melting point (a "CF1C"), and a formula 1 compound that is unknown or at least partially uncharacterized, i.e., is uncharacerized for at least one of the same analytical characteristics (a "UCF1C"), (b) obtaining one, two or more analytical characteristics of the UCF1C, and (c) comparing the 1, 2 or more analytical characteristics of the CF1C with the analytical characteristics of the UCF1C. The steps in this method may be conducted in any suitable order, e.g., analytical or chemical data for the CF1C will usually be obtained before or at about the same time as one obtains the analytical or chemical data for the UCF1C. Usually the CF1C will be more completely characterized than the UCF1C, particularly with regard to its chemical structure or its relative degree of purity or with regard to the analytical or chemical data that is being sought. This method allows further characterization of the UCF1C, e.g., by confirming the UCF1C's chemical structure or by determining the UCF1C's stability under various storage or temperature conditions or in various formulations or by determining other analytical or chemical properties of interest. In this method, the CF1C itself may not be completely characterized, however, for the one, two or more analytical characteristics of interest, the CF1C will usually have a known or confirmed property or properties, while the UCF1C is unknown or at least unconfirmed for the same property or properties.

In some embodiments the characterization method is conducted by comparing dissimilar analytical characteristics. For example, the CF1C may be well characterized by GC-MS or by NMR, while an insufficient amount of the UCF1C is available for analysis with the same technique. In these cases, one can then, e.g., compare the GC-MS of the CF1C with the NMR of the UCF1C to obtain the same or essentially the same information for the UCF1C. Other examples of where this can be done is where DSC data is available for the CF1C, and only melting point data is available for the UCF1C. In this case, the CF1C DSC data is compared to the UCF1C's melting point data. Also, in conducting the characterization method, one can optionally derivatize or chemically modify the CF1C and/or the UCF1C to facilitate analysis of the compound(s). For example, in conducting MS, GC-MS or NMR analysis, one or more free hydroxyl or ketone moieties on the CF1C and/or the F2C can be silylated using, e.g., trimethylsilyl chloride, t-butyl-dimethylsilyl chloride or other suitable silylating agents. Similarly, the UCF1C may be treated or incubated with a cell line or tissue or with a glucuronidase, sulfatase, phosphatase, esterase, lipase, oxidoreductase or other enzyme and then characterized. This treatment may in some cases convert the UCF1C into the CF1C, but this conversion would usually be confirmed by one, two or more suitable analytical methods. Such treatments will usually generate additional data about the structure, properties or origin of the UCF1C.

Embodiments include modifications of the characterization method that use a CF1C and a second formula 1 compound that is believed or known to have a related structure or empirical formula. In these modifications, the CF1C is used as described and a second formula 1 compound or a UCF1C that is believed or known to be, e.g., an epimer or a salt, of the CF1C is compared to the CF1C. Invention embodiments include other modifications of the characterization method such as (1) comparing analytical or chemical data from a single CF1C with 2, 3, 4 or more UCF1C, (2) comparing analytical or chemical data from 2, 3, 4 or more CF1C with a single UCF1C and (3) comparing analytical or chemical data from 2, 3, 4 or more CF1C with 2, 3, 4 or more UCF1C. In these modifications, the CF1C or UCF1C are used essentially as described for the characterization method, except that data is obtained for the added formula 1 compounds.

Typically, when the 1, 2 or more analytical characteristics of a CF1C or a UCF1C are obtained, which may be for use in the characterization method or for other purposes, each compound is analyzed under the same or essentially the same analytical conditions using the same or essentially the same analytical technique or instrument. Variations in an analytical technique may be used where the properties of a CF1C or a UCF1C require slightly different handling or specimen preparation. An example of a variation in analytical conditions is the comparison of a property of a CF1C, e.g., its stability to heat, humidity or prolonged storage at a given temperature, with the same property of the CF1C in a composition containing an excipient(s) or in a formulation (where the CF1C in a composition is then considered the UCF1C for the characterization method). This allows the determination of the stability of the CF1C as a pure compound compared to its stability in any desired composition.

When characterizing a CF1C by MS, particularly by GC-MS, one will usually conduct an initial characterization of a formula 1 compound or a CF1C in the characterization method using a known GC-MS method (e.g., H. L. J. Makin et al., *Mass Spectra and GC Data of Steroids: Androgens and Estrogens* 1999 John Wiley & Sons, pages XIII-XIV) or a suitable variation of this method. For F1Cs that contain free hydroxyls or oxo groups, the hydroxyl groups can be derivatized to an ester such as acetate, hydroxyl and oxo or groups can be derivatized to trimethylsilyl ether, i.e., —O—Si(CH$_3$)$_3$, and oxo groups can be derivatized to a an oxime such as =N—O—CH$_3$ before GC-MS analysis. Other functional groups can also be suitably derivatized. For embodiments of the characterization method that use a GC-MS analysis method, the CF1C or the UCF1C is analyzed by the GC-MS method or a suitable variation to obtain or to confirm chemical structure information about the CF1C or the UCF1C. Suitable variations include, e.g., a change in the carrier gas from helium to hydrogen to increase the sensitivity of detection or a decrease in the ionization from 70 eV to 50 eV can give a better parent mass ion.

As is apparent from the present disclosure, the F1C may be prepared synthetically and typical embodiments will utilize purified a F1C. Purified F1C can be free, essentially free or partially free, of other F1C or other compounds such as excipients. Thus, any given purified F1C can be present as a solid that contains, e.g., less than about 15% w/w or less than about 10% w/w or less than about 8% w/w or less than about 5% w/w or less than about 3% w/w or less than about 1% w/w of one, two or more other F1Cs, excipients, synthetic by-products, decomposition products or synthesis or purification reactants or reagents. Similarly, the F1C can be present in a solution or suspension that contains at least about 90% w/w or at least about 95% w/w or at least about 97% w/w of the F1C and one or more excipients and less than about 10% or 8% or 5% or 3% w/w or 1% w/w of one, two or more other F1Cs, excipients, synthetic by-products, decomposition products or synthesis or purification reactants or reagents.

Various groups that F1Cs contain as described herein, e.g., hydroxyl groups or ketones bonded to the steroid nucleus, or substituted alkyl groups, substituted heterocycles, amino acids and peptides, which can contain one or more reactive moieties such as hydroxyl, oxo, carboxyl, amino or thiol moieties. Intermediates used to make F1Cs may be protected as is apparent in the art, e.g., using suitable R$^{PR}$ moieties. Noncyclic and cyclic protecting groups and corresponding cleavage reactions are described in "Protective Groups in Organic Chemistry", Theodora W. Greene (John Wiley & Sons, Inc., New York, 1991, ISBN 0-471-62301-6) (hereafter "Greene") and will not be detailed here. In the context of the present invention, these protecting groups are groups that can be removed from a F1C without irreversibly changing the covalent bond structure or oxidation/reduction state of the remainder of the molecule. For example, the protecting group, —R$^{PR}$, that is bonded to an —OR$^{PR}$ or —NHR$^{PR}$ group can be removed to form —OH or —NH$_2$, respectively, without affecting other covalent bonds in the molecule. Protecting groups for carbonyl or ketone moieties include ethylene ketals, e.g., —O—CH$_2$—CH$_2$—O—. At times, when desired, more than one protecting group can be removed at a time, or they can be removed sequentially. In F1Cs containing more than one protecting group, the protecting groups are the same or different.

Protecting groups are removed by known procedures, although it will be understood that the protected intermediates fall within the scope of this invention. The removal of the protecting group may be arduous or straightforward, depending upon the economics and nature of the conversions involved. In general, one will use a protecting group with exocyclic amines or with carboxyl groups during synthesis of a F1C. For most therapeutic applications amine groups should be deprotected. Protecting groups commonly are employed to protect against covalent modification of a sensitive group in reactions such as alkylation or acylation. Ordinarily, protecting groups are removed by, e.g. hydrolysis, elimination or aminolysis. Thus, simple functional considerations will suffice to guide the selection of a reversible or an irreversible protecting group at a given locus on the F1Cs. Suitable protecting groups and criteria for their selection are described in T. W. Greene and P. G. M. Wuts, Eds. "Protective Groups in Organic Synthesis" 2nd edition, Wiley Press, at pps. 10-142, 143-174, 175-223, 224-276, 277-308, 309-405 and 406-454.

Characterization of a protecting group is made in the conventional manner, e.g., as described by Kocienski, Philip J.; "*Protecting Groups*" (Georg Thieme Verlag Stuttgart, New York, 1994) (hereafter "Kocienski"), Section 1.1, page 2, and Greene Chapter 1, pages 1-9. In particular, a group is a protecting group if when, based on mole ratio, 90% of that protecting group has been removed by a deprotection reaction, no more than 50%, typically 25%, more typically 10%, of the deprotected product molecules have undergone changes to their covalent bond structure or oxidation/reduction state other than those occasioned by the removal of the protecting group. When multiple protecting groups of the same type are present in the molecule, the mole ratios are determined when all of the groups of that type are removed. When multiple protecting groups of different types are present in the molecule, each type of protecting group is treated (and the mole ratios are determined) independently or together with others depending on whether the deprotection reaction conditions pertinent to one type are also pertinent to the other types present. In one embodiment, a group is a protecting group if when, based on mole ratio determined by conventional techniques, 90% of that protecting group has been removed by a conventional deprotection reaction, no more than 50%, typically 25%, more typically 10%, of the deprotected product molecules have undergone irreversible changes to their covalent bond structure or oxidation/reduction state other than those occasioned by the removal of the protecting group. Irreversible changes require chemical reactions (beyond those resulting from aqueous hydrolysis, acid/base neutralization or conventional separation, isolation or purification) to restore the covalent bond structure or oxidation/reduction state of the deprotected F1C.

Protecting groups are also described in detail together with general concepts and specific strategies for their use in Kocienski, Philip J.; "Protecting Groups" (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184, Chapter 6, Amino Protecting Groups, pages 185-243, Chapter 7, Epilog, pages 244-252, and Index, pages 253-260, are incorporated with specificity in the context of their contents. More particularly, Sections 2.3 Silyl Ethers, 2.4 Alkyl Ethers, 2.5 Alkoxyalkyl Ethers (Acetals), 2.6 Reviews (hydroxy and thiol protecting groups), 3.2 Acetals, 3.3 Silylene Derivatives, 3.4 1,1,3,3-Tetraisopropyldisiloxanylidene Derivatives, 3.5 Reviews (diol protecting groups), 4.2 Esters, 4.3 2,6,7-Trioxabicyclo[2.2.2]octanes [OBO] and Other Ortho Esters, 4.4 Oxazolines, 4.5 Reviews (carboxylprotecting groups), 5.2 O,O-Acetals, 5.3 S,S-Acetals, 5.4 O,S-Acetals, 5.5 Reviews (carbonyl protecting groups), 6.2 N-Acyl Derivatives, 6.3 N-Sulfonyl Derivatives, 6.4 N-Sulfenyl Derivatives, 6.5 N-Alkyl Derivatives, 6.6 N-Silyl Derivatives, 6.7 Imine Derivatives, and 6.8 Reviews (amino protecting groups), are each incorporated with specificity where protection/deprotection of the requisite functionalities is discussed. Further still, the tables "Index to the Principal Protecting Groups" appearing on the inside front cover and facing page, "Abbreviations" at page xiv, and "reagents and Solvents" at page xv are each incorporated in their entirety herein at this location.

Groups capable of biological cleavage typically include prodrugs. Some exemplary groups are described in "Design of Prodrugs", Hans Bundgaard (Elsevier, N.Y., 1985, ISBN 0-444-80675-X) (Bundgaard) and will not be detailed here. In particular, Bundgaard, at pages 1-92, describes prodrugs and their biological cleavage reactions for a number of functional group types. Prodrugs for carboxyl and hydroxyl groups are detailed in Bundgaard at pages 3 to 10, for amides, imides and other NH-acidic compounds at pages 10 to 27, amines at pages 27 to 43, and cyclic prodrugs at pages 62 to 70. These moieties are optionally bonded to the steroid at one, two or more of the variable groups that are bonded to the rings in the F1Cs, e.g., one or more $R^1$-$R^6$, $R^{10}$, $R^{15}$, $R^{17}$ and $R^{18}$.

In some embodiments one or more F1Cs or groups of F1Cs may be excluded from one or more of the uses disclosed herein. For example, if the subject has or is susceptible to developing a memory impairing neurological disorder or memory impairment condition, excluded compounds can include 5-androstene-3β-ol-7,17-dione or 5-androstene-3β,7-diol-17-one or a derivative of these compounds that can has a group at the 7-position that can convert to —OH or ═O by hydrolysis. In other cases, the F1Cs can exclude one or more of 4-pregnene-11β,17α,21-triol-3,20-dione, 17α,21-dihydroxypregn-4-ene-3,11,20-trione, 11β,21-dihydroxy-3,20-dioxopregn-4-en-18-al, 11β,17α,21-trihydroxypregna-1,4-diene-3,20-dione, 17α,21-dihydroxypregna-1,4-diene-3,11,20-trione, 3β-hydroxypregn-5-ene-20-one, 3β-hydroxyandrost-5-ene-17-one, pregn-4-ene-3,20-dione, 21-hydroxypregn-4-ene-3,20-dione, 9-fluoro-11β,16α,21-trihydroxy-16-methylpregna-1,4-diene-3,20-dione, 9-fluoro-11β,16α,17,21-tetrahydroxypregna-1,4-diene-3,20-dione, 9-fluoro-11β,17α,21-trihydroxy-16-methylpregna-1,4-diene-3,20-dione, dehydroepiandrosterone-3-sulfate, 1,4-pregnadiene-17α,21-diol-3,11,20-trione, androsterone, androsterone acetate, androsterone propionate, androsterone benzoate, androst-5-ene-3β,17β-diol, androst-5-ene-3β,17β-diol-3-acetate, androst-5-ene-3β,17β-diol-17-acetate, androst-5-ene-3β,17β-diol-3,17-diacetate, androst-5-ene-3β,17β-diol-17-benzoate, androst-5-ene-3β,17β-diol-3-acetate-17-benzoate, androst-4-ene-3,17-dione, androst-5-ene-3β,7β,17β-triol, androst-5-ene-3(3,7α,17β-triol, dehydroepiandrosterone, 4-dihydrotestosterone, 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol, testosterone, methyl testosterone, testolactone, oxymetholone, fluoxymesterone, acetoxypregnenolone, allylestrenol, anagestone acetate, chlormadinone acetate, cyproterone, cyproterone acetate, desogestrel, dihydrogesterone, dimethisterone, ethisterone (17α-ethynyltestosterone), ethynodiol diacetate, fluorogestone acetate, gestadene, hydroxyprogesterone, hydroxyprogesterone acetate, hydroxyprogesterone caproate, 3-ketodesogestrel, hydroxymethylprogesterone, hydroxymethylprogesterone acetate, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone, progesterone, cyproterone acetate, norethindrone, norethindrone acetate, levonorgestrel, an ester of any of the foregoing compounds (e.g., acetate, enanthate, propionate, isopropionate, cyclopropionate, isobutyrate, butyrate, valerate, caproate, isocaproate, hexanoate, heptanoate, octanoate, nonanoate, decanoate, undecanoate, phenylacetate or benzoate esters, e.g., hydroxyl esters), a naturally occurring glucorcorticoid, a species disclosed herein or a derivative of any of these that can convert to these molecules by hydrolysis or metabolism, e.g., a metabolizable or hydrolyzable ester or ether such as a cyclic ketal, an acetate, a diacetete, a proprionate, a diprorionate, or an an O-alkyl, an acyl, e.g., —C(O)—C1-C6 alkyl or another moiety that is bonded at, e.g., a variable group such as for $R^1$-$R^6$.

Dosages of F1C and Dosing Protocols or Methods.

In treating any of the conditions or symptoms disclosed herein, one can continuously or intermittently administer the F1C(s) to a subject having or susceptible to developing the condition or symptom. In treating a condition such as an infection, a hyperproliferation condition, an inflammation condition or another condition disclosed herein with a F1C using an intermittent dosing can avoid or ameliorate some of the undesired aspects normally associated with discontinuous dosing. Such undesired aspects include development of resistance of a pathogen such as a pathogen disclosed herein, e.g., a virus or bacterium such as HIV or *Staphylococcus aureus* or a parasite such as a *Plasmodium* parasite, to the therapeutic agent, failure of the patient or subject to adhere to a daily dosing regimen or reduction of the dosages of other therapeutic agents and/or their associated unwanted side effects or toxicities, e.g., reduction or a toxic effect of a chemotherapy or radiation exposure. In any of the continuous or intermittent dosing protocols described herein, other appropriate treatments can be applied as the subject's clinical situation dictates. Suitable other appropriate treatments or therapeutic agents are described elsewhere herein and in the cited references.

In any of the continuous or in any step(s) in the intermittent dosing protocols described herein, or in treating any of the diseases, conditions or symptoms described herein, the F1C(s) can be administered by one or more suitable routes, e.g., oral, buccal, sublingual, intramuscular (i.m.), subcutaneous (s.c.), intravenous (i.v.), intradermal, another parenteral route or by an aerosol. The effective daily dose in such methods will typically comprise about 0.05 mg/kg/day to about 200 mg/kg/day, or about 0.1 to about 100 mg/kg/day, including about 0.2 mg/kg/day, 0.5 mg/kg/day, about 1 mg/kg/day, about 2 mg/kg/day, about 4 mg/kg/day, about 6 mg/kg/day, about 10 mg/kg/day, about 20 mg/kg/day, about 40 mg/kg/day or about 100 mg/kg/day. Higher dosages, e.g., about 250 mg/kg/day, about 300 mg/kg/day or about 350 mg/kg/day can also be utilized, e.g., in veterinary applications. One can administer the F1C(s) orally using about 4 to about 60 mg/kg/day, usually about 6-30 mg/kg/day. In some embodiments, the intermittent dosing methods exclude dosing protocols that are commonly used to deliver contraceptive steroids to, e.g., human females, such as daily dosing for 21 days, followed by no dosing for 7 days. For humans, dosing is generally about 0.005 mg/kg/day to about 30 mg/kg/day, typically about 0.5-5 mg/kg/day. Low dosages for humans such as about 0.005 mg/kg/day to about 0.2 mg/kg/day or about 0.25-10 mg/day, can be used with, e.g., local, topical, transmucosal or intravenous administration and higher dosages such as about 0.1 mg/kg/day to about 20 mg/kg/day or about 5-200 mg/day, can be used, e.g., for oral, subcutaneous or other systemic or local administration route. For non-human subjects, e.g., mammals such as rodents or primates, the effective daily dosage may comprise about 0.05 mg/kg/day to about 350 mg/kg/day. F1C formulation dosages or daily doses or unit doses or subdoses for subjects such as humans and mammals include, e.g., about 1, 5, 10, 15, 20, 25, 50, 75, 100, 125, 150, 175, 200, 225, 250, 275, 300, 325, 350, 400 or 450 mg of the F1C.

An effective dosage or an effective amount of a F1C(s) is one that is sufficient to result in, e.g., a detectable change in a symptom or an immune parameter such as one described herein. An effective dosage (or daily dosage) may be administered to a subject over a period of time, e.g., at least about 1-14 days before a symptom change or an immune parameter detectably changes. Effective amounts of a F1C can be delivered using the dosages and dosing protocols described herein.

In some embodiments, F1C are used to treat, ameliorate, prevent or slow the progression of a condition or disease described herein by continuous daily dosing of the F1C for 1 day to 1, 2, 3 years or more. In related embodiments, F1C are used to treat, ameliorate, prevent or slow the progression of a condition or disease described herein by continuous dosing the F1C every other day or dosing every third, fourth, fifth, sixth, seventh or $14^{th}$ day over a time period of 3 days to 1, 2, 3 years or more, e.g., dosing for about 2, 3, 4, 5, 6 or 7 days or about 1, 2, 3, 4, 6, 8, 10, 12, 16, 20, 24 or more weeks. Daily doses in any of these dosing regimens or protocols may be subdivided into 2 or 3 subdoses.

Intermittent dosing protocols include administration of a F1C, e.g., orally, topically or parenterally as follows: (1) daily dosing or dosing every other day or dosing every third day or dosing every fourth day or dosing every fifth day or dosing every seventh day for about 2, 3, 4, 5, 6, 7, 8, 9, 10, 11, 12, 13, 14, 15, 16, 17, 18, 19, 20, 21 or 28 days to about 190 days or more, e.g., 1 or 2 years, (2) no dosing of the F1C for 1 to about 190 consecutive days (e.g., about 2, 3, 4, 5, 6, 7, 8, 9, 10, 11 or 12 days to about 20 days), (3) daily dosing for about 3 to about 190 days (e.g., about 3 to about 20 days), and (4) optionally repeating step (2) or a variation of step (2) and (5) optionally repeating the steps (1), (2), (3) and (4) 1, 2, 3, 4, 5, 6, 10, 15, 20, 30 or more times. In some embodiments, the dosing of steps (1) and (3) are the same, while in others, step (1) dosing is for a longer time than step β). Less frequently, step (1) dosing will be for a shorter time. In some embodiments, steps (1)-(4) or (1)-(5) of the dosing protocol described above where step (4) is included, is repeated at least one time, e.g., at least 2, 3, 4, 5 or 6 times. For conditions that tend to remain chronic, e.g., HIV infection or other chronic conditions described herein, any of these intermittent dosing protocols can be maintained over a relatively long time period, e.g., for at least about 4 months or 6 months to about 5 or more years.

In some embodiments, the number of days of dosing in steps (1) and (3) is the same in each round of treatment, i.e., each time period in step (1) and (3) is the same in the initial and subsequent rounds of the method. In other embodiments they differ. Thus, in some embodiments, step (1) may comprise dosing of about 1 mg/day to about 1500 mg/day of a F1C for 1, 2, 3, 4, 5, 6, 7, 8, 9 or 10 or more consecutive days. Then, step (2) may comprise not administering any F1C for at least about 2, 3, 4, 5, 6, 7, 14, 21, 28, 42, 56, 84, 98, 112 or more consecutive days. Step (3) could comprise dosing of a F1C for 1, 2, 3, 4, 5, 6, 7, 8, 9, 10 or more consecutive days. When step (4) is included it is typically about 1 day to about 3 months, usually 3 days to about 6 weeks. On days when the F1C is administered to the subject, it may be delivered in a single dose or in two, three or more subdoses at, e.g., about 12 hour or about 8 hour time intervals.

One aspect of invention intermittent dosing is monitoring the subject's response to a particular dosing regimen or schedule, e.g., to any intermittent administration method disclosed herein. For example, while dosing a subject who has a viral infection (e.g., HCV, HIV, SIV, SHIV), one can measure the subject's or pathogen's response, e.g., amelioration of one or more symptoms or a change in infectious particles or viral DNA or RNA in the serum or a change in an immune parameter of interest. Once a response is observed dosing can be continued for one, two or three additional days, followed by discontinuing the dosing for at least one day (at least 24 hours), usually for at least about 2, 3, 4, 5, 6, 7, 14, 21, 28, 42, 56, 70, 84, 98, 112 or more days. Once the subject's response shows signs of remission (e.g., a symptom begins to intensify, viral serum DNA or RNA begins to increase or an immune parameter, e.g., as described herein, begins to deteriorate), dosing can be resumed for another course. An aspect of the subject's response to F1C(s) is that the subject may show a measurable response within a short time, usually about 5-10 days, which allows straightforward tracking of the subject's response, e.g., by monitoring viral titer in peripheral white blood cells ("PBMC"), by measuring viral nucleic acid levels in the blood or by measuring a white blood cell population(s) or expression of a cytokine or interleukin by e.g., white blood cells or a subset(s) thereof. One may monitor one or more immune cell subsets, e.g., NK, LAK, dendritic cells or cells that mediate ADCC immune responses, during and after intermittent dosing to monitor the subject's response and to determine when further administration of the F1C is indicated. These cell subsets are monitored as described herein, e.g., by flow cytometry.

Dosages of the F1C, continuous or intermittent dose protocols, routes of administration and the use of combination therapies with other standard therapeutic agents or treatments could be applied essentially as described above for any of the diseases or conditions that are disclosed herein. Thus, the F1Cs may be administered prophylactically or therapeutically in chronic or acute conditions. In acute conditions, the F1Cs may also be administered at the time of occurrence or relatively soon after an acute event such as the onset of surgery, a migraine or the occurrence of trauma, e.g., a central nervous system injury, a cerebral stroke or myocardial infarction. For acute events, a F1C may thus be administered concurrently, e.g., within about 15 minutes or about 30 minutes or about 45 minutes of the onset or occurrence of the acute event, or at a later time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours after the onset or occurrence of the acute event or at any range of times defined by any two of these later times. The F1Cs may thus be administered at about 4-120 hours, about 6-120 hours, about 8-48 hours, 8-24 hours, 8-12 hours, 10-12 hours, 10-14 hours, 10-16 hours, about 10-24 hours, 12-14 hours or about 12-16 hours after an acute event starts, occurs or is believed to have begun, e.g., after a surgical procedure has been completed or after a radiation treatment has ended or after a cytotoxic chemotherapy or a myelosuppressive cancer chemotherapy has been administered to the subject.

Alternatively, the F1Cs may be administered before, e.g., within about 15 minutes, about 30 minutes or about 45 minutes before the onset or occurrence of a planned or anticipated acute event, or at an earlier time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours before the onset or occurrence of the acute event. The F1Cs may thus be administered at about 6-120 hours, about 8-48 hours, about 10-24 hours, about 10-16, or about 12-16 hours before the planned or anticipated acute event, e.g., before a planned surgery or a radiation treatment starts or occurs.

Formulations and Compositions for Preparing Formulations.

Invention embodiments include formulations described here and elsewhere in this disclosure. While it is possible for the F1C(s) to be administered to a subject or incubated with a subject's cells in vitro as the compound alone, it is usual to use F1C in a formulation or at least in a composition that contains 1, 2, 3, 4, 5, 6 or more excipients. The formulations, which are useful for veterinary or human pharmaceutical use, comprise at least one F1C, together with 1, 2, 3, 4, 5, 6 or more excipients and optionally one or more additional therapeutic ingredients.

The invention includes compositions comprising one or more pharmaceutically acceptable excipients or carriers. The compositions are used to prepare formulations suitable for human or animal use. Formulations may be designed or intended for oral, rectal, nasal, topical or transmucosal (including buccal, sublingual, ocular, vaginal and rectal) and parenteral (including subcutaneous, intramuscular, intravenous, intradermal, intrathecal, intraocular and epidural) administration. In general, aqueous and non-aqueous liquid or cream formulations are delivered by a parenteral, oral or topical route. In other embodiments, the F1C(s) may be present as an aqueous or a non-aqueous liquid formulation or a solid formulation suitable for administration by any route, e.g., oral, topical, buccal, sublingual, parenteral, aerosol, a depot such as a subcutaneous depot or an intraperitoneal or intramuscular depot or a rectal or vaginal suppository. The preferred route may vary with, for example, the subject's pathological condition or weight or the subject's response to therapy with a F1C or other therapy that is used or that is appropriate to the circumstances. The F1C formulations can also be administered by two or more routes, e.g., subcutaneous injection and buccal or sublingual, where these delivery methods are essentially simultaneous or they may be essentially sequential with little or no temporal overlap in the times at which the compound is administered to the subject.

The formulations include those suitable for the foregoing administration routes. The formulations may conveniently be presented in unit dosage form and may be prepared by any of the methods known in the art of pharmacy. Techniques, excipients and dosage forms are found in, e.g., *Remington's Pharmaceutical Sciences*, Mack Publishing Co., Easton, Pa. 1985, 17$^{th}$ edition; Nema et al., *PDA J. Pharm. Sci. Tech.* 1997 51:166-171; *Pharmaceutical Coating Technology,* 1995, G. Cole, et al., editors, Taylor & Francis, ISBN 0136628915; *Pharmaceutical Dosage Forms,* 1992 2$^{nd}$ revised edition, volumes 1 and 2, H. A. Lieberman, et al., editors, Marcel Dekker, ISBN 0824793870; *Pharmaceutical Preformulation,* 1998, pages 1-306, J. T. Carstensen, Technomic Publishing Co. ISBN 1566766907; and *Encyclopedia of Pharmaceutical Technology*, volumes 1, 2 and 3, 2$^{nd}$ edition, 2002, J. Swarbrick and J.0 Boylan, editors, Marcel Dekker, Inc., New York, N.Y.

Methods to make invention formulations include the step of bringing into association or contacting a F1C(s) with one or more excipient, such as one described herein or in the cited references. In general the formulations are prepared by uniformly and intimately bringing into association the F1C(s) with liquid excipients or finely divided solid excipients or both, and then, if appropriate, shaping the product.

Formulations suitable for oral administration are prepared as discrete units such as capsules, soft gelatin capsules (softgels), cachets, tablets or caplets each containing a predetermined amount of the F1C(s). F1C formulations can also be present as a powder or granules or as a solution or a suspension, colloid or gel in an aqueous liquid or base or in a non-aqueous liquid or base; or as an oil-in-water liquid emulsion or a water-in-oil liquid emulsion. The F1C formulations may also be a bolus, electuary or paste. Suspension formulations will typically contain about 0.5% w/w or about 1% w/w to about 5%, 10%, 15% or 20% w/w of the F1C, which can be for parenteral use or for other routes of administration, e.g., oral softgels.

A tablet is made by compression or molding, optionally with one or more accessory ingredients. Compressed tablets may be prepared by compressing in a suitable machine the F1C(s) in a free-flowing form such as a powder or granules, optionally mixed with a binder, lubricant, inert diluent, preservative, surface active or dispersing agent. Molded tablets may be made by molding in a suitable machine a mixture of the powdered or granulated F1C and one or more excipients, which are optionally moistened, with an inert liquid diluent or excipient. The tablets may optionally be coated or scored and optionally are formulated so as to provide slow or controlled release of the F1C(s) therefrom. An exemplary tablet or caplet formulation suitable for buccal or sublingual delivery of a F1C to a subject's tissues comprises about 25 or 50 mg of a F1C comprising per 25 mg of the F1C about 6.2 mg povidone, about 0.62 mg magnesium stearate, about 45 mg mannitol and about 48 mg of compressible sucrose.

For infections of the eye or other external tissues e.g., the mouth or skin, the formulations are typically applied as a topical ointment or cream containing the F1C(s) in an amount of, for example, about 0.075 to about 20% w/w (including F1C(s) in a range between about 0.1% and 20% in increments of 0.1% w/w such as about 0.6% w/w, about 0.7% w/w, about 1% w/w, about 1.5% w/w, about 2% w/w, about 2.5 w/w, about 3% w/w, about 5% w/w, about 7% w/w, about 10% w/w etc.), including about 0.2 to 15% w/w and about 0.5 to 10% w/w. When formulated in an ointment, the F1C(s) may be employed with either a paraffinic or a water-miscible ointment base. Alternatively, they may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, butane 1,4-diol, mannitol, sorbitol, glycerol and a polyethylene glycol (including, e.g., PEG 300 and PEG 400) and mixtures thereof. The topical formulations may include a compound that enhances absorption or penetration of the F1C(s) through the skin or other affected areas. Examples of such dermal penetration enhancers include dimethyl sulphoxide and related analogs.

The oily phase of the emulsion formulations may be constituted from known excipients in a known manner. While the phase may comprise an emulsifier or emulgent, it typically comprises a mixture of at least one emulsifier with a fat or an oil or with both a fat and an oil. A hydrophilic emulsifier may be included together with a lipophilic emulsifier, which acts as a stabilizer. Some embodiments include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulations include Tween60™, Span80™, cetostearyl alcohol, benzyl alcohol, myristyl alcohol, glyceryl monostearate and sodium lauryl sulfate. Other excipients include emulsifying wax, propyl gallate, citric acid, lactic acid, polysorbate 80, sodium chloride, isopropyl palmitate, glycerin and white petrolatum.

Formulations suitable for topical administration to the eye include eye drops, which are usually sterile, wherein the F1C(s) is dissolved or suspended in a suitable excipient(s), including an aqueous solvent for a F1C(s) that comprise at least about 0.5, one, two or more charges at pH values near neutrality, e.g., about pH 6-8. The F1C(s) is typically present in such formulations in a concentration of about 0.5-20% w/w, about 1-10% w/w or about 2-5% w/w.

Formulations suitable for topical administration to oral mucosa include lozenges or tablets comprising the F1C(s) in a flavored basis or a monosaccharide or disaccharide such as sucrose, lactose or glucose and acacia or tragacanth; pastilles comprising the F1C(s) in an inert basis such as gelatin and glycerin, or sucrose and acacia; and mouthwashes comprising the F1C(s) in a suitable liquid excipient(s). In some embodiments, the lozenges or tablets optionally comprise the property of rapid dissolution or disintegration, e.g., disintegration within about 15 seconds to about 2 minutes, while in others, the lozenges or tablets comprise the property of slower dissolution or disintegration, e.g., disintegration within about 2 minutes to about 10 minutes or more.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the F1C(s) such excipients as are known in the art to be appropriate.

Formulations suitable for parenteral administration include aqueous and non-aqueous sterile injection solutions which may contain anti-oxidants, buffers, bacteriostats, salts (e.g., NaCl, potassium or sodium carbonate or bicarbonate or potassium or sodium phosphates) and solutes which render the formulation isotonic with the blood of the intended subject; and aqueous and non-aqueous sterile suspensions which may include suspending agents or thickening agents. In general, the F1C that is present in liquid compositions or formulations is completely dissolved in aqueous or non-aqueous excipients. However, in some embodiments, e.g., transient compositions or some formulations, the F1C is partially dissolved while the remaining portion is present as a solid, which can be a suspension or a colloid.

Formulations suitable for parenteral delivery of F1Cs to subjects such as humans or animals typically comprise 1, 2, 3, 4, 5, 6 or more excipients. Exemplary embodiments include (1) any two, three or four of propylene glycol, PEG200, PEG300, ethanol, benzyl alcohol and benzyl benzoate and (2) any two, three or four of propylene glycol, PEG100, PEG200, PEG300, PEG400, benzyl alcohol and benzyl benzoate. Typically such formulations will contain both propylene glycol and one or more PEGs, e.g., PEG100, PEG200, PEG300 or PEG400, which enhance the solublity of the F1C by a cosolvent effect.

Formulations, or compositions disclosed herein for use to make formulations suitable for administration by the routes disclosed herein optionally comprise an average particle size in the range of about 0.01 to about 500 microns, about 0.1 to about 100 microns or about 0.5 to about 75 microns. Average particle sizes include a range between 0.01 and 500 microns in 0.05 micron or in 0.1 micron or other increments, e.g., an average particle size of about 0.05, 0.1, 0.2, 0.3, 0.4, 0.5, 0.7, 1, 1.5, 2.0, 2.5, 3.0, 3.5, 4.0, 4.5, 5.0, 5.5, 6, 7, 8, 9, 10, 15, 20, 25, 30, 35, 40, 50, 60, 75, 85, 100, 120, 150, etc. microns). The F1C itself that is used to make a formulation can have one, two or more of these average particle sizes. When F1Cs or compositions that comprise a F1C are used as intermediates to make a formulation, they may comprise one, two, three or more of these average particle sizes, or size ranges. In preparing any of the compositions or formulations that are disclosed herein and that comprise a F1C (and optionally one or more excipients), one may optionally mill, sieve or otherwise granulate the compound or composition to obtain a desired particle size, e.g., as described above.

Milling or micronization by any other method may occur before or after the F1C is contacted with one or more excipients. For example, one may mill a F1C to obtain an average particle size (or diameter) of about 0.05-50 μM or about 0.5-10 μM (e.g., about 0.02, 0.04, 0.05, 0.07, 0.1, 0.5, 1, 1.5, 2, 2.5, 5, 10, 15, 20, 30, 40, 50, 60, 80, 100 or 120 μM average particle size or diameter) before contacting the milled F1C with a liquid or solid excipient. In some cases the F1C is milled or sieved to obtain an average particle size of about 5 μm or about 10 μm before it is contacted with a solid or liquid excipient(s) to obtain a solution or suspension or a powder suitable for making a tablet, capsule or other dosage form as described herein or in the cited references. Micronized compound may be prepared using any suitable process for obtaining small particles, e.g., controlled precipitation from a solution, micronizing or milling, a number of which are known in the art. The micronized particles may include a percentage of particles that are less than or equal to about 0.1-20 μm in diameter. Ranges of average particle sizes include F1Cs of about 0.04-0.6 μm, about 0.04-1.0 μm, about 0.05-0.6 μm, about 0.05-1.0 μm, about 0.1-0.4 μm, about 0.5-1 μm, about 1-20 μm or about 2-50 μm.

As used herein, reference to an average particle size or an average particle diameter means that the material, e.g., a F1C(s), an excipient(s) or a composition that comprises both, is ground, milled, sieved or otherwise treated so as to comprise the specified average size. It is to be understood that some particles may be larger or smaller, but the composition or the F1C(s) will comprise a significant proportion of the material with the specified size or within an acceptable range of the specified size, e.g., at least about 70% or about 80% of the particles within about 30% to about 50% of the average size or diameter. Micronization methods include milling by ball mills, pin mills, jet mills (e.g., fluid energy jet mills) and grinding, sieving and precipitation of a compound(s) from a solution, see, e.g., U.S. Pat. Nos. 4,919,341, 5,202,129, 5,271,944, 5,424,077 and 5,455,049. Average particle size is determined by known methods, e.g., transmission electron microscopy, scanning electron microscopy, light microscopy, X-ray diffractometry, light scattering methods or Coulter counter analysis.

Thus, the F1Cs may comprise a powder that consists of one, two or more of these average particle sizes and the powder may be contacted with a solid excipient(s), suitably mixed and optionally compressed or formed into a desired shape. Alternatively, such a F1C(s) is contacted with a liquid excipient(s) to prepare a liquid formulation or a liquid composition that is incorporated into a solid formulation. Suitable micronized formulations thus include aqueous or oily solutions or suspensions of the F1C(s).

Formulations suitable for aerosol administration typically will comprise a fine powder, e.g., having an average particle size of about 0.1 to about 20 microns or any one, two or more of the average particle sizes within this range that are described above. The powder is typically delivered by rapid inhalation through the nasal passage or by inhalation through the mouth so as to reach the bronchioles or alveolar sacs of the lungs.

Formulations suitable for aerosol, dry powder or tablet administration may be prepared according to conventional methods and may be delivered with other therapeutic agents such as compounds heretofore used in the treatment or prophylaxis of viral or other infections as described herein. Such formulations may be administered, e.g., orally, parenterally (e.g., intravenous, intramuscular, subcutaneous, intradermal, intrathecal), topically, sublingually or by a buccal or sublingual route.

Micronized F1C is useful, e.g., to facilitate mixing, dissolution or uniform suspension of the F1C in one or more liquid or solid excipients, e.g., a PEG such as PEG 300 or PEG 400, propylene glycol, benzyl benzoate, a complexing agent, such as a cyclodextrin (e.g., an α-, β- or γ-cyclodextrin such as hydroxypropyl-β-cyclodextrin). Micronized F1C is also useful to facilitate uniformly distributing drug substance when the micronized compound is contacted with one or more solid excipients (e.g., a filler, a binder, a disintegrant, complexing agent (e.g., a cyclodextrin such as hydroxypropyl-β-cyclodextrin), a preservative, a buffer or a lubricant).

In related embodiments, suitable compositions or formulations comprise a F1C that is present in two or more physical forms. For example, a liquid composition or formulation may comprise a F1C that is present in solution and as undissolved particles, which may be milled as described herein. Alternatively, a solid composition or formulation may comprise a F1C that is present as an amorphous form and as a crystal or in an encapsulated granule. Such encapsulated granules may comprise a slow release type formulation and the F1C that is present may be in one or more physical forms, e.g., liquids or solids as described herein, but usually as a solid in tablets or other solid formulations.

The formulations are presented in unit-dose or multi-dose containers, for example sealed ampules and vials, and may be stored in a freeze-dried (lyophilized) condition requiring only the addition of the sterile liquid excipient, for example water for injection, immediately prior to use. In general, solid, liquid or other formulations or compositions that comprise a F1C, e.g., unit dosages for solid or liquid formulations, are stored in a sealed container, which may optionally be opaque or nearly opaque (e.g., amber or blue glass or brown plastic) to reduce the amount of light that reaches the formulation or composition. Such containers are also optionally sealed, e.g., hermetically sealed, to prevent or limit exchange of air, water or other gases between the container's contents and air. Extemporaneous injection solutions and suspensions are prepared from sterile powders, granules and tablets as described above. Unit dosage formulations are those containing a daily dose or unit daily sub-dose, as recited herein, or an appropriate fraction thereof, of the F1C(s).

Invention formulations include controlled release or slow release formulations containing a F1C(s) in which the release of the F1C(s) is controlled or regulated to allow less frequency dosing or to improve the pharmacokinetic or toxicity profile of a given F1C(s). Polymers and other materials that are suitable to prepare controlled release formulations that comprise a F1C have been described, e.g., U.S. Pat. Nos. 4,652,443, 4,800,085, 4,808,416, 5,013,727, 5,188,840.

Formulations may thus contain microcapsules, granules or other shaped forms and may comprise a F1C and a slow release polymer or polymer matrix that comprises or consists of one or more of ethylene dimethacrylate, diethylene glycol dimethacrylate, diethylene glycol diacrylate, triethylene glycol dimethacrylate, triethylene glycol diacrylate, tetrathylene glycol dimethacrylate, tetraethylene glycol diacrylate, polyethylene glycol dimethacrylate, polyethylene glycol diacrylate, diethylaminoethyl dimethacrylate, glycidyl methacrylate, epoxy acrylate, glycidyl acrylate, hydroxyethyl methacrylate, hydroxyethyl acrylate, hydroxypropyl methacrylate, hydroxypropyl acrylate, hydroxybutyl methacrylate, hydroxybutyl acrylate, hydroxyhexyl methacrylate, hydroxyhexyl acrylate, butanediol dimethacrylate, butanediol diacrylate, propanediol dimethacrylate, propanediol diacrylate, pentanediol dimethacrylate, pentanediol diacrylate, hexanediol dimethacrylate, hexanediol diacrylate, neopentyl glycol dimethacrylate, neopentyl glycol diacrylate, trimethylopropane triacrylate, trimethylolpropane trimethacrylate, trimethyloethane triacrylate, trimethylolethane trimethacrylate, polypropyleneglycol diacrylate, and polypropylene glycol dimethacrylate.

Invention embodiments include the product made by a process of combining, mixing or otherwise contacting a F1C and one, two or more excipients. Such products are produced by routine methods of contacting the ingredients. Such products optionally contain a diluent, a disintegrant, a lubricant, a binder, or other excipients described herein or in references cited herein.

When a F1C and an excipient(s) is contacted or mixed, the final composition may comprise a homogenous mixture or it may comprise a mixture that is not homogenous for one or more of the compounds that are present in the composition. Compositions and formulations that are either homogenous or non-homogenous are included in the scope of the invention. Non-homogenous compositions can be used, e.g., to make controlled release formulations.

Other embodiments include the product obtained by storing invention compositions or formulations, e.g., unit dosage forms or compositions used to make formulations, at about 4-40° C. for at least about 30 days, e.g., storage at ambient temperature for about 1-24 months. Invention formulations will typically be stored in hermetically or induction sealed containers for these time periods. Compositions and formulations that comprise a F1C will typically be held in closed or sealed containers, particularly when the composition is a formulation for pharmaceutical or veterinary use.

Typical containers for storage of compositions and formulations that comprise a F1C will limit the amount of water that reaches the materials contained therein. Typically, formulations are packaged in hermetically or induction sealed containers. The containers are usually induction sealed. Water permeation characteristics of containers have been described, e.g., Containers—Permeation, chapter, USP 23 <671>, United States Pharmacopeial Convention, Inc., 12601 Twinbrook Parkway, Rockville, Md. 20852, pp.: 1787 et seq. (1995).

Immune Modulation.

The F1Cs, or the biologically active substances produced from these compounds by hydrolysis or metabolism in vivo, have a number of clinical and non-clinical applications. The compounds are generally useful to correct immune dysregulation, e.g., imbalanced immune responses to disease conditions, pathogens or the like, suppression of an innate or acquired immune response(s) and inflammation conditions in vertebrate or mammalian subjects, e.g., as disclosed herein. Thus, while the compounds will generally enhance a deficient immune response in a given clinical condition, they will generally reduce the same immune response when it is too active in a different clinical condition. For example, they can enhance insufficient or suboptimal Th1 immune responses, reduce excess or undesirable Th2 immune responses, reduce excess or undesirable Th1 immune responses or enhance insufficient or suboptimal Th2 immune responses or they can reduce excess or undesirable inflammation or one or more of its symptoms. The compounds will generally also modulate dysregulated Tc1 and Tc2 immune responses (associated with CD8$^+$ T cells) in a similar manner, e.g., excessive Tc1 or Tc2 responses will be detectably decreased and deficient or suboptimal Tc1 or Tc2 responses will generally be detectably enhanced.

Invention embodiments include a method to modulate a subject's innate immunity, Th1 immune responses, Tc1 immune responses, Th2 immune responses or Tc2 immune responses comprising administering an effective amount of a F1C to a subject or delivering the F1C to the subject's tissues. Other methods include modulating an immune or cellular response in a subject in need thereof comprising administering to the subject, or delivering to the subject's tissues, an effective amount of a compound of formula 1. Immune and cellular response modulation includes enhancing Th1 immune responses, reducing Th2 immune responses, reducing Th1 immune responses, enhancing Th2 immune responses, reducing unwanted or pathological inflammation, enhancing hematopoiesis or modulating the synthesis, level or a biological activity of a biomolecule such as (1) a transcription factor such as a nuclear hormone receptor or an associated receptor factor, (2) a purine such as adenosine, (3) a nucleotide cofactor such as NADPH, (4) a cytokine or interleukin or a receptor for a cytokine or interleukin, or (5) another biomolecule as disclosed herein. Such enhancements, reductions, levels or activities are usually in an easily detectable range, e.g., a change compared to a suitable control of at least about 5%, 10%, 20%, 30%, 40%, 50%, 60%, 70%, 80%, 90%, 95% or a range that is between about any two of these values. Typically the subject is in need of such treatment, e.g., by having a clinical condition disclosed herein or being subject to developing such a condition, e.g., having been exposed or potentially exposed to a pathogen or having a predisposing condition such as precancer.

In modulating one or more activities of Th1, Th2, Tc1 or Tc2 cells or their function(s), the F1Cs will typically detectably modulate one, two, three or more factors, e.g., immune cell subsets or populations, cytokines, interleukins, surface antigens such as a CD molecule(s) and/or their receptors that affect the development, migration, numbers or biological function(s) of such cells. When a Th1 or Tc1 cell or population is affected, the F1Cs will typically increase or decrease the synthesis or level of one, two or more of an associated effector factor, e.g., IFNγ, IL-2, IL-12, IL-18, T-bet, PPARα and PPARγ or a cell surface molecule, e.g., as disclosed herein or in the cited references, that is associated with or needed for normal, optimal or enhanced Th1 or Tc1 cells or cell function. Such molecules are generally associated with development or enhancement of Th1 or Tc1 cells or their biological function(s). When a Th2 or Tc2 cell or population is affected, the F1Cs will typically increase or decrease the synthesis or level of one, two or more of an associated effector factor, e.g., IL-4, IL-5, IL-6, IL-8, IL-10, IL-13, GATA-3, COX-2 or a cell surface molecule, e.g., as disclosed herein or in the cited references, that is associated with or needed for normal, optimal or enhanced Th2 or Tc2 cells or cell function(s). Such molecules are generally associated with development or enhancement of Th2 or Tc2 cells or their biological function(s).

Similarly, when a subject has or is subject to developing an unwanted or excessive inflammation, the F1Cs will generally detectably modulate one or more relevant effector factors for inflammation, e.g., a detectable decrease of one, two, three or more of IL-1α, IL-1β, TNFα, TNF-β, MIP-1α, MIP-2, TGF-β1, IP-10, LT-β, γIFN, IL-6, IL-8, IL-10 and COX-2, lipoxygenase, or an increase of one or more suppressor factors or antagonists of inflammation. Such modulation can comprise increases or decreases of at least about 2%, 5%, 10%, 15%, 20%, 25%, 30%, 40%, 50%, 60%, 70%, 75%, 80%, 85%, 90%, 95%, 98%, 100%, 200%, 300%, 500%, 1000%, 5000% or within a range between any two of these values, e.g., between about 5-95%, about 10-90%, about 5-60% or about 40-95%. In general, such changes leads to a detectable amelioration of an inflammation-associated disease, condition, symptom or to the detectable slowing of the progression thereof or to a detectably reduced incidence or severity of or susceptibility to developing an unwanted inflammatory response.

In conditions where an unwanted or excessive Th1, Tc1, Th2 or Tc2 response is associated with or causes a disease(s), disease(s) progression, disease(s) state maintenance, condition(s) or symptom(s), the F1Cs will generally decrease the level or one or more biological activity of one, two or more of their respective associated effector molecules. In conditions where a deficient or suboptimal Th1, Tc1, Th2 or Tc2 response is associated with or causes a disease(s), disease(s) progression, disease(s) state maintenance, condition(s) or symptom(s), the F1Cs will generally increase the level or one or more biological activity of one, two, three or more of their respective associated effector molecules. Such changes in the level or biological activity(ies) the associated effector molecules is generally detectable using standard methods and is typically an increase (when a response is insufficient) or a decrease (when a response is in excess) of at least about 2%, 5%, 10%, 15%, 20%, 25%, 30%, 40%, 50%, 60%, 70%, 75%, 80%, 85%, 90%, 95%, 98% or within a range between any two of these values, e.g., between about 5-95%, about 10-90%, about 5-60% or about 40-95%. In general, such changes leads to a detectable amelioration of a disease, condition, symptom or to the detectable slowing of the progression thereof or to a detectably reduced incidence or severity of or susceptibility to developing a disease(s) or the occurrence of a symptom(s) for a at least a portion of subjects that are treated with a F1C, e.g., at least about 5%, 10%, 20%, 40%, 60% or 80% of treated subjects. The F1Cs may facilitate the clinical cure of a disease(s), prolong remission of a disease(s) or eliminate or ameliorate a clinically detectable symptom(s).

The F1C will generally also affect the function of other immune cell subsets in a similar manner. Thus, when an insufficient macrophage, dendritic cell or neutrophil response is associated with the establishment, maintenance or progression of a disease, symptom or a condition, the F1Cs will generally enhance of the level or a biological activity(ies) of one or more effector molecule associated with or needed for an optimal or more normal response or immune function that is mediated by the macrophages, dendritic cells or neutrophils. Similarly, when the subject suffers from a excessive or pathological activity associated with macrophages, dendritic cells or neutrophils, which is associated with the establishment, maintenance or progression of a disease, symptom or a condition, the F1Cs will generally detectably reduce the level or a biological activity(ies) of one or more effector molecule associated with or needed for an optimal or more normal response or immune function that is mediated by the macrophages, dendritic cells or neutrophils. Such effector molecules are as described herein or in the cited references.

As used herein, reference to Th1 or Th2 immune responses means such responses as observed in mammals generally and not as observed in the murine system, from which the Th1 and Th2 terminology originated. Thus, in humans, Th1 cells are $CD4^+$ T lymphocytes and they usually preferentially display chemokine receptors CXCR3 and CCR5, while Th2 cells are $CD4^+$ T lymphocytes and usually preferentially express the CCR4, CCR8 and/or CXCR4 chemokine receptor molecule(s) and generally a smaller amount of CCR3, see, e.g., U. Syrbe et al., *Springer Semin. Immunopathol.* 1999 21:263-285, S. Sebastiani et al., *J. Immunol.* 2001 166:996-1002. Tc1 and Tc2 immune responses are mediated by $CD8^+$ lymphocytes and means to identify these cells and their associated lymphokines, cell specific antigens and biological activities have been described, see, e.g., M. B. Faries et al., Blood 2001 98:2489-2497, W. L. Chan et al., *J. Immunol.* 2001 167:1238-1244, C. Prezzi et al., *Eur. J. Immunol.* 2001 31:894-906, H. Ochi et al., *J. Neuroimmunol.* 2001 119:297-305, D. H. Fowler and R. E. Gress, *Leukemia and Lymphoma* 2000 38:221-234.

The F1Cs are useful in reestablishing normal immune function in various immune dysregulation or immune suppression conditions. For example, they are useful to treat, slow progression of or to ameliorate one or more symptoms associated with one or more of an autoimmune condition(s), a inflammation condition(s), an infection(s), a cancer(s), a precancer(s), a chemotherapy(ies), radiation therapy, a burn(s), a trauma(s), a surgery(ies), a pulmonary condition, a cardiovascular disease(s) and a neurological or neurodegenerative disease(s). Without being limited to any theory, the F1Cs are believed to act through several mechanisms, including by directly or indirectly modulating nuclear hormone receptor activity or by affecting or modulating other biological targets such as transcription factors, steroid binding proteins or enzymes in at least some of the diseases, conditions or symptoms disclosed herein.

The F1Cs are useful to modulate delayed-type hypersensitivity ("DTH") responses and anergic conditions in subjects having to subject to developing abnormal DHT responses or anergy. Means to measure such responses and conditions are known and can be used to characterize the effects of the F1Cs on these responses and conditions. See, e.g., A. E. Brown, et al., *J. Med. Assoc. Thailand* 83:633-6392000, R. A. Smith et al., *J. Adolesc. Health* 27:384-3902000, N. M. Ampel, *Med. Mycology*37:245-2501999. The compounds will generally detectably enhance or restore DTH in immune suppression conditions. They will also generally detectably reduce or eliminate anergy in subjects having significantly reduced or no immune response to, e.g., specific antigens or pathogens.

Clinical indications that have an association with or have a symptom(s) that is consistent or associated with an excessive or unwanted Th2 immune response include, e.g., fatigue, pain, fever or an increased incidence of infection, schizophrenia, acute myelitis, tumor progression, progressive systemic sclerosis, Omenn's syndrome, atopic disease, atopy, allergen hypersensitivity, atopic asthma, atopic dermatitis, burns, trauma (e.g., bone fracture, hemorrhage, surgery), immune responses to xenotransplantation, chronic periodontitis, SLE (systemic lupus erythematosus), discoid lupus erythematosus, osteoporosis, myasthenia gravis, Graves disease, mite-associated ulcerative dermatitis, rheumatoid arthritis and osteoarthritis. Excessive Th2 immune responses are also associated with an unwanted symptom or pathology, e.g., fatigue, pain, fever or an increased incidence of infection, that is associated with aging, allergy and inflammation conditions such as allergic bronchopulmonary aspergillosis in cystic fibrosis patients, allergic respiratory disease, allergic rhinitis, atopic dermatitis, subepithelial fibrosis in airway hyperresponsiveness, chronic sinusitis, perennial allergic rhinitis, fibrosing alveolitis (lung fibrosis). This common underlying immune component is at least part of the pathology or symptoms of all of these conditions. This allows a F1C to be effectively used to prevent or treat the condition or to treat or ameliorate one or more symptoms that are associated with these conditions. Thus, in some embodiments, an unwanted or excessive Th2 response is present and amelioration of one or more symptoms associated with this condition is accomplished by administering an effective amount of a F1C according to the methods described herein, e.g., F1C is administered using a formulation and a route of administration essentially as described herein on an intermittent or a daily basis.

Typically, unwanted Th2 immune responses are associated with, or caused by, increased expression of one or more cytokines or interleukins such as one, two, three or more of cortisol, IL-4, IL-5, IL-6, IL-10 and IL-13. Administration of a F1C will generally reduce the expression of one or more of the Th2-associated cytokines or interleukins. At the same time, the compounds generally enhance the expression of one or more cytokines or interleukins associated with Th1 immune responses. Because of their capacity to modulate or to balance Th1 and Th2 immune responses, the compounds are useful for a variety of clinical conditions, e.g., infection, immunosuppression or cancer, where an enhanced Th1 immune response is desired. Effects of the F1Cs in treating, preventing or slowing the progression of the clinical conditions described herein can include one or more of (1) enhancing the Th1 character of a subject's immune response or immune status, (2) increasing the intensity of a Th1 or a Th2 immune response or both and (3) decreasing inflammation or a symptom thereof.

Exemplary conditions where an immune imbalance or an excessive Th1 immune response is involved include autoimmune diseases such as multiple sclerosis, Crohn's disease (regional enteritis), ulcerative colitis, inflammatory bowel disease, rheumatoid arthritis, reactive arthritis, acute allograft rejection, sarcoidosis, type 1 diabetes mellitus, *Helicobacter pylori* associated peptic ulcer, graft versus host disease and Hashimotos' thyroiditis. Because these conditions are associated with a similar type immune dysfunction, a F1C can be effectively used to prevent or treat these conditions or to treat or ameliorate one or more symptoms associated therewith. Thus, in some embodiments, an unwanted or excessive Th1 response is present and amelioration of one or more symptoms associated with this condition is accomplished by administering an effective amount of a F1C according to the methods described herein, e.g., F1C is administered using a formulation and a route of administration essentially as described herein on an intermittent or a daily basis. In other embodiments, a deficient Th1 response is enhanced, which is optionally observed as a detectable increase in one or more of IFNγ, IL-2, IL-12 or IL-18 in Th1 cells or in accessory cells such as a dendritic cell or macrophage. In all of the conditions where an insufficient or excess Th1, Th2, Tc1 or Tc2 response is present, amelioration of one or more symptoms associated with the condition is accomplished by administering an effective amount of a F1C according to the methods described herein.

Aspects of the invention include the use or administration of compositions or formulations that comprise a carrier and an amount of at least one F1C effective to detectably modulate an immune parameter. For example, to enhance the relative proportion of a desired immune cell subset, e.g., $CD4^+$ T cells, $CD8^+$ T cells, NK cells, LAK cells, neutrophils, granulocytes, basophils, eosinophils or dendritic cells, or to modulate (detectably increase or decrease) one or more functions of immune cell subsets. The F1Cs can modulate the expression of CD molecules or alter the proportion of cell subsets, e.g., $CD4^+$ or $CD8^+$ T cells, or their relative numbers in a subject's blood or tissues. CD and related molecules participate in the function of various immune cell subsets and can be useful as markers for immune function in vivo. In some aspects, the F1Cs activate immune cells which generally alters (increases or decreases) expression of, or changes the numbers of cells that express one or more of, CD4, CD6, CD8, CD25, CD27, CD28, CD30, CD36, CD38, CD39, CD43, CD45RA, CD45RO, CD62L, CD69, CD71, CD90 or HLA-DR molecules. Often, the numbers of cells that express these molecules are increased, e.g., CD25, CD36, CD16 or CD69. Typically, such increases are observed as an increased proportion of circulating white blood cells that express one or more of these molecules or white blood cells, e.g., T cells or dendritic cells, that express CXCR3, CCR5, CCR4, CCR8 and/or CXCR4. In some cases the number of such molecules per cell is detectably altered.

Expression of one or more adhesion molecules CD2, CD5, CD8, CD11a, CD11b, CD11c, CD18, CD29, CD31, CD36, CD44, CD49a, CD49b, CD49c, CD49d, CD49e, CD49f, CD50, CD54, CD58, CD103 or CD104 are also detectably modulated after administration of the F1Cs to a subject. Often, the numbers of cells that express these molecules are increased, e.g., CD5 or CD56. The adhesion molecules function in various aspects of immune responses, such as binding to class I MHC molecules, transducing signals between cells or binding to molecules in the extracellular matrix associated with endothelial or other cell types. Administration of the F1Cs to a subject also affects the numbers of certain immune cell subsets, e.g., NK cells (e.g., $CD8^-$, $CD56^+$ or $CD8^+$, $CD56^+$) or lymphokine activated killer cells (LAK). Increased circulating NK or LAK cells are typically observed, which is reflected in increased numbers of cells that express one or more of CD16, CD38, CD56, CD57 or CD94. Also, increased numbers of circulating dendritic cell precursors are observed, as shown by increases in cells that express one or more of CD11c, CD80, CD83, CD106 or CD123. Although one can observe an increased proportion of circulating white blood cells that express one or more of these molecules, in some instances the number of such molecules per cell is detectably altered. Both the cell numbers and the density of CD molecule per cell can also be detectably modulated. Modulation of immune cell subsets typically occurs on intermittent dosing of a F1C, but will arise from any suitable dosing regimen, e.g., as described herein.

Expression of one or more homing or other receptors or receptor subunits such as CD62L, CLA-1, LFA1, CD44, ICAM, VCAM or ECAM may also be detectably affected after administration of the F1Cs to a subject. The numbers of cells that express these molecules, or the relative amounts per cell of, e.g., CD44 or CD62L, may be increased where a desired immune response is desired, e.g., migration of T cells to mucosal tissues or exposure of naïve T cells to antigen in lymph nodes. Alternatively, numbers of cells that express these molecules, or the relative amounts per cell of, e.g., CLA-1, may be decreased where inhibition of an undesired immune response, such as an inflammatory response is desired. The subject's response to such enhanced expression includes migration of cells such as movement of naïve T cells to peripheral lymph nodes in response to modulation of CD62L or other homing receptor expression. Thus, the F1Cs can also facilitate migration of various immune cell types, e.g., dendritic cells, NK cells, LAK cells, macrophages or lymphocytes, from one location to another within a subject. For example, the compounds can enhance dendritic cell or lymphocyte migration from areas such as the skin tissues to the gut associated lymphoid tissue ("GALT"), lymph nodes or spleen. Such migration may facilitate the function of those cell types by increasing their transit to tissues where their effector functions, e.g., antigen presentation by dendritic cells, normally occur. The migration period is often relatively transient (e.g., observable over about 1-7 days) or occasionally longer (e.g., occurring for about 8-40 days), depending on the dosing regimen and other factors. This migration can be observed by standard methods, e.g., by cell staining, by PCR analyses or by determining the presence of a given cell type in circulation or determining a decrease in the number circulating cells. A decrease would generally reflect sequestration of an immune cell population(s) in a tissue(s) where the immune cell normally exercises its effector functions.

Thus, in some embodiments, the migration of one or more immune cell subsets such as CD11C$^+$ cells from tissue such as skin or lung through the blood to immune tissue such as lymph nodes or GALT is seen as a transient increase in the level of circulating CD11C$^+$ cells in response to exposure of the subject's tissues to a suitable amount of a F1C. Thus, the level of CD11C$^+$ cells in the blood will generally detectably increase, e.g., a statistically significant increase, plateau and then decrease as migration of the cells to immune tissue subsides. In these embodiments, the proportion of the cells of the affected immune cell subset is typically relatively low in most physiological immune states, e.g., normal or abnormal immune conditions, compared to the total white blood cell population in circulation. In other embodiments, the migration of one or more immune cell subsets such as CD123$^+$ cells from the circulation to immune tissue such as lymph nodes or GALT results in a decrease. In these embodiments, the decrease in the numbers of circulating immune cells reflects the migration of the immune cells from the blood to immune tissue such as lymph nodes or GALT. Such a decrease may be transient and followed by recovery of the affected immune cell subset(s) over about 2 to 24 weeks. In conducting these embodiments, administration of the F1C to the subject is accomplished using the formulations or the methods as described herein.

Thus, an aspect of the invention is a method to enhance the migration of one or more immune cell types in a subject from one location (e.g., bone marrow, circulating blood or a tissue such as the skin, liver, central nervous system or lung) to another (e.g., to the blood or to a lymphoid tissue such as a lymph node, spleen or a mucosal tissue such as GALT) by administration to a subject as described herein of an effective amount of a F1C essentially as described by any of the methods disclosed herein. A related aspect is the monitoring, e.g., by suitable blood counts or tissue biopsy, of the subject's response to determine the timing and extent of such immune cell migration.

Other CD molecules that are modulated by the presence of the F1Cs in a subject include cytokine receptor molecules such as one or more of CD115, CDW116, CD117, CD118, CDW119, CD120a, CD120b, CD121a, CD121b, CD122, CD123, CD124, CD125 CD126, CDW127, CDW128 or CDW130. Often, the numbers of receptor molecules per cell will be modulated. For example, receptors for cytokines that mediate or facilitate Th1 immune responses or innate immune responses (e.g., one or more of IL-1α, IL-1β, IL-2, IL-4, IL-12, γIFN or α-interferon) will typically increase in or on cells that mediate Th1 or innate immune responses. Modulation of these molecules may be by direct interactions with a receptor(s) in the cell that expresses the cytokine receptor or indirectly by modulation of cytokine synthesis in the affected cells or in other cells, typically immune cells that may interact with the cells whose receptor synthesis is being modulated. Thus, autocrine or paracrine mechanisms may underlie some of the effects associated with administration of a F1C(s) such as altered cytokine profiles in immune cells or altered immune cell populations. Endocrine cytokine mechanisms may also contribute to desired immune responses.

Treatment of a subject with a F1C can result in a change of at least about 20-80% or about 25-50% above or below (e.g., at least 30% or at least 40% above or below) the control or basal level of affected immune cell subsets. For example, increases of more than about 30% in the total numbers of activated CD8$^+$ T cells, e.g., CD8$^+$, CD69$^+$, CD25$^+$ T cells, CD8$^+$, CD69$^+$, CD25$^-$ T cells or CD8$^+$, CD69$^-$, CD25$^+$ T cells, can occur by 7 days after a single dose of a F1C to a subject. Such increases may be greater than 50%, 60% or 100% in the total numbers of activated CD8$^+$ T cells or subsets of activated CD8$^+$ T cells in individual subjects. Typically such increases are about in the total numbers of activated CD8$^+$ T cells or subsets of activated CD8$^+$ T cells averages about 30-40%, with individual subjects experiencing increases over 100% in the numbers of activated CD8$^+$ T cells per unit blood volume compared to the basal level.

Administration of the F1Cs can affect other immune cell subsets. For example, the concentration of circulating CD4$^+$, CD69$^+$, CD25$^-$ (Th1 helper cells) and CD8$^+$, CD16$^+$, CD38$^+$ LAK cells or CD8$^-$, CD16$^+$, CD38$^+$ LAK cells typically increases during or after the course of dosing a subject with a F1C. Also, CD8$^-$, CD16$^+$, CD38$^+$ and CD8$^+$, CD16$^+$, CD38$^+$ (ADCC effector cells) and low side scatter Lin$^-$, DR$^+$, CD123$^+$ (dendritic precursors) or low side scatter Lin$^-$, DR$^+$, CD11c$^+$ (dendritic cells or precursors) may show modest to significant increases.

In subjects that are immunosuppressed, e.g., from certain infections (e.g., viral (HIV, HCV), bacterial infection or parasite infection) or from chemotherapy (e.g., an antiviral therapy, a cancer chemotherapy or a radiation therapy), administration of the F1Cs to the subject results in a favorable shift in the balance of Th1 or Th2 responses the subject can mount in the face of immunosuppression. When Th1 responses are suboptimal or insufficient, treatment with a F1C results in enhancement of Th1 responses or a reduction in Th2 responses. Conversely, when Th2 responses are suboptimal or insufficient, treatment with a F1C results in enhancement of Th2 responses, which may occur with a concomitant modulation (increase or decrease) in Th1 responses. The F1Cs can thus be used to shift the nature of a subject's immune response to result in a more balanced immune response from immunosuppression. Alternatively, the compounds can selectively suppress inappropriate or unwanted immune responses. Enhanced Th1 responses appears to be at least partly due to one or more of (i) a reduction in biological restraints, e.g., high levels of IL-4 or IL-10, on Th1 functions by preexisting primed Th1 effector cells, (ii) enhanced differentiation of Th0 cells to Th1 cells or enhanced responses mediated by Th1 cells, (iii) enhanced function of accessory cell function, e.g., antigen presentation by dendritic cells, dendritic precursor or progenitor cells or by macrophages or their precursors or progenitors, (iv) enhanced proliferation and differentiation of Th1 precursor or progenitor cells, (v) enhanced IL-12 expression in dendritic cells or their precursors, which results in enhanced differentiation of Th1 cells from Th0 precursors, (vi) enhanced expression or activity of factors associated with Th1 functions, e.g., IL-2, gamma interferon (γIFN or IFNγ), IL-18 or lymphotoxin.

An aspect of the invention methods is an alteration in the expression of IL-4 or IL-10 that occurs after administration of a F1C to a subject. A consistent observation is that extracellular IL-4 or IL-10 levels rapidly decrease to levels that are undetectable by ELISA. Intracellular IL-10 levels are reduced to levels that are near or below the limits of detection by flow cytometry. The administration of a F1C to a subject thus provides a means to inhibit either or both of these interleukins. Such inhibition may be associated with enhancement of Th1 immune responses relative to Th2 or Th0 responses, e.g., in subjects where Th1 responses are suppressed (e.g., from viral, bacterial or parasite infection (HIV, HCV, etc) or chemotherapy) or are otherwise suboptimal. In many subjects, levels of either IL-4 or IL-10, usually IL-10, before dosing with a F1C is low or undetectable. In these subjects, dosing with the F1C results in a rapid drop in the interleukin that is detectable, usually IL-4.

Clinical conditions are described in more detail below where the F1Cs are useful for treating, preventing, slowing the progression of, or ameliorating one or more symptoms associated with the described conditions. In any these conditions, any F1C disclosed herein can be used according to one or more of the dosing methods that are disclosed herein. For these conditions, dosages for the F1Cs, formulations and routes of administration are as described herein. Additional information regarding these and other clinical conditions or symptoms that can be treated, prevented or ameliorated with the F1Cs are found at e.g., *The Merck Manual*, $17^{th}$ edition, M. H. Beers and R. Berkow editors, 1999, Merck Research Laboratories, Whitehouse Station, N.J., ISBN 0911910-10-7, or in other references cited herein.

Responses to treatment of a subject having a condition disclosed herein with a F1C is optionally monitored by observing changes in one or more immune or other appropriate clinical parameters, e.g., as described herein or in D. S. Jacobs et al., editors, *Laboratory Test Handbook*, $4^{th}$ edition, pages 11-686, Lexi-Comp Inc., Hudson, Ohio, ISBN 0-916589-36-6, or in any of the references cited herein, or by monitoring the progression or severity of the underlying condition according to known methods, e.g., J.B. Peter, editor, *Use and Interpretation of Laboratory Tests in Infectious Disease*, $5^{th}$ Edition, pages 1-309, 1998, Specialty Laboratories, Santa Monica, Calif., ISBN 1-889342-13-0.

Although the forgoing combination therapies have been described in the context of viral or other infections, the protocols and methods that employ a F1C can be used in conjunction with any suitable new or known therapeutic agent(s) or treatment protocol(s) for other any other clinical condition described herein. Any of these additional treatments can be coupled with the administration of any of the F1Cs in any of the embodiments described herein. Exemplary conditions include one or more of a non-viral pathogen infection(s), a cancer(s), a precancer(s), an inflammation condition(s), an autoimmune condition(s), an immunosuppression condition(s), a neurological disorder(s), a cardiovascular disorder(s), a neurological disorder(s), diabetes, obesity, wasting, anorexia, anorexia nervosa, a cancer chemotherapy(ies) side-effect(s), a side-effect(s) of a chemotherapy(ies) or a radiation therapy(ies) of any other clinical condition disclosed herein or in the cited references, or the like. Thus, invention embodiments include the use of a F1C before, during or after a treatment that uses another suitable therapeutic agent(s) or therapeutic treatment(s) for any of the diseases or conditions disclosed herein, any of which diseases or conditions may be acute, chronic, severe, mild, moderate, stable or progressing.

Other uses for the F1C(s) include administering the compound(s) to a subject who suffers from a pathological condition(s). The treatment may treat or ameliorate the source of the condition(s) and/or symptoms associated with the pathological condition(s) such as infection with a pathogen(s) (viruses, bacteria, fungi), a malignancy, unwanted immune response, i.e., an immune response that causes pathology and/or symptoms, e.g., autoimmune conditions or allergy or conditions such as hypoproliferation conditions, e.g., normal or impaired tissue growth, or wound healing or burn healing, or in immunosuppression conditions, e.g., conditions characterized by an absence of a desired response and/or an inadequate degree of a desired response.

Cancer and Hyperproliferation Conditions.

Many cancers, precancers, malignancies or hyperproliferation conditions are associated with an unwanted Th2 immune response, a deficient Th1 response or unwanted inflammation. An insufficient Th1 immune response may play a role in the capacity of malignant or premalignant cells to escape immune surveillance. Any of the F1Cs disclosed herein, may thus be used to treat, prevent or slow the progression of one or more cancers, precancers or cell hyperproliferation conditions or they may be used to ameliorate one or more symptoms thereof. In these conditions, the F1Cs are useful to enhance the subject's Th1 responses or to reestablish a more normal Th1-Th2 balance in the subject's immune responses. The F1Cs may function at least in part by decreasing inflammation or inflammation associated markers such as IL-6 and/or by enhancing hematopoiesis in many of these conditions.

These conditions include cancers or precancers comprising carcinomas, sarcomas, adenomas, blastoma, disseminated tumors and solid tumors such as one associated with or arising from prostate, lung, breast, ovary, skin, stomach, intestine, pancreas, neck, larynx, esophagus, throat, tongue, lip, oral cavity, oral mucosa, salivary gland, testes, liver, parotid, biliary tract, colon, rectum, cervix, uterus, vagina, pelvis, endometrium, kidney, bladder, central nervous system, glial cell, astrocyte, squamous cell, blood, bone marrow, muscle or thyroid cells or tissue. The F1Cs are thus useful to treat, prevent, slow the progression of, or ameliorate one or more symptoms of a precancer, cancer or related hyperproliferation condition such as myelodysplastic syndrome, actinic keratoses, endometriosis, Barrett's esophagus, leiomyoma, fibromyoma, benign or precancerous intestinal or bowel polyps or benign prostatic hyperplasia. The compounds can also be used to treat, prevent, slow the progression of, slow the replication or growth of, or to ameliorate one or more symptoms of a primary tumor, a metastasis, an advanced malignancy, a blood born malignancy, a leukemia or a lymphoma. Any of these conditions may be in an early or mild form or can be moderate or advanced in the existent or progression of the disease or a symptom.

In treating endometriosis, the use of an F1C will slow the rate of disease progression and decrease the severity or frequency of one or more symptoms such as irregular menstrual periods, infertility abdominal pain or cramping and pain in the lower back or pelvic area, which may precede menstruation or may accompany sexual intercourse or bowel movements. Beneficial effects from F1C treatment will be mediated in patients with endometriosis at least partially by increasing the patient's Th1 immune responses and/or by decreasing anti-endometrial antibodies or aberrent Th2 immune responses. Treatment of emdometriosis could be accompanied by other suitable treatments, e.g., treatment with one or more of estrogen, progesterone, danazol, follicle stimulating hormone antagonists, leutinizing hormone antagonists, gonadotropin-releasing hormone antagonists such as nafarelin acetate or analgesics such as codeine, tylenol or aspirin.

The F1Cs can be used to treat paraneoplastic syndromes or conditions such as ones associated with lung or breast cancers that secrete calcitonin or that enhance osteoclast activity. Such conditions include hypercalcemia, Cushing's syndrome, acromegaly and non-islet cell tumor hypoglycemia. The compounds are used to decrease osteoclast activity or other symptoms associated with such conditions.

Hyperproliferation conditions that can be treated include melanoma, Kaposi's sarcoma, leiomyosarcoma, non-small cell lung cancer, small cell lung cancer, bronchogenic carcinoma, renal cell cancer or carcinoma, glioma, glioblastoma, pancreatic or gastric adenocarcinoma, gastrointestinal adenocarcinoma, human papillomavirus associated cervical intraepithelial neoplasia, cervical carcinoma, hepatoma, hepatocellular carcinoma, hepatocellular adenoma, cutaneous T-cell lymphoma (mycosis fungoides, Sezary syndrome), colorectal cancer, chronic lymphocytic leukemia, chronic myelogenous leukemia, ALL or follicular lymphoma, multiple myeloma, carcinomas with p53 mutations, colon cancer, cardiac tumors, adrenal tumors, pancreatic cancer, retinoblastoma, a small cell lung cancer, a non-small cell lung cancer, intestinal cancer, testicular cancer, stomach cancer, neuroblastoma, neuroma, myxoma, myoma, endothelioma, osteoblastoma, osteoclastoma, osteosarcoma, chondrosarcoma, adenoma, breast cancer, prostate cancer, Kaposi's sarcoma, ovarian cancer, squamous cell carcinoma of the gastrointestinal tract and non-myeloid tumors. Treating a subject with a F1C can ameliorate one or more side effects of chemotherapy or cancer symptoms such as alopecia, pain, fever, malaise, chronic fatigue and cachexia or weight loss. Other cancers, precancers or their symptoms that can be treated, prevented or ameliorated are described in, e.g., *Holland•Frei Cancer Medicine$^e$* 5, 5$^{th}$ edition, R. C. Bast et al., editors, 2000, ISBN 1-55009-1,3-1, pages 168-2453, B. C. Becker Inc. Hamilton, Ontario, Canada or *The Merck Manual*, 17$^{th}$ edition, M. H. Beers and R. Berkow editors, 1999, Merck Research Laboratories, Whitehouse Station, N.J., ISBN 0911910-10-7.

In some of these embodimants, the subject's hyperproliferation or malignant condition may be associated with or caused by one or more pathogens. Such conditions include hepatocellular carcinoma associated with HCV or HBV, Kaposi's sarcoma associated with HIV-1 or HIV-2, T cell leukemia associated with HTLV I, Burkitt's lymphoma associated with Epstein-Barr virus or papillomas or carcinoma associated with papilloma viruses (e.g., human HPV 6, HPV 11, HPV 16, HPV 18, HPV 31, HPV 45) or gastric adenocarcinoma, gastric MALT lymphoma or gastric inflammation associated with *Helicobacter pylori, lactobacillus, enterobacter, staphylococcus* or propionibacteria infection.

In some of these embodiments, the F1Cs may be used to treat, prevent or slow the progression of or ameliorate one or more conditions in a subject having or subject to developing a hyperproliferation condition where angiogenesis contributes to the pathology. Abnormal or unwanted angiogenesis or neovascularization contributes to the development or progression of solid tumor growth and metastases, as well as to arthritis, some types of eye diseases such as diabetic retinopathy, retinopathy of prematurity, macular degeneration, corneal graft rejection, neovascular glaucoma, rubeosis, retinoblastoma, uvietis and pterygia or abnormal blood vessel growth of the eye, and psoriasis. See, e.g., Moses et al., *Biotech.* 9:630-6341991, Folkman et al., *N. Engl. J. Med.*, 333:1757-1763 1995, and Auerbach et al., *J. Microvasc. Res.* 29:401-411 1985.

Dosages of the F1C, routes of administration and the use of combination therapies with other standard therapeutic agents or treatments could be applied essentially as described above for cancer or hyperproliferation conditions or other conditions as disclosed herein. Thus, in some embodiments, the use of the F1C is optionally combined with one, two or more additional therapies for a cancer or precancer(s), e.g., one, two or more of surgery and treatment with an antiandrogen or an antiestrogen as described herein or in the cited references, an antineoplastic agent such as an alkylating agent, a nitrogen mustard, a nitrosourea, an antimetabolite, a cytotoxic agent, a cytostatic agent, platinum agents, anthracyclines, taxanes or treatment with an analgesic such as propoxyphene napsylate, acetaminophen, morphine or codeine. Exemplary anticancer and adjunct agents include tamoxifen, paclitaxel, taxol, docetaxil, methotrexate, vincristine, vinblastine, 5-fluorouracil, thioguanine, mercaptopurine, adriamycin, chlorambucil, cyclophosphamide, cisplatin, carboplatin, transplatinum, irinotecan, procarbazine, hydroxyurea, erythropoietin, G-CSF, bicalutamide, anastrozole, fludarabine phosphate, doxorubicin and any suitable form of any of these agents, e.g., salts and solvates. Such therapies would be used essentially according to standard protocols and they would precede, be essentially concurrent with and/or follow treatment with a F1C. In some embodiments, such additional therapies will be administered at the same time that a F1C is being used or within about 1 day to about 16 weeks before or after at least one round of treatment with the F1C is completed. In other embodiments, a course of therapy is administered to the subject, e.g., treatment with a myelosuppressive amount of a myelosuppressive agent such as 5-fluorouracil, cyclophosphamide or a platinum compound such as cisplatin, followed within about 1, 2, 3, 4, 5 or 6 days by administration of one or more courses of treatment with a F1C. Other suitable exemplary therapeutic agents and their use have been described in detail, see, e.g., *Physicians Desk Reference* 54$^{th}$ edition, 2000, pages 303-3250, ISBN 1-56363-330-2, Medical Economics Co., Inc., Montvale, N.J. One or more of these exemplary agents can be used in combination with a F1C to ameliorate, slow the establishment or progression of, prevent or treat any of the appropriate cancers, precancers or related conditions described herein, or any of their symptoms.

In treating cancers or hyperproliferation conditions, the F1Cs may detectably modulate, e.g., decrease or increase, the expression or level or activity of one or more biomolecules associated with the prevention, establishment, maintenance or progression of the cancer or hyperproliferation condition. Such biomolecules include one or more of carcinoembryonic antigen, prostate specific antigen, her2/neu, Bcl-XL, bcl-2, p53, 1L-1α, IL-1β, IL-6, or TNFα, GATA-3, COX-2, NFκB, IkB, an IkB kinase, e.g., IkB kinase-α, IkB kinase-β or IkB kinase-γ, NFAT, calcineurin, calmodulin, a ras protein such as H-ras or K-ras, cyclin D, cyclin E, xanthine oxidase, or their isoforms, orthologs, homologs or mutant forms, which may be observed as either reduced or increased levels or biological activity(ies). Biomolecule levels or their activity(ies) that can be at least transiently detectably increased include one or more IL-2, IFNγ, IL-12, T-bet, O6-methylguanine-DNA-methyltransferase, calcineurin, calmodulin, a superoxide dismutase (e.g., Mn, Zn or Cu), a tumor suppressor protein such as the retinoblastoma protein (Rb) or CDKN2A (p16), BRCA1, BRCA2, MeCP2, MBD2, PTEN, NBR1, NBR2 or the isoforms, orthologs, homologs or mutant forms, which may have either attenuated or enhanced biological activity(ies), of any of these molecules. In treating a cancer described herein such as prostate cancer, one or more of ELAC2, 2',5'-oligoadenylate dependnet RNAse L (RNASEL), macrophage scavenger receptor 1 (MSR1), BRCA2 can be modulated or decreased.

The F1Cs can modulate the synthesis or a biological activity of one or more other gene products such as transcription factors, enzymes or steroid or other receptors that are associated with the establishment, progression or maintenance of a cancer or precancer or associated symptom. The compounds can inhibit AIB-1 coactivator or HER2/neu synthesis or activity in breast cancer cells or breast cancer conditions. They can enhance the synthesis or an activity of an estrogen receptor such as ERα, ERβ1 or ERβ2 or progesterone receptor in breast cancer or colon cancer cells or conditions. These effects can include modulation of the expression or one or more biological activities of proteins or enzymes that contribute to disease establishment or progression. Thus, the compounds can decrease IL-4, IL-6 or IL-13 expression by stromal cells or immune cells that are in proximity to or adjacent to solid or diffuse tumor cells in a subject such as a human or another mammal. In the cancers or precancers described herein, the compounds can thus directly or indirectly modulate (e.g., decrease) the activity or expression of relevant enzymes such as STAT-6, neutral endopeptidase, a hydroxysteroid dehydrogenase, such as a 17β-hydroxysteroid dehydrogenase, 11β-hydroxysteroid dehydrogenase, 7β-hydroxysteroid dehydrogenase or a 3β-hydroxysteroid dehydrogenase.

In some embodiments, the F1Cs are used to treat tumors or cancers wherein proliferation of the tumor or cancer cells is enhanced in response to sex steroids such as natural or synthetic androgens or estrogens. In other embodiments, the tumor or cancer cells are not responsive to such hormones or they are only slightly responsive to the presence of such compounds.

Cardiovascular Applications.

Any of the F1Cs disclosed herein, may be used to treat, prevent or slow the progression of one or more of congenital heart defects, cardiovascular diseases, disorders, abnormalities and/or conditions, or to ameliorate one or more symptoms thereof in a subject. These include peripheral artery disease, arterio-arterial fistula, arteriovenous fistula, cerebral arteriovenous malformations, aortic coarctation, cor triatum, coronary vessel anomalies, patent ductus arteriosus, Ebstein's anomaly, hypoplastic left heart syndrome, levocardia, transposition of great vessels, double outlet right ventricle, tricuspid atresia, persistent truncus arteriosus, and heart septal defects, such as aortopulmonary septal defect, endocardial cushion defects, Lutembacher's Syndrome, ventricular heart septal defects, cardiac tamponade, endocarditis (including bacterial), heart aneurysm, cardiac arrest, congestive heart failure, congestive cardiomyopathy, paroxysmal dyspnea, cardiac edema, post-infarction heart rupture, ventricular septal rupture, heart valve diseases, myocardial diseases, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, cardiovascular syphilis, cardiovascular tuberculosis, arrhythmias such as sinus arrhythmia, atrial fibrillation, atrial flutter, bradycardia, extrasystole, Adams-Stokes Syndrome, bundle-branch block, sinoatrial block, long QT syndrome, parasystole, sick sinus syndrome, ventricular fibrillations, tachycardias such as paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia and heart valve diseases such as aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

The F1Cs can be used to treat, prevent or ameliorate one or more symptoms of myocardial diseases or pathological myocardial or vascular conditions such as alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, myocardial fibrosis, endomyocardial fibrosis, Kearns Syndrome, myocardial reperfusion injury, myocarditis, cardiovascular or vascular diseases such as dissecting aneurysms, false aneurysms, infected aneurysms, ruptured aneurysms, aortic aneurysms, cerebral aneurysms, coronary aneurysms, heart aneurysms, and iliac aneurysms, angiodysplasia, angiomatosis, bacillary angiomatosis, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, thrombosis, erythromelalgia, hemorrhoids, hepatic veno-occlusive disease, hypertension, hypotension, idiopathic pulmonary fibrosis, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, venous insufficiency and arterial occlusive diseases such as arteriosclerosis, intermittent claudication, carotid stenosis, fibromuscular dysplasias, mesenteric vascular occlusion, Moyamoya disease retinal artery occlusion, thromboangiitis obliterans or atherosclerosis, any of which may be at an early stage or at a more advanced or late stage.

The F1Cs can also be used to treat, prevent or ameliorate one or more symptoms of cerebrovascular diseases, thrombosis, and/or conditions such as carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subarachnoid hemorrhage, cerebral infarction, cerebral ischemia (including transient), subclavian steal syndrome, periventricular leukomalacia, vascular headache, cluster headache, migraine, vertebrobasilar insufficiency, air embolisms, embolisms such as cholesterol embolisms, fat embolisms, pulmonary embolisms or amniotic fluid embolism, thromoboembolisms, thrombosis such as coronary thrombosis, hepatic vein thrombosis, retinal vein occlusion, carotid artery thrombosis, sinus thrombosis, Wallenberg's syndrome, and thrombophlebitis.

The F1Cs can also be used to treat, prevent or ameliorate one or more symptoms of vascular ischemia or myocardial ischemias, vasculitis and coronary diseases, including angina pectoris, coronary aneurysm, coronary arteriosclerosis, coronary thrombosis, coronary vasospasm, myocardial infarction and myocardial stunning, cerebral ischemia, ischemic colitis, compartment syndromes, anterior compartment syndrome, myocardial ischemia, reperfusion injuries, peripheral limb ischemia, aortitis, arteritis, Behcet's Syndrome, mucocutaneous lymph node syndrome, thromboangiitis obliterans, hypersensitivity vasculitis, Schoenlein-Henoch purpura, allergic cutaneous vasculitis, Wegener's granulomatosis or metabolic syndrome, which may be accompanied by one, two or more of obesity, insulin resistance, dyslipidemia, hypertension or other related symptoms or conditions.

Exemplary symptoms that the use of the F1Cs can ameliorate include one or more of pain such as arm, jaw or chest pain, edema or swelling, high blood pressure, shortness of breath or dyspnea, e.g., on exertion or while prone, fatigue or malaise and low cardiac injection fraction. In treating a cardiovascular condition in a subject or in improving one or more symptoms thereof, the F1Cs may accomplish one or more of increasing cardiac ejection volume or fraction, decreasing levels of IL-6, decreasing levels of C reactive protein, fibrinogen, cardiac creatinine kinase, increasing fatty acid metabolism or utlization by cardiac tissue, increasing carnityl palmitoyl fatty acid transferase or other cardiac metabolic enzymes, activating potassium dependent calcium channels, vasodilating or enhancing oxygen delivery to ischemic tissues or decreasing levels of scarring or plaque formation that occurs, e.g., after vascular damage. Symptoms associated with a cardiovascular condition such as ischemia that can be ameliorated also include acidosis, expression of one or more immediate early genes in, e.g., glial cells, vascular smooth muscle cells or endothelial cells, neuronal membrane depolarization and increased neuronal extracellular calcium and glutamate concentration. Other biological effects associated with treatment using a F1C may also be monitored, e.g., and increase or decrease of a cell surface antigen, a cytokine or an interleukin as disclosed herein.

Useful biological effects of the F1Cs in cardiovascular indications such as myocardial ischemias also include preventing or reducing heart or vascular cell death and subsequent fibrosis. These effects are associated with a decreased oxidative capacity of heart cells or myocytes, which is associated with a decreased capacity of the cells to metabolize fatty acids efficiently. The compounds enhance fatty acid metabolism and ameliorate the deleterious effects of a limited oxidative capacity.

The F1Cs also can limit inflammation or cell injury that is associated with ischemia or oxygen reperfusion after ischemia. Ischemia, which is a detrimental decrease in oxygenated blood delivery to affected cells or tissues, may arise from a cardiovascular condition or event such as an infarction, or from thermal injury or burns. Ischemia may also arise from accidental or surgical trauma. Reperfusion after cells have become hypoxic for a sufficient period of time can lead to tissue or cell injury that varies from slight to lethal. The compounds can reduce cell or tissue injury or death associated with ischemia and reperfusion, by, e.g., reducing inflammation or the level of a molecule associated with inflammation. Thus, levels of a proinflammatory cytokine or molecule such as leukotriene B4, platelet activating factor or levels of extracellular P-selectin may result from administration of a F1C to a subject who may experience reperfusion injury. Thus, the compounds can reduce injury or death of, e.g., neuron, cardiac, vascular endothelium, myocardial, pulmonary, hepatic or renal cells or tissues. Without wishing to be bound by any theory, the compounds may act in part by reducing one or more of neutrophil activation, platelet activation, platelet aggregation, endothelial cell activation and neutrophil adherence or adhesion to endothelial cells in these conditions.

The F1Cs are useful to treat autoimmune or metabolic conditions or disorders, or their symptoms, in subjects such as mammals or humans, that relate to impaired insulin synthesis or use or that relate to abnormal or pathological lipid or cholesterol metabolism or levels. Such conditions and symptoms include polycystic ovarian syndrome, Type 1 diabetes (including Immune-Mediated Diabetes Mellitus and Idiopathic Diabetes Mellitus), Type 2 diabetes (including forms with (1) predominant or profound insulin resistance, (2) predominant insulin deficiency and some insulin resistance, (3) forms intermediate between these), obesity, hyperglycemia and dyslipidemia, unwanted hyperlipidemia conditions such as hypertriglyceridemia and hypercholesterolemias such as hyper-LDL cholesterolemia, (4) unwanted hypolipidemias, e.g., hypo-HDL cholesterolemia or low HDL cholesterol levels and (5) angina pectoris. In diabetes, the compounds are useful to (1) enhance β-cell function in the islets of Langerhans (e.g., increase insulin secretion), (2) reduce the rate of islet cell damage, (3) increase insulin receptor levels or activity to increase cell sensitivity to insulin and/or (4) modulate glucocorticoid receptor activity to decrease insulin resistance in cells that are insulin resistant. The compounds are thus useful to treat, prevent, ameliorate or slow the progression of a metabolic or cardiovascular condition such as diabetes or hyperglycemia, or a related symptom or condition such as a dyslipidemia in a subject such as a human or a mammal.

Beneficial effects that can the F1Cs can exert on such related symptoms or conditions include improved glucose tolerance, improved glucose utilization, decreased severity or slowed progression of vascular disease (e.g., microvascular or macrovascular disease, including nephropathy, neuropathy, retinopathy, hypertension, cerebrovascular disease and coronary heart disease) or a decreased severity or slowed progression of atherosclerosis, an arteriosclerosis condition (e.g., coronary arteriosclerosis, hyperplastic arteriosclerosis, peripheral arteriosclerosis or hypertensive arteriosclerosis), decreased severity or slowed progression of diabetic osteoarthropathy, skin lesions, rhabdomyolysis, ketosis, detectably decreased generation of islet cell autoantibodies, decreased levels or activity of inflammatory macrophages (foam cells) in atherosclerotic plaques, or detectably decreased expression or levels of one or more of human (or mammalian) angiopoietin-like 3 gene product, apolipoprotein C-1, inducible or constitutive nitric oxide synthase, e.g., in endothelial cells, macrophages or the like, pyruvate dehydrogenase kinase 4, carboxyl ester lipase, cholesteryl ester transfer protein, endothelial lipase, vascular wall lipoprotein lipase, antilipoprotein lipase autoantibodies, triglyceride-rich lipoproteins, LDL cholesterol, C-reactive protein, high sensitivity C-reactive protein, fibrinogen, plasma homocysteine, VCAM-1, IL-1 (e.g., IL-1β), IL-6, a TNF (e.g., TNFα), AP-1, NF-κB, and IFN-γ. In these any of these diseases or conditions, the F1Cs can also modulate, e.g., detectably increase, the activity or level of one, two or more of human (or mammalian) LOX-1, apolipoprotein A-1, apolipoprotein A-2, LPDL lipase, hormone sensitive lipase, paraoxonase, brain natriuretic peptide, a brain natriuretic peptide receptor, e.g., Npr1 or Npr3, hepatic lipase, LDL receptor, HDL apoliporpotein E, HDL apoliporpotein J, HDL cholesterol, VLDL receptor, ATP-binding casette transporter 1, leukemia inhibitory factor, CD36, LXRα, LXIRβ, CARβ, RXR, PPARα, PPARβ, PPARγ or a lipoprotein lipase, e.g., marophage lipoprotein lipase. As used herein, obesity includes a human with a body mass index of at least about 25, 26, 27, 28, 29, 30, 31, 32, 33, 34, 35, 36 or greater. Obese humans that are treated with a F1C may have one or more of the conditions descrbed here.

The F1Cs are useful in treating insulin resistance and associated symptoms and conditions. Insulin resistance is typically observed as a diminished ability of insulin to exert its biological action across a broad range of concentrations. This leads to less than the expected biologic effect for a given level of insulin. Insulin resistant subjects or human have a diminished ability to properly metabolize glucose or fatty acids and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, impaired glucose tolerance, gestational diabetes, hypertension, obesity, atherosclerosis and a variety of other disorders. Insulin resistant individuals can progress to a diabetic state. The compounds can also be used in the treatment or amelioration of one or more condition associated with insulin resistance or glucose intolerance including an increase in plasma triglycerides and a decrease in high-density lipoprotein cholesterol, high blood pressure, hyperuricemia, smaller denser low-density lipoprotein particles, and higher circulating levels of plasminogen activator inhibitor-1. Such diseases and symptoms have been described, see, e.g., G. M. Reaven, *J. Basic Clin. Phys. Pharm.* 1998, 9: 387-406, G. M. Reaven, *Physiol. Rev.* 1995, 75: 473-486 and J. Flier, *J. Ann. Rev. Med.* 1983, 34:145-60.

The compounds can thus be used in diabetes, obesity, hyperlipidemia or hypercholesterolemia conditions to reduce body fat mass, increase muscle mass or to lower one or more of serum or blood low density lipoprotein, triglyceride, cholesterol, apolipoprotein B, free fatty acid or very low density lipoprotein compared to a subject that would otherwise be considered normal for one or more of these characteristics. These beneficial effects are typically obtained with little or no effect on serum or blood high density lipoprotein levels. The F1Cs are useful to reduce or slow the rate of myocardial tissue or myocyte damage, e.g., fibrosis, or to enhance cardiac fatty acid metabolism in conditions, such as inflammation, where fatty acid metabolism is depressed or decreased. Elevated cholesterol levels are often associated with a number of other disease states, including coronary artery disease, angina pectoris, carotid artery disease, strokes, cerebral arteriosclerosis, and xanthoma, which the F1Cs can ameliorate or slow the progression or severity of. Abnormal lipid and cholesterol conditions that can be treated include exogenous hypertriglyceridemia, familial hypercholesterolemia, polygenic hypercholesterolemia, biliary cirrhosis, familial combined hyperlipidemia, dysbetalipoproteinemia, endogenous hypertriglyceridemia, mixed hypertriglyceridemia and hyperlipidemia or hypertriglycidemia secondary to alcohol consumption, diabetic lipemia, nephrosis or drug treatments, e.g., corticosteroid, estrogen, colestipol, cholestyramine or retinoid treatments. Dosages, routes of administration and dosing protocols for the F1Cs are essentially as described herein. Where the condition is chronic, the F1Cs will generally be administered to a subject such as a human for a relatively long time period, e.g., for about 3 months to about 10 years or more. Dosages, routes of administration and dosing protocols for the F1Cs are essentially as described herein. Dosing of the compound can be daily or intermittent using a dosing protocol using dosages as described herein, e.g., about 0.01 to about 20 mg/kg of a F1C administered to a subject once or twice per day daily or intermittently. The use of the F1Cs can be combined with one, two or more other suitable treatments, e.g., treatment for cessation of smoking, diet control, e.g., caloric restriction or reduced fat intake, or treatment with fibrates, non-steroidal anti-inflammatory drugs, angiotensin-converting enzyme inhibitors or HMG-CoA reductase inhibitors such as aspirin, clofibrate, fenofibrate, ciprofibrate, gemfibrozil, Simvastatin™, Pravastatin™, Mevastatin™ or Lovastatin™.

The use of any F1C or species in any genus of F1Cs disclosed herein to treat, prevent or ameliorate any of these cardiovascular or metabolic disorders or symptoms will generally use one or more of the routes of administration, dosages and dosing protocols as disclosed herein. Thus, in exemplary embodiments, about 0.5 to about 100 mg/kg or about 1 to about 25 mg/kg, of the F1C will be administered per day by an oral, buccal, sublingual or parenteral route. Such administration can be, e.g., daily for about 5 to about 60 days in acute conditions or it can be intermittent for about 3 months to about 2 years or more for chronic conditions. Alternatively, intermittent dosing can be used essentially as described herein for acute cardiovascular conditions. In some embodiments, for conditions such as ischemia or trauma, administration of the F1C is provided before or as soon after the ischemic or traumatic event as possible, e.g., within about 6 hours of an ischemic or traumatic event or about 12-24 hours before an anticiapted ischemic or traumatic event. In other embodiments, administration of the F1C can be delayed for, e.g., about 6, 7, 8, 9, 10, 11, 12, 13, 14, 15, 16, 18, 19, 20, 21, 24, 28, 32, 36, 40, 48 or more hours after an ischemic or traumatic event has occurred and a course of daily or intermittent dosing is initiated of one of these times, or in a range between any of these times after the event. Thus, administration of the F1C can begin at about 10-14 hours, at about 11-13 hours or at about 8-16 hours after the ischemic or traumatic event.

In another aspect of the invention, the F1Cs can be used to prevent, treat or to reduce the severity of vascular or microvascular occlusions in human sickle cell diseases (SCD). SCD is heterogenous and includes subgroups with high transcranial velocities, which is a group with an increased risk of infarctive stroke or cereberal thrombosis. SCD types also include sickle cell-$\beta^+$ thalassemia, sickle cell-$\beta^o$ thalassemia, sickle cell-$\delta\beta^o$ thalassemia and sickle cell-HPFH (hereditary of persistent fetal hemoglobin). Another subgroup of SCD patients is characterized by the presence of a *Plasmodium* parasite infection. SCD is usually accompanied by acute vaso-occlusive episodes such as microvascular occlusions, ischemia and infarctions that arise from adhesion of sickle cells and other blood cell types, e.g., platelets or leukocytes, to vascular endothelial cells. Reduced sickle cell adhesion in response to treatment with a F1C and related responses is facilitated at least in part by decreased production or activity of one or more biological response mediators such as one, two, three or more of thrombospondin, von Willebrand factor, epinephrine, C reactive protein, cAMP, basal cell adhesion molecule/Lutheran (BCAM/Lu), P-selectin, L-selectin, E-selectin, VCAM-1, ICAM-1, fibronectin, annexin V, placenta growth factor, superoxide, CD11a, CD11b, CD11c, CD15, CD18, CD31, CD36, TNFα, NF-κB, IL-1β or IL-6 by endothelial cells or one or more immune cell types as described herein. In treating sickle cell disease, the F1Cs will also increase the activity or levels of one, two or more desired response mediators including fetal hemoglobin, erythropoietin, heme oxygenase, nitric oxide, PPARα, PPARγ or GM-CSF. The F1Cs will thus ameliorate one or more symptoms of sickle cell disease such as anemia, stroke, pain, e.g., chest or abdominal pain, skin ulcers, dyspnea, organ damage, retinopathy or the level of infected red cells in *Plasmodium*-infected subjects. Treatment of acute SCD episodes or of chronic SCD with F1Cs can be combined with other suitable therapies, e.g., inhaled nitric oxide, hydroxyurea treatment, anti-adhesion molecule antibody treatment or analgesic use such as morphine, oxycodone, or codeine. The F1Cs can also be used to reduce cellular damage from reactive oxygen species associated with hydroxyurea treatment, since the F1Cs will enhance cellular antioxidant capacity.

As is apparent from the foregoing, the use of the F1C is optionally combined with one or more additional therapies for cardiovascular or related disorders, e.g., insulin therapy, vascular surgery, cardiac surgery, angioplasty, or treatment with andrenergic blockers, coronary vasodilators, calcium channel blockers, nitrates, angiotensin converting enzyme inhibitors, anti-hypertensives, anti-inflammatory agents, diuretics, anti-arrhythmia agents, thrombolytic agents, enzyme inhibitors such as hydroxymethylglutaryl CoA reductase inhibitors or xanthine oxidase inhibitors. Exemplary hydroxymethylglutaryl CoA reductase inhibitors include statins such as mevastatin, lovastatin, pravastatin, simvastatin or compounds described in U.S. Pat. Nos. 4,346, 227, 4,448,979, 4,739,073, 5,169,857, 5,006,530 or 5,401,746. Other therapies that can be applied include diet control, dietary calorie restriction or diet modification for subjects who are or who are susceptible to developing a cardiovascular or related condition such as pulmonary hypertension, diabetes, a dyslipidemia or obesity, e.g., humans having a body mass index of 27, 28, 29, 30, 31, 32, 33, 34, 35, 36 or greater. Diet modifications include limiting or restricting salt, alcohol, caffeine, cigarette, drugs, e.g., opiate, hallucinogen, sedative, narcotic or amphetamine, sugar, refined sugar and/or fat or cholesterol intake, use or abuse. Additional therapies include treatment with one or more of digoxin, nitroglycerin, doxazosin mesylate, nifedipine, enalapril maleate, indomethicin, tissue plasminogin activator, urokinase, acetylsalicylic acid or the like. Any of such additional therapies would be used essentially according to standard protocols and such therapies would precede, be concurrent with or follow treatment with a F1C. In some embodiments, such additional therapies will be administered at the same time that a F1C is being used or within about 1 day to about 16 weeks before or after at least one round of treatment with the F1C is completed. Other exemplary therapeutic agents and their use have been described in detail, see, e.g., *Physicians Desk Reference* 54$^{th}$ edition, 2000, pages 303-3251, ISBN 1-56363-330-2, Medical Economics Co., Inc., Montvale, N.J.; *Harrison's Principles of Internal Medicine*, 15$^{th}$ edition, 2001, E. Braunwald, et al., editors, McGraw-Hill, New York, N.Y., ISBN 0-07-007272-8, especially chapters 231, 241-248 and 258-265 at pages 1309-1318, 1377-1442 and 1491-1526. One or more of these exemplary agents or treatments can be used in combination with a F1C to treat any of the appropriate cardiovascular and related disorders described herein and in the references cited herein.

Respiratory and Pulmonary Conditions.

F1Cs can be used to treat, ameliorate, prevent or slow the progression of a number of pulmonary conditions or their symptoms such as 1, 2, 3 or more of cystic fibrosis, bronchiectasis, cor pulmonale, pneumonia, lung abcess, acute bronchitis, chronic bronchitis, chronic obstructive pulmonary diseases, emphysema, pneumonitis, e.g., hypersensitivity pneumonitis or pneumonitis associated with radiation exposure, alveolar lung diseases and interstitial lung diseases, e.g., associated with asbestos, fumes or gas exposure, aspiration pneumonia, pulmonary hemorrhage syndromes, amyloidosis, connective tissue diseases, systemic sclerosis, ankylosing spondylitis, allergic granulomatosis, granulomatous vasculitides, asthma, e.g., acute asthma, chronic asthma, atopic asthma, allergic asthma or idiosyncratic asthma, cystic fibrosis and associated conditions, e.g., allergic bronchopulmonary aspergillosis, chronic sinusitis, pancreatic insufficiency, inflammation or *Haemophilus influenzae, S. aureus* or *Pseudomonas aeruginosa* infection. In some of these conditions where inflammation plays a role in the pathology of the condition, the F1Cs can ameliorate or slow the progression of the condition by reducing damage from inflammation. In other cases, the F1Cs act to limit pathogen replication or pathogen-associated lung tissue damage.

For these conditions, the severity of the disease or the type or severity of associated symptoms can vary. For example, in humans having pediatric, e.g., infants or children of about 1 month or about 4 months of age to about 16 or 17 years of age, or adult cystic fibrosis ("CF"), the disease may be associated with the presence of one or more symptoms, syndromes, genetic mutations or the like. Symptoms or syndromes that can be observed in human CF patients include 1, 2, 3, 4 or more of *Staphylococcus* (e.g., *S. aureus*), *Haemophilus influenzae, Pseudomonas* or *Burkholderia* respiratory tract or lung infection or propensity to develop detectable infection or colonization, coughing, wheezing, cyanosis, bronchiolitis, bronchospasm, pneumothorax, hemoptysis, pancreatic exocrine insufficiency, bronchiectatic lung disease, atelectasisconsolidation, pulmonary edema, increased lung vascular hydrostatic pressure, increased lung vascular permeability, sinusitis, respiratory insufficiency, bronchial wall or interlobular septa thickening, reduction of forced expiratory volume in 1 second, dyspnea, impaired male fertility, elevated sweat chloride (e.g., >60 mmol/L), mucous plugging, tree-in-bud sign, mosaic perfusion pattern, glucose intolerance or abnormal elevation of one or more of IL-4, IL-8, RANTES, neutrophil elastase, eosinophils, macrophages, neutrophils, eosinophil cationic protein or cysteinyl leukotrienes. Any of these symptoms or syndromes can be acute, intermittent or chronic and/or mild, moderate or severe. Relevant mutations include, e.g., a homozygous or heterozygous, dominant or recessive deletion, insertion and/or point mutation in (1) the cationic trypsinogen gene or (2) the cystic fibrosis transmembrane conductance regulator (CFTR) gene, such as one, two or more of, a CFTR F508del deletion mutation or CFTR lacking phe508, 3272-26A>G/F508del, 3659delC, 394delTT, S1455X or Δ26, I1234V, 2183AA>G, 2043delG, 548A>T, I148T, R334W, S1196X, 4041C>G, 1161delC, 1756G>T or 3120+1G>A mutation.

The use of a F1C to treat, ameliorate or slow the progression of conditions such as CF can be optionally combined with other suitable treatments. For CF, this includes, e.g., one, two or more of oral or aerosol corticosteroid treatment, ibuprofen treatment, DNAse or IL-10 treatment, diet control, e.g., vitamin E supplementation, vaccination against pathogens, e.g., *Haemophilus influenzae*, or chest physical therapy, e.g., chest drainage or percussion.

Humans or other subjects who have one or more of these conditions can be treated with other suitable therapeutics. Pulmonary conditions that can be treated with the F1Cs and other therapeutic methods and agents that can be used in conjunction with the F1Cs have been described in detail, see, e.g., *Harrison's Principles of Internal Medicine*, 15$^{th}$ edition, 2001, E. Braunwald, et al., editors, McGraw-Hill, New York, N.Y., ISBN 0-07-007272-8, especially chapters 252-265 at pages 1456-1526; *Physicians Desk Reference* 54$^{th}$ edition, 2000, pages 303-3251, ISBN 1-56363-330-2, Medical Economics Co., Inc., Montvale, N.J. One or more of these exemplary agents or treatments can be used in combination with a F1C to treat any of the appropriate cardiovascular and related disorders described herein and in the references cited herein. Treatment of any of these respiratory and pulmonary conditions using a F1C is accomplished using the treatment regimens described herein. For chronic conditions, intermittent dosing of the F1C can be used to reduce the frequency of treatment. Intermittent dosing protocols are as described herein.

Applications in Autoimmunity, Allergy, Inflammation and Related Conditions.

As mentioned above, the F1Cs may be used to treat, prevent or slow the progression of one or more autoimmune allergic or inflammatory diseases, disorders, or conditions, or to ameliorate one or more symptoms thereof in a subject. These diseases and conditions include Addison's Disease, autoimmune hemolytic anemia, autoimmune sensorineural hearing loss, antiphospholipid syndrome, acute or chronic rheumatoid arthritis and other synovial disorders, an osteoarthritis including post-traumatic osteoarthritis and hypertrophic pulmonary osteoarthropathy, psoriatic arthritis, polyarthritis, epichondylitis, type I diabetes, type II diabetes, rheumatic carditis, bursitis, ankylosing spondylitis, multiple sclerosis, a dermatitis such as contact dermatitis, atopic dermatitis, exfoliative dermatitis or seborrheic dermatitis, mycosis fungoides, allergic encephalomyelitis, autoimmune glomerulonephritis, Goodpasture's Syndrome, Graves' Disease, Hashimoto's Thyroiditis, multiple sclerosis, myasthenia gravis, neuritis, bullous pemphigoid, pemphigus, polyendocrinopathies, purpura, Reiter's Disease, autoimmune thyroiditis, systemic lupus erythematosus, scleroderma, fibromyalgia, chronic fatigue syndrome, autoimmune pulmonary inflammation, Guillain-Barre Syndrome, type 1 or insulin dependent diabetes mellitus, autoimmune inflammatory eye disease, hepatitis C virus associated autoimmunity, postinfectious autoimmunity associated with, e.g., virus or bacterial infection such as a parvovirus such as human parvovirus B19 or with rubella virus, autoimmune skin and muscle conditions such as pemphigus vulgaris, pemphigus foliaceus, systemic dermatomyositis or polymyositis or another inflammatory myopathy, myocarditis, asthma such as allergic asthma, allergic encephalomyelitis, allergic rhinitis, a vasculitis condition such as polyarteritis nodosa, giant cell arteritis or systemic necrotizing vasculitis, chronic and an acute or chronic inflammation condition such as chronic prostatitis, granulomatous prostatitis and malacoplakia, ischemia-reperfusion injury, endotoxin exposure, complement- mediated hyperacute rejection, nephritis, cytokine or chemokine induced lung injury, cachexia, sarcoidosis, inflammatory bowel disease, regional enteritis, ulcerative colitis, Crohn's disease, inflammatory bowel disease or inflammation associated with an infection, e.g., septic shock, sepsis, or systemic inflammatory response syndrome. Any of these diseases or conditions or their symptoms may be acute, chronic, mild, moderate, severe, stable or progressing before, during or after the time administration of the F1C to a subject such as a human, is initiated. In general, a detectable improvement is observed in the subject within a period of about 3 days to about 12 months after initiation of a dosing protocol, e.g., the severity of the disease or condition will detectably decrease, the rate of progression will detectably slow or the severity of a symptom(s) will detectably decrease.

As used herein, acute inflammation conditions are characterized as an inflammation that typically has a fairly rapid onset, quickly becomes moderate or severe and usually lasts for only a few days or for a few weeks. Chronic inflammation conditions as used herein are characterized as an inflammation that may begin with a relatively rapid onset or in a slow, or even unnoticed manner, tends to persist for at least several weeks, e.g., about 3-6 weeks, months, or years and may have a vague or indefinite termination. Chronic inflammation may result when the injuring agent (or products resulting from its presence) persists in the lesion, and the subject's tissues respond in a manner (or to a degree) that is not sufficient to overcome completely the continuing effects of the injuring agent. Other exemplary conditions are described in, e.g., *Textbook of Autoimmune Diseases*, R. G. Lahita, editor, Lippincott Williams & Wikins, Philadelphia, Pa., 2000, ISBN 0-7817-1505-9, pages 175-851 and *Rheumatology*, $2^{nd}$ edition, J. H. Klippel et al., editors, 1998, ISBN 0-7234-2405-5, volume 1, sections 1-5 and volume 2, sections 6-8, Mosby International, London, UK.

A F1C can be used to inhibit or ameliorate one or more inappropriate immune responses or their symptoms in autoimmunity, inflammation, allergy or related conditions. The effects of the F1Cs include detectably ameliorating one or more of (1) the proliferation, differentiation or chemotaxis of T cells, (2) reducing unwanted cytotoxic T cell responses, (3) reducing unwanted autoantibody or other antibody synthesis, e.g., an unwanted IgA, IgE, IgG or IgM, in allergy, asthma or another autoimmune or inflammation condition, (4) inhibiting the development, proliferation or unwanted activity of autoreactive T or B cells, (5) altering the expression of one or more cytokines, interleukins or cell surface antigens, e.g., a cytokine, interleukin or cell surface antigen described herein (decreasing IL-8 in an autoimmune condition, decreasing the level of acute phase proteins such as C reactive protein or fibrinogen in inflammation conditions, (6) decreasing eosinophilia in allergy conditions, (7) detectably decreasing the level or activity of one or more of ICAM-1, IL-1α, IL-1β, TNFα, IL-6 or IL-8 in, e.g., inflammation conditions or in autoimmune conditions such as an arthritis or a myocarditis condition such as osteoarthritis, rheumatoid arthritis, toxic myocarditis, indurative myocarditis or idiopathic myocarditis, (8) decreasing the level or biological activity of one or more of anti-islet antibody, TNF, IFN-γ, IL-1, an arthritis symptom(s), nephritis, skin rash, photosensitivity, headache frequency or pain, migraine frequency or pain, abdominal pain, nausea or anti-DNA antibodies in, e.g., insulin dependent diabetes mellitus or an autoimmune or inflammation condition such as systemic lupus erythematosus, rheumatoid arthritis or Crohn's disease, (9) reducing induction of arachidonic acid metabolism or reducing eicosanoid metabolites such as thromboxanes or prostaglandins in, e.g., inflammation, asthma or allergy, (10) reducing IL-4, IL-8 or IL-10 synthesis, levels or activity in, e.g., allergy or inflammation such as idiopathic pulmonary fibrosis or allergic asthma or (11) reducing or interfering with neutrophil chemotaxis by, e.g., reducing thioredoxin release from affected cells in conditions such as cancer, infections, inflammation or autoimmunity.

Exemplary symptoms that the use of the F1Cs can ameliorate in these autoimmune, inflammatory and allergy conditions include one or more of pain such as shoulder, hip, joint, abdominal or spine pain, joint stiffness or gelling, bursitis, tendonitis, edema or swelling, fatigue or malaise, headache, dyspnea, skin rash, fever, night sweats, anorexia, weight loss, skin or intestine ulceration, muscle weakness, pericarditis, coronary occlusion, neuropathy and diarrhea. In treating one of these conditions in a subject or in improving one or more symptoms thereof, the F1Cs may accomplish one or more of decreasing levels of one or more of IL-1, IL-4, IL-6 or TNFα, decreasing levels of C reactive protein, fibrinogen or creatinine kinase. Other biological effects associated with treatment using a F1C may also be monitored or observed, e.g., an increase or decrease of a cell surface antigen, a cytokine or an interleukin as disclosed herein.

In another aspect of the invention, the F1Cs can be used to treat or to reduce the severity of chronic allergies or atopic diseases such as allergic rhinitis, psoriasis, eczema, gastrointestinal allergies, atopic dermatitis conditions, allergic asthma, food allergies and hay fever. These conditions are typically characterized by the presence of elevated levels of allergen specific antibodies of the IgE isotype. In treating or ameliorating these conditions, the F1Cs reduce the generation of IgE by "isotype switching", which is increasing allergen-specific IgA production and/or decreasing IgE production from preexisting allergen-primed cells. Allergen specific IgG may also be increased from new cells that might otherwise have responded to allergen exposure by generating unwanted IgE.

The IgA and IgG are allergen specific, which will enhance clearance of allergen from mucosa or other tissue and reduction of chronic or late phase allergic responses. The F1C can thus also be used to increase the biological clearance of allergens from tissue and mucosa. Reduced generation of the levels or activity of IgE by B cells in response to treatment with a F1C and related responses is facilitated at least in part by decreased production of one or more biological response mediators, e.g., cytokines or response mediators such as protein kinase A inhibitors, substance P neuropeptide, thymus- and activation-regulated chemokine, e.g., by airway smooth muscle cells, proteinase activated receptor-2 by neurons, intracellular signal-transducing protein-6 (STAT6), Janus kinase 1, Janus kinase 6, CD40, CD86 and/or NF-kB by B cells, CD154 in T cells, and suppressor of cytokine signalling-3, phosphodiesterase 4, TNF-α, MCP-1, RANTES, CXCL10, CXCL8 (IL-8), prostaglandin E2 receptor, IL-1β, IL-4, IL-5, IL-6, IL-9, IL-10, IL-13, and IL-23, by one or more other cell types such as immune cells as described herein, airway smooth muscle cells, mucosal cells or keratinocytes. In these treatments, the F1Cs will also increase the activity or levels of one or more desired response mediators including soluble CD23, cathepsin E, epidermal growth factor receptor, IFNγ, IL-2, IL-12 or IL-18. In treating these conditions, Treatment can be combined with other suitable therapies, e.g., corticosteroids such as fluticasone propionate. The F1Cs can also be used to reduce rebound phenomena following withdrawal of corticosteroid therapies, since the F1Cs have an anti-inflammatory effect without having immunosuppressive side effects. Use of the F1Cs to generate any of these biological responses or treatments can be by daily or intermittent administration of the F1C to the subject.

In a related embodiment, the F1Cs are used in allergen vaccination protocols to enhance levels or activity of allergen specific IgA or IgG, which contributes to reducing IgE responses to allergen exposure. Such protocols are used to decrease a subject's sensitivity to allergen exposure. Typically such allergies are chronic or atopic. In these applications, the vaccination protocol typically uses the allergen(s) or an active fragment(s) of the allergen that is associated with the allergy or atopic condition. In these methods, a F1C is administered to a subject who has an IgE mediated allergy or atopy condition in conjunction with administration of the allergen. Allergens typically used include dermatophagoides, house dust, cat allergen and pollen. In any of these methods isotype switching or vaccination methods, the F1C is typically administered as described herein, e.g., by administering the F1C about 1, 2, 3, 4, 5, 6, 7, 8, or more days before the allergen is administered to the subject. The subject may receive about 1-20 mg/kg of a F1C at 2, 3 and 4 days before the allergen is administered or injected. The F1C treatment increases allergen specific IgA or IgG responses or levels relative to untreated controls. The use of F1C with allergens will reduce the total number of anti-allergic vaccinations that are needed, increase the quality or length of an effective response and/or increase the proportion of subjects in which allergy shots are effective. An effective response is seen in about 55%, 60%, 65%, 70%, 75%, 80% or more of vaccinated patients who also receive the F1C compared to about 40-50% of vaccinated patients who do not receive the F1C.

In treating inflammation or any condition described herein where inflammation contributes to the condition, the F1Cs may detectably modulate, e.g., decrease or increase, the expression or level or activity of one or more biomolecules associated with the prevention, establishment, maintenance or progression of the inflammation condition. Such biomolecules include one or more of carcinoembryonic antigen, prostate specific antigen, her2/neu, Bcl-XL, bcl-2, p53, IL-1α, IL-1β, IL-6, or TNFα, GATA-3, COX-2, NFκB, IkB, an IkB kinase, e.g., IkB kinase-α, IkB kinase-β or IkB kinase-γ, NFAT, a ras protein such as H-ras or K-ras, cyclin D, cyclin E xanthine oxidase, or their isoforms, orthologs, homologs or mutant forms, which may have either reduced or enhanced biological activity(ies), and which may be detectably decreased. Biomolecules that can be detectably increased include IL-2, IFNγ, IL-12, T-bet, O6-methylguanine-DNA-methyltransferase, calcineurin, calmodulin, a superoxide dismutase (e.g., Mn, Zn or Cu), a tumor suppressor protein such as the retinoblastoma protein (Rb) or CDKN2A (p16), BRCA1, BRCA2, MeCP2, MBD2, PTEN, NBR1, NBR2 or the isoforms, orthologs, homologs or mutant forms, which may have either attenuated or enhanced biological activity(ies), of any of these molecules. One or more of these biomolecules may be modulated in any inflammation condition described herein.

The use of any F1C or species in any genus of F1Cs disclosed herein to treat, prevent or ameliorate any of these autoimmune, inflammatory or allergy conditions or symptoms will generally use one or more of the routes of administration, dosages and dosing protocols as disclosed herein. Thus, in exemplary embodiments, about 0.5 to about 100 mg/kg or about 1 mg/kg to about 15 mg/kg, of the F1C will be administered per day by, e.g., an oral, buccal, sublingual, topical or parenteral route. Such administration can be, e.g., daily for about 5 to about 60 days in acute conditions or it can be intermittent for about 3 months to about 2 years or more for chronic conditions. Alternatively, intermittent dosing can be used essentially as described herein for acute autoimmune, inflammatory and allergy conditions.

In another aspect of the invention, the F1Cs can be used to treat or to reduce the severity of chronic allergies or atopic diseases such as allergic rhinitis, psoriasis, eczema, gastrointestinal allergies, atopic dermatitis conditions, allergic asthma, food allergies and hay fever. These conditions are typically characterized by the presence of elevated levels of the IgE isotype and of B cells that generate IgE. In treating or ameliorating these conditions, the F1Cs reduce the generation of IgE by facilitating an isotype switch from B cells that produce IgE to cells that produce antigen-specific IgA and/or IgG4. The IgA and IgG4 are allergen specific, which will facilitate clearance of allergen from mucosa or other tissue and reduction of chronic or late phase allergic responses. The F1c can thus be used to increase the biological clearance of allergens from tissue. Reduced generation of the levels or activity of IgE by B cells in response to treatment with a F1C and related responses is facilitated at least in part by decreased production of one or more biological response mediators, e.g., cytokines or response mediators such as protein kinase A inhibitors, substance P neuropeptide, thymus- and activation-regulated chemokine, e.g., by airway smooth muscle cells, proteinase activated receptor-2 by neurons, intracellular signal-transducing protein-6 (STAT6), Janus kinase 1, Janus kinase 6, CD40, CD86 and/or NF-κB by B cells, CD154 in T cells, and suppressor of cytokine signalling-3, phosphodiesterase 4, TNF-α, MCP-1, RANTES, CXCL10, CXCL8 (IL-8), prostaglandin $E_2$ receptor, IL-1β, IL-4, IL-5, IL-6, IL-10, IL-13 and IL-18 by one or more other cell types such as immune cells as described herein, airway smooth muscle cells, mucosal cells or keratinocytes. In these treatments, the F1Cs will also increase the activity or levels of one or more desired response mediators including cathepsin E, epidermal growth factor receptor, IFNγ, IL-2, IL-12. In treating these conditions, Treatment can be combined with other suitable therapies, e.g., corticosteroids such as fluticasone propionate. The F1Cs can also be used to reduce rebound phenomena following withdrawal of corticosteroid therapies, since the F1Cs have an anti-inflammatory effect without having immunosuppressive side-effects. Use of the F1Cs to effect any of these biological responses or treatments can be by daily or intermittent administration of the F1C to the subject.

In a related embodiment, the F1Cs are used to enhance isotype switching from IgE to IgG in these chronic allergies or atopic diseases in vaccination protocols that use the allergen(s) or an active fragment(s) of the allergen that is associated with the allergy or atopic condition. In these methods, a F1C is administered to a subject who has an elevated IgE allergy or atopy condition in conjunction with administration of the allergen. The subject's response to the allergen is an enhanced proportion of B cells that produce IgG compared to B cells that generate IgE. Allergens typically used include *dermatophagoides*, house dust, cat allergen and pollen. In these methods, the F1C is typically administered about 1, 2, 3, 4, 5, 6, 7, 8, or more days before the allergen is administered to the subject, e.g., the subject receives about 1-20 mg/kg of a F1C at 2, 3 and 4 days before the allergen is administered or injected. The F1C facilitates isotype switching to IgG. The use of F1C with allergens will reduce the total number of anti-allergic vaccinations that are needed, increase the quality or length of an effective response and/or increase the proportion of subjects in which allergy shots are effective, e.g., an effective response is seen in about 55%, 60%, 65%, 70%, 75%, 80% or more of vaccinated patients who also receive the F1C compared to about 40-50% of vaccinated patients who do not receive the F1C.

The F1Cs are suitable for enhancing immune responses in aging in subjects such as humans or primates. In humans at about 50 to 60 years of age and later, one or more aspects of immune responses will typically decrease by a detectable amount compared to typical immune responses at younger ages, e.g., at about 18-50 years of age. The F1Cs can be used on an intermittent basis or continuously in aged subjects. Intermittent administration of a F1C can occur as described herein, e.g., daily dosing or dosing every other day or every third day for about 1, 2, 3, 4, 5, 6, 7, 8 or 9 days, followed by about 2, 3, 4, 5, 6, 7, 8, 9 or 10 weeks of no dosing, optionally followed by about 1, 2, 3, 4, 5, 6, 7 or 8 days of daily dosing or dosing every other day or every third day and then followed by about 2, 3, 4, 5, 6, 7, 8, 9 or 10 weeks of no dosing. Such dosing cycles can be repeated indefinitely or as needed. Such treatments can be used prophylactically or therapeutically. In prophylaxis the F1C are administered, e.g., before or during influenza outbreaks, or in aged patients in hospitals or in aged patients in long term living or care facilities such as retirement communities or nursing homes. In therapeutic applications, the F1C are used to treat trauma, e.g., bone fractures or active infections. The F1C treatments in these embodiments will result in enhanced immune responses, including increased innate and specific responses to, e.g., infectious agents. These treatments will typically also have other beneficial effects including enhancing bone marow production of blood cells or blood components such as neutrophils or improving levels of dysregulated immune response mediators, e.g., decreasing elevated cortisol, IL-6, IL-10, COX-2 or C reactive protein levels or increasing low IL-2 or IL-12 levels.

In related embodiments, the use of the F1C is optionally combined with one or more additional known or experimental therapies for an autoimmune, inflammatory or allergy disorder(s), e.g., one or more of surgery and treatment with a corticosteroid or glucocorticoid such as hydrocortisone, hydrocortisone acetate, fludrocortisone, prednisone, prednisolone, prednisolone acetate, methylprednisolone, dexamethasone, dexamethasone acetate or triamcinolone acetonide, leflunomide, an antibody, e.g., a human or humanized monoclonal antibody, that decreases the activity or level of C5 complement, TNFα or TNFα receptor, an antirheumatic drug such as methorexate, D-penicillamine, sodium aurothiomalate, sulfasalazine or hydroxychloroquine, immunosuppressive agents such as 6-thioguanylic acid, chlorambucil, cyclophosphamide or cyclosporin, a non-steroidal antiinflammatory agent such as celecoxib, ibuprofin, piroxicam or naproxin, an antihistamine such as loratidine or promethazine hydrochloride, an analgesic such as propoxyphene napsylate, acetaminophen or codeine or administration of vitamins (e.g., multivitamins, individual vitamins), antioxidants or other agents (e.g., vitamin E, folinic acid, carnitine, a C2-8 alkanoyl carnitine such as acetyl or propionyl L-carnitine) or nutritional supplements (e.g., liquid protein or carbohydrate preparations). Such therapies would be used essentially according to standard protocols and such they would precede, be concurrent with or follow treatment with a F1C. In some embodiments, such additional therapies will be administered at the same time that a F1C is being used or within about 1 day to about 16 weeks before or after at least one round of treatment with the F1C is completed. Other exemplary therapeutic agents and their use have been described in detail, see, e.g., *Physicians Desk Reference* $54^{th}$ edition, 2000, pages 303-3267, ISBN 1-56363-330-2, Medical Economics Co., Inc., Montvale, N.J. One or more of these exemplary agents can be used in combination with a F1C to ameliorate, prevent or treat any of the appropriate autoimmune, inflammatory or allergy conditions or disorders described herein or any of their symptoms.

Where a natural or synthetic antiinflammatory glucocorticoid is used to treat one more of the conditions disclosed herein or wherein endogenous levels of glucocorticoid such as cortisol are elevated to an unwanted level in a subject, the use of a F1C will ameliorate unwanted side-effects of such glucocorticoid use or excess. Typically the F1C will be administered during, before and/or after glucocorticoid levels are elevated or during, before and/or after a therapeutic glucocorticoid is administered to the subject, e.g., within about 1, 2, 3, 4, 5, 6 or 7 days or within about 2, 3, 4, 5, 6, 7, 8, 9, 10, 11, 12, 14, 16, 20 or 24 weeks before or after glucocorticoid use or elevated glucocorticoid levels exist. Typically, the use of the F1C to counteract unwanted side-effects of therapeutic glucocorticoid use In these embodiments, will reduce or ameliorate the onset, severity or progression of one or more unwanted side-effects of glucocorticoid therapy such as a detectable immune suppression, an increased occurrence or incidence of infection, an undesirable alteration of mood (e.g., increased anxiety, depression or schizophrenia) or a detectable loss or alteration of memory.

Neurological Conditions.

Nervous system diseases, disorders, conditions, or their symptoms (collectively 'neurological conditions') that can be ameliorated, treated or prevented with any of the F1Cs disclosed herein include, but are not limited to, nervous system trauma or injury, and neurological conditions that result in an unwanted pathology or symptom, e.g., demyelination, pain, impairment of cognitive function, discernable memory loss, depression, anxiety, a disconnection of axons, a diminution of neuron, astrocyte or glia function or degeneration or death of nervous system cells or tissues such as one or more of those described herein.

Neurological conditions, including nervous system lesions that may be treated, prevented, or ameliorated in a subject include but are not limited to, the following lesions of either the central (including spinal cord, brain) or peripheral nervous systems. Exemplary neurological conditions include (1) ischemic lesions, in which a lack of oxygen in a portion of the nervous system results in neuronal injury or death, including cerebral infarction, ischemia or stroke, or spinal cord infarction or ischemia, (2) traumatic lesions, including lesions caused by physical injury or associated with surgery, for example, lesions which sever a portion of the nervous system, or compression injuries, (3) malignant lesions, in which a portion of the nervous system is destroyed or injured by malignant tissue which is either a nervous system associated malignancy or a malignancy derived from non-nervous system tissue, (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis or syphilis, (5) degenerative lesions or conditions, in which a portion of the nervous system is destroyed or injured as a result of a degenerative process including but not limited to degeneration associated with Parkinson's disease, Alzheimer's disease, Huntington's chorea, AIDS associated dementia, epliepitic dementia, presenile dementia, senile dementia, vascular dementia, post stroke dementia, post traumatic dementia or amyotrophic lateral sclerosis (ALS), (6) lesions associated with nutritional diseases, disorders, and/or conditions, in which a portion of the nervous system is destroyed or injured by a nutritional disorder or disorder of metabolism including but not limited to, vitamin B 12 deficiency, folic acid deficiency, Wernicke disease, tobacco-alcohol amblyopia, Marchiafava-Bignami disease (primary degeneration of the corpus callosum), and alcoholic cerebellar degeneration, (7) neurological lesions associated with systemic diseases including, but not limited to, diabetes (diabetic neuropathy, Bell's palsy), systemic lupus erythematosus, carcinoma, or sarcoidosis, (8) lesions caused by toxic substances including alcohol, lead, or neurotoxins, (9) demyelinated lesions in which a portion of the nervous system is destroyed or injured by a demyelinating disease including, but not limited to, multiple sclerosis, human immunodeficiency virus-associated myelopathy, progressive multifocal leukoencephalopathy, and central pontine myelinolysis or a myelopathy, e.g., diabetic meylopathy or a transverse myelopathy, (10) neurological conditions such as insomnia (e.g., transient or chronic), epilepsy, schizophrenia, psychosis, delusion, a unipolar mood disorder, a bipolar mood disorder, psychomotor dysfunction, depression, anxiety, addiction to or abuse of a drug substance such as tobacco, nicotine, caffeine, alcohol, a barbiturate, a tranquilizer, a narcotic such as hydromorphone HCl, propoxyphene napsylate, meperidine HCl, valium, codeine, cocaine, morphine, heroin or methadone, (11) cognitive dysfunction conditions or diseases such as one or more of impaired long-term or short-term memory, impaired concentration, impaired attention or impaired learning, where the cognitive dysfunction condition or disease is optionally associated with chemotherapy, radiation therapy or exposure, aging, trauma, e.g., CNS trauma, or neurodegeneration and (12) genetic disorders with a neurological pathology or component such as Down's syndrome or Tay Sach's disease.

The F1Cs are useful to ameliorate, treat or prevent the onset, severity or length of other neurological diseases or conditions such as headache or a migraine condition or symptom such as classic migraine, cluster headache, abdominal migraine, common migraine, hemiplegic migraine, ocular migraine, fulminating migraine, complicated migraine or a symptom of any of these such as head pain, vertigo, nausea, vomiting or potophobia.

In some embodiments, the F1C is used to protect neural cells from the damaging effects of cerebral hypoxia, cerebral ischemia or neural cell injury associated with cerebral infarction, heart attack, stroke or elevated levels of glucocorticoids such as cortisol. The compounds that are also useful for treating or preventing a nervous system disorder may be selected, e.g., by assaying their biological activity in promoting the survival or differentiation of neurons. For example, and not by way of limitation, the F1Cs can be used to elicit any of the following useful effects: (1) increased survival time of neurons in culture, (2) increased sprouting of neurons in culture or in vivo, (3) increased production of a neuron-associated molecule in culture or in vivo, e.g., dopamine or choline acetyltransferase or acetylcholinesterase with respect to motor neurons or (4) decreased symptoms of neuron dysfunction in vivo. Such effects may be measured by any method known in the art. Increased survival of neurons may be measured using known methods, such as, for example, the method set forth in Arakawa et al. (*J. Neurosci.* 10:3507-3515 1990); increased sprouting of neurons may be detected by methods known in the art, such as the methods set forth in Pestronk et al. (*Exp. Neurol.* 70:65-821980) or Brown et al. (*Ann. Rev. Neurosci.* 4:17-421981). Increased production of neuron-associated molecules may be measured by, e.g., bioassay, enzymatic assay, antibody binding or Northern blot assay, using techniques known in the art and depending on the molecule to be measured. Motor neuron dysfunction may be measured by assessing the physical manifestation of motor neuron disorder, e.g., weakness, motor neuron conduction velocity, or functional disability. Motor neuron conditions may arise from infarction, cancer, infection, exposure to toxin, trauma, surgical damage or a degenerative disease that affects motor neurons as well as other components of the nervous system.

Other neurological condtions that can be treated using F1Cs include conditions that selectively affect neurons or adjacent tissues such as amyotrophic lateral sclerosis, progressive spinal muscular atrophy, progressive bulbar palsy, primary lateral sclerosis, infantile and juvenile muscular atrophy, poliomyelitis and the post polio syndrome, hereditary motorsensory neuropathy, spinal cord compression and a myelitis such as necrotizing myelitis, transverse myelitis, ascending myelitis, bulbar myelitis, concussion myelitis, demyelinated myelitis, postinfectious myelitis, systemic myelitis or transverse myelitis.

In some neurological conditions such as mood changes, depression, anxiety, memory loss or motor function impairment, the F1Cs can modulate one or more biological activities of a transcription factor or a nuclear hormone receptor such as ERα in tissue such as the hypothalamus or amygdala or ERβ in tissue such as the hippocampus, thalamus or entorhinal cortex.

In neurological conditions or other conditions where loss or damage to nervous system cells or tissue is typically present, e.g., multiple sclerosis, cerebral infarction, cerebral trauma, elevated glucocorticoid levels or Alzheimer's disease, use of the F1Cs can lead to detectable repair of damaged cells or replacement of at least some killed cells. Elevated glucocorticoids can result from endogenous production of natural glucocorticoids, e.g., cortisol or hydrocortisone, or from administration of synthetic glucocorticoids, e.g., dexamethasone, triamcinolone, betamethasone or other synthetic agents disclosed herein or in the cited references. Repair or replacement can occur for cell types that are present in nervous system tissues, e.g., neurons, Schwann cells, glial cells, astrocytes, oligodendrocytes, macroglia cells, endothelial cells, or stem or progenitor cells of any of these cell types. The cells may reside in discrete regions of nervous organs, e.g., hippocampus, cerebrum or cerebellum, or they may reside in multiple regions. Any of the neurological conditions that cen be treated with the F1Cs may be acute, subacute or chronic and they may be subclinical (having few or no overt symptoms), mild, moderate or severe.

In treating neurological conditions, the F1Cs will generally enhance function, self renewal and/or differentiation of stem or progenitor cells and/or they will reduce the severity of cell damage or impairment compared to similar subjects that are not treated with the F1Cs. In cases where myelin damage or nerve death occurs, the F1Cs can reduce the rate at which damage or death occurs or they can detectably reverse damage or enhance replacement of killed cells, particularly where the extent of such damage or killing is mild or moderate. Without wishing to be bound to any theory, the F1Cs may exert these properties (1) by directly acting as a hormone, growth factor or modulator of a biomolecule disclosed herein such as an enzyme, a glucocorticoid receptor, PPARα, a neural stem cell helix-loop-helix transcription factor such as HES1 or an estrogen receptor to enhance replication, synaptogenesis or other repair or maintenance functions, (2) by enhancing recruitment and/or differentiation of cells involved in cell or tissue repair, e.g., enhanced recruitment and differentiation of oligodendrocyte cells to a demyelinated lesion in multiple sclerosis and/or (3) indirectly by modulating the level or activity of autocrine, paracrine or endocrine factors such as one or more inflammatory cytokines or markers as disclosed herein that can modulate disease progression, e.g., cortisol, IL-1α, IL-1β, TNF-α, IL-6, a thromboxane, a prostaglandin or a neuregulin.

In treating chronic or progressive disorders such as multiple sclerosis or Alzheimer's disease, the F1Cs will typically slow the rate of progression of the disease. The F1Cs act at least in part by decreasing the activity or levels of chemokines and/or pro-inflammatory cytokines, e.g., one, two or more of MCP-1, MIP-1, ICAM, V-CAM, E-selectin, RANTES, IL-1α, IL-1β, IL-6, IL-8 and TNF-α. This reduction can be accompanied by a reduced rate of deposition of amyloid-β (AJ3) protein, which results in slowed disease progression and in reduced severity and/or frequency of one or more symptoms such as short term memory loss, impaired concentration, impaired judgement, episodes of disorientation or confusion and periods of mood or behavior changes such as irritability, anxiety or aggression. Treatment of chronic or progressive disorders such as Alzheimer's disease with a F1C is optionally accompanied by other suitable treatments, e.g., treatment with one or more non-steroidal anti-inflammatory drugs or other palliative measures.

Factors such as increased levels of cortisol or thromboxane, that are associated with increased cell or tissue damage or with inhibition of cell growth or differentiation are generally decreased or reregulated to express in a normal manner by the appropriate cells such as neurons, astrocytes, glial cells or their stem or precursor cells. Factors that facilitate normal differentiation or repair, e.g., basic fibroblast growth factor 2 or neuregulin, are generally increased or reregulated to express in a normal manner by the appropriate cells such as neurons, astrocytes, glial cells or their stem or precursor cells.

Because of these properties, the F1Cs can be used in various protocols or methods to enhance differentiation or proliferation of these cell types in vivo or in vitro. Typically, the concentration of the F1Cs will exert one or more of these beneficial effects at extracellular concentrations of about $1 \times 10^{-12}$ M to about $5 \times 10^{-6}$ M, e.g., about $1 \times 10^{-11}$ M to about $5 \times 10^{-7}$ M or about $1 \times 10^{-10}$ M to about $1 \times 10^{-7}$ M. Such concentrations can suitably be established transiently, e.g., for about 10 minutes to about 6 hours or about 12 hours once or twice per day on one, two or more days. Alternatively, such concentrations may be maintained more or less constantly, e.g., within these ranges for at least about 12 hours per day for one, two or more days, particularly for in vitro use to enhance cell or tissue growth, differentiation or viability in tissue culture. Methods to administer the F1Cs for in vivo use are essentially as described herein.

For any of these neurological conditions or their associated symptoms, the presence of the condition or its pathological manifestation, e.g., cell or tissue damage, or symptom may be determined by suitable objective or subjective means, e.g., assays to detect tissue damage, levels of diagnostic markers or an etiological agent, performance of histopathological examination of cells or tissues, patient questionnaires or behavior performance tests, measurement of a diagnostic marker(s), e.g., an enzyme, hormone, cytokine or drug substance in blood or tissue, electroencephalography, imaging methods such as X-ray, MRI scan or CAT scan, observation and diagnosis of clinical features or symptoms or biopsy of affected tissue or cells, e.g., aspiration biopsy, needle biopsy, incision biopsy or punch biopsy of tissue or cells. Neurological conditions, diseases and symptoms, which the F1Cs can be used to treat or ameliorate and methods to diagnose and characterize such conditions or diseases have been described. See, e.g., Ph. Demaerel, A. L. Baert et al., eds. *Recent Advances in Diagnostic Neuroradiology* (*Medical Radiology: Diagnostic Imaging*) 2001 Springer Verlag, ISBN: 3504657231, W. G. Bradley et al., *Neurology in Clinical Practice: Principles of Diagnosis and Management* 1995, see, e.g., vol. 1 Ch. 1-55 and vol. 2. Ch. 1-66, Butterworth-Heinemann Medical, ISBN 0750694777, H. J. M. Barnett et al., eds. *Stroke: Pathophysiology, Diagnosis and Management* $3^{rd}$ edition, 1998, see, e.g., pages 10-1450, Churchill Livingstone, ISBN 0443075514, P. J. Vinken et al., eds. *Neurodystrophies and Neurolipidoses* $2^{nd}$ ed. 1996, see, e.g., pages 8-780, Elsevier Science, ISBN 0444812857, P. L. Peterson and J. W. Phillis eds. *Novel Therapies for CNS Injuries: Rationales and Results* 1995, see, e.g., pages 8-380, CRC Press, ISBN 0849376521, D. Schiffer, *Brain Tumors: Pathology and Its Biological Correlates* $2^{nd}$ ed. 1997, see, e.g., pages 5-450, Springer Verlag, ISBN 3540616225 and E. Niedermeyer and F. Lopes Da Silva, eds. *Electroencephalography: Basic Principles, Clinical Applications and Related Fields* $4^{th}$ ed. 1999 see, e.g., pages 13-1238, Lippincott, Williams & Wilkins, ISBN 0683302841.

The use of the F1Cs in these conditions is optionally combined with one or more of the therapeutic treatments that are described in these references. The F1C may be administered before, during or after another treatment is employed to prevent, treat or ameliorate a given neurological condition or symptom thereof. Any of these neurological conditions or symptoms may be mild or at an early stage, moderate or severe or advanced.

Dosages of the F1C, routes of administration and the use of combination therapies with other standard therapeutic agents or treatments could be applied essentially as described above for cardiovascular conditions or as disclosed elsewhere herein. Thus, the F1Cs may be administered prophylactically or therapeutically in chronic conditions or they may be administered at the time of or relatively soon before or after an acute event such as an epileptic seizure, onset of a migraine or occurrence of trauma, before, during or after surgery, accidental head or central nervous system injury or a cerebral stroke or infarction. For acute events, the formula] compounds may thus be administered concurrently, e.g., within about 15 minutes or about 30 minutes of the onset or occurrence of the acute event, or at a later time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours after the onset or occurrence of the acute event. The F1Cs may thus be administered at about 6-120 hours, or about 8-48 hours, about 10-24 hours or about 12-16 hours after an acute event starts or occurs. In other embodiments, the F1C can be administered before an expected acute event such as a planned surgery. In these cases, the F1Cs may be administered before, e.g., within about 15 minutes or about 30 minutes of the onset or occurrence of the acute event, or at an earlier time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours before the onset or occurrence of the acute event.

Skin Treatments.

The affect of the F1Cs on immune function permits their use to improve the function of organs or organ systems that rely on the optimal functioning of one or more immune responses. Thus, the F1Cs can be administered to a subject to prevent, treat, ameliorate, slow the progression of or enhance the healing of certain skin conditions such as skin inflammation, lesions, atrophy or rash. Conditions that can give rise to skin pathology or an unwanted skin condition include autoimmune diseases, inflammation, allergy, age, exposure to sunlight, cancer, infection or the like.

As used here, skin includes external skin and internal skin or surfaces such as oral, intestinal and rectal mucosa. These conditions include lesions, rashes or inflammation associated with, e.g., burns, infections and the thinning or general degradation of the dermis often characterized by a decrease in collagen or elastin as well as decreased number, size and doubling potential of fibroblast cells. Such skin conditions include keratoses such as actinic keratosis, psoriasis, eczema, warts such as papillomavirus-induced warts, ulcers or lesions such as herpesvirus-induced ulcers or lesions or diabetes associated ulcers or lesions, discoid lupus erythematosus, erythema nodosum, erythema multiform, cutaneous T cell lymphoma, atopic dermatitis, inflammatory vasculitis, relapsing polychondritis, exfoliative dermatitis, sarcoidosis, burns, melanoma, rash or irritation from poison oak, poison ivy or poison Sumac, blemished or hyperpigmented skin, hyperkeratotic skin, dry skin, dandruff, acne, inflammatory dermatoses, scarring such as from a chemical or thermal burn and age-related skin changes. In these embodiments, treatment with the F1Cs is optionally combined with other appropriate treatments or therapies essentially as described herein, e.g., one or more of a corticosteroid such as hydrocortisone or cortisol, prednisone, or prednisolone, an α-hydroxybenzoic acid or an α-hydroxycarboxylic acid(s) is coadministered with a F1C to treat, prevent or ameliorate a skin condition such as atrophy or a lesion. α-Hydroxybenzoic acids and α-hydroxycarboxylic acids suitable for use in these embodiments are described in, e.g., U.S. Pat. Nos. 5,262,407, 5,254,343, 4,246,261, 4,234,599 and 3,984,566. The F1C can be used to minimize cutaneous atrophy caused by corticosteroids, a side effect of their application to the skin.

In these embodiments that address skin conditions, dosages, routes of administration and dosing protocols for the F1Cs are essentially as described herein. In some embodiments, the F1C is administered to the subject in the form of a topical cream, ointment, spray, foam or gel. These topical formulations will optionally comprise about 0.1% w/w to about 20% w/w, or about 0.2% w/w to about 10% w/w of a F1C in a composition that comprises one or more excipients that are suitable for such topical formulations, including, e.g., one or more agents that enhance penetration or delivery of the F1C into the skin. Such topical formulations can be administered, e.g., once, twice or three times per day using about 0.1 g to about 8 g or about 0.2 g to about 5 g of the topical formulation on each occasion. Administration may be daily for about 1 to about 28 days, or it may be intermittent and used as needed. The amount of a topical formulation that can be administered may be higher, e.g., about 15 g or about 20 g, if the size of the area to be treated is relatively large, e.g., at least about 30 cm$^2$ to about 100 cm$^2$ or more. Alternatively, systemic administration of the F1C such as oral, parenteral, sublingual or buccal delivery may be used, particularly when the area of the skin to be treated is relatively large. In some cases, both topical and systemic administration of a F1C can be used. Excipients that topical or other formulations may contain include those described herein, or agents that enhance permeation or solubilization of the F1C, e.g., DMSO or an alkylalkanol, such as a 2-alkylalkanol or a 3-alkyloctanol that comprises about 8-36 carbon atoms (e.g., 8, 9, 10, 11, 12, 13, 14, 15, 16, 17, 18, 19 or 20 carbon atoms) such as 2-ethyloctanol, 2-propyloctanol, 2-octyldodecanol, 2-butyloctanol, 2-hexyldecanol, 2-pentylnonanol, 3-ethyloctanol, 3-propyloctanol, 3-octyldodecanol, 3-butyloctanol, 3-hexyldecanol, 3-pentylnonanol, isostearyl alcohol, isocetyl alcohol, or mixtures thereof. Such alkylalkanol moieties include those having the structure HO—CH$_2$—(CH$_2$)$_{0-4}$—CH(C1-10 alkyl)-(CH$_2$)$_{0-6}$—CH$_3$, any of which are optionally substituted at the alkanol or the alkyl moiety with one, two, three or more independently selected substituents as described herein, e.g., with one, two, three or more independently selected —O—, —F, —OH, —CN or —CH=CH— moieties. Such formulations can be used in therapeutic applications described herein or in cosmetic applications.

Modulation of Transcription Factors, Receptors and Gene Expression.

In treating any of the diseases, conditions or symptoms disclosed herein, the F1Cs can modulate, i.e., detectably enhance or increase or detectably inhibit or decrease, the expression or a biological activity(ies) of one or more transcription factors or receptors. This can lead to detectable modulation of target gene activity or expression as part of the treatment or amelioration of the disease, condition or symptom. Such modulation can arise from changes in the capacity of a transcription factor or receptor to bind to or form a complex with other natural ligands such as a target DNA sequence(s), another transcription factor(s), a transcription cofactor, a receptor such as a nuclear hormone receptor or cell membrane receptor (e.g., a lipid, peptide, protein or glycoprotein receptor such as an interleukin receptor or a growth factor receptor), a receptor cofactor or an enzyme such as a polymerase, kinase, phosphatase or transferase. The effects of F1Cs on these biomolecules can be exerted in immune cells or in non-immune tissue, e.g., cells or tissue adjacent to diseased tissue such as infected or malignant cells. The F1Cs may directly or indirectly modulate the capacity of any of these molecules to transduce signals that are part of normal signal trandsuction processes.

In many of the clinical conditions described herein, e.g., in cancers, infections, acute inflammation, chronic inflammation, trauma, neurological conditions or autoimmunity, the F1Cs can modulate, e.g., detectably decrease or increase, a biological activity(ies), protein or molecule level or RNA level of 1, 2, 3, 4, 5, 6 or more biomolecules that are involved in establishment, maintenance or progression of a disease, condition or symptom. Such biomolecules include 1, 2, 3, 4, 5, 6 or more of AP-1, a cyclooxygenase such as mammalian or human cyclooxygenase-1 (COX-1) or cyclooxygenase-2 (COX-2), a mammalian or human lipoxygenase, e.g., 5-lipoxygenase, TNFα, TNFα receptor 1, TNFα receptor 2, TNF receptor-associated factor, TNFβ, TNFβ receptor, MIP-1α, monocyte chemoattractant-1 (MCP-1), interferon gamma (IFNγ or γIFN), IL-1α, IL-1β, IL-1α receptor, IL-1β receptor, IL-2, IL-3, IL-4, IL-4 receptor (IL-4R), IL-5, IL-6, IL-6 receptor (IL-6R), IL-8, IL-8 receptor (IL-8R), IL-10, IL-10 receptor (IL-10R), IL-12, an IL-12 receptor, (e.g., IL-12Rβ2), IL-13, IL-15, IL-17, IL-18, nuclear factor kappa B (NFκB), AP-1, c-maf, v-maf, maf B, Nrl, mafK, mafG, the maf family protein p18, reactive oxygen species, e.g., peroxynitrite, hydrogen peroxide or superoxide ion (collectively ROS), a 17β-hydroxysteroid dehydrogenase (17β-HSD) or an 11β-hydroxysteroid dehydrogenase (11β-HSD), e.g., 11β-HSD type 1, 11β-HSD type 2, 17β-HSD type 1, 17β-HSD type 2 or 17β-HSD type 5, a steroid aromatase, e.g., cytochrome P450 aromatase, steroid 5α-reductase, serum or blood cortisol, cytosolic phospholipase A2 (cPLA2), calcium-independent phospholipase A2 (iPLA2), a prostaglandin, e.g., prostaglandin E2 (PGE2) or prostaglandin D2 (PGD2), a leukotriene, e.g., leukotriene B4, inducible nitric oxide synthetase (iNOS), nitric oxide (NO), GM-CSF, RANTES (regulated on activation, normal T cells expressed and secreted), eotaxin, GATA-3, CCR1, CCR3, CCR4, CCR5, CXCR4, in, e.g., a subject's cell(s) or tissue(s) or in enzyme, tissue or cell-based assays. In these subjects, the levels of other biomolecules, their RNAs or the level of their activity can be detectably modulated include IFNα, INFα receptor, PPARα, PPARγ, PPARδ or a transcription factor such as T-bet is detectably increased. Other biomolecules or their isoforms, polymorphs, orthologs, or homologs that the F1Cs directly or indirectly modulate include one or more of, e.g., Janus kinase 1 (JAK1), Janus kinase 2 (JAK2), Janus kinase 3 (JAK3), signal transducer and activator of transcription 1 (STAT1), signal transducer and activator of transcription 2 (STAT2) and signal transducer and activator of transcription 3 (STAT3). The F1Cs can modulate the other biologically active analogs of any these enzymes, chemokines, cytokines, their receptors or ligands, including their isoforms, polymorphs, orthologs or homologs. In some cells or tissues, one or more of these biomolecules may be detectably increased, while in other cells or tissues, the same biomolecule may be detectably decreased. Thus, the biomolecules that the F1Cs can modulate, e.g., detectably increase or decrease, include the intracellular or extracellular level or biological activity of one or more enzyme, cytokine, cytokine receptor, chemokine and/or chemokine receptor. Exemplary chemokine receptors include one, two or more of CCR-1, CCR-2, CCR-2A, CCR-2B, CCR-3, CCR-4, CCR-5, CXCR-3 and CXCR-4.

The F1Cs can modulate the activity of certain biomolecules that mediate various biological responses that affect establishment or progression of a disease or that enhance or inhibit specific immune responses. Thus, in conditions where unwanted inflammation is present, the F1Cs can reduce inflammation, while enhancing Th1 or Tc1 immune responses at the same time. The biomolecules that the F1Cs can modulate include, e.g., transcription factors or receptors, including orphan nuclear receptors, and the homologs, isoforms, orthologs and co-factors (e.g., co-repressors, co-activators, transcription factors, gene promoter regions, sequences or messenger moieties such as calcium ions, potassium ions or cAMP) of any of these molecules and related molecules that participate in their function. The compounds can directly or indirectly from complexes with such molecules or they can modulate (detectably increase or decrease) the synthesis, level or one or more biological activities of those molecules. These complexes include receptors or transcription factor complexes, which can comprise heterodimers, homodimers and trimer, tetramer, pentamer or higher homo or hetero complexes. A number of the orphan receptors or their isoforms, orthologs or homologs, e.g., PPARα, PPARβ, PPARγ, PPARγ1, PPARγ2, PPARγ3, LXRα, LXRβ, SXR, PXR, CARα and CARβ, can form heterodimers with one or more of RXRα, RXRβ and RXRγ. Exemplary mammalian, human or other biomolecules include steroidogenic factor-1 (SF-1), steroidogenic acute regulatory protein (StAR), a chicken ovalbumin upstream promoter-transcription factor (COUP-TF), chicken ovalbumin upstream promoter-transcription factor (COUP-TFI) and its mammalian isoforms, orthologs and homologs, silencing mediator for retinoid and thyroid hormone receptor (SMRT) and its mammalian isoforms, orthologs and homologs, sterol regulatory element binding protein (SREBP) 1a (SREBP-1a), SREBP-1c, SREPB-2, NF-E3, FKHR-L1, COUP-TFII and its mammalian isoforms, orthologs and homologs, and the isoforms, orthologs and homologs of IκB, IκBα, AML-3, PEBP2αA1, Osf2, Cbfa1, RUNX2, activating transcription factor 2 (ATF2), c-Jun, c-Fos, a mitogen activated kinase (MAP) such as p38 or JNK, a mitogen activated kinase kinase (MKK), a p160 or steroid receptor coactivator-1 family (SRC-1, SRC-1/serum response factor), SRC-2, SRC-3, SET, nerve growth factor inducible protein B, StF-IT, NFAT, NFAT interacting protein 45 (NIP45), IkB, an IkB kinase, NFATp, NFAT4, an AP-1 family protein, a p300 protein, CREB, CREB-binding protein (CPB), p300/CBP, p300/CPB-associated factor, SWI/SNF and their human and other homologs, BRG-1, OCT-1/OAF, AP-1, AF-2, Ets, androgen receptor associated protein 54 (ARA54), androgen receptor associated protein 55 (ARA55), androgen receptor associated protein 70 (ARA70), androgen receptor-interacting protein 3 (ARIP3), ARIP3/PIASx α complex, PIASx α, Miz1, Miz1/PIASx β complex, PIASx β, PIAS1, PIAS3, GBP, GBP/PIAS1 complex, RAC3/ACTR complex, SRC-1α, receptor interacting protein-140 (RIP-140), transcription factor activator protein-1, activation function-2, glucocorticoid receptor-interacting protein-1 (GRIP-1), receptor interacting protein-160 (RIP-160), suppressor of gal4D lesions (SUG-1), transcription intermediary factor-1 (TIF-1), transcription intermediary factor-2 (TIF-2), SMRT, N—CoR, N—CoA-1, p/CIP, p65 (ReIA), the 120 KD rel-related transcription factor, heat shock proteins (HSP) such as HSP90, HSP70 and HSP72, heat shock factor-1, Vpr encoded by the human immunodeficiency virus and its isoforms and homologs thereof, testicular orphan receptor 2 (TR2), testicular orphan receptor 4 (TR4), a thyroid hormone receptor α, thyroid hormone receptor α1 (TRα1), thyroid hormone receptor α2 (TRα2), thyroid hormone receptor β (TRβ), retinoid X receptor α (RXRα), retinoid X receptor β (RXRβ), retinoid X receptor γ (RXRγ), TR α1/RXR α heterodimer, direct repeat-4 thyroid hormone response element (DR4-TRE), an estrogen receptor (ER) such as ERα or ERβ, estrogen receptor related receptor a (ERRα or EER1), estrogen receptor related receptor β (ER-IRβ or EER2), estrogen receptor related receptor γ (ERRγ or EER3), steroid xenobiotic receptor (SXR), a hepatocyte nuclear factor 4 (HNF-4), hepatocyte nuclear factor 4γ (HNF-4γ), hepatocyte nuclear factor 3 (HNF-3), liver X receptors (LXRs), LXRα, LXIRβ, estrogen receptor α (ERα), constitutive androstane receptor-α (CAR-α), constitutive androstane receptor-β (CAR-β), RXR/CAR-β heterodimer, short heterodimer partner (SHP; NR0B2), SHP/ERα heterodimer, estrogen receptor β, SHP/ERβ heterodimer, testicular orphan receptor TR4, TR2/TR4 heterodimer, pregnane X receptor (PXR) and isoforms, cytochrome P-450 monooxygenase 3A4, including its gene promoter region and isoforms thereof, HNF-4/cytochrome P-450 monooxygenase 3A4 gene promoter region and isoforms complex, HIV-1 long terminal repeat (LTR), HIV-2 LTR, TR2/HIV-1 LTR complex, TR4/HIV-1 LTR complex, TR4/HIV-1 LTR complex, TR α1/TR4/HIV-1 LTR complex, TR2 isoforms (TR2-5, TR7, TR9, TR11), DAX-1 (NR0B1), DAX-1/steroidogenic acute regulatory protein gene promoter region, RevErb, Rev-erbA α, Rev-erb β, steroid receptor coactivator amplified in breast cancer (AIB 1), p300/CREB binding protein-interacting protein (p/CIP), thyroid hormone receptor (TR, T3R), thyroid hormone response elements (T3REs), retinoblastoma protien (Rb), tumor suppressor factor p53, transcription factor E2F, mammalian acute phase response factor (APRF), constitutive androstane receptor (CAR), Xenopus xSRC-3 and mammalian (e.g., human) isoforms, orthologs and homologs, TAK1, TAK1/peroxisome proliferator-activated receptor α (PPARα) complex, PPARα/RXRα complex, peroxisome proliferator-activated receptor β (PPARβ), peroxisome proliferator-activated receptor γ (PPARγ), peroxisome proliferator-activated receptor δ (PPARδ), farnesoid X receptor, retina X receptor, TAK-1/RIP-140 complex, a retinoic acid receptor (RAR), retinoic acid receptor-β (RARβ), retinoic acid receptor-γ (RARγ), TR4/RXRE complex, SF-1/steroid hydroxylase gene promoter region, SF-1/oxytocin, including its gene promoter region, a bile acid receptor (FXR), nuclear receptor corepressor (NcoR), liver receptor homologous protein-1 (LRH-1; NR5A2), SF-1/ACTH receptor gene promoter region, rat Ear-2 and mammalian homologs, human TR3 orphan receptor (TR3), RLD-1, OR-1, androgen receptor, glucocorticoid receptor, estrogen receptor, progesterone receptor, mineralcorticoid receptor, aldosterone receptor, E6-associated protein (E6-AP), OR1, OR1/RXRα complex, TIF-1, CBP/P300 complex, TRIP1/SUG-1 complex, RIP-140, steroid receptor coactivator 1 (SRC1), SRC1a/P160 complex and TIF-2/GRIP-1 complex, RAR/N—CoR/RIP13 complex, RAR/SMRT/TRAC-2 complex and protein X of hepatitis B virus. The homologs, orthologs and isoforms of these transcription factors, receptors and other molecules are included among the molecules that the F1Cs can modulate the synthesis or one or more biological activities of. Such factors are biologically active or function in one or more of a number of cell types such as T cells, B cells, macrophages, dendritic cells, platelets, monocytes, neutrophils, neurons, epithelial cells, endothelial cells, cartilage cells, osteoblasts, osteoclasts, splenocytes, thymocytes and GALT associated cells. Methods to identify these molecules and their biological activities have been described, e.g., U.S. Pat. Nos. 6,248,781, 6,242,253, 6,180, 681, 6,174,676, 6,090,561, 6,090,542, 6,074,850, 6,063,583, 6,051,373, 6,024,940, 5,989,810, 5,958,671, 5,925,657, 5,958,671, 5,844,082, 5,837,840, 5,770,581, 5,756,673, and PCT publication Nos. WO 00/24245, WO 0073453 and WO 97/39721.

In one aspect, the compounds are used to treat, prevent or to ameliorate conditions or symptoms that are associated with unwanted or expression or activity of one or more of these molecules in conditions such as, e.g., acute inflammation, chronic inflammation or their symptoms, acute allergy, chronic allergy or their symptoms, e.g., allergic rhinitis or acute or chronic asthma, psoriatic arthritis, osteoporosis, osteoarthritis, rheumatoid arthritis, neurological dysfunction or their symptoms, e.g., dementias such as Alzheimer's Disease, Parkinson's Disease, or memory loss conditions, in osteoporosis or in cancer such as breast cancer. The compounds can prevent NFκB from translocating from the cytoplasm into the nucleus and thus can increase the ratio of cytoplasmic NFκB to nuclear NFκB. The F1Cs may inhibit activation of NFκB-mediated transcription while NFκB is bound to target DNA sequences in the nucleus. Alternatively, the F1Cs can activate or enhance the expression of or one or more activity of a transcription factor such as T-bet in, e.g., a subject's cell(s) or tissue(s) or in enzyme or cell-based assays. In this aspect the compounds are used to treat, prevent or to ameliorate conditions or symptoms that are associated with deficient expression or activity of T-bet in conditions such as immune dysfunction in an immunosuppression condition, aging, an infection, a cancer or precancer as described herein or in the cited references.

The invention provides methods to identify compounds to regulate immune or other biological responses in a context-sensitive manner. Such compounds modulate differential expression in a cell of the level of or an activity of, eg., 4, 5, 6, 7, 8 or more genes or gene products, comprising administering an effective amount of a F1C. The genes or gene products are USF1, c-Fos, EGR1, Cul1, RIPK2, IκBα, IκBKb, NF-κB, NF-κB2, NF-κB1 p50, Fn14 (fibroblast growth factor-inducible 14), TWEAK (TNF-like weak inducer of apoptosis), NEMO (NF-κB essential modifier), FCAR, c-Fos/ C/EBPβ, RANTES, ICAM1, TSG (TNFAIP6), IL-2 receptor α, GRO2, GRO3, HO1, Jun B, c-Fos/JunB complex, JunB/ATF3 complex, c-Jun, c-Fos/c-Jun complex, ATF-3, MMP1, TSG-6 (TNFAIP3), AP-1, EGR1, TGFβ, ATF-3/c-Jun complex, c-Fos, MMP3, IL-8, STAT5A, STAT5B, CDKN1A, IFNγ receptor 2 (IFNγR2), T-bet, C reactive protein, immunoglobulin E, an AP-1 family protein, GATA-3, Jak2, Tyk2, stat1, stat3, stat4, stat5, MIP-1α, MIP-2, IP-10, MCP-1, TNF-α, TNF-β, LT-β, IFN-α, IFN-β, TGF-β1, NF-κB, IL-1α, IL-1β, IL-4, IL-6, IL-10, IL-12 receptor β1, IL-12p35, IL-12p40, IL-23, IL-23 receptor or another gene or gene product disclosed herein, including in Table 1. The compounds identified by the screening methods modulate the expression of dysregulated genes and restore or enhance normal immune responses in conditions where unwanted dysregulation contributes to the establishment or progression a pathological condition such as an infection, an autoimmune disorder, a cardiovascular condition or a neurological condition.

Thus, in some embodiments, the level or a biological activity of 4, 5, 6, 7, 8, 9, 10, 11, 12, 13, 14, 15 or more of COX-2, IL-1β, TNFα, TNFα receptor 1, TNFα receptor 2, TNF receptor-associated factor, MIP-1α, MCP-1, IFNγ, IL-4, IL-4R, IL-6, IL-6R, IL-8, IL-8R, IL-10, IL-10R, IL-12, IL-12R, IL-18, IL-18R NFκB, IkBα, AP-1, GATA-3, 11β-HSD1, cPLA2, iPLA2, cortisol, ROS, PGE2, PGD2, leukotriene A4, leukotriene B4, leukotriene C4, iNOS or GM-CSF are optionally measured and they are generally detectably reduced, e.g., RNA or protein levels are reduced by about 10-95% or about 20-95% or more compared to suitable untreated controls. In these embodiments, the level or a biological activity of 4, 5, 6 or more of IFNα, INFα receptor, IL-12, an IL-12 receptor, (e.g., IL-12Rβ2), PPARα, PPARγ, and T-bet are optionally measured and they are generally detectably increased. In a chronic infection condition, e.g., HIV in humans, autoimmunity, a chronic fungal or parasite infection or in a precancer or cancer condition, e.g., benign prostatic hyperplasia, the progression of the condition may be slowed over a period of 1, 2, 3, 4, 5 or more years. In these embodiments, the subject's condition becomes more manageable with a reduced incidence or severity of side effects, e.g., a detectable halt, slowing, reversal or decreased incidence of wasting, dementia, CD4 cell count decreases or viral load increases, which tend to occur over time in HIV infected humans or a halt, slowing or reversal of pathogen or precancer or cancer cell replication.

These effects are typically observed after administration of an effective amount of a F1C using, e.g., a method or dose essentially as disclosed herein. The simultaneous reduction of multiple biomolecules provides a method to modulate immune responses by modulating multiple pathways that lead to a common condition such as inflammation. This provides a method to treat or ameliorate, e.g., acute or chronic inflammation, a cancer, an infection or a symptom associated therewith, or to slow the progression of or reduce the severity of these conditions or their symptoms.

Previously described methods can be used to measure the amount, activity or cellular location of various biomolecules such as cytokines or transcription factors. See, e.g., U.S. Pat. Nos. 6,107,034, 5,925,657, 5,658,744, 4,016,043 and 3,850,752, S. Szabo et al., Cell 2000 100:655-669, Y. Nakamura et al., J. Allergy Clin. Immunol. 1999103(2 pt. 1):215-222., R. V. Hoch et al., Int. J. Cancer 1999 84:122-128. These methods can be used to measure the effects of the F1Cs on transcription factors or receptors in cells or tissues that have been exposed to the compounds.

Without wishing to be bound to any theory, the F1Cs may modulate multiple biomolecules in a microenvironment sensitive manner or context. The effects of the compounds can provide a decrease in a particular molecule such as IFNγ and a decrease in inflammation associated with elevated IFNγ levels or activity without eliminating beneficial effects of the molecule. This effect arises from decreasing the level or activity of a biomolecule such as IFNγ in cells that are dysregulated, while allowing normal immune cells to produce sufficient amounts of the same molecule to perform normal immune functions. In locations where the biomolecule is needed for activity, e.g., in lymph nodes or spleen cells, sufficient amounts of the modulated molecule are present to elicit a desired response, while the level of the molecule in cells in circulation decreases. The compounds can increase IL-13, IL-15, IL-17 or IL-18 in conditions where a subject has a deficient Th1 immune response, e.g., in infection or cancer. Conversely, the compounds can decrease IL-13, IL-15 or IL-18 in conditions such as allergy or autoimmune conditions, e.g., multiple sclerosis, where an excess Th1 immune status may prevail.

In general, the F1Cs will detectably decrease the synthesis or one or more biological activity of one or more of these molecules (or other transcription factors or receptors disclosed herein) when such synthesis or activities is associated with the establishment, maintenance, progression or enhanced severity of a clinical condition or symptom disclosed herein. Conversely, the F1Cs will generally detectably increase the synthesis or one or more biological activities of one or more of these molecules (or other transcription factors or receptors disclosed herein) when such synthesis or activity is associated with the treatment, prevention, cure or amelioration of a clinical condition or symptom disclosed herein.

These decreases or increases compared to suitable controls can be relatively small, including changes near the lower limits of delectability for such molecules using known or new assays, e.g., a decrease or increase in the synthesis or biological activity of at least about 2%, about 5%, about 10% or about 20%. Such changes can be modest or relatively large, e.g., at least about a 50% change, at least about a 90% change, or at least about a 200% change, up to about a 5-fold, about a 10-fold, about a 100-fold or greater decrease or increase in the synthesis or biological activity of the affected molecule(s) compared to suitable controls. These changes are typically measured relative to controls that lack a F1C or that use known agonists or antagonists of one or more relevant molecules. Assays can be based on measuring decreases or increases in, e.g., one or more of protein levels, RNA or mRNA levels, a ligand binding activity, transcription of a target gene(s) and the like. Suitable assay protocols include any suitable polymerase chain reaction assay to measure an RNA or mRNA, any suitable blotting protocol for nucleic acid or for protein such as a Northern or Western blot method or any transcription assay, including DNA footprinting or a gene expression or gene function assay. Typically the F1Cs will effect detectable changes in the synthesis or one or more biological activities in a concentration range of about $0.5 \times 10^{-9}$ M to about $3 \times 10^{-5}$ M. Exemplary compositions that comprise a F1C for use in, e.g., in vivo animal assays, in vitro cell or tissue culture assays or in cell free assays, will comprise one or more suitable solvents or vehicles including DMSO, ethanol, water and a suitable tissue culture medium.

One or more of these transcription factors, receptors or complexes can be a component in methods when, e.g., they are used with a F1C in cell-free assays or in tissue culture assays. Formation of these complexes in cells or analysis of the effects of F1Cs on one or more of their biological activities is facilitated by inserting into the cells a DNA construct(s) that expresses one or more of these proteins, e.g., mammalian or yeast cells containing a stable DNA construct or a construct used for transient transfection assays. Methods to perform assays or to induce biological responses in vitro or in vivo using the F1Cs as agonists, antagonists or as reference standards are essentially as described, see, e.g., U.S. Pat. Nos. 5,080,139, 5,696,133, 5,932,431, 5,932,555, 5,935,968, 5,945,279, 5,945,404, 5,945,410, 5,945,412, 5,945,448, 5,952,319, 5,952,371, 5,955,632, 5,958,710, 5,958,892 and 5,962,443; International Publication Numbers WO 96/19458, WO 99/41257 and WO 99/45930. The complexes or assay systems, that comprise a F1C and one or more of these molecules are embodiments of the invention, as are the use of these compositions when employed in the practice of any of the assay methods or in any of the clinical treatment methods disclosed herein or in the cited references.

Invention embodiments include a method comprising contacting a F1C(s) with a cell(s), whereby the F1C(s) forms a complex with a steroid hormone receptor or results directly or indirectly in the modulation of a biological activity of the steroid hormone receptor or a gene that it regulates. The steroid hormone receptor may be an orphan nuclear hormone receptor or a characterized receptor such as the glucocorticoid receptor, estrogen receptor or the androgen receptor that displays a moderate or high binding affinity for the F1C(s). In some embodiments, the nuclear hormone receptor is a known receptor. Biological effects from interaction of a F1C and a receptor can lead to interference with the replication or development of a pathogen or the cell(s) itself, e.g., detectably inhibited proliferation of cancer cells. For example, expression of HIV transcripts in HIV-infected cells may be altered. The receptor-F1C complex may directly interfere with LTR-dependent transcription of HIV genes, leading to reduced viral replication. Alternatively, such effects can include the decreased synthesis or biological activity of a protein or gene product that is associated with the establishment, maintenance or progression of a disease condition described herein or in the cited references.

An aspect of F1C biological activity is their capacity to modulate the cpacity of cells or tissues described herein to express one or more enzymes that mediate phase II detoxification and reduction of damaging or reactive species such as xenobiotics, including electrophiles and chemical carcinogens, and superoxide radicals or hydrogen peroxide. Modulation of these genes is mediated by one or more transcription factors or complexes of factors that include bZip transcription factors such as Nrf2 (NF-E2 related factor 2, Unigene symbol Nfe2L2) and Maf proteins such as MafG, MafK or MafF. These factors bind to cis-elements such as EpRE (electrophile response element) or ARE (antioxident response element).

EpRE and/or ARE elements present in the promoters of phase II detoxification enzymes including NAD(P)H:quinine oxidoreductase-1 (NQO1) and glutathione-S-transferase (GST) as well as cellular defensive enzymes such as thioredoxins, heme oxygenase 1 (HO 1, or HMOX1), the catalytic and regulatory subunit γ-glutamylcysteine syhthetase (γGCS or GCLM) and xCT (SLC7A11), a subunit of the cystine/glutamate exchange transporter. EpRE and ARE mediate upregulation of these genes following exposure of the cells to many xenobiotics. In situations where enhanced expression of these genes or transcription factors is desirable, the F1C upregulate the activity or levels of one or more of these factors and/or enzymes.

Thus, in some embodiments the F1C are used to modulate the level or activity of one or more of Nrf2, a thioredoxin, NQO1, GST, HO 1, the catalytic subunit of γGCS, the regulatory subunit of γGCS and xCT in cells or tissues that are exposed to a F1C. In some embodiments, the cells or tissues are treated with a F1C when an unwanted acute or chronic condition such as toxin exposure or elevated oxidative stress is present in the cells or tissues. Such conditions can occur, e.g., as described elsewhere herein, including in acute or chronic pathological inflammation conditions, acute or chronic infections and trauma conditions. The effect of the F1Cs is restoration of normal expression or establishment of desired levels of expression of one or more of these transcription factors or enzymes, e.g., decreased expression in situations where chronic over-expression occurs. Thus, the F1C can be used to modulate these or other genes described herein, e.g., to decrease expression or mRNA levels or protein levels of one or more of these or other genes in clinical conditions where excess or unwanted expression or levels of the gene is associated with establishment, maintenance, severity or progression of the clinical condition resulting in clincal improvement in the disease or an unwanted symptom.

Homologs of these genes or proteins in other species, e.g., primates, are also modulated by the F1C. Modulation of these genes can be observed, e.g., as increased expression or mRNA levels or protein levels of the biomolecules in clinical conditions where insufficient or suboptimal expression or levels of the gene is associated with establishment, maintenance, severity or progression of the clinical condition to produce a desired clincal improvement.

Other Therapeutic and Biological Applications and Activities.

The F1Cs are useful for preventing, slowing the progression of or treating certain chronic conditions in a subject such as a mammal or a human. Chronic conditions include diseases and conditions that arise or develop over a relatively long time period, e.g., over about 3 months to 10 years or more. Such conditions include chronic renal failure, which may result from polycystic kidney disease, from, e.g., an autoimmune condition such as acute or chronic glomerulonephritis, or from diabetes, interstitial nephritis, hypertension and other conditions discussed elsewhere herein. Chronic conditions include chronic pulmonary conditions such as chronic bronchitis, lung fibrosis, right ventricular hypertrophy, pulmonary hypertension, emphysema, asthma and chronic obstructive pulmonary disease, which may be treated with a F1C. These conditions or their symptoms may be mild, moderate or severe. The subject may be suffering from the disease or condition or may be subject to developing the condition, e.g., the subject may display early signs or a predisposition to develop a chronic condition. Such treatment will generally facilitate prevention of the disease, delay the onset or severity of the disease or condition, ameliorate one or more symptoms, e.g., reduce shortness of breath, coughing or dyspnea, or slow progression of the disease or condition. In these and other chronic conditions described herein, the F1Cs will generally be administered to a subject such as a human for a relatively long time period, e.g., for at least about 3 months to about 10 years or more. Dosages, routes of administration and dosing protocols for the F1Cs are essentially as described herein. Dosing of the compound can be daily or intermittent using a dosing protocol using dosages as described herein, e.g., about 0.1 to about 20 mg/kg of a F1C administered to a subject once or twice per day daily or intermittently. The use of the F1Cs can be combined with other treatments, e.g., β-agonists such as metaproterenol or albuterol, or corticosteroids, e.g., prednisone, for asthma or chronic obstructive pulmonary disease.

The F1Cs can modulate the biological activity of cytokines or interleukins that are associated with various immune deficiency or dysregulation conditions, which may be transient or chronic. They can thus be used to ameliorate, treat or prevent naturally occurring age-related decline in immune function in a subject or immune deficiency or dysregulation resulting from trauma, stress, burns, surgery, autoimmunity or infections as described herein. Such immune deficiency dysregulation may be associated with, e.g., an age-related increase in production of one or more of IL-4, IL-5 and IL-6 or an age-related decrease in production of one or more of IL-2, IL-3, γ-IFN, GM-CSF or antibodies. In these embodiments, the F1C is administered to the subject to detectably decrease production or levels of one or more of IL-4, IL-5 and IL-6 or to detectably increase production or levels of one or more of IL-2, IL-3, IL-5, IL-12, GM-CSF and γ-IFN. These cytokine changes facilitate normalization of the subject's immune responses. Such normalization can be observed by various means. These means include monitoring appropriate cytokine RNA or protein level(s) in the subject or by measuring biological responses such as restoration or detectable improvement of contact hypersensitivity in a subject with depressed or suboptimal contact hypersensitivity response. The F1Cs can thus be used to enhance or restore a deficient or suboptimal immune response such as contact hypersensitivity response in a subject with a chronic or transient state of immune deficiency or dysregulation. In these embodiments, the F1C is administered using the dosages, routes of administration and dosing protocols for the F1Cs essentially as described herein. Treatment with the F1Cs is optionally combined with other appropriate treatments or therapies essentially as described herein, e.g., a antibacterial or antiviral agent(s) is coadministered with a F1C to treat, prevent or ameliorate an infection in an infected subject or a subject suffering from, e.g., a burn. Methods to measure changes in cytokine levels or contact hypersensitivity are known and can optionally be applied in these embodiments, see, e.g., U.S. Pat. Nos. 5,919,465, 5,837,269, 5,827,841, 5,478,566.

The capacity of the F1Cs to modulate immune functions permits their use for treating, preventing, slowing the progression of or alleviating the a symptom(s) of subjects with psychological disorders, metabolic disorders, chronic stress, sleep disorders, conditions associated with sexual senescence, aging, or premature aging. Metabolic disorders include parathyroidism, pseudoparathyroidism, hypoparathyroidism, hypercalcemia, hypocalcemia and detectable symptoms thereof such as fatigue, constipation, kidney stones and kidney malfunction. Chronic stress and related disorders include fibromyalgia, chronic fatigue syndrome, hypothalamic-pituitary axis dysregulation. Other related pathological conditions that can be treated with the F1Cs include hormone deficiency associated with aging or with a pathological condition, hypogonadism, vaginal atrophy, diminished libido, urinary incontinence, skin collagen loss, loss or impairment of skin, organ or joint connective tissue and menopause or its symptoms such as hot flashes, unwanted mood changes, fatigue and insomnia. In these embodiments, treatment of subjects with a F1C is optionally combined with other suitable agents such as triiodothyronine, tetraiodothyronine, an insulin-like growth factor, insulin-like growth factor binding protein-3, an estrogen or a progestin.

As noted above, in some embodiments a treatment with a F1C is combined with a corticosteroid or glucocorticoid. Corticosteroids are used in a number of clinical situations to, e.g., decrease the intensity or frequency of flares or episodes of inflammation or autoimmune reactions in conditions such as acute or chronic rheumatoid arthritis, acute or chronic osteoarthritis, ulcerative colitis, acute or chronic asthma, bronchial asthma, psoriasis, systemic lupus erythematosus, hepatitis, pulmonary fibrosis, type I diabetes, type II diabetes or cachexia. However, many corticosteroids have significant side effects or toxicities that can limit their use or efficacy. The F1Cs are useful to counteract such side effects or toxicities without negating all of the desired therapeutic capacity of the corticosteroid. This allows the continued use, or a modified dosage of the corticosteroid, e.g., an increased dosage, without an intensification of the side effects or toxicities or a decreased corticosteroid dosage. The side-effects or toxicities that can be treated, prevented, ameliorated or reduced include one or more of bone loss, reduced bone growth, enhanced bone resorption, osteoporosis, immunosuppression, increased susceptibility to infection, mood or personality changes, depression, headache, vertigo, high blood pressure or hypertension, muscle weakness, fatigue, nausea, malaise, peptic ulcers, pancreatitis, thin or fragile skin, growth suppression in children or preadult subjects, thromboembolism, cataracts, and edema. Dosages, routes of administration and dosing protocols for the F1C would be essentially as described herein. An exemplary dose of F1C of about 0.5 to about 20 mg/kg/day is administered during the period during which a corticosteroid is administered and optionally over a period of about 1 week to about 6 months or more after dosing with the corticosteroid has ended. The corticosteroids are administered essentially using known dosages, routes of administration and dosing protocols, see, e.g., *Physicians Desk Reference* 54$^{th}$ edition, 2000, pages 323-2781, ISBN 1-56363-330-2, Medical Economics Co., Inc., Montvale, N.J. However, the dosage of the corticosteroid may optionally be adjusted, e.g., increased about 10% to about 300% above the normal dosage, without a corresponding increase in all of the side effects or toxicities associated with the corticosteroid. Such increases would be made incrementally over a sufficient time period and as appropriate for the subject's clinical condition, e.g., daily corticosteroid dose increases of about 10% to about 20% to a maximum of about 300% over about 2 weeks to about 1 year.

Such corticosteroids include hydrocortisone (cortisol), corticosterone, aldosterone, ACTH, triamcinolone and derivatives such as triamcinolone diacetate, triamcinolone hexacetonide, and triamcinolone acetonide, betamethasone and derivatives such as betamethasone dipropionate, betamethasone benzoate, betamethasone sodium phosphate, betamethasone acetate, and betamethasone valerate, flunisolide, prednisone, fluocinolone and derivatives such as fluocinolone acetonide, diflorasone and derivatives such as diflorasone diacetate, halcinonide, dexamethasone and derivatives such as dexamethasone dipropionate and dexamethasone valerate, desoximetasone (desoxymethasone), diflucortolone and derivatives such as diflucortolone valerate), fluclorolone acetonide, fluocinonide, fluocortolone, flu-prednidene, flurandrenolide, clobetasol, clobetasone and derivatives such as clobetasone butyrate, alclometasone, flumethasone, and fluocortolone.

In some clinical conditions, the F1Cs can inhibit activated T lymphocytes in vivo, and they can inhibit the expression or biological activity of one or more of TNF-α, IFN-γ, IL-6, IL-8 or insulin like growth factor-1 receptor (IGF-1 R) or IL-6 receptor. The compounds are thus useful to treat, prevent or ameliorate conditions where this is a component of pathology. Such conditions include inflammation conditions such as psoriasis, psoriatic arthritis, osteoarthritis, and rheumatoid arthritis. The compound can thus ameliorate the inflammation, e.g., by inhibiting expression of one or more of TNF-α, IFN-γ, IL-6, IL-8 or IGF-1 R. Also, the compounds can inhibit unwanted T cell activity. They can thus ameliorate one or more psoriasis symptoms such as skin scaling, skin thickening, keratinocyte hyperproliferation, deficient filaggrin expression (B. Baker et al., *Br. J. Dermatol.* 1984, 111:702), deficient strateum corneum lipid deposition or they can improve a clinical assessment such as the Psoriasis Activity and Severity Index. The F1Cs can be delivered to a subject with psoriasis using topical or systemic formulations as described herein. Topical formulations include gels, lotions and creams, e.g., as described herein. Daily or intermittent administration of the compound can be used essentially as described herein. The use of the F1Cs is optionally combined with one more current psoriasis treatments, e.g., topical emollients or moisturizers, tars, anthralins, systemic or topical corticosteroids, vitamin D analogs such as calcitriol, methotrexate, etretinate, acitretin, cyclosporin, FK 506, sulfasalazine, ultraviolet B radiation optionally combined with one or more of a topical corticosteroid, tar, anthralin, emollient or moisturizer or ultraviolet A plus psoralen. Such additional treatments essentially would use known dosages and routes of administration, which are applied, e.g., within a month before, during or within a month after a treatment course with a F1C.

Specific Embodiments.

Aspects of the invention and related subject matter include the following specific embodiments and are not intended to limit the invention in any way.

1A. A compound having the structure

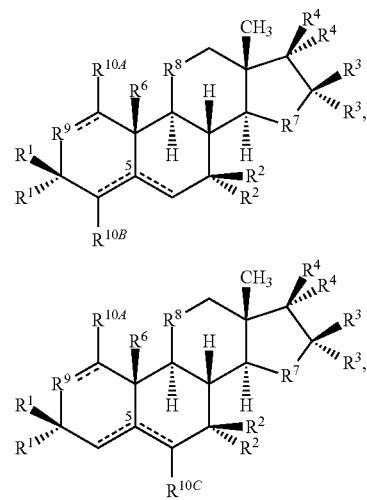

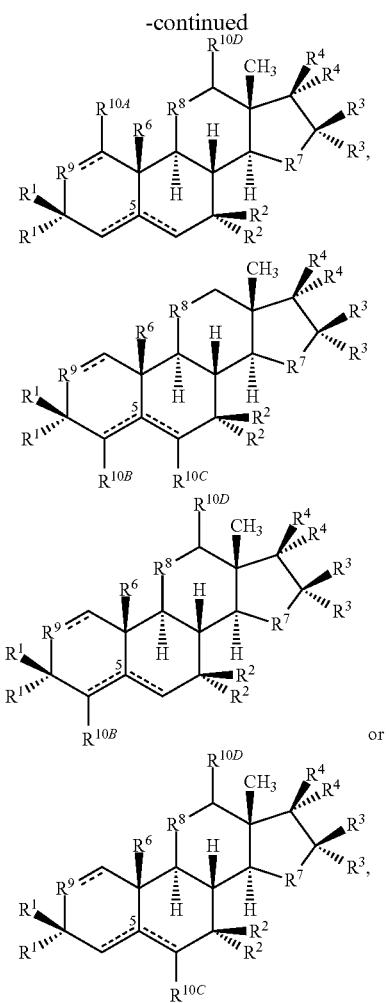

or a salt thereof, provided that if a double bond is present at the 4-5- or 5-6-positions, then —H at the 5-position is absent and is otherwise present in the α- or β-configuration or if a double bond is present at the 1-2-, 4-5- or 5-6-positions, then $R^{10A}$, $R^{10B}$ or $R^{10C}$, respectively, are bonded to the ring to which they are linked by a single bond;

wherein one each of $R^1$, $R^2$ and $R^3$ is —H; one of $R^4$ is —H or an optionally substituted alkyl group; the other $R^1$ is —OH; the other $R^2$ is —H, —OH, —CH$_3$, a halogen or an alkoxy or both $R^2$ together are =O or =CH$_2$; the other $R^3$ is —H, halogen, —OH or an ester or both $R^3$ together are =O or =CH$_2$; the other $R^4$ is —NH$_2$, —N($R^{PR}$)$_2$, an optionally substituted amine moiety, an optionally substituted amide group, an N-linked amino acid or both $R^4$ together are =N—OH or =NO-optionally substituted alkyl; $R^6$ is —H or —CH$_3$; $R^7$ is —CH($R^{10}$)$_2$— or =CH($R^{10}$)—; $R^8$ and $R^9$ independently are —C($R^{10}$)$_2$—; $R^{10}$ independently are —H, —OH, an ester, an alkoxy group or a halogen; $R^{10A}$, $R^{10B}$, $R^{10C}$ and $R^{10D}$ independently are —H, an optionally substituted alkyl group, a halogen, —OR$^{PR}$, —SR$^{PR}$ or =O; $R^{PR}$ independently are —H or a protecting group; wherein the protecting group defines —OR$^{PR}$ as an ester or an alkoxy group;

wherein (1) $R^{10A}$ in $R^{10A}$ and $R^{10B}$, $R^{10A}$ and $R^{10C}$ or $R^{10A}$ and $R^{10D}$ is an optionally substituted alkyl group, a halogen, an ester, an alkoxy group, —OR$^{PR}$, —SR$^{PR}$ or =O, and the other $R^{10B}$, $R^{10C}$ or $R^{10D}$ are as defined, (2)$R^{10B}$ and $R^{10C}$, $R^{10B}$ and $R^{10D}$ or $R^{10C}$ and $R^{10D}$ independently are an optionally substituted alkyl group, a halogen, —OR$^{PR}$, —SR$^{PR}$ or =O, or (3) one $R^2$ is as defined and the other $R^2$ is —OH, —CH$_3$, a halogen or an alkoxy group or both $R^2$ together are =O; one $R^3$ is as defined and the other $R^3$ is a halogen, —OH or an ester or both $R^3$ together are =O; and wherein the optionally substituted alkyl groups independently are —CH$_3$, —CH$_2$CH$_3$, —CH$_2$OH, or —CH$_2$-(ester), the alkoxy groups independently are —OCH$_3$, —OC$_2$H$_5$ or —OC$_3$H$_7$, the esters independently are a hydroxyl ester.

2A. The compound of embodiment 1A wherein $R^{10}$, $R^{10A}$, $R^{10B}$, $R^{10C}$ and $R^{10D}$ independently are —H, an optionally substituted alkyl group, a halogen, —OH or an alkoxy group, wherein (1) $R^{10A}$ in $R^{10A}$ and $R^{10B}$, $R^{10A}$ and $R^{10C}$ or $R^{10A}$ and $R^{10D}$ is an optionally substituted alkyl group, a halogen, —OH or an alkoxy group and the other $R^{10B}$, $R^{10C}$ or $R^{10D}$ is as defined, or (2) $R^{10B}$ and $R^{10C}$, $R^{10B}$ and $R^{10D}$ or $R^{10C}$ and $R^{10D}$ independently are an optionally substituted alkyl group, a halogen, —OH or an alkoxy group.

3A. The compound of embodiment 1A wherein $R^{10}$, $R^{10A}$, $R^{10B}$, $R^{10C}$ and $R^{10D}$ independently are —H, an optionally substituted alkyl group, a halogen, —OH, an alkoxy group or an ester, wherein the optionally substituted alkyl group is —CH$_3$ or —CH$_2$CH$_3$, the halogen atom is —F, —Cl or —Br, the alkoxy group is —OCH$_3$ or —OC$_2$H$_5$ and the ester is —O—C(O)—CH$_3$ or —O—C(O)—CH$_2$CH$_3$, wherein (1) $R^{10A}$ in $R^{10A}$ and $R^{10B}$, $R^{10A}$ and $R^{10C}$ or $R^{10A}$ and $R^{10D}$ is —CH$_3$, —CH$_2$CH$_3$, —F, —Cl, —Br, —OCH$_3$, —OC$_2$H$_5$, —O—C(O)—CH$_3$ or —O—C(O)—CH$_2$CH$_3$ and the other $R^{10B}$, $R^{10C}$ or $R^{10D}$ is as defined, or (2) $R^{10B}$ and $R^{10C}$, $R^{10B}$ and $R^{10D}$ or $R^{10C}$ and $R^{10D}$ independently are —CH$_3$, —CH$_2$CH$_3$, —F, —Cl, —Br, —OCH$_3$, —OC$_2$H$_5$, —O—C(O)—CH$_3$ or —O—C(O)—CH$_2$CH$_3$.

4A. The compound of embodiment 1A wherein $R^{10A}$, $R^{10B}$, $R^{10C}$ and $R^{10D}$ independently are —H, —F, —Cl, —Br, —OH, —OCH$_3$, —OC$_2$H$_5$ or an ester, wherein (1) $R^{10A}$ in $R^{10A}$ and $R^{10B}$, $R^{10A}$ and $R^{10C}$ or $R^{10A}$ and $R^{10D}$ is —F, —Cl, —Br, —OH, —OCH$_3$, —OC$_2$H$_5$ or an ester and the other $R^{10B}$, $R^{10C}$ or $R^{10D}$ is as defined, or (2) $R^{10B}$ and $R^{10C}$, $R^{10B}$ and $R^{10D}$ or $R^{10C}$ and $R^{10D}$ independently are —F, —Cl, —Br, —OH, —OCH$_3$, —OC$_2$H$_5$ or an ester.

5A. The compound of embodiment 1A wherein $R^{10}$, $R^{10A}$, $R^{10B}$, $R^{10C}$ and $R^{10D}$ independently are —H, α-OH, β-OH or =O, wherein (1) $R^{10A}$ in $R^{10A}$ and $R^{10B}$, $R^{10A}$ and $R^{10C}$ or $R^{10A}$ and $R^{10D}$ is α-OH, β-OH or =O and the other $R^{10B}$, $R^{10C}$ or $R^{10D}$ is as defined, or (2) $R^{10B}$ and $R^{10C}$, $R^{10B}$ and $R^{10D}$ or $R^{10C}$ and $R^{10D}$ independently are α-OH, β-OH or =O.

6A. The compound of embodiment 1A wherein $R^7$, $R^8$, $R^9$ independently are —C($R^{10}$)$_2$— or =C($R^{10}$)— wherein one $R^{10}$ is —H, —OH, an ester, an alkoxy group or a halogen, in the α- or β-configuration, and the other $R^{10}$, if present, is —H.

7A. The compound of embodiment 1A wherein $R^7$ and $R^8$ independently are —CH$_2$—, —CF$_2$—, —CH(OH)—, —CH($R^{10}$)—, —CH(ester)-, —CH(alkoxy)- or —CH(halogen)-, wherein —OH, $R^{10}$, the ester, the alkoxy group or the halogen atom is present in the α-configuration; wherein the halogen atom is —F, —Cl or —Br, the alkoxy group is —OCH$_3$, —OC$_2$H$_5$ or —OC$_3$H$_7$ and the ester is —OC(O)—CH$_3$ or —OC(O)CH$_2$CH$_3$.

8A. The compound of embodiment 1A wherein the other $R^2$ is —H, —OH or an alkoxy group, wherein the alkoxy group is —OCH$_3$, or both $R^2$ together are =O; the other $R^3$ is —H, halogen, —OH or an ester, wherein the ester is —O—C(O)—CH$_3$ or —O—C(O)—CH$_2$CH$_3$, or both $R^3$ together are =O; the other $R^4$ is an optionally substituted amine moiety or an optionally substituted amide group; $R^6$ is —H or —CH$_3$; $R^7$ is —CH($R^{10}$)$_2$— or =CH($R^{10}$)— and $R^8$ and $R^9$ independently are —C($R^{10}$)$_2$, wherein $R^{10}$ independently are —H, —OH or a halogen; $R^{10A}$ is halogen or $R^{10A}$ and $R^{10B}$, $R^{10A}$ and $R^{10C}$ or $R^{10A}$ and $R^{10D}$, $R^{10B}$ and $R^{10C}$, $R^{10B}$ and $R^{10D}$ or $R^{10C}$ and $R^{10D}$ independently are —OH or a halogen; and wherein the halogens independently are —F, —Cl or —Br.

9A. The compound of embodiment 1A wherein the hydroxyl ester is acetate, enanthate, propionate, isopropionate, isobutyrate, butyrate, valerate, caproate, isocaproate, hexanoate, heptanoate, octanoate, nonanoate, decanoate, undecanoate, phenylacetate or benzoate.

10A. The compound of embodiment 1A wherein the compound has the structure

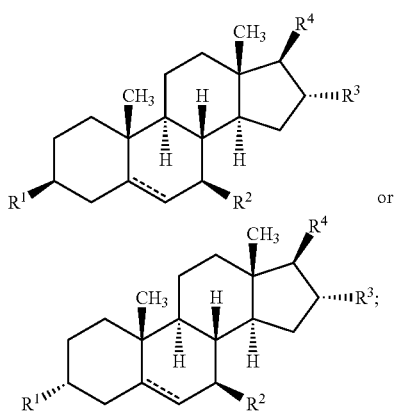

wherein $R^1$ is —OH; $R^2$ is —OH, an alkoxy group or =O; $R^3$ is a halogen, —OH, an ester or =O; and $R^4$ is an optionally substituted amine moiety or =NOH.

11A. The compound of embodiment 10A wherein $R^1$ and $R^2$ are —OH; $R^3$ is —OH, =O, a halogen or an ester, wherein the halogen atom is —F or —Br and the ester is —O—C(O)—CH$_3$ or —O—C(O)—CH$_2$CH$_3$; and $R^4$ is an optionally substituted amine moiety, wherein the optionally substituted amine moiety is —NH$_2$, —NHCH$_3$, —N(CH$_3$)$_2$, —N$^+$(CH$_3$)$_3$, —NH—C$_2$H$_5$ or —NHOH, or an optionally substituted amide group, wherein the optionally substituted amide group is —NH—C(O)CH$_3$.

12A. The compound of embodiment 11A wherein the compound has the structure

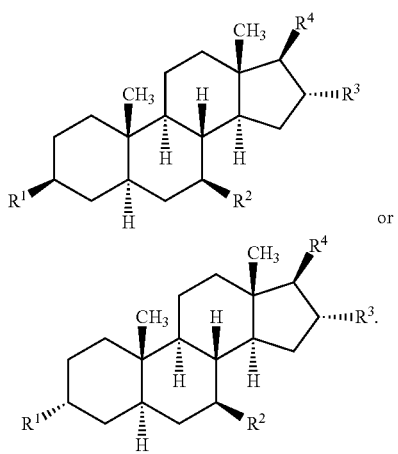

13A. The compound of embodiment 11A wherein the compound has the structure

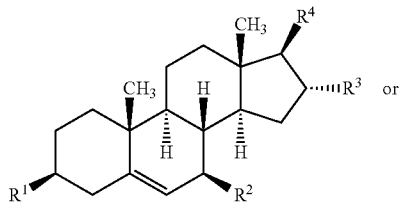

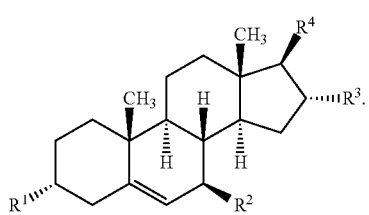

14A. The compound of embodiment 1A wherein the compound is 3β,7β-dihydroxy-6-chloro-16-oxo-17β-aminoandrost-5-ene, 3β-hydroxy-6-chloro-16α-fluoro-17β-aminoandrost-5-ene, 3β,7β-dihydroxy-6α-bromo-16-oxo-17β-aminoandrostane or 3β-hydroxy-6α-bromo-16α-fluoro-17β-aminoandrostane.

15A. The compound of embodiment 1A wherein the compound is 3β,7β-dihydroxy-16-oxo-17β-aminoandrost-5-ene or 3β,7β-dihydroxy-16α-fluoro-17β-aminoandrostane.

16A. A formula 1 compound having the structure

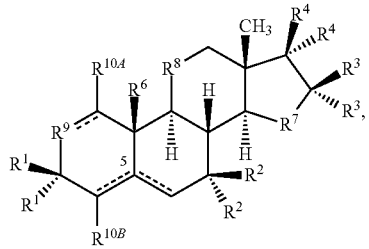

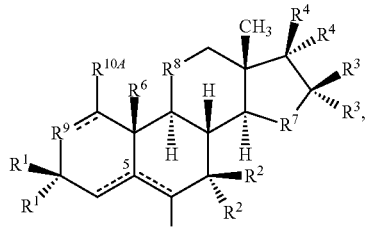

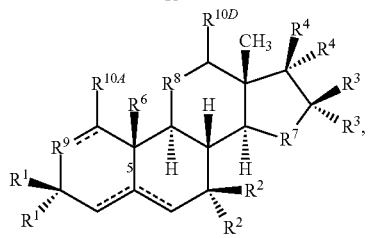

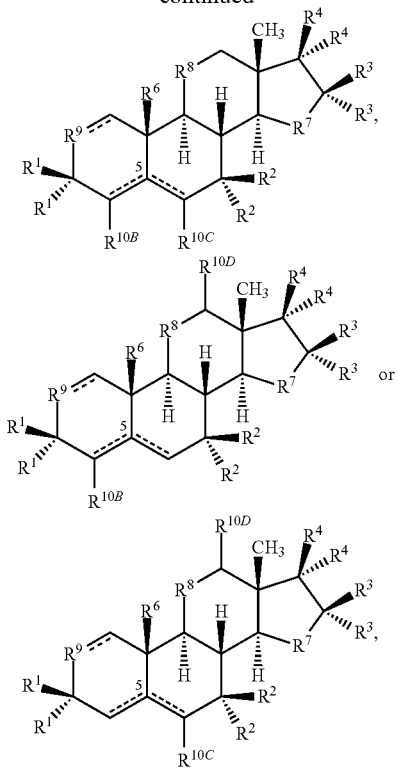

or a salt thereof, provided that if a double bond is present at the 4-5 or 5-6 positions, then $R^{10}$ at the 5-position is absent and is otherwise present in the α- or β-configuration or if a double bond is present at the 1-2, 4-5 or 5-6 positions, then $R^{10A}$, $R^{10B}$ or $R^{10C}$ respectively are bonded to the ring to which they are linked by a single bond;

wherein one of $R^1$ is —H, an optionally substituted alkyl group, an optionally substituted alkenyl group, an optionally substituted alkynyl group, an optionally substituted aryl moiety or an optionally substituted heteroaryl moiety and the other $R^1$ is —OH, —$OR^{PR}$, —O—Si—$(R^{13})_3$, —$OSO_3H$, —$OPO_3H$, an ester, an ether, a carbonate, a carbamate, an optionally substituted monosaccharide, an optionally substituted disaccharide or an optionally substituted oligosaccharide or both of $R^1$ together are =O or both $R^1$ comprise a ketal or thioketal; $R^2$ and $R^3$ independently are —H, —OH, —$OR^{PR}$, —O—Si—$(R^{13})_3$, an ester, an ether, a carbonate, a carbamate, a halogen, an optionally substituted alkyl group, an optionally substituted alkenyl group, an optionally substituted alkynyl group, an optionally substituted aryl moiety or an optionally substituted heteroaryl moiety or both of $R^2$ or $R^3$ together are =O or both of $R^2$ or $R^3$ comprise an independently selected ketal or thioketal; one $R^4$ is —H, an optionally substituted alkyl group, an optionally substituted alkenyl group, an optionally substituted alkynyl group or an optionally substituted aryl moiety and the other $R^4$ is an optionally substituted N-linked heterocycle; $R^5$ and $R^6$ independently are —H, —OH, —$OR^{PR}$, an optionally substituted alkyl group, an optionally substituted alkenyl group, an optionally substituted alkynyl group, an optionally substituted aryl moiety; or an optionally substituted heteroaryl moiety; $R^7$, $R^8$ and $R^9$ independently are —$C(R^{10})_2$—, =$C(R^{10})$—, —O—, —S— or —$NR^{PR}$—, wherein $R^{10}$ are independently selected; $R^{10}$ independently or together are —H, —OH, —$OR^{PR}$, —O—Si—$(R^{13})_3$, an ester, an ether, a carbonate, a carbamate, a halogen, —$SR^{PR}$, an optionally substituted alkyl group, an optionally substituted alkenyl group, an optionally substituted alkynyl group, an optionally substituted aryl moiety or an optionally substituted heteroaryl moiety or =O; wherein $R^{10}$ moieties at the 5 (if present), 8, 9 and 14 positions independently are —H, —OH, —$OR^{PR}$, —O—Si—$(R^{13})_3$, an ester, an ether, a carbonate, a carbamate or a halogen; $R^{10A}$, $R^{10B}$, $R^{10C}$ and $R^{10D}$ independently are —H, —OH, —$OR^{PR}$, —O—Si—$(R^{13})_3$, an ester, an ether, a carbonate, a carbamate, a halogen, —$SR^{PR}$, an optionally substituted alkyl group, an optionally substituted alkenyl group, an optionally substituted alkynyl group, an optionally substituted aryl moiety or an optionally substituted heteroaryl moiety or =O or $R^{10A}$, $R^{10B}$, $R^{10C}$ or $R^{10D}$ is =O; $R^{13}$ independently are a C1-C6 alkyl group or an aryl moiety; and $R^{PR}$ independently are —H or a protecting group; and wherein (1) when the double bonds at the 1-2-, 4-5- and 5-6 positions are absent (i) one $R^2$ is as defined and the other $R^2$ is —OH, —$OR^{PR}$, —O—Si—$(R^{13})_3$, an ester, an ether, a carbonate, a carbamate, both $R^2$ together are =O or both $R^2$ comprise a ketal or thioketal, (ii) one of $R^{10A}$ and $R^{10B}$, $R^{10A}$ and $R^{10C}$, $R^{10A}$ and $R^{10D}$, $R^{10B}$ and $R^{10C}$, $R^{10}B$ and $R^{10D}$ or $R^C$ and $R^{10D}$ are an optionally substituted alkyl group, —$CH_3$, —OH, —$OR^{PR}$, —O—Si—$(R^{13})_3$, an ester, an ether, a carbonate, a carbamate, a halogen, —$SR^{PR}$ or =O and the other $R^{10A}$, $R^{10B}$, $R^{10C}$ or $R^{10D}$ are as defined, or (2) when a double bond at the 1-2-, 4-5- or 5-6 position is present (i) one $R^2$ or one $R^3$ is as defined and the other $R^2$ or $R^3$ is —OH, —$OR^{PR}$, —O—Si—$(R^{13})_3$, an ester, an ether, a carbonate, a carbamate, both $R^2$ or $R^3$ together are =O or both $R^2$ or $R^3$ comprise a ketal or thioketal, (ii) one of $R^{10A}$ and $R^{10B}$, $R^{10A}$ and $R^{10C}$, $R^{10A}$ and $R^{10D}$, $R^{10B}$ and $R^{10C}$, $R^{10B}$ and $R^{10D}$ or $R^{10C}$ and $R^{10D}$ are an optionally substituted alkyl group, —$CH_3$, —OH, —$OR^{PR}$, —O—Si—$(R^{13})_3$, an ester, an ether, a carbonate, a carbamate, a halogen, —$SR^{PR}$ or =O and the other $R^{10A}$, $R^{10B}$, $R^{10C}$ or $R^{10D}$ are as defined.

17A. The compound of embodiment 16A wherein one each of $R^1$, $R^2$, $R^3$ and $R^4$ are —H, and, when no double bond links the other $R^1$, $R^2$, $R^3$ and $R^4$ to the ring to which it is bonded, then the other $R^1$, $R^2$, $R^3$ and $R^4$ respectively are in the α,α, α,α-, α,α,α,β-, α,α,β,α-, α,β,α,α-, β,α,α,α-, α,α,β,β-, α,β, α,β-, β,α,α,β-, β,α,β,α-, β,β,α,α-, α,β,β,α-, α,β,β,β-, β,α,β, β-, β,β,α,β-, β,β,β,α- or β,β,β,β-configurations; the other $R^1$, $R^2$ independently are —OH, —$OCH_3$, —$OC_2H_5$, a carbamate, a carbonate, an optionally substituted C1-C20 ether, an optionally substituted C1-C20 ester, an optionally substituted C1-C20 monosaccharide, an optionally substituted disaccharide or an optionally substituted oligosaccharide; and the other $R^3$ is —H, —F, —Cl, —Br, —I, —OH, —$CH_3$, —$C_2H_5$, —$C(CH_3)_3$, —$OCH_3$, —$OC_2H_5$, —$CF_3$, —$CH_2OH$, a carbamate, a carbonate, an optionally substituted C1-C20 alkyl group, an optionally substituted C1-C20 ether or an optionally substituted C1-C20 ester.

18A. The compound of embodiment 16A or 17A wherein the compound has the structure

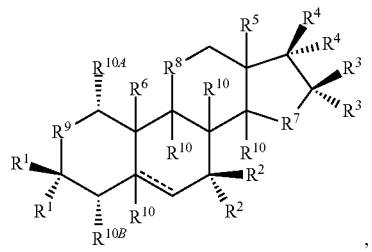

129
-continued
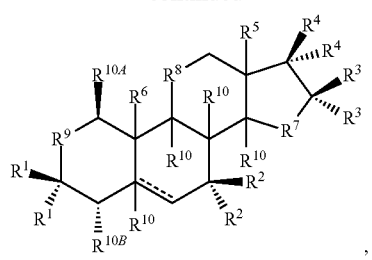
,
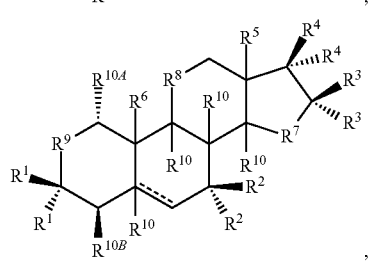
,
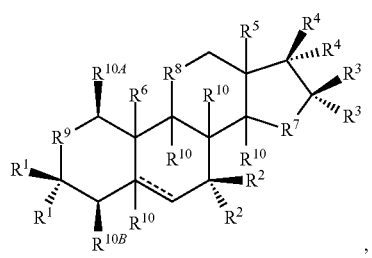
,
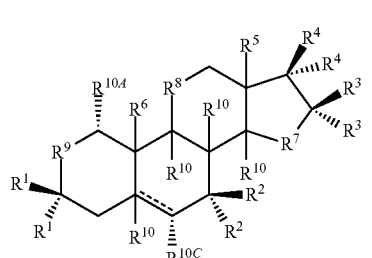
,
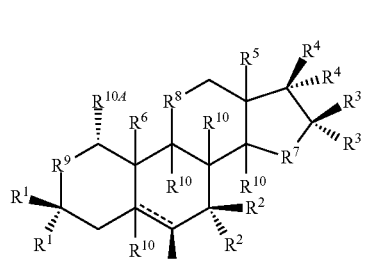
,
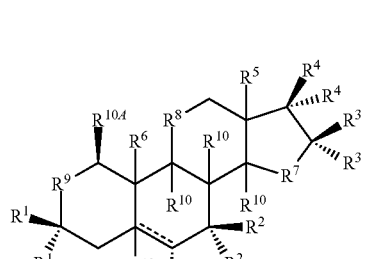
,
130
-continued
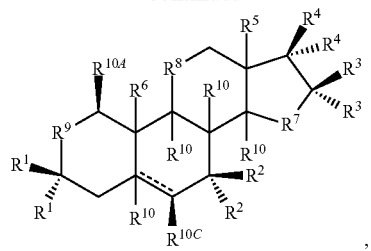
,
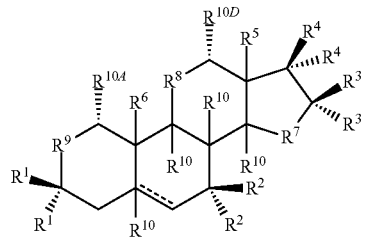
,
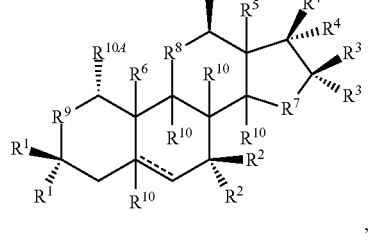
,
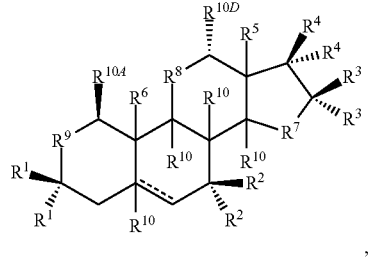
,
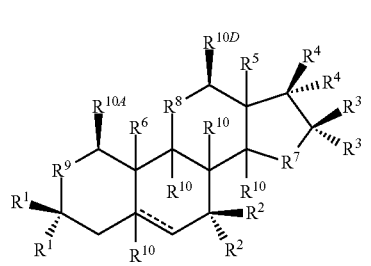
,
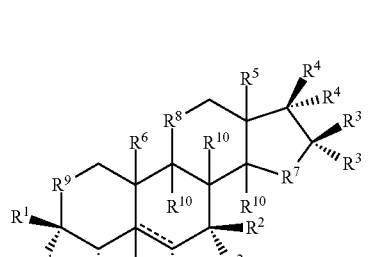
, -continued

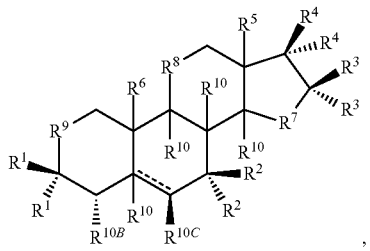

,

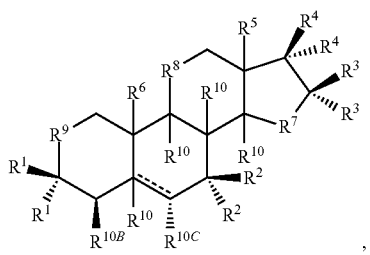

,

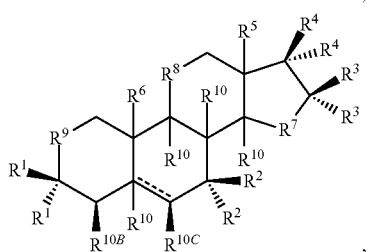

,

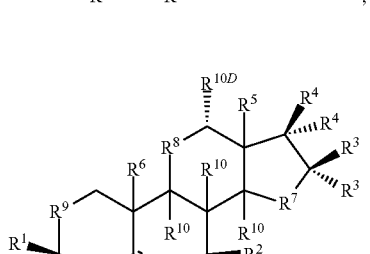

,

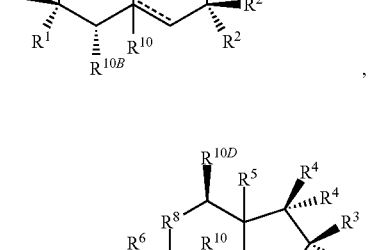

,

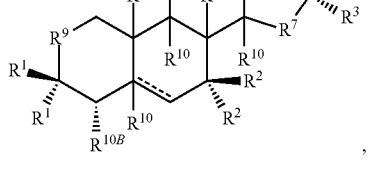

,

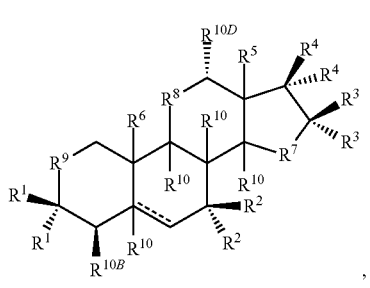

-continued

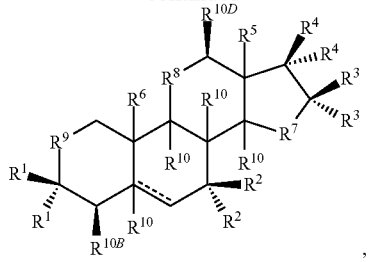

,

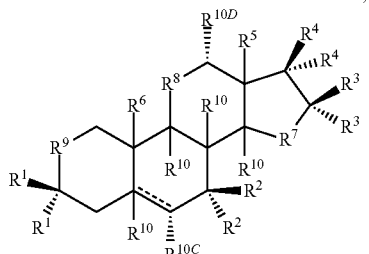

,

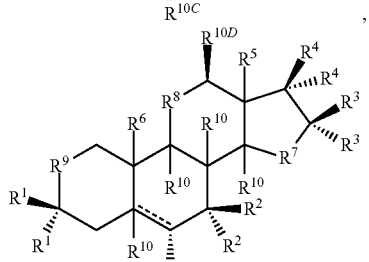

,

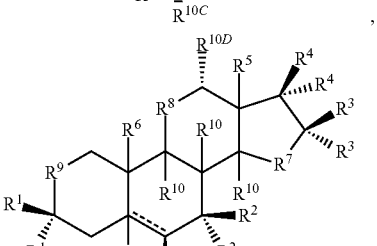

or

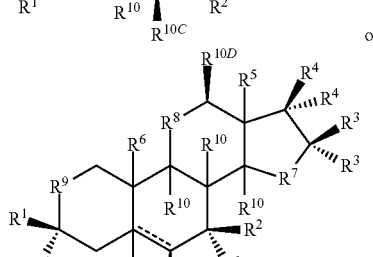

.

19A. The compound of embodiment 16A, 17A or 18A wherein (1) $R^5$ and $R^6$ respectively are in the α,α-, α,β-, β,α- or β,β-configurations and $R^5$ and $R^6$ are both —CH$_3$ or are selected from —CH$_3$ and —CH$_2$OH or (2) $R^5$ and $R^6$ are both in the β-configuration and $R^5$ and $R^6$ are both —CH$_3$ or are selected from —CH$_3$ and —CH$_2$OH.

20A. The compound of any one of embodiments 16 through 19 wherein 1$R^{10}$ at the 5, 8, 9 and 14-positions respectively are (1) —H, —H, —H, —H, (2) —H, —H, halogen (—F, —Cl, —Br or —I), —H, (3) —H, —H, —H, —OH, (4) —H, —H, halogen (—F, —Cl, —Br or —I), —OH, (5) -optionally substituted alkyl (optionally —CH$_3$, —CH$_2$OH, —CH$_2$O-ester, —C$_2$H$_5$), —H, —H, —H, (6) -optionally substituted alkyl (optionally —CH$_3$, —CH$_2$OH, —CH$_2$O-ester, —C₂H₅), —H, halogen (—F, —Cl, —Br or —I), —H, (7) -optionally substituted alkyl (optionally —CH₃, —CH₂OH, —CH₂O-ester, —C₂H₅), —H, —H, —OH, (8) -acyl (optionally —C(O)—(CH₂)₀₋₂—CH₃), —H, —H, —H, (9) -ester (optionally acetoxy or propionoxy), —H, —H, —H, (10) -ether (optionally —O—(CH₂)₀₋₂—CH₃), —H, —H, —H, (11) -ester (optionally acetoxy, propionoxy, —O—C(O)—(CH₂)₁₋₆—H), —H, halogen (optionally —F, —Cl, —Br), —H, (12) -ester (optionally acetoxy or propionoxy), —H, —H, —OH, (13) —H, —H, —H, -acyl (optionally —C(O)—(CH₂)₀₋₂—CH₃), (14) —H, —H, —H, -ester (optionally acetoxy or propionoxy), or (15) —H, —H, —H, -ether (optionally —O—(CH₂)₀₋₂—OH₃, —OCH₃, —OC₂H₅, —OCH₂OH, —OCH₂F, —OCH₂Br, —OCH₂COOH, —OCH₂NH₂, —OCH₂CH₂OH, —OCH₂CH₂F, —OCH₂CH₂Br, —OCH₂CH₂COOH or —OCH₂CH₂NH₂).

21A. The compound of any one of embodiments 16A through 20A wherein $R^7$ is —CH₂—, —CHOH—, —CH($\alpha R^{10}$)—, —CH(ester)-, —CH(alkoxy)- or —CH(halogen)- wherein hydroxyl, the ester, the alkoxy group or the halogen atom is present in the α-configuration and the alkoxy group is optionally selected from —OCH₃, —OC₂H₅ and —OC₃H₇ and the halogen atom is —F, —Cl, —Br or —I.

22A. The compound of any one of embodiments 16A through 21A wherein $R^8$ is —CH₂—, —CF₂—, —CHOH—, —CH($\alpha R^{10}$)—, —CH(ester)-, —CH(alkoxy)- or —CH(halogen)- wherein hydroxyl, the ester, the alkoxy group or the halogen atom is present in the α-configuration and the alkoxy group is optionally selected from —OCH₃, —OC₂H₅ and —OC₃H₇ and the halogen atom is —F, —Cl, —Br or —I.

23A. The compound of embodiment 16A wherein the compound has the structure

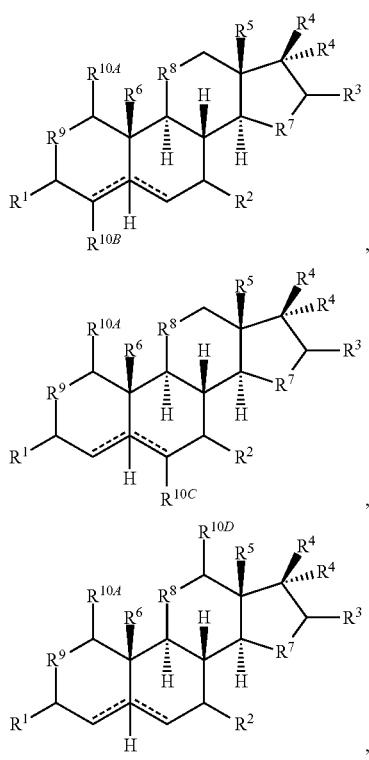

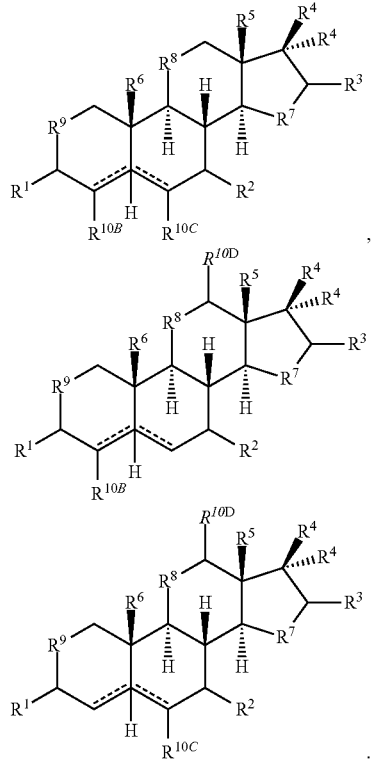

$R^1$ is —OH, =O, an ester or an ether; $R^2$ is —H, —OH, =O, an ester or an ether; $R^3$ is —H, an optionally substituted alkyl group, a halogen, —OH, an ester or an ether; and one $R^4$ is —H and other $R^4$ is an optionally substituted N-linked heterocycle moiety.

24A. The compound of embodiment 23A wherein $R^5$ and $R^6$ independently are —H, —CH₃ or —CH₂OH; $R^7$, $R^8$ and $R^9$ are —CH₂—; and $R^{10A}$ and $R^{10B}$ independently are an optionally substituted alkyl group, —CH₃, a halogen, —SR^{PR} or —OR^{PR}.

25A. The compound of embodiment 24A wherein the compound has the structure

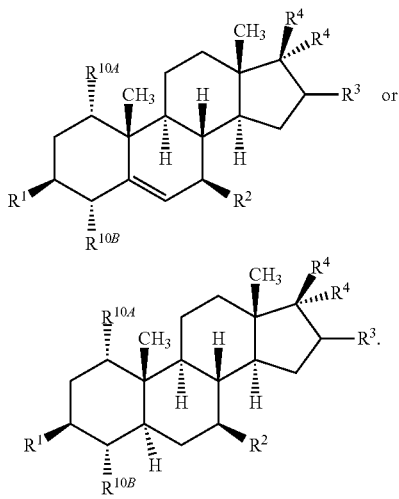

26A. The compound of embodiment 16A wherein the compound has the structure

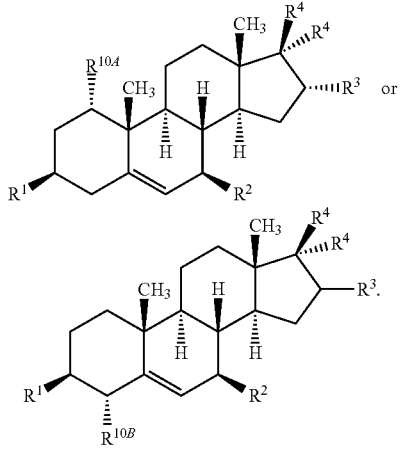 or

27A. The compound of embodiment 26A wherein $R^1$ is —OH, =O, an ester or an ether; $R^2$ is —H, —OH, =O, an ester or an ether; $R^3$ is —H, an optionally substituted alkyl group, a halogen, —OH, an ester or an ether; and one $R^4$ is —H and the other $R^4$ is an optionally substituted N-linked heterocycle moiety.

28A. The compound of embodiment 27A wherein $R^5$ and $R^6$ independently are —H, —CH$_3$ or —CH$_2$OH; $R^7$, $R^8$ and $R^9$ are —CH$_2$—; and $R^{10A}$ or $R^{10B}$ is a halogen, —SR$^{PR}$ or —OR$^{PR}$.

29A. The compound of embodiment 16A wherein the compound has the structure

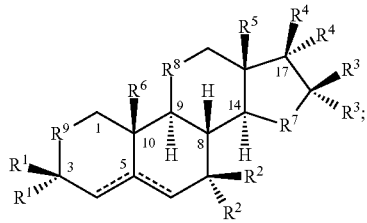

wherein one each of $R^1$ and $R^2$ are —H; the other $R^1$ and $R^2$ independently are —OH or an ester; one of $R^3$ is —H and the other $R^3$ is —OH, a halogen, an ester or both or $R^3$ together are =O; one $R^4$ is —H and the other $R^4$ is an optionally substituted N-linked heterocycle moiety; $R^5$ is —CH$_3$, —CH$_2$CH$_3$ or —CH$_2$OH; $R^6$ is —H, —CH$_3$ or —CH$_2$OH; and $R^7$, $R^8$ and $R^9$ are —CH$_2$—.

30A. The compound of embodiment 29A wherein the compound has the structure

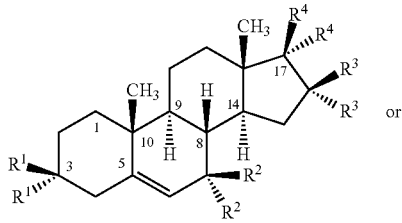

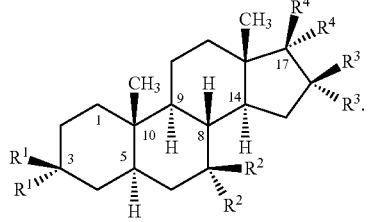

31A. The compound of embodiment 30 wherein the optionally substituted N-linked heterocycle moiety has the structure

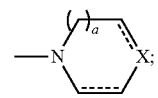

wherein the dotted lines are optional double bonds; a is 0 or 1; —X— is —C(R$^{10}$)$_2$—, =C(R$^{10}$)—, —O— or —N(R$^{12}$)— provided the optional double bonds are absent when —X— is —N(R$^{12}$)— or —O— or —X— is an amide or a sulfonamide wherein the amide or sulfonamide nitrogen comprises the heterocycle ring and the double bond to X is not present; wherein $R^{10}$ in —X— independently are —H, —OH, —OR$^{PR}$, an ester or an ether and $R^{12}$ is —H, an optionally substituted alkyl group, formyl, an optionally substituted alkylsulfonyl moiety, an optionally substituted arylsulfonyl moiety, an optionally substituted aryl moiety or an optionally substituted heteroaryl moiety.

32A. The compound of embodiment 30A wherein the N-linked heterocycle moiety is —N-pyrrolidine, —N1-pyrazolone, —N2-pyrazolone, —N-imidazolidin-2-one, —N1-imidazole, —N1-4,5-dihydroimidazole, —N-morpholine, —N-piperidine, —N-indole, —N-indoline, —N-quinolidine or —N1-piperazine, optionally substituted at N4 with an optionally substituted alkyl, aryl or heteroaryl moiety.

33A. A formula 1A compound having a structure of

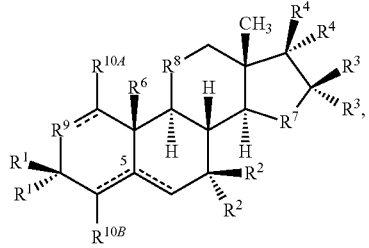

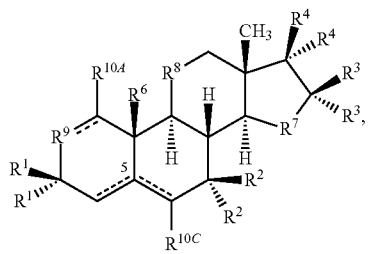

-continued

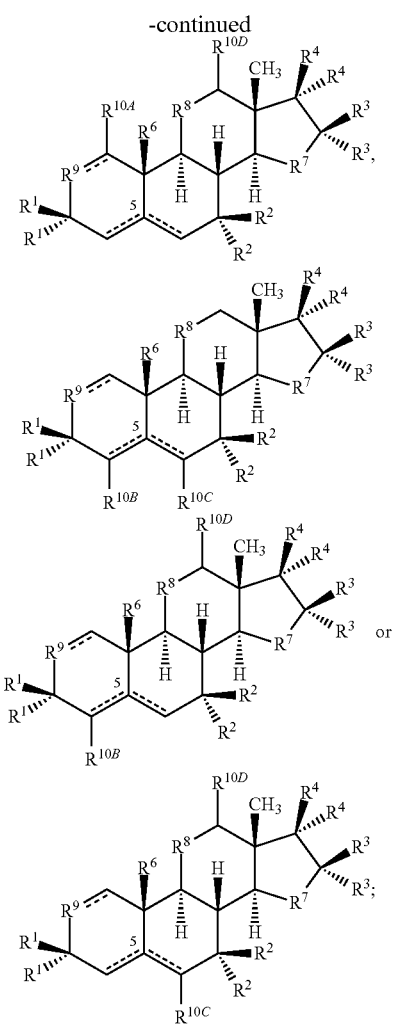

provided that if a double bond is present at the 4-5 or 5-6 positions, then $R^{10}$ at the 5-position is absent and is otherwise present in the α- or β-configuration or if a double bond is present at the 1-2, 4-5 or 5-6 positions, then $R^{10A}$, $R^{10B}$ or $R^{10C}$ respectively are bonded to the ring to which they are linked by a single bond;

wherein one of $R^1$ is —H, an optionally substituted alkyl group, an optionally substituted alkenyl group, an optionally substituted alkynyl group, an optionally substituted aryl moiety or an optionally substituted heteroaryl moiety and the other $R^1$ is —OH, —OR$^{PR}$, —O—Si—(R$^{13}$)$_3$, —OSO$_3$H, —OPO$_3$H, an ester, an ether, a carbonate, a carbamate, an optionally substituted monosaccharide, an optionally substituted disaccharide or an optionally substituted oligosaccharide; $R^2$ and $R^3$ independently are —H, —OH, —OR$^{PR}$, —O—Si—(R$^{13}$)$_3$, an ester, an ether, a carbonate, a carbamate, a halogen, an optionally substituted alkyl group, an optionally substituted alkenyl group, an optionally substituted alkynyl group, an optionally substituted aryl moiety or an optionally substituted heteroaryl moiety or both of $R^2$ or $R^3$ together are =O or both of $R^2$ or $R^3$ comprise an independently selected ketal or thioketal; one $R^4$ is —OH, —OR$^{PR}$, —O—Si—(R$^{13}$)$_3$, an ester, an ether, a carbonate or a carbamate and the other $R^4$ is an optionally substituted C-linked heterocycle moiety; $R^5$ and $R^6$ independently are —H, —OH, —OR$^{PR}$, an optionally substituted alkyl group, an optionally substituted alkenyl group, an optionally substituted alkynyl group, an optionally substituted aryl moiety; or an optionally substituted heteroaryl moiety; $R^7$, $R^8$ and $R^9$ independently are —C(R$^{10}$)$_2$—, =C(R$^{10}$)—, —O—, —S— or —NR$^{PR}$—, wherein R$^{10}$ are independently selected; R$^{10}$ independently or together are —H, —OH, —OR$^{PR}$, —O—Si—(R$^{13}$)$_3$, an ester, an ether, a carbonate, a carbamate, a halogen, —SR$^{PR}$, an optionally substituted alkyl group, an optionally substituted alkenyl group, an optionally substituted alkynyl group, an optionally substituted aryl moiety or an optionally substituted heteroaryl moiety or =O; wherein R$^{10}$ moieties at the 5 (if present), 8, 9 and 14 positions independently are —H, —OH, —OR$^{PR}$, —O—Si—(R$^{13}$)$_3$, an ester, an ether, a carbonate, a carbamate or a halogen; $R^{10A}$, $R^{10B}$, $R^{10C}$ and $R^{10D}$ independently are —H, —OH, —OR$^{PR}$, —O—Si—(R$^{13}$)$_3$, an ester, an ether, a carbonate, a carbamate, a halogen, —SR$^{PR}$, an optionally substituted alkyl group, an optionally substituted alkenyl group, an optionally substituted alkynyl group, an optionally substituted aryl moiety or an optionally substituted heteroaryl moiety or =O or $R^{10A}$, $R^{10B}$, $R^{10C}$ or $R^{10D}$ is =O; $R^{13}$ independently are a C1-C6 alkyl group or an aryl moiety; and R$^{PR}$ independently are —H or a protecting group;

wherein (1) one of $R^{10A}$ and $R^{10B}$, $R^{10A}$ and $R^{10C}$, $R^{10A}$ and $R^{10D}$, $R^{10B}$ and $R^{10C}$, $R^{10B}$ and $R^{10D}$ or $R^{10C}$ and $R^{10D}$ are an optionally substituted alkyl group, —CH$_3$, —OH, —OR$^{PR}$, —O—Si—(R$^{13}$)$_3$, an ester, an ether, a carbonate, a carbamate, a halogen, —SR$^{PR}$ or =O and the other $R^{10A}$, $R^{10B}$, $R^{10C}$ or $R^{10D}$ are as defined, (2) one $R^2$ is as defined and the other $R^2$ is —OH, —OR$^{PR}$, —O—Si—(R$^{13}$)$_3$, an ester, an ether, a carbonate, a carbamate, both $R^2$ or $R^3$ together are =O or both $R^2$ or $R^3$ comprise a ketal or thioketal, or (3) one or more of $R^7$, $R^8$ and $R^9$ independently are —C(R$^{10}$)$_2$— or =C(R$^{10}$)—, wherein one R$^{10}$ is —OH, a halogen, an optionally substituted alkyl group, an ester or an ether and the other R$^{10}$ is —H or an optionally substituted alkyl group or both R$^{10}$ together are =O;

34A. The compound of embodiment 33A wherein one each of $R^1$, $R^2$, $R^3$ and $R^4$ are —H, and, when no double bond links the other $R^1$, $R^2$, $R^3$ and $R^4$ to the ring to which it is bonded, then the other $R^1$, $R^2$, $R^3$ and $R^4$ respectively are in the α,α, α,α-, α,α,α,β-, α,α,β,α-, α,β,α,α-, β,α,α,α-, α,α,β,β-, α,β, α,β-, β,α,α,β-, β,α,β,α-, β,β,α,α-, α,β,β,α-, α,β,β,β-, β,α,β, β-, β,β,α,β-, β,β,β,α or β,β,β,β-configurations; the other $R^1$, $R^2$ independently are —OH, —OCH$_3$, —OC$_2$H$_5$, a carbamate, a carbonate, an optionally substituted C1-C20 ether, an optionally substituted C1-C20 ester, an optionally substituted C1-C20 monosaccharide, an optionally substituted disaccharide or an optionally substituted oligosaccharide; and the other $R^3$ is —H, —F, —Cl, —Br, —I, —OH, —CH$_3$, —C$_2$H$_5$, —C(CH$_3$)$_3$, —OCH$_3$, —OC$_2$H$_5$, —CF$_3$, —CH$_2$OH, a carbamate, a carbonate, an optionally substituted C1-C20 alkyl group, an optionally substituted C1-C20 ether or an optionally substituted C1-C20 ester.

35A. The compound of embodiment 33A or 34A wherein the compound has a structure of

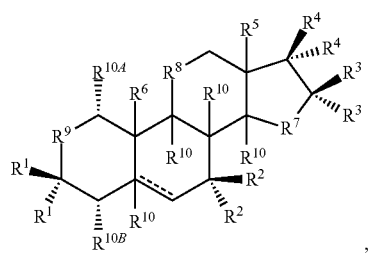

,

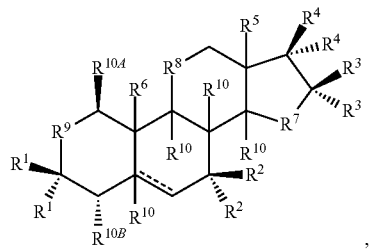
,
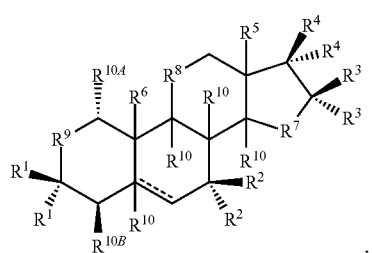
,
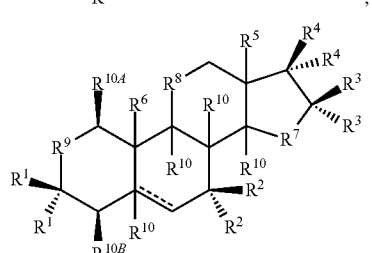
,
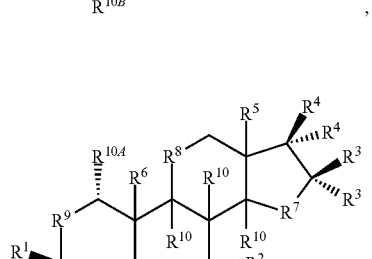
,
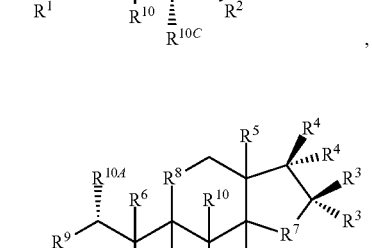
,
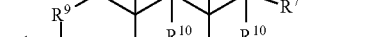
,
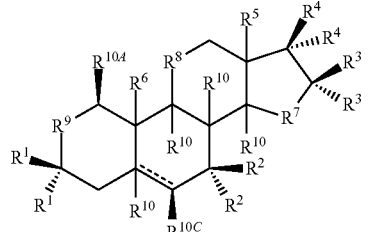
,
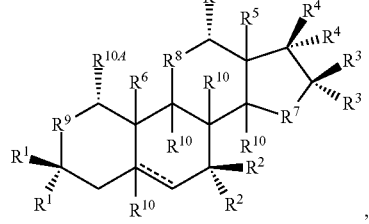
,
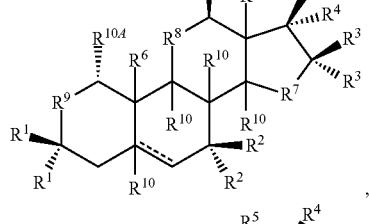
,
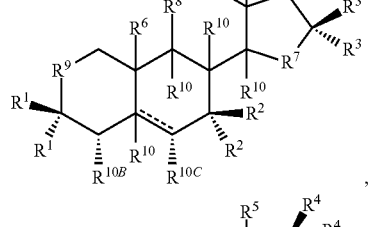
,
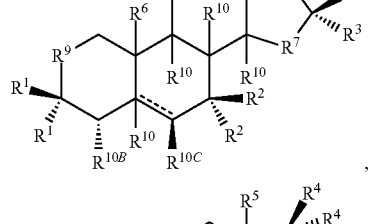
,
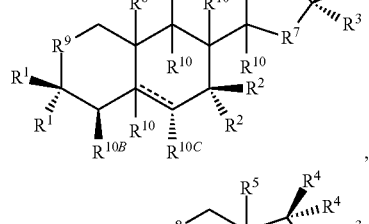
,
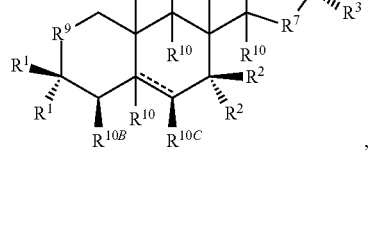
, -continued

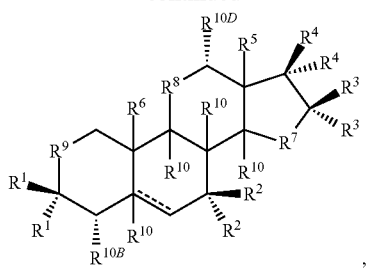

,

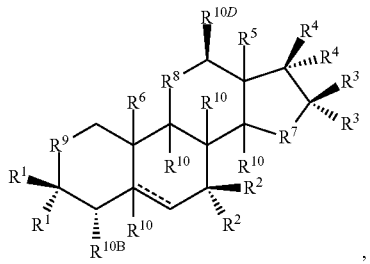

,

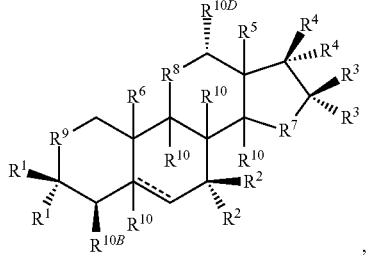

,

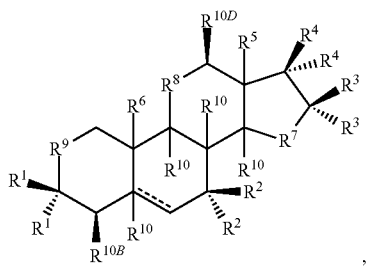

,

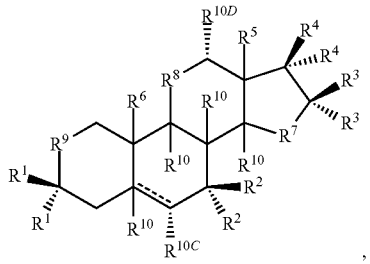

,

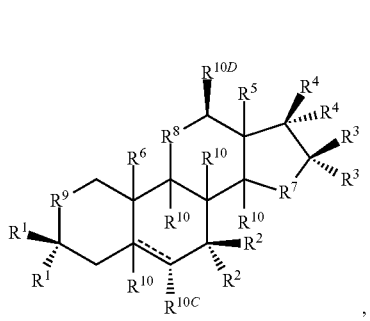

,

-continued

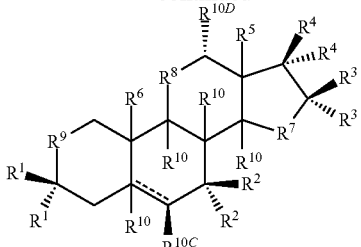

or

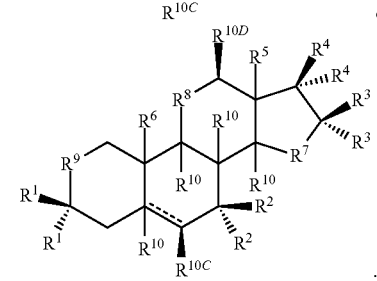

.

36A. The compound of embodiment 33A, 34A or 35A wherein (1) $R^5$ and $R^6$ respectively are in the α,α-, α,β-, β,α- or β,β-configurations and $R^5$ and $R^6$ are both —$CH_3$ or are selected from —$CH_3$ and —$CH_2OH$ or (2) $R^5$ and $R^6$ are both in the β-configuration and $R^5$ and $R^6$ are both —$CH_3$ or are selected from —$CH_3$ and —$CH_2OH$.

37A. The compound of any one of embodiments 33A through 36A wherein $R^{10}$ at the 5, 8, 9 and 14-positions respectively are (1) —H, —H, —H, —H, (2) —H, —H, halogen (—F, —Cl, —Br or —I), —H, (3) —H, —H, —H, —OH, (4) —H, —H, halogen (—F, —Cl, —Br or —I), —OH, (5) -optionally substituted alkyl (optionally —$CH_3$, —$CH_2OH$, —$CH_2O$-ester, —$C_2H_5$), —H, —H, —H, (6) -optionally substituted alkyl (optionally —$CH_3$, —$CH_2OH$, —$CH_2O$-ester, —$C_2H_5$), —H, halogen (—F, —Cl, —Br or —I), —H, (7) -optionally substituted alkyl (optionally —$CH_3$, —$CH_2OH$, —$CH_2O$-ester, —$C_2H_5$), —H, —H, —OH, (8) -acyl (optionally —C(O)—$(CH_2)_{0-2}$—$CH_3$), —H, —H, —H, (9) -ester (optionally acetoxy or propionoxy), —H, —H, —H, (10) -ether (optionally —O—$(CH_2)_{0-2}$—$OH_3$), —H, —H, —H, (11) -ester (optionally acetoxy, propionoxy, —O—C(O)—$(CH_2)_{1-6}$—H), —H, halogen (optionally —F, —Cl, —Br), —H, (12) -ester (optionally acetoxy or propionoxy), —H, —H, —OH, (13) —H, —H, —H, -acyl (optionally —C(O)—$(CH_2)_{0-2}$—$CH_3$), (14) —H, —H, —H, -ester (optionally acetoxy or propionoxy), or (15) —H, —H, —H, -ether (optionally —O—$(CH_2)_{0-2}$—$CH_3$, —$OCH_3$, —$OC_2H_5$, —$OCH_2OH$, —$OCH_2F$, —$OCH_2Br$, —$OCH_2COOH$, —$OCH_2NH_2$, —$OCH_2CH_2OH$, —$OCH_2CH_2F$, —$OCH_2CH_2Br$, —$OCH_2CH_2COOH$ or —$OCH_2OH_2NH_2$).

38A. The compound of any one of embodiments 33A through 37A wherein $R^7$ is —$CH_2$—, —CHOH—, —CH(α$R^{10}$)—, —CH(ester)-, —CH(alkoxy)- or —CH(halogen)- wherein hydroxyl, the ester, the alkoxy group or the halogen atom is present in the α-configuration and the alkoxy group is optionally selected from —$OCH_3$, —$OC_2H_5$ and —$OC_3H_7$ and the halogen atom is —F, —Cl, —Br or —I.

39A. The compound of any one of embodiments 33A through 38A wherein $R^8$ is —$CH_2$—, —$CF_2$—, —CHOH—, —CH(α$R^{10}$)—, —CH(ester)-, —CH(alkoxy)- or —CH(halogen)- wherein hydroxyl, the ester, the alkoxy group or the halogen atom is present in the α-configuration and the alkoxy group is optionally selected from —$OCH_3$, —$OC_2H_5$ and —$OC_3H_7$ and the halogen atom is —F, —Cl, —Br or —I.

40A. The compound of embodiment 33A wherein the compound has a structure

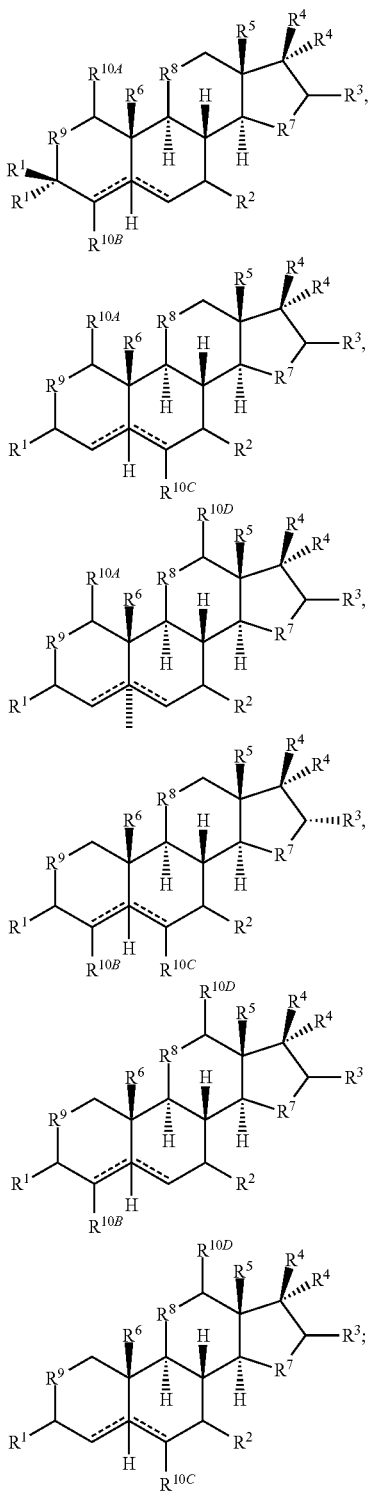

wherein $R^1$ is —OH, =O, an ester or an ether; $R^2$ is —H, —OH, =O, an ester or an ether; $R^3$ is —H, an optionally substituted alkyl group, a halogen, —OH, an ester or an ether; one $R^4$ is —OH, an ester or an ether and the other $R^4$ is an optionally substituted C-linked heterocycle moiety.

41A. The compound of embodiment 40 wherein $R^5$ and $R^6$ independently are —H, —CH$_3$ or —CH$_2$OH; $R^7$, $R^8$ and $R^9$ are —CH$_2$—; and $R^{10A}$, $R^{10B}$, $R^{10C}$ and $R^{10D}$ independently are an optionally substituted alkyl group, —CH$_3$, a halogen, —SR$^{PR}$ or —OR$^{PR}$.

42A. The compound of embodiment 41A wherein the compound has the structure

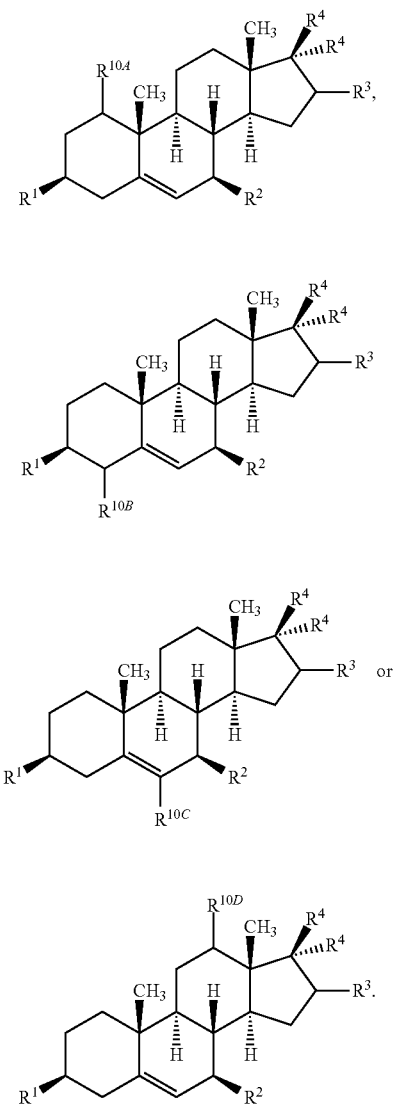

43A. The compound of embodiment 41A wherein the compound has the structure

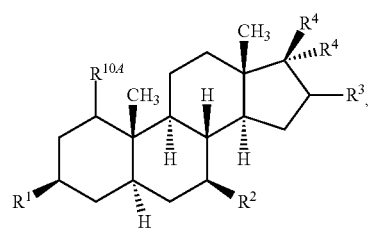

-continued

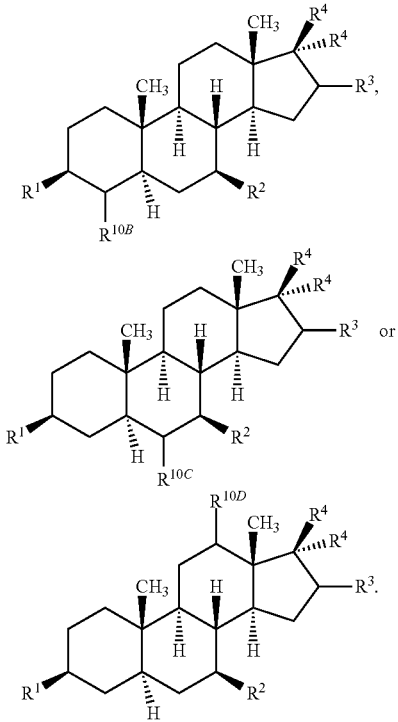

44A. The compound of embodiment 42A or 43A wherein R$^1$ is —OH or ═O; R$^2$ is —OH, ═O or an ether wherein the ether is —OCH$_3$; R$^3$ is —H, a halogen or an ester wherein the ester is —O—C(O)CH$_3$ or —O—C(O)CH$_2$CH$_3$; one R$^4$ is an optionally substituted C-linked heterocycle moiety, wherein the C-linked heterocycle is 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-thiazolyl, 4-thiazolyl or 5-thiazolyl and the other R$^4$ is —OH; and R$^{10A}$, R$^{10B}$, R$^{10C}$ or R$^{10D}$ is —H, —OR$^{PR}$ or a halogen.

45A. The compound of embodiment 44A wherein R$^1$ and R$^2$ are —OH; R$^3$ is —H or —O—C(O)CH$_3$; R$^4$ is 3-pyridyl; and R$^{10A}$ or R$^{10B}$ is —OR$^{PR}$ or —F.

46A. A formula 1 compound having the structure

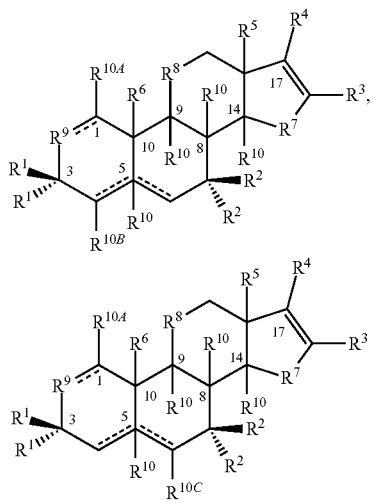

-continued

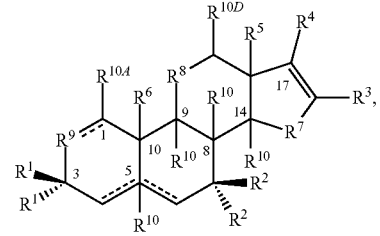

or a salt thereof; wherein the dotted lines are optional double bonds; R$^{10}$ at the 5 (if present), 8, 9 and 14 positions respectively are in the α,α,α,α-, α,α,α,β-, α,α,β,α-, α,β,α, α-, β,α,α,α-, α,α,β,β-, α,β,β,α,β-, β,α,α,β-, β,α,β,α-, β,β,α, α-, α,β,β,α-, α,β,β,α-, β,α,β,β-, β,β,α,β-, β,β,β,α- or β,β,β, β-configurations; R$^{10A}$ and R$^{10B}$, R$^{10A}$ and R$^{10C}$, R$^{10A}$ and R$^{10D}$, R$^{10B}$ and R$^{10C}$, R$^{10B}$ or R$^{10D}$ and R$^{10C}$ respectively are in the α,α-, α,β-, β,α- or β,β-configurations, provided that if a double bond is present at the 4-5 or 5-6 positions, then R$^{10}$ at the 5-position is absent and is otherwise present in the α- or β-configuration or if a double bond is present at the 1-2, 4-5 or 5-6 positions, then R$^{10A}$, R$^{10A}$, R$^{10B}$ or R$^{10C}$ respectively are bonded to the ring to which they are linked by a single bond; one of R$^1$ is —H, an optionally substituted alkyl group, an optionally substituted alkenyl group, an optionally substituted alkynyl group, an optionally substituted aryl moiety or an optionally substituted heteroaryl moiety and the other R$^1$ is —OH, —OR$^{PR}$, —SR$^{PR}$, —O—Si—(R$^{13}$)$_3$, —OSO$_3$H, —OPO$_3$H, an ester, an ether, a carbonate, a carbamate, an optionally substituted monosaccharide, an optionally substituted disaccharide or an optionally substituted oligosaccharide or both of R$^1$ together are ═O or both R$^1$ comprise a ketal or thioketal; R$^2$ and R$^3$ independently are —H, —OH, —OR$^{PR}$, —SR$^{PR}$, —O—Si—(R$^{13}$)$_3$, an ester, an ether, a carbonate, a carbamate, a halogen, an optionally substituted alkyl group, an optionally substituted alkenyl group, an optionally substituted alkynyl group, an optionally substituted aryl moiety or an optionally substituted heteroaryl moiety or both of R$^2$ or R$^3$ together are ═O or both of R$^2$ or R$^3$ comprise an independently selected ketal or thioketal; R⁴ is an optionally substituted N-linked heterocycle moiety, an optionally substituted amine moiety, an optionally substituted amide group or an optionally substituted C-linked heterocycle moiety; R⁵ and R⁶ independently are —H, —OH, —OR$^{PR}$, an optionally substituted alkyl group, an optionally substituted alkenyl group, an optionally substituted alkynyl group, an optionally substituted aryl moiety; or an optionally substituted heteroaryl moiety; R⁷, R⁸ and R⁹ independently are —C(R¹⁰)₂—, =C(R¹⁰)—, —O—, —S— or —NR$^{PR}$—, wherein R¹⁰ are independently selected; R¹⁰ independently or together are —H, —OH, —OR$^{PR}$, —O—Si—(R¹³)₃, an ester, an ether, a carbonate, a carbamate, a halogen, —SR$^{PR}$, an optionally substituted alkyl group, an optionally substituted alkenyl group, an optionally substituted alkynyl group, an optionally substituted aryl moiety or an optionally substituted heteroaryl moiety or =O; wherein R¹⁰ moieties at the 5 (if present), 8, 9 and 14 positions are —H, —OH, —OR$^{PR}$, —O—Si—(R¹³)₃, an ester, an ether, a carbonate, a carbamate or a halogen; R$^{10A}$, R$^{10B}$, R$^{10C}$ and R$^{10D}$ independently are —H, —OH, —OR$^{PR}$, —O—Si—(R¹³)₃, an ester, an ether, a carbonate, a carbamate, =O, a halogen, —SR$^{PR}$, an optionally substituted alkyl group, an optionally substituted alkenyl group, an optionally substituted alkynyl group, an optionally substituted aryl moiety or an optionally substituted heteroaryl moiety or =O; R¹³ independently are a C1-C6 alkyl group or an aryl moiety; and R$^{PR}$ independently are —H or a protecting group;

wherein when R⁹ is —CH₂— or =CH—, R⁷ or R⁸ is —CH₂—, —CH(OH)— or —C(O)—, R⁵ and R⁶ are —CH₃ and (1) R⁴ is an optionally substituted C-linked heterocycle moiety and R³ is —H or an ether, or (2) R⁴ is an optionlly substituted N-linked heterocycle moiety and R³ is —H or an optionally substituted alkyl group, then (i) one R² is as defined an the other R² is —OH, an ester, an ether, a carbonate or a carbamate or both R² together are =O or both R² comprise a ketal or thioketal or (ii) one of R$^{10A}$ and R$^{10B}$, R$^{10A}$ and R$^{10C}$, R$^{10A}$ and R$^{10D}$, R$^{10B}$ and R$^{10C}$, R$^{10B}$ and R$^{10D}$ or R$^{10C}$ and R$^{10D}$ is a halogen, —SR$^{PR}$ or —OR$^{PR}$ and the other R$^{10A}$, R$^{10B}$, R$^{10C}$ or R$^{10D}$ are as defined.

47A. The compound of embodiment 46A wherein one each of R¹, R² and R³ are —H, and, when no double bond links the other R¹, R² and R³ to the ring to which it is bonded, then the other R¹, R² and R³ respectively are in the α,α,α-, α,α,β-, α,β,α-, β,α,α-, β,α,β-, β,β,α-, α,β,β- or β,β,β-configurations; the other R¹, R² independently are —OH, —OCH₃, —OC₂H₅, a carbamate, a carbonate, an optionally substituted C1-C20 ether, an optionally substituted C1-C20 ester, an optionally substituted C1-C20 monosaccharide, an optionally substituted disaccharide or an optionally substituted oligosaccharide; and the other R³ is —H, —F, —Cl, —Br, —I, —OH, —CH₃, —C₂H₅, —C(CH₃)₃, —OCH₃, —OC₂H₅, —CF₃, —CH₂OH, a carbamate, a carbonate, an optionally substituted C1-C20 alkyl group, an optionally substituted C1-C20 ether or an optionally substituted C1-C20 ester.

48A. The compound of embodiment 46A or 47A wherein the compounds have the structure

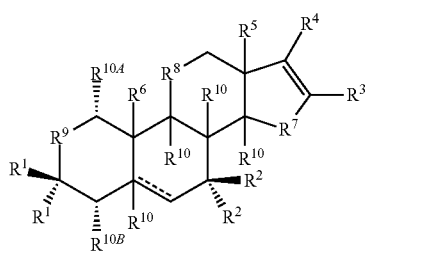

-continued

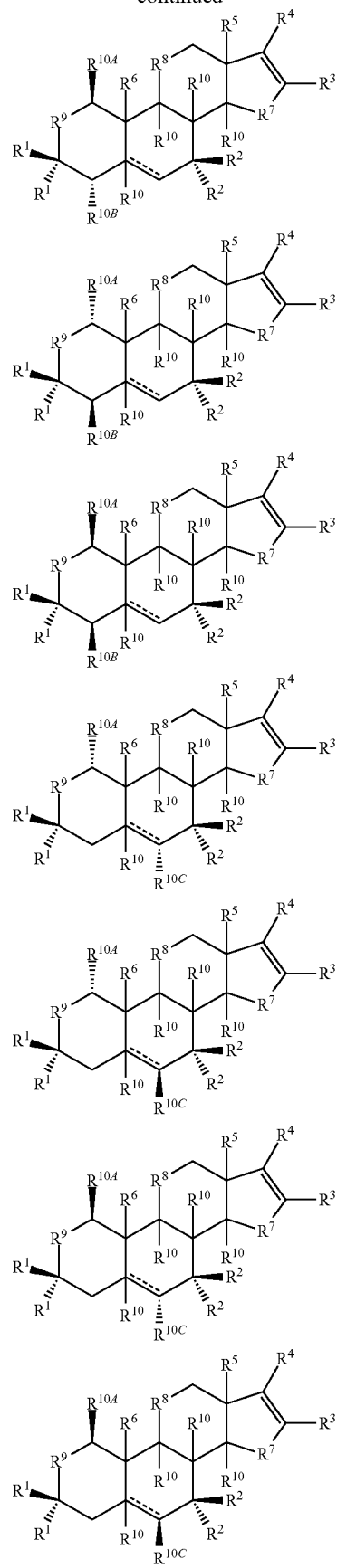

149
-continued
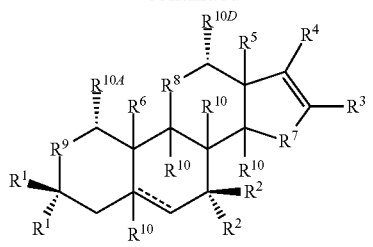
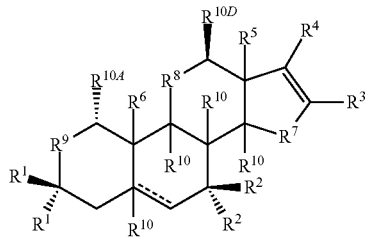
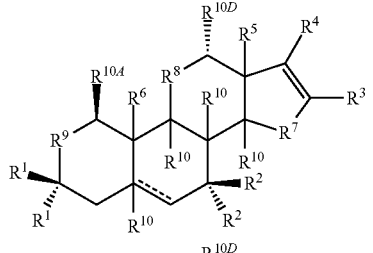
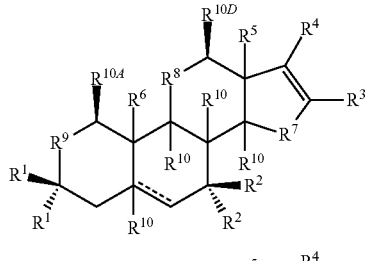
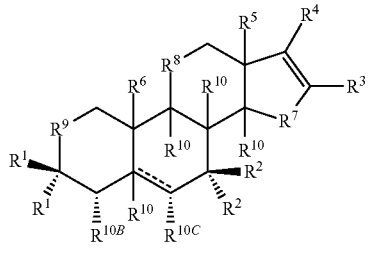
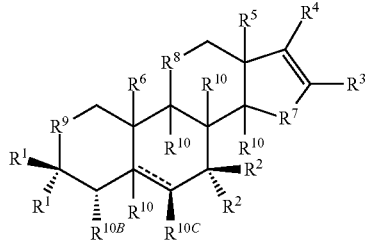
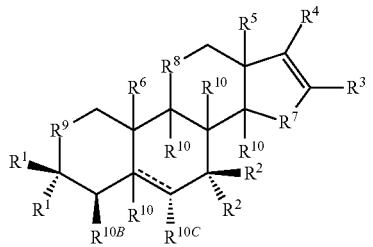
150
-continued
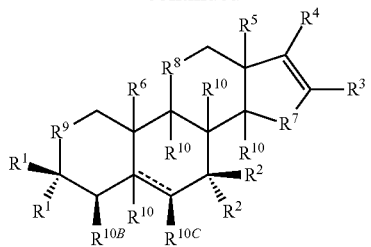
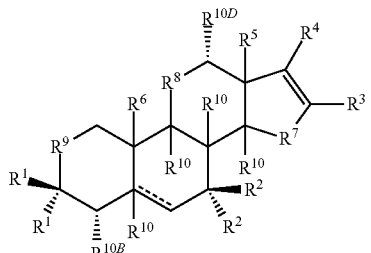
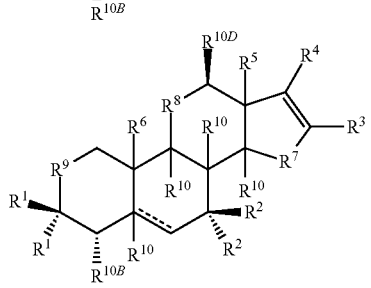
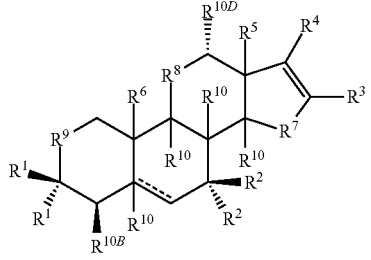
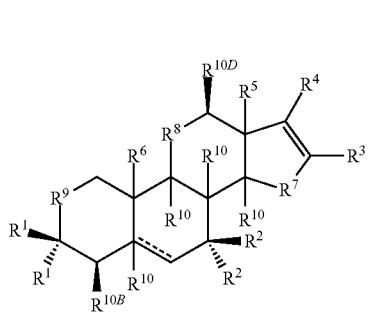
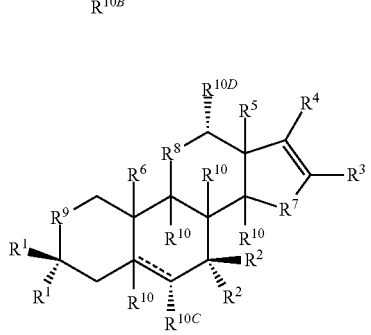

-continued

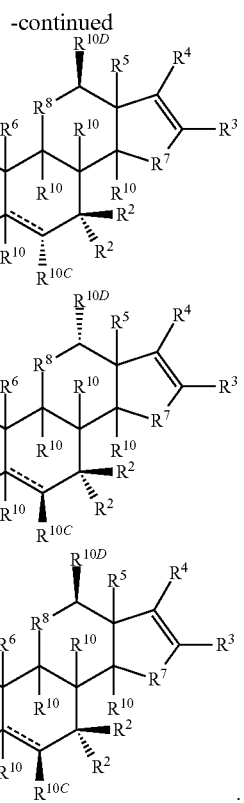

49A. The compound of embodiment 46A, 47A or 48A wherein (1) $R^5$ and $R^6$ respectively are in the α,α-, α,β-, β,α- or β,β-configurations and $R^5$ and $R^6$ are both —$CH_3$ or are selected from —$CH_3$ and —$CH_2OH$ or (2) $R^5$ and $R^6$ are both in the β-configuration and $R^5$ and $R^6$ are both —$CH_3$ or are selected from —$CH_3$ and —$CH_2OH$.

50A. The compound of any one of embodiments 46A through 49A wherein $R^{10}$ at the 5, 8, 9 and 14-positions respectively are (1) —H, —H, —H, —H, (2) —H, —H, halogen (—F, —Cl, —Br or —I), —H, (3) —H, —H, —H, —OH, (4) —H, —H, halogen (—F, —Cl, —Br or —I), —OH, (5) -optionally substituted alkyl (optionally —$CH_3$, —$CH_2OH$, —$CH_2O$-ester, —$C_2H_5$), —H, —H, —H, (6) -optionally substituted alkyl (optionally —$CH_3$, —$CH_2OH$, —$CH_2O$-ester, —$C_2H_5$), —H, halogen (—F, —Cl, —Br or —I), —H, (7) -optionally substituted alkyl (optionally —$CH_3$, —$CH_2OH$, —$CH_2O$-ester, —$C_2H_5$), —H, —H, —OH, (8) -acyl (optionally —C(O)—$(CH_2)_{0-2}$—$CH_3$), —H, —H, —H, (9) -ester (optionally acetoxy or propionoxy), —H, —H, —H, (10) -ether (optionally —O—$(CH_2)_{0-2}$—$CH_3$), —H, —H, —H, (11) -ester (optionally acetoxy, propionoxy, —O—C(O)—$(CH_2)_{1-6}$—H), —H, halogen (optionally —F, —Cl, —Br), —H, (12) -ester (optionally acetoxy or propionoxy), —H, —H, —OH, (13) —H, —H, —H, -acyl (optionally —C(O)—$(CH_2)_{0-2}$—$CH_3$), (14) —H, —H, —H, -ester (optionally acetoxy or propionoxy), or (15) —H, —H, —H, -ether (optionally —O—$(CH_2)_{0-2}$—$CH_3$, —$OCH_3$, —$OC_2H_5$, —$OCH_2OH$, —$OCH_2F$, —$OCH_2Br$, —$OCH_2COOH$, —$OCH_2NH_2$, —$OCH_2CH_2OH$, —$OCH_2CH_2F$, —$OCH_2CH_2Br$, —$OCH_2CH_2COOH$ or —$OCH_2CH_2NH_2$).

51A. The compound of any one of embodiments 46A through 50A wherein $R^7$ is —$CH_2$—, —CHOH—, —CH($αR^{10}$)—, —CH(ester)-, —CH(alkoxy)- or —CH(halogen)- wherein hydroxyl, the ester, the alkoxy group or the halogen atom is present in the α-configuration and the alkoxy group is optionally selected from —$OCH_3$, —$OC_2H_5$ and —$OC_3H_7$ and the halogen atom is —F, —Cl, —Br or —I.

52A. The compound of any one of embodiments 46A through 51A wherein $R^8$ is —$CH_2$—, —$CF_2$—, —CHOH—, —CH($αR^{10}$)—, —CH(ester)-, —CH(alkoxy)- or —CH(halogen)- wherein hydroxyl, the ester, the alkoxy group or the halogen atom is present in the α-configuration and the alkoxy group is optionally selected from —$OCH_3$, —$OC_2H_5$ and —$OC_3H_7$ and the halogen atom is —F, —Cl, —Br or —I.

53A. The compound of embodiment 46A wherein $R^1$ is —OH, =O, an ester or an ether; $R^2$ is —H, —OH, =O, an ester or an ether; $R^3$ is —H, an optionally substituted alkyl group, a halogen, —OH, an ester or an ether; and $R^{10A}$, $R^{10B}$, $R^{10C}$ and $R^{10D}$ independently are —H, a halogen, —$SR^{PR}$ or —$OR^{PR}$, wherein one of $R^{10A}$ and $R^{10B}$, $R^{10A}$ and $R^{10C}$, $R^{10A}$ and $R^{10D}$, $R^{10B}$ and $R^{10C}$, $R^{10B}$ and $R^{10D}$ or $R^{10C}$ and $R^{10D}$ is a halogen, —$SR^{PR}$ or —$OR^{PR}$ or $R^3$ is a halogen, —OH or an ester when $R^2$ is —H.

54A. The compound of embodiment 53A wherein $R^5$ and $R^6$ independently are —H, —$CH_3$ or —$CH_2OH$; and $R^7$, $R^8$ and $R^9$ are —$CH_2$—.

55A. The compound of embodiment 46A wherein the compound has the structure

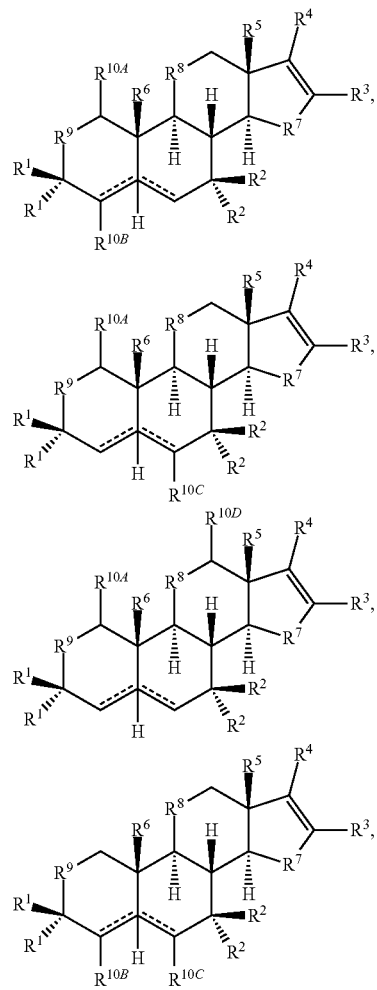

153

-continued

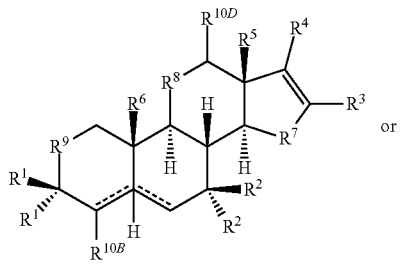

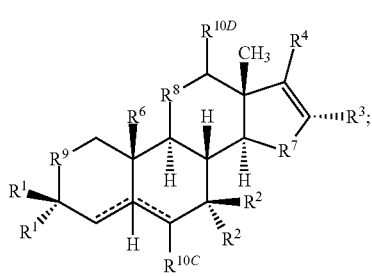

wherein one R[1] is —H and the other R[1] is —OH, an ester or an ether or both R[1] together are =O; one R[2] is —H, and the other R[2] is —H, —OH, an ester or an ether or both R[2] together are =O; R[3] is —H, a halogen, —OH, an ester or an ether; R[4] is an optionally substituted amine moiety, and optionally substituted amide group, an optionally substituted N-linked heterocycle moiety or an optionally substituted C-linked heterocycle moiety; R[5] and R[6] independently are —H or an optionally substituted alkyl group; R[7], R[8] and R[9] independently are —C(R[10])$_2$—, wherein R[10] independently or together are —H, —OH, =O, an ester or an ether; R[10A], R[10B], R[10C] and R[10D] independently are —H, a halogen —SR[PR] or —OR[PR]; and R[PR] independently are —H or a protecting group;

wherein (1) when R[4] is an optionally substituted N-linked heterocycle moiety and R[3] is —H or optionally substituted alkyl or (2) when R[4] is an optionally substituted C-linked heterocycle moiety and R[3] is —H or an ether, (i) one R[2] is as defined and the other R[2] is —OH, an ester or an ether or (ii) one of R[10A] and R[10B], R[10A] and R[10C], R[10A] and R[10D], R[10B] and R[10C], R[10B] and R[10D] or R[10C] and R[10D] is a halogen, —SR[PR] or —OR[PR].

56A. The compound of embodiment 55A wherein R[5] and R[6] independently are —H, —CH$_3$ or —CH$_2$OH; and R[7], R[8] and R[9] are —CH$_2$— or =CH—.

57A. The compound of embodiment 46 wherein the compound has the structure

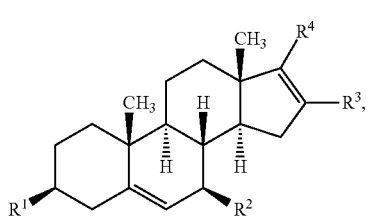

154

-continued

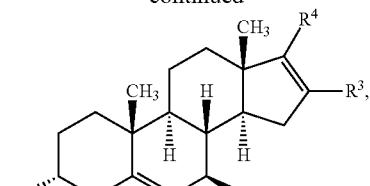

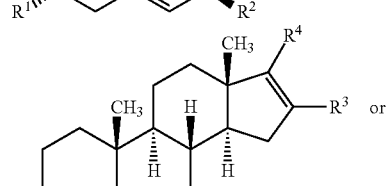

wherein, R[1] is —OH, =O, —SH, an ester or an ether; R[2] is —OH, an ester or an ether; R[3] is —H, a halogen, —OH, an ester or an ether; and R[4] is an optionally substituted amine moiety, an optionally substituted amide group or an optionally substituted N-linked heterocycle moiety.

58A. The compound of embodiment 57A wherein the compound has the structure

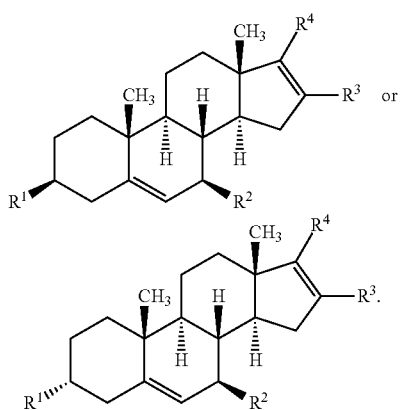

59A. The compound of embodiment 57A wherein the compound has the structure

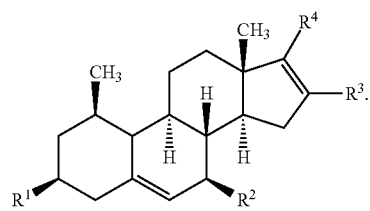

60A. The compound of embodiment 59A wherein R[1] is —OH, —SH or =O; R[2] is —OH, =O or —OCH$_3$; R[3] is —H, —F, —Cl, —Br, —OH, —O—C(O)CH$_3$ or —O—C(O)

CH$_2$CH$_3$; and R$^4$ is an optionally substituted amine moiety or an optionally substituted amide group wherein the amine moiety or amide group is —NH$_2$, —NHOH, —NH—C(O)CH$_3$, —NHCH$_3$ or —NH(CH$_3$)$_2$.

61A. The compound of embodiment 59A wherein R$^1$ is —OH, —SH or =O; R$^2$ is —OH, =O or —OCH$_3$; R$^3$ is —H, —F, —Cl, —Br, —OH, —O—C(O)CH$_3$ or —O—C(O)CH$_2$CH$_3$; and R$^4$ is an optionally substituted N-linked heterocycle moiety, wherein the N-linked heterocycle moiety is —N-pyrrolidine, —N1-pyrazolone, —N$^2$-pyrazolone, —N-imidazolidin-2-one, —N1-imidazole, —N1-4,5-dihydroimidazole, —N-morpholine, —N1-pyridine, —N-piperidine or —N-piperazine.

62A. The compound of embodiment 59A wherein R$^1$ is —OH, —SH or =O; R$^2$ is —OH, =O or —OCH$_3$; R$^3$ is —H, —F, —Cl, —Br, —OH, —O—C(O)CH$_3$ or —O—C(O)CH$_2$CH$_3$; and R$^4$ is an optionally substituted amide group or an optionally substituted N-linked heterocycle moiety, wherein the N-linked heterocycle moiety is —N-piperazine substituted at N4 with optionally substituted alkyl, —N-indole, —N-indoline, —N-quinolidine, and the amide group is —NH—C(O)—CH$_2$—CH$_2$—C(O)—CH, —NH—C(O)—CH$_2$—C(O)—OH, —NH—C(O)—CH$_2$—CH$_2$—C(O)—OR$^{PR}$, —NH—C(O)—CH$_2$—C(O)—OR$^{PR}$, —NH—C(O)—(CH$_2$)$_3$—C(O)—OH or —NH—C(O)—(CH$_2$)$_3$—C(O)—OR$^{PR}$, wherein R$^{PR}$ is a protecting group.

63A. The compound of embodiment 59A wherein R$^1$ is —OH, —SH or =O; R$^2$ is —OH, =O or —OCH$_3$; R$^3$ is —H, —F, —Cl, —Br, —OH, —O—C(O)CH$_3$ or —O—C(O)CH$_2$CH$_3$; and R$^4$ is an optionally substituted amine moiety wherein the amine moiety is —NH—CH(CH$_3$)—C(O)OH, —NH—CH(CH$_3$)—C(O)OR$^{PR}$, —NH—CH(CH$_2$OH)—C(O)OH, —NH—CH(CH$_2$OH)—C(O)OR$^{PR}$, —NH—CH$_2$—CH$_2$—C(O)—OH, —NH—CH$_2$—C(O)—OH, —NH—CH$_2$—CH$_2$—C(O)—OR$^{PR}$, —NH—CH$_2$—C(O)—OR$^{PR}$, —NH—(CH$_2$)$_3$—C(O)—OH or —NH—(CH$_2$)$_3$—C(O)—OR$^{PR}$, wherein R$^{PR}$ is a protecting group.

64A. The compound of embodiment 46A wherein the compound has the structure

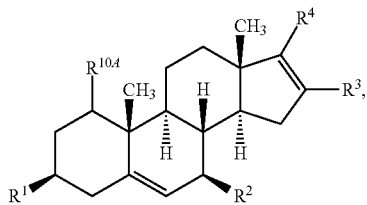

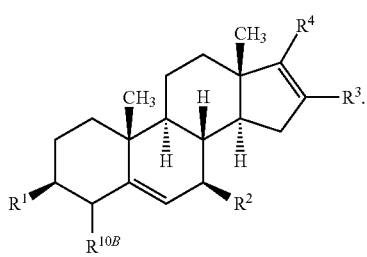

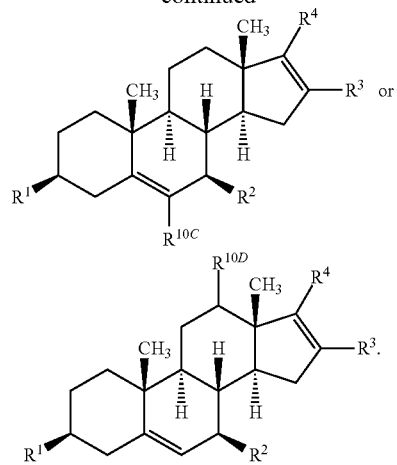

65A. The compound of embodiment 64A wherein R$^1$ is —OH or =O; R$^2$ is —H, —OH or an ether wherein the ether is —OCH$_3$; R$^3$ is —H, a halogen or an ester wherein the ester is —O—C(O)CH$_3$ or —O—C(O)CH$_2$CH$_3$; R$^4$ is an optionally substituted N-linked heterocycle moiety, wherein the N-linked heterocycle moiety is —N-pyrrolidine, —N1-pyrazolone, —N-2-pyrazolone, —N-imidazolidin-2-one, —N1-imidazole, —N1-4,5-dihydroimidazole, —N-morpholine, —N-piperidine, —N-indole, —N-indoline, —N-quinolidine or —N1-piperazine, optionally substituted at N4 with optionally substituted alkyl, aryl or heteroaryl; and R$^{10A}$, R$^{10B}$ R$^{10C}$ or R$^{10D}$ are —H, a halogen or —OR$^{PR}$, wherein R$^{10}$A, R$^{10B}$R$^{10C}$ or R$^{10D}$ is a halogen or —OR$^{PR}$ or R$^3$ is a halogen or an ester when R$^2$ is —H.

66A. The compound of embodiment 46A wherein the compound has the structure

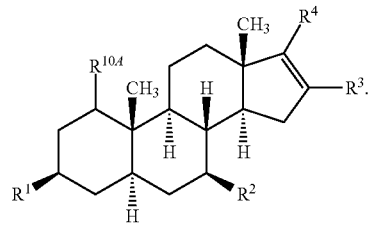

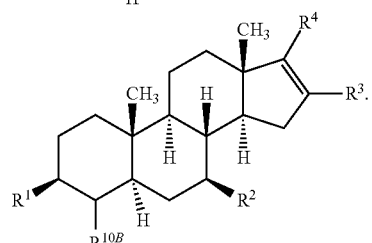

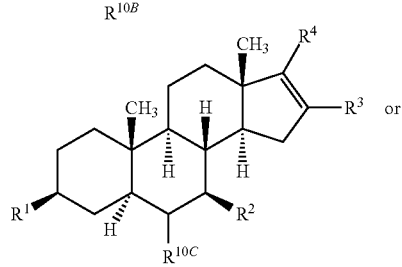

-continued

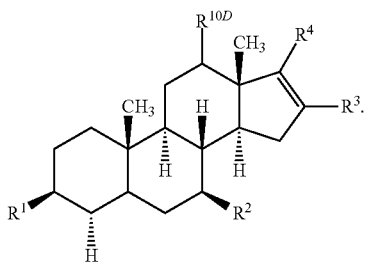

67A. The compound of embodiment 66A wherein $R^1$ is —OH or =O; $R^2$ is —H, —OH or an ether wherein the ether is —OCH$_3$; $R^3$ is —H or an ester wherein the ester is —O—C(O)CH$_3$ or —O—C(O)CH$_2$CH$_3$; $R^4$ is an optionally substituted N-linked heterocycle moiety, wherein the N-linked heterocycle moiety is —N-pyrrolidine, —N1-pyrazolone, —N$^2$-pyrazolone, —N-imidazolidin-2-one, —N1-imidazole, —N1-4,5-dihydroimidazole, —N-morpholine, —N-piperidine, —N-indole, —N-indoline, —N-quinolidine or —N1-piperazine, optionally substituted at N4 with optionally substituted alkyl, aryl or heteroaryl; and $R^{10A}$, $R^{10B}$, $R^{10C}$ or $R^{10D}$ are —H, a halogen or —OR$^{PR}$, wherein $R^{10A}$, $R^{10B}$, $R^{10C}$ or $R^{10D}$ is a halogen or —OR$^{PR}$ when $R^2$ and $R^3$ are —H.

68A. The compound of embodiment 46A wherein the compound has the structure

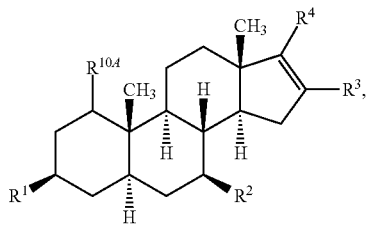

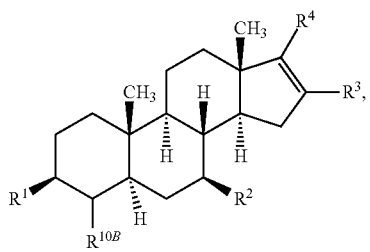

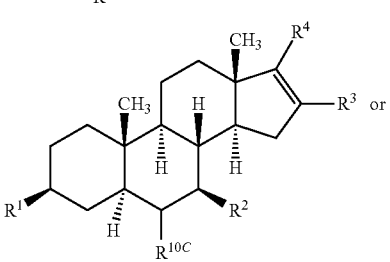

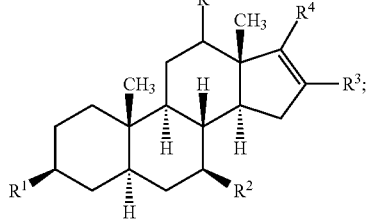

wherein $R^1$ is —OH or =O; $R^2$ is —H, —OH, =O or an ether wherein the ether is —OCH$_3$; $R^3$ is —H, a halogen or an ester wherein the ester is —O—C(O)CH$_3$ or —O—C(O)CH$_2$CH$_3$; $R^4$ is an optionally substituted C-linked heterocycle moiety, wherein the C-linked heterocycle moiety is 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-thiazolyl, 4-thiazolyl or 5-thiazolyl; and $R^{10A}$, $R^{10B}$, $R^{10C}$ or $R^{10D}$ is —H, a halogen, —SR$^{PR}$ or —OR$^{PR}$; wherein $R^{10A}$, $R^{10B}$, $R^{10C}$ or $R^{10D}$ is a halogen, —SR$^{PR}$ or —OR$^{PR}$ when $R^2$ and $R^3$ are —H.

68A. The compound of embodiment 69A wherein $R^1$ and $R^2$ are —OH; $R^3$ is —H or —O—C(O)CH$_3$; $R^4$ is 3-pyridyl; and $R^{10A}$ or $R^{10B}$ is —H, —OR$^{PR}$ or —F.

69A. The compound of embodiment 46A wherein the compound is 3β,16-dihydroxy-17-N-pyrrolidinylandrost-5,16-diene, 3β,7β-dihydroxy-17-N-pyrrolidinylandrost-5,16-diene, 3β-hydroxy-16α-fluoro-17β-N-pyrrolidinylandrost-1,16-diene.

70A. The compound of embodiment 46A wherein the compound is 17-(3-pyridyl)-androst-1,5,16 triene-3β-ol or 17-(3-pyridyl)-16-fluoro-androst-1,5,16 triene-3β-ol, 3β,7β-dihydroxy-17-(3-pyridyl)-5α-androst-16-ene or 3β,7β-dihydroxy-17-(3-pyridyl)-androst-5,16-diene.

71A. A compound having the structure

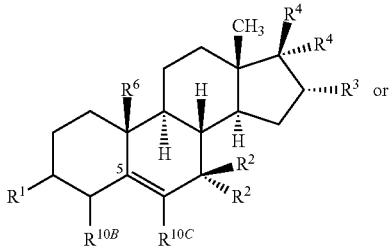

wherein one R⁴ is —OH, —NH₂, —NH—C(O)CH₃, —NHCH₃, —NH(CH₃)₂, —N⁺(CH₃)₃, —NH—CH₂CH₃, —NHOH or an N-linked heterocycle moiety, wherein the heterocycle moiety is —N-pyrrolidine, —N1-pyrazolone, —N2-pyrazolone, —N-imidazolidin-2-one, —N1-imidazole, —N1-4,5-dihydroimidazole, —N-morpholine, —N1-pyridine, —N-piperidine, —N-piperazine, —N-piperazine substituted at N⁴ with optionally substituted alkyl, —N-indole, —N-indoline, —N-quinolidine, and the other R⁴ is —H or both R⁴ together are =O or =NHOH.

72A. The compound of embodiment 71A wherein R¹ is in the α- or β-configuration and is —OH; one R² is —OH and the other R² is —H or both R² together are =O; R³ is —H, halogen, —OH, —O—C(O)—CH₃ or —O—C(O)—CH₂CH₃; R⁴ in the β-configuration is —OH or an N-linked heterocycle moiety, wherein the heterocycle moiety is pyrrolidine or piperidine; R⁴ in the α-configuration is —H; R⁶ is —H or —CH₃; R¹⁰ᴮ is halogen; and R¹⁰ᶜ is halogen or —OR^PR;

and wherein the halogens independently are —F, —Cl or —Br.

73A. The compound of embodiment 72 wherein the compound has the structure

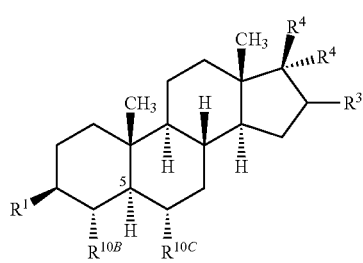

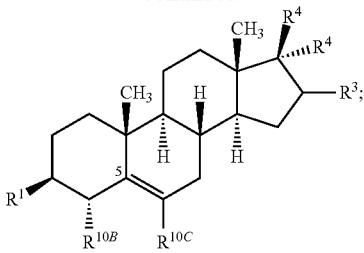

wherein R¹ is —OH; R³ is in the α- or β-configuration and is —H, halogen, —OH, —O—C(O)—CH₃ or —O—C(O)—CH₂CH₃; R⁴ in the β-configuration is —OH and R⁴ in the α-configuration is —H; R¹⁰ᴮ is F, —Br or —Cl; and R¹⁰ᶜ is halogen or —OR^PR, wherein R^PR is —H.

74A. The compound of embodiment 73A wherein the compound has the structure

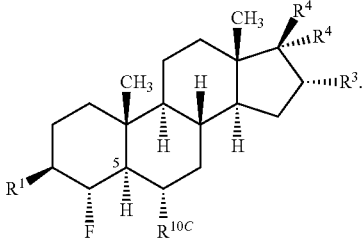

75A. The compound of embodiment 74 wherein the compound is 4α-fluoro-3β,6α,17β-trihydroxyandrostane.

1B. A formula 1 compound having the structure

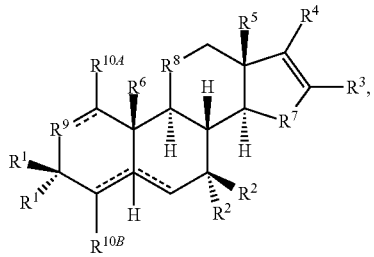

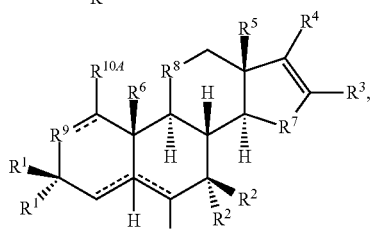

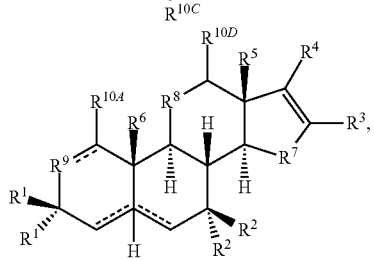

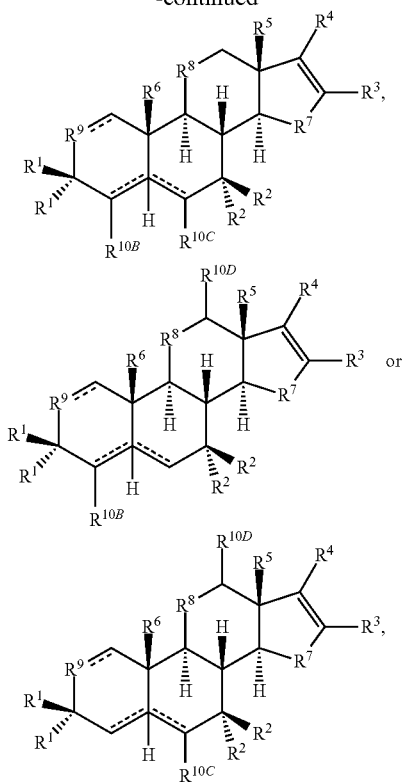

or a salt thereof; wherein the dotted lines are optional double bonds and —H at the 5-position (if present) is in the α- or β-configuration or if a double bond is present at the 1-2, 4-5 or 5-6 positions, then $R^{10A}$, $R^{10B}$ or $R^{10C}$ respectively are bonded to the ring to which they are linked by a single bond; $R^{10A}$ and $R^{10B}$, $R^{10A}$ and $R^{10C}$, $R^{10A}$ and $R^{10D}$, $R^{10B}$ and $R^{10C}$, $R^{10B}$ or $R^{10D}$ and $R^{10C}$ respectively are in the α,α-, α,β-, β,α- or β,β-configurations;

wherein one of $R^1$ is —H, an optionally substituted alkyl group, an optionally substituted alkenyl group or an optionally substituted alkynyl group and the other $R^1$ is —OH, an ester, or an alkoxy group; $R^2$ and $R^3$ independently are —H, —OH, an ester, an alkoxy group or a halogen; $R^4$ is an optionally substituted N-linked heterocycle moiety, an optionally substituted amine moiety, an optionally substituted amide group or an optionally substituted C-linked heterocycle moiety, wherein the C-linked heterocycle moiety is 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-thiazolyl, 4-thiazolyl or 5-thiazolyl; $R^5$ and $R^6$ independently are —H or an optionally substituted alkyl group, $R^7$ is —C($R^{10}$)$_2$— and $R^8$ and $R^9$ independently are —C($R^{10}$)$_2$— or =C($R^{10}$)—, wherein $R^{10}$ are independently selected; $R^{10}$, $R^{10A}$, $R^{10B}$, $R^{10C}$ and $R^{10D}$ independently are —H, halogen, —SR$^{PR}$ or —OR$^{PR}$; R$^{PR}$ independently are —H or a protecting group, wherein R$^{PR}$ of —OR$^{PR}$ defines an ester or an alkoxy group;

wherein (1) one $R^2$ is as defined and the other $R^2$ is —OH, an ester, an alkoxy group or a halogen or $R^3$ is a halogen, an ester or an alkoxy group, or (2) one of $R^{10A}$ and $R^{10B}$, $R^{10A}$ and $R^{10C}$, $R^{10A}$ and $R^{10D}$, $R^{10B}$ and $R^{10}$, $R^{10B}$ and $R^{10D}$ or $R^{10C}$ and $R^{10D}$ is a halogen, —SR$^{PR}$ or —OR$^{PR}$ and the other $R^{10A}$, $R^{10B}$, $R^{10C}$ or $R^{10D}$ is as defined.

2B. The compound of embodiment 1B, wherein $R^7$, $R^8$ and $R^9$ independently are —CH$_2$—, —CHOH—, —CH(αR$^{10}$)—, —CH(ester)-, —CH(alkoxy)- or —CH(halogen)-, wherein hydroxyl, the ester, the alkoxy group or the halogen atom is present in the α-configuration and the alkoxy group is —OCH$_3$, —OC$_2$H$_5$ and —OC$_3$H$_7$ and the halogen atom is —F, —Cl or —Br.

3B. The compound of embodiment 2B, wherein $R^1$ is —OH, an ester or an alkoxy group; $R^2$ is —H, —OH, an ester or an alkoxy group; $R^3$ is —H, a halogen, —OH, an ester or an alkoxy group; and $R^{10A}$, $R^{10B}$, $R^{10C}$ and $R^{10D}$ independently are —H, a halogen or —OR$^{PR}$, wherein one of $R^{10A}$ and $R^{10}$B, $R^{10A}$ and $R^{10C}$, $R^{10A}$ and $R^{10D}$, $R^{10B}$ and $R^{10C}$, $R^{10B}$ and $R^{10D}$ or $R^{10C}$ and $R^{10D}$ is a halogen or —OR$^{PR}$ when $R^2$ is —H.

4B. The compound of embodiment 3B, wherein $R^5$ and $R^6$ independently are —H, —CH$_3$ or —CH$_2$OH; and $R^7$, $R^8$ and $R^9$ are —CH$_2$—.

5B. The compound of embodiment 4B, wherein the compound has the structure

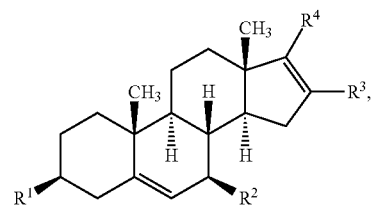

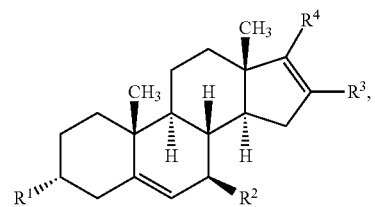

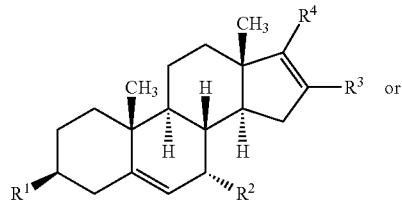

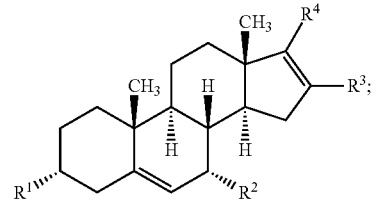

wherein $R^1$ and $R^2$ independently are —OH, an ester or an alkoxy group; $R^3$ is —H, a halogen, —OH or an ester; and $R^4$ is an optionally substituted amine moiety, an optionally substituted amide group or an optionally substituted N-linked heterocycle moiety.

6B. The compound of embodiment 5B, wherein the compound has the structure

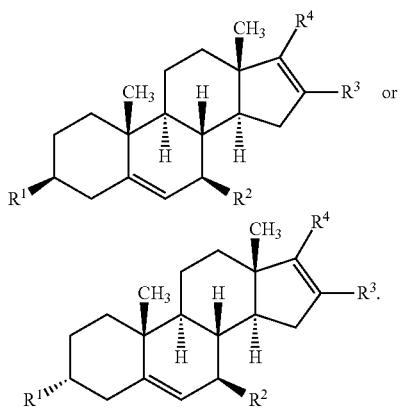

7B. The compound of embodiment 5B, wherein the compound has the structure

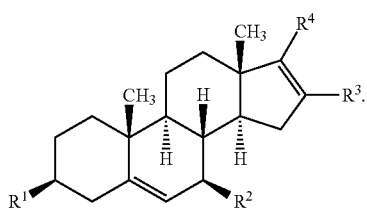

8B. The compound of embodiment 7B, wherein R$^1$ is —OH; R$^2$ is —OH or —OCH$_3$; R$^3$ is —H, —F, —Cl, —Br, —OH, —O—C(O)CH$_3$ or —O—C(O)CH$_2$CH$_3$; and R$^4$ is an optionally substituted amine moiety or an optionally substituted amide group, wherein the amine moiety or amide group is —NH$_2$, —NHOH, —NH—C(O)CH$_3$, —NHCH$_3$ or —NH(CH$_3$)$_2$.

9B. The compound of embodiment 7B, wherein R$^1$ is —OH; R$^2$ is —OH or —OCH$_3$; R$^3$ is —H, —F, —Cl, —Br, —OH, —O—C(O)CH$_3$ or —O—C(O)CH$_2$CH$_3$; and R$^4$ is an optionally substituted N-linked heterocycle moiety, wherein the N-linked heterocycle moiety is —N-pyrrolidine, —N1-pyrazolone, —N2-pyrazolone, —N-imidazolidin-2-one, —N1-imidazole, —N1-4,5-dihydroimidazole, —N-morpholine, —N1-pyridine, —N-piperidine or —N-piperazine.

10B. The compound of embodiment 7B, wherein R$^1$ is —OH; R$^2$ is —OH or —OCH$_3$; R$^3$ is —H, —F, —Cl, —Br, —OH, —O—C(O)CH$_3$ or —O—C(O)CH$_2$CH$_3$; and R$^4$ is an optionally substituted amide group or an optionally substituted N-linked heterocycle moiety, wherein the N-linked heterocycle moiety is —N-piperazine substituted at N4 with optionally substituted alkyl, —N-indole, —N-indoline or —N-quinolidine, and the amide group is —NH—C(O)—CH$_2$—CH$_2$—C(O)—OH, —NH—C(O)—CH$_2$—C(O)—OH, —NH—C(O)—CH$_2$—CH$_2$—C(O)—OR$^{PR}$, —NH—C(O)—CH$_2$—C(O)—OR$^{PR}$, —NH—C(O)—(CH$_2$)$_3$—C(O)—OH or —NH—C(O)—(CH$_2$)$_3$—C(O)—OR$^{PR}$, wherein R$^{PR}$ is a protecting group.

11B. The compound of embodiment 7B, wherein R$^1$ is —OH; R$^2$ is —OH or —OCH$_3$; R$^3$ is —H, —F, —Cl, —Br, —OH, —O—C(O)CH$_3$ or —O—C(O)CH$_2$CH$_3$; and R$^4$ is an optionally substituted amine moiety, wherein the amine moiety is —NH—CH(CH$_3$)—C(O)OH, —NH—CH(CH$_3$)—C(O)OR$^{PR}$, —NH—CH(CH$_2$OH)—C(O)OH, —NH—CH(CH$_2$OH)—C(O)OR$^{PR}$, —NH—CH$_2$—CH$_2$—C(O)—OH, —NH—CH$_2$—C(O)—OH, —NH—CH$_2$—CH$_2$—C(O)—OR$^{PR}$, —NH—CH$_2$—C(O)—OR$^{PR}$, —NH—(CH$_2$)$_3$—C(O)—OH or —NH—(CH$_2$)$_3$—C(O)—OR$^{PR}$, wherein R$^{PR}$ is a protecting group.

12B. The compound of embodiment 1B, wherein the compound has the structure

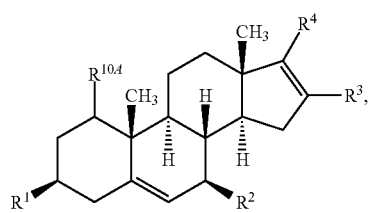

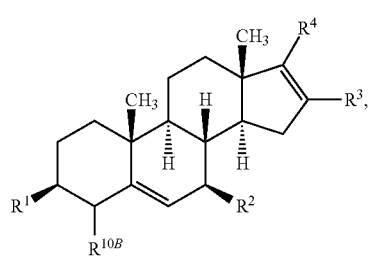

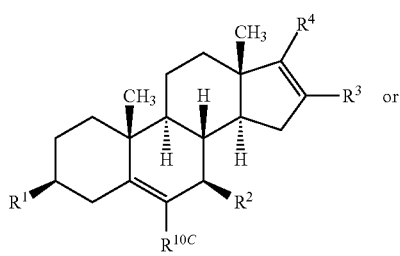

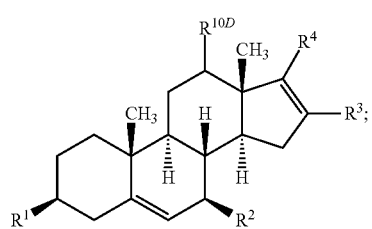

wherein R$^1$ is —OH; R$^2$ is —H, —OH or —OCH$_3$; R$^3$ is —H, a halogen, —O—C(O)CH$_3$ or —O—C(O)CH$_2$CH$_3$; R$^4$ is an optionally substituted N-linked heterocycle moiety, wherein the N-linked heterocycle moiety is —N-pyrrolidine, —N1-pyrazolone, —N2-pyrazolone, —N-imidazolidin-2-one, —N1-imidazole, —N1-4,5-dihydroimidazole, —N-morpholine, —N-piperidine, —N-indole, —N-indoline, —N-quinolidine or —N1-piperazine, optionally substituted at N4 with optionally substituted alkyl, aryl or heteroaryl; and R$^{10A}$, R$^{10B}$ R$^{10C}$ or R$^{10D}$ are —H, a halogen or —OR$^{PR}$;

wherein R$^2$ is —OH or —OCH$_3$ when R$^{10A}$, R$^{10B}$ R$^{10C}$ or R$^{10D}$ is —H.

13B. The compound of embodiment 1B, wherein the compound has the structure

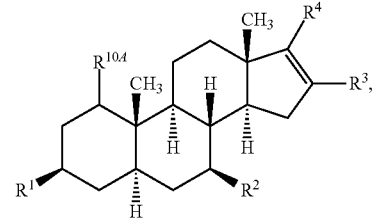

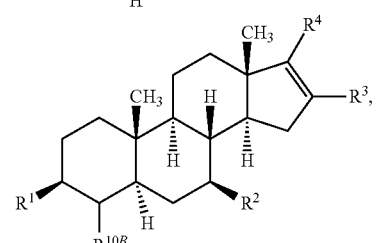

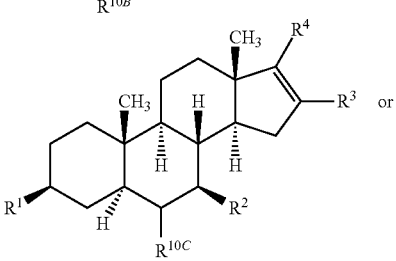 or

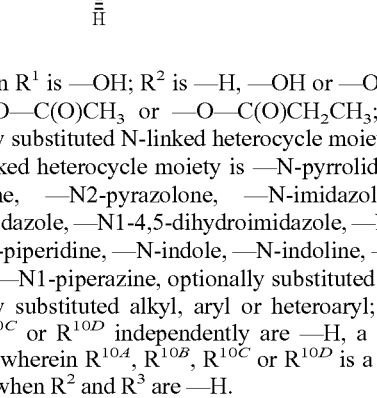

wherein R$^1$ is —OH; R$^2$ is —H, —OH or —OCH$_3$; R$^3$ is —H, —O—C(O)CH$_3$ or —O—C(O)CH$_2$CH$_3$; R$^4$ is an optionally substituted N-linked heterocycle moiety, wherein the N-linked heterocycle moiety is —N-pyrrolidine, —N1-pyrazolone, —N2-pyrazolone, —N-imidazolidin-2-one, —N1-imidazole, —N1-4,5-dihydroimidazole, —N-morpholine, —N-piperidine, —N-indole, —N-indoline, —N-quinolidine or —N1-piperazine, optionally substituted at N4 with optionally substituted alkyl, aryl or heteroaryl; and R$^{10A}$, R$^{10B}$, R$^{10C}$ or R$^{10D}$ independently are —H, a halogen or —OR$^{PR}$, wherein R$^{10A}$, R$^{10B}$, R$^{10C}$ or R$^{10D}$ is a halogen or —OR$^{PR}$ when R$^2$ and R$^3$ are —H.

14B. The compound of embodiment 1B, wherein the compound has the structure

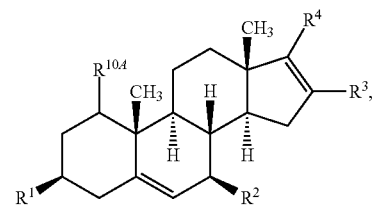

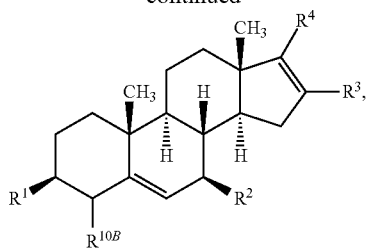

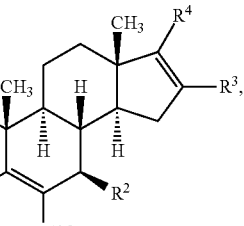

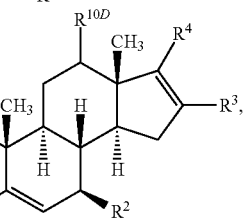

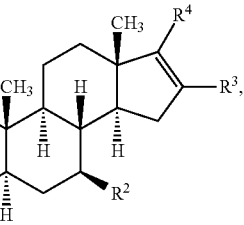

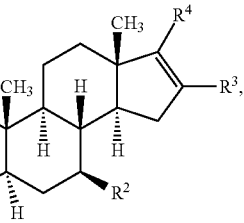

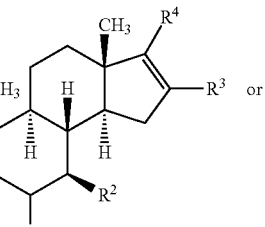 or

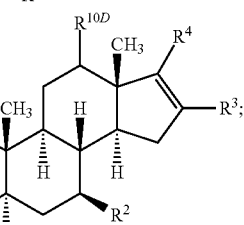

wherein R$^1$ is —OH; R$^2$ is —H, —OH or —OCH$_3$; R$^3$ is —H, a halogen, —O—C(O)CH$_3$ or —O—C(O)CH$_2$CH$_3$; R$^4$ is an optionally substituted C-linked heterocycle moiety, wherein the C-linked heterocycle moiety is 2-pyridyl, 3-pyridyl, 4-pyridyl, 5-pyridyl or 6-pyridyl; and $R^{10A}$, $R^{10B}$, $R^{10C}$ or $R^{10D}$ is —H, a halogen or —$OR^{PR}$ wherein $R^{10A}$, $R^{10B}$, $R^{10C}$ or $R^{10D}$ is a halogen or —$OR^{PR}$ when $R^2$ and $R^3$ are —H.

15B. The compound of embodiment 14B wherein $R^1$ and $R^2$ are —OH; $R^3$ is —H or —O—C(O)CH$_3$; $R^4$ is 3-pyridyl; and $R^{10A}$ or $R^{10B}$ is —H, —$OR^{PR}$ or —F.

16B. The compound of claim 1B, wherein the compound has the structure

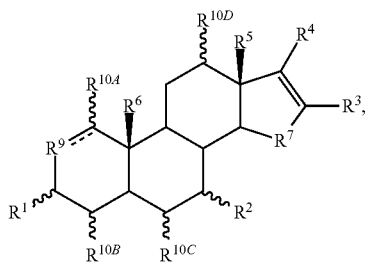

or a salt thereof, wherein the dotted lines are optional double bonds;

wherein $R^1$ is —OH, =O, —SH, amide, ester or ether; $R^2$ is —OH, =O, halogen, optionally substituted alkyl, ester or ether; $R^3$ is —H, —OH, halogen, optionally substituted alkyl, ester or ether; $R^4$ is optionally substituted heterocycle; $R^5$ and $R^6$ independently are —H, —CH$_3$, —C$_2$H$_5$, —C$_3$H$_7$, optionally substituted alkyl, —OH, —F, —Cl, —Br or —I; $R^7$ is —CH$_2$—, —C(halogen)$_2$-, —CH(α-optionally substituted alkyl), —CH(β-optionally substituted alkyl), —CH(α-OH), —CH(β-OH) or —C(optionally substituted alkyl)$_2$-; $R^9$ is —CH$_2$—, —CH(α-OH), —CH(β-OH) or —C(optionally substituted alkyl)$_2$-; and $R^{10A}$, $R^{10B}$, $R^{10C}$ and $R^{10D}$ independently are —H, optionally substituted alkyl, —CH$_3$, halogen, —$SR^{PR}$ or —$OR^{PR}$ and each $R^{10A}$, $R^{10B}$, $R^{10C}$ and $R^{10D}$ is independently in the α-configuration or the β-configuration and wherein $R^{PR}$ independently are —H or a protecting group.

17B. The compound of embodiment 16B, wherein the compound has the structure

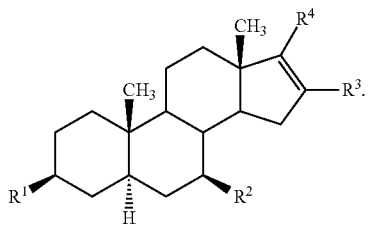

18B. The compound of embodiment 16B, wherein the compound has the structure

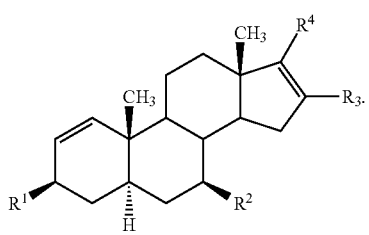

19B. The compound of embodiment 17B, wherein $R^1$ is —OH, =O or —NH—C(O)CH$_3$; $R^2$ is —OH or —OCH$_3$; and $R^3$ is —H, —OH, —O—C(O)CH$_3$ or —O—C(O)CH$_2$CH$_3$.

20B. The compound of embodiment 17B, wherein $R^4$ is —N-pyrrolidine, —N1-pyrazolone, —N2-pyrazolone, —N-imidazolidin-2-one, —N1-imidazole, —N1-4,5-dihydroimidazole, —N-morpholine, —N1-pyridine, —N-piperidine or —N-piperazine.

21B. The compound of embodiment 17B, wherein $R^4$ is 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

22B. The compound of embodiment 17B, wherein $R^4$ is 1-aziridyl, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, 2-isoindole, 2-isoindoline, 4- morpholine, 9-carbazole or β-carboline.

23B. The compound of embodiment 16B, wherein the compound has the structure

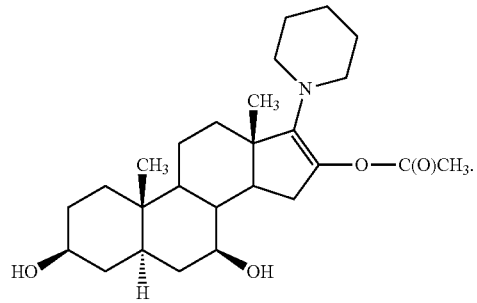

24B. The compound of embodiment 16B, wherein the compound is 3β,16-dihydroxy-17-N-pyrrolidinylandrost-5,16-diene, 3β,7β-dihydroxy-17-N-pyrrolidinylandrost-5,16-diene, 3β-hydroxy-16α-fluoro-17β-N-pyrrolidinylandrost-1,16-diene.

25B. The compound of embodiment 16B, wherein the compound is 17-(3-pyridyl)-androst-1,5,16 triene-3β-ol or 17-(3-pyridyl)-16-fluoro-androst-1,5,16 triene-3β-ol, 3β,7β-dihydroxy-17-(3-pyridyl)-5α-androst-16-ene or 3β,7β-dihydroxy-17-(3-pyridyl)-androst-5,16-diene.

26B. The compound of embodiment 1B, wherein the compound has the structure

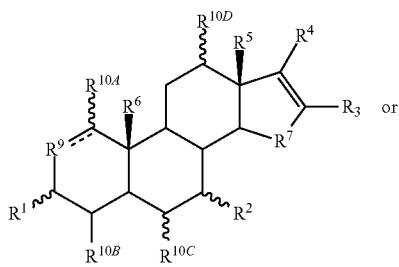 or

-continued

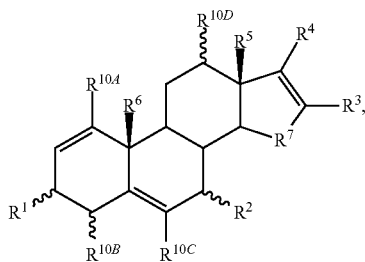

or a salt thereof, wherein the dotted lines are optional double bonds;

wherein $R^1$ is —OH, =O, —SH, amide, ester or ether; $R^2$ is —OH, =O, halogen, optionally substituted alkyl, ester or ether; $R^3$ is —H, —OH, halogen, optionally substituted alkyl, ester or ether; $R^4$ is optionally substituted heterocycle; $R^5$ and $R^6$ independently are —H, —CH$_3$, —C$_2$H$_5$, —C$_3$H$_7$, optionally substituted alkyl, —OH, —F, —Cl, —Br or —I; $R^7$ is —CH$_2$—, —C(halogen)$_2$-, —CHα-optionally substituted alkyl), —CH(β-optionally substituted alkyl), —CH(α-OH), —CH(β-OH) or —C(optionally substituted alkyl)$_2$-; $R^9$ is —CH$_2$—, —CH(α-OH), —CH(β-OH) or —C(optionally substituted alkyl)$_2$-; and $R^{10A}$, $R^{10B}$, $R^{10C}$ and $R^{10D}$ independently are —H, optionally substituted alkyl, —CH$_3$, halogen, —SR$^{PR}$ or —OR$^{PR}$ and each $R^{10A}$, $R^{10B}$, $R^{10C}$ and $R^{10D}$ is independently in the α-configuration or the β-configuration and wherein $R^{PR}$ independently are —H or a protecting group.

27B. The compound of embodiment 26B, wherein the compound has the structure

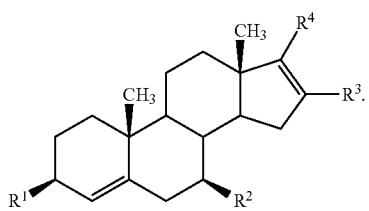

28B. The compound of embodiment 27B, wherein the compound has the structure

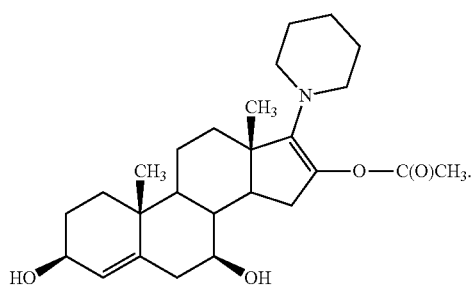

29B. The compound of embodiment 26B, wherein the compound has the structure

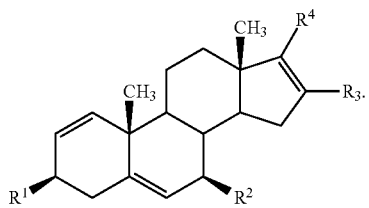

30B. The compound of embodiment 27B, wherein $R^1$ is —OH, =O or —NH—C(O)CH$_3$; $R^2$ is —OH or —OCH$_3$; and $R^3$ is —H, —OH, —O—C(O)CH$_3$ or —O—C(O)CH$_2$CH$_3$.

31B. The compound of embodiment 27B, wherein $R^4$ is —N-pyrrolidine, —N1-pyrazolone, —N2-pyrazolone, —N-imidazolidin-2-one, —N1-imidazole, —N1-4,5-dihydroimidazole, —N-morpholine, —N1-pyridine, —N-piperidine or —N-piperazine.

32B. The compound of embodiment 27, wherein $R^4$ is 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

33B. The compound of embodiment 27B, wherein $R^4$ is 1-aziridyl, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, 2-isoindole, 2-isoindoline, 4- morpholine, 9-carbazole or β-carboline.

34B. A compound having a structure of

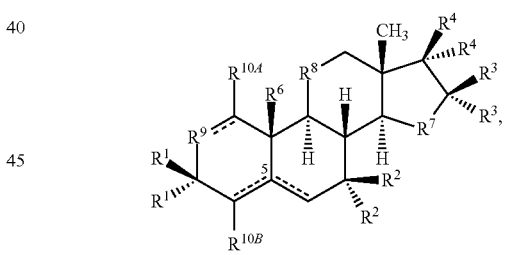

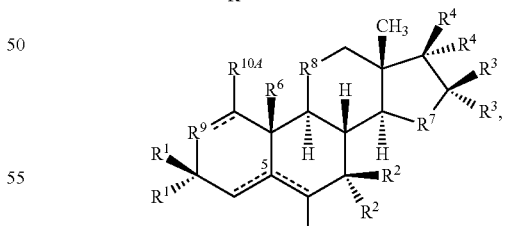

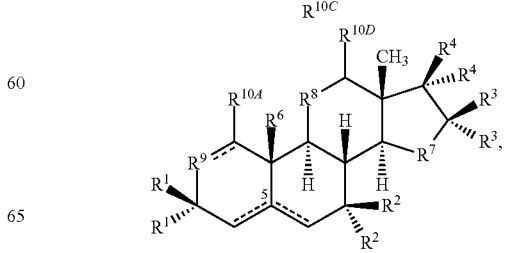

-continued

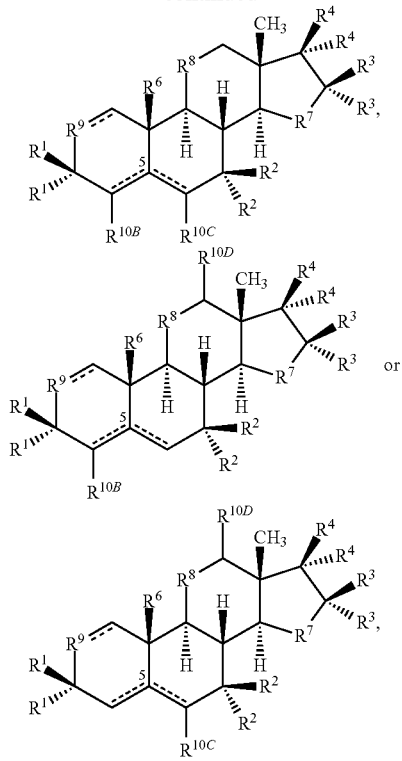

or a salt thereof; wherein the dotted lines are optional double bonds and —H at the 5-position (if present) is in the α- or β-configuration or if a double bond is present at the 1-2, 4-5 or 5-6 positions, then $R^{10A}$, $R^{10B}$ or $R^{10C}$ respectively are bonded to the ring to which they are linked by a single bond; wherein $R^{10A}$ and $R^{10B}$, $R^{10A}$ and $R^{10C}$, $R^{10A}$ and $R^{10D}$, $R^{10B}$ and $R^{10C}$, $R^{10B}$ or $R^{10D}$ and $R^{10C}$ respectively are in the α,α-, α,β-, β,α- or β,β-configurations; one of $R^1$ is —H, an optionally substituted alkyl group, an optionally substituted alkenyl group or an optionally substituted alkynyl group and the other $R^1$ is —OH, an ester, or an alkoxy group; $R^2$ and $R^3$ independently are —H, —OH, an ester, an ether or a halogen; one $R^4$ is —OH, an ester or an alkoxy group and the other $R^4$ is an optionally substituted C-linked heterocycle moiety, wherein the C-linked heterocycle moiety is 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-thiazolyl, 4-thiazolyl or 5-thiazolyl; $R^5$ and $R^6$ independently are —H or an optionally substituted alkyl group; $R^7$, $R^8$ and $R^9$ independently are —C($R^{10}$)$_2$— or =C($R^{10}$)—, wherein $R^{10}$ are independently selected; $R^{10}$, $R^{10A}$, $R^{10B}$, $R^{10C}$ and $R^{10D}$ independently are —H, halogen, —SR$^{PR}$ or —OR$^{PR}$, wherein one of $R^{10A}$ and $R^{10B}$, $R^{10A}$ and $R^{10C}$, $R^{10A}$ and $R^{10D}$, $R^{10B}$ and $R^{10C}$, $R^{10B}$ and $R^{10D}$ or $R^{10C}$ and $R^{10D}$ are halogen, —SR$^{PR}$ or —OR$^{PR}$ and the other $R^{10A}$, $R^{10B}$, $R^{10C}$ or $R^{10D}$ are as defined; and R$^{PR}$ independently are —H or a protecting group, wherein R$^{PR}$ of —OR$^{PR}$ defines an ester or an alkoxy group.

35B. The compound of embodiment 34B wherein $R^7$, $R^8$ and $R^9$ independently are —CH$_2$—, —CF$_2$—, —CHOH—, —CH(αR$^{10}$)—, —CH(ester)-, —CH(alkoxy)- or —CH(halogen)-, wherein hydroxyl, the ester, the alkoxy group or the halogen atom is present in the α-configuration and the alkoxy group is —OCH$_3$, —OC$_2$H$_5$ and —OC$_3$H$_7$ and the halogen atom is —F, —Cl or —Br.

36B. The compound of embodiment 35B wherein the compound has a structure

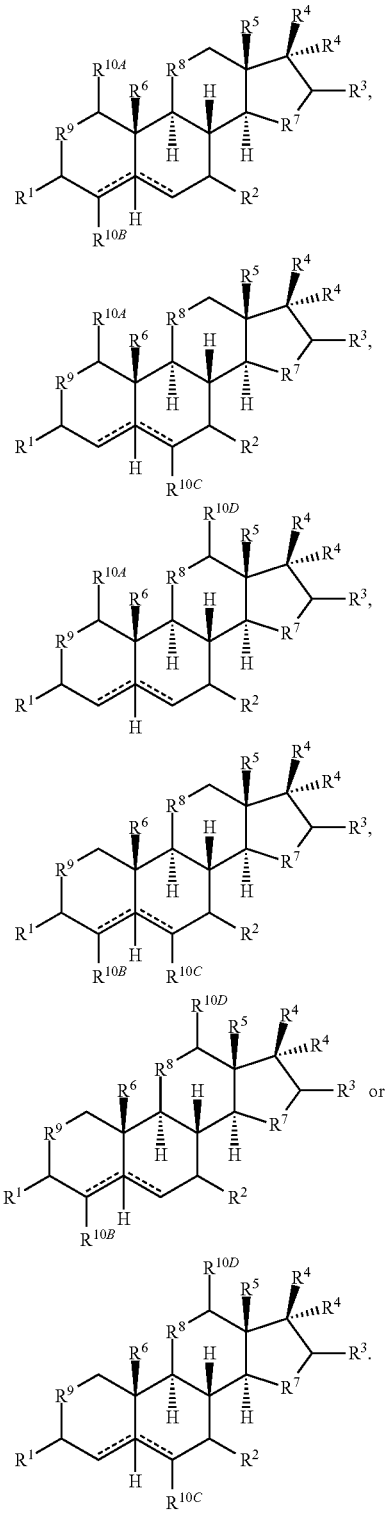

37B. The compound of embodiment 36B wherein $R^5$ and $R^6$ independently are —H, —CH$_3$ or —CH$_2$OH; $R^7$, $R^8$ and $R^9$ are —CH$_2$—; and $R^{10A}$, $R^{10B}$, $R^{10C}$ and $R^{10D}$ is a halogen or —OR$^{PR}$.

38B. The compound of embodiment 34B wherein the compound has the structure

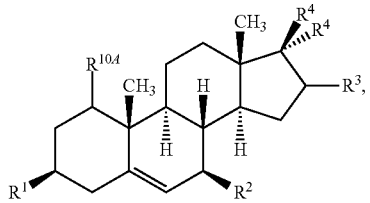
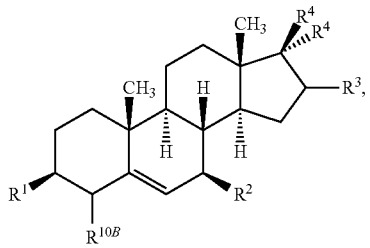
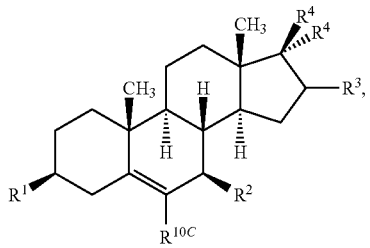
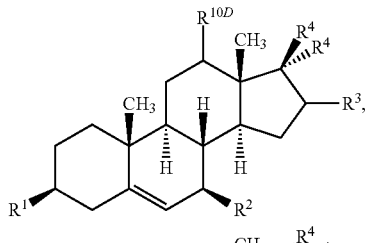
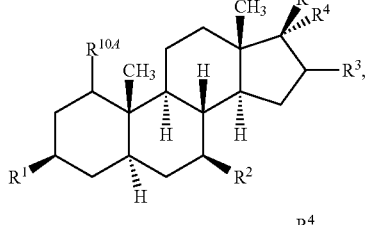
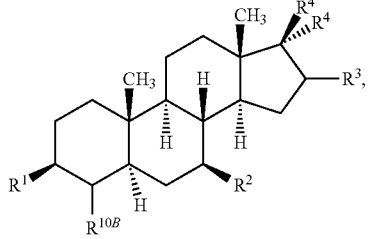
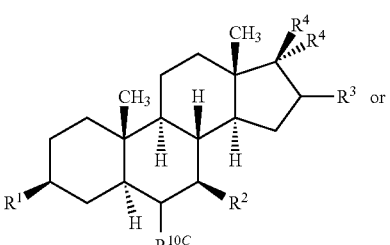 or

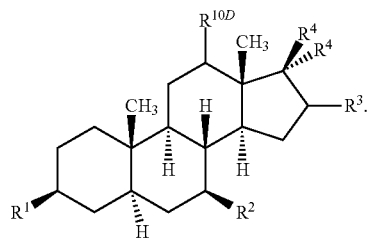

39B. The compound of embodiment 38B, wherein $R^1$ is —OH; $R^2$ is —OH or —OCH$_3$; $R^3$ is —H, a halogen, —O—C(O)CH$_3$ or —O—C(O)CH$_2$CH$_3$; one $R^4$ is an optionally substituted C-linked heterocycle moiety, wherein the C-linked heterocycle is 2-pyridyl, 3-pyridyl, 4-pyridyl, 5-pyridyl or 6-pyridyl and the other $R^4$ is —OH; and $R_{10A}$, $R_{10B}$, $R_{10C}$ or $R^{10D}$ is —H, —OR$^{PR}$ or a halogen.

40B. The compound of embodiment 39B, wherein $R^1$ and $R^2$ are —OH; $R^3$ is —H or —O—C(O)CH$_3$; $R^4$ is 3-pyridyl; and $R^{10A}$, $R^{10B}$, $R^{10C}$ $R^{10D}$ or is —OR$^{PR}$ or —F.

41B. A compound having the structure

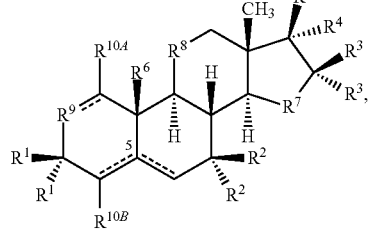
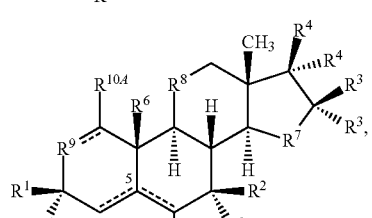
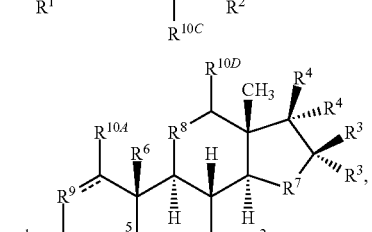
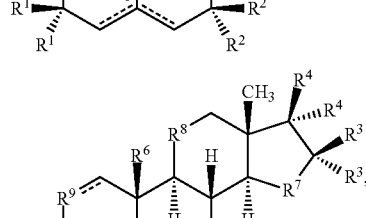
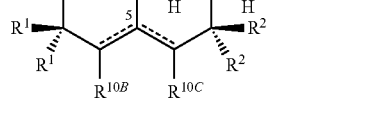

-continued

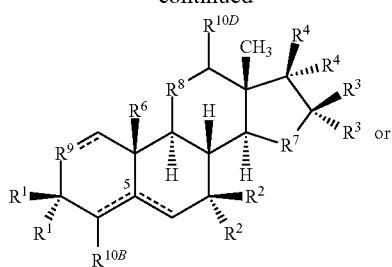

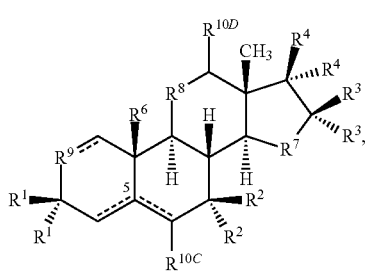

or a salt thereof, wherein the dotted lines are optional double bonds and —H at the 5-position (if present) is in the α- or β-configuration or if a double bond is present at the 1-2, 4-5 or 5-6 positions, then $R^{10A}$, $R^{10B}$ or $R^{10C}$ respectively are bonded to the ring to which they are linked by a single bond; $R^{10A}$ and $R^{10B}$, $R^{10A}$ and $R^{10C}$, $R^{10A}$ and $R^{10D}$, $R^{10B}$ and $R^{10C}$, $R^{10B}$ or $R^{10D}$ and $R^{10C}$ respectively are in the α,α-, α,β-, β,α- or β,β-configurations;

wherein one of $R^1$ is —H, an optionally substituted alkyl group, an optionally substituted alkenyl group or an optionally substituted alkynyl group and the other $R^1$ is —OH, an ester, or an alkoxy group; $R^2$ and $R^3$ independently are —H, —OH, an ester, an alkoxy group or a halogen; one $R^4$ is —OH, an ester or an alkoxy group and the other $R^4$ is an optionally substituted N-linked heterocycle; $R^5$ and $R^6$ independently are —H or an optionally substituted alkyl group; $R^7$, $R^8$ and $R^9$ independently are —C($R^{10}$)$_2$— or =C($R^{10}$)—, wherein $R^{10}$ are independently selected; $R^{10}$, $R^{10A}$, $R^{10B}$, $R^{10C}$ and $R^{10D}$ independently are —H, halogen, —$SR^{PR}$ or —$OR^{PR}$; $R^{PR}$ independently are —H or a protecting group, wherein $R^{PR}$ of —$OR^{PR}$ defines an ester or an alkoxy group;

wherein (1) one $R^2$ is as defined and the other $R^2$ is —OH, an ester or an ether, or (2) one of $R^{10A}$ and $R^{10B}$, $R^{10A}$ and $R^{10C}$, $R^{10A}$ and $R^{10D}$, $R^{10B}$ and $R^{10C}$, $R^{10B}$ and $R^{10D}$ or $R^{10C}$ and $R^{10D}$ are halogen, —$SR^{PR}$ or —$OR^{PR}$ and the other $R^{10A}$, $R^{10B}$, $R^{10C}$ or $R^{10D}$ are as defined.

42B. The compound of embodiment 41B wherein $R^7$, $R^8$ and $R^9$ independently are —CH$_2$—, —CHOH—, —CH(αR$^{10}$)—, —CH(ester)-, —CH(alkoxy)- or —CH(halogen)-, wherein hydroxyl, the ester, the alkoxy group or the halogen atom is present in the α-configuration and the alkoxy group is —OCH$_3$, —OC$_2$H$_5$ and —OC$_3$H$_7$ and the halogen atom is —F, —Cl or —Br.

43B. The compound of embodiment 42B, wherein the compound has the structure

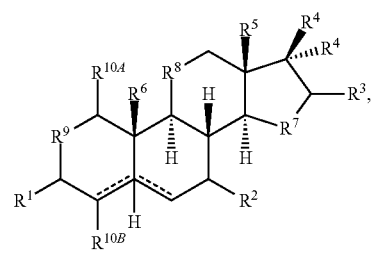

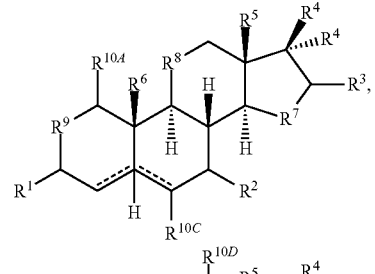

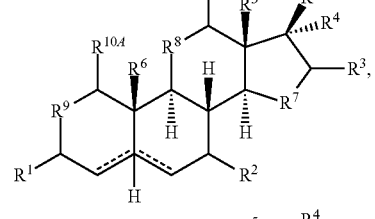

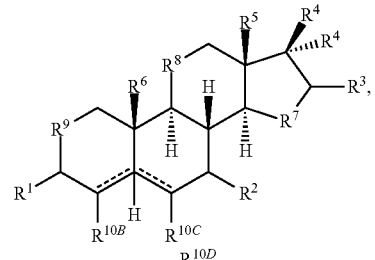

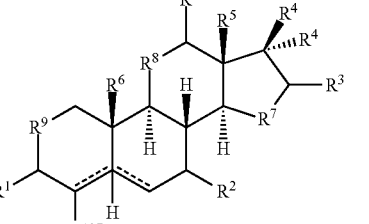

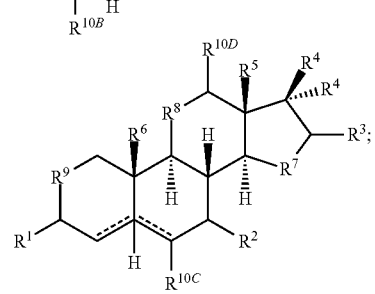

wherein $R^1$ is —OH, an ester or an alkoxy group; $R^2$ is —H, —OH, an ester or an alkoxy group; $R^3$ is —H, a halogen, —OH, an ester or an alkoxy group; one $R^4$ is —H and other $R^4$ is an optionally substituted N-linked heterocycle moiety; $R^5$ and $R^6$ independently are —H, —CH$_3$ or —CH$_2$OH; and $R^7$, $R^8$ and $R^9$ are —CH$_2$—;

wherein one of $R^{10A}$ and $R^{10B}$, $R^{10A}$ and $R^{10C}$, $R^{10A}$ and $R^{10D}$, $R^{10B}$ and $R^{10C}$, $R^{10B}$ and $R^{10D}$ or $R^{10C}$ and $R^{10D}$ are hydrogen or —$OR^{PR}$ and the other $R^{10A}$, $R^{10B}$, $R^{10C}$, $R^{10D}$ and $R^{10D}$ or $R^{10C}$ and $R^{10D}$ are halogen or —$OR^{PR}$ and the other $R^{10A}$, $R^{10B}$, $R^{10C}$ or $R^{10D}$ are as defined.

44B. The compound of embodiment 43B, wherein the compound has the structure

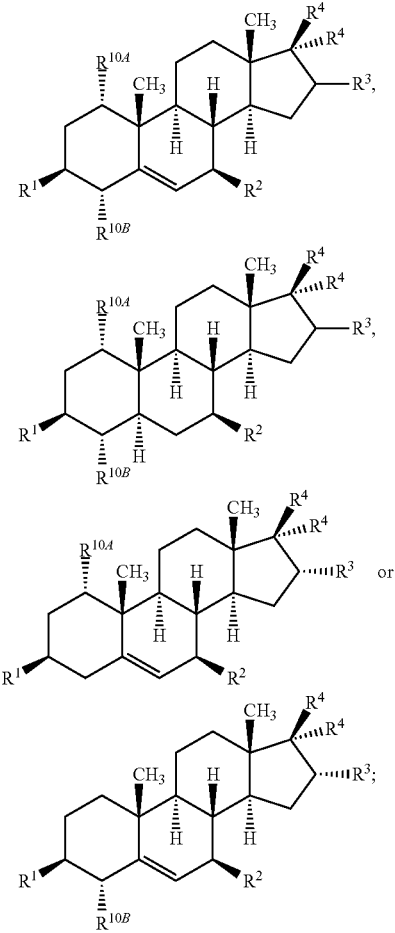

wherein $R^1$ is —OH, an ester or an alkoxy group; $R^2$ is —H, —OH, an ester or an alkoxy group; $R^3$ is —H a halogen, —OH, an ester or an alkoxy group; one $R^4$ is —H and the other $R^4$ is an optionally substituted N-linked heterocycle moiety; $R^{10A}$ or $R^{10B}$ is halogen or —$OR^{PR}$.

45B. The compound of embodiment 41B, wherein the compound has the structure

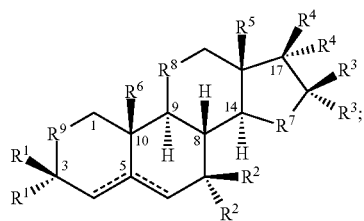

wherein one each of $R^1$ and $R^2$ are —H and the other $R^1$ and $R^2$ independently are —OH or an ester; one of $R^3$ is —H and the other $R^3$ is —OH, a halogen, an ester or an alkoxy group; one $R^4$ is —H and the other $R^4$ is an optionally substituted N-linked heterocycle moiety; $R^5$ is —CH$_3$, —CH$_2$CH$_3$ or —CH$_2$OH; $R^6$ is —H, —CH$_3$ or —CH$_2$OH; and $R^7$, $R^8$ and $R^9$ are —CH$_2$—.

46B. The compound of embodiment 45B, wherein the compound has the structure

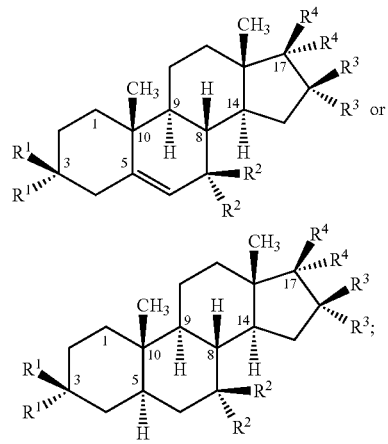

wherein one $R^4$ is —OH and the other $R^4$ is a N-linked heterocycle moiety wherein the N-linked heterocycle moiety is —N-pyrrolidine, —N1-pyrazolone, —N2-pyrazolone, —N-imidazolidin-2-one, —N1-imidazole, —N1-4,5-dihydroimidazole, —N-morpholine, —N-piperidine, —N-indole, —N-indoline, —N-quinolidine or —N1-piperazine, optionally substituted at N4 with an optionally substituted alkyl, aryl or heteroaryl moiety.

47B. A compound having the structure

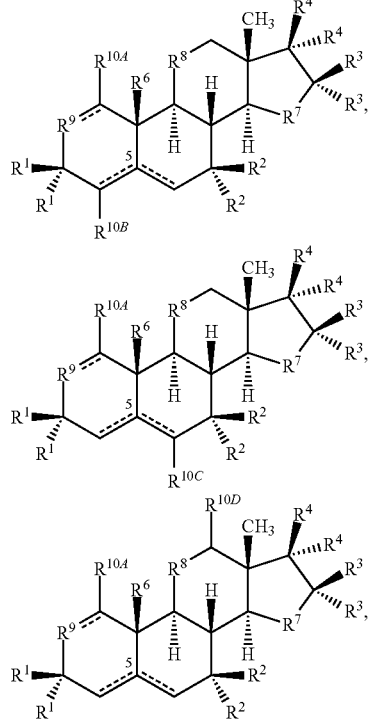

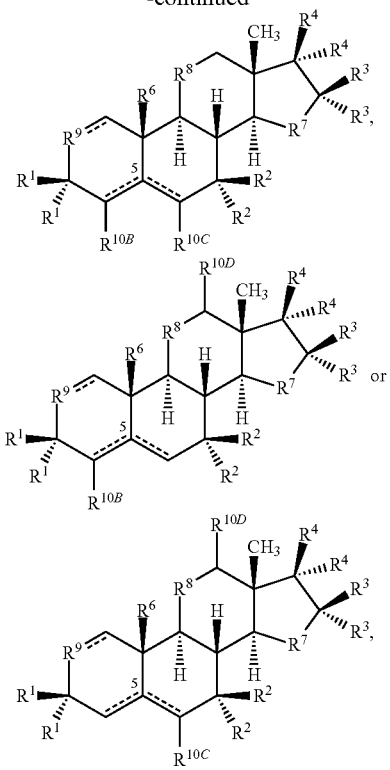

or a salt thereof, wherein the dotted lines are optional double bonds and —H at the 5-position (if present) is in the α- or β-configuration or if a double bond is present at the 1-2,4-5 or 5-6 positions, then $R^{10A}$, $R^{10B}$ or $R^{10C}$ respectively are bonded to the ring to which they are linked by a single bond;

wherein one each of $R^1$, $R^2$ and $R^3$ is —H and the other $R^1$ is —OH, the other $R^2$ and $R^3$ independently are —H, —OH, a halogen, an ester or an alkoxy group; one of $R^4$ is —H or an optionally substituted alkyl group the other $R^4$ is —NH$_2$, —N(R$^{PR}$)$_2$, an optionally substituted amine moiety or an optionally substituted amide group or both $R^4$ together are =N—OH or =NO-optionally substituted alkyl; $R^6$ is —H or —CH$_3$; $R^7$ is —CH(R$^{10}$)$_2$— or =CH(R$^{10}$)— and $R^8$ and $R^9$ independently are —C(R$^{10}$)$_2$—, wherein $R^{10}$ are independently selected; $R^{10}$, $R^{10A}$, $R^{10B}$, $R^{10C}$ and $R^{10D}$ independently are —H, a halogen, —SR$^{PR}$ or —OR$^{PR}$; R$^{PR}$ independently are —H or a protecting group; wherein the protecting group defines —OR$^{PR}$ as an ester or an alkoxy group;

wherein (1) $R^{10A}$ in $R^{10A}$ and $R^{10B}$, $R^{10A}$ and $R^{10C}$ or $R^{10A}$ and $R^{10D}$ is a halogen, —OH, —SR$^{PR}$ or —OR$^{PR}$, and the other $R^{10B}$, $R^{10C}$ or $R^{10D}$ are as defined, or (2) $R^{10B}$ and $R^{10C}$, $R^{10B}$ and $R^{10B}$ or $R^{10C}$ and $R^{10D}$ independently are a halogen, —SR$^{PR}$ or —OR$^{PR}$, or (3) one $R^2$ and one $R^3$ is as defined and the other $R^2$ and $R^3$ independently are —OH, a halogen, an ester or an alkoxy group; and wherein the optionally substituted alkyl groups independently are —CH$_3$, —CH$_2$CH$_3$, —CH$_2$OH, or —CH$_2$-(ester), the alkoxy groups independently are —OCH$_3$, —OC$_2$H$_5$ or —OC$_3$H$_7$, the esters independently are a hydroxyl ester.

48B. The compound of embodiment 47B wherein the hydroxyl ester is acetate, enanthate, propionate, isopropionate, isobutyrate, butyrate, valerate, caproate, isocaproate, hexanoate, heptanoate, octanoate, nonanoate, decanoate, undecanoate, phenylacetate or benzoate.

49B. The compound of embodiment 47B wherein $R^{10}$, $R^{10A}$, $R^{10B}$, $R^{10C}$ and $R^{10D}$ independently are —H, a halogen, —OH, an alkoxy group or a hydroxyl ester, wherein the halogen atom is —F, —Cl or —Br, the alkoxy group is —OCH$_3$ or —OC$_2$H$_5$ and the hydroxyl ester is —O—C(O)—CH$_3$ or —O—C(O)—CH$_2$CH$_3$.

50B. The compound of embodiment 49B, wherein $R^{10}$, $R^{10A}$, $R^{10B}$, $R^{10C}$ and $R^{10D}$ independently are —H, α-OH, or β-OH, wherein (1) $R^{10A}$ in $R^{10A}$ and $R^{10B}$, $R^{10A}$ and $R^{10C}$ or $R^{10A}$ and $R^{10D}$ is α-OH or β-OH and the other $R^{10B}$, $R^{10C}$ or $R^{10D}$ is as defined, or (2) $R^{10B}$ and $R^{10C}$, $R^{10B}$ and $R^{10D}$ or $R^{10C}$ and $R^{10D}$ independently are α-OH or β-OH.

51B. The compound of embodiment 47B, wherein $R^7$ is —C(R$^{10}$)$_2$— or —C(R$^{10}$)$_2$— and $R^8$ and $R^9$ independently are —C(R$^{10}$)$_2$— or =C(R$^{10}$)—, wherein one $R^{10}$ is —H, —OH, an ester, an alkoxy group or a halogen, in the α- or β-configuration, and the other $R^{10}$, if present, is —H.

52B. The compound of embodiment 51B, wherein $R^7$, $R^8$ and $R^9$ independently are —CH$_2$—, —CF$_2$—, —CH(OH)—, —CH(R$^{10}$)—, —CH(ester)-, —CH(alkoxy)- or —CH(halogen)-, wherein —OH, $R^{10}$, the ester, the alkoxy group or the halogen atom is present in the α-configuration; and wherein the halogen atom is —F, —Cl or —Br, the alkoxy group is —OCH$_3$, —OC$_2$H$_5$ or —OC$_3$H$_7$ and the ester is —OC(O)—CH$_3$ or —OC(O)CH$_2$CH$_3$.

53B. The compound of embodiment 47B, wherein the other $R^2$ is —H, —OH or an alkoxy group, wherein the alkoxy group is —OCH$_3$, and the other $R^3$ is —H, halogen, —OH or a hydroxyl ester, wherein the hyroxyl ester is —O—C(O)—CH$_3$ or —O—C(O)—CH$_2$CH$_3$; the other $R^4$ is an optionally substituted amine moiety or an optionally substituted amide group; $R^6$ is —H or —CH$_3$; $R^7$, $R^8$ and $R^9$ independently are —C(R$^{10}$)$_2$, wherein $R^{10}$ independently are —H, —OH or a halogen; $R^{10A}$ is halogen or $R^{10A}$ and $R^{10B}$, $R^{10A}$ and $R^{10C}$ or $R^{10A}$ and $R^{10D}$, $R^{10B}$ and $R^{10C}$, $R^{10B}$ and $R^{10D}$ or $R^{10C}$ and $R^{10D}$ independently are —OH or a halogen; and wherein the halogens independently are —F, —Cl or —Br.

54B. The compound of embodiment 47B, wherein the compound has the structure

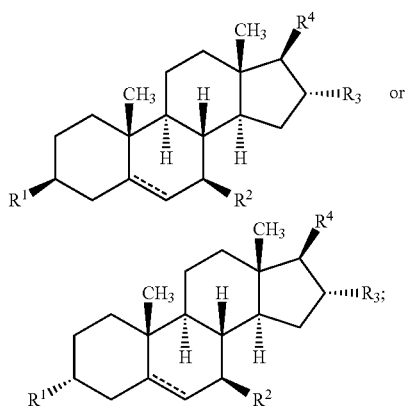

wherein $R^1$ is —OH; $R^2$ is —OH or an alkoxy group; $R^3$ is a halogen, —OH, a hydroxyl ester; and $R^4$ is an optionally substituted amine moiety or =NOH.

55B. The compound of embodiment 47B, wherein $R^1$ and $R^2$ are —OH; $R^3$ is —OH, =O, a halogen or a hydroxyl ester, wherein the halogen atom is —F or —Br and the hydroxyl ester is —O—C(O)—CH$_3$ or —O—C(O)—CH$_2$CH$_3$; and $R^4$ is an optionally substituted amine moiety, wherein the optionally substituted amine moiety is —NH$_2$, —NHCH$_3$, —N(CH$_3$)$_2$, —N$^+$(CH$_3$)$_3$, —NH—C$_2$H$_5$ or —NHOH, or an optionally substituted amide group, wherein the optionally substituted amide group is —NH—C(O)CH$_3$.

56B. The compound of embodiment 55B, wherein the compound has the structure

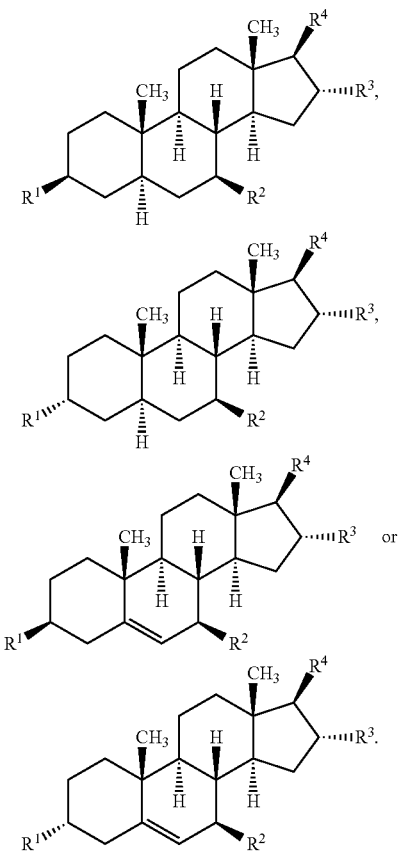

57B. The compound of embodiment 47B, wherein the compound is 3β,7β-dihydroxy-6-chloro-16-oxo-17β-aminoandrost-5-ene, 3β-hydroxy-6-chloro-16α-fluoro-17β-aminoandrost-5-ene, 3β,7β-dihydroxy-6α-bromo-16-oxo-17β-aminoandrostane or 3β-hydroxy-6α-bromo-16α-fluoro-17β-aminoandrostane.

58B. The compound of embodiment 47B, wherein the compound is 3β,7β-dihydroxy-16-oxo-17β-aminoandrost-5-ene or 3β,7β-dihydroxy-16α-fluoro-17β-aminoandrostane.

59B. A pharmaceutical formulation comprising one or more excipients and a compound according to claim 1B, 16B, 34B, 41B or 47B.

1C. A compound having the structure

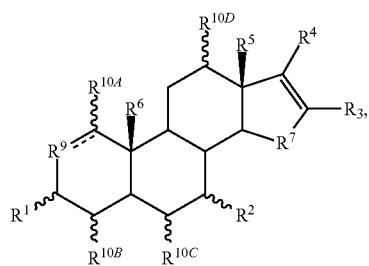

or a salt thereof, wherein the dotted line is an optional double bond;

R$^1$ is —OH, =O, —SH, amide, ester or ether; R$^2$ is —OH, =O, halogen, optionally substituted alkyl, ester or ether; R$^3$ is —H, —OH, halogen, optionally substituted alkyl, ester or ether; R$^4$ is optionally substituted heterocycle; R$^5$ and R$^6$ independently are —H, —CH$_3$, —C$_2$H$_5$, —C$_3$H$_7$, optionally substituted alkyl, —OH, —F, —Cl, —Br or —I; R$^7$ is —CH$_2$—, —C(halogen)$_2$-, —CH(α-optionally substituted alkyl), —CH(β-optionally substituted alkyl), —CH(α-OH), —CH(β-OH) or —C(optionally substituted alkyl)$_2$-; R$^9$ is —CH$_2$—, —CH(α-OH), —CH(β-OH) or —C(optionally substituted alkyl)$_2$-; and R$^{10A}$, R$^{10B}$, R$^{10C}$ and R$^{10D}$ independently are —H, optionally substituted alkyl, —CH$_3$, halogen, —SR$^{PR}$ or —OR$^{PR}$ and each R$^{10A}$, R$^{10B}$, R$^{10C}$ and R$^{10D}$ is independently in the α-configuration or the β-configuration and wherein R$^{PR}$ independently are —H or a protecting group.

2C. The compound of embodiment 1C wherein the compound has the structure

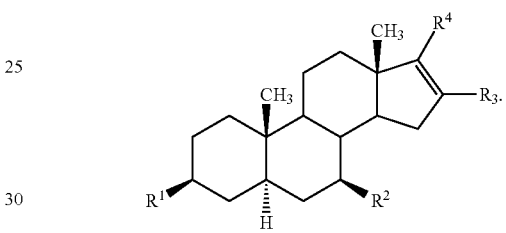

3C. The compound of embodiment 1C wherein the compound has the structure

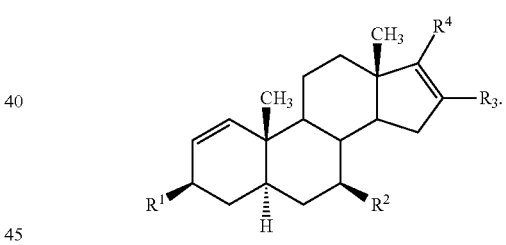

4C. The compound of embodiment 2C wherein R$^1$ is —OH, =O or —NH—C(O)CH$_3$; R$^2$ is —OH or —OCH$_3$; and R$^3$ is —H, —OH, —O—C(O)CH$_3$ or —O—C(O)CH$_2$CH$_3$.

5C. The compound of embodiment 1C wherein R$^4$ is —N-pyrrolidine, —N1-pyrazolone, —N2-pyrazolone, —N-imidazolidin-2-one, —N1-imidazole, —N1-4,5-dihydroimidazole, —N-morpholine, —N1-pyridine, —N-piperidine or —N-piperazine.

6C. The compound of embodiment 1C wherein R$^4$ is 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

7C. The compound of embodiment 1C wherein R$^4$ is 1-aziridyl, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, 2-isoindole, 2-isoindoline, 4- morpholine, 9-carbazole or β-carboline.

8. The compound of embodiment 1 wherein the compound has the structure

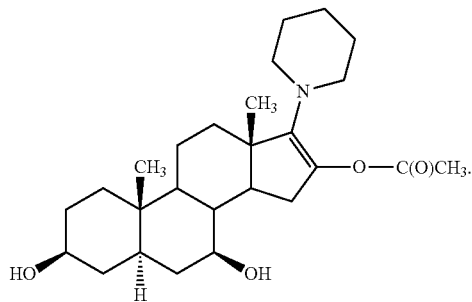

9C. A pharmaceutical formulation comprising one or more excipients and a compound according to embodiment 1C.

10C. A compound having the structure

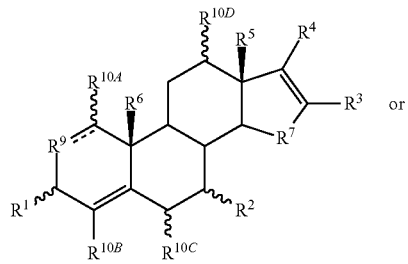

or

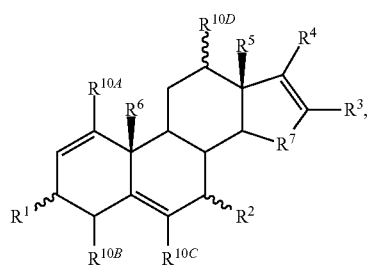

or a salt thereof, wherein the dotted line is an optional double bond;
$R^1$ is —OH, =O, —SH, amide, ester or ether; $R^2$ is —OH, =O, halogen, optionally substituted alkyl, ester or ether; $R^3$ is —H, —OH, halogen, optionally substituted alkyl, ester or ether; $R^4$ is optionally substituted heterocycle; $R^5$ and $R^6$ independently are —H, —CH$_3$, —C$_2$H$_5$, —C$_3$H$_7$, optionally substituted alkyl, —OH, —F, —Cl, —Br or —I; $R^7$ is —CH$_2$—, —C(halogen)$_2$-, —CH(α-optionally substituted alkyl), —CH(β-optionally substituted alkyl), —CH(α-OH), —CH(β-OH) or —C(optionally substituted alkyl)$_2$-; $R^9$ is —CH$_2$—, —CH(α-OH), —CH(β-OH) or —C(optionally substituted alkyl)$_2$-; and $R^{10A}$, $R^{10B}$, $R^{10C}$ and $R^{10D}$ independently are —H, optionally substituted alkyl, —CH$_3$, halogen, —SR$^{PR}$ or —OR$^{PR}$ and each $R^{10A}$, $R^{10B}$, $R^{10C}$ and $R^{10D}$ is independently in the α-configuration or the β-configuration and wherein $R^{PR}$ independently are —H or a protecting group.

11C. The compound of embodiment 10C wherein the compound has the structure

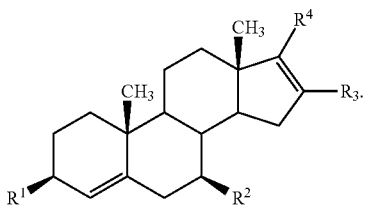

12C. The compound of embodiment 11C wherein the compound has the structure

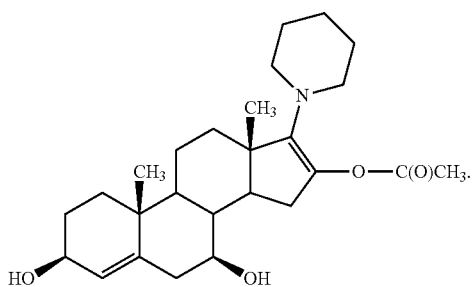

13C. The compound of embodiment 10C wherein the compound has the structure

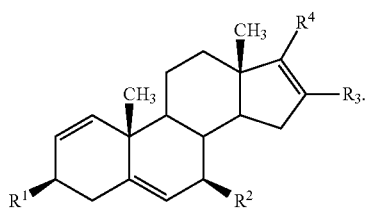

14C. The compound of embodiment 11C wherein $R^1$ is —OH, =O or —NH—C(O)CH$_3$; $R^2$ is —OH or —OCH$_3$; and $R^3$ is —H, —OH, —O—C(O)CH$_3$ or —O—C(O)CH$_2$CH$_3$.

15C. The compound of embodiment 1C wherein $R^4$ is —N-pyrrolidine, —N1-pyrazolone, —N2-pyrazolone, —N-imidazolidin-2-one, —N1-imidazole, —N1-4,5-dihydroimidazole, —N-morpholine, —N1-pyridine, —N-piperidine or —N-piperazine.

16C. The compound of embodiment 1C wherein $R^4$ is 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl or 5-thiazolyl.

17C. The compound of embodiment 1C wherein $R^4$ is 1-aziridyl, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, 2-isoindole, 2-isoindoline, 4- morpholine, 9-carbazole or β-carboline.

18C. A pharmaceutical formulation comprising one or more excipients and a compound according to embodiment 10C.

19C. A compound having the structure

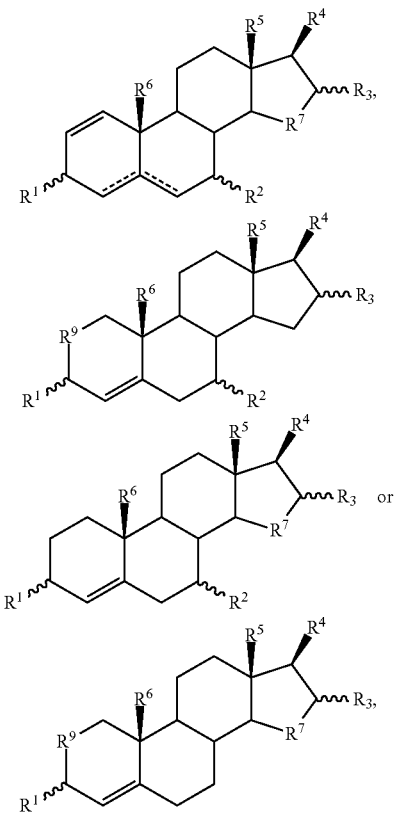

or a salt thereof, wherein the dotted lines are optional double bonds;

$R^1$ is —OH, =O, —SH, amide, ester or ether; $R^2$ is —OH, =O, halogen, optionally substituted alkyl, ester or ether; $R^3$ is —H, —OH, halogen, optionally substituted alkyl, ester or ether; $R^4$ is —OH, ester, ether, —NH$_2$, —NH—C(O)CH$_3$, —NH—CH$_3$, —N(CH$_3$)$_2$, —NHOH or optionally substituted heterocycle; $R^5$ and $R^6$ independently are —H, —CH$_3$, —C$_2$H$_5$, —C$_3$H$_7$, optionally substituted alkyl, —OH, —F, —Cl, —Br or —I; $R^7$ is —C(halogen)$_2$-, —CH($\alpha$-optionally substituted alkyl), —CH($\beta$-optionally substituted alkyl), —CH($\alpha$-OH), —CH($\beta$-OH) or —C(optionally substituted alkyl)$_2$-; and $R^9$ is —CH($\alpha$-OH), —CH($\beta$-OH) or —C(optionally substituted alkyl)$_2$-.

20C. The compound of embodiment 19C wherein the compound has the structure

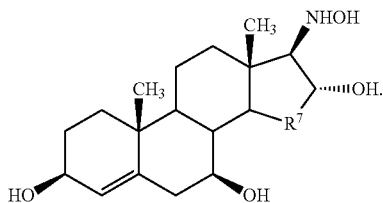

21C. A pharmaceutical formulation comprising one or more excipients and a compound according to embodiment 19.

22C. A compound having the structure

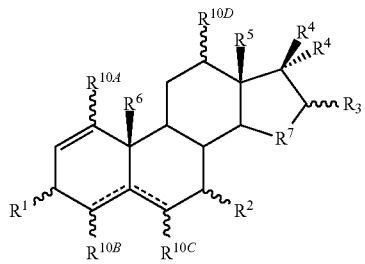

or a salt thereof, wherein the dotted lines are optional double bonds;

$R^1$ is —OH, =O, —SH, amide, ester or ether; $R^2$ is —OH, =O, halogen, optionally substituted alkyl, ester or ether; $R^3$ is —H, —OH, halogen, optionally substituted alkyl, ester or ether; one $R^4$ is —OH, ester, ether, —NH$_2$, —NH—C(O)CH$_3$, —NH—CH$_3$, —N(CH$_3$)$_2$, —NHOH or optionally substituted heterocycle; the other $R^4$ is —H, optionally substituted alkyl, halogen, —SH or —OH; $R^5$ and $R^6$ independently are —H, —CH$_3$, —C$_2$H$_5$, —C$_3$H$_7$, optionally substituted alkyl, —OH, —F, —Cl, —Br or —I; $R^7$ is —CH$_2$—, —C(halogen)$_2$-, —CH($\alpha$-optionally substituted alkyl), —CH($\beta$-optionally substituted alkyl), —CH($\alpha$-OH), —CH($\beta$-OH) or —C(optionally substituted alkyl)$_2$-; $R^9$ is —CH$_2$—, —CH($\alpha$-OH), —CH($\beta$-OH) or —C(optionally substituted alkyl)$_2$-; and $R^{10A}$, $R^{10B}$, $R^{10C}$ and $R^{10D}$ independently are —H, optionally substituted alkyl, —CH$_3$, halogen, —SR$^{PR}$ or —OR$^{PR}$ and each $R^{10A}$, $R^{10B}$, $R^{10C}$ and $R^{10D}$ is independently in the $\alpha$-configuration or the $\beta$-configuration, wherein R$^{PR}$ independently are —H or a protecting group and wherein one or two of $R^{10A}$, $R^{10B}$, $R^{10C}$ and $R^{10D}$ are not —H.

23C. The compound of embodiment 22C wherein the compound has the structure

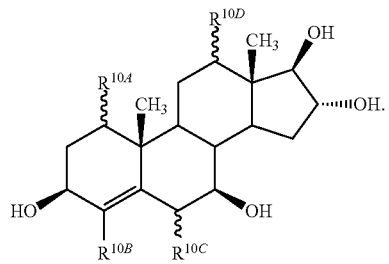

24C. A compound having the structure

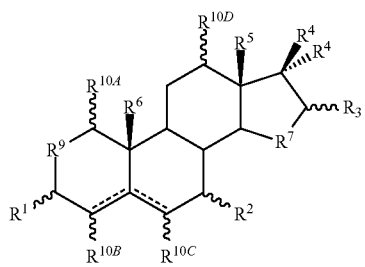

or a salt thereof, wherein the dotted lines are optional double bonds;

$R^1$ is —OH, =O, —SH, amide, ester or ether; $R^2$ is —H, —OH, =O, halogen, optionally substituted alkyl, ester or ether; $R^3$ is —H, —OH, halogen, optionally substituted alkyl, ester or ether; one $R^4$ is —OH, ester, ether, —NH$_2$, —NH—C(O)CH$_3$, —NH—CH$_3$, —N(CH$_3$)$_2$, —NHOH or optionally substituted heterocycle; the other $R^4$ is —H, optionally substituted alkyl, halogen, —SH or —OH; $R^5$ and $R^6$ independently are —H, —CH$_3$, —C$_2$H$_5$, —C$_3$H$_7$, optionally substituted alkyl, —OH, —F, —Cl, —Br or —I; $R^7$ is —CH$_2$—, —C(halogen)$_2$-, —CH($\alpha$-optionally substituted alkyl), —CF($\beta$-optionally substituted alkyl), —CH($\alpha$-OH), —CH($\beta$-OH) or —C(optionally substituted alkyl)$_2$-; $R^9$ is —CH$_2$—, —CH($\alpha$-OH), —CH($\beta$-OH) or —C(optionally substituted alkyl)$_2$-; and $R^{10A}$, $R^{10B}$, $R^{10C}$ and $R^{10D}$ independently are —H, optionally substituted alkyl, —CH$_3$, halogen, —SR$^{PR}$, —OR$^{PR}$, $\alpha$-OH, $\beta$-OH or =O and each $R^{10A}$, $R^{10B}$, $R^{10C}$ and $R^{10D}$ is independently in the $\alpha$-configuration or the $\beta$-configuration, wherein $R^{PR}$ independently are —H or a protecting group and wherein $R^{10A}$ and $R^{10C}$, $R^{10B}$ and $R^{10C}$ or $R^{10C}$ and $R^{10D}$ are not —H.

25C. The compound of embodiment 24C wherein the compound has the structure

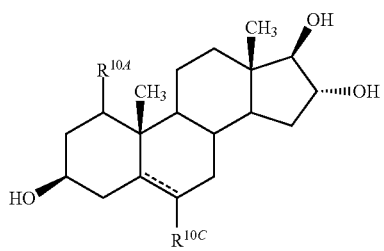

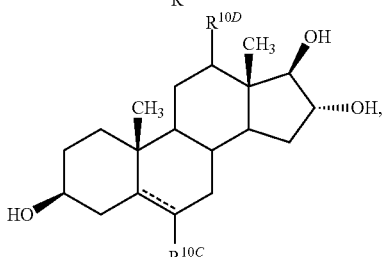

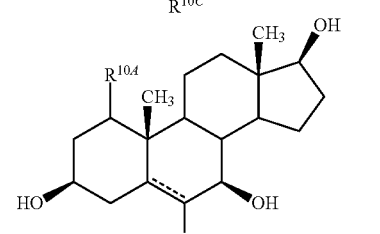

or

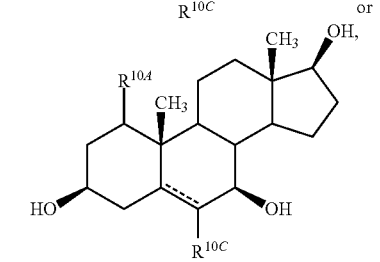

wherein $R^{10A}$ and $R^{10C}$ or $R^{10C}$ and $R^{10D}$ independently are $\alpha$-OH, $\beta$-OH or =O.

26. A pharmaceutical formulation comprising one or more excipients and a compound according to claim 24.

1. A method to prevent, treat, ameliorate or slow the progression of cystic fibrosis, sickle cell disease, neutropenia or thrombocytpoenia in a subject, or to treat a symptom of the neutropenia or thrombocytopenia, comprising administering to a subject, or delivering to the subject's tissues, an effective amount of a formula 1 compound having the structure 5, 6, 7, 8, 9, 10, 11, 12, 13 or 14

5

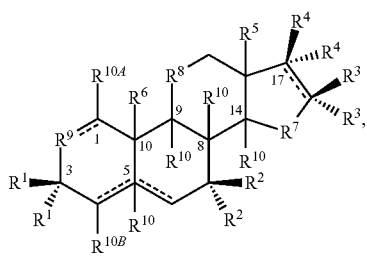

6

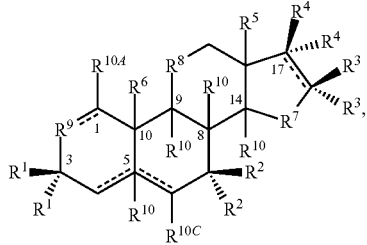

7

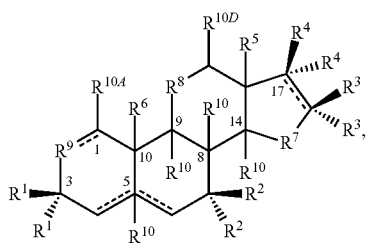

8

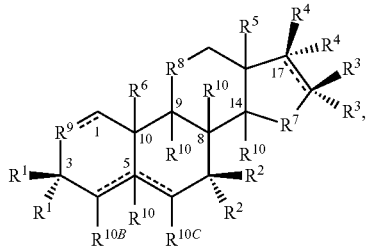

9

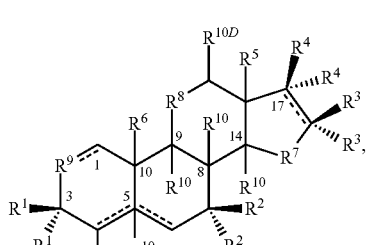

-continued

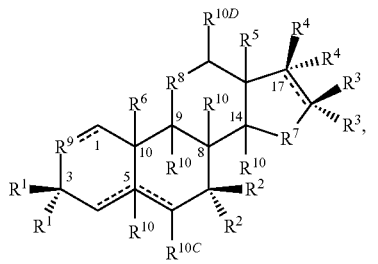

10

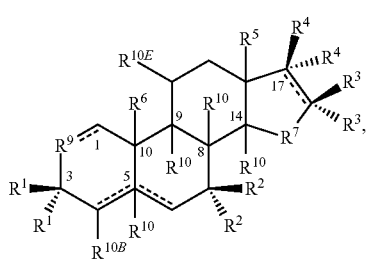

11

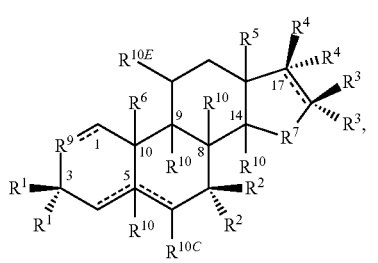

12

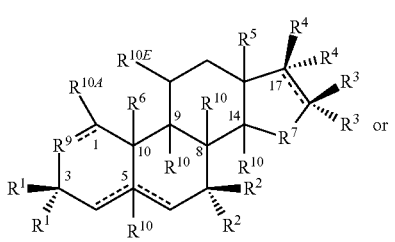

13

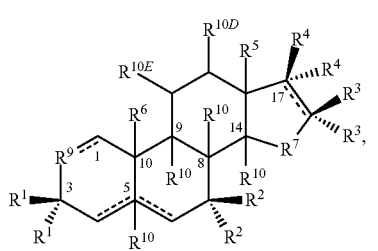

14 or a metabolic precursor or a metabolite thereof, wherein $R^{10}$ moieties at the 5 (if present), 8, 9 and 14 positions respectively are in the α,α,α,α, α,α,α,β, α,α,β,α, α,β,α,α, β,α,α,α, α,α,β,β, α,β,α,β, β,α,α,β, β,α,β,α, β,β,α,α, α,β,β,α, α,β,β,β, β, β,α,β,β, β,β,α,β, β,β,β,α or β,β,β,β configurations, wherein $R^{10A}$, $R^{10B}$, $R^{10C}$, $R^{10D}$ and $R^{10E}$ respectively are in the α,α, α,β, β,α or β,β configurations, wherein, each $R^1$, $R^2$, $R^3$, $R^4$, $R^5$, $R^6$, $R^{10}$, $R^{10A}$, $R^{10B}$, $R^{10C}$, $R^{10D}$ and $R^{10E}$ independently are —H, —OH, —OR$^{PR}$, —SR$^{PR}$, —N(R$^{PR}$)$_2$, —O—Si—(R$^{13}$)$_3$, —CHO, —CHS, —CN, —SCN, —NO$_2$, —NH$_2$, —COOH, —OSO$_3$H, —OPO$_3$H, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate, a carbamate, a halogen, an optionally substituted alkyl group, an optionally substituted alkenyl group, an optionally substituted alkynyl group, an optionally substituted aryl moiety, an optionally substituted heteroaryl moiety, an optionally substituted heterocycle, an optionally substituted monosaccharide, an optionally substituted oligosaccharide, a nucleoside, a nucleotide, an oligonucleotide, a polymer, or one or more of $R^1$, $R^2$, $R^3$, $R^4$, $R^5$, $R^6$, $R^{10}$, $R^{10A}$, $R^{10B}$, $R^{10C}$, $R^{10D}$ and $R^{10E}$ are =O, =S, =N—OH, =CH$_2$, =CH—CH$_3$, or an independently selected spiro ring and the hydrogen atom or the second variable group that is bonded to the same carbon atom is absent, or one or more of two adjacent $R^1$-$R^6$, $R^{10}$, $R^{10A}$, $R^{10B}$, $R^{10C}$, $R^{10D}$ and $R^{10E}$ comprise an independently selected epoxide, acetal, a thioacetal, ketal or thioketal;

$R^7$ is —C(R$^{10}$)$_2$—, —C(R$^{10}$)$_2$—C(R$^{10}$)$_2$—, —C(R$^{10}$)$_2$—C(R$^{10}$)$_2$—C(R$^{10}$)$_2$—, —C(R$^{10}$)$_2$—O—C(R$^{10}$)$_2$—, —C(R$^{10}$)$_2$—S—C(R$^{10}$)$_2$—, —C(R$^{10}$)$_2$—NR$^{PR}$—C(R$^{10}$)$_2$—, —O—, —O—C(R$^{10}$)$_2$—, —S—, —S—C(R$^{10}$)$_2$—, —NR$^{PR}$— or —NR$^{PR}$—C(R$^{10}$)$_2$—; $R^8$ and $R^9$ independently are —C(R$^{10}$)$_2$—, —C(R$^{10}$)$_2$—C(R$^{10}$)$_2$—, —O—, —O—C(R$^{10}$)$_2$—, —S—, —S—C(R$^{10}$)$_2$—, —NR$^{PR}$— or —NR$^{PR}$—C(R$^{10}$)$_2$—, or one or both of $R^8$ or $R^9$ independently are absent, leaving a 5-membered ring; $R^{13}$ independently is C$_{1-6}$ alkyl; and R$^{PR}$ independently is —H or a protecting group;

optionally provided that (1) one or two of $R^{10A}$, $R^{10B}$, $R^{10C}$, $R^{10D}$ and $R^{10E}$ are not hydrogen or (2) one $R^4$ is —NH$_2$, an opotionally substituted amine, —N(R$^{PR}$)$_2$, =NOH, =NO-optionally substituted alkyl, an amide or an N-linked amino acid. In these embodiments, the subject may have or be subject to developing the listed condition and the subject can be a human or a primate.

2. The method of embodiment 1 wherein one each of $R^1$, $R^2$, $R^3$ and $R^4$ are —H, and, when no double bond links the second $R^1$, $R^2$, $R^3$ and $R^4$ to the ring to which it is bonded and no double bond is present at the 16-17 position, then the second $R^1$, $R^2$, $R^3$ and $R^4$ respectively are in the α,α,α,α, α,α,α,β, α,α,β,α, α,β,α,α, β,α,α,α, α,α,β,β, α,β,α,β, β,α, α,β, β,α,β,α, β,β,α,α, α,β,β,α, α,β,β,β, β,α,β,β, β,β,α,β, β,β,β, α or β,β,β,β configurations and the second $R^1$, $R^2$, $R^3$ and $R^4$ are optionally independently selected from —H, —F, —Cl, —Br, —I, —OH, —SH, —NH$_2$, —COOH, —CH$_3$, —C$_2$H$_5$, —C(CH$_3$)$_3$, —OCH$_3$, —OC$_2$H$_5$, —CF$_3$, —CH$_2$OH, —C(O)CH$_3$, —C(O)CH$_2$OH, —C(O)CH$_2$F, —C(O)CH$_2$Cl, —C(O)CH$_2$Br, —C(O)CH$_2$I, —C(O)CF$_3$, —C$_2$F$_5$, =O, =CH$_2$, =CHCH$_3$, amino acid, carbamate, carbonate, optionally substituted C1-C20 alkyl, optionally substituted C1-C20 ether, optionally substituted C1-C20 ester, optionally substituted C1-C20 thioether, optionally substituted C1-C20 thioester, optionally substituted monosaccharide, optionally substituted disaccharide, optionally substituted oligosaccharide.

3. The method of embodiment 1 or 2 wherein (a) $R^{10A}$ is bonded to the ring to which it is attached by a single bond and a double bond is present at (i) the 1-2 position, or (ii) the 1-2 and 16-17 positions; or (b) $R^{10B}$ is bonded to the ring to which it is attached by a single bond and a double bond is present at the 4-5 position; or (c) $R^{10C}$ is bonded to the ring to which it is attached by a single bond and a double bond is present at the 5-6 position; or (d) $R^{10A}$ and $R^{10B}$ are bonded to the rings to which they are attached by a single bond and a double bond is present at (i) the 1-2 and 4-5 positions, or (ii) the 1-2, 4-5 and 16-17 positions; and (e) $R^{10A}$ and $R^{10C}$ are bonded to the rings to which they are attached by a single bond and a double bond is present at (i) the 1-2 and 5-6 positions, or (ii) the 1-2, 5-6 and 16-17 positions; or (f) no double bond is present.
4. The method of embodiment 1, 2 or 3 wherein the compounds of structure 5, 6, 7, 8, 9, 10, 11 and 12 have the structure
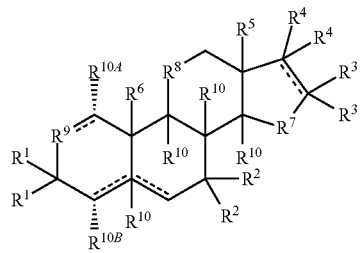
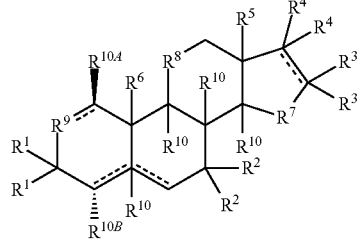
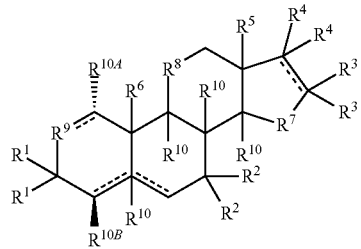
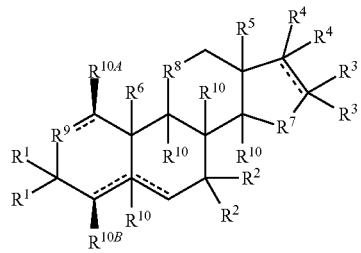
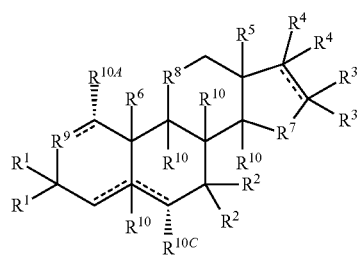
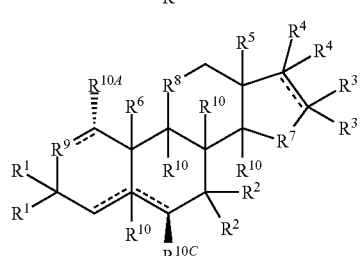
-continued
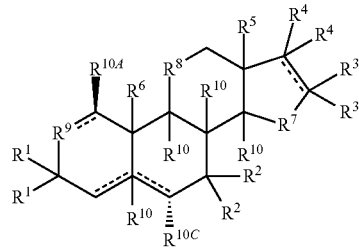
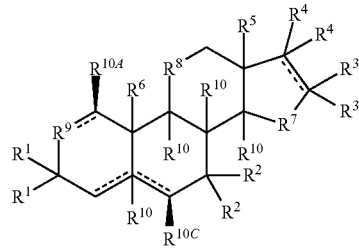
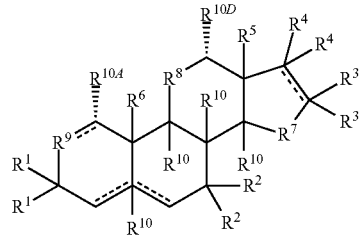
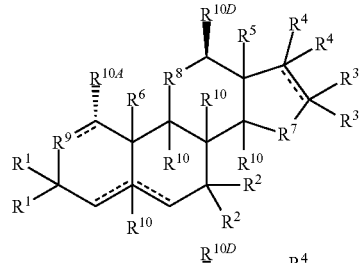
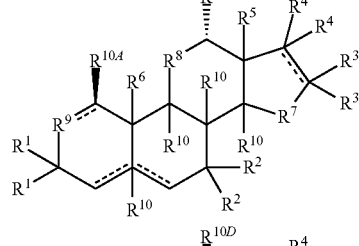
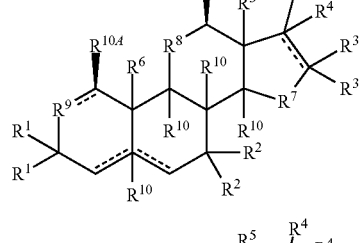
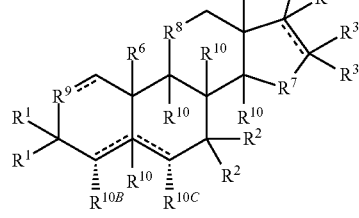

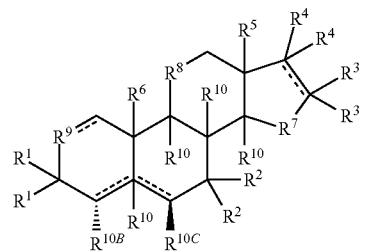
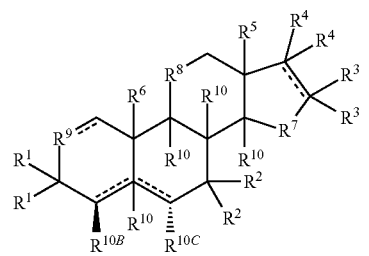
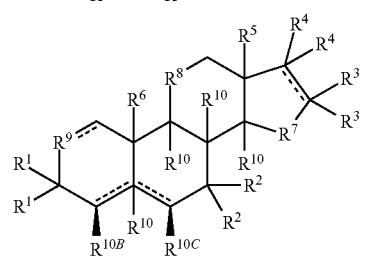
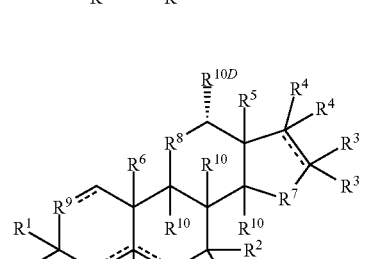
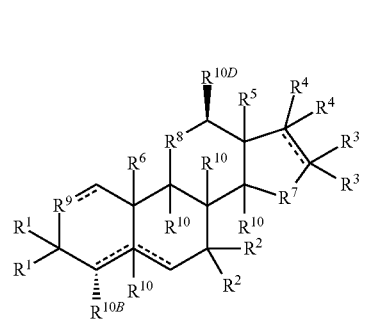
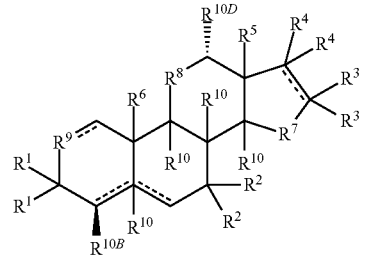
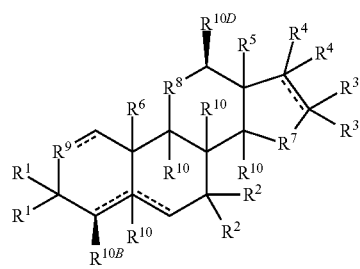
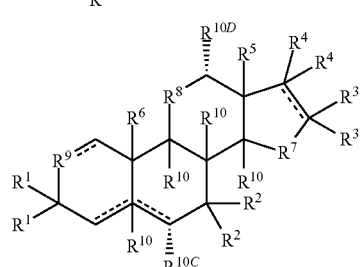
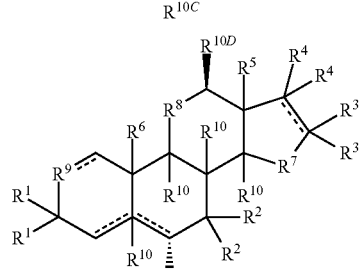
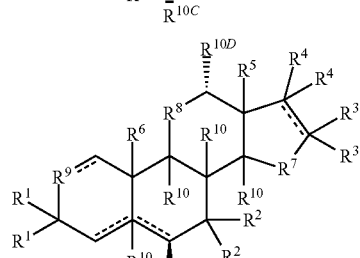
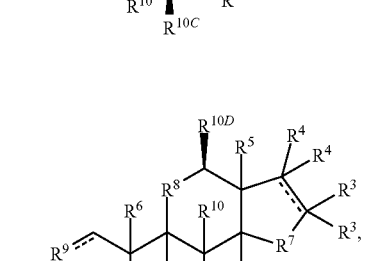
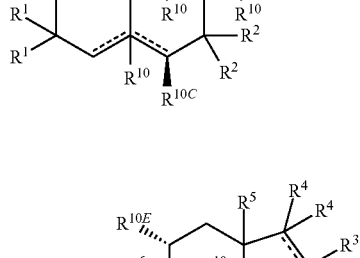
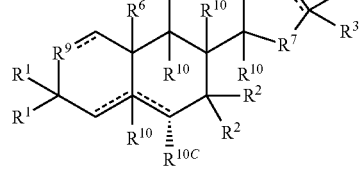

-continued

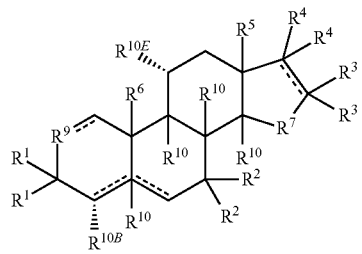

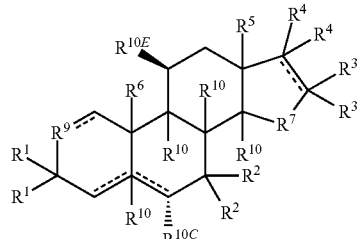

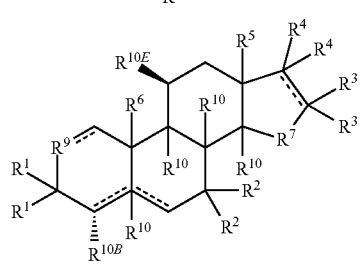

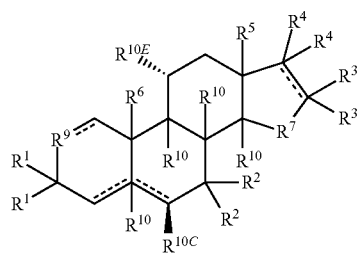

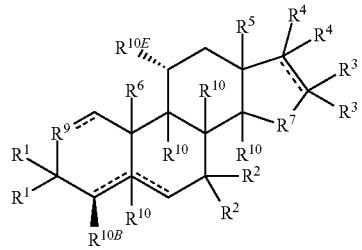

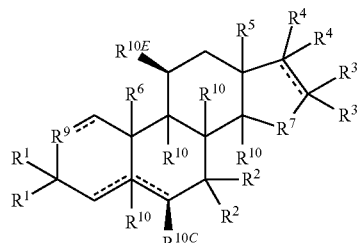

-continued

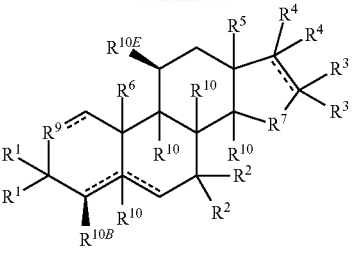

provided that if a double bond is present at the 1-2, 4-5 or 5-6 positions, then $R^{10A}$, $R^{10B}$ or $R^{10C}$ respectively are bonded to the ring to which they are linked by a single bond and wherein, when $R^1$, $R^2$, $R^3$ and $R^4$ are single bonded, one is in the α-configuration and the other $R^1$, $R^2$, $R^3$ and $R^4$ is in the β-configuration.

5. The method of embodiment 1, 2, 3 or 4 wherein (1) $R^5$ and $R^6$ respectively are in the α,α, α,β, β,α or β,β configuration and $R^5$ and $R^6$ are optionally both —CH$_3$ or are optionally selected from —CH$_3$ and —CH$_2$OH or (2) $R^5$ and $R^6$ are both in the β-configuration and $R^5$ and $R^6$ are optionally both —CH$_3$ or are optionally —CH$_3$ and —CH$_2$OH.

6. The method of embodiment 1, 2, 3, 4 or 5 wherein $R^5$ and $R^6$ are optionally both in the β-configuration and are optionally independently selected from —H, —F, —Br, —CH$_3$, —C$_2$H$_5$, —C(CH$_3$)$_3$, —CH$_2$CH$_2$OH, —CH(O), —CH$_2$OH, —CH$_2$-ester, —CH$_2$-ether, —CH$_2$-amino acid, —CH$_2$-carbamate, —CH$_2$OR$^{PR}$, —CHS, —CH$_2$SH, —CH$_2$SR$^{PR}$, —CH$_2$-thioester, —CH$_2$-thioether, —CH$_2$NH$_2$, —CH$_2$NHR$^{PR}$, —CF$_3$, —CH$_2$CH$_3$, —CH$_2$CH$_2$F, —CH$_2$CF$_3$, —CH$_2$OC(O)—(CH$_2$)$_n$—CH$_3$, —CH$_2$OC(O)—(CH$_2$)$_n$—CO$_2$H, —CH$_2$OC(O)—(CH$_2$)n-CO$_2$R$^{PR}$, —CH$_2$OC(O)—(CH$_2$)$_n$—C(O)SH, —CH$_2$OC(O)—(CH$_2$)n-C(O)SR$^{PR}$, —CH$_2$OC(O)—(CH$_2$)$_n$—NH$_2$, —CH$_2$OC(O)—(CH$_2$)n-NHR$^{PR}$, a monosaccharide, and an ester wherein n is 0, 1, 2, 3 or 4 and R$^{PR}$ are independently selected protecting groups for atoms to which they are bonded.

7. The method of embodiment 1, 2, 3, 4, 5 or 6 wherein one each of $R^1$, $R^2$, $R^3$ and $R^4$ are —H and wherein (i) no double bond is present at the 16-17 position, the second $R^1$, $R^2$, $R^3$ and $R^4$ respectively are bonded to the ring to which they are attached by a single bond in the β,β,α,β configurations (i.e., $R^1$ is in the β-configuration, $R^2$ is in the β-configuration, $R^3$ is in the α-configuration and $R^4$ is in the β-configuration when no double bond is present at 16-17), or (ii) a double bond is present at the 16-17 position and $R^1$ and $R^2$ respectively are in the β,β configurations (i.e., $R^1$ is in the β-configuration and $R^2$ is in the β-configuration when a double bond is present at 16-17).

8. The method of embodiment 1, 2, 3, 4, 5 or 6 wherein (i) no double bond is present at the 16-17 position, one each of $R^1$, $R^2$, $R^3$ and $R^4$ are —H, and the second $R^1$, $R^2$, $R^3$ and $R^4$ respectively are bonded to the ring to which they are attached by a single bond in the β, β, β, β configurations or (ii) one each of $R^1$, $R^2$ and $R^3$ are —H, no double bond is present at the 16-17 position, the second $R^1$, $R^2$ and $R^3$ respectively are bonded to the ring to which they are attached by a single bond in the β,β,β, β,β,α, β,α,β, α,β,β, β,α,α, α,β,α, α,α,β or α,α,α configurations and both $R^4$ together are bonded to the ring by a double bond (i.e., both $R^4$ together are a double bonded moiety described herein such as =O, =NOH, =CH$_2$ or =CH—CH$_3$).

9. The method of embodiment 1, 2, 3, 4, 5 or 6 wherein (i) no double bond is present at the 16-17 position, one each of $R^1$, $R^2$, $R^3$ and $R^4$ are —H and the second $R^1$, $R^2$, $R^3$ and $R^4$ respectively are bonded to the ring to which they are attached by a single bond in the β,β,β,α configurations or (ii) one each of $R^1$, $R^2$ and $R^4$ are —H, no double bond is present at the 16-17 position, the second $R^1$, $R^2$ and $R^4$ respectively are bonded to the ring to which they are attached by a single bond in the β,β,β, β,β,α, β,α,β, α,β,β, β,α,α, α,β,α, α,α,β or α,α,α configurations and both $R^3$ together are bonded to the ring by a double bond (i.e., both $R^3$ together are a double bonded moiety described herein such as =O, =NOH, =CH$_2$ or =CH—CH$_3$).

10. The method of embodiment 1, 2, 3, 4, 5 or 6 wherein no double bond is present at the 16-17 position, one each of $R^1$, $R^2$, $R^3$ and $R^4$ are —H and the second $R^1$, $R^2$, $R^3$ and $R^4$ respectively are bonded to the ring to which they are attached by a single bond in the β,β,α,α configurations.

11. The method of embodiment 1, 2, 3, 4, 5 or 6 wherein (i) no double bond is present at the 16-17 position, one each of $R^1$, $R^2$, $R^3$ and $R^4$ are —H, the second $R^1$, $R^2$, $R^3$ and $R^4$ respectively are bonded to the ring to which they are attached by a single bond in the β,α,β,β configurations (i.e., $R^1$ is in the β-configuration, $R^2$ is in the α-configuration, $R^3$ is in the β-configuration and $R^4$ is in the β-configuration when no double bond is present at 16-17), or (ii) a double bond is present at the 16-17 position and $R^1$ and $R^2$ respectively are in the β,α configurations (i.e., $R^1$ is in the β-configuration and $R^2$ is in the α-configuration when a double bond is present at 16-17).

12. The method of embodiment 1, 2, 3, 4, 5 or 6 wherein (i) no double bond is present at the 16-17 position, one each of $R^1$, $R^2$, $R^3$ and $R^4$ are —H, and the second $R^1$, $R^2$, $R^3$ and $R^4$ respectively are bonded to the ring to which they are attached by a single bond in the β,α,β,α configurations or (ii) one each of $R^1$, $R^3$ and $R^4$ are —H, no double bond is present at the 16-17 position, the second $R^1$, $R^3$ and $R^4$ respectively are bonded to the ring to which they are attached by a single bond in the β,β,β, β,β,α, β,α,β, α,β,β, β,α,α, α,β,α, α,α,β or α,α,α configurations and both $R^2$ together are bonded to the ring by a double bond (i.e., both $R^2$ together are a double bonded moiety described herein such as =O, =NOH, =CH$_2$ or =CH—CH$_3$).

13. The method of embodiment 1, 2, 3, 4, 5 or 6 wherein (i) no double bond is present at the 16-17 position, one each of $R^1$, $R^2$, $R^3$ and $R^4$ are —H, and the second $R^1$, $R^2$, $R^3$ and $R^4$ respectively are bonded to the ring to which they are attached by a single bond in the β,α,α,β configurations or (ii) one each of $R^2$, $R^3$ and $R^4$ are —H, no double bond is present at the 16-17 position, the second $R^2$, $R^3$ and $R^4$ respectively are bonded to the ring to which they are attached by a single bond in the β,β,β, β,β,α, β,α,β, α,β,β, β,α,α, α,β,α, α,α,β or α,α,α configurations and both $R^1$ together are bonded to the ring by a double bond (i.e., both $R^1$ together are a double bonded moiety described herein such as =O, =NOH, =CH$_2$ or =CH—CH$_3$).

14. The method of embodiment 1, 2, 3, 4, 5 or 6 wherein no double bond is present at the 16-17 position, one each of $R^1$, $R^2$, $R^3$ and $R^4$ are —H, and the second $R^1$, $R^2$, $R^3$ and $R^4$ respectively are bonded to the ring to which they are attached by a single bond in the β,α,α,α configurations.

15. The method of embodiment 1, 2, 3, 4, 5 or 6 wherein (i) no double bond is present at the 16-17 position, one each of $R^1$, $R^2$, $R^3$ and $R^4$ are —H, the second $R^1$, $R^2$, $R^3$ and $R^4$ respectively are bonded to the ring to which they are attached by a single bond in the α,β,β,β configurations (i.e., $R^1$ is in the α-configuration, $R^2$ is in the β-configuration, $R^3$ is in the β-configuration and $R^4$ is in the β-configuration when no double bond is present at 16-17), or (ii) a double bond is present at the 16-17 position and $R^1$ and $R^2$ respectively are in the α,β configurations (i.e., $R^1$ is in the α-configuration and $R^2$ is in the β-configuration when a double bond is present at 16-17).

16. The method of embodiment 1, 2, 3, 4, 5 or 6 wherein (i) no double bond is present at the 16-17 position, one each of $R^1$, $R^2$, $R^3$ and $R^4$ are —H, and the second $R^1$, $R^2$, $R^3$ and $R^4$ respectively are bonded to the ring to which they are attached by a single bond in the α,β,α,β configurations or (ii) one each of $R^1$ and $R^3$ are —H, no double bond is present at the 16-17 position, the second $R^1$ and $R^3$ respectively are bonded to the ring to which they are attached by a single bond in the β,β, β,α, α,β or α,α configurations and both $R^2$ together and both $R^4$ together are bonded to the ring by a double bond (i.e., both $R^2$ together and both $R^4$ together are an independently selected double bonded moiety described herein such as =O, =NOH, =CH$_2$ or =CH—CH$_3$).

17. The method of embodiment 1, 2, 3, 4, 5 or 6 wherein (i) no double bond is present at the 16-17 position, one each of $R^1$, $R^2$, $R^3$ and $R^4$ are —H, and the second $R^1$, $R^2$, $R^3$ and $R^4$ respectively are bonded to the ring to which they are attached by a single bond in the α,β,β,α configurations or (ii) one each of $R^2$ and $R^3$ are —H, no double bond is present at the 16-17 position, the second $R^2$ and $R^3$ respectively are bonded to the ring to which they are attached by a single bond in the β,β, β,α, α,β or α,α configurations and both $R^1$ together and both $R^4$ together are bonded to the ring by a double bond (i.e., both $R^1$ together and both $R^4$ together are an independently selected double bonded moiety described herein such as =O, =NOH, =CH$_2$ or =CH—CH$_3$).

18. The method of embodiment 1, 2, 3, 4, 5 or 6 wherein no double bond is present at the 16-17 position, one each of $R^1$, $R^2$, $R^3$ and $R^4$ are —H, and the second $R^1$, $R^2$, $R^3$ and $R^4$ respectively are bonded to the ring to which they are attached by a single bond in the α,β,α,α configurations.

19. The method of embodiment 1, 2, 3, 4, 5 or 6 wherein (i) no double bond is present at the 16-17 position, one each of $R^1$, $R^2$, $R^3$ and $R^4$ are —H, the second $R^1$, $R^2$, $R^3$ and $R^4$ respectively are bonded to the ring to which they are attached by a single bond in the α,α,β,β configurations (i.e., $R^1$ is in the α-configuration, $R^2$ is in the α-configuration, $R^3$ is in the β-configuration and $R^4$ is in the β-configuration when no double bond is present at 16-17), or (ii) a double bond is present at the 16-17 position and $R^1$ and $R^2$ respectively are in the α,α configurations (i.e., $R^1$ and $R^2$ are both in the α-configuration when a double bond is present at 16-17).

20. The method of embodiment 1, 2, 3, 4, 5 or 6 wherein (i) no double bond is present at the 16-17 position, one each of $R^1$, $R^2$, $R^3$ and $R^4$ are —H, and the second $R^1$, $R^2$, $R^3$ and $R^4$ respectively are bonded to the ring to which they are attached by a single bond in the α,α,α,β configurations or (ii) one each of $R^1$ and $R^4$ are —H, no double bond is present at the 16-17 position, the second $R^1$ and $R^4$ respectively are bonded to the ring to which they are attached by a single bond in the β,β, β,α, α,β or α,α configurations and both $R^2$ together and both $R^3$ together are bonded to the ring by a double bond (i.e., both $R^2$ together and both $R^3$ together are an independently selected double bonded moiety described herein such as =O, =NOH, =CH$_2$ or =CH—CH$_3$).

21. The method of embodiment 1, 2, 3, 4, 5 or 6 wherein (i) no double bond is present at the 16-17 position, one each of $R^1$, $R^2$, $R^3$ and $R^4$ are —H, and the second $R^1$, $R^2$, $R^3$ and $R^4$ respectively are bonded to the ring to which they are attached by a single bond in the α,α,β,α configurations or (ii) one each of $R^2$ and $R^4$ are —H, no double bond is present at the 16-17 position, the second $R^2$ and $R^4$ respectively are bonded to the ring to which they are attached by a single bond in the β,β, β,α, α,β or α,α configurations and both $R^1$ together and both $R^3$ together are bonded to the ring by a double bond (i.e., both $R^1$ together and both $R^3$ together are an independently selected double bonded moiety described herein such as =O, =NOH, =CH$_2$ or =CH—CH$_3$).

22. The method of embodiment 1, 2, 3, 4, 5 or 6 wherein (i) no double bond is present at the 16-17 position, one each of $R^1$, $R^2$, $R^3$ and $R^4$ are —H, and the second $R^1$, $R^2$, $R^3$ and $R^4$ respectively are bonded to the ring to which they are attached by a single bond in the α,α,α,α configurations or (ii) one each of $R^1$ and $R^2$ are —H, no double bond is present at the 16-17 position, the second $R^1$ and $R^2$ respectively are bonded to the ring to which they are attached by a single bond in the β,β, β,α, α,β or α,α configurations and both $R^3$ together and both $R^4$ together are bonded to the ring by a double bond (i.e., both $R^3$ together and both $R^4$ together are an independently selected double bonded moiety described herein such as =O, =NOH, =CH$_2$ or =CH—CH$_3$) or (iii) one each of $R^3$ and $R^4$ are —H, no double bond is present at the 16-17 position, the second $R^3$ and $R^4$ respectively are bonded to the ring to which they are attached by a single bond in the β,β, β,α, α,β or α,α configurations and both $R^1$ together and both $R^2$ together are bonded to the ring by a double bond (i.e., both $R^1$ together and both $R^2$ together are an independently selected double bonded moiety described herein such as =O, =NOH, =CH$_2$ or =CH—CH$_3$).

23. The method of any of embodiments 1 through 22 wherein no double bond is present at the 4-5 or the 5-6 positions and $R^{10}$ at the 5, 8, 9 and 14 positions respectively are in the α,β,α,α configurations or, if a double bond is present at the 4-5 or the 5-6 positions, then $R^{10}$ at the 8, 9 and 14 positions respectively are in the β,α,α configurations.

24. The method of any of embodiments 1 through 22 wherein no double bond is present at the 4-5 or the 5-6 positions and $R^{10}$ at the 5, 8, 9 and 14 positions respectively are in the β,β,α,α configurations.

25. The method of any of embodiments 1 through 22 wherein no double bond is present at the 4-5 or the 5-6 positions and $R^{10}$ at the 5, 8, 9 and 14 positions respectively are in the α,β,α,β configurations or, if a double bond is present at the 4-5 or the 5-6 positions, then $R^{10}$ at the 8, 9 and 14 positions respectively are in the β,α,β configurations.

26. The method of any of embodiments 1 through 22 wherein no double bond is present at the 4-5 or the 5-6 positions and $R^{10}$ at the 5, 8, 9 and 14 positions respectively are in the β,β,α,β configurations.

27. The method of any of embodiments 1 through 22 wherein no double bond is present at the 4-5 or the 5-6 positions and $R^{10}$ at the 5, 8, 9 and 14 positions respectively are in the α,β,β,α configurations or, if a double bond is present at the 4-5 or the 5-6 positions, then $R^{10}$ at the 8, 9 and 14 positions respectively are in the β,β,α configurations.

28. The method of any of embodiments 1 through 22 wherein no double bond is present at the 4-5 or the 5-6 positions and $R^{10}$ at the 5, 8, 9 and 14 positions respectively are in the β,β,β,α configurations.

29. The method of any of embodiments 1 through 22 wherein no double bond is present at the 4-5 or the 5-6 positions and $R^{10}$ at the 5, 8, 9 and 14 positions respectively are in the α,α,α,α configurations or, if a double bond is present at the 4-5 or the 5-6 positions, then $R^{10}$ at the 8, 9 and 14 positions respectively are in the α,α,α configurations.

30. The method of any of embodiments 1 through 22 wherein no double bond is present at the 4-5 or the 5-6 positions and $R^{10}$ at the 5, 8, 9 and 14 positions respectively are in the β,α,α,α configurations.

31. The method of any of embodiments 1 through 22 wherein no double bond is present at the 4-5 or the 5-6 positions and $R^{10}$ at the 5, 8, 9 and 14 positions respectively are in the α,α,α,β, α,α,β,α, α,α,β,β, β,α,α,β, β,α,β,α, α,β, β,β, β,α,β,β, or β,β,β,β configurations or, if a double bond is present at the 4-5 or the 5-6 positions, then $R^{10}$ at the 8, 9 and 14 positions respectively are in the α,α,β, α,β,α, α,β,β or β,β,β configurations.

32. The method of any of embodiments 1 through 31 wherein $R^{10}$ at the 5, 8, 9 and 14-positions are independently selected from —H, —F, —Cl, —Br, —I, —OH, —OR$^{PR}$, —SH, —NH$_2$, —COOH, —CH$_3$, —C$_2$H$_5$, —C(CH$_3$)$_3$, —CH$_2$OH, —CH$_2$OR$^{PR}$, —CH$_2$F, —CH$_2$Cl, —CH$_2$Br, —CH$_2$I, —CHO, —CHS, —CH$_2$SH, —CH$_2$SR$^{PR}$, —CH$_2$NH$_2$, —CH$_2$NHR$^{PR}$, —CF$_3$, —CH$_2$CH$_3$, —CH$_2$CH$_2$F, —CH$_2$CF$_3$, —CH$_2$OC(O)—(CH$_2$)$_n$—CH$_3$, —CH$_2$OC(O)—(CH$_2$)$_n$—CO$_2$H, —CH$_2$OC(O)—(CH$_2$)n—CO$_2$R$^{PR}$, —CH$_2$OC(O)—(CH$_2$)$_n$—C(O)SH, —CH$_2$OC(O)—(CH$_2$)n-C(O)SR$^{PR}$, —CH$_2$OC(O)—(CH$_2$)$_n$—NH$_2$, —CH$_2$OC(O)—(CH$_2$)n-NHR$^{PR}$, a monosaccharide, an amino acid, a carbonate, a carbamate, an ester, optionally substituted C1-C20 alkyl optionally selected from —CH$_3$, —C$_2$H$_5$ and —C$_3$H$_7$, optionally substituted C1-C20 ether optionally selected from —OCH$_3$, —OC$_2$H$_5$ and —OC$_3$H$_7$, optionally substituted C1-C20 ester optionally selected from acetoxy and propionoxy, optionally substituted aryl optionally selected from —O-phenyl, —O-(alkoxy)$_{1-3}$-phenyl where each alkoxy is optionally independently selected (e.g., methoxy or ethoxy) and —O-(halo)$_{1-3}$-phenyl where each halogen is optionally independently selected (e.g., —F or —Cl).

33. The method of any of embodiments 1 through 31 wherein $R^{10}$ at the 5, 8, 9 and 14-positions respectively are (1) —H, —H, —H, —H, (2) —H, —H, halogen (—F, —Cl, —Br or —I), —H, β) —H, —H, —H, —OH, (4) —H, —H, halogen (—F, —Cl, —Br or —I), —OH, (5) -optionally substituted alkyl (e.g., —CH$_3$, —CH$_2$OH, —CH$_2$O-ester, —C$_2$H$_5$), —H, —H, —H, (6) -optionally substituted alkyl (e.g., —CH$_3$, —CH$_2$OH, —CH$_2$O-ester, —C$_2$H$_5$), —H, halogen (—F, —Cl, —Br or —I), —H, (7) -optionally substituted alkyl (e.g., —CH$_3$, —CH$_2$OH, —CH$_2$O-ester, —C$_2$H$_5$), —H, —H, —OH, (8) -acyl (e.g., —C(O)—(CH$_2$)$_{0-2}$—CH$_3$), —H, —H, —H, (9) -ester (e.g., acetoxy or propionoxy), —H, —H, —H, (10) -ether (e.g., —O—(CH$_2$)$_{0-2}$—CH$_3$), —H, —H, —H, (11) -ester (e.g., acetoxy, propionoxy, —O—C(O)—(CH$_2$)$_{1-6}$—H), —H, halogen (e.g., —F, —Cl, —Br), —H, (12) -ester (e.g., acetoxy or propionoxy), —H, —H, —OH, (13) —H, —H, —H, -acyl (e.g., —C(O)—(CH$_2$)$_{0-2}$—OH$_3$), (14) —H, —H, —H, -ester (e.g., acetoxy or propionoxy), or (15) —H, —H, —H, -ether (e.g., —O—(CH$_2$)$_{0-2}$—CH$_3$, —OCH$_3$, —OC$_2$H$_5$, —OCH$_2$OH, —OCH$_2$F, —OCH$_2$Br, —OCH$_2$COOH, —OCH$_2$NH$_2$, —OCH$_2$CH$_2$OH, —OCH$_2$CH$_2$F, —OCH$_2$CH$_2$Br, —OCH$_2$CH$_2$COOH or —OCH$_2$CH$_2$NH$_2$).

34. The method of any of embodiments 1 through 33 wherein $R^{10}$ at the 5-position is in the α-configuration and is optionally selected from —H, —F, —Cl, —Br, —I, —OH, —OR$^{PR}$, —CH$_3$, —C$_2$H$_5$, —C(CH$_3$)$_3$, —CH$_2$OH, —CH$_2$OR$^{PR}$, —CH$_2$F, —CH$_2$Cl, —CH$_2$Br, —CH$_2$I, —CH(O), —CH(S), —CH$_2$SH, —CH$_2$SR$^{PR}$, —CH$_2$NH$_2$, —CH$_2$NHR$^{PR}$, —CF$_3$, —CH$_2$CH$_3$, —CH$_2$CH$_2$F, —CH$_2$CF$_3$, —CH$_2$OC(O)—(CH$_2$)$_n$—CH$_3$, —CH$_2$OC(O)—(CH$_2$)$_n$—CO$_2$H, —CH$_2$OC(O)—(CH$_2$)$_n$—CO$_2$R$^{PR}$, —CH$_2$OC(O)—(CH$_2$)$_n$—C(O)SH, —CH$_2$OC(O)—(CH$_2$)n-C(O)SR$^{PR}$, —CH$_2$OC(O)—(CH$_2$)$_n$—NH$_2$, —CH$_2$OC(O)—(CH$_2$)n-NHR$^{PR}$, a monosaccharide, an amino acid, a carbonate, a carbamate and an ester.

35. The method of any of embodiments 1 through 33 wherein $R^{10}$ at the 5-position is in the β-configuration and is optionally selected from —H, —F, —Cl, —Br, —I, —OH, —OR$^{PR}$, —CH$_3$, —C$_2$H$_5$, —C(CH$_3$)$_3$, —CH$_2$OH, —CH$_2$OR$^{PR}$, —CH$_2$F, —CH$_2$Cl, —CH$_2$Br, —CH$_2$I, —CHO, —CHS, —CH$_2$SH, —CH$_2$SR$^{PR}$, —CH$_2$NH$_2$, —CH$_2$NHR$^{PR}$, —CF$_3$, —CH$_2$CH$_3$, —CH$_2$CH$_2$F, —CH$_2$CF$_3$, —CH$_2$OC(O)—(CH$_2$)$_n$—CH$_3$, —CH$_2$OC(O)—(CH$_2$)$_n$—CO$_2$H, —CH$_2$OC(O)—(CH$_2$)n-CO$_2$R$^{PR}$, —CH$_2$OC(O)—(CH$_2$)$_n$—C(O)SH, —CH$_2$OC(O)—(CH$_2$)n-C(O)SR$^{PR}$, —CH$_2$OC(O)—(CH$_2$)$_n$—NH$_2$, —CH$_2$OC(O)—(CH$_2$)n-NHR$^{PR}$, a monosaccharide, an amino acid, a carbonate, a carbamate and an ester.

36. The method of any of embodiments 1 through 35 wherein R$^{10}$ at the 8-position is in the α-configuration and is optionally selected from —H, —F, —Cl, —Br, —I, —OH, —OR$^{PR}$, —CH$_3$, —C$_2$H$_5$, —C(CH$_3$)$_3$, —CH$_2$OH, —CH$_2$OR$^{PR}$, —CH$_2$F, —CH$_2$Cl, —CH$_2$Br, —CH$_2$I, —CHO, —CHS, —CH$_2$SH, —CH$_2$SR$^{PR}$, —CH$_2$NH$_2$, —CH$_2$NHR$^{PR}$, —CF$_3$, —CH$_2$CH$_3$, —CH$_2$CH$_2$F, —CH$_2$CF$_3$, —CH$_2$OC(O)—(CH$_2$)$_n$—CH$_3$, —CH$_2$OC(O)—(CH$_2$)$_n$—OC$_2$H, —CH$_2$OC(O)—(CH$_2$)$_n$—CC$_2$R$^{PR}$, —CH$_2$OC(O)—(CH$_2$)n-C(O)SH, —CH$_2$OC(O)—(CH$_2$)n-C(O)SR$^{PR}$, —CH$_2$OC(O)—(CH$_2$)$_n$—NH$_2$, —CH$_2$OC(O)—(CH$_2$)n-NHR$^{PR}$, a monosaccharide, an amino acid, a carbonate, a carbamate and an ester.

37. The method of any of embodiments 1 through 35 wherein IR$^{10}$ at the 8-position is in the β-configuration and is optionally selected from —H, —F, —Cl, —Br, —I, —OH, —OR$^{PR}$, —CH$_3$, —C$_2$H$_5$, —C(CH$_3$)$_3$, —CH$_2$OH, —CH$_2$OR$^{PR}$, —CH$_2$F, —CH$_2$C$_1$, —CH$_2$Br, —CH$_2$I, —CHO, —CHS, —CH$_2$SH, —CH$_2$SR$^{PR}$, —CH$_2$NH$_2$, —CH$_2$NHR$^{PR}$, —CF$_3$, —CH$_2$CH$_3$, —CH$_2$CH$_2$F, —CH$_2$CF$_3$, —CH$_2$OC(O)—(CH$_2$)$_n$—CH$_3$, —CH$_2$OC(O)—(CH$_2$)n-CO$_2$H, —CH$_2$OC(O)—(CH$_2$)$_n$—CC$_2$R$^{PR}$, —CH$_2$OC(O)—(CH$_2$)$_n$—C(O)SH, —CH$_2$OC(O)—(CH$_2$)n-C(O)SR$^{PR}$, —CH$_2$OC(O)—(CH$_2$)$_n$—NH$_2$, —CH$_2$OC(O)—(CH$_2$)n-NHR$^{PR}$, a monosaccharide, an amino acid, a carbonate, a carbamate and an ester.

38. The method of any of embodiments 1 through 37 wherein R$^{10}$ at the 9-position is in the α-configuration and is optionally selected from —H, —F, —Cl, —Br, —I, —OH, —OR$^{PR}$, —CH$_3$, —C$_2$H$_5$, —C(CH$_3$)$_3$, —CH$_2$OH, —CH$_2$OR$^{PR}$, —CH$_2$F, —CH$_2$Cl, —CH$_2$Br, —CH$_2$I, —CHO, —CHS, —CH$_2$SH, —CH$_2$SR$^{PR}$, —CH$_2$NH$_2$, —CH$_2$NHR$^{PR}$, —CF$_3$, —CH$_2$CH$_3$, —CH$_2$CH$_2$F, —CH$_2$CF$_3$, —CH$_2$OC(O)—(CH$_2$)$_n$—CH$_3$, —CH$_2$OC(O)—(CH$_2$)$_n$—CC$_2$H, —CH$_2$OC(O)—(CH$_2$)n-CO$_2$R$^{PR}$, —CH$_2$OC(O)—(CH$_2$)$_n$—C(O)SH, —CH$_2$OC(O)—(CH$_2$)n-C(O)SR$^{PR}$, —CH$_2$OC(O)—(CH$_2$)$_n$—NH$_2$, —CH$_2$OC(O)—(CH$_2$)n-NHR$^{PR}$, a monosaccharide, an amino acid, a carbonate, a carbamate and an ester.

39. The method of any of embodiments 1 through 37 wherein R$^{10}$ at the 9-position is in the β-configuration and is optionally selected from —H, —F, —Cl, —Br, —I, —OH, —OR$^{PR}$, —CH$_3$, —C$_2$H$_5$, —C(CH$_3$)$_3$, —CH$_2$OH, —CH$_2$OR$^{PR}$, —CH$_2$F, —CH$_2$C$_1$, —CH$_2$Br, —CH$_2$I, —CHO, —CHS, —CH$_2$SH, —CH$_2$SR$^{PR}$, —CH$_2$NH$_2$, —CH$_2$NHR$^{PR}$, —CF$_3$, —CH$_2$CH$_3$, —CH$_2$CH$_2$F, —CH$_2$CF$_3$, —CH$_2$OC(O)—(CH$_2$)$_n$—CH$_3$, —CH$_2$OC(O)—(CH$_2$)$_n$—CC$_2$H, —CH$_2$OC(O)—(CH$_2$)n-CO$_2$R$^{PR}$, —CH$_2$OC(O)—(CH$_2$)n-C(O)SH, —CH$_2$OC(O)—(CH$_2$)n-C(O)SR$^{PR}$, —CH$_2$OC(O)—(CH$_2$)$_n$—NH$_2$, —CH$_2$OC(O)—(CH$_2$)n-NHR$^{PR}$, a monosaccharide, an amino acid, a carbonate, a carbamate and an ester.

40. The method of any of embodiments 1 through 39 wherein R$^{10}$ at the 14-position is in the α-configuration and is optionally selected from —H, —F, —Cl, —Br, —I, —OH, —OR$^{PR}$, —CH$_3$, —C$_2$H$_5$, —C(CH$_3$)$_3$, —CH$_2$OH, —CH$_2$OR$^{PR}$, —CH$_2$F, —CH$_2$Cl, —CH$_2$Br, —CH$_2$I, —CHO, —CHS, —CH$_2$SH, —CH$_2$SR$^{PR}$, —CH$_2$NH$_2$, —CH$_2$NHR$^{PR}$, —CF$_3$, —CH$_2$CH$_3$, —CH$_2$CH$_2$F, —CH$_2$CF$_3$, —CH$_2$OC(O)—(CH$_2$)$_n$—CH$_3$, —CH$_2$OC(O)—(CH$_2$)$_n$—CO$_2$H, —CH$_2$OC(O)—(CH$_2$)n-CO$_2$R$^{PR}$, —CH$_2$OC(O)—(CH$_2$)n-C(O)SH, —CH$_2$OC(O)—(CH$_2$)n-C(O)SR$^{PR}$, —CH$_2$OC(O)—(CH$_2$)$_n$—NH$_2$, —CH$_2$OC(O)—(CH$_2$)n-NHR$^{PR}$, a monosaccharide, an amino acid, a carbonate, a carbamate and an ester.

41. The method of any of embodiments 1 through 39 wherein R$^{10}$ at the 14-position is in the β-configuration and is optionally selected from —H, —F, —Cl, —Br, —I, —OH, —OR$^{PR}$, —CH$_3$, —C$_2$H$_5$, —C(CH$_3$)$_3$, —CH$_2$OH, —CH$_2$OR$^{PR}$, —CH$_2$F, —CH$_2$Cl, —CH$_2$Br, —CH$_2$I, —CHO, —CHS, —CH$_2$SH, —CH$_2$SR$^{PR}$, —CH$_2$NH$_2$, —CH$_2$NHR$^{PR}$, —CF$_3$, —CH$_2$CH$_3$, —CH$_2$CH$_2$F, —CH$_2$CF$_3$, —CH$_2$OC(O)—(CH$_2$)$_n$—CH$_3$, —CH$_2$OC(O)—(CH$_2$)$_n$—CC$_2$H, —CH$_2$OC(O)—(CH$_2$)n-CO$_2$R$^{PR}$, —CH$_2$OC(O)—(CH$_2$)$_n$—C(O)SH, —CH$_2$OC(O)—(CH$_2$)n-C(O)SR$^{PR}$, —CH$_2$OC(O)—(CH$_2$)$_n$—NH$_2$, —CH$_2$OC(O)—(CH$_2$)n—NHR$^{PR}$, a monosaccharide, an amino acid, a carbonate, a carbamate and an ester.

42. The method of any of embodiments 1 through 41 wherein R$^7$ is —CH$_2$—, —CHOH—, —CH(αR$^{10}$)—, —CH(ester)-, —CH(alkoxy)- or —CH(halogen)- where the hydroxyl, ester or alkoxy group or the halogen atom is present in the α-configuration and the alkoxy group is optionally selected from —OCH$_3$, —OC$_2$H$_5$ and —OC$_3$H$_7$ and the halogen atom is —F, —Cl, —Br or —I.

43. The method of any of embodiments 1 through 41 wherein R$^7$ is (i)-CHOH—, —CF$_2$—, —C(R$^{10}$)$_2$—, —CH(βR$^{10}$)—, —CH(ester)-, —CH(alkoxy)- or —CH(halogen)-, wherein the hydroxyl, ester or alkoxy group or the halogen atom is present in the β-configuration and the alkoxy group is optionally selected from —OCH$_3$, —OC$_2$H$_5$ and —OC$_3$H$_7$ and the halogen atom is —F, —Cl, —Br or —I or (ii) wherein R$^7$ is —C(βCH$_3$)(αOH)—, —CαCH$_3$)(βOH)—, —C(βCH$_3$)(αF)—, —C(αCH$_3$)(βF)—, —CF$_2$—, —C(βCH$_3$)(αCl)—, —C(αCH$_3$)(βCl)—, —CCl$_2$—, —C(βCH$_3$)(αBr)—, —C(αCH$_3$)(βBr)—, —CBr$_2$—, —C(βCH$_3$)(αI)—, —C(αCH$_3$)(βI)—, or —CI$_2$—.

44. The method of any of embodiments 1 through 41 wherein R$^7$ is —C(O)—, —C(=CHCH$_3$)—, —C(=CH$_2$)—, —C(=CH—(CH$_2$)$_n$—CH$_3$)—, —C(=CH—(CH$_2$)$_n$—CH$_2$OH)—, —C(=CH—(CH$_2$)$_n$—CH$_2$F)—, —C(=CH—(CH$_2$)$_n$—CH$_2$Cl)—, —C(=CH—(CH$_2$)$_n$—CH$_2$Br)—, —C(=CH—(CH$_2$)$_n$—CH$_2$I)—, —C(=NOH)—, —C(=NO—(CH$_2$)$_n$—CH$_3$), wherein n is 0, 1, 2, 3 or 4.

45. The method of any of embodiments 1 through 44 wherein R$^8$ is —CH$_2$—, —CHOH—, —CH(αR$^{10}$)—, —CH(ester)-, —CH(alkoxy)- or —CH(halogen)- where the hydroxyl, ester or alkoxy group or the halogen atom is present in the α-configuration and the alkoxy group is optionally selected from —OCH$_3$, —OC$_2$H$_5$ and —OC$_3$H$_7$ and the halogen atom is —F, —Cl, —Br or —I.

46. The method of any of embodiments 1 through 44 wherein R$^8$ is (i)-CHOH—, —CF$_2$—, —C(R$^{10}$)$_2$—, —CH(βR$^{10}$)—, —CH(ester)-, —CH(alkoxy)- or —CH(halogen)-, wherein the hydroxyl, ester or alkoxy group or the halogen atom is present in the β-configuration and the alkoxy group is optionally selected from —OCH$_3$, —OC$_2$H$_5$ and —OC$_3$H$_7$ and the halogen atom is —F, —Cl, —Br or —I or (ii) wherein R$^8$—C(βCH$_3$)(αOH)—, —C(αCH$_3$)(βOH)—, —C(βCH$_3$)(αF)—, —C(αCH$_3$)(βF)—, —CF$_2$—, —C(βCH$_3$)(αCl)—, —C(αCH$_3$)(βCl)—, —CCl$_2$—, —C(βCH$_3$)(αBr)—, —C(αCH₃)(βBr)—, —CBr₂—, —C(βCH₃)(αI)—, —C(αCH₃)(βI)—, or —CI₂—.

47. The method of any of embodiments 1 through 44 wherein R⁸ is —C(O)—, —CH₂—, —C(=CHCH₃)—, —C(=CH₂)—, —C(=CH—(CH₂)ₙ—CH₃)—, —C(=CH—(CH₂)ₙ—CH₂OH)—, —C(=CH—(CH₂)ₙ—CH₂F)—, —C(=CH—(CH₂)ₙ—CH₂Cl)—, —C(=CH—(CH₂)ₙ—CH₂Br)—, —C(=CH—(CH₂)ₙ—CH₂I)—, —C(=NOH)—, —C(=NO—(CH₂)ₙ—CH₃), wherein n is 0, 1, 2, 3 or 4.

48. The method of any of embodiments 1 through 47 wherein R⁹ is —CH₂—, —CHOH—, —CH(αR¹⁰)—, —CH(ester)-, —CH(alkoxy)- or —CH(halogen)-, wherein the hydroxyl, ester or alkoxy group or the halogen atom is present in the α-configuration and the alkoxy group is optionally selected from —OCH₃, —OC₂H₅ and —OC₃H₇ and the halogen atom is —F, —Cl, —Br or —I.

49. The method of any of embodiments 1 through 47 wherein R⁹ is (i) —CHOH—, —CF₂—, —C(R¹⁰)₂—, —CH(βR¹⁰)—, —CH(ester)-, —CH(alkoxy)- or —CH(halogen)-, wherein the hydroxy, ester or alkoxy group or the halogen atom is present in the β-configuration and the alkoxy group is optionally selected from —OCH₃, —OC₂H₅ and —OC₃H₇ and the halogen atom is —F, —Cl, —Br or —I, or (ii) wherein R⁹ is —C(βCH₃)(αOH)—, —C(αCH₃)(βOH)—, —C(βCH₃)(αF)—, —C(αCH₃)(βF)—, —CF₂—, —C(βCH₃)(αCl)—, —C(αCH₃)(βCl)—, —CCl₂—, —C(βCH₃)(αBr)—, —C(αCH₃)(βBr)—, —CBr₂—, —C(βCH₃)(αI)—, —C(αCH₃)(βI)—, or —CI₂—.

50. The method of any of embodiments 1 through 47 wherein R⁹ is —C(O)—, —CH₂—, —C(=CHCH₃)—, —C(=CH₂)—, —C(=CH—(CH₂)ₙ—CH₃)—, —C(=CH—(CH₂)ₙ—CH₂OH)—, —C(=CH—(CH₂)ₙ—CH₂F)—, —C(=CH—(CH₂)ₙ—CH₂Cl)—, —C(=CH—(CH₂)ₙ—CH₂Br)—, —C(=CH—(CH₂)ₙ—CH₂I)—, —C(=NOH)—, —C(=NO—(CH₂)ₙ—CH₃), wherein n is 0, 1, 2, 3 or 4.

51. The method of any of embodiments 1 through 50 wherein the subject has, or is subject or susceptible to developing, neutropenia.

52. The method of any of embodiments 1-50 wherein the subject is a mammal.

53. The method of embodiment 52 wherein the mammal is a human.

54. The method of any preceeding embodiment wherein R⁷ is —CH₂—, —C(α-OH, β-H)—, —C(β-CH, α-H)— or —C(O)—.

55. The method of any preceeding embodiment wherein R⁸ is —CH₂—, —C(α-OH, β-H)—, —C(β-OH, α-H)—, —C(α-OH, β-F)—, —C(β-OH, α-F)—, —C(α-F, β-H)—, —C(β-F, α-H)— or —C(O).

56. The method of any preceeding embodiment wherein R⁹ is —CH₂—, —C(α-OH, β-H)—, —C(β-OH, α-H)— or —C(O)—.

57. The method of any preceeding embodiment wherein R¹⁰ᴬ is —H, α-OH, β-OH or =O.

58. The method of any preceeding embodiment wherein R¹⁰ᴮ is —H, α-OH, β-OH or =O.

59. The method of any preceeding embodiment wherein R¹⁰ᶜ is —H, α-OH, β-OH or =O.

60. The method of any preceeding embodiment wherein R¹⁰ᴰ is —H, α-OH, β-OH or =O.

61. The method of any preceeding embodiment wherein R¹⁰ᴱ is —H, α-OH, β-OH or =O.

62. The method of any preceeding embodiment wherein R⁴ are (α-OH, β-H), (β-OH, α-H), (α-C(O)CH₃, β-H), (β-C(O)CH₃, α-H), (α-OH, β-F), (β-OH, α-F), (α-H, β-F), (β-H, α-F), (α-NH₂, β-H), (β-NH₂, α-H), =O, =CH₂ or =CH₃.

63. The method of any preceeding embodiment wherein R¹ are (H, H), (α-OH, β-H), (β-OH, α-H) or =O.

64. The method of any preceeding embodiment wherein R² are (H, H), (α-OH, β-H), (β-OH, α-H) or =O.

65. The method of any preceeding embodiment wherein R³ are (H, H), (α-OH, (β-H), (β-OH, α-H), (α-H, β-F), (β-H, α-F) or =O.

66. The method of any of embodiments 1-65 wherein the formula 1 compound is 16α-bromo-3β-hydroxy-5α-androstan-17-one, 16α-fluoro-3β-hydroxy-5α-androstan-17-one, 16α-chloro-3β-hydroxy-5α-androstan-17-one, 16β-bromo-3β-hydroxy-5α-androstan-17-one, 16β-fluoro-3β-hydroxy-5α-androstan-17-one, 16β-chloro-3β-hydroxy-5α-androstan-17-one, 16α,3β-dihydroxy-5α-androstan-17-one, 16β,3β-dihydroxy-5α-androstan-17-one, 16α,3α-dihydroxy-5α-androstan-17-one, 16β,3α-dihydroxy-5α-androstan-17-one, 16α-bromo-3,3-hydroxy-5α-androstan-17-one hemihydrate, 3α-hydroxy-16α-fluoroandrostane-17-one, 3β-hydroxy-16α-fluoroandrostane-17-one, 17α-hydroxy-16α-fluoroandrostane-3-one, 17β-hydroxy-16α-fluoroandrostane-3-one, 17α-hydroxy-16α-fluoroandrostane-4-one, 17β-hydroxy-16α-fluoroandrostane-4-one, 17α-hydroxy-16α-fluoroandrostane-6-one, 17β-hydroxy-16α-fluoroandrostane-6-one, 17α-hydroxy-16α-fluoroandrostane-7-one, 17β-hydroxy-16α-fluoroandrostane-7-one, 17α-hydroxy-16α-fluoroandrostane-11-one, 17β-hydroxy-16α-fluoroandrostane-11-one, 16α-fluoroandrost-5-ene-17-one, 7α-hydroxy-16α-fluoroandrost-5-ene-17-one, 71β-hydroxy-16α-fluoroandrost-5-ene-17-one, 4α-hydroxy-16α-fluoroandrost-5-ene-17-one, 3α-hydroxy-16α-fluoroandrost-5-ene-17-one, 3β-hydroxy-16α-fluoroandrost-5-ene-17-one, 4β-hydroxy-16α-fluoroandrost-5-ene-17-one, 6α-hydroxy-16α-fluoroandrost-5-ene-17-one, 6β-hydroxy-16α-fluoroandrost-5-ene-17-one, 11α-hydroxy-16α-fluoroandrost-5-ene-17-one, 11β-hydroxy-16α-fluoroandrost-5-ene-17-one, 4α,17β-dihydroxy-16α-fluoroandrost-5-ene, 4β,17β-dihydroxy-16α-fluoroandrost-5-ene, 6α,17β-dihydroxy-16α-fluoroandrost-5-ene, 6β,17β-dihydroxy-16α-fluoroandrost-5-ene, 11α,17β-dihydroxy-16α-fluoroandrost-5-ene, 11β,17β-dihydroxy-16α-fluoroandrost-5-ene, 4α,17α-dihydroxy-16α-fluoroandrost-5-ene, 4β,17α-dihydroxy-16α-fluoroandrost-5-ene, 6α,17α-dihydroxy-16α-fluoroandrost-5-ene, 6β,17α-dihydroxy-16α-fluoroandrost-5-ene, 11α,17α-dihydroxy-16α-fluoroandrost-5-ene, 11β,17α-dihydroxy-16α-fluoroandrost-5-ene, 7α,17β-dihydroxy-16α-fluoroandrost-5-ene, 7β,17β-dihydroxy-16α-fluoroandrost-5-ene, 3α,17β-dihydroxy-16α-fluoroandrost-5-ene, 3β,17β-dihydroxy-16α-fluoroandrost-5-ene, 3α,17α-dihydroxy-16α-fluoroandrost-5-ene, 3β,17α-dihydroxy-16α-fluoroandrost-5-ene, 1α,17β-dihydroxy-16α-fluoroandrost-5-ene, 1β,17β-dihydroxy-16α-fluoroandrost-5-ene, 2α,17β-dihydroxy-16α-fluoroandrost-5-ene, 2β,17β-dihydroxy-16α-fluoroandrost-5-ene, 12α,17β-dihydroxy-16α-fluoroandrost-5-ene, 12β,17β-dihydroxy-16α-fluoroandrost-5-ene, 1α,17α-dihydroxy-16α-fluoroandrost-5-ene, 1β,17α-dihydroxy-16α-fluoroandrost-5-ene, 2α,17α-dihydroxy-16α-fluoroandrost-5-ene, 2β,17α-dihydroxy-16α-fluoroandrost-5-ene, 12α,17α-dihydroxy-16α-fluoroandrost-5-ene, 12β,17α-dihydroxy-16α-fluoroandrost-5-ene, 15α,17β-dihydroxy-16α-fluoroandrost-5-ene, 15β,17β-dihydroxy-16α-fluoroandrost-5-ene, 17l3,18-dihydroxy-16α-fluoroandrost- 5-ene, 17β,19-dihydroxy-16α-fluoroandrost-5-ene, 15α,17α-dihydroxy-16α-fluoroandrost-5-ene, 15β,17α-dihydroxy-16α-fluoroandrost-5-ene, 17α,18-dihydroxy-16α-fluoroandrost-5-ene, 17α,19-dihydroxy-16α-fluoroandrost-5-ene, 16α-fluoroandrost-4-ene-17-one, 7α-hydroxy-16α-fluoroandrost-4-ene-17-one, 7β-hydroxy-16α-fluoroandrost-4-ene-17-one, 3α-hydroxy-16α-fluoroandrost-4-ene-17-one, 3β-hydroxy-16α-fluoroandrost-4-ene-17-one, 4α-hydroxy-16α-fluoroandrost-4-ene-17-one, 4β-hydroxy-16α-fluoroandrost-4-ene-17-one, 6α-hydroxy-16α-fluoroandrost-4-ene-17-one, 6β-hydroxy-16α-fluoroandrost-4-ene-17-one, 11α-hydroxy-16α-fluoroandrost-4-ene-17-one, 11β-hydroxy-16α-fluoroandrost-4-ene-17-one, 4α,17β-dihydroxy-16α-fluoroandrost-4-ene, 4β,17β-dihydroxy-16α-fluoroandrost-4-ene, 6α,17β-dihydroxy-16α-fluoroandrost-4-ene, 6β,17β-dihydroxy-16α-fluoroandrost-4-ene, 11α,17β-dihydroxy-16α-fluoroandrost-4-ene, 11β,17β-dihydroxy-16α-fluoroandrost-4-ene, 4α,17α-dihydroxy-16α-fluoroandrost-4-ene, 4β,17α-dihydroxy-16α-fluoroandrost-4-ene, 6α,17α-dihydroxy-16α-fluoroandrost-4-ene, 6β,17α-dihydroxy-16α-fluoroandrost-4-ene, 11α,17α-dihydroxy-16α-fluoroandrost-4-ene, 11β,17α-dihydroxy-16α-fluoroandrost-4-ene, 7α,17β-dihydroxy-16α-fluoroandrost-4-ene, 7β,17β-dihydroxy-16α-fluoroandrost-4-ene, 3α,17β-dihydroxy-16α-fluoroandrost-4-ene, 3β,17β-dihydroxy-16α-fluoroandrost-4-ene, 3α,17α-dihydroxy-16α-fluoroandrost-4-ene, 3β,17α-dihydroxy-16α-fluoroandrost-4-ene, 1α,17β-dihydroxy-16α-fluoroandrost-4-ene, 1β,17β-dihydroxy-16α-fluoroandrost-4-ene, 2α,17β-dihydroxy-16α-fluoroandrost-4-ene, 2β,17β-dihydroxy-16α-fluoroandrost-4-ene, 12α,17β-dihydroxy-16α-fluoroandrost-4-ene, 12β,17β-dihydroxy-16α-fluoroandrost-4-ene, 1α,17α-dihydroxy-16α-fluoroandrost-4-ene, 1β,17α-dihydroxy-16α-fluoroandrost-4-ene, 2α,17α-dihydroxy-16α-fluoroandrost-4-ene, 2β,17α-dihydroxy-16α-fluoroandrost-4-ene, 12α,17α-dihydroxy-16α-fluoroandrost-4-ene, 12β,17α-dihydroxy-16α-fluoroandrost-4-ene, 15α,17β-dihydroxy-16α-fluoroandrost-4-ene, 15β,17β-dihydroxy-16α-fluoroandrost-4-ene, 17β,18-dihydroxy-16α-fluoroandrost-4-ene, 17β,19-dihydroxy-16α-fluoroandrost-4-ene, 15α,17α-dihydroxy-16α-fluoroandrost-4-ene, 15β,17α-dihydroxy-16α-fluoroandrost-4-ene, 17α,18-dihydroxy-16α-fluoroandrost-4-ene, 17α,19-dihydroxy-16α-fluoroandrost-4-ene, 3β,17β-dihydroxyandrost-5-ene, 3β-hydroxy-7,17-dioxoandrost-5-ene, 3α-hydroxy-7,17-dioxoandrost-5-ene, 3,17-dioxoandrost-5-ene, 3,17-dioxoandrost-4-ene, 3,17-dioxoandrost-1,4-diene, 3β,7β,17β-trihydroxyandrost-5-ene, 3β,7β,17β-trihydroxyandrostane, 3β,16α-dihydroxy-17-oxoandrostane, 3α,16α-dihydroxy-17-oxoandrostane, 3β,16β-dihydroxy-17-oxoandrostane, 3α,16β-dihydroxy-17-oxoandrostane, 3β,16α,17β-trihydroxyandrostane, 3β,16β,17β-trihydroxyandrostane, 3β,16α,17α-trihydroxyandrostane, 3β,16β,17α-trihydroxyandrostane, 3α,16α,17β-trihydroxyandrostane, 3α,16β,17β-trihydroxyandrostane or an analog of any of the foregoing compounds that is suitably substituted to fall within the scope of the embodiment, e.g., wherein an $R^{10}$ is a hydroxyl, thiol, optionally substituted alkyl or a halogen such as fluorine or bromine at the 1-, 2-, 4-, 6-, 7-, 9-11-, 12-, 14-, 15- or 16-position, wherein the $R^{10}$ is present in the α-configuration or the β-configuration.

67. A method to treat, ameliorate or slow the progression of cystic fibrosis in a human comprising administering to the human an effective amount of a formula 1 compound of any preceeding embodiment.

68. The method of embodiment 67, wherein one or more symptoms or syndromes are ameliorated, or wherein the progression of the disease is reduced.

69. The method of embodiment 68, wherein the one or more symptoms or syndromes are 1, 2, 3 or more of *Staphylococcus* (e.g., *S. aureus*), *Haemophilus influenzae, Pseudomonas* or *Burkholderia* respiratory tract or lung infection or propensity to develop a detectable infection or colonization, coughing, wheezing, cyanosis, bronchiolitis, bronchospasm, pneumothorax, hemoptysis, pancreatic exocrine insufficiency, bronchiectatic lung disease, atelectasis-consolidation, pulmonary edema, increased lung vascular hydrostatic pressure, increased lung vascular permeability, sinusitis, respiratory insufficiency, bronchial wall or interlobular septa thickening, reduction of forced expiratory volume in 1 second, dyspnea, impaired male fertility, elevated sweat chloride, mucous plugging, tree-in-bud sign, mosaic perfusion pattern, glucose intolerance or abnormal elevation of one or more of IL-4, IL-8, RANTES, neutrophil elastase, eosinophils, macrophages, neutrophils, eosinophil cationic protein or cysteinyl leukotrienes.

70. The method of embodiment 67, 68 or 69 wherein the method further comprises another suitable CF treatment, which is optionally selected from oral or aerosol corticosteroid treatment, ibuprofen treatment, DNAse treatment, IL-10 treatment, diet control, vaccination against pathogens, or chest physical therapy.

71. The method of embodiment 67, 68, 69 or 70 wherein the F1C is 16α-bromoepiandrosterone, 16α-bromoepiandrosterone hemihydrate, 16α-hydroxyepiandrosterone, 16β-hydroxyepiandrosterone, 3α,17β-dihydroxyandrostane, 3β,17β-dihydroxyandrostane, 3α,16α,17β-trihydroxyandrostane, 3α,16β,17βtrihydroxyandrostane, 3β,16α,17β-trihydroxyandrostane, 3β,16β,17β-trihydroxyandrostane, or an ester, carbonate or other analog of any of these compounds that can convert to the compound by metabolism or hydrolysis.

72. A method to prevent, treat or ameliorate neutropenia in a human comprising administering to the human an effective amount of a formula 1 compound of any of embodiments 1-66, wherein the neutropenia is postinfectious neutropenia, autoimmune neutropenia, chronic idiopathic neutropenia or a neutropenia resulting from or potentially resulting result from a cancer chemotherapy, chemotherapy for an autoimmune disease, an antiviral therapy, radiation exposure, tissue or solid organ allograft or xenograft rejection or immune suppression therapy in tissue or solid organ transplantation or aging or immunesenescence.

73. The method of embodiment 72 wherein one $R^4$ is in the β-configuration or the α-configuration and is —NH$_2$, a substituted amine or an amide, which is optionally selected from —NH$_2$, —NHCH$_3$, —N(CH$_3$)$_2$, —NHR$^{PR}$, —NH—C(O)—H and —NH—C(O)-optionally substituted alkyl, e.g., —NH—C(O)—CH$_3$.

74. The method of embodiment 73 wherein the other $R^4$ is —H, optionally substituted alkyl, —CN, —SCN or —OH.

75. The method of embodiment 72 wherein the F1C is 3β-hydroxy-17β-aminoandrost-5-ene, 3β-hydroxy-16α-fluoro-17β-aminoandrost-5-ene, 3β-hydroxy-16β-fluoro-17β-aminoandrost-5-ene, 3β-hydroxy-16,16-difluoro-17β-aminoandrost-5-ene, 3β,16α-dihydroxy-17β-aminoandrost-5-ene, 3β,16β-dihydroxy-17β-aminoandrost-5-ene, 3β-hydroxy-16,16-dimethyl-17β-aminoandrost-5-ene, an ester or carbonate of any of these compounds or an analog of any of the foregoing compounds where the double bond at the 5-6 position is absent and a hydrogen or other $R^{10}$ moiety is present at the 5-position in the α- or β-configuration and/or wherein the hydroxyl group (or ester or carbonate analog) at the 3-position is present in the α-configuration.

76. A compound of formula 1 as defined in embodiment 1.

77. The compound of embodiment 76 wherein one $R^3$ is a halogen, the other $R^3$ is not a halogen and one $R^4$ is —$NH_2$, a subtituted amine, an N-linked amino acid, —$N(R^{PR})_2$ or an amide, where $R^{PR}$ independently or together are —H or a protecting group.

78. The compound of embodiment 77 wherein one $R^4$ is —$NH_2$.

79. The compound of embodiment 77 wherein the compound is 3β-hydroxy-16α-fluoro-17β-aminoandrost-5-ene, 3β-hydroxy-16β-fluoro-17β-aminoandrost-5-ene, 3α-hydroxy-16α-fluoro-17β-aminoandrost-5-ene, 3α-hydroxy-16β-fluoro-17β-aminoandrost-5-ene, 3β-hydroxy-16α-fluoro-17β-aminoandrost-4-ene, 3β-hydroxy-16β-fluoro-17β-aminoandrost-4-ene, 3α-hydroxy-16α-fluoro-17β-aminoandrost-4-ene, 3α-hydroxy-16β-fluoro-17β-aminoandrost-4-ene, 3β-hydroxy-16α-fluoro-17β-aminoandrostane, 3β-hydroxy-16β-fluoro-17β-aminoandrostane, 3α-hydroxy-16α-fluoro-17β-aminoandrostane, 3α-hydroxy-16β-fluoro-17β-aminoandrostane, 3β-hydroxy-16α-fluoro-17β-amino-5,3-androstane, 3β-hydroxy-16β-fluoro-17β-amino-5β-androstane, 3α-hydroxy-16α-fluoro-17β-amino-5,3-androstane, 3α-hydroxy-16β-fluoro-17β-amino-5,3-androstane or an analog of any of these compounds wherein (1) the compound is substituted with an $R^{10}$ moiety other than —H at the 1, 2, 4, 6, 7, 11, 12, 14 or 15 position and/or (2) the compound is substituted at one or two of the 2, 11 or 15 positions with an independently selected —O—, —S— or —NH-moiety that replaces the one or two —$CH_2$— moieties.

80. A composition comprising a compound of formula 1 as defined in any preceding embodiment and one, two, three, four, five or more excipients.

81. A method to treat or to reduce the severity of a chronic allergy or an atopic disease, or one or more symptoms of the chronic allergy or atopic disease in a subject in need thereof, comprising administering an effective amount of a formula 1 compound of embodiment 1, wherein one $R^1$ is, or both $R^1$ together are, —OH, —$OR^{PR}$, —$SR^{PR}$, —O—Si—$(R^{13})_3$, —COOH, —$OSO_3H$, —$OPO_3H$, =O, =S, an ester, a thioester, a thionoester, a phosphoester, a phosphothioester, a phosphonoester, a phosphiniester, a sulfite ester, a sulfate ester, an amide, an amino acid, a peptide, an ether, a thioether, a carbonate or a carbamate, and the other $R^1$ is independently chosen; and one $R^4$ is, or both $R^4$ together are, —OH, —$OR^{PR}$, —$SR^{PR}$, —$N(R^{PR})_2$, —O—Si—$(R^{13})_3$, —CHO, —CHS, —CN, —SCN, —$NO_2$, —$NH_2$, —COOH, —$OSO_3H$, —$OPC_3H$, =O, =S, =N—OH, =N—O-optionally substituted alkyl, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate or a carbamate, and the other $R^4$ is independently chosen.

82. The method of embodiment 81 wherein the compound is 16α-bromoepiandrosterone, 16α-bromoepiandrosterone hemihydrate, 16α-iodoepiandrosterone, 16-oxoepiandrosterone, 16-oxoandrosterone, 3β,16α-dihydroxyandrostane-17-one, 3α,16α-dihydroxyandrostane-17-one, 3β,16β-dihydroxyandrostane-17-one, 3α,16β-dihydroxyandrostane-17-one, 3β,16α,17β-trihydroxyandrostane, 3α,16α,17β-trihydroxyandrostane, 3β,16β,17β-trihydroxyandrostane, 3α,16β,17β-trihydroxyandrostane, or an analog of any of these compounds that is (1) 2-oxa or 11-oxa substituted, (2) substituted at the 7-position with an α-halogen, β-halogen, α-hydroxyl, β-hydroxyl or oxo moiety, (3) a D-ring homo analog, (4) a 19-nor analog and/or (5) an analog of any of the foregoing compounds that is substituted with an $R^{10}$ substituent disclosed herein, e.g., wherein the $R^{10}$ is a hydroxyl, thiol, optionally substituted alkyl or a halogen such as fluorine or bromine at the 1-, 2-, 4-, 6-, 9-11-, 12-, 14-, 15- or 16-positions, wherein the $R^{10}$, e.g., the hydroxyl, thiol, optionally substituted alkyl or halogen is present in the α-configuration or the β-configuration.

83. The method of embodiment 81 or 82 wherein the level or activity of IgE in the subject is at least transiently detectably reduced, e.g., shortly after allergen exposure (such as within about 1 hour to about 1 week) or at one mor more later times.

84. A method to increase the efficacy of an immune response to dendritic cells in a subject, comprising (1) contacting for a sufficient time an effective amount of a formula 1 compound of any of embodiments 1-66 and an effective amount of a non-self antigen with the subject's dendritic cells in vitro, (2) optionally expanding the dendritic cells in vitro in the presence or absence of the formula 1 compound and/or the antigen, (3) infusing the dendritic cells into the subject, (4) optionally administering an effective amount of the formula 1 compound to the subject and/or optionally administering an effective amount of the non-self antigen to the subject.

85. The method of embodiment 84 wherein the non-self antigen comprises an antigen derived or obtained from an infectious agent or from a malignant cell or a pre-malignant cell, wherein the malignant or pre-malignant cell is from the subject or is from another individual of the same species as the subject.

86. The method of embodiment 84 or 85 wherein one $R^1$ is, or both $R^1$ together are, —H, —OH, —$OR^{PR}$, —$SR^{PR}$, —O—Si—$(R^{13})_3$, —COOH, —$OSO_3H$, —$OPO_3H$, =O, =S, an ester, a thioester, a thionoester, a phosphoester, a phosphothioester, a phosphonoester, a phosphiniester, a sulfite ester, a sulfate ester, an amide, an amino acid, a peptide, an ether, a thioether, a carbonate or a carbamate, and the other $R^1$ is independently chosen; and one $R^4$ is, or both $R^4$ together are, —OH, —$OR^{PR}$, —$SR^{PR}$, —$N(R^{PR})_2$, —O—Si—$(R^{13})_3$, —CHO, —CHS, —CN, —SCN, —$NO_2$, —$NH_2$, —COOH, —$OSO_3H$, —$OPO_3H$, =O, =S, =N—OH, =N—O-optionally substituted alkyl, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate or a carbamate, and the other $R^4$ is independently chosen.

87. The method of embodiment 86 wherein the compound is 3β,17β-dihydroxyandrost-5-ene, 3β,7β,17β-trihydroxyandrost-5-ene, 3β,17β-dihydroxyandrost-1,5-diene, 3β,7β,17β-trihydroxyandrost-1,5-diene, 3β,17β-dihydroxy-16-haloandrost-5-ene, 3β,7β,17β-trihydroxy-16-haloandrost-5-ene, 16α-fluoro-17-oxoandrost-5-ene, 3α-hydroxy-16α-fluoro-17-oxoandrost-5-ene, 3β-hydroxy-16α-fluoro-17-oxoandrost-5-ene, 3β,17β-dihydroxy-16α-fluoroandrost-5-ene, 3α,17β-dihydroxy-16α-fluoroandrost-5-ene, 16α-bromoepiandrosterone, 16α-bromoepiandrosterone hemihydrate, 16α-iodoepiandrosterone, 16-oxoepiandrosterone, 16-oxoandrosterone, 3β,16α-dihydroxyandrostane-17-one, 3α,16α-dihydroxyandrostane-17-one, 3β,16β-dihydroxyandrostane-17-one, 3α,16β-dihydroxyandrostane-17-one, 3β,16α,17β-trihydroxyandrostane, 3α,16α,17β-trihydroxyandrostane, 3β,16β,17β-trihydroxyandrostane, 3α,16β,17β-trihydroxyandrostane, or an analog of any of these compounds that is (1) 11-oxa substituted or 2-oxa substituted if no double bond is present at the 1-2 position, (2)

substituted at the 7-position with an α-halogen, β-halogen, α-hydroxyl, β-hydroxyl or oxo moiety (3), (3) a D-ring homo analog, (4) a 19-nor analog and/or (5) an analog of any of the foregoing compounds that is substituted with an 1:1¹º substituent disclosed herein, e.g., wherein the $R^{10}$ is a hydroxyl, thiol, optionally substituted alkyl or a halogen such as fluorine or bromine at the 1-, 2-, 4-, 6-, 9- 11-, 12-, 14-, 15- or 16-positions, wherein the $R^{10}$, e.g., the hydroxyl, thiol, optionally substituted alkyl or halogen is present in the α-configuration or the β-configuration.

88. A method to increase the efficacy of allergy vaccinations in a subject having an allergy, comprising (1) at an effective time before or during vaccination of the subject with an allergen, administering to the subject an effective amount of a formula 1 compound of embodiment 1, (2) optionally administering to the subject an effective amount of the formula 1 compound daily or intermittently for 2, 3, 4, 5, 6, 7, 14 or more days after the vacination of step (1), (3) after passage of sufficient time, repeating step (1) and (4) after passage of sufficient time, optionally repeating steps (1), (3) and/or (2).

89. The method of embodiment 88 wherein the subject has a chronic allergy or atopic disease, optionally selected from allergic rhinitis, psoriasis, eczema, gastrointestinal allergies, atopic dermatitis conditions, allergic asthma, food allergies and hay fever and (1) wherein the level of IgE in the subject is at least transiently detectably reduced during or after exposure to the allergen, or (2) wherein the total number of anti-allergic vaccinations that are needed to reduce allergy reactions or symptoms to allergen exposure is reduced or there is an increase in the quality or length of an effective response to allergen vaccination or there is an increase the proportion of subjects in which allergy vaccination is effective.

90. The method of embodiment 88 or 89 wherein one $R^1$ is, or both $R^1$ together are, —H, —OH, —$OR^{PR}$, —$SR^{PR}$, —O—Si—$(R^{13})_3$, —COOH, —$OSO_3H$, —$OPO_3H$, =O, =S, an ester, a thioester, a thionoester, a phosphoester, a phosphothioester, a phosphonoester, a phosphiniester, a sulfite ester, a sulfate ester, an amide, an amino acid, a peptide, an ether, a thioether, a carbonate or a carbamate, and the other $R^1$ is independently chosen; and one $R^4$ is, or both $R^4$ together are, —OH, —$OR^{PR}$, —$SR^{PR}$, —$N(R^{PR})_2$, —O—Si—$(R^{13})_3$, —CHO, —CHS, —CN, —SCN, —$NO_2$, —$NH_2$, —COOH, —$OSO_3H$, —$OPO_3H$, =O, =S, =N—OH, =N—O-optionally substituted alkyl, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate or a carbamate, and the other $R^4$ is independently chosen.

91. The method of embodiment 90 wherein the compound is 3β,17β-dihydroxyandrost-5-ene, 3β,7β,17β-trihydroxyandrost-5-ene, 3β,17β-dihydroxyandrost-1,5-diene, 3β,7β,17β-trihydroxyandrost-1,5-diene, 3β,17β-dihydroxy-16-haloandrost-5-ene, 3β,7β,17β-trihydroxy-16-haloandrost-5-ene, 16α-fluoro-17-oxoandrost-5-ene, 3α-hydroxy-16α-fluoro-17-oxoandrost-5-ene, 3β-hydroxy-16α-fluoro-17-oxoandrost-5-ene, 3β,17β-dihydroxy-16α-fluoroandrost-5-ene, 3α,17β-dihydroxy-16α-fluoroandrost-5-ene, 16α-bromoepiandrosterone, 16α-bromoepiandrosterone hemihydrate, 16α-iodoepiandrosterone, 16-oxoepiandrosterone, 16-oxoandrosterone, 3β,16α-dihydroxyandrostane-17-one, 3α,16α-dihydroxyandrostane-17-one, 3β,16β-dihydroxyandrostane-17-one, 3α,16β-dihydroxyandrostane-17-one, 3β,16α,17β-trihydroxyandrostane, 3α,16α,17β-trihydroxyandrostane, 3β,16β,17β-trihydroxyandrostane, 3α,16β,17β-trihydroxyandrostane, or an analog of any of these compounds that is (1) 11-oxa substituted or 2-oxa substituted if no double bond is present at the 1-2 position, (2) substituted at the 7-position with an α-halogen, β-halogen, α-hydroxyl, β-hydroxyl or oxo moiety, (3) a D-ring homo analog, (4) a 19-nor analog and/or (5) an analog of any of the foregoing compounds that is substituted with an $R^{10}$ substituent disclosed herein, e.g., wherein the $R^{10}$ is a hydroxyl, thiol, optionally substituted alkyl or a halogen such as fluorine or bromine at the 1-, 2-, 4-, 6-, 9-11-, 12-, 14-, 15- or 16-positions, wherein the $R^{10}$, e.g., the hydroxyl, thiol, optionally substituted alkyl or halogen is present in the α-configuration or the β-configuration.

92. A method to prevent, treat or to reduce the severity of vascular or microvascular occlusions in human sickle cell or thalassemia diseases, comprising administering to the patient an effective amount of a formula 1 compound of any of embodiments 1-66.

93. The method of embodiment 92 further comprising daily or intermittent administration of the formula 1 compound.

94. The method of embodiment 92 or 93 further comprising monitoring the subject's blood cell status to determine if further administration of the formula 1 compound is desirable, and, if further treatment is desirable, administering to the patient an effective amount of the formula 1 compound.

95. The method of embodiment 92, 93 or 94 wherein the frequency of observed vascular occlusion events in the subject or the severity of the subject's symptoms of vascular occlusions is at least transiently detectably reduced.

96. The method of embodiment 92, 93, 95 or 95 wherein one $R^1$ is, or both $R^1$ together are, —H, —OH, —$OR^{PR}$, —$SR^{PR}$, —O—Si—$(R^{13})_3$, —COOH, —$OSO_3H$, —$OPO_3H$, =O, =S, an ester, a thioester, a thionoester, a phosphoester, a phosphothioester, a phosphonoester, a phosphiniester, a sulfite ester, a sulfate ester, an amide, an amino acid, a peptide, an ether, a thioether, a carbonate or a carbamate, and the other $R^1$ is independently chosen; and one $R^4$ is, or both $R^4$ together are, —OH, —$OR^{PR}$, —$SR^{PR}$, —$N(R^{PR})_2$, —O—Si—$(R^{13})_3$, —CHO, —CHS, —CN, —SCN, —$NO_2$, —$NH_2$, —COOH, —$OSO_3H$, —$OPO_3H$, =O, =S, =N—OH, =N—O-optionally substituted alkyl, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate or a carbamate, and the other $R^4$ is independently chosen.

97. The method of embodiment 90 wherein the compound is 3β,17β-dihydroxyandrost-5-ene, 3β,7β,17β-trihydroxyandrost-5-ene, 3β,17β-dihydroxyandrost-1,5-diene, 3β,7β,17β-trihydroxyandrost-1,5-diene, 3β,17β-dihydroxy-16-haloandrost-5-ene, 3β,7β,17β-trihydroxy-16-haloandrost-5-ene, 16α-fluoro-17-oxoandrost-5-ene, 3α-hydroxy-16α-fluoro-17-oxoandrost-5-ene, 3β-hydroxy-16α-fluoro-17-oxoandrost-5-ene, 3β,17βdihydroxy-16α-fluoroandrost-5-ene, 3α,17β-dihydroxy-16α-fluoroandrost-5-ene, 16α-bromoepiandrosterone, 16α-bromoepiandrosterone hemihydrate, 16α-iodoepiandrosterone, 16-oxoepiandrosterone, 16-oxoandrosterone, 3β,16α-dihydroxyandrostane-17-one, 3α,16α-dihydroxyandrostane-17-one, 3β,16β-dihydroxyandrostane-17-one, 3α,16β-dihydroxyandrostane-17-one, 3β,16α,17β-trihydroxyandrostane, 3α,16α,17β-trihydroxyandrostane, 3β,16β,17β-trihydroxyandrostane, 3α,16β,17β-trihydroxyandrostane, or an analog of any of these compounds that is (1) 11-oxa substituted or 2-oxa substituted if no double bond is present at the 1-2 position, (2) substituted at the 7-position with an α-halogen, β-halogen, α-hydroxyl, β-hydroxyl or oxo moiety, (3) a D-ring homo analog, (4) a 19-nor analog and/or (5) an analog of any of the foregoing compounds that is substituted with an R" substituent disclosed herein, e.g., wherein the $R^{10}$ is a hydroxyl, thiol, optionally substituted alkyl or a halogen such as fluorine or bromine at the 1-, 2-, 4-, 6-, 9-11-, 12-, 14-, 15- or 16-positions, wherein the $R^{10}$, e.g., the hydroxyl, thiol, optionally substituted alkyl or halogen is present in the α-configuration or the β-configuration.

98. A method to identify a compound that modulates the expression in a cell of the level of or an activity of 1, 2, 3, 4, 5, 6, 7, 8, 9, 10 or more genes or gene products or gene transcripts in the cell, comprising contacting an effective amount of the compound with the cell under suitable conditions and for a sufficient time to detectably modulate the activity or level of the genes, or gene products in the cell, wherein the compound is a compound of any of embodiments 1-65.

99. The method of embodiment 98 wherein the genes or gene products are optionally selected from the group consisting of the genes or gene products disclosed herein.

100. The method of embodiment 98 or 99 wherein the genes or gene products are selected from the group consisting of USF1, c-Fos, EGR1, Cul1, RIPK2, IκBα, IκBKb, NF-κB1 p50, FCAR, c-Fos/ C/EBPβ, RANTES, ICAM1, TSG (TNFAIP6), IL-2 receptor α, GRO2, GRO3, HO1, Jun B, c-Fos/JunB complex, JunB/ATF3 complex, c-Jun, c-Fos/c-Jun complex, ATF-3, MMP1, TSG-6 (TNFAIP3), EGR1, TGFβ, ATF-3/c-Jun complex, c-Fos, MMP3, IL-8, STAT5A, STAT5B, CDKN1A, IFNγ receptor 2 (IFNγR2), T-bet, C reactive protein, immunoglobulin E, an AP-1 family protein, SOD2, GATA-3, Jak2, Tyk2, stat1, stat3, stat4, stat5, stat6, MIP-1α, MIP-2, IP-10, MCP-1, TNF-α, TNF-β, LT-β, IFN-α, IFN-β, TGF-β1, NF-κB, IL-1α, IL-1β, IL-4, IL-6, IL-10, IL-12 receptor β1, IL-12p35, IL-12p40, IL-23 and IL-23 receptor.

101. The method of embodiment 98, 99 or 100 wherein the level or activity of 1, 2, 3, 4, 5, 6, 7, 8, 9, 10, 11, 12, 13, 14, 15, 16, 17, 18, 19, 20, about 30, about 50, about 100, about 150, about 200, about 250, about 300, about 500, about 700 or about 1000 of the genes or gene products is detectably modulated at least transiently.

102. The method of any of embodiments 98-101 wherein the level or an activity of the gene product is a detectable increase in the level of the mRNA, the protein or one or more biological activities associated with the gene product.

103. The method of embodiment 102 wherein the increase is a transient increase of about 1 hour to about 12 hours.

104. The method of embodiment 102 wherein the level or an activity of the gene product is a detectable decrease in the level of the mRNA, the protein or one or more biological activities associated with the gene product.

105. The method of embodiment 104 wherein the increase is a transient decrease of about 1 hour to about 12 hours.

106. The method of any of embodiments 98-101 wherein the modulation is an increase or a decrease of at least about 2-fold to about 1000-fold in the level or an activity of the mRNA, the protein or at least one biological activity associated with the gene product.

107. The method of any of embodiments 98-106 wherein one $R^1$ is, or both $R^1$ together are, —H, —OH, —$OR^{PR}$, —$SR^{PR}$, —O—Si—$(R^{13})_3$, —COOH, —$OSO_3H$, —$OPO_3H$, =O, =S, an ester, a thioester, a thionoester, a phosphoester, a phosphothioester, a phosphonoester, a phosphiniester, a sulfite ester, a sulfate ester, an amide, an amino acid, a peptide, an ether, a thioether, a carbonate or a carbamate, and the other $R^1$ is independently chosen; and one $R^4$ is, or both $R^4$ together are, —OH, —$OR^{PR}$, —$SR^{PR}$, —$N(R^{PR})_2$, —O—Si—$(R^{13})_3$, —CHO, —CHS, —CN, —SCN, —$NO_2$, —$NH_2$, —COOH, —$OSO_3H$, —$OPO_3H$, =O, =S, =N—OH, =N—O-optionally substituted alkyl, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate or a carbamate, and the other $R^4$ is independently chosen.

108. The method of any of embodiments 98-106 wherein the formula 1 compound is 16α-bromo-3β-hydroxy-5α-androstan-17-one, 16α-bromo-3β-hydroxy-5α-androstan-17-one hemihydrate, 16α-fluoro-3β-hydroxy-5α-androstan-17-one, 16α-chloro-3β-hydroxy-5α-androstan-17-one, 16β-bromo-3β-hydroxy-5α-androstan-17-one, 16β-fluoro-3β-hydroxy-5α-androstan-17-one, 16β-chloro-3β-hydroxy-5α-androstan-17-one, 16α,3β-dihydroxy-5α-androstan-17-one, 16β,3β-dihydroxy-5α-androstan-17-one, 16α,3α-dihydroxy-5α-androstan-17-one, 16β,3α-dihydroxy-5α-androstan-17-one, 16α-bromo-3,3-hydroxy-5α-androstan-17-one hemihydrate, 3α-hydroxy-16α-fluoroandrostane-17-one, 3β-hydroxy-16α-fluoroandrostane-17-one, 17α-hydroxy-16α-fluoroandrostane-3-one, 17β-hydroxy-16α-fluoroandrostane-3-one, 17α-hydroxy-16α-fluoroandrostane-4-one, 17β-hydroxy-16α-fluoroandrostane-4-one, 17α-hydroxy-16α-fluoroandrostane-6-one, 17β-hydroxy-16α-fluoroandrostane-6-one, 17α-hydroxy-16α-fluoroandrostane-7-one, 17β-hydroxy-16α-fluoroandrostane-7-one, 17α-hydroxy-16α-fluoroandrostane-11-one, 17β-hydroxy-16α-fluoroandrostane-11-one, 16α-fluoroandrost-5-ene-17-one, 7α-hydroxy-16α-fluoroandrost-5-ene-17-one, 7β-hydroxy-16α-fluoroandrost-5-ene-17-one, 4α-hydroxy-16α-fluoroandrost-5-ene-17-one, 3α-hydroxy-16α-fluoroandrost-5-ene-17-one, 3β-hydroxy-16α-fluoroandrost-5-ene-17-one, 4β-hydroxy-16α-fluoroandrost-5-ene-17-one, 6α-hydroxy-16α-fluoroandrost-5-ene-17-one, 6β-hydroxy-16α-fluoroandrost-5-ene-17-one, 11α-hydroxy-16α-fluoroandrost-5-ene-17-one, 11β-hydroxy-16α-fluoroandrost-5-ene-17-one, 4α,17β-dihydroxy-16α-fluoroandrost-5-ene, 4β,17β-dihydroxy-16α-fluoroandrost-5-ene, 6α,17β-dihydroxy-16α-fluoroandrost-5-ene, 6β,17β-dihydroxy-16α-fluoroandrost-5-ene, 11α,17β-dihydroxy-16α-fluoroandrost-5-ene, 11β,17β-dihydroxy-16α-fluoroandrost-5-ene, 4α,17α-dihydroxy-16α-fluoroandrost-5-ene, 4β,17α-dihydroxy-16α-fluoroandrost-5-ene, 6α,17α-dihydroxy-16α-fluoroandrost-5-ene, 6β,17α-dihydroxy-16α-fluoroandrost-5-ene, 11α,17α-dihydroxy-16α-fluoroandrost-5-ene, 11β,17α-dihydroxy-16α-fluoroandrost-5-ene, 7α,17β-dihydroxy-16α-fluoroandrost-5-ene, 7β,17β-dihydroxy-16α-fluoroandrost-5-ene, 3α,17β-dihydroxy-16α-fluoroandrost-5-ene, 3β,17β-dihydroxy-16α-fluoroandrost-5-ene, 3α,17α-dihydroxy-16α-fluoroandrost-5-ene, 3β,17α-dihydroxy-16α-fluoroandrost-5-ene, 1α,17β-dihydroxy-16α-fluoroandrost-5-ene, 1β,17β-dihydroxy-16α-fluoroandrost-5-ene, 2α,17β-dihydroxy-16α-fluoroandrost-5-ene, 2β,17β-dihydroxy-16α-fluoroandrost-5-ene, 12α,17β-dihydroxy-16α-fluoroandrost-5-ene, 12β,17β-dihydroxy-16α-fluoroandrost-5-ene, 1α,17α-dihydroxy-16α-fluoroandrost-5-ene, 1β,17α-dihydroxy-16α-fluoroandrost-5-ene, 2α,17α-dihydroxy-16α-fluoroandrost-5-ene, 2β,17α-dihydroxy-16α-fluoroandrost-5-ene, 12α,17α-dihydroxy-16α-fluoroandrost-5-ene, 12β,17α-dihydroxy-16α-fluoroandrost-5-ene, 15α,17β-dihydroxy-16α-fluoroandrost-5-ene, 15β,17β-dihydroxy-16α-fluoroandrost-5-ene, 17β,18-dihydroxy-16α-fluoroandrost-5-ene, 17β,19-dihydroxy-16α-fluoroandrost-5-ene, 15α, 17α-dihydroxy-16α-fluoroandrost-5-ene, 15β,17α-dihydroxy-16α-fluoroandrost-5-ene, 17α,18-dihydroxy-16α-fluoroandrost-5-ene, 17α,19-dihydroxy-16α-fluoroandrost-5-ene, 16α-fluoroandrost-4-ene-17-one, 7α-hydroxy-16α-fluoroandrost-4-ene-17-one, 7β-hydroxy-16α-fluoroandrost-4-ene-17-one, 3α-hydroxy-16α-fluoro-androst-4-ene-17-one, 3β-hydroxy-16α-fluoroandrost-4-ene-17-one, 4α-hydroxy-16α-fluoroandrost-4-ene-17-one, 4β-hydroxy-16α-fluoroandrost-4-ene-17-one, 6α-hydroxy-16α-fluoroandrost-4-ene-17-one, 6β-hydroxy-16α-fluoro-androst-4-ene-17-one, 11α-hydroxy-16α-fluoroandrost-4-ene-17-one, 11β-hydroxy-16α-fluoroandrost-4-ene-17-one, 4α,17β-dihydroxy-16α-fluoroandrost-4-ene, 4β,17β-dihydroxy-16α-fluoroandrost-4-ene, 6α,17β-dihydroxy-16α-fluoroandrost-4-ene, 6β,17β-dihydroxy-16α-fluoroandrost-4-ene, 11α,17β-dihydroxy-16α-fluoroandrost-4-ene, 11β,17β-dihydroxy-16α-fluoroandrost-4-ene, 4α,17α-dihydroxy-16α-fluoroandrost-4-ene, 4β,17α-dihydroxy-16α-fluoroandrost-4-ene, 6α,17α-dihydroxy-16α-fluoroandrost-4-ene, 6β,17α-dihydroxy-16α-fluoroandrost-4-ene, 11α,17α-dihydroxy-16α-fluoroandrost-4-ene, 11β,17α-dihydroxy-16α-fluoroandrost-4-ene, 7α,17β-dihydroxy-16α-fluoroandrost-4-ene, 7β,17β-dihydroxy-16α-fluoroandrost-4-ene, 3α,17β-dihydroxy-16α-fluoroandrost-4-ene, 3β,17β-dihydroxy-16α-fluoroandrost-4-ene, 3α,17α-dihydroxy-16α-fluoroandrost-4-ene, 3β,17α-dihydroxy-16α-fluoroandrost-4-ene, 1α,17β-dihydroxy-16α-fluoroandrost-4-ene, 1β,17β-dihydroxy-16α-fluoroandrost-4-ene, 2α,17β-dihydroxy-16α-fluoroandrost-4-ene, 2β,17β-dihydroxy-16α-fluoroandrost-4-ene, 12α,17β-dihydroxy-16α-fluoroandrost-4-ene, 12β,17β-dihydroxy-16α-fluoroandrost-4-ene, 1α,17α-dihydroxy-16α-fluoroandrost-4-ene, 1β,17α-dihydroxy-16α-fluoroandrost-4-ene, 2α,17α-dihydroxy-16α-fluoroandrost-4-ene, 2β,17α-dihydroxy-16α-fluoroandrost-4-ene, 12α,17α-dihydroxy-16α-fluoroandrost-4-ene, 12β,17α-dihydroxy-16α-fluoroandrost-4-ene, 15α,17β-dihydroxy-16α-fluoroandrost-4-ene, 15β,17β-dihydroxy-16α-fluoroandrost-4-ene, 17β,18-dihydroxy-16α-fluoroandrost-4-ene, 17β,19-dihydroxy-16α-fluoroandrost-4-ene, 15α,17α-dihydroxy-16α-fluoroandrost-4-ene, 15β,17α-dihydroxy-16α-fluoroandrost-4-ene, 17α,18-dihydroxy-16α-fluoroandrost-4-ene, 17α,19-dihydroxy-16α-fluoroandrost-4-ene, 3β,17β-dihydroxyandrost-5-ene, 3β-hydroxy-7,17-dioxoandrost-5-ene, 3α-hydroxy-7,17-di-oxoandrost-5-ene, 3,17-dioxoandrost-5-ene, 3,17-dioxoandrost-4-ene, 3,17-dioxoandrost-1,4-diene, 3β,7β,17β-trihydroxyandrost-5-ene, 3β,7β,17β-trihydroxyandrostane, 3β,16α-dihydroxy-17-oxoandrostane, 3α,16α-dihydroxy-17-oxoandrostane, 3β,16β-dihydroxy-17-oxoandrostane, 3α,16β-dihydroxy-17-oxoandrostane, 3β,16α,17β-trihydroxyandrostane, 3β,16β,17β-trihydroxyandrostane, 3β,16α,17α-trihydroxyandrostane, 3β,16β,17α-trihydroxyandrostane, 3α,16α,17β-trihydroxyandrostane, 3α,16β,17β-trihydroxyandrostane or an analog of any of these compounds that is (1) 11-oxa substituted or 2-oxa substituted if no double bond is present at the 1-2 position, (2) substituted at the 7-position with an α-halogen, β-halogen, α-hydroxyl, β-hydroxyl or oxo moiety, (3) a D-ring homo analog, (4) a 19-nor analog and/or (5) an analog of any of the foregoing compounds that is substituted with an $R^{10}$ substituent disclosed herein, e.g., wherein the $R^{10}$ is a hydroxyl, thiol, optionally substituted alkyl or a halogen such as fluorine or bromine at the 1-, 2-, 4-, 6-, 9-11-, 12-, 14-, 15- or 16-positions, wherein the $R^{10}$, e.g., the hydroxyl, thiol, optionally substituted alkyl or halogen is present in the α-configuration or the β-configuration.

109. A method to enhance the healing of a trauma or an acute injury in a subject who has experienced or who is expected to experience a trauma or an acute injury comprising administering an effective amount of a compound to the subject, wherein the compound is (1) 3β,17β-dihydroxyandrost-5-ene, 3β,7β,17β-trihydroxyandrost-5-ene, a 16-halo analog of either compound, a 16-hydroxy analog of either compound, an 11-oxa analog of either compound, a 2-oxa analog of either compound, an ester or a carbonate of either compound, a derivative of either compound that can convert to either compound by hydrolysis or by metabolism or (2) a formula 1 compound of any of embodiments 1-66.

110. The method of embodiment 109 wherein the subject will experience or has experienced an immune suppressive event within about 2-3 weeks or about 3-4 weeks of the occurrence of the trauma or acute injury, wherein the immune suppressive event is exposure of the subject to an immune suppressive amount of ionizing radiation.

111. The method of embodiment 110 wherein the ionizing radiation exposure is about 0.3 Gy to about 30 Gy of the ionizing radiation.

112. The method of embodiment 110 wherein the radiation exposure is about 0.5 Gy to about 8 Gy of the ionizing radiation.

113. The method of embodiment 109 wherein the subject has experienced an immune suppressive event within within 3 weeks of the occurrence of the trauma or acute injury, wherein the immune suppressive event is selected from an immune suppressive amount of an immunosuppressive chemotherapy.

114. The method of embodiment 113 wherein the immunosuppressive chemotherapy is an immunosuppressive cancer chemotherapy, an immunosuppressive amtimicrobial therapy or an immunosuppressive glucocorticoid therapy.

115. The method of embodiment 113 wherein the immunosuppressive cancer chemotherapy is treatment of the subject with an immunosuppressive amount of cyclophosphamide, 5-fluorouracil or a platinum compound optionally selected from cisplatin and carboplatin.

116. The method of embodiment 113 wherein the immunosuppressive glucocorticoid chemotherapy is treatment of the subject with an immunosuppressive amount of dexamethasone, prednisone, hydrocortisone or cortisol.

117. The method of any of embodiments 109-116 wherein the subject is a human or a primate.

118. The method of any of embodiments 109-117 wherein the formula 1 compound has the structure

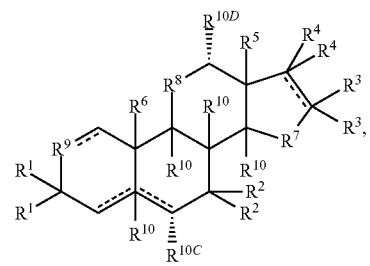

-continued

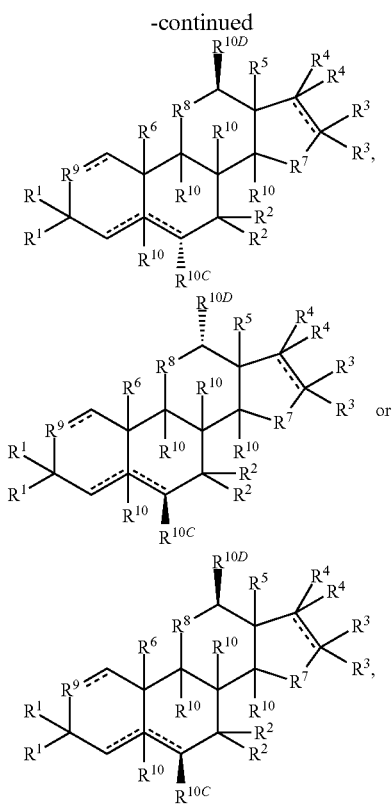

119. The method of embodiment 118 wherein the compound is 3β-hydroxy-17β-aminoandrost-5-ene.

120. The method of embodiment 118 wherein the compound is 3β-hydroxy-17β-amino-17α-optionally substituted alkyl-androst-5-ene, 3β-hydroxy-9α-fluoro-17β-aminoandrost-5-ene or 3β-hydroxy-17β-amino-19-norandrost-5-ene.

121. The method of any of embodiments 109-117 wherein the compound is 3β,17β-dihydroxyandrost-5-ene.

122. A method to modulate the expression of one or more transcription factors or enzymes in a subject who has a dysregulated oxidative stress condition comprising administering an effective amount of a compound to the subject, wherein the compound is (1) 3β,16α,17β-trihydroxyandrostane, 3α,16α,17β-trihydroxyandrostane, 3β,16α-dihydroxyandrostane-17-one, 3α,16α-dihydroxyandrostane-17-one, 3β,17β-dihydroxy-16α-haloandrostane, 3α,17β-dihydroxy-16α-haloandrostane, 3β,17β-dihydroxy-16α-bromoandrostane, 3α,17β-dihydroxy-16α-bromoandrostane, 3β-hydroxy-16α-bromoandrostane-17-one, 3β-hydroxy-16α-bromoandrostane-17-one hemihydrate, 3β,17β-dihydroxyandrost-5-ene, 3β,713,17β-trihydroxyandrost-5-ene, 3β,17β-dihydroxy-16α-haloandrost-5-ene, 3α,17β-dihydroxy-16α-haloandrost-5-ene, 3β,16α,17β-trihydroxyandrost-5-ene, 3α,16α,17β-trihydroxyandrost-5-ene, an 11-oxa analog of any of these compounds, a 2-oxa analog of any of these compounds, a 19-nor analog of any of these compounds, a 9α-fluoro analog of any of these compounds, or an ester or a carbonate of any of these compounds or analogs, or (2) a derivative of any of these compounds or analogs that can convert to these compounds or analogs by hydrolysis or by metabolism, or β) a formula 1 compound of any of embodiments 1-66.

123. The method of embodiment 122 wherein the compound modulates the level or activity of a transcription factor or enzyme selected from one or more of Nrf2, a Maf protein, a thioredoxin, NQO1, GST, HO 1, SOD2, the catalytic subunit of γGCS, the regulatory subunit of γGCS and xCT.

124. The method of embodiment 122 or 123 wherein the dysregulated oxidative stress condition is associated with exposure of the subject to a toxin that can cause cell or tissue damage or wherein elevated oxidative stress is present in one or more of the subject's cell types or tissues.

125. The method of embodiment 122, 123 or 124 wherein the subject has an acute or chronic inflammation condition, an acute or chronic infection or a trauma.

126. The method of embodiment 122, 123, 124 or 125 wherein the levels or activity of one, two or more of Nrf2, a Maf protein, a thioredoxin, NQO1, GST, HO 1, the catalytic subunit of γGCS, the regulatory subunit of γGCS and xCT is increased.

127. The method of embodiment 122, 123, 124, 125 or 126 wherein the compound is 3β,16α,17β-trihydroxyandrostane, 3α,16α,17β-trihydroxyandrostane, 3β,16α-dihydroxyandrostane-17-one or 3α,16α-dihydroxyandrostane-17-one.

128. A product produced by the process of (1) contacting a F1C(s) and an excipient or (2) contacting a composition comprising a F1C(s) and one or more excipients with one or more additional excipients.

129. Use of a compound, composition, formulation or product of any of embodiments 1-129 or of any species or group of F1Cs disclosed herein for the preparation of a medicament. The medicament can be for the prophylaxis or treatment of a disease or condition disclosed herein in a subject having or susceptible to developing the disease or condition.

130. The use of a compound, composition, formulation or product of any of embodiments 1-129 or of any species or group of F1Cs disclosed herein to prepare a medicament for use to prevent or to treat, or to ameliorate one or more symptoms associated, with one, two or more acute or chronic diseases or conditions disclosed herein, e.g., an infection, an immunesuppression condition, an allergy, a cardiovascular condition, a metabolic disorder, a pulmonary condition, a skin condition, aging, a trauma such as a burn or a bone fracture, immune suppression, a neurological or centeral or peripheral nervous system condition or disorder, an unwanted or pathological inflammatory condition, toxicity or unwanted side-effects of a chemotherapy orof radiation exposure such as a glucocorticoid treatment or a cancer chemotherapy, an autoimmune disease or condition, a malignancy or cancer, a pre-malignant condition or to modulate a mammal's immune response, such as enhancing a Th1 response or decreasing a Th2 response, in a subject, e.g., a human or a mammal, having the acute or chronic disease or condition or subject to developing the acute or chronic disease or condition.

131. The use of embodiment 130, wherein the infection is a viral, bacterial, fungal, yeast or parasite infection, e.g., as described herein.

132. Use according to embodiment 130 or 131 wherein the medicament is for intermittently administering the F1C(s) to a subject or delivering to the subject's tissues the F1C(s), e.g., using an intermittent dosing protocol disclosed herein.

133. Use of a compound, composition, formulation or product of any of embodiments 1-129 or of any species or group of F1Cs disclosed herein to prepare a medicament for use to enhacnce a specific or an innate humoral or cellular response to vaccination or to the presence of 1, 2, 3, 4, 5, 6 or more endogenous antigens or epitopes associated with establishing or maintaining a disease or pathogenic agent such as a tumor antigen or an antigen associated with a pathogen.

134. Use according to embodiment 133 wherein the subject's innate immunity is enhanced.

135. Use according to embodiment 13 or 134 wherein the subject's innate or adaptive immunity is enhanced or wherein an unwanted immune response is decreased, or wherein number or activity of one, two or more of the subject's Th1 cells, tumor-infiltrating lymphocytes (TIL cells), NK cells, peripheral blood lymphocytes, phagocytes, monocytes, macrophage, neutrophils, eosinophils, dendritic cells, fibrocytes, astrocytes, gilal cells or stromal cells, e.g., bone marrow, lymph node or spleen stroma, are increased or activated at least transiently (e.g., for at least 10 minutes to 10 days or more), which is optionally as measured by, e.g., enhanced $^3$H-thymidine uptake compared to untreated controls or by an increase in the number of the cell type in circulation or demonstrable movement of the cell type from one tissue or compartment (e.g., skin or blood) to another tissue or compartment (e.g., blood, lymph node, spleen, Peyer's patches, GALT or thymus), or wherein the transcription rate, protein level or biological activity of one or more genes in the subject's NK cells, TIL cells, phagocytes, monocytes, macrophages, neutrophils, eosinophils, dendritic cells, fibrocytes, astrocytes, gilal cells or stromal cells are detectably modulated, e.g., increased (e.g., as measured by increased enzyme or biological activity of a biomolecule such as a nuclear hormone receptor such as an orphan nuclear hormone receptor, a transcription factor, a chemokine or a cytokine, which is optionally compared to suitable control cells or tissues).

136. A method to (a) modulate (detectably increase or decrease) the expression of at least one immune cell antigen by an immune cell in a subject, wherein the immune cell antigen is selected from CD3, CD11c, CD14, CD16, CD19, CD25, CD38, CD56, CD62L, CD69, CD45RA, CD45RO, CD123, HLA-DR, IL-1, IL-2, IL-4, IL-6, IL-8, IL-10, IL-12, TNFα, IGF$_1$ and γIFN, or (b) activate CD8$^+$ T cells or CD8$^-$ T cells in a subject, wherein the activation comprises at least transiently enhanced expression of CD25 or CD69 by the T cells, or (c) increase the proportion of CD8$^+$ or CD8$^-$ lymphokine activated killer cells in a subject's CD16+ cells (e.g., CD8$^+$, CD16$^+$, CD38$^+$ or cells CD8$^-$, CD16$^+$, CD38$^+$), or (d) increase the proportion of (i) CD8$^-$, CD16$^+$ natural killer cells, (ii) CD8$^+$, CD16$^+$ natural killer cells or (iii) CD8$^-$, CD16$^+$ cells that mediate antibody-dependent cell-mediated cytotoxicity, or (iv) CD8$^+$, CD16$^+$ cells that mediate antibody-dependent cell-mediated cytotoxicity, or (e) increase the proportion of dendritic cell precursors in a subject's circulating white blood cells (e.g., Lin$^-$, HLA-DR$^+$, CD123$^+$ or Lin$^-$ HLA-DR$^+$, CD11c$^+$ cells) or (f) increase the proportion of CD45RA$^+$ T cells or CD45$^+$, R0$^+$ T cells in a subject's circulating white blood cells, or (g) change (increase or decrease) the proportion or relative numbers of CD62L$^+$ T cells in a subject's circulating white blood cells, or (h) increase the proportion of CD8$^+$ or CD4$^+$ T cells that express CD62L in a subject's circulating CD8$^+$ or CD4$^+$ T cells, or (i) decrease the proportion of CD8$^+$ or CD4$^+$ T cells that express CD62L in a subject's circulating CD8$^+$ or CD4$^+$ T cells, or (j) increase the proportion of HLA-DR$^+$, CD8$^+$, CD38$^+$ cells in a subject's circulating white blood cells, or (k) decrease the level of IL-4 or IL-10 that is expressed by or present in a subject's white blood cells or in a subject's plasma (or that is expressed after the subject's white cells are stimulated in vitro), (l) at least transiently increase the number of dendritic cell precursors or dendritic cells that are present in a subject's white blood cells or in a subject's plasma, or (m) enhance the capacity of an immune cell, e.g., macrophages, CD4$^+$ T cells, CD8$^+$ T cells to express IL-2, IL-12 or γIFN or to activate such cells, the method comprising administering to the subject an effective amount of a F1C, which is optionally present in a composition or a formulation comprising 1, 2, 3, 4, 5, 6 or more pharmaceutically acceptable excipients. The F1c is any compound as described herein, e.g., a compound of embodiments 1-66 or in any chemical structure or any compound group.

137. A method to detect or to characterize a biological response (e.g., increased or decreased cytokine or cell surface antigen expression or activity, increased numbers of circulating neutrophils, increased phagocytic activity by phagocytic cells or modulation of a disease or symptom described herein) associated with the administration of a F1C to a subject comprising (1) obtaining a first biological sample from the subject and analyzing the sample to obtain a baseline value for the response, (2) administering the F1C to the subject to obtain a treated subject (3) within about 15 minutes to about 28 days after administering the F1C, obtaining a second biological sample from the treated subject and analyzing the sample to obtain a treated value for the response, and (4) optionally comparing the control information with the experimental information to detect the presence, absence, relative magnitude or absolute magnitude of the biological response.

138. The method of embodiment 137 wherein the biological response is modulation of CD8$^+$ T cells, CD4$^+$ T cells, CD8$^+$ lymphokine activated killer cells, CD8$^-$, CD16$^+$ natural killer cells, circulating dendritic cell precursors, circulating dendritic cells, tissue dendritic cell precursors, tissue dendritic cells, CD8$^+$ lymphokine activated killer cells, CD8$^-$ lymphokine activated killer cells, CD8$^-$, CD16$^+$ natural killer cells, CD8$^+$, CD16$^+$ natural killer cells, CD8$^-$, CD16$^+$ cells that mediate antibody-dependent cell-mediated cytotoxicity, CD8$^+$, CD16$^+$ cells that mediate antibody-dependent cell-mediated cytotoxicity, CD45RA$^+$ T cells, CD45RA$^+$, CD45RO$^+$ T cells, CD45RO$^+$ T cells, CD8$^+$, CD62L T cells, CD4$^+$, CD62L$^+$ T cells or HLA-DR$^+$, CD8$^+$, CD38$^+$ T cells, monocytes, macrophages, glial cells or astrocytes, or wherein the biological response is at least transient modulation of an immune cell antigen or an immune accessory cell antigen (e.g., an adhesion molecule at the surface of endothelial cells or a cytokine receptor at the surface of T cells or B cells or a CD molecule, an interleukin or a cytokine, optionally selected from CD16, CD25, CD38, CD62L, CD69, CD45RA, CD45RO, IL-1, IL-2, IL-4, IL-6, IL-8, IL-10, TNFα, IGF$_1$ and γIFN).

139. A kit comprising a formulation that comprises a unit dosage or a multiple dosage comprising a F1C, e.g., any compound described or within any structure disclosed herein, and one or more excipients wherein the formulation is dispensed in a suitable closed container, wherein the kit optionally further comprises a label that provides information about one or more of (1) the F1C's chemical structure, (2) any recommended dosing regimen, (3) any adverse effects of administering the F1C to a subject that are required to be disclosed and (4) the amount of the F1C that is present in each unit dose or in the entire container.

140. A method to treat a symptom or condition associated with one or more delayed adverse or unwanted effects of radiation exposure or therapy in a subject in need thereof comprising administering to the subject, or delivering to the subject's tissues, an effective amount of a compound of formula 1, wherein the F1C is administered or delivered to the subject's tissues beginning at least 2 weeks after the subject has been exposed to a dose of radiation that will cause or could potentially cause the one or more delayed adverse or unwanted effects of the radiation exposure, or wherein the F1C is administered or delivered to the subject's tissues beginning at least 2 weeks after the subject has been exposed to at least one subdose of a planned course of radiation exposures that will cause or could potentially cause the one or more delayed adverse effects or unwanted effects of the radiation exposure.

141. The method of embodiment 140 wherein the subject has received, or is anticipated to receive, a total radiation dose of at least about 0.5 Gy to about 300 Gy, wherein the subject received the radiation dose in a single dose or in two or more divided doses, e.g., a total radiation dose of at least about Gy 1 to about 12 Gy, or at least about Gy 1 to about 8 Gy.

142. The method of embodiment 140 or 141 wherein the symptom or condition associated with one or more delayed adverse effect of radiation is one or more of encephalopathy, myelopathy, nausea, vomiting, diarrhea, acute inflammation, e.g., of the lung, chronic inflammation, e.g., of the lung, edema, pain, headache, depression, fever, malaise, weakness, hair loss, skin atrophy, skin ulceration, skin lesion, keratosis, telangiectasia, infection, hypoplasia, atrophy, fibrosis, pneumonitis, bone marrow hypoplasia, hemorrhage, leukopenia or thrombocytopenia.

143. The method of embodiment 140, 141 or 142 wherein the symptom or condition associated with one or more delayed adverse or unwanted effect of the radiation exposure or therapy is caused by or associated with radiation damage to one or more of bone marrow cells, bowel epithelium, bone marrow, testicles, ovaries, brain nerves or tissue, peripheral nerves, spinal cord nerves or tissue or skin epithelium.

Variations and modifications of these embodiments, the claims and the remaining portions of this disclosure will be apparent to the skilled artisan after a reading thereof. Such variations and modifications are within the scope and spirit of this invention. All citations herein are incorporated herein by reference in their entirety. All citations herein are incorporated herein by reference with specificity.

EXAMPLES

The following examples further illustrate the invention and they are not intended to limit it in any way. Variations of these examples that are included in the invention may include, e.g., any of the F1Cs described herein or parts or all of any of the methods, formulations, treatment protocols and/or assays described herein.

Example 1

Cystic fibrosis treatment. Treatment with a F1C is conducted on human cystic fibrosis ("CF") patients, e.g., 18 years of age or older, who may have two or more of the following characteristics: (1) sweat chloride ≥60 mEq/L, e.g., by quantitative pilocarpine iontophoresis test, (2) homozygosity for the F508 genetic mutation, or heterozygosity for 2 well-characterized mutations, e.g., as described herein, associated with CF, (3) $FEV_1 \geq 40\%$ predicted at screening, (4) $SaC_2 \geq 90\%$ at screening, (5) ability to perform pulmonary function tests and (6) clinical stability, with no evidence of acute upper or lower respiratory tract infection or current pulmonary exacerbation. The treatment regimen consists of 1, 2, 3, 4 or 5 consecutive days of once daily dosing of a F1C or placebo equivalent followed by a 40-day observation period. Daily dosages are about 10-150 mg/day, e.g., about 25 mg/day, 50 mg/day, 75 mg/day or 100 mg/day. The F1C is administered as described herein such as by a parenteral route, e.g., intramuscular or subcutaneous delivery, or by transmucosal delivery, e.g., buccal or sublingual. A follow-up visit will occur 6 weeks after the last treatment course to collect final samples for safety and activity. Patients receive, e.g., 3 treatment courses over a 14-week period, 6 treatment courses over a 28-week period or more courses of treatment over a longer period. F1Cs that are used include 3β-hydroxy-16α-bromo-17-oxoandrostane, 3β-hydroxy-16α-bromo-17-oxoandrostane hemihydrate, 3β,16α-dihydroxy-17-oxoandrostane, 3α,16α-dihydroxy-17-oxoandrostane, 3β,16α,17β-trihydroxyandrostane or 3α,16α,17β-trihydroxyandrostane or another F1C disclosed herein. The patients are optionally monitored for the status of their condition or in improvement of one or more CF symptoms after dosing, e.g., reduction in the numbers of neutrophils in bronchiolar or alveolar lavage samples, e.g., about a 30%, 40%, 50% or greater reduction, or levels of one or more CF-related inflammation markers, e.g., reduced levels or activity of IL-6, IL-8, IKK-β kinase or neutrophil elastase, or in the reduced occurrence, severity or progression of infections such as a *Burkholderia* (*Pseudomonas*) cepacia infection.

Example 2

Cyclodextrin formulation. A cyclodextrin formulation containing a F1C is prepared by mixing a sulfobutyl β-cyclodextrin and the F1C in one or more liquids such as ethanol, DMSO, N-methylpyrrolidine, pyridine or water. The sulfobutyl β-cyclodextrin contains one or more butyl sulfonate or —O—$(CH_2)_4$—$SO_3^-Na^+$ moieties, typically about 5, 6 or 7 per cyclodextrin molecule. F1Cs that contain a positive charge are especially helpful in forming complexes with the multiple negative charges of sulfobutyl cyclodextrin. For parenteral formulations, the maximum concentrations could be achieved at about the maximum cyclodextrin concentration that is still syringable, about 50% w:v. The F1C can be added to a solution of sulfobutyl β-cyclodextrin at a molar ratio of about 1:1, e.g., 0.5:1 to about 2:1, and stirred with or without heat for up to about 1 week to form the complex. The solution is optionally filtered or sterilized before filling in vials or injection delivery by any route. The vials can be sterilized by radiation or by sterilie filtration. An exemplary preparation is made using 500 grams of sulfobutyl β-cyclodextrin (about 230 mmoles) combined with about 230 mmoles of the F1C. Solutions containing about 20-80 mg/mL of the F1C are typically obtained. For pharmaceutical formulations, the complex is prepared under GMP compliance conditions. The dried complex is prepared by lyophilization and can be reconstituted, e.g., using sterile 0.9% NaCl. The cyclodextrin complex can also be dried for preparation of formulations for oral or transmucosal administration or reconstituted with water for parenteral delivery, e.g., by subcutaneous or intramuscular injection. F1Cs that are used include 3β,17β-dihydroxyandrost-5-ene, 3β,17β-dihydroxy-16α-fluoroandrost-5-ene, 3β,713,17β-trihydroxyandrost-5-ene, 3β-hydroxy-3α-methyl-17β-aminoandrost-4-ene, 3α-hydroxy-3β-methyl-17β-aminoandrost-4-ene and 3β-hydroxy-17β-aminoandrost-5-ene.

Example 3

Inhibition of inflammation. The capacity of formula 1 compounds to limit or inhibit inflammation or symptoms of inflammation is shown using animal models for inflammatory bowel disease. In an exemplary protocol, groups of 3 male Wistar rats (180±20 grams) fasted for 24 hours before 2,4-dinitrobenzene sulfonic acid (DNBS) or saline challenge are used. Distal colitis is induced by intra-colonic instillation of 0.5 mL of an ethanolic solution of DNBS (30 mg in 0.5 mL of a 30% ethanol in saline solution) after which 2 mL of air is injected through the cannula to ensure that the solution remained in the colon. The volume used is 0.1 mL per injection of 2 and 20 mg/mL of a F1C in a liquid formulation, which is administered by subcutaneous injection once a day for 6 days. The formulation contained 100 mg/mL of the F1C in a non-aqueous suspension, e.g., 2% benzyl alcohol w/v, 0.1% Brij 96 w/v and equal volumes of PEG 300 and propylene glycol. Concentrations of 2 mg/mL and 20 mg/mL are obtained by diluting the 20 mg/mL formulation with vehicle that lacked the F1C.

The first F1C dose is given 30 minutes after DNBS challenge. Sulfasalazine (30 mg/mL in 2% Tween 80 in distilled water) is administered orally (PO) once a day (10 mL/kg/day) for 7 days, the first two doses beginning 24 hours and 2 hours before DNBS challenge. The presence of diarrhea is recorded daily by examining the anal area. Animals are fasted for 24 hours prior to being sacrificed. Animals are sacrificed on day 7 or day 8 and their colons are removed and weighed. Before removal of the colon, signs of adhesion between the colon and other organs are recorded. Also, the presence of ulcerations is noted after weighing of each colon. The "net" change of colon-to-body weight (BW) ratio is normalized relative to saline-challenged baseline group. A 30% decrease in "net" colon-to-body weight ratio is considered significant.

Example 4

Modulation of delayed type hypersensitivity. The capacity of F1Cs to modulate delayed type hypersensitivity (DTH) is determined in mice. Groups of five female BALB/cByJ mice (20-25 grams) are anesthetized and 100 µl of a 3% solution of oxazolone is applied on day 0 to the shaved abdomen and dried. Seven days later, on day 7, the mice are challenged by applying 5 µL of oxazolone topically to each side of the right ear. The F1C (at about 20-100 mg/mL) in vehicle is administered by subcutaneous injection (2 mg/day) one time on day 6, 24 hours before the oxazolone challenge. The vehicle as a non-aqueous suspension of the F1C in, e.g., 2% benzyl alcohol w/v, 0.1% Brij 96 w/v and equal volumes of PEG 300 and propylene glycol.

Dexamethasone in saline (0.2 mg/mL) is administered daily for 9 days (day −1 to 7), first dose 24 hours before sensitization, last dose at challenge by subcutaneous injection (0.01 mg/dose, 50 µL/injection). On Day 8, 24 hours following the oxazolone challenge, both the right and left ear thicknesses are measured using a micrometer caliper and the differences are determined. The differential ear thickness is measured as an indicator of the DTH response to topical oxazolone challenge. The DTH response is expressed as the difference in the thickness (mm) between the right and the left ears for each animal.

The differential ear thickness in animals receiving vehicle alone is 0.225 mm and treatment with dexamethasone (high dose) or cyclophosphamide reduced the DTH response (0.144 mm and 0.092 mm, respectively).

Example 5

Supression of TNF-α induced adhesion molecule expression. The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-α), is a proinflammatory cytokine and stimulates all three CAMs on endothelial cells. It may be involved in a wide variety of inflammatory responses, often resulting in a pathological outcome. The capacity of a formula 1 compound to mediate a suppression of TNF-α induced CAM expression can be examined. A modified ELISA assay which uses Ecs as a solid phase absorbent is employed to measure the amount of CAM expression on TNF-a treated Ecs when co-stimulated with a member of the FGF family of proteins. To perform the experiment, human umbilical vein endothelial cell (HUVEC) cultures are obtained from pooled cord harvests and maintained in growth medium (EGM-2, Clonetics, San Diego, Calif.) supplemented with 10% FCS and 1% penicillin/streptomycin in a 37° C. humidified incubator containing 5% $CO_2$. HUVECs are seeded in 96-well plates at concentrations of about $1 \times 10^4$ cells/well in EGM medium at 37° C. for 18-24 hrs or until confluent. The monolayers are subsequently washed 3 times with a serum-free solution of RPMI-1640 optionally supplemented with 100 U/mL penicillin and 100 mg/mL streptomycin, and treated with a given cytokine and/or growth 5 factor (s) for 24 h at 37° C. Following incubation, the cells are then evaluated for CAM expression.

HUVECs are grown in a standard 96 well plate to confluence. Growth medium is removed from the cells and replaced with 90 µL of 199 Medium (10% FBS). Samples for testing and positive or negative controls are added to the plate in triplicate (in 10 µL volumes). Plates are incubated at 37° C. for either 5 h (selectin and integrin expression) or 24 h (integrin expression). Plates are aspirated to remove medium and 100 pL of 0.1% paraformaldehyde-PBS (with $Ca^{++}$ and $Mg^{++}$) is added to each well. Plates are held at 4° C. for 30 min. Fixative is then removed from the wells and wells are washed 1× with PBS(+Ca,Mg)+0.5% BSA and drained. Do not allow the wells to dry. 10 pL of diluted primary antibody is added to the test and control wells. Anti-ICAM-1-Biotin, Anti-VCAM-1-Biotin and Anti-E-selectin-Biotin are used at a concentration of 10 pg/ml (1:10 dilution of 0.1 mg/ml stock antibody). Cells are incubated at 37° C. for 30 min. in a humidified environment. Wells are washed ×3 with PBS (with Ca, Mg) and 0.5% BSA. Then add 20 pL of diluted ExtrAvidin-Alkaline Phosphotase (1:5,000 dilution) to each well and incubate at 37° C. for 30 min. Wells are washed ×3 with PBS (with Ca, Mg) and 0.5% BSA. 1 tablet of p-Nitrophenol Phosphate pNPP is dissolved in 5 mL of glycine buffer (pH 10.4). 100 µl of pNPP substrate in glycine buffer is added to each test well. Standard wells in triplicate are prepared from the working dilution of the ExtrAvidin-Alkaline Phosphotase in glycine buffer: 5 pL of each dilution is added to triplicate wells and the resulting AP content in each well is 5.50 ng, 1.74 ng, 0.55 ng, 0.18 ng. 100 pl of pNNP reagent is then be added to each of the standard wells. The plate is incubated at 37° C. for 4 h. A volume of 50 µL of 3M NaOH is added to all wells. The results are quantified on a plate reader at 405 nm. The background subtraction option is used on blank wells filled with glycine buffer only. The template is set up to indicate the concentration of AP-conjugate in each standard well. Results are indicated as amount of bound APconjugate in each sample.

Example 6

Effects on the CNS. The effects of the formula 1 compounds on memory, learning, motor function or the status of a neurological condition or neurodegeneration condition are assayed using standard methods. For example, aged, two year old mice are tested in the Morris water maze procedure by training the mice to locate a pedestal in less than 15 seconds in three consecutive trials. Immediately upon completion of training one group of mice is treated with a formula 1 compound (5-30 mg/kg) and a second group is treated with a placebo. The treatment comprises one, two or three intraperitoneal, subcutaneous, intramuscular or intravenous injections of the formula 1 compound and the vehicle placebo. The injections are given once per day. Two weeks after treatment, the time to rescue is timed in the Morris water maze procedure and the control result is compared to the placebo control. The use of Morris water maze and other procedures to measure the effect of various conditions or compounds on learning, memory or neurological conditions have been described, see e.g., R. Gerlai *Trends Neurosci.* 1996, 19:177-181, J. L. W. Lau et al., *Proc. Nat'l. Acad. Sci.* 2001, 98:4716-4721, U.S. Pat. Nos. 6,348,489, 6,251,942 and 6,277,886.

Scopolamine induced amnesia is examined essentially as follows. Groups of 13 to 16 C57BL76 mice (about 35 gm) are trained in the Morris water maze procedure to locate a pedestal in less than 15 seconds in three consecutive trials. Immediately upon completion of training the mice in each of three groups are treated with scopolamine (1 mg/kg), scopolamine plus a formula 1 compound at one or more dosages (e.g., about 5-50 mg/kg), and scopolamine plus a placebo. The treatment comprises one, two or three intraperitoneal, subcutaneous, intramuscular or intravenous injections of the formula 1 compound and the vehicle placebo. The injections are given once per day. Six days after treatment the average time (sec) to rescue is timed using the Morris water maze procedure and the results from each group are compared. Results for a F1C such as 3α,17β-dihydroxy-16α-fluoroandrost-5-ene or 3β-hydroxy-17β-aminoandrost-5-ene are optionally compared to the results that are obtained in these protocols using another control compound, e.g., (S)-(−)-N-propargyl-1-aminoindan or nefiracetam, or another F1C.

Example 7

Ischemia treatment. The capacity of F1Cs to limit injury associated with ischemia and reperfusion is determined in an animal model essentially as follows. Male Sprague-Dawley rats weighing 130-170 g are randomly assigned to no pre-treatment, vehicle pre-treatment or formula 1 compound pre-treatment using one or more dosages, e.g., about 1-10 mg/kg. Animals are treated with vehicle or F1C the day before and the day of surgery. Anesthesia is induced with intraperitoneal pentobarbital (60-70 mg/kg). The rats are placed on a heating pad, and body temperature is maintained at about 36° C. Detection of the cremaster muscle on its neurovascular pedicle is performed essentially according to conventional techniques, e.g., Anderson, G. L. et al., *Microvascular Res.* 1988 36:56-63, Siemionow, M. et al., *Microcirc. Endoth. Lymphatics* 1991 7:183-197, Siemionow, M. et al., *J. Hand Surgery* 1993 18A:963-971.

Briefly, a skin incision is made from the anterior iliac spine to the tip of the scrotum. The testis with cremaster muscle intact is then dissected away from the scrotum. An opening of 1 cm is made on the ventral surface of the cremaster, and the testis and spermatic cord are removed. Under a microscope, the neurovascular pedicle, consisting of the pubic-epigastric arteries, vein, and genitofemoral nerve, is then completely isolated by dissecting to the origin of the vessels from the external iliac artery and vein. The front wall of the cremaster muscle sac is opened and the island cremaster muscle flap is prepared for intravital videomicroscopy. The rat is secured on a tissue bath, and the cremaster muscle flap is spread over the coverglass in the opening at the bottom of the bath and fixed with 5-0 silk sutures. It is then transilluminated from below, using a fiber optic tungsten lamp. The muscle is kept moist and covered with impermeable plastic film. The tissue bath, designed specifically for temperature control, is filled with 0.9% saline and the temperature maintained at between 35-36° C. The microscope is equipped with a color video camera. The video image of the microcirculation is displayed on a 19" monitor, where the final magnification is 1800×. Measurement of microvascular activity is recorded after isolation of the muscle to establish the pre-ischemia baseline. After proper positioning of clamps to completely shut down blood flow to the muscle flap, the duration of the ischemic period is six hours. Following removal of clamps to induce reperfusion injury, activity in the microvasculature is measured at e.g., 30, 60 and 90 minutes post-reperfusion. In all experimental subjects, ischemia is followed by reflow and then by an initial period of flow of blood through the microcirculation. This burst of circulatory activity is followed by marked reperfusion injury that induces loss of flow.

One or more of the following parameters are used to evaluate the state of the cremaster muscle microvasculatory system prior to ischemia and after reperfusion. The density of perfused capillaries in each of three flap regions is measured by counting the number of flowing capillaries in proximity to the preselected post-capillary venule. Nine visual fields of capillaries are counted at each postcapillary venule site, for a total of 27 fields per cremaster muscle flap.

A leukocyte count in postcapillary venules is taken using video scans of three pre-selected post-capillary venules in proximal, middle and distal flap regions. For each venule, the number of leukocytes rolling through the lumen, the number adhering to the endothelium and the number migrating across the endothelium over a two-minute period are recorded. Results are optionally obtained for rollers, strikers and diapedesis.

Red blood cell velocities in first order and second order arterioles are measured. Red blood cell velocities are recorded in the main arterioles of the cremaster flap using an optical Doppler velocimeter. Results are obtained for velocity of venous and arterial blood.

In an exemplary protocol, six rats are untreated and six rats are pre-treated with vehicle. Under conditions of six hours of ischemia and 90 minutes of reperfusion, the absolute number of rolling, sticking and transmigrated leukocytes is determined within 60 minutes of reperfusion and at 90 minutes. Rats are pre-treated with a formula 1 compound by subcutaneous injection the day before and the day of surgery to measure any protective effect of the therapy. One or more of the three parameters are determined and are compared to normal values. The endothelial-adherent properties compared to baseline values are optionally determined, using numbers of rolling, sticking and transmigrating leukocytes. Red cell velocities in second order arterioles are compared to normal rates of flow at, e.g., 90 minutes post-reperfusion.

Example 8

Pulmonary vasoconstriction. The capacity of F1Cs to limit hypoxia induced pulmonary vasoconstriction is demonstrated using an animal model essentially as follows. Isolated perfused ferret lungs are an established animal model to study secondary pulmonary hypertension. In brief, male ferrets are anesthetized with intraperitoneal pentobarbital sodium and the chest is opened. Stainless steel cannulae are secured in the left atrium and pulmonary artery, and the pulmonary artery and the aorta are ligated. The lungs are perfused with a mixture of autologous blood and Krebs-Henseleit buffer in a circulating manner at a constant rate of about 85 mL/min. The perfusion circuit includes a perfusate reservoir, a roller perfusion pump, filter, and a heat exchanger. The perfusion system is made of, e.g., tygon tubing, which is used for connections and for passage through the perfusion pump. The temperature of the perfusate is kept about 37-38° C. and the pH is maintained at 7.35 to 7.40 by adding sodium bicarbonate to the reservoir as needed. The venous reservoir is placed below the lowermost portion of the lung.

The lungs are ventilated with a hypoxic gas mixture of 5% $CO_2$, 4% $O_2$, and 91% $N_2$ by a tracheotomy with a Harvard animal respirator for 30 minutes. The animals are ventilated with a tidal volume of 30 mL, at a rate of 18 breaths/min. and with 2 cm of $H_2O$ positive end-expiatory pressure. For measurements, pulmonary arterial, left atrial and tracheal pressures are monitored using Gould Statha P231 D pressure transducers or an equivalent connected to the inflow circulation and recorded on, e.g., a Grass polygraph. After 30 minutes of ventilation with hypoxic gas mixture, a formula 1 compound in a dose between about 5-25 mg/kg body weight is added to the reservoir, and perfusate is allowed to perfuse the ferret lungs for 1.5 hours. Pulmonary artery pressure is measured until the end of the experiment, i.e., a total of two hours. Pressure that remains at or near basal level indicates the vasodilatory effect of the F1C in pulmonary circulation that is otherwise constricted in response to hypoxia. The effects of the F1Cs can be compared to the effects and duration of nitric oxide, a therapeutic agent that is optionally used in this model as a control.

Example 9

Antiglucocorticoid effects of formula 1 compounds. A series of tests is run in triplicate using BALB/c mouse spleen cells to demonstrate the effect of the F1Cs and hydrocortisone ("Hycort") on cellular proliferation in the absence of a mitogen. Cultures of spleen cells are prepared and F1Cs are added at, e.g., 0.1, 0.5, 1 and 5 µM. Suitable controls are used. Twenty four hours after setup, about 50 µCi [$^3$H]-thymidine is added to each cell. Four to six hours later, the cells are harvested and counted on a scintillation counter.

Spleen cells are obtained from normal BALB/c mice and prepared as a single cell suspension at a concentration of about $1\times10^7$ cells/ml in RPMI 1640 supplemented with 2 mM L-glutamine, $5\times10^{-5}$ M 2-mercaptoethanol, 20 µg/ml gentamycin-sulfate, and 1% Nutridona-NS (Boehringer-Mannheim). Individual aliquots of cells are then pulsed for 30 minutes at 37° C. with selected concentrations of formula 1 compounds. After pulsing, the cells are washed several times in balanced salt solution, resuspended in fresh medium, and then dispensed into 24-well culture plates with a stimulatory concentration of anti-CD3 (e.g., Leo et al. Proc. Natl. Acad. Sci. U.S.A., 84:1374 (1987)). After a 24-hour incubation period, culture supernatants are harvested for assessment of proliferation or cytokine production, e.g., IL-2, IL-3 or IL-4 using, e.g., the method of Mossman (J. Immunol. Meth. 65:55 (1983)). 100% control titers of IL-3, IL-2 or IL-4 from normal stimulated splenocytes are obtained, exemplary values may be about 640 units/mL or IL-2 and 160 units/mL for IL-4.

Effects of formula 1 compounds and Hydrocortisone on Proliferation in the Presence of a Mitogen. A series of spleen cell cultures is run using a formula 1 compound and/or hydrocortisone with cell cultures to which concanavalin A is added. Preliminary tests on cultures to which concanavalin A is added at concentrations of 10.0, 5.0, 2.5 and 1.0 ng/mL. All tests on the effects of invention compounds on cultures stimulated with concanavalin A are performed with concanavalin A at, e.g., about 2.5 ng/mL. A mitogen such as ConA generally increases cell proliferation and the glucocorticoid steroid ("GCS") can decrease proliferation. Detectable partial or complete reversal of the inhibitor effects of hydrocortisone indicate an anti-glucorticoid effect by the formula 1 compounds.

Effect of formula 1 compounds on IL-3 production. Exemplary formula 1 compounds are characterized for their effect on the level of the cytokine IL-3 expresion by spleen cells in tissue culture and for their capacity to reverse the effects of a GCS in IL-3 expression. The spleen cell cultures are prepared in accordance with the general method above. After 30 hours the level of IL-3 in the supernatants of the cultures was measured using the IL-3 ELISA kit manufactured by EndoGen Inc., Boston, Mass. A GCS such as hydrocortisone will generally suppress the production of IL-3 and the invention compounds are examined for their capacity to modify this effect. The IL-3 expressed by cells in culture may be recovered from the media containing IL-3 by known methods such as single or sequential reverse-phase HPLC steps on a preparative HPLC column. (See Urdal, et al., J. Chromatog. 296:171 (1984) and U.S. Pat. No. 5,128,450).

Example 10

Treatment of neurodegenerative conditions. Experimental allergic encephalomyelitis (EAE), is demyelinating disease of the central nervous system with many pathological and clinical similarities with multiple sclerosis (MS). EAE is thus a recognized animal model for human autoimmune conditions such as MS. F1Cs such as 3β,7β-dihydroxy-17β-aminoandrost-5-ene and 3β-hydroxy-17β-aminoandrost-5-ene are tested for their capacity to delay the onset of EAE or to reduce its symptoms. Female SJL mice (5 animals per group) are immunized with 150 to 200 µg of PLP-139-151 peptide/CFA to induce EAE. Starting 7 days before injection of the peptide, the animals are given daily injections (s.c.) of the compounds (3.0 mg) in 0.1 mL vehicle, or vehicle alone for 33 days. The vehicle consisted of a suspension of the formula 1 compound in saline and carboxymethylcellulose. Delayed onset, reduced peak clinical score (from 5.2±0.6 to 2.8±1.8) and cumulative disease index (>60%) of EAE, and prevention of or significant attenuation of relapses are measured. Reduced numbers of PLP-139-151 specific T cell responses and reduced numbers of TNF-α producing cells in the CNS indicate reduced disease progression or severity. Reduced production of autoimmune Th-1 associated cytokines, is consistent with restoration of a more normal Th-1/Th-2 immune balance and/or with reduction of inflammation in this model.

The efficacy of the formula 1 compounds to treat other autoimmune conditions can be determined by incorporating their use with suitable animal models or assay methods, e.g., collagen-induced arthritis as a model for human autoimmune polyarthritis (e.g., L. K. Myers et al., *Clin. Immunol.* 2002, 102:185-191, A. Matejuk et al., *Endocrinology* 2002, 143: 313-319, S. Thornton et al., *J. Immunol.* 165:1557-1563). The effect of the compounds on markers of inflammation such as TNFα, MIP-1β, IL-13, IL-15, IL-17 or IL-18, e.g., reduced expression or activity, is optionally observed in any autoimmune or inflammatory condition.

Example 11

Modulation of transcription. The effect of 16α-bromoepiandrosterone ("BrEA") on transcript levels in cells in vitro was studied using a microarray to allow simultaneous monitoring of the expression of many genes to allow detailed analysis of the molecular pathways involved in biological responses to the compound.

In general, microarray technology works by covalently linking short DNA sequences that are complementary to the transcripts of many different genes on a single slide or array chip. mRNAs from test and control samples are generated and labeled with one or more colored fluorescent dyes or probes. The probes are hybridized with the array, which is then scanned by laser. The color and intensity of the fluorescent signal at each spot denotes relative expression level of each gene. The capacity of other F1Cs described herein, e.g., a F1C in compound group 1, 2, 3, 4 or 5, to modulate gene expression is characterized in a similar manner.

The array used in the experiment described below, contained about 12,000 known genes. The experiment used U937 human promonocytic leukemia cells that differentiate to monocyte/macrophage cells in the presence of phorbol-12-myristate-13-acetate ("PMA"). The U937 cells were PMA treated and then exposed to BrEA for 1 hr, 2 hrs, or 4 hrs, followed by bacterial lipopolysaccharide ("LPS") stimulation for 1 hr, 2 hrs or 4 hrs. The level of transcripts of the genes on the array was measured at the time points using RNA prepared from BrEA-treated and control (no BrEA) cells. U937 cells were plated at $1\times10^5$ cells/mL in the presence of 3 ng/mL PMA (Sigma, Catalog #P-8139) for 48 hrs. Cells were then treated with either 10 µM BrEA or DMSO (vehicle) for 1 hr, 2 hr, and 4 hrs. At each time point, cells were harvested and total RNA was extracted using Qiagen Rneasy kit according to manufacturer's specification. Total RNA samples were then analyzed by Mergen Ltd. (San Leandro, Calif. www.mergen.com) to perform microarray assay.

For the microarray assay, Dnase-treated total RNA (20 micrograms) was reverse-transcribed using an oligo[$(dT)_{24}$ T7 promoter]$_{65}$ primer (consisting of the nucleotide binding sequence for the T7 RNA polymerase followed by 24 thymidine nucleotides). This was followed by second strand synthesis. The reaction mixture was then treated with Rnase I to digest the remaining RNA. The double-stranded cDNA was phenol-chloroform extracted and used as template for in vitro transcription (T7 MEGAscript, Ambion, Inc.) to generate biotin-labeled cRNA probes. These probes were hybridized overnight at 30° C. with continuous agitation to Mergen's ExpressChip HO5 DNA Microarray System (catalog number HO5-001) containing 12,000 genes. The arrays were then washed, and hybridized probes were detected using Mergen's cyanine-3 fluorescent dye-conjugated protein. Chips were imaged using an Affymetrix 417-418 form Affymetrix/Genetic MicroSystems (www.affymetrix.com) and spot intensity was quantitated using ImaGene from BioDiscovery Inc. (www.biodiscovery.com).

The results showed that BrEA was capable of substantially up-regulating a number of genes. A number of genes were differentially regulated by BrEA based on two criteria: 1) the expression level of any particular gene in a BrEA-treated sample is at least two-fold higher than that of the control-treated sample; and 2) the expression level of any particular gene in a BrEA-treated sample is significantly higher than background. The up-regulation of many of these genes most apparent at 4 hr after treatment, at which time roughly 700 genes were within the above criteria. Some examples are shown in the following list. The ratios given in the list are from BrEA treated cells compared to control cells not treated with BrEA.

| Ratio* | UniGene ID | UniGene symbol | HO5 gene description |
|---|---|---|---|
| 5.3 | Hs.460 | ATF3 | Activating transcription factor 3 |
| 5.4 | Hs.78546 | ATP2B1 | ATPase, Ca++ transporting, plasma membrane 1 |
| 10.2 | Hs.2128 | DUSP5 | Dual specificity phosphatase 5 |
| 9.7 | Hs.155119 | EHD1 | EH-domain containing 1 |
| 9.6 | Hs.75765 | GRO2 | GRO2 oncogene |
| 124.7 | Hs.89690 | GRO3 | GRO3 oncogene |
| 7.8 | Hs.274402 | HSPA1B | Heat shock 70 kD protein 1B |
| 32.0 | Hs.177781 | MGC5618 | Hypothetical protein MGC5618 |
| 6.6 | Hs.75063 | HIVEP2 | immunodeficiency virus type I enhancer-binding protein 2 |
| 21.5 | Hs.727 | INHBA | Inhibin, beta A (activin A, activin AB alpha polypeptide) |
| 53.0 | Hs.81134 | IL1RN | Interleukin 1 receptor antagonist |
| 27.5 | Hs.126256 | IL1B | Interleukin 1, beta |
| 7.6 | Hs.12503 | IL15RA | Interleukin 15 receptor, alpha |
| 131.8 | Hs.98309 | IL23A | Interleukin 23, alpha subunit p19 |
| 16.9 | Hs.50640 | SSI-1 | JAK binding protein |
| 7.7 | Hs.24684 | KIAA1376 | KIAA1376 protein |
| 6.9 | Hs.164719 | KIAA1726 | KIAA1726 protein |
| 7.1 | Hs.151988 | MAP3K5 | Mitogen-activated protein kinase kinase kinase 5 |
| 25.5 | Hs.301183 | MAIL | Molecule possessing ankyrin repeats induced by lipopolysaccharide (MAIL), homolog of mouse |
| 30.0 | Hs.75607 | MACS | Myristoylated alanine-rich protein kinase C substrate (MARCKS, 80K-L) |
| 6.4 | Hs.109281 | NAF1 | Nef-associated factor 1 |
| 11.3 | Hs.81328 | NFKBIA | Nuclear factor of kappa light polypeptide gene enhancer in B-cells inhibitor, alpha |
| 26.1 | Hs.77729 | OLR1 | Oxidised low density lipoprotein receptor 1 |
| 1348.4 | Hs.2050 | PTX3 | Pentaxin-related gene, rapidly induced by IL-1 beta |
| 14.5 | Hs.80205 | PIM2 | Pim-2 oncogene |
| 9.2 | Hs.239138 | PBEF | Pre-B-cell colony-enhancing factor |
| 5.4 | Hs.3407 | PKIG | Protein kinase (cAMP-dependent, catalytic) inhibitor gamma |

-continued

| Ratio* | UniGene ID | UniGene symbol | HO5 gene description |
|---|---|---|---|
| 6.6 | Hs.103755 | RIPK2 | Receptor-interacting serine-threonine kinase 2 |
| 29.2 | Hs.183601 | RGS16 | Regulator of G-protein signalling 16 |
| 5.3 | Hs.115521 | REV3L | REV3 (yeast homolog)-like, catalytic subunit of DNA polymerase zeta |
| 5.9 | Hs.27018 | LOC51285 | Ris |
| 8.4 | Hs.82085 | SERPINE1 | Serine (or cysteine) proteinase inhibitor, clade E (nexin, plasminogen activator inhibitor type 1), member 1 |
| 9.0 | Hs.1087 | STK2 | Serine/threonine kinase 2 |
| 5.9 | Hs.167503 | STAT5A | Signal transducer and activator of transcription 5A |
| 40.4 | Hs.72918 | SCYA1 | Small inducible cytokine A1 (I-309, homologous to mouse Tca-3) |
| 67.3 | Hs.75703 | SCYA4 | Small inducible cytokine A4 (homologous to mouse Mip-1b) |
| 174.0 | Hs.75498 | SCYA20 | Small inducible cytokine subfamily A (Cys-Cys), member 20 |
| 7.0 | Hs.271387 | SCYA8 | Small inducible cytokine subfamily A (Cys-Cys), member 8 (monocyte chemotactic protein 2) |
| 39.7 | Hs.318885 | SOD2 | Superoxide dismutase 2, mitochondrial |
| 17.4 | Hs.112259 | TRG@ | T cell receptor gamma locus |
| 15.0 | Hs.2134 | TRAF1 | TNF receptor-associated factor 1 |
| 10.3 | Hs.17839 | GG2-1 | TNF-induced protein |
| 17.4 | Hs.101382 | TNFAIP2 | Tumor necrosis factor, alpha-induced protein 2 |
| 5.1 | Hs.211600 | TNFAIP3 | Tumor necrosis factor, alpha-induced protein 3 |
| 1733.0 | Hs.29352 | TNFAIP6 | Tumor necrosis factor, aloha-induced protein 6 |

*Ratio of BrEA treated cells compared to control cells not treated with BrEA

As seen from the data shown above, BrEA was capable of inducing an increase in the level of transcription of a number of genes. These increases ranged from about a 2-fold increase to an increase of greater than about 1700-fold. For some genes, levels of mRNA increased from a nearly undetectable level to a very high level. For genes that are modulated by the formula 1 compounds, the level of mRNA, protein or one or more biological activities associated with the gene product can thus include an increase or a decrease of at least about 3-fold, at least about 5-fold, at least about 10-fold, at least about 20-fold, at least about 50-fold or at least about 100-fold. This increase or decrease may occur for 1, 2, 3, 4, 5, 6 or more of the affected genes.

Pathways through which BrEA may mediate its effects include one or more of the following. At 1 hr, transcripts of USF1, c-Fos, EGR1, and Cul1 were increased. Cul1 activates NFkB1 p50. At 2 hrs, USF1 increases FCAR transcript levels. At 4 hrs, c-Fos/C/EBPβ stimulate transcription of RANTES, NFκB1 p50, 1L6, ICAM1, TSG (TNFAIP6), and IL1β. NFκB1p50/RelA induces IL-2Rα, IL6, GRO2 and GRO3. At 5 hrs, USF1 increases HO1 transcript levels. Alternatively, at 4 hrs, Jun B is also increased, and c-Fos/JunB & JunB/ATF3 increase c-Jun. c-Fos/c-Jun increases ATF-3, MMP1, TNFα and TSG-6 (TNFAIP3). Elevated AP1 or EGR1 increases TGFβ. ATF-3/c-Jun & c-Fos increase MMP3. Activity associated with the presence of the NFkBp50/RelA complex increases IL-8. NFkBp50, STAT5A and STAT5B induce IL2Rα (interleukin-2 receptor α). STAT5B Induces CDKN1A. IFNγR2 induces T-bet. Other formula 1 compounds will generally affect one or more of these pathways in a similar manner.

In general, the genes showing the greatest increases in expression belong to the following families: chemokines (GRO2, GRO3, SCYA1, SCYA4, SCYA20, and SCYA8), cytokines and their receptors ( IL1RN, IL1B, IL15RA, and IL23A), TNFα-related/induced genes (TRAF1, GG2-1, TNFAIP2, TNFAIP3, and TNFAIP6), and members of several different signal transduction pathways (e.g. MAP3K5, STAT5A, SSI-1, RGS16, and NFκBIA). Changes in the expression level of 1, 2, 3, 4, 5, 6, 7, 8, 9, 10, 11, 12 or more of these genes or other genes described herein are useful as a screening assay or method to analyze other test compounds or other formula 1 compounds. The assay can identify the relative potency of the test compound compared to the activity of BrEA or a formula 1 compound, or the assay can identify a distinct subset of the activities seen with BrEA or another formula 1 compound, for example.

As discussed above, BrEA was found to increase immunity in a non-inflammatory cellular context, e.g., in the absence of LPS here, but BrEA decreased inflammation when the cells were in the presence of a strong inducer of inflammation. Thus, BrEA was capable of mediating both apparently contradictory activities by context-specific regulation of activities. The formula 1 compounds act differently in different tissues, depending on the physiological condition of cells or tissues in a subject or cells or tissues in vitro. In multiple systems, both in animals and in humans, the formula 1 compounds appear to drive immune function toward homeostasis. This was observed in the context of HIV where BrEA stimulated immune response in a condition of immune suppression. But, in the context of autoimmunity, the formula 1 compounds generally limit unwanted autoimmune responses. Depending on the state of the target cell, genes will be regulated in a manner that optimizes desired immune responses while limiting unwanted immune responses. Responses to formula 1 compounds in resting cells (e.g. at vaccination) will be different than responses in activated cells (e.g. chronic inflammation).

Screening assays using a formula 1 compound or another compound would include any method that measures the expression level of one or more of these genes in the presence of a test compound as compared to their expression in the absence of the test compound and/or compared to the expression seen with BrEA or another formula 1 compound. This can be done by microarray essentially as described above, as well as by mini or custom array on a focused list of genes (such as the list above and optionally including 1, 2, 3, 4, 5, 6, 7, 8, 9, 10, 11, 12 or more of the genes disclosed herein), quantitative PCR assays such as eXpres Profiling or real-time PCR (www.altheatech.com), and Northern blot analysis. In some cases, when a target gene product is a secreted protein, such as SCYA1, measuring protein level in the culture media for cells in tissue culture by ELISA could also be used as a screening assay. Also, cells for this type of analysis can be obtained from a subject who has been dosed with a formula 1 compound or another test compound. In this case, the cells could be obtained from blood, e.g., white blood cells, or from bone marrow, lymph tissue, spleen tissue or thymus tissue.

It will be appreciated that the methods and compositions of the instant invention can be incorporated in the form of a variety of embodiments, some of which are disclosed herein. It will be apparent to the artisan that other embodiments exist and do not depart from the scope of the invention. Thus, the described embodiments are illustrative and should not be construed as restrictive.

For any of the uses of formula 1 compounds described herein, e.g., in any of the examples above, the results or biological effects that are obtained using individual formula 1 compounds are optionally compared to the results or biological effects that are obtained using a reference formula 1 compound such as 3β,17β-dihydroxyandrost-5-ene, 3β,7β, 17β-trihydroxyandrost-5-ene or BrEA. A reference F1C can serve as a positive control or negative control for modulation of gene transcription or activity. Other known modulators of a gene whose biological activity is associatiated with a symptom or clinical condition of interest could also be used as a reference control with or without a reference F1C control. Such comparisons provide guidance for using the formula 1 compounds in the different methods or clinical conditions. Such comparison information allows, e.g., tailoring of dosages, dosing schedules, routes of administration or drug interactions with other therapeutic treatments in any selected application for the F1Cs.

Example 12

The effect of F1Cs on transcript or gene product levels in cells in vitro is studied in vitro using a cell type of interest, e.g., the murine macrophage cell line designated RAW264.7 ("RAW" cells). For the RAW cells, the cells are maintained in a suitable medium, e.g., RPMI 1640 supplemented with 10% FBS, standard Penn/Strep antibiotic solution and 2 mM glutamine. The T1C is dissolved in a suitable solvent, e.g., DMSO or pyrrolidone, to generate a 10 mM stock solution. For DMSO solutions, appropriate dilutions are made to give a F1C final concentration in culture media of about 1 nM to about 10 μM, with a final DMSO content of no more than 0.1% v/v. The cells are induced with LPS at 100 ng/ml (stock solution in water, diluted in serum-free culture media).

In a typical protocol, on day 0 the cells are plated at a density to reach a sub-confluent state of greater than about 75% confluency on the following day. For 6-well plates, about 500,000 to 700,000 cells/well are plated. On the following day, day 1, the cells are treated with the F1C or vehicle, e.g., DMSO, with or without LPS, for selected times, e.g., 0.5, 1, 2, 4, 6, 8, 10, 12, 16, 24, 36, 48 hours. After incubation, cells are harvested with a cell scraper and total RNA is extracted to generate samples for PCR analysis. 1 mL of culture media is optionally saved at −20° C. for future ELISA analysis to determine gene transcript levels. On day 2, cells are harvested after, e.g., 24 hr of F1C in DMSO treatment. LPS induction is started in cells pre-treated with F1C in, e.g., DMSO. Exemplary treatment conditions and time points for cell harvesting are as follows:

| | | | | | | |
|---|---|---|---|---|---|---|
| No treatment | 0 hr | | | | | 24 hr |
| DMSO + LPS | | | 1 hr | 4 hr | 8 hr | 24 hr |
| F1C 10 μM + LPS | | | 1 hr | 4 hr | 8 hr | 24 hr |
| F1C 1 μM + LPS | | | 1 hr | 4 hr | 8 hr | 24 hr |
| F1C 10 nM + LPS | | | 1 hr | 4 hr | 8 hr | 24 hr |
| DMSO | 24 hr | +LPS | 1 hr | 4 hr | 8 hr | 24 hr |
| F1C 10 μM | 24 hr | +LPS | 1 hr | 4 hr | 8 hr | 24 hr |
| F1C 1 μM | 24 hr | +LPS | 1 hr | 4 hr | 8 hr | 24 hr |
| F1C 10 nM | 24 hr | +LPS | 1 hr | 4 hr | 8 hr | 24 hr |

Exemplary genes of interest that can be analyzed by this or a similar protocol include 1, 2, 3, 4, 5, 6 or more of iNOS (inducible nitric oxide synthase), eNOS (constitutive nitric oxide synthase), COX-2 (cycloxygenase-2, PGE2 synthase), IκBβ, TNFα, IL-1β, IL-1Ra (interleukin 1 receptor antagonist), NFκB1 (p105), NFκB2 (p49/p100), IL-6, MCP-1 (monocyte chemoattractant prtein-1 or CCL2), MIP-2 (macrophage inflammatory protein-2), MMP9 (matrix metalloproteinase 9), gelatinase B, HO-1 (heme oxygenase 1), HIF1α (hypoxia inducible factor 1, alpha subunit), GCLC (gamma glutamylcycteine synthetase catalytic (heavy) subunit or γGCS-hs), GCLM (gamma glutamylcycteine synthetase modifier (light) subunit or γGCS-ls), xCT (cystine/glutamate exchange transporter), NQO1 (NAD(P)H: quinone oxidoreductase 1), TXNRD1 (thioredoxin reduatase 1), EBBP (estrogen responsive B-box protein), CYP1A1 (cytochrome P450), CD36 (SR-B), SR-A (scavenger receptor A or Msr1), ABCA1 (ATP-binding cassette transporter A1), ABCG1 (ATP-binding cassette transporter G1), LDLR (low-density lipoprotein receptor), NR1H3 (nuclear receptor 1H3 or LXRα), NR1C3 (nuclear receptor 1C3 or PPARγ), SCD-1 (stearoyl-CoA desaturase 1) and NR4A1 (nuclear receptor 4A1 or Nur77). F1C that can be characterized in this manner include the F1Cs in the compound groups described above, e.g., one or more of 16α-bromoepiandrosterone, 3β,16α-dihydroxyandrostane-17-one, 3β,16α,17β-trihydroxyandrostane, 3α,16α,17β-trihydroxyandrostane, 3β,17β-dihydroxy-16α-fluoroandrost-5-ene, 3β,17β-dihydroxy-16α-fluoroandrost-1,5-diene, 3β-hydroxy-17β-aminoandrost-5-ene, 3β,7β-dihydroxy-17β-aminoandrost-5-ene, 3β-hydroxy-7-oxo-17β-aminoandrost-5-ene, 3α-hydroxy-17β-aminoandrost-5-ene, 3β-hydroxy-17β-aminoandrost-1,5-ene, 3α-hydroxy-17β-aminoandrost-1,5-diene, 3β-hydroxy-16α-fluoro-17(3-aminoandrost-5-ene or 3β-hydroxy-16α-fluoro-17β-aminoandrost-1,5-diene.

To the extent not already indicated, it will be understood by those of ordinary skill in the art that any of the various specific embodiments, compounds or compositions described herein may be modified to incorporate other appropriate features, e.g., as shown in any other of the specific embodiments disclosed herein or in the cited references.

What is claimed is:

1. A compound having the structure

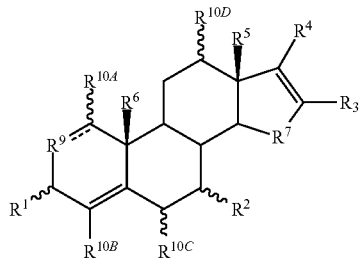

or a salt thereof, wherein the dotted line is an optional double bond;

$R^1$ is —OH, =O, —SH, amide, ester or ether;

$R^2$ is —OH, =O, halogen, alkyl, ester or ether;

$R^3$ is —H, —OH, halogen, alkyl, ester or ether;

$R^4$ is a heterocycle;

$R^5$ and $R^6$ independently are —H, —CH$_3$, —C$_2$H$_5$, —C$_3$H$_7$, —OH, —F, —Cl, —Br or —I;

$R^7$ is —CH$_2$—, —C(halogen)$_2$-, —CH($\alpha$-alkyl), —CH($\beta$-alkyl), —CH($\alpha$-OH), —CH($\beta$-OH) or —C(alkyl)$_2$;

$R^9$ is —CH$_2$—, —CH($\alpha$-OH), —CH($\beta$-OH) or —C(alkyl)$_2$-, or $R^9$ is =CH— when the optional double bond is present $R^{10A}$, $R^{10B}$, $R^{10C}$ and $R^{10D}$ independently are —H, alkyl, —CH$_3$, halogen, —SR$^{PR}$ or —OR$^{PR}$ and each $R^{10A}$, $R^{10B}$, $R^{10C}$ and $R^{10D}$ is independently in the $\alpha$-configuration or the $\beta$-configuration; and $R^{PR}$ independently are —H or a protecting group.

2. The compound of claim 1 wherein the compound has the structure

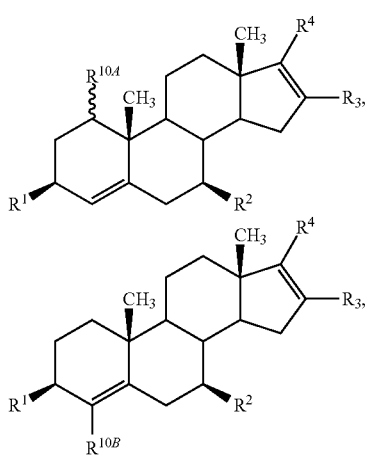

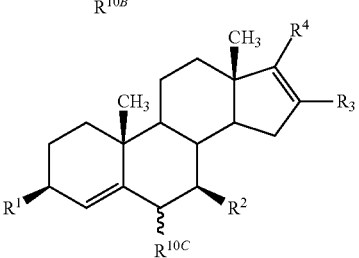

or

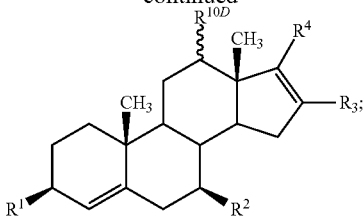

wherein $R^1$ is —OH;

$R^2$ is —OH or —OCH$_3$;

$R^3$ is —H, a halogen, —O—C(O)CH$_3$ or —O—C(O)CH$_2$OH$_3$;

$R^4$ is a heterocycle wherein the heterocycle is 1-aziridyl, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, 2-isoindole, 2-isoindoline, 4-morpholine, 9-carbazole or β-carboline.

3. The compound of claim 1 wherein the compound has the structure

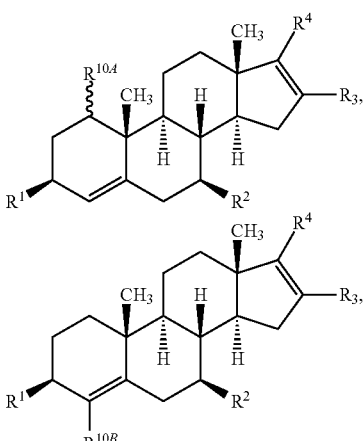

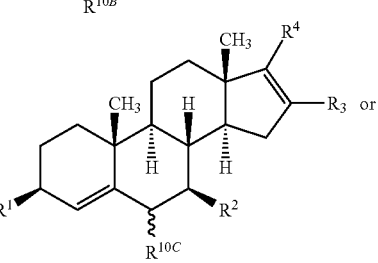

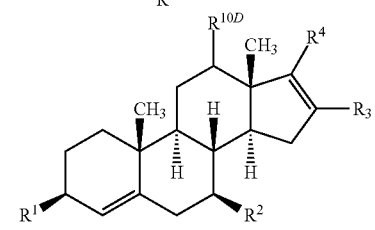

wherein $R^1$ is —OH;

$R^2$ is —OH or —OCH$_3$;

$R^3$ is —H, a halogen, —O—C(O)CH$_3$ or —O—C(O)CH$_2$OH$_3$;

$R^4$ is a C-linked heterocycle; and $R^{10A}$, $R^{10B}$, $R^{10C}$ or $R^{10D}$ is —H, a halogen or —OR$^{PR}$.

4. The compound of claim 3 wherein the C-linked heterocycle is 2-pyridyl, 3-pyridyl, 4-pyridyl, 5-pyridyl or 6-pyridyl.

5. The compound of claim 4 wherein the compound has the structure

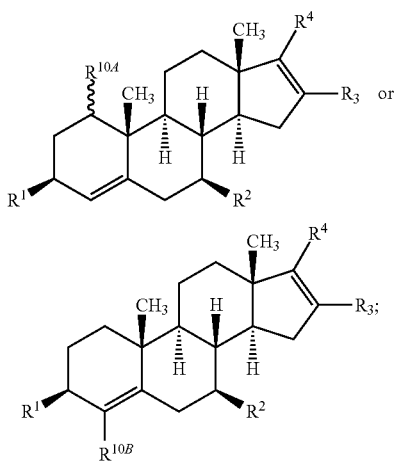

wherein $R^1$ and $R^2$ are —OH;
$R^3$ is —H or —O—C(O)CH$_3$;
$R^4$ is 3-pyridyl; and
$R^{10A}$ or $R^{10B}$ is —H, —OR$^{PR}$ or —F.

6. The compound of claim 1 wherein the compound has the structure

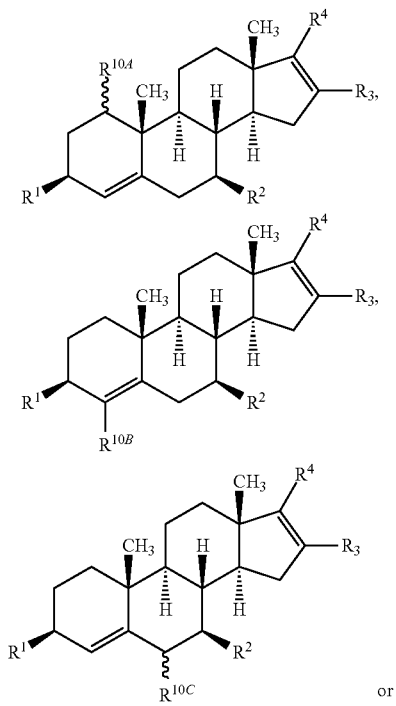

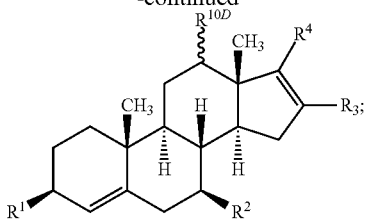

wherein $R^1$ is —OH;
$R^2$ is —OH or —OCH$_3$;
$R^3$ is —H, —O—C(O)CH$_3$ or —O—C(O)CH$_2$OH$_3$;
$R^4$ is an N-linked heterocycle; and
$R^{10A}$, $R^{10B}$, $R^{10C}$ or $R^{10D}$ independently are —H, a halogen or —OR$^{PR}$.

7. The compound of claim 6 wherein $R^4$ is an N-linked heterocycle wherein the N-linked heterocycle is —N-pyrrolidine, —N1-pyrazolone, —N2-pyrazolone, —N-imidazolidin-2-one, —N1-imidazole, —N1-4,5-dihydroimidazole, —N-morpholine, —N-piperidine, —N-indole, —N-indoline, —N-quinolidine or —N1-piperazine, optionally substituted at N4 with alkyl, aryl or heteroaryl.

8. The compound of claim 1 wherein the compound has the structure

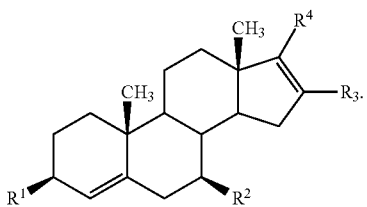

9. The compound of claim 8 wherein
$R^1$ is —OH, =O or —NH—C(O)CH$_3$;
$R^2$ is —OH or —OCH$_3$;
$R^3$ is —H, —OH, —O—C(O)CH$_3$ or —O—C(O)CH$_2$CH$_3$; and
$R^4$ is an N-linked heterocycle.

10. The compound of claim 9, wherein the N-linked heterocycle is —N-pyrrolidine, —N1-pyrazolone, —N2-pyrazolone, —N-imidazolidin-2-one, —N1-imidazole, —N1-4,5-dihydroimidazole, —N-morpholine, —N1-pyridine, —N-piperidine or —N-piperazine.

11. The compound of claim 8 wherein
$R^1$ is —OH, =O or —NH—C(O)CH$_3$;
$R^2$ is —OH or —OCH$_3$;
$R^3$ is —H, —OH, —O—C(O)CH$_3$ or —O—C(O)CH$_2$CH$_3$; and
$R^4$ is a C-linked heterocycle.

12. The compound of claim 11 wherein the C-linked heterocycle is 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

13. The compound of claim 1 wherein the compound is 7β-hydroxy-17-(3-pyridyl)-androst-4,16-dien-3-one.

14. A pharmaceutical formulation comprising one or more pharmaceutically acceptable excipients and a compound according to claim 1.

* * * * *